US012617762B2

(12) United States Patent
Cooke et al.

(10) Patent No.: US 12,617,762 B2
(45) Date of Patent: May 5, 2026

(54) CARBOXY DERIVATIVES WITH ANTIINFLAMATORY PROPERTIES

(71) Applicant: Sitryx Therapeutics Limited, Oxford (GB)

(72) Inventors: Michael Liam Cooke, Nottingham (GB); David Cousin, Nottingham (GB); Matthew Colin Thor Fyfe, Oxford (GB); Thomas Michael Waugh, Nottingham (GB); Saleh Ahmed, Nottingham (GB); Alessio De Simone, Nottingham (GB); Barry John Teobald, Oxford (GB)

(73) Assignee: Sitryx Therapeutics Limited, Oxford (GB)

( * ) Notice: Subject to any disclaimer, the term of this patent is extended or adjusted under 35 U.S.C. 154(b) by 934 days.

(21) Appl. No.: 17/787,870

(22) PCT Filed: Dec. 23, 2020

(86) PCT No.: PCT/GB2020/053357
§ 371 (c)(1),
(2) Date: Jun. 21, 2022

(87) PCT Pub. No.: WO2021/130492
PCT Pub. Date: Jul. 1, 2021

(65) Prior Publication Data

US 2023/0219907 A1 Jul. 13, 2023

(30) Foreign Application Priority Data

Dec. 23, 2019 (EP) .................................... 19219531
Mar. 11, 2020 (EP) .................................... 20162545
(Continued)

(51) Int. Cl.
*C07D 271/06* (2006.01)
*A61K 45/06* (2006.01)
(Continued)

(52) U.S. Cl.
CPC ............ *C07D 271/06* (2013.01); *A61K 45/06* (2013.01); *A61P 37/06* (2018.01); *C07D 263/32* (2013.01); *C07D 277/24* (2013.01)

(58) Field of Classification Search
CPC ........ C07D 271/06; A61P 37/06; A61K 45/06
(Continued)

(56) References Cited

U.S. PATENT DOCUMENTS 4,028,377 A 6/1977 Meyer et al.
4,267,338 A 5/1981 Stetter et al.
(Continued)

FOREIGN PATENT DOCUMENTS

CN 103097365 A 5/2013
CN 103923105 A 7/2014
(Continued)

OTHER PUBLICATIONS

Zhang Y, Zhang Z, Wang B, Liu L, Che Y. Design and synthesis of natural product derivatives with selective and improved cytotoxicity based on a sesquiterpene scaffold. Bioorganic & Medicinal Chemistry Letters. Apr. 15, 2016;26(8):1885-8. (Year: 2016).*
(Continued)

*Primary Examiner* — Jeffrey S Lundgren
*Assistant Examiner* — Heather Dahlin
(74) *Attorney, Agent, or Firm* — Faegre Drinker Biddle & Reath LLP

(57) ABSTRACT

The invention relates to compounds of formula (I) and to their use in treating or preventing an inflammatory disease or
(Continued)

a disease associated with an undesirable immune response: (I) wherein, $R^{A1}$, $R^{A2}$, $R^C$ and $R^D$ are as defined herein.

(I)

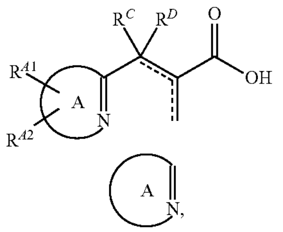

21 Claims, 3 Drawing Sheets

(30) Foreign Application Priority Data

Aug. 5, 2020 (EP) .................................... 20189623
Nov. 4, 2020 (EP) .................................... 20205768

(51) Int. Cl.

| | |
|---|---|
| ***A61P 37/06*** | (2006.01) |
| ***C07D 263/32*** | (2006.01) |
| ***C07D 277/24*** | (2006.01) |

(58) Field of Classification Search
USPC .......................................................... 514/364
See application file for complete search history.

(56) References Cited

U.S. PATENT DOCUMENTS

| | | | |
|---|---|---|---|
| 4,714,765 A | 12/1987 | Ogawa et al. | |
| 5,965,718 A | 10/1999 | Nicolaou et al. | |
| 6,042,991 A | 3/2000 | Aoai et al. | |
| 2003/0207889 A1 | 11/2003 | Owen et al. | |
| 2012/0142717 A1 | 6/2012 | Jin et al. | |
| 2020/0377510 A1* | 12/2020 | Protter et al. | C07D 491/056 |

FOREIGN PATENT DOCUMENTS

| | | |
|---|---|---|
| DE | 1963672 A1 | 6/1971 |
| JP | 2001354625 | 12/2001 |
| JP | 2002107918 | 4/2002 |
| NL | 7112959 A | 3/1972 |
| WO | 1993/001198 A1 | 1/1993 |
| WO | 95/11235 A1 | 4/1995 |
| WO | 2004087636 | 10/2004 |
| WO | 2014/152263 A1 | 9/2014 |
| WO | 2015010107 A | 1/2015 |
| WO | 2017/142855 A1 | 8/2017 |
| WO | 2019/036509 A1 | 2/2019 |
| WO | 2019066827 A1 | 4/2019 |
| WO | 2020006557 A1 | 1/2020 |
| WO | 2020/222010 A1 | 11/2020 |
| WO | 2020/222011 A1 | 11/2020 |
| WO | 2022/029438 A1 | 2/2022 |
| WO | 2022/038365 A2 | 2/2022 |
| WO | 2022/090714 A1 | 5/2022 |
| WO | 2022/090723 A1 | 5/2022 |
| WO | 2022/090724 A1 | 5/2022 |

OTHER PUBLICATIONS

4-Octyl Itaconate, CAS Registry No. 3133-16-2, SciFinder, p. 1, Retrieved Jul. 2025. (Year: 2025).*

Orlek BS, Blaney FE, Brown F, Clark MS, Hadley MS, Hatcher J, Riley GJ, Rosenberg HE, Wadsworth HJ, Wyman P. Comparison of azabicyclic esters and oxadiazoles as ligands for the muscarinic receptor. Journal of medicinal chemistry. Sep. 1991;34(9):2726-35. (Year: 1991).*

Zarghi A, Hajimahdi Z. Substituted oxadiazoles: a patent review (2010-2012). Expert Opinion on Therapeutic Patents. Sep. 1, 2013;23(9):1209-32. (Year: 2013).*

McCurdy & Cohen, Bioisosterism, Drug Design Org, p. 1-138, Feb. 2007. (Year: 2007).*

Liao ST, Han C, Xu DQ, Fu XW, Wang JS, Kong LY. 4-Octyl itaconate inhibits aerobic glycolysis by targeting GAPDH to exert anti-inflammatory effects. Nature communications. Nov. 8, 2019;10(1):5091. (Year: 2019).*

Giacomelli R. et al. "IL-1β at the crossroad between rheumatoid arthritis and type 2 diabetes: may we kill two birds with one stone?", Expert Review of Clinical Immunology, 2016, vol. 12, No. 8, p. 849-p. 855.

Al-Hwas Z. S. et al. "A distinct inflammasome IL-1β gene expression profile in patients with psoriatic arthritis in Basra city", International Journal of Health Sciences, Mar. 27, 2022, vol. 6, p. 4570-p. 4577.

Sung S. J. et al. "Interactions among glomerulus infiltrating macrophages and intrinsic cells via cytokines in chronic lupus glomerulonephritis" Journal of Autoimmunity, 106 (2020) 102331, p. 1-p. 13.

Mendiola et al., "The IL-1b phenomena in neuroinflammatory diseases", A.E. J. Neural. Transm. 2018, 125, p. 781-p. 795.

Tsuji, G et al., "Metformin inhibits IL-1β secretion via impairment of NLRP3 inflammasome in keratinocytes: implications for preventing the development of psoriasis" Cell Death Discovery, 2020, 6:11, p. 1-p. 11.

Piotrowska M. et al., "The Nrf2 in the pathophysiology of the intestine: Molecular mechanisms and therapeutic implications for inflammatory bowel diseases", Pharmacological Research 163 (2021) 105243, p. 1-p. 12.

Liso M. et al., "Interleukin 1b Blockade Reduces Intestinal Inflammation in a Murine Model of Tumor Necrosis Factor-Independent Ulcerative Colitis", Cellular Molecular Gastroenterology and Hepatology, 2022, vol. 14, No. 1, p. 151-p. 171.

Toplak N. et al., "The role of IL-1 inhibition in systemic juvenile idiopathic arthritis: current status and future perspectives" Drug Design, Development and Therapy, 2018, 12, p. 1633-p. 1643.

Fabiani C. et al., "Interleukin (IL)-1 inhibition with anakinra and canakinumab in Behçet's disease-related uveitis: a multicenter retrospective observational study", Clin. Rheumatology, (2017), 36, p. 191-p. 197.

Ferrándiz M. L. et al., "Nrf2 as a therapeutic target for rheumatic diseases", Biochemical Pharmacology, 152, 2018, p. 338-p. 346.

Italiani P. et al., "IL-1 family cytokines and soluble receptors in systemic lupus erythematosus", Arthritis Research & Therapy, (2018), 20;27, p. 1-p. 10.

Karpenko M. N. et al., "Interleukin-1β, interleukin-1 receptor antagonist, interleukin-6, interleukin-10, and tumor necrosis factor-α levels in CSF and serum in relation to the clinical diversity of Parkinson's disease", Cellular Immunology, 327, 2018, 7p. 7-p. 82.

Friedrich M. et al., "IL-1-driven stromal-neutrophil interactions define a subset of patients with inflammatory bowel disease that does not respond to therapies", Nature Medicine, vol. 27, Nov. 2021, p. 1970-p. 1981.

Nasserinejad M. et al., "The effects of IL-8, IL-6, and IL-1 on the risk of celiac disease: a Bayesian regression analysis", Gastroenterology and Hepatology From Bed to Bench, 2019, 12(S1), S117-S122.

Authier F. J. et al., "Interleukin-1 expression in inflammatory myopathies: evidence of marked immunoreactivity in sarcoid granulomas and muscle fibres showing ischaemic and regenerative changes", Neuropathology and Applied Neurobiology, 1997, 23(2), p. 132-p. 40.

Witte-Händel E. et al., "The IL-1 Pathway Is Hyperactive in Hidradenitis Suppurativa and Contributes to Skin Infiltration and Destruction", Journal of Investigative Dermatology, 2019, vol. 139, p. 1294-p. 1305.

(56) References Cited

OTHER PUBLICATIONS

Bårdsen K. et al., "Interleukin-1-related activity and hypocretin-1 in cerebrospinal fluid contribute to fatigue in primary Sjögren's syndrome", Journal of Neuroinflammation, 2019, 16, 102, p. 1-p. 9.
Ly Kim-Heang. et al., "Interleukin-1 blockade in refractory giant cell arteritis", Joint Bone Spine, (2014), 81, p. 76-p. 78.
Migita K. et al., "Dysregulated mature IL-1b production in familial Mediterranean fever" Rheumatology, 2015, 54(4), p. 660-p. 665.
Dandekar P. et al., "Living with Tumour necrosis factor receptor-associated periodic fever syndrome (TRAPS)", Pediatric Rheumatology, 2015, 13(Suppl 1):p. 23.
Kaneko N. et al., "The role of interleukin-1 in general pathology", Inflammation and Regeneration, 2019, 39, 12, p. 1-p. 16.
Dhimolea Eugen, "Interleukin-1β inhibitors for the treatment of cryopyrin-associated periodic syndrome", The Application of Clinical Genetics, 2011, 4, p. 21-p. 27.
Takanohashi A. et al., "Elevation of proinflammatory cytokines in patients with Aicardi-Goutières syndrome", Neurology 2013, 80(11), p. 997-p. 1002.
H. Lindahl et al."Neuroinflammation Associated With Inborn Errors of Immunity", Frontiers in Immunology, Jan. 2022, vol. 12, Article 827815, p. 1-p. 21.
CAS Registry number 2286651-47-4 Cited in official action dated Oct. 16, 2023 on corresponding Canadian Patent application No. 3,161,424.
Rohand, T. et al., Synthesis, Structure Elucidation and Antimicrobial Properties of New Bis-1,3,4-Oxadiazole Derivatives. Pharmaceutical Chemistry Journal, May 2019, vol. 53, No. 2, pp. 152-156.
CAS RN: 1359822-69-7, ACS, STN Registry database, published on Mar. 5, 2012.
Kozbekçi Cansu et al, Journal of Applied Polymer Science, 45039 (2017).
Amrendra K Roy et al., Synthesis, No. 15, pp. 2325-2330, 2003.
Amrendra K. Roy et al., Cheminform, vol. 34, No. 47, pp. 1347-1356, 2003, Jan. 11, 2003.
Bagavant G et al., Indian J Pharm Sci, vol. 56, pp. 80-85, 1994.
Brennan M. S. et al. PLOS One, vol. 10, No. 3 e0120254, 2015.
Cocco et al., J. Med. Chem ; vol. 60, No. 9 pp. 3656-3671, 2017.
Haas Diana et al; Organic Letters; vol. 15, No. 24, pp. 6162-6165, 2013.
Haopeng Sun et al., Expert Opinion on Therapeutics Patents, vol. 27, No. 7, pp. 763-785, 2017.
Joachimiak et al; Chemmedchem; vol. 13, No. 8, pp. 842-851, 2018.
Patra et al., Isoxazole-Based Derivatives from Baylis-Hillman Chemistry: Assessment of Preliminary Hypolipidemic Activity, Bioorg. Med. Chem. 2003, 11, 2269-2276.
Shen et al., Discovery of Biaryl Anthranilides as Full Agonists for the High Affinity Niacin Receptor, J. Med. Chem. 2007, 50, 6303-6306.
Zhang et al., Design and synthesis of natural product derivatives with selective and improved cytotoxicity base on a sesquiterpene scaffold, Bioorg. Med. Chem. Lett. 2016, 26, 1885-1888.
Sun, H. et al., Expert Opinion on Therapeutic Patents, May 10, 2017, vol. 27, No. 7, pp. 763-785.
Paprocka et al., Bioorganic & Medicinal Chemistry Letters, 2015, vol. 25, No. 13, p. 2664-2667.
Cocco et al., Journal of Medicinal Chemistry, 2014, vol. 57, No. 24,p. 10366-10382.
Chobanian et al., ACS Med. Chem. Lett. 2014, 5, 6, 717-721.
Omar et al., Eur J med Chem (1996) 31, 819-825.

* cited by examiner

CARBOXY DERIVATIVES WITH ANTIINFLAMATORY PROPERTIES

CROSS-REFERENCE TO RELATED APPLICATIONS

This application is the National Stage of International Application No. PCT/GB2020/053357 filed Dec. 23, 2020, which claims priority to and benefit of European Application Nos. 19219531.1 filed Dec. 23, 2019, 20162545.6 filed Mar. 11, 2020, 20189623.0 filed Aug. 5, 2020, and 20205768.3 filed Nov. 4, 2020, each of which is herein incorporated by reference in its entirety.

FIELD OF THE INVENTION

The present invention relates to compounds for use in treating or preventing inflammatory diseases or diseases associated with an undesirable immune response, and to related compositions, methods, uses and intermediate compounds.

BACKGROUND OF THE INVENTION

Chronic inflammatory diseases such as rheumatoid arthritis, systemic lupus erythematosus (SLE), multiple sclerosis, psoriasis, Crohn's disease, ulcerative colitis, uveitis and chronic obstructive pulmonary disease (COPD) represent a significant burden to society because of life-long debilitating illness, increased mortality and high costs for therapy and care (Straub R. H. and Schradin C., 2016). Non-steroidal anti-inflammatory drugs (NSAIDs) are the most widespread medicines employed for treating inflammatory disorders, but these agents do not prevent the progression of the inflammation and only treat the accompanying symptoms. Glucocorticoids are powerful anti-inflammatory agents, making them emergency treatments for acute inflammatory flares, but given longer term these medicines give rise to a plethora of unwanted side-effects and may also be subject to resistance (Straub R. H. and Cutolo M., 2016). Thus, considerable unmet medical need still exists for the treatment of inflammatory disorders and extensive efforts to discover new medicines to alleviate the burden of these diseases is ongoing (Hanke T. et al., 2016).

Dimethyl fumarate (DMF), a diester of the citric acid cycle (CAC) intermediate fumaric acid, is utilised as an oral therapy for treating psoriasis (Brück J. et al., 2018) and multiple sclerosis (Mills E. A. et al., 2018). Importantly, following oral administration, none of this agent is detected in 35 plasma (Dibbert S. et al., 2013), the only drug-related compounds observed being the hydrolysis product monomethyl fumarate (MMF) and glutathione (GSH) conjugates of both the parent (DMF) and metabolite (MMF). DMF's mechanism of action is complex and controversial. This compound's efficacy has been attributed to a multiplicity of different phenomena involving covalent modification of proteins and the conversion of "prodrug" DMF to MMF. In particular, the following pathways have been highlighted as being of relevance to DMF's anti-inflammatory effects: 1) activation of the anti-oxidant, anti-inflammatory, nuclear factor (erythroid-derived 2)-like 2 (NRF2) pathway as a consequence of reaction of the electrophilic α,β-unsaturated ester moiety with nucleophilic cysteine residues on kelch-like ECH-associated protein 1 (KEAP1) (Brennan M. S. et al., 2015); 2) induction of activating transcription factor 3 (ATF3), leading to suppression of pro-inflammatory cytokines interleukin (IL)-6 and IL-8 (Müller S. et al., 2017); 3) inactivation of the glycolytic enzyme glyceraldehyde 3-phosphate dehydrogenase (GAPDH) through succination of its catalytic cysteine residue with a Michael accepting unsaturated ester (Kornberg M. D. et al., 2018; Angiari S. and O'Neill L. A., 2018); 4) inhibition of nuclear factor-kappaB (NF-κB)-driven cytokine production (Gillard G. O. et al., 2015); 5) prevention of the association of PKCθ with the costimulatory receptor CD28 to reduce the production of IL-2 and block T-cell activation (Blewett M. M. et al., 2016); 6) reaction of the electrophilic α,β-unsaturated ester with the nucleophilic thiol group of anti-oxidant GSH, impacting cellular responses to oxidative stress (Lehmann J. C. U. et al., 2007); 7) agonism of the hydroxycarboxylic acid receptor 2 (HCA2) by the MMF generated in vivo through DMF hydrolysis (von Glehn F. et al., 2018); 8) allosteric covalent inhibition of the p90 ribosomal S6 kinases (Andersen J. L. et al., 2018); 9) inhibition of the expression and function of hypoxia-inducible factor-1α (HIF-1α) and its target genes, such as IL-8 (Zhao G. et al., 2014); and 10) inhibition of Toll-like receptor (TLR)-induced M1 and K63 ubiquitin chain formation (McGuire V. A. et al., 2016). In general, with the exception of HCA2 agonism (Tang H. et al., 2008), membrane permeable diester DMF tends to exhibit much more profound biological effects in cells compared to its monoester counterpart MMF. However, the lack of systemic exposure of DMF in vivo has led some researchers to assert that MMF is, in fact, the principal active component following oral DMF administration (Mrowietz U. et al., 2018). As such, it is evident that some of the profound biology exerted by DMF in cells is lost because of hydrolysis in vivo to MMF.

Recently, it has been discovered that, during inflammatory macrophage activation, the CAC becomes anaplerotic and is diverted such that the unsaturated diacid itaconic acid, "itaconate", is generated (Murphy M. P. and O'Neill L. A. J., 2018; O'Neill L. A. J. and Artyomov M. N., 2019; Yu X.-H. et al., 2019). Instead of being hydrated to isocitrate by aconitate hydratase, the CAC intermediate aconitate is decarboxylated by the protein product of immune-responsive gene 1 (IRG1), one of the most highly upregulated genes in macrophages under proinflammatory conditions, subsequently named aconitate decarboxylase 1, to produce itaconic acid (Michelucci A. et al., 2013). This unsaturated diacid is an inhibitor of the bacterial enzyme isocitrate lyase and, as such, it exerts anti-bacterial activity. In addition, itaconic acid has been shown to inhibit the CAC enzyme succinate dehydrogenase (SDH) (Ackermann et al., 1949), leading accordingly to succinate accumulation (Cordes T. et al., 2016). By inhibiting SDH, an enzyme critical for the inflammatory response (E. L. Mills et al., 2016), itaconate ameliorates inflammation in vitro and in vivo during macrophage activation and ischemia-reperfusion injury (Lampropoulou V. et al., 2016).

Like fumaric acid, itaconic acid is an α,β-unsaturated carboxylic acid. As such, it is a Michael acceptor which induces a global electrophilic stress response. In this regard, the itaconic acid diester dimethyl itaconate (DMI), like DMF, produces an anti-inflammatory response, reducing the expression levels of pro-inflammatory cytokines IL-1β, IL-6, IL-12 and IL-18 in lipopolysaccharide (LPS)-stimulated bone marrow-derived macrophages (WO2017/142855A1, incorporated herein by reference). This response appears to be mediated, in part, by NRF2 activation, via alkylation of KEAP1 cysteine residues by the electrophilic α,β-unsaturated ester moiety (Mills E. L. et al., 2018), which enhances the expression of downstream genes with anti-oxidant and anti-inflammatory capacities. Nevertheless, not all of the pronounced immunoregulatory effects engendered by DMI can be attributed to NRF2 activation. In particular, the modulation of IKK by DMI is independent of NRF2 and is mediated via upregulation of ATF3, a global negative regulator of immune activation that downregulates various cytokines, such as IL-6 (Bambouskova M. et al., 2018). Moreover, by inhibiting IκBζ protein production, DMI ameliorates IL-17-mediated pathologies, highlighting the therapeutic potential of this regulatory pathway (WO2019/036509A1, incorporated herein by reference). Further highlighting its pharmacologic potential, DMI has recently been reported to 1) demonstrate a protective effect on cerebral ischemia/reperfusion injury, thereby offering potential for the treatment of ischemic stroke (Zhang D. et al., 2019); 2) provide protection from the cardiotoxic effects of doxorubicin (Shan Q. et al., 2019); 3) protect against lippolysacchride-induced mastitis in mice by activating MAPKs and NRF2 while inhibiting NF-κB signaling pathways (Zhao C. et al., 2019). Furthermore, DMI is said to have utility in preventing and treating ulcerative colitis and canceration thereof (CN110731955, Sun Yat-sen University Cancer Center); and has been reported to protect against fungal keratitis by activating the NRF2/HO-1 signaling pathway (Gu L. et al., 2020). Nevertheless, it should be noted that DMI is not metabolised to itaconic acid intracellularly (ElAzzouny M. et al., 2017). Other α,β-unsaturated esters and acids exhibit IL-1β-lowering effects in macrophages by inhibiting the NLRP3 inflammasome (Cocco M. et al., 2017 and 2014), and have been demonstrated to inhibit the TLR4 pathway, leading ultimately to suppression of LPS-induced stimulation of NF-κB, tumour necrosis factor (TNF)-α, IL-1β and nitric oxide release (Zhang S. et al., 2012). WO2014/152263A1 (Karyopharm Therapeutics, Inc.) describes α,β-unsaturated esters which are said to be chromosomal region maintenance 1 (CRM1) inhibitors. CRM-1 plays a role in exporting several key proteins that are involved in many inflammatory processes.

Other itaconic acid derivatives have been demonstrated to elicit anti-inflammatory effects (Bagavant G. et al., 1994). A notable example is 4-octyl itaconic acid (4OI), an itaconate derivative with improved cellular uptake. Since the α,β-unsaturated carboxylic acid is not esterified in 4OI, this electrophile exhibits low reactivity with biological thiols (Schmidt T. J. et al., 2007), much like the situation encountered with itaconic acid itself. As a result of its low reactivity/electrophilicity, the NRF2-activating effects of 4OI are not attenuated by GSH, in contrast to the findings with the much more reactive DMI. In this latter case, the α,β-unsaturated carboxylic acid is esterified and, as a consequence, the IL-6-lowering and NRF2-activating effects of DMI are reversed by the thiols N-acetylcysteine and GSH, respectively. Through the reaction with KEAP1 and the resulting NRF2 activation, as well as GAPDH inhibition (Liao S.-T. et al., 2019), 4OI has been demonstrated to produce a wide range of interesting biological effects, including: 1) protection of neuronal cells from hydrogen peroxide (Liu H. et al., 2018); 2) inhibition of proinflammatory cytokine production in peripheral blood mononuclear cells of SLE patients (Tang C. et al., 2018); 3) protection of human umbilical vein endothelial cells from high glucose (Tang C. et al., 2019); 4) inhibition of osteoclastogenesis by suppressing the E3 ubiquitin ligase Hrd1 and activating NRF2 signaling (Sun X. et al., 2019); 5) induction of repression of STING by NRF2 and type I IFN production in cells from patients with STING-dependent interferonopathies (Olagnier D. et al., 2018); 6) protection against renal fibrosis via inhibiting the TGF-beta/Smad pathway, autophagy and reducing generation of reactive oxygen species (Tian F. et al., 2020); 7) reduction of brain viral burden in mice intracranially injected with Zika virus (Daniels B. P. et al. 2019); and 8) protection against liver ischemia-reperfusion injury (Yi F. et al. 2020). Furthermore, itaconate has been reported to modulate tricarboxylic acid and redox metabolism to mitigate reperfusion injury (Cordes T. et al., 2020). In addition, raised plasma itaconate levels demonstrate a clear correlation with reduction in rheumatoid arthritis disease activity scores following commencement of therapy with conventional disease modifying anti-rheumatic drug (cDMARD) therapy (Daly R. et al., 2019).

In spite of the above findings, there remains a need to identify and develop new α,β-unsaturated carboxyl compounds such as itaconate and acrylate derivatives possessing enhanced properties compared to currently marketed anti-inflammatory agents, such as DMF. The present inventors have now discovered, surprisingly, that certain α,β-unsaturated methacrylic acids possessing heteroaryl groups are effective at reducing cytokine release, activating NRF2 in cells and/or have improved metabolic stability. These properties make them potentially more effective than 4-octyl itaconate in particular. Such compounds are therefore expected to possess excellent anti-inflammatory properties.

SUMMARY OF THE INVENTION

In a first aspect, the present invention provides a compound of formula (I):

(I)

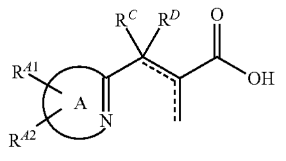

wherein,

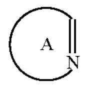

represents a 5 membered heteroaryl ring, which in addition to the C═N shown contains one or more further heteroatoms independently selected from N, O and S;

or

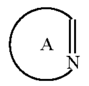

represents a 6 membered heteroaryl ring, which in addition to the C═N shown optionally contains one or more further N atoms;

$R^{A1}$ is selected from the group consisting of $C_{1-10}$ alkyl, $C_{2-10}$ alkenyl, $C_{2-10}$ alkynyl, $-(CH_2)_{0-6}-C_{3-10}$ cycloalkyl, $-(CH_2)_{0-6}-C_{5-10}$ spirocycloalkyl, $-(CH_2)_{0-6}$-aryl and O-aryl;

wherein $R^{A1}$ is optionally substituted by one or more substituents selected from the group consisting of halo, $C_{1-6}$ alkyl, $C_{1-6}$ haloalkyl, hydroxy, cyano, $OG^1$, $S(O)_{0-2}G^1$, $SF_5$, $(CH_2)_{0-3}C_{3-7}$ cycloalkyl and 5-7-membered heterocyclyl wherein said $C_{3-7}$ cycloalkyl and said 5-7-membered heterocyclyl are optionally substituted by one or more groups selected from halo, $C_{1-3}$ alkyl and $C_{1-3}$ haloalkyl; wherein two alkyl groups which are attached to the same carbon atom are optionally joined to form a $C_{3-7}$ cycloalkyl ring; wherein the $C_{3-10}$ cycloalkyl group is optionally fused to a phenyl ring which phenyl ring is optionally substituted by one or more halo atoms;

or $R^{A1}$ is optionally substituted by one phenyl ring which is optionally substituted by $C_{1-2}$ haloalkyl, $C_{1-2}$ haloalkoxy or one or more halo atoms;

wherein $G^1$ is $C_{1-6}$ alkyl, $C_{3-7}$ cycloalkyl, $C_{1-6}$ haloalkyl, or $(CH_2)_{0-1}$phenyl, wherein $G^1$ is optionally substituted by one or more substituents selected from the group consisting of halo, $C_{1-2}$ alkyl, $C_{1-2}$ haloalkyl, hydroxy, cyano, nitro, $C_{1-2}$ alkoxy and $C_{1-2}$ haloalkoxy;

$R^{A2}$ is selected from the group consisting of halo, $C_{1-6}$ alkyl, $C_{2-6}$ alkenyl, $C_{2-6}$ alkynyl, $C_{1-6}$ haloalkyl, hydroxy, cyano, nitro, $NR^1R^2$, $OG^2$ and $S(O)_{0-2}G^2$;

wherein $G^2$ is $C_{1-6}$ alkyl, $C_{3-7}$ cycloalkyl, $C_{1-6}$ haloalkyl, or phenyl which is optionally substituted by one or more substituents selected from the group consisting of halo, $C_{1-2}$ alkyl, $C_{1-2}$ haloalkyl, hydroxy, cyano, nitro, $C_{1-2}$ alkoxy and $C_{1-2}$ haloalkoxy; and wherein $R^1$ and $R^2$ are independently H or $C_{1-2}$ alkyl or, taken together, $R^1$ and $R^2$ may combine to form a 5-7-membered heterocyclic ring;

or $R^{A2}$ is absent; and $R^C$ and $R^D$ are each independently H, $C_{1-2}$ alkyl, hydroxy, fluoro or $C_{1-2}$ alkoxy; or $R^C$ and $R^D$ may join to form a $C_{3-5}$ cycloalkyl ring;

wherein

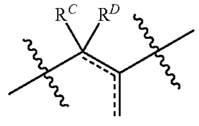

in the compound of formula (I) represents:

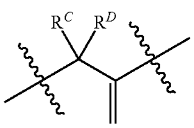 or 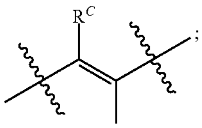;

and wherein the total number of carbon atoms in groups $R^{A1}$ and $R^{A2}$ taken together including their optional substituents is 6-14; and wherein, when

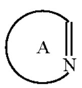

represents an isoxazole, $R^{A1}$ does not represent phenyl, phenyl substituted by bromo, or phenyl substituted by methyl;

or a pharmaceutically acceptable salt and/or solvate thereof.

In a further aspect, the present invention provides a pharmaceutical composition comprising a compound of formula (I) or a pharmaceutically acceptable salt and/or solvate thereof.

In a further aspect, the present invention provides a compound of formula (I) or a pharmaceutically acceptable salt and/or solvate thereof for use as a medicament.

In a further aspect, the present invention provides a compound of formula (I) or a pharmaceutically acceptable salt and/or solvate thereof for use in treating or preventing an inflammatory disease or a disease associated with an undesirable immune response.

In a further aspect, the present invention provides the use of a compound of formula (I) or a pharmaceutically acceptable salt and/or solvate thereof in the manufacture of a medicament for treating or preventing an inflammatory disease or a disease associated with an immune response.

In a further aspect, the present invention provides a method of treating or preventing an inflammatory disease or a disease associated with an undesirable immune response, which comprises administering a compound of formula (I) or a pharmaceutically acceptable salt and/or solvate thereof.

DETAILED DESCRIPTION OF THE INVENTION

FIGURES

COMPOUNDS OF FORMULA (I)

Figure 1:
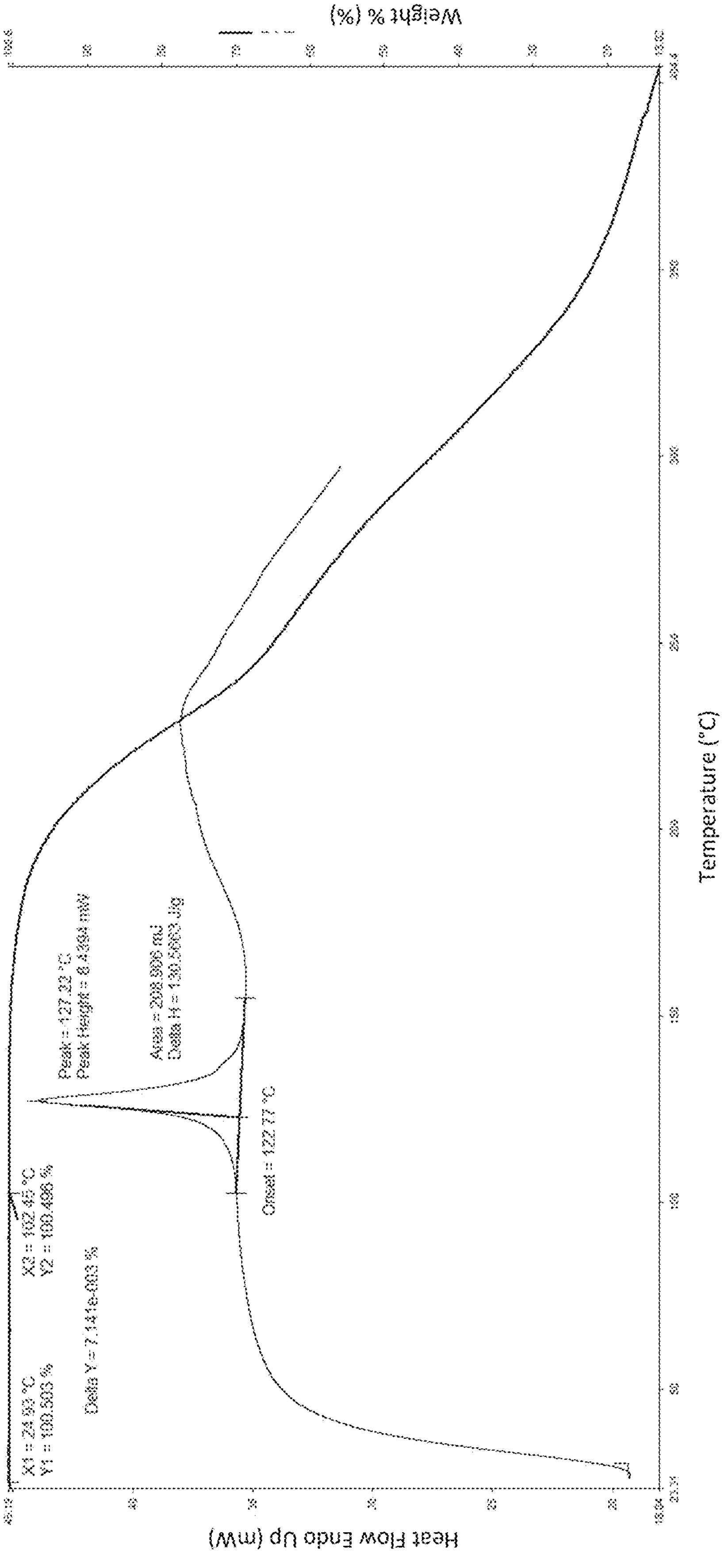
FIG. 1 shows the combined DSC/TGA thermographs of a crystalline form of Example 1, tromethamine salt.

Embodiments and preferences set out herein with respect to the compound of formula (I) apply equally to the pharmaceutical composition, compound for use, use and method aspects of the invention.

In a first aspect, the present invention provides a compound of formula (I) as defined above.

Suitably, the present invention provides a compound of formula (I):

(I)

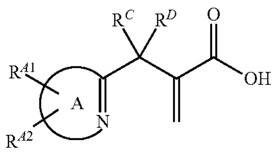

wherein,

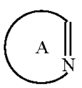

represents a 5 membered heteroaryl ring, which in addition to the C═N shown contains one or more further heteroatoms independently selected from N, O and S;

or

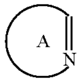

represents a 6 membered heteroaryl ring, which in addition to the C═N shown optionally contains one or more further N atoms;

$R^{A1}$ is selected from the group consisting of $C_{1-10}$ alkyl, $C_{2-10}$ alkenyl, $C_{2-10}$ alkynyl, $—(CH_2)_{0-6}—C_{3-10}$ cycloalkyl, $—(CH_2)_{0-6}—C_{5-10}$ spirocycloalkyl and $—(CH_2)_{0-6}$-aryl; wherein $R^{A1}$ is optionally substituted by one or more substituents selected from the group consisting of halo, $C_{1-6}$ alkyl, $C_{1-6}$ haloalkyl, hydroxy, cyano, $OG^1$, $S(O)_{0-2}G^1$, $SF_5$ and $C_{3-7}$ cycloalkyl wherein said $C_{3-7}$ cycloalkyl is optionally substituted by one or more groups selected from halo, $C_{1-3}$ alkyl and $C_{1-3}$ haloalkyl; wherein two alkyl groups which are attached to the same carbon atom are optionally joined to form a $C_{3-7}$ cycloalkyl ring; or $R^{A1}$ is optionally substituted by one phenyl ring which is optionally substituted by $C_{1-2}$ haloalkyl, $C_{1-2}$ haloalkoxy or one or more halo atoms;

wherein $G^1$ is $C_{1-6}$ alkyl, $C_{3-7}$ cycloalkyl, $C_{1-6}$ haloalkyl, or $(CH_2)_{0-1}$phenyl which is optionally substituted by one or more substituents selected from the group consisting of halo, $C_{1-2}$ alkyl, $C_{1-2}$ haloalkyl, hydroxy, cyano, nitro, $C_{1-2}$ alkoxy and $C_{1-2}$ haloalkoxy;

$R^{A2}$ is selected from the group consisting of halo, $C_{1-6}$ alkyl, $C_{2-6}$ alkenyl, $C_{2-6}$ alkynyl, $C_{1-6}$ haloalkyl, hydroxy, cyano, nitro, $NR^1R^2$, $OG^2$ and $S(O)_{0-2}G^2$;

wherein $G^2$ is $C_{1-6}$ alkyl, $C_{3-7}$ cycloalkyl, $C_{1-6}$ haloalkyl, or phenyl which is optionally substituted by one or more substituents selected from the group consisting of halo, $C_{1-2}$ alkyl, $C_{1-2}$ haloalkyl, hydroxy, cyano, nitro, $C_{1-2}$ alkoxy and $C_{1-2}$ haloalkoxy; and wherein $R^1$ and $R^2$ are independently H or $C_{1-2}$ alkyl or, taken together, $R^1$ and $R^2$ may combine to form a 5-7-membered heterocyclic ring;

or $R^{A2}$ is absent;

$R^C$ and $R^D$ are each independently H, $C_{1-2}$ alkyl, hydroxy, fluoro or $C_{1-2}$ alkoxy; and wherein, the total number of carbon atoms in groups $R^{A1}$ and $R^{A2}$ taken together including their optional substituents is 6-14; and wherein, when

represents an isoxazole, $R^{A1}$ does not represent phenyl, phenyl substituted by bromo, or phenyl substituted by methyl;

or a pharmaceutically acceptable salt and/or solvate thereof.

Suitably, the present invention provides a compound of formula (I):

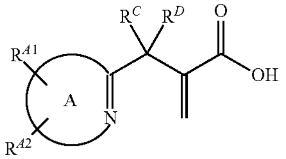

(I)

wherein,

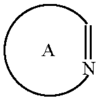

represents a 5 membered heteroaryl ring, which in addition to the C═N shown contains one or more further heteroatoms independently selected from N, O and S;

or

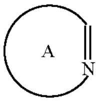

represents a 6 membered heteroaryl ring, which in addition to the C═N shown optionally contains one or more further N atoms;

$R^{A1}$ is selected from the group consisting of $C_{1-10}$ alkyl, $C_{2-10}$ alkenyl, $C_{2-10}$ alkynyl, $—(CH_2)_{0-6}—C_{3-10}$ cycloalkyl, $—(CH_2)_{0-6}—C_{5-10}$ spirocycloalkyl and $—(CH_2)_{0-6}$aryl; wherein $R^{A1}$ is optionally substituted by one or more substituents selected from the group consisting of halo, $C_{1-6}$ alkyl, $C_{1-6}$ haloalkyl, hydroxy, cyano, $OG^1$ and $S(O)_{0-2}G^1$, wherein two alkyl groups which are attached to the same carbon atom are optionally joined to form a $C_{3-7}$ cycloalkyl ring, or $R^{A1}$ is optionally substituted by one phenyl ring which is optionally substituted by $C_{1-2}$ haloalkyl, $C_{1-2}$ haloalkoxy or one or more halo atoms;

wherein $G^1$ is $C_{1-6}$ alkyl, $C_{3-7}$ cycloalkyl, $C_{1-6}$ haloalkyl, or phenyl which is optionally substituted by one or more substituents selected from the group consisting of halo, $C_{1-2}$ alkyl, $C_{1-2}$ haloalkyl, hydroxy, cyano, nitro, $C_{1-2}$ alkoxy and $C_{1-2}$ haloalkoxy;

$R^{A2}$ is selected from the group consisting of halo, $C_{1-6}$ alkyl, $C_{2-6}$ alkenyl, $C_{2-6}$ alkynyl, $C_{1-6}$ haloalkyl, hydroxy, cyano, nitro, $NR^1R^2$, $OG^2$ and $S(O)_{0-2}G^2$;

wherein $G^2$ is $C_{1-6}$ alkyl, $C_{3-7}$ cycloalkyl, $C_{1-6}$ haloalkyl, or phenyl which is optionally substituted by one or more substituents selected from the group consisting of halo, $C_{1-2}$ alkyl, $C_{1-2}$ haloalkyl, hydroxy, cyano, nitro, $C_{1-2}$ alkoxy and $C_{1-2}$ haloalkoxy; and wherein $R^1$ and $R^2$ are independently H or $C_{1-2}$ alkyl or, taken together, $R^1$ and $R^2$ may combine to form a 5-7-membered heterocyclic ring;

or $R^{A2}$ is absent;

$R^C$ and $R^D$ are each independently H, $C_{1-2}$ alkyl, hydroxy or fluoro; and wherein, the total number of carbon atoms in groups $R^{A1}$ and $R^{A2}$ taken together including their optional substituents is 6-14; and wherein, when

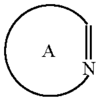

represents an isoxazole, $R^{A1}$ does not represent phenyl, phenyl substituted by bromo, or phenyl substituted by methyl;

or a pharmaceutically acceptable salt and/or solvate thereof.

Suitably, the compound of formula (I) is:

(I)

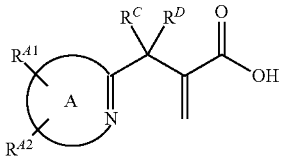

wherein,

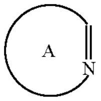

represents a 5 membered heteroaryl ring, which in addition to the C═N shown contains one or more further heteroatoms independently selected from N, O and S;

or

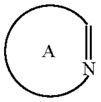

represents a 6 membered heteroaryl ring, which in addition to the C═N shown optionally contains one or more further N atoms;

$R^{A1}$ is selected from the group consisting of $C_{1-10}$ alkyl, $C_{2-10}$ alkenyl, $C_{2-10}$ alkynyl, $—(CH_2)_{1-6}—C_{3-10}$ cycloalkyl, $—(CH_2)_{0-6}—C_{5-10}$ spirocycloalkyl and $—(CH_2)_{0-6}$-aryl; wherein $R^{A1}$ is optionally substituted by one or more substituents selected from the group consisting of halo, $C_{1-6}$ alkyl, $C_{1-6}$ haloalkyl, hydroxy, cyano, $OG^1$ and $S(O)_{0-2}G^1$ and wherein two alkyl groups which are attached to the same carbon atom are optionally joined to form a $C_{3-7}$ cycloalkyl ring;

wherein $G^1$ is $C_{1-6}$ alkyl, $C_{3-7}$ cycloalkyl, $C_{1-6}$ haloalkyl, or phenyl which is optionally substituted by one or more substituents selected from the group consisting of halo, $C_{1-2}$ alkyl, $C_{1-2}$ haloalkyl, hydroxy, cyano, nitro, $C_{1-2}$ alkoxy and $C_{1-2}$ haloalkoxy;

$R^{A2}$ is selected from the group consisting of halo, $C_{1-6}$ alkyl, $C_{2-6}$ alkenyl, $C_{2-6}$ alkynyl, $C_{1-6}$ haloalkyl, hydroxy, cyano, nitro, $NR^1R^2$, $OG^2$ and $S(O)_{0-2}G^2$;

wherein $G^2$ is $C_{1-6}$ alkyl, $C_{3-7}$ cycloalkyl, $C_{1-6}$ haloalkyl, or phenyl which is optionally substituted by one or more substituents selected from the group consisting of halo, $C_{1-2}$ alkyl, $C_{1-2}$ haloalkyl, hydroxy, cyano, nitro, $C_{1-2}$ alkoxy and $C_{1-2}$ haloalkoxy; and wherein $R^1$ and $R^2$ are independently H or $C_{1-2}$ alkyl;

or $R^{A2}$ is absent;

$R^C$ and $R^D$ are each independently H, $C_{1-2}$ alkyl, hydroxy or fluoro; and wherein, the total number of carbon atoms in groups $R^{A1}$ and $R^{A2}$ taken together including their optional substituents is 6-12; and wherein, when

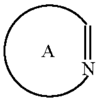

represents an isoxazole, $R^{A1}$ does not represent phenyl, phenyl substituted by bromo, or phenyl substituted by methyl;

or a pharmaceutically acceptable salt and/or solvate thereof.

Suitably, there is provided a compound of formula (I):

(I)

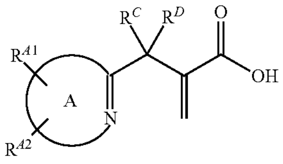

wherein,

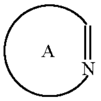

represents a 5 membered heteroaryl ring, which in addition to the C═N shown contains one or more further heteroatoms independently selected from N, O and S;

or

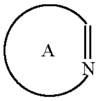

represents a 6 membered heteroaryl ring, which in addition to the C═N shown optionally contains one or more further N atoms;

$R^{A1}$ is selected from the group consisting of $C_{1-10}$ alkyl, $C_{2-10}$ alkenyl, $C_{2-10}$ alkynyl, $—(CH_2)_{0-6}—C_{3-10}$ cycloalkyl, $—(CH_2)_{0-6}—C_{5-10}$ spirocycloalkyl and $—(CH_2)_{0-6}$-aryl; wherein $R^{A1}$ is optionally substituted by one or more substituents selected from the group consisting of halo, $C_{1-6}$ alkyl, $C_{1-6}$ haloalkyl, hydroxy, cyano, $OG^1$ and $S(O)_{0-2}G^1$;

wherein $G^1$ is $C_{1-6}$ alkyl, $C_{3-7}$ cycloalkyl, $C_{1-6}$ haloalkyl, or phenyl which is optionally substituted by one or more substituents selected from the group consisting of halo, $C_{1-2}$ alkyl, $C_{1-2}$ haloalkyl, hydroxy, cyano, nitro, $C_{1-2}$ alkoxy and $C_{1-2}$ haloalkoxy;

$R^{A2}$ is selected from the group consisting of halo, $C_{1-6}$ alkyl, $C_{2-6}$ alkenyl, $C_{2-6}$ alkynyl, $C_{1-6}$ haloalkyl, hydroxy, cyano, nitro, $NR^1R^2$, $OG^2$ and $S(O)_{0-2}G^2$;

wherein $G^2$ is $C_{1-6}$ alkyl, $C_{3-7}$ cycloalkyl, $C_{1-6}$ haloalkyl, or phenyl which is optionally substituted by one or more substituents selected from the group consisting of halo, $C_{1-2}$ alkyl, $C_{1-2}$ haloalkyl, hydroxy, cyano, nitro, $C_{1-2}$ alkoxy and $C_{1-2}$ haloalkoxy; and wherein $R^1$ and $R^2$ are independently H or $C_{1-2}$ alkyl;

or $R^{A2}$ is absent;

$R^C$ and $R^D$ are each independently H, $C_{1-2}$ alkyl, hydroxy or fluoro; and wherein, the total number of carbon atoms in groups $R^{A1}$ and $R^{A2}$ taken together including their optional substituents is 6-12; and wherein, when

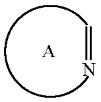

represents an isoxazole, $R^{A1}$ does not represent phenyl, phenyl substituted by bromo, or phenyl substituted by methyl;

or a pharmaceutically acceptable salt and/or solvate thereof.

The term "$C_{1-10}$ alkyl" refers to a straight or branched fully saturated hydrocarbon group having from 1 to 10 carbon atoms. The term encompasses methyl, ethyl, n-propyl, isopropyl, n-butyl, isobutyl, sec-butyl, tert-butyl, n-pentyl, n-heptyl, n-hexyl and n-octyl. Other branched variants such as heptyl-$CH(CH_3)$— and hexyl-$CH(CH_3)$— are also included. Other alkyl groups, for example $C_{1-9}$ alkyl, $C_{1-8}$ alkyl, $C_{1-7}$ alkyl, $C_{1-6}$ alkyl, $C_{1-5}$ alkyl, $C_{1-4}$ alkyl, $C_{1-3}$ alkyl, $C_{1-2}$ alkyl, $C_{2-10}$ alkyl, $C_{2-9}$ alkyl, $C_{2-8}$ alkyl, $C_{2-7}$ alkyl, $C_{2-6}$ alkyl, $C_{2-5}$ alkyl, $C_{2-4}$ alkyl, $C_{2-3}$ alkyl, $C_{3-10}$ alkyl, $C_{3-9}$ alkyl, $C_{3-8}$ alkyl, $C_{3-7}$ alkyl, $C_{3-6}$ alkyl, $C_{3-5}$ alkyl, $C_{3-4}$ alkyl, $C_{4-10}$ alkyl, $C_{4-9}$ alkyl, $C_{4-8}$ alkyl, $C_{4-7}$ alkyl, $C_{4-6}$ alkyl, $C_{4-5}$ alkyl, $C_{5-10}$ alkyl, $C_{5-9}$ alkyl, $C_{5-8}$ alkyl, $C_{5-7}$ alkyl, $C_{5-6}$ alkyl, $C_{6-10}$ alkyl, $C_{6-9}$ alkyl, $C_{6-8}$ alkyl, $C_{7-10}$ alkyl, $C_{7-9}$ alkyl, $C_{7-8}$ alkyl, $C_{8-10}$ alkyl, $C_{8-9}$ alkyl and $C_{9-10}$ alkyl are as defined above but contain different numbers of carbon atoms. The term "$C_{1-10}$ alkyl" also encompasses "$C_{1-10}$ alkylene" which is a bifunctional straight or branched fully saturated hydrocarbon group having the stated number of carbon atoms. Example "alkylene" groups include methylene, ethylene, n-propylene, n-butylene, n-pentylene, n-hexylene, n-heptylene, n-octylene, and stereoisomers thereof such as 2-propylene, 2-butylene, 2-pentylene, 3-pentylene, 2-hexylene, 3-hexylene, 2-heptylene, 3-heptylene, 4-heptylene, 2-octylene, 3-octylene and 4-octylene.

The term "$C_{2-10}$ alkenyl" refers to a straight or branched hydrocarbon group having from 2 to 10 carbon atoms and at least one carbon-carbon double bond. The term encompasses, $CH{=}CH_2$, $CH_2CH{=}CH_2$, $CH{=}CHCH_3$, $CH_2CH_2CH{=}CH_2$, $CH{=}CHCH_2CH_3$, $CH_2CH{=}CHCH_3$, $CH_2CH_2CH_2CH{=}CH_2$, $CH{=}CHCH_2CH_2CH_3$, $CH_2CH{=}CHCH_2CH_3$, $CH_2CH_2CH{=}CHCH_3$, $CH{=}CHCH{=}CHCH_3$ and $CH_2CH{=}CHCH{=}CH_2$. Branched variants such as $CH(CH_3)CH{=}CH_2$ and $CH{=}C(CH_3)CH_2$ are also included. Other alkenyl groups, for example $C_{2-9}$ alkenyl, $C_{2-8}$ alkenyl, $C_{2-7}$ alkenyl, $C_{2-6}$ alkenyl, $C_{2-5}$ alkenyl, $C_{2-4}$ alkenyl, $C_{2-3}$ alkenyl, $C_{3-10}$ alkenyl, $C_{3-9}$ alkenyl, $C_{3-8}$ alkenyl, $C_{3-7}$ alkenyl, $C_{3-6}$ alkenyl, $C_{3-5}$ alkenyl, $C_{3-4}$ alkenyl, $C_{4-10}$ alkenyl, $C_{4-9}$ alkenyl, $C_{4-8}$ alkenyl, $C_{4-7}$ alkenyl, $C_{4-6}$ alkenyl, $C_{4-5}$ alkenyl, $C_{5-10}$ alkenyl, $C_{5-9}$ alkenyl, $C_{5-8}$ alkenyl, $C_{5-7}$ alkenyl, $C_{5-6}$ alkenyl, $C_{6-10}$ alkenyl, $C_{6-9}$ alkenyl, $C_{6-8}$ alkenyl, $C_{7-10}$ alkenyl, $C_{7-9}$ alkenyl, $C_{7-8}$ alkenyl, $C_{8-10}$ alkenyl, $C_{8-9}$ alkenyl and $C_{9-10}$ alkenyl are as defined above but contain different numbers of carbon atoms.

The term "$C_{2-10}$ alkynyl" refers to a straight or branched hydrocarbon group having from 2 to 10 carbon atoms and at least one carbon-carbon triple bond. The term encompasses, $C{\equiv}CH$, $CH_2C{\equiv}CH$, $C{\equiv}C{-}CH_3$, $CH_2CH_2C{\equiv}CH$, $C{\equiv}CCH_2CH_3$, $CH_2C{\equiv}CCH_3$, $CH_2CH_2CH_2C{\equiv}CH$, $C{\equiv}CCH_2CH_2CH_3$, $CH_2C{\equiv}CCH_2CH_3$, $CH_2CH_2C{\equiv}CCH_3$, $C{\equiv}CC{\equiv}CCH_3$ and $CH_2C{\equiv}CC{\equiv}CH$. Branched variants such as $CH(CH_3)C{\equiv}CH$ are also included. Other alkynyl groups, for example $C_{2-9}$ alkynyl, $C_{2-8}$ alkynyl, $C_{2-7}$ alkynyl, $C_{2-6}$ alkynyl, $C_{2-5}$ alkynyl, $C_{2-4}$ alkynyl, $C_{2-3}$ alkynyl, $C_{3-10}$ alkynyl, $C_{3-9}$ alkynyl, $C_{3-8}$ alkynyl, $C_{3-7}$ alkynyl, $C_{3-6}$ alkynyl, $C_{3-5}$ alkynyl, $C_{3-4}$ alkynyl, $C_{4-10}$ alkynyl, $C_{4-9}$ alkynyl, $C_{4-8}$ alkynyl, $C_{4-7}$ alkynyl, $C_{4-6}$ alkynyl, $C_{4-5}$ alkynyl, $C_{5-10}$ alkynyl, $C_{5-9}$ alkynyl, $C_{5-8}$ alkynyl, $C_{5-7}$ alkynyl, $C_{5-6}$ alkynyl, $C_{6-10}$ alkynyl, $C_{6-9}$ alkynyl, $C_{6-8}$ alkynyl, $C_{7-10}$ alkynyl, $C_{7-9}$ alkynyl, $C_{7-8}$ alkynyl, $C_{8-10}$ alkynyl, $C_{8-9}$ alkynyl and $C_9$-10 alkynyl are as defined above but contain different numbers of carbon atoms.

The term "$C_{3-10}$ cycloalkyl" refers to a fully saturated cyclic hydrocarbon group having from 3 to 10 carbon atoms. The term encompasses cyclopropyl, cyclobutyl, cyclopentyl, cyclohexyl, cycloheptyl, cyclooctyl, cyclononyl and cyclodecyl as well as bridged systems such as bicyclo[1.1.1]pentyl, bicyclo[2.2.1]heptyl, bicyclo[2.2.2]octyl and adamantyl. Other cycloalkyl groups, for example $C_{3-9}$ cycloalkyl, $C_{3-8}$ cycloalkyl, $C_{3-7}$ cycloalkyl, $C_{3-6}$ cycloalkyl, $C_{3-5}$ cycloalkyl, $C_{3-4}$ cycloalkyl, $C_{4-10}$ cycloalkyl, $C_{4-9}$ cycloalkyl, $C_{4-8}$ cycloalkyl, $C_{4-7}$ cycloalkyl, $C_{4-6}$ cycloalkyl, $C_{4-5}$ cycloalkyl, $C_{5-10}$ cycloalkyl, $C_{5-9}$ cycloalkyl, $C_{5-8}$ cycloalkyl, $C_{5-7}$ cycloalkyl, $C_{5-6}$ cycloalkyl, $C_{6-10}$ cycloalkyl, $C_{6-9}$ cycloalkyl, $C_{6-8}$ cycloalkyl, $C_{6-7}$ cycloalkyl, $C_{7-10}$ cycloalkyl, $C_{7-9}$ cycloalkyl, $C_{7-8}$ cycloalkyl, $C_{8-10}$ cycloalkyl, $C_{8-9}$ cycloalkyl and $C_{9-10}$ cycloalkyl are as defined above but contain different numbers of carbon atoms.

The term "$C_{5-10}$ spirocycloalkyl" refers to a bicyclic cycloalkyl group wherein the two rings are connected through just one atom. The rings can be different or identical. The term encompasses spiro[3.3]heptyl. Other spirocycloalkyl groups, for example $C_{5-9}$ spirocycloalkyl, $C_{5-8}$ spirocycloalkyl and $C_{5-7}$ spirocycloalkyl are as defined above but contain different numbers of carbon atoms.

The term "5-7 membered heterocyclic ring" refers to a non-aromatic cyclic group having 5 to 7 ring atoms and wherein at least one of the ring atoms is a heteroatom selected from N, O, S and B. The term "heterocyclic ring" is interchangeable with "heterocyclyl". The term encompasses pyrrolidinyl, tetrahydrofuranyl, tetrahydrothienyl, tetrahydropyranyl, piperidinyl, piperazinyl, morpholinyl, thiomorpholinyl and homomorpholinyl. 5-7 membered heterocyclyl groups can typically be substituted by one or more (e.g. one or two) oxo groups. Suitably, thietanyl is substituted by one or two oxo groups. Bicyclic heterocyclic compounds are also encompassed, such as the following:

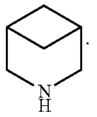

The term "aryl" refers to a cyclic group with aromatic character having from 6 to 10 ring carbon atoms and containing one or two rings. Where an aryl group contains more than one ring, both rings must be aromatic in character. Suitably "aryl" encompasses only phenyl and naphthyl. Most suitably, "aryl" is phenyl.

The term "hydroxy" (which may also be referred to as "hydroxyl") refers to an —OH group.

The term "halo" as used herein, refers to fluorine, chlorine, bromine or iodine. Particular examples of halo are fluorine and chlorine, especially fluorine.

The term "$C_{1-6}$ haloalkyl" refers to a $C_{1-6}$ alkyl group (e.g. a $C_1$ alkyl group i.e. methyl) as defined above, which is substituted by one or more (e.g., one, two or three) halo atoms. Examples include trifluoromethyl, difluoromethyl, 2,2,2-trifluoroethyl and 1,1-difluoroethyl.

The term "$C_{1-2}$ alkoxy" refers to a $C_{1-2}$ alkyl group (e.g. a $C_1$ alkyl group i.e. methyl) as defined above, singularly bonded to oxygen. The term encompasses methoxy and ethoxy.

The term "$C_{1-2}$ haloalkoxy" refers to a $C_{1-2}$ alkoxy as defined above, which is substituted by one or more (e.g., one, two or three) halo atoms. An example includes trifluoromethoxy.

As referred to herein, the term "leaving group" includes groups such as halo, e.g., chloro, bromo, iodo, alkanesulfonate, e.g., methanesulfonate, or arenesulfonate, e.g., para-toluenesulfonate or benzenesulfonate.

Where substituents are indicated as being optionally substituted in formula (I) in the embodiments and preferences set out below, said substituents are optionally substituted as specified in the given formula unless stated otherwise, even if the possible substitution is not explicitly listed in the embodiment. Suitably, the optional substituent may be attached to an available carbon atom, which means a carbon atom which is attached to a hydrogen atom i.e. a C—H group. The optional substituent replaces the hydrogen atom attached to the carbon atom.

The group

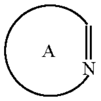

may also be written as

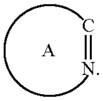

In one embodiment,

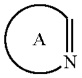

represents a 5 membered heteroaryl ring, which in addition to the C═N shown contains one or more (e.g., one or two) further heteroatoms independently selected from N, O and S.

In one embodiment,

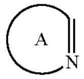

represents a 5 membered heteroaryl ring selected from the group consisting of imidazole, pyrazole, oxazole, isoxazole, thiazole, isothiazole, 1,2,3-triazole, 1,2,4-triazole, 1,2,4-oxadiazole, 1,2,5-oxadiazole, 1,3,4-oxadiazole, 1,2,4-thiadiazole, 1,2,5-thiadiazole, 1,3,4-thiadiazole and tetrazole.

When

represents imidazole, it is intended to represent

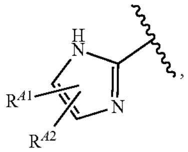

in formula (I). For the avoidance of doubt, substituent $R^{A1}$ and/or $R^{A2}$ (if present) can be bound to a carbon or nitrogen atom of the imidazole moiety.

When

represents pyrazole, it is intended to represent

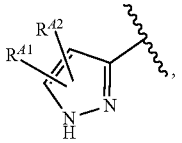

in formula (I). For the avoidance of doubt, substituent $R^{A1}$ and/or $R^{A2}$ (if present) can be bound to a carbon or nitrogen atom of the pyrazole moiety.

When

represents oxazole, it is intended to represent

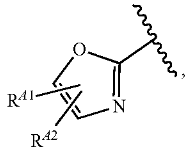

in formula (I).

When

represents isoxazole, it is intended to represent

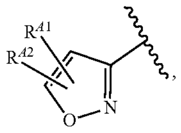

in formula (I).

When

represents thiazole, it is intended to represent

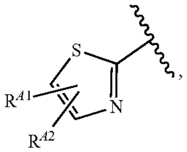

in formula (I).

When

represents isothiazole, it is intended to represent

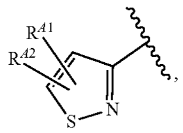

in formula (I).

When

represents 1,2,3-triazole, it is intended to represent

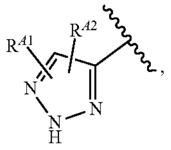

in formula (I). For the avoidance of doubt, substituent $R^{A1}$ and/or $R^{A2}$ (if present) can be bound to a carbon or nitrogen atom of the 1,2,3-triazole moiety.

When

represents 1,2,4-triazole, it is intended to represent

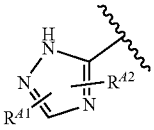

and/or

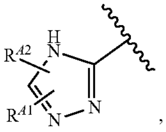

, in formula (I). For the avoidance of doubt, substituent $R^{A1}$ and/or $R^{A2}$ (if present) can be bound to a carbon or nitrogen atom of the 1,2,4-triazole moiety.

When

represents 1,2,4-oxadiazole, it is intended to represent

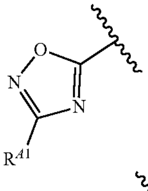

and/or

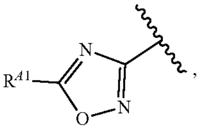

in formula (I).

When

represents 1,2,5-oxadiazole, it is intended to represent

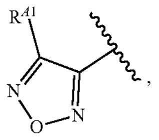

in formula (I).

When

represents 1,3,4-oxadiazole, it is intended to represent

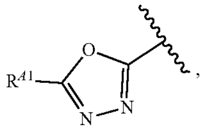

in formula (I).

When

represents 1,2,4-thiadiazole, it is intended to represent

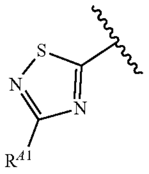

and/or

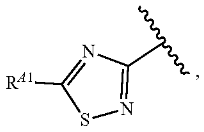

in formula (I).

When

represents 1,2,5-thiadiazole, it is intended to represent

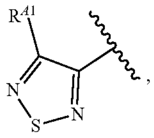

in formula (I).

When

represents 1,3,4-thiadiazole, it is intended to represent

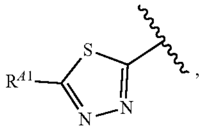

in formula

When

represents tetrazole, it is intended to represent

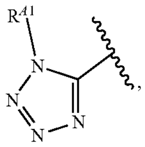

in formula (I).

In one embodiment,

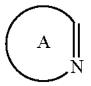

represents an oxadiazole, in particular 1,2,4-oxadiazole.

Suitably, the 1,2,4-oxadiazole is

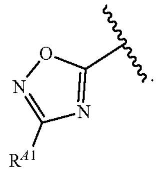

In one embodiment,

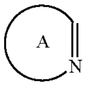

represents 1,3,4-oxadiazole.

In one embodiment,

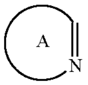

represents a 6 membered heteroaryl ring, which in addition to the C═N shown optionally contains one or more (e.g., one or two) further N atoms.

In one embodiment,

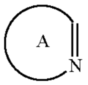

represents a 6 membered heteroaryl ring selected from the group consisting of pyridine, pyridazine, pyrimidine, pyrazine and triazine.

When

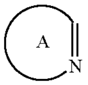

represents pyridine, it is intended to represent

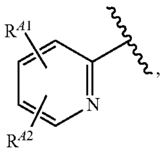

in formula (I).

When

represents pyridazine, it is intended to represent

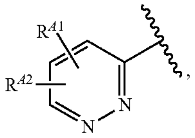

in formula (I).

When

represents pyrimidine, it is intended to represent

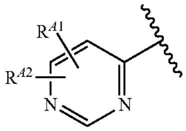

and/or

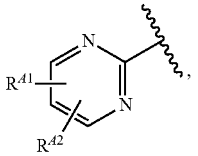

in formula (I).

When

represents pyrazine, it is intended to represent

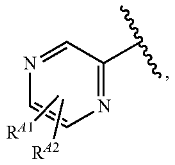

in formula (I).

When

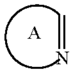

represents triazine, it is intended to represent

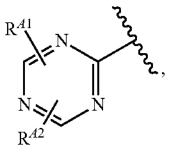

in formula (I).

In the representations above, where a substituent is not indicated as being bound to a carbon atom or nitrogen atom and is instead shown as intersecting a double or single bond of a heteroaryl compound, this indicates that the point of attachment is undefined, and may be any attachment point which is chemically feasible. Furthermore, each of the above mentioned heteroaryl groups is shown as a single tautomer. The skilled person recognises that although a single tautomer is shown, the compound may exist as a mixture of tautomeric forms. Thus, the invention extends to all tautomeric forms of the compounds of formula (I).

In one embodiment, $R^{A1}$ is selected from the group consisting of $C_{1-10}$ alkyl, $C_{2-10}$ alkenyl, $C_{2-10}$ alkynyl, $—(CH_2)_{0-6}—C_{3-10}$ cycloalkyl, $—(CH_2)_{0-6}—C_{5-10}$ spirocycloalkyl, $—(CH_2)_{0-6}$-aryl and O-aryl (e.g. O-phenyl).

In one embodiment, $R^{A1}$ is selected from the group consisting of $C_{1-10}$ alkyl, $C_{2-10}$ alkenyl, $C_{2-10}$ alkynyl, $—(CH_2)_{0-6}—C_{3-10}$ cycloalkyl, $—(CH_2)_{0-6}—C_{5-10}$ spirocycloalkyl and $—(CH_2)_{0-6}$-phenyl.

Suitably, $R^{A1}$ is selected from the group consisting of $C_{1-10}$ alkyl, $C_{2-10}$ alkenyl, $C_{2-10}$ alkynyl, $—(CH_2)_{1-6}—C_{3-10}$ cycloalkyl, $—(CH_2)_{0-6}—C_{5-10}$ spirocycloalkyl and $—(CH_2)_{0-6}$-phenyl.

Suitably, $R^{A1}$ is selected from the group consisting of $C_{1-10}$ alkyl, $C_{2-10}$ alkenyl, $C_{2-10}$ alkynyl, $—(CH_2)_{1-6}C_{3-10}$ cycloalkyl, $—(CH_2)_{1-6}C_{5-10}$ spirocycloalkyl and $—(CH_2)_{1-6}$-phenyl.

In one embodiment, $R^{A1}$ is $C_{2-10}$ alkyl, in particular $C_{3-10}$ alkyl, $C_{4-10}$ alkyl, $C_{5-10}$ alkyl, $C_{6-10}$ alkyl, $C_{7-10}$ alkyl or $C_{8-10}$ alkyl. Suitably, $R^{A1}$ is $C_{7-8}$ alkyl. In one embodiment, $R^{A1}$ is selected from the group consisting of ethyl, n-propyl, iso-propyl, n-butyl, sec-butyl, iso-butyl, tert-butyl, n-pentyl, 2-methylbutan-2-yl, 2,2-dimethylpropyl, 3-methylbutyl, 2-pentyl, 3-pentyl, 3-methylbutan-2-yl, 2-methylbutyl, 1-hexyl, 2-hexyl, 3-hexyl, 1,1-dimethylpentyl, 1,1-dimethylhexyl, 1-heptyl, 1-octyl, 2-octyl, 3-octyl, 4-octyl, 1-nonyl and 5-nonyl.

In one embodiment, the alkyl group is linear (i.e. n-alkyl). In another embodiment, the alkyl group is branched.

Suitably, $R^{A1}$ is $C_7$ alkyl wherein the alkyl group has a linear configuration i.e.

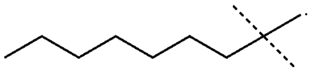

Suitably, $R^{A1}$ is $C_8$ alkyl wherein the alkyl group has a linear configuration i.e.

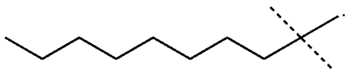

Suitably, $R^{A1}$ is $C_8$ alkyl wherein the alkyl group has a branched configuration. For example, the branched $C_8$ alkyl group may be

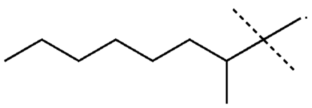

Alternatively, when $R^{A1}$ is $C_{1-10}$ alkyl such as $C_{7-8}$ alkyl, the alkyl group may be substituted by another alkyl group leading to a branched configuration.

For example, suitably $R^{A1}$ is $C_7$ alkyl wherein the alkyl group is substituted by an alkyl group. For example, the $C_7$ alkyl may be substituted by a $C_1$ alkyl (i.e. methyl) such that the following group is formed:

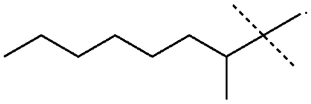

In one embodiment, $R^{A1}$ is $—(CH_2)_{0-6}—C_{3-10}$ cycloalkyl, in particular $—(CH_2)_{0-6}—C_{4-10}$ cycloalkyl, $—(CH_2)_{0-6}—C_{5-10}$ cycloalkyl or $—(CH_2)_{0-6}—C_{5-8}$ cycloalkyl. In one embodiment, $R^{A1}$ is selected from the group consisting of $—(CH_2)_{0-6}$-cyclopropyl, $—(CH_2)_{0-6}$-cyclobutyl, $—(CH_2)_{0-6}$-cyclopentyl, $—(CH_2)_{0-6}$-cyclohexyl, $—(CH_2)_{0-6}$-cycloheptyl, $—(CH_2)_{0-6}$-cyclooctyl and $—(CH_2)_{0-6}$-bicyclo[2.2.1]heptyl; and in particular is selected from the group consisting of $—(CH_2)_{0-6}$-cyclopentyl, $—(CH_2)_{0-6}$-cyclohexyl, $—(CH_2)_{0-6}$-cycloheptyl, $—(CH_2)_{0-6}$-cyclooctyl or $—(CH_2)_{0-6}$-bicyclo[2.2.1]heptyl.

Suitably, $R^{A1}$ is $—(CH_2)_0—C_{3-10}$ cycloalkyl, such as $—(CH_2)_0—C_6$ cycloalkyl, $—(CH_2)_0—C_7$ cycloalkyl or $—(CH_2)_0—C_8$ cycloalkyl.

In one embodiment, $R^{A1}$ is $—(CH_2)_{1-6}—C_{3-10}$ cycloalkyl, in particular $—(CH_2)_{1-6}—C_{4-10}$ cycloalkyl, $—(CH_2)_{1-6}—C_{5-10}$ cycloalkyl or $—(CH_2)_{1-6}—C_{5-8}$ cycloalkyl. In one embodiment, $R^{A1}$ is selected from the group consisting of $—(CH_2)_{1-6}$-cyclopropyl, $—(CH_2)_{1-6}$-cyclobutyl, $—(CH_2)_{0-6}$-cyclopentyl, $—(CH_2)_{1-6}$-cyclohexyl, $—(CH_2)_{1-6}$cycloheptyl, $—(CH_2)_{1-6}$-cyclooctyl and $—(CH_2)_{1-6}$-bicyclo[2.2.1]heptyl; and in particular is $—(CH_2)_{1-6}$-cyclopentyl, $—(CH_2)_{1-6}$-cyclohexyl, $—(CH_2)_{1-6}$-cycloheptyl, $—(CH_2)_{1-6}$-cyclooctyl or $—(CH_2)_{1-6}$-bicyclo[2.2.1]heptyl.

In one embodiment, $C_{3-10}$ cycloalkyl group is fused to a phenyl ring which phenyl ring is optionally substituted by one or more (such as one, two or three, e.g., two) halo atoms. Suitably, $C_{3-10}$ cycloalkyl is a $C_5$ cycloalkyl group. Suitably, the phenyl group is substituted by one or more (such as one, two or three, e.g., two) halo atoms, and most suitably the one or more such as two halo atoms are chloro.

In one embodiment, $R^{A1}$ is $—(CH_2)_{0-6}—C_{5-10}$ spirocycloalkyl, in particular $—(CH_2)_{0-6}$-spiro[3.3]heptyl. Suitably, $R^{A1}$ is $—(CH_2)_{1-6}—C_{5-10}$ spirocycloalkyl.

In one embodiment, $R^{A1}$ is $—(CH_2)_{0-6}$-aryl, for example $—(CH_2)_{0-6}$-phenyl or $—(CH_2)_{0-6}$-naphthyl. Suitably, $R^{A1}$ is $—(CH_2)_{1-6}$-aryl. Suitably, $R^{A1}$ is $—(CH_2)_{0-6}$-phenyl. Suitably, $R^{A1}$ is $—(CH_2)_{1-6}$-phenyl.

Suitably, $R^{A1}$ is $—(CH_2)_{0-2}$-phenyl such as $—(CH_2)_{1-2}$-phenyl. In one embodiment, $R^{A1}$ is phenyl. In another embodiment $R^{A1}$ is $CH_2$-phenyl. In another embodiment, $R^{A1}$ is $(CH_2)_2$-phenyl. Most suitably, $R^{A1}$ is phenyl or $—CH_2$-phenyl.

In one embodiment, $R^{A1}$ is O-aryl e.g. O-phenyl.

In one embodiment, $R^{A1}$ is $C_{7-8}$ alkyl or $—(CH_2)_{0-2}$-phenyl, such as $C_{7-8}$ alkyl or $—(CH_2)_{1-2}$-phenyl.

In another embodiment, $R^{A1}$ is $C_{7-8}$ alkyl or $—(CH_2)_{0-2}$-phenyl, such as $C_{7-8}$ alkyl or $—(CH_2)_{0-1}$-phenyl.

In one embodiment, $R^{A1}$ is not substituted.

In one embodiment, $R^{A1}$ is substituted by one or more such as one, two, three, four, or five e.g., one substituent(s) selected from the group consisting of halo, $C_{1-6}$ alkyl, $C_{1-6}$ haloalkyl, hydroxy, cyano, $OG^1$, $S(O)_{0-2}G^1$, $SF_5$, $(CH_2)_{0-3}C_{3-7}$ cycloalkyl and 5-7-membered heterocyclyl wherein said $C_{3-7}$ cycloalkyl and said 5-7-membered heterocyclyl are optionally substituted by one or more groups selected from halo, $C_{1-3}$ alkyl and $C_{1-3}$ haloalkyl; wherein two alkyl groups which are attached to the same carbon atom are optionally joined to form a $C_{3-7}$ cycloalkyl ring; or $R^{A1}$ is optionally substituted by one phenyl ring which is optionally substituted by $C_{1-2}$ haloalkyl, $C_{1-2}$ haloalkoxy or one or more halo atoms.

In one embodiment, $R^{A1}$ is substituted by one or more such as one, two, three or four, e.g., one substituent(s) selected from the group consisting of halo, $C_{1-6}$ alkyl, $C_{1-6}$ haloalkyl, hydroxy, cyano, $OG^1$, $S(O)_{0-2}G^1$, $SF_5$ and $(CH_2)_{0-3}C_{3-7}$ cycloalkyl wherein said $C_{3-7}$ cycloalkyl is optionally substituted by one or more groups selected from halo, $C_{1-3}$ alkyl and $C_{1-3}$ haloalkyl; wherein two alkyl groups which are attached to the same carbon atom are optionally joined to form a $C_{3-7}$ cycloalkyl ring; or $R^{A1}$ is optionally substituted by one phenyl ring which is optionally substituted by $C_{1-2}$ haloalkyl, $C_{1-2}$ haloalkoxy or one or more halo atoms.

In one embodiment, $R^{A1}$ is substituted by one or more such as one, two, three or four, e.g., one substituent(s) selected from the group consisting of halo, $C_{1-6}$ alkyl, $C_{1-6}$ haloalkyl, hydroxy, cyano, $OG^1$ and $S(O)_{0-2}G^1$, wherein two alkyl groups which are attached to the same carbon atom are optionally joined to form a $C_{3-7}$ cycloalkyl; or $R^{A1}$ is substituted by one phenyl ring which is optionally substituted by $C_{1-2}$ haloalkyl, $C_{1-2}$ haloalkoxy or one or more halo atoms.

In one embodiment, $R^{A1}$ is substituted by one substituent. In another embodiment, $R^{A1}$ is substituted by two substituents. In another embodiment, $R^{A1}$ is substituted by three substituents. In another embodiment, $R^{A1}$ is substituted by four substituents. In another embodiment, $R^{A1}$ is substituted by five substituents in particular when the substituent is halo. Suitably, $R^{A1}$ is substituted by one substituent or three substituents.

In one embodiment, $R^{A1}$ is substituted by halo, e.g., fluoro, chloro or bromo. In a second embodiment, $R^{A1}$ is substituted by $C_{1-6}$ alkyl, e.g., methyl. In a third embodiment, $R^{A1}$ is substituted by $C_{1-6}$ haloalkyl e.g., $CF_3$. In a fourth embodiment, $R^{A1}$ is substituted by hydroxy. In a fifth embodiment, $R^{A1}$ is substituted by cyano. In a sixth embodiment, $R^{A1}$ is substituted by $OG^1$. In a seventh embodiment, $R^{A1}$ is substituted by $S(O)_{0-2}G^1$. In an eighth embodiment, $R^{A1}$ is substituted by $SF_5$. In a ninth embodiment, $R^{A1}$ is substituted by $(CH_2)_{0-3}C_{3-7}$ cycloalkyl wherein said $C_{3-7}$ cycloalkyl is optionally substituted by one or more groups selected from halo, $C_{1-3}$ alkyl and $C_{1-3}$ haloalkyl. In a tenth embodiment, $R^{A1}$ is substituted by 5-7-membered heterocyclyl such as pyrrolidinyl wherein said 5-7-membered heterocyclyl is optionally substituted by one or more groups selected from halo, $C_{1-3}$ alkyl and $C_{1-3}$ haloalkyl.

Suitably, $R^{A1}$ is substituted by one $SF_5$. Alternatively, $R^{A1}$ is substituted by one $SG^1$ wherein $G^1$ is $CF_3$.

In one embodiment, the one or more substituent is $SG^1$. In a second embodiment, the one or more substituent is $S(O)G^1$. In a third embodiment, the one or more substituent is $S(O)_2G^1$. Suitably, the one or more (e.g. one) substituent is $SG^1$.

In an embodiment, $R^{A1}$ is substituted by $(CH_2)_{0-3}C_{3-7}$ cycloalkyl (e.g. one $(CH_2)_{0-3}C_{3-7}$ cycloalkyl) wherein said $C_{3-7}$ cycloalkyl is optionally substituted by one or more groups selected from halo, $C_{1-3}$ alkyl and $C_{1-3}$ haloalkyl.

In one embodiment, $R^{A1}$ is substituted by $C_{3-7}$ cycloalkyl e.g. cyclopentyl. In a second embodiment, $R^{A1}$ is substituted by $CH_2C_{3-7}$ cycloalkyl. In a third embodiment, $R^{A1}$ is substituted by $(CH_2)_2C_{3-7}$ cycloalkyl e.g., $CH_2CH_2$cyclopropyl. In a fourth embodiment, $R^{A1}$ is substituted by $(CH_2)C_{3-7}$ cycloalkyl.

In one embodiment, $R^{A1}$ is substituted by $(CH_2)_{0-3}C_{3-7}$ cycloalkyl wherein said $C_{3-7}$ cycloalkyl is not substituted.

In one embodiment, $R^{A1}$ is substituted by $(CH_2)_{0-3}C_{3-7}$ cycloalkyl wherein said $C_{3-7}$ cycloalkyl is substituted by one or more (such as one, two or three, e.g. one) groups selected from halo, $C_{1-3}$ alkyl and $C_{1-3}$ haloalkyl.

Suitably, the substituent is halo e.g. fluoro. Alternatively, the substituent is $C_{1-3}$ alkyl such as methyl, ethyl or n-propyl, e.g. n-propyl. Alternatively, the substituent is $C_{1-3}$ haloalkyl such as $CF_3$.

In one embodiment, $R^{A1}$ is substituted by $C_3$ cycloalkyl wherein said $C_3$ cycloalkyl is substituted by $C_{1-3}$ haloalkyl such as $CF_3$.

In another embodiment, $R^{A1}$ is substituted by $C_3$ cycloalkyl wherein said $C_3$ cycloalkyl is substituted by n-propyl.

In another embodiment, $R^{A1}$ is substituted by $(CH_2)_2C_3$ cycloalkyl.

Suitably one of the following moieties is formed:

(I)

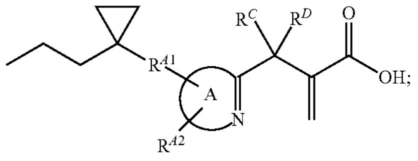

(I)

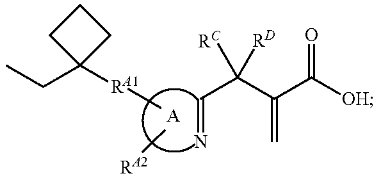

(I)

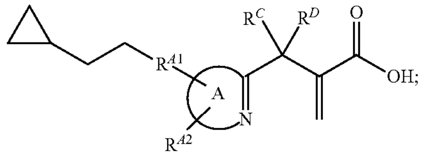

or (I)

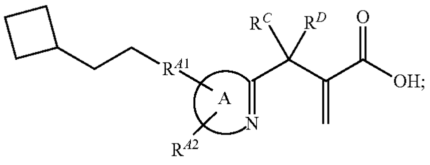

(I)

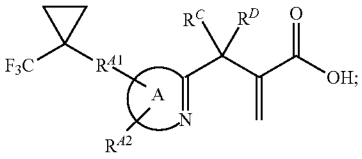

(I)

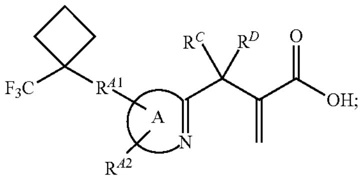

-continued (I)

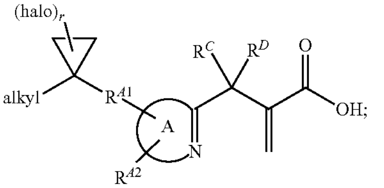

or (I)

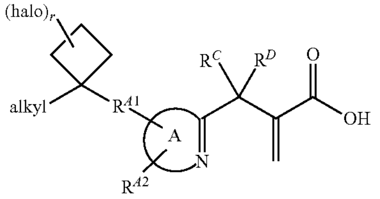

r=1-3

Other variations with different arrangements and number of carbon atoms will be readily envisaged by the skilled person.

When $R^{A1}$ is substituted by 5-7-membered heterocyclyl, suitably, $R^{A1}$ is phenyl. In this embodiment, the 5-7-membered heterocyclyl is suitably connected to $R^{A1}$ via a heteroatom (such as N) present in the 5-7-membered heterocyclyl. Suitably, the 5-7-membered heterocyclyl is pyrrolidinyl and the pyrrolidinyl is connected to $R^{A1}$ (e.g. phenyl) via the nitrogen atom.

In one embodiment, the 5-7-membered heterocyclyl is not substituted. In another embodiment, the 5-7-membered heterocyclyl is substituted by one or more groups selected from halo, $C_{1-3}$ alkyl and $C_{1-3}$ haloalkyl.

In another embodiment, $R^{A1}$ is substituted by one phenyl ring which is optionally substituted by $C_{1-2}$ haloalkyl e.g., $CF_3$, $C_{1-2}$ haloalkoxy e.g., $OCF_3$, or one or more such as one, two, three or four, e.g., one halo atoms (e.g., bromo, chloro and/or fluoro).

Suitably, $R^{A1}$ is substituted by one $C_{1-6}$ alkyl group e.g. n-butyl. Alternatively, $R^{A1}$ is substituted by one $OG^1$ group wherein suitably, $G^1$ is $C_{1-6}$ alkyl e.g. n-butyl. Alternatively, $R^{A1}$ is substituted by two alkyl groups e.g. $C_{1-6}$ alkyl, e.g. $C_{1-2}$ alkyl such as two methyl groups, which are attached to the same carbon atom are optionally joined to form a $C_{3-7}$ cycloalkyl such as a cyclopropyl ring, and $R^{A1}$ is further substituted by one halo atom such as bromo. Suitably in these embodiments, $R^{A1}$ is $-(CH_2)_{0-1}$-phenyl. Most suitably, the phenyl ring is substituted in the para-position.

In one embodiment, $R^{A1}$ is optionally substituted by one or more such as one, two, three or four, e.g., one substituent(s) selected from the group consisting of halo (e.g. fluoro or chloro), $C_{1-2}$ alkyl, $C_{1-2}$ haloalkyl (e.g., $CF_3$), hydroxy, cyano, $O(C_{1-2}$ alkyl) and $S(O)_2C_{1-2}$ alkyl. Suitably, $R^{A1}$ is substituted by $C_1$ alkyl (i.e. methyl), fluoro or chloro.

In another embodiment, $R^{A1}$ is optionally substituted by two alkyl groups such as $C_{1-6}$ alkyl for example $C_{1-2}$ alkyl wherein the alkyl groups are attached to the same carbon atom in $R^{A1}$ and are joined to form a $C_{3-7}$ cycloalkyl group. Suitably, the two alkyl groups are alkyl groups present in $R^{A1}$ substituents $C_{1-6}$ alkyl, $C_{1-6}$ haloalkyl or $OG^1$ (i.e. $C_{1-6}$ alkyl or $C_{1-6}$ haloalkyl $G^1$ groups).

When $R^{A1}$ is optionally substituted by $C_{1-6}$ alkyl and two alkyl groups which are attached to the same carbon atom are optionally joined to form a $C_{3-7}$ cycloalkyl ring, groups of the following structure form:

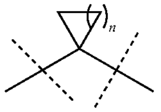

wherein n is an integer selected from 1, 2, 3, 4 and 5. Suitably n is 3.

Suitably, the $C_{3-7}$ cycloalkyl group is a $C_3$ cycloalkyl group:

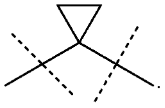

Suitably, the $C_{3-7}$ cycloalkyl group is a $C_4$ cycloalkyl group:

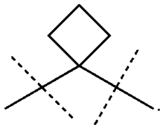

Suitably, the $C_{3-7}$ cycloalkyl group is a $C_5$ cycloalkyl group:

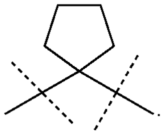

Suitably, the $C_{3-7}$ cycloalkyl group is a $C_6$ cycloalkyl group:

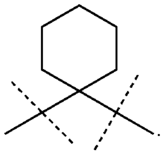

Suitably, the $C_{3-7}$ cycloalkyl group is a $C_7$ cycloalkyl group:

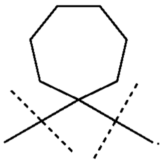

Most suitably, the $C_{3-7}$ cycloalkyl group is a $C_{3-4}$ cycloalkyl group.

In this embodiment, suitably $R^{A1}$ is $-(CH_2)_{1-6}$-phenyl such as $-CH_2$-phenyl. The phenyl ring may be optionally substituted, for example by halo e.g. chloro and/or fluoro e.g. chloro. Alternatively, the phenyl ring may be optionally substituted by bromo.

Suitably, when $R^{A1}$ is —$(CH_2)_{0-2}$-phenyl, for example —$(CH_2)_{1-2}$-phenyl, the phenyl group is substituted by chloro, for example the phenyl group is substituted by chloro in the para position. The phenyl group may be additionally substituted by fluoro. Most suitably, when $R^{A1}$ is —$(CH_2)_{0-2}$-phenyl, for example —$CH_2$-phenyl, the phenyl group is substituted by bromo, for example in the para position.

Suitably, when $R^{A1}$ is —$(CH_2)_{0-2}$-phenyl, for example —$(CH_2)_{1-2}$-phenyl, the phenyl group may be substituted by an additional phenyl ring, which is optionally substituted by one or more (such as one) halo atoms. Suitably, the additional phenyl ring is substituted by one or more (such as one) halo atoms such as one or more (such as one) chloro atoms. Alternatively, the additional phenyl ring is not substituted.

Suitably, when $R^{A1}$ is $C_{1-10}$ alkyl, $R^{A1}$ is optionally substituted by one or more (such as one, two, three or four e.g. one) substituents selected from the group consisting of halo, $C_{1-6}$ haloalkyl, hydroxy, cyano, $OG^1$, $S(O)_{0-2}G^1$, $SF_5$, $(CH_2)_{0-3}C_{3-7}$ cycloalkyl and 5-7-membered heterocyclyl wherein said $C_{3-7}$ cycloalkyl and said 5-7-membered heterocyclyl are optionally substituted by one or more groups selected from halo, $C_{1-3}$ alkyl and $C_{1-3}$ haloalkyl; wherein two alkyl groups which are attached to the same carbon atom are optionally joined to form a $C_{3-7}$ cycloalkyl ring.

Suitably, when $R^{A1}$ is $C_{1-10}$ alkyl, $R^{A1}$ is optionally substituted by one or more (such as one, two, three or four e.g. one) substituents selected from the group consisting of halo, $C_{1-6}$ haloalkyl, hydroxy, cyano, $OG^1$ and $S(O)_{0-2}G^1$, wherein two alkyl groups which are attached to the same carbon atom are optionally joined to form a $C_{3-7}$ cycloalkyl ring; or $R^{A1}$ is optionally substituted by one phenyl ring which is optionally substituted by $C_{1-2}$ haloalkyl, $C_{1-2}$ haloalkoxy or one or more (such as one, two, three or four, e.g., one) halo atoms.

Suitably, when $R^{A1}$ is $C_{2-10}$ alkenyl, $C_{2-10}$ alkynyl, —$(CH_2)_{0-6}$—$C_{3-10}$ cycloalkyl, —$(CH_2)_{0-6}$—$C_{5-10}$ spirocycloalkyl and —$(CH_2)_{0-6}$-aryl, $R^{A1}$ is optionally substituted by one or more (such as one, two, three or four e.g. one) substituents selected from the group consisting of halo, $C_{1-6}$ alkyl, $C_{1-6}$ haloalkyl, hydroxy, cyano, $OG^1$, $S(O)_{0-2}G^1$, $SF_5$, $(CH_2)_{0-3}C_{3-7}$ cycloalkyl and 5-7-membered heterocyclyl wherein said $C_{3-7}$ cycloalkyl and said 5-7-membered heterocyclyl are optionally substituted by one or more groups selected from halo, $C_{1-3}$ alkyl and $C_{1-3}$ haloalkyl; wherein two alkyl groups which are attached to the same carbon atom are optionally joined to form a $C_{3-7}$ cycloalkyl ring; wherein the $C_{3-10}$ cycloalkyl group is optionally fused to a phenyl ring which phenyl ring is optionally substituted by one or more halo atoms.

Suitably, when $R^{A1}$ is $C_{2-10}$ alkenyl, $C_{2-10}$ alkynyl, —$(CH_2)_{0-6}$—$C_{3-10}$ cycloalkyl, —$(CH_2)_{0-6}$—$C_{5-10}$ spirocycloalkyl and —$(CH_2)_{0-6}$-aryl, $R^{A1}$ is optionally substituted by one or more (such as one, two, three or four e.g. one) substituents selected from the group consisting of halo, $C_{1-6}$ alkyl, $C_{1-6}$ haloalkyl, hydroxy, cyano, $OG^1$ and $S(O)_{0-2}G^1$, wherein two alkyl groups which are attached to the same carbon atom are optionally joined to form a $C_{3-7}$ cycloalkyl ring, or $R^{A1}$ is optionally substituted by one phenyl ring which is optionally substituted by $C_{1-2}$ haloalkyl, $C_{1-2}$ haloalkoxy or one or more (such as one, two, three or four, e.g., one) halo atoms.

In one embodiment, $G^1$ is $C_{1-6}$ alkyl, $C_{3-7}$ cycloalkyl, $C_{1-6}$ haloalkyl, or $(CH_2)_{0-1}$phenyl (such as phenyl) wherein $G^1$ is optionally substituted by one or more substituents selected from the group consisting of halo, $C_{1-2}$ alkyl, $C_{1-2}$ haloalkyl, hydroxy, cyano, nitro, $C_{1-2}$ alkoxy and $C_{1-2}$ haloalkoxy.

In one embodiment, $G^1$ is $C_{1-6}$ alkyl, $C_{3-7}$ cycloalkyl, $C_{1-6}$ haloalkyl, or phenyl which is optionally substituted by one or more (such as one, two or three, e.g. one) substituents selected from the group consisting of halo, $C_{1-2}$ alkyl, $C_{1-2}$ haloalkyl, hydroxy, cyano, nitro, $C_{1-2}$ alkoxy and $C_{1-2}$ haloalkoxy.

In one embodiment, $G^1$ is $C_{1-6}$ alkyl e.g. n-butyl. In a second embodiment, $G^1$ is $C_{3-7}$ cycloalkyl, e.g., cyclopropyl. In a third embodiment, $G^1$ is $C_{1-6}$ haloalkyl, such as $CF_3$. In a fourth embodiment, $G^1$ is $(CH_2)_{0-1}$phenyl which is optionally substituted by one or more (such as one, two or three, e.g. one) substituents selected from the group consisting of halo, $C_{1-2}$ alkyl, $C_{1-2}$ haloalkyl, hydroxy, cyano, nitro, $C_{1-2}$ alkoxy and $C_{1-2}$ haloalkoxy. In another embodiment, $G^1$ is phenyl which is optionally substituted by one or more substituents selected from the group consisting of halo, $C_{1-2}$ alkyl, $C_{1-2}$ haloalkyl, hydroxy, cyano, nitro, $C_{1-2}$ alkoxy and $C_{1-2}$ haloalkoxy. In another embodiment, $G^1$ is $CH_2$-phenyl which is optionally substituted by one or more substituents selected from the group consisting of halo, $C_{1-2}$ alkyl, $C_{1-2}$ haloalkyl, hydroxy, cyano, nitro, $C_{1-2}$ alkoxy and $C_{1-2}$ haloalkoxy. Suitably, $G^1$ is not further substituted. Alternatively, $G^1$ is substituted by $C_{1-2}$ alkoxy. Most suitably, $G^1$ is $C_{1-6}$ alkyl e.g. n-butyl.

In one embodiment, $R^{A2}$ is not substituted.

In one embodiment, $R^{A2}$ is absent.

In one embodiment, $R^{A2}$ is $C_{1-6}$ alkyl such as $C_{1-4}$ alkyl, e.g. n-butyl.

$R^C$ and $R^D$ are each independently H, $C_{1-2}$ alkyl, hydroxy, fluoro or $C_{1-2}$ alkoxy; or $R^C$ and $R^D$ may join to form a $C_{3-5}$ cycloalkyl ring.

In one embodiment, $R^C$ and $R^D$ are each independently H, $C_{1-2}$ alkyl, hydroxy or fluoro.

In one embodiment, $R^C$ is H. In a second embodiment, $R^C$ is $C_{1-2}$alkyl e.g. methyl. In a third embodiment, $R^C$ is hydroxy. In a fourth embodiment, $R^C$ is fluoro. In a fifth embodiment, $R^C$ is $C_{1-2}$ alkoxy e.g. OMe.

In one embodiment, $R^D$ is H. In a second embodiment, $R^D$ is $C_{1-2}$ alkyl e.g. methyl. In a third embodiment, $R^D$ is hydroxy. In a fourth embodiment, $R^D$ is fluoro. In a fifth embodiment, $R^D$ is $C_{1-2}$ alkoxy e.g. OMe.

In one embodiment, both $R^C$ and $R^D$ are H.

In another embodiment, $R^C$ and $R^D$ may join to form a $C_{3-5}$ cycloalkyl ring, such as a cyclopropyl ring.

In one embodiment, the compound of formula (I) is:

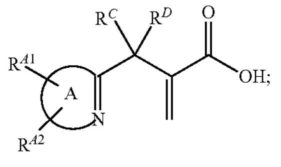

or a pharmaceutically acceptable salt and/or solvate thereof;

wherein A, $R^{A1}$, $R^{A2}$, $R^C$ and $R^D$ are as defined elsewhere herein. The carbon-carbon double bond in this structure is referred to as "exo".

In another embodiment, the compound of formula (I) is:

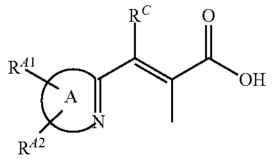

or a pharmaceutically acceptable salt and/or solvate thereof;

wherein A, $R^{A1}$, $R^{A2}$ and $R^C$ are as defined elsewhere herein. The carbon-carbon double bond in this structure is referred to as “endo”.

In the endo embodiment, the double bond may be cis or trans such that both of the following moieties are covered:

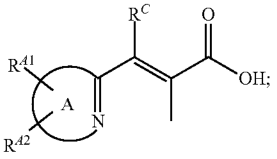

*trans*

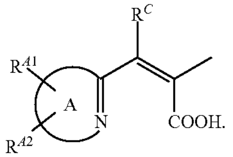

*cis*

Similarly, as used herein, the following structure:

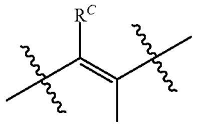

encompasses both cis and trans isomers:

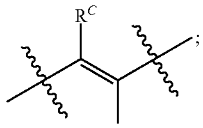

*trans*

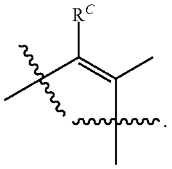

*cis*

Suitably, the endo double bond in the compound of formula (I) is trans.

Typically, e.g. as shown in the Biological Examples section, the compounds of formula (I) in which the carbon-carbon double bond is exo are more potent (e.g. have a lower $IC_{50}$, lower $EC_{50}$ and/or higher $E_{max}$ in the assays described herein) than the equivalent compounds of formula (I) in which the carbon-carbon double bond is endo.

The compounds of formula (I) in which the carbon-carbon double bond is endo can generally be obtained by isomerisation from compounds of formula (I) in which the carbon-carbon double bond is exo and such isomerisation may occur in in vitro assays or in vivo following administration of the exo compound. In some cases, isomerisation in in vitro assays, such as in vitro hepatocyte stability assays, or in vivo following administration of the exo compound may be partial and thus lead to a mixture of the endo and exo compound resulting. In some cases, the mixture of endo and exo isomers may contribute to the activity observed in a particular assay. Suitably, compounds of formula (I), such as those in which the carbon-carbon double bond is exo, are stable to isomerisation.

The total number of carbon atoms in groups $R^{A1}$ and $R^{A2}$ taken together including their optional substituents is 6-14 such as 6-12, suitably, 7-12 or 8-12 e.g. 6-10, 7-10 or 8-10.

In an embodiment, $R^{A2}$ is absent and the total number of carbon atoms in group $R^{A1}$ including any optional substituents is 7-12 or 8-12, or 6-10, 7-10 or 8-10.

When

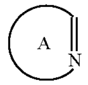

represents an isoxazole, $R^{A1}$ does not represent phenyl, phenyl substituted by bromo, or phenyl substituted by methyl. In one embodiment, when

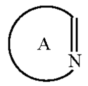

represents an isoxazole, $R^{A1}$ does not represent phenyl, phenyl substituted by halo, or phenyl substituted by $C_{1-10}$ alkyl. In one embodiment, when

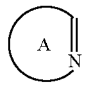

represents an isoxazole, $R^{A1}$ does not represent phenyl or substituted phenyl.

In one embodiment, the compound of formula (I) is selected from the group consisting of:

2-((3-octyl-1,2,4-oxadiazol-5-yl)methyl)acrylic acid;
2-((5-octyl-1,3,4-oxadiazol-2-yl)methyl)acrylic acid; and
2-((5-octyl-1,2,4-oxadiazol-3-yl)methyl)acrylic acid;

or a pharmaceutically acceptable salt and/or solvate thereof.

In one embodiment, the compound of formula (I) is selected from the group consisting of:

2-((3-(4-chlorobenzyl)-1,2,4-oxadiazol-5-yl)methyl)acrylic acid;
2-((3-(4-chlorophenethyl)-1,2,4-oxadiazol-5-yl)methyl) acrylic acid;
2-((3-heptyl-1,2,4-oxadiazol-5-yl)methyl)acrylic acid;
2-((3-(4-chlorophenyl)-1,2,4-oxadiazol-5-yl)methyl)acrylic acid;
2-((3-(octan-2-yl)-1,2,4-oxadiazol-5-yl)methyl)acrylic acid;
2-((3-(naphthalen-2-ylmethyl)-1,2,4-oxadiazol-5-yl) methyl)acrylic acid;
2-((3-(1-(4-chlorophenyl)cyclopropyl)-1,2,4-oxadiazol-5-yl)methyl)acrylic acid; and
2-((3-(8,8,8-trifluorooctyl)-1,2,4-oxadiazol-5-yl)methyl) acrylic acid;

or a pharmaceutically acceptable salt and/or solvate thereof.

In one embodiment, the compound of formula (I) is selected from the group consisting of:

2-((3-(2-methylheptan-2-yl)-1,2,4-oxadiazol-5-yl)methyl)acrylic acid;
2-((1-octyl-1H-1,2,4-triazol-3-yl)methyl)acrylic acid;
2-((3-(3,4-dichlorobenzyl)-1,2,4-oxadiazol-5-yl)methyl)acrylic acid;
2-((3-(4-(tert-butyl)benzyl)-1,2,4-oxadiazol-5-yl)methyl)acrylic acid;
2-((3-(3,5-dichlorobenzyl)-1,2,4-oxadiazol-5-yl)methyl)acrylic acid;
2-((3-(7,7,8,8,8-pentafluorooctyl)-1,2,4-oxadiazol-5-yl)methyl)acrylic acid;
2-((3-(4-butylphenyl)-1,2,4-oxadiazol-5-yl)methyl)acrylic acid;
2-((3-((4'-chloro-[1,1'-biphenyl]-4-yl)methyl)-1,2,4-oxadiazol-5-yl)methyl)acrylic acid;
2-((3-(4-butylbenzyl)-1,2,4-oxadiazol-5-yl)methyl)acrylic acid;
2-((3-(1-(3-chlorophenyl)cyclopropyl)-1,2,4-oxadiazol-5-yl)methyl)acrylic acid;
2-((3-(1-(4-(trifluoromethyl)phenyl)cyclopropyl)-1,2,4-oxadiazol-5-yl)methyl)acrylic acid;
2-((3-(4-pentylphenyl)-1,2,4-oxadiazol-5-yl)methyl)acrylic acid;
2-((3-(1-(2-chlorophenyl)cyclopropyl)-1,2,4-oxadiazol-5-yl)methyl)acrylic acid;
2-((3-(1-(4-chlorophenyl)cyclobutyl)-1,2,4-oxadiazol-5-yl)methyl)acrylic acid;
2-((3-(2-methyloctan-2-yl)-1,2,4-oxadiazol-5-yl)methyl)acrylic acid;
2-((3-(3-butylphenyl)-1,2,4-oxadiazol-5-yl)methyl)acrylic acid;
2-((3-(4-pentylbenzyl)-1,2,4-oxadiazol-5-yl)methyl)acrylic acid;
2-((3-(3-butylbenzyl)-1,2,4-oxadiazol-5-yl)methyl)acrylic acid;
2-((3-(2-(4-chlorophenyl)propan-2-yl)-1,2,4-oxadiazol-5-yl)methyl)acrylic acid;
2-((3-(7,7-difluorooctyl)-1,2,4-oxadiazol-5-yl)methyl)acrylic acid;
2-((3-(cyclohexylmethyl)-1,2,4-oxadiazol-5-yl)methyl)acrylic acid;
2-((3-(3-(4-chlorophenyl)propyl)-1,2,4-oxadiazol-5-yl)methyl)acrylic acid;
2-((3-(octyl-d17)-1,2,4-oxadiazol-5-yl)methyl)acrylic acid;
2-((3-(oct-7-yn-1-yl)-1,2,4-oxadiazol-5-yl)methyl)acrylic acid;
2-((3-(4-propylphenethyl)-1,2,4-oxadiazol-5-yl)methyl)acrylic acid;
2-((5-octyl-1,3,4-thiadiazol-2-yl)methyl)acrylic acid;
2-((4-octylthiazol-2-yl)methyl)acrylic acid;
2-((4-octyloxazol-2-yl)methyl)acrylic acid;
(R)-2-((3-(octan-2-yl)-1,2,4-oxadiazol-5-yl)methyl)acrylic acid;
2-((3-(4-ethylphenethyl)-1,2,4-oxadiazol-5-yl)methyl)acrylic acid;
2-((3-(4-(trifluoromethyl)benzyl)-1,2,4-oxadiazol-5-yl)methyl)acrylic acid;
(S)-2-((3-(octan-2-yl)-1,2,4-oxadiazol-5-yl)methyl)acrylic acid;
2-((3-(1-(4-fluorophenyl)cyclopropyl)-1,2,4-oxadiazol-5-yl)methyl)acrylic acid;
2-((3-(1-(4-methoxyphenyl)cyclopropyl)-1,2,4-oxadiazol-5-yl)methyl)acrylic acid;
2-((3-(4-(trifluoromethoxy)benzyl)-1,2,4-oxadiazol-5-yl)methyl)acrylic acid;
2-((3-(7,7,8-trifluorooctyl)-1,2,4-oxadiazol-5-yl)methyl)acrylic acid;
2-((3-(4-(1-(trifluoromethyl)cyclopropyl)benzyl)-1,2,4-oxadiazol-5-yl)methyl)acrylic acid;
2-((3-(1-(4-(trifluoromethoxy)phenyl)cyclopropyl)-1,2,4-oxadiazol-5-yl)methyl)acrylic acid;
2-((3-(1-(4-bromophenyl)cyclopropyl)-1,2,4-oxadiazol-5-yl)methyl)acrylic acid;
2-((3-(4-butoxybenzyl)-1,2,4-oxadiazol-5-yl)methyl)acrylic acid;
2-((3-(1-(4-chloro-3-fluorophenyl)cyclopropyl)-1,2,4-oxadiazol-5-yl)methyl)acrylic acid;
2-((3-nonyl-1,2,4-oxadiazol-5-yl)methyl)acrylic acid;
2-((3-(8,8,8-trifluorooctan-2-yl)-1,2,4-oxadiazol-5-yl)methyl)acrylic acid;
2-((5-octylthiazol-2-yl)methyl)acrylic acid;
2-((3-undecyl-1,2,4-oxadiazol-5-yl)methyl)acrylic acid;
2-((3-(oct-3-yn-1-yl)-1,2,4-oxadiazol-5-yl)methyl)acrylic acid;
2-((3-(8,8-difluorooctyl)-1,2,4-oxadiazol-5-yl)methyl)acrylic acid;
2-((5-octyloxazol-2-yl)methyl)acrylic acid;
2-((3-(9,9,9-trifluorononyl)-1,2,4-oxadiazol-5-yl)methyl)acrylic acid;
2-((3-(4-butoxyphenyl)-1,2,4-oxadiazol-5-yl)methyl)acrylic acid;
2-((3-(dispiro[3.1.3$^6$.1$^4$]decan-2-yl)-1,2,4-oxadiazol-5-yl)methyl)acrylic acid;
2-((3-cyclooctyl-1,2,4-oxadiazol-5-yl)methyl)acrylic acid;
2-((3-cyclohexyl-1,2,4-oxadiazol-5-yl)methyl)acrylic acid;
2-((3-cycloheptyl-1,2,4-oxadiazol-5-yl)methyl)acrylic acid; and
2-((3-(adamantan-1-yl)-1,2,4-oxadiazol-5-yl)methyl)acrylic acid;

or a pharmaceutically acceptable salt and/or solvate thereof.

In one embodiment, the compound is selected from the group consisting of:

2-((3-(1-(3,5-dichlorophenyl)cyclopropyl)-1,2,4-oxadiazol-5-yl)methyl)acrylic acid;
2-((3-(6-methylheptyl)-1,2,4-oxadiazol-5-yl)methyl)acrylic acid;
2-((3-(4-neopentylbenzyl)-1,2,4-oxadiazol-5-yl)methyl)acrylic acid;
2-((3-(4-propylbenzyl)-1,2,4-oxadiazol-5-yl)methyl)acrylic acid;
2-((3-(4-(1,1-difluoropropyl)phenyl)-1,2,4-oxadiazol-5-yl)methyl)acrylic acid;
2-((3-(4-(1-propylcyclopropyl)phenyl)-1,2,4-oxadiazol-5-yl)methyl)acrylic acid;
2-((3-(4-(3,3,3-trifluoropropyl)phenyl)-1,2,4-oxadiazol-5-yl)methyl)acrylic acid;
2-((3-((4-chlorophenyl)difluoromethyl)-1,2,4-oxadiazol-5-yl)methyl)acrylic acid;
2-((3-(4-(5,5,5-trifluoropentyl)phenyl)-1,2,4-oxadiazol-5-yl)methyl)acrylic acid;
2-((3-(4-(2-cyclopropylethyl)phenyl)-1,2,4-oxadiazol-5-yl)methyl)acrylic acid;
2-((3-(1-(4-(pentafluoro-$\lambda^6$-sulfaneyl)phenyl)cyclopropyl)-1,2,4-oxadiazol-5-yl)methyl)acrylic acid;
2-((3-(1-(4-(difluoromethoxy)phenyl)cyclopropyl)-1,2,4-oxadiazol-5-yl)methyl)acrylic acid;
2-((3-(4-(1,1-difluoropentyl)phenyl)-1,2,4-oxadiazol-5-yl)methyl)acrylic acid;
2-((3-(1-(4-butoxyphenyl)cyclopropyl)-1,2,4-oxadiazol-5-yl)methyl)acrylic acid;
2-((3-(4-(1,1,2,2-tetrafluoroethoxy)benzyl)-1,2,4-oxadiazol-5-yl)methyl)acrylic acid;

2-((3-(1-(4-(1,1,2,2-tetrafluoroethoxy)phenyl)cyclopropyl)-1,2,4-oxadiazol-5-yl)methyl)acrylic acid;
2-((5-(1,1-difluorooctyl)-1,2,4-oxadiazol-3-yl)methyl)acrylic acid;
2-((5-((4-chlorophenyl)difluoromethyl)-1,2,4-oxadiazol-3-yl)methyl)acrylic acid;
2-((5-((4-bromophenyl)difluoromethyl)-1,2,4-oxadiazol-3-yl)methyl)acrylic acid;
2-((3-(1-(4-((trifluoromethyl)thio)phenyl)cyclopropyl)-1,2,4-oxadiazol-5-yl)methyl)acrylic acid;
2-((3-(6,6,8,8,8-pentafluorooctyl)-1,2,4-oxadiazol-5-yl)methyl)acrylic acid;
2-((3-(1,1-difluorooctyl)-1,2,4-oxadiazol-5-yl)methyl)acrylic acid;
2-((5-((4-chlorophenyl)difluoromethyl)-1,2,4-oxadiazol-3-yl)methyl)acrylic acid;
2-((3-((4-bromophenyl)difluoromethyl)-1,2,4-oxadiazol-5-yl)methyl)acrylic acid;
2-((3-((4-butylphenyl)difluoromethyl)-1,2,4-oxadiazol-5-yl)methyl)acrylic acid;
2-((3-(difluoro(4-(trifluoromethyl)phenyl)methyl)-1,2,4-oxadiazol-5-yl)methyl)acrylic acid;
2-((3-(4-(1,1-difluoropentyl)benzyl)-1,2,4-oxadiazol-5-yl)methyl)acrylic acid;
2-((3-(difluoro(4-(trifluoromethoxy)phenyl)methyl)-1,2,4-oxadiazol-5-yl)methyl)acrylic acid;
2-((5-(4-butylbenzyl)-1,2,4-oxadiazol-3-yl)methyl)acrylic acid;
2-((5-(4-butoxyphenyl)-1,2,4-oxadiazol-3-yl)methyl)acrylic acid;
2-((5-(difluoro(4-(trifluoromethyl)phenyl)methyl)-1,2,4-oxadiazol-3-yl)methyl)acrylic acid;
2-((3-(4-(1,1-difluorobutyl)phenyl)-1,2,4-oxadiazol-5-yl)methyl)acrylic acid;
2-((5-(1-(4-(trifluoromethoxy)phenyl)cyclopropyl)-1,2,4-oxadiazol-3-yl)methyl)acrylic acid;
2-((3-(4-(benzyloxy)phenyl)-1,2,4-oxadiazol-5-yl)methyl)acrylic acid;
2-((4-(4-butylphenyl)oxazol-2-yl)methyl)acrylic acid;
2-((5-octylisoxazol-3-yl)methyl)acrylic acid;
2-((4-(1-(4-(trifluoromethyl)phenyl)cyclopropyl)oxazol-2-yl)methyl)acrylic acid;
2-((4-octylpyridin-2-yl)methyl)acrylic acid trifluoroacetic acid salt;
2-((5-octylpyridin-2-yl)methyl)acrylic acid trifluoroacetic acid salt;
2-((5-octylpyrimidin-2-yl)methyl)acrylic acid;
2-((5-octylpyrazin-2-yl)methyl)acrylic acid;
2-((6-octylpyridazin-3-yl)methyl)acrylic acid;
2-((5-methyl-4-octyloxazol-2-yl)methyl)acrylic acid;
2-(hydroxy(3-octyl-1,2,4-oxadiazol-5-yl)methyl)acrylic acid;
2-((5-butyl-4-(4-chlorophenyl)oxazol-2-yl)methyl)acrylic acid;
2-(methoxy(3-octyl-1,2,4-oxadiazol-5-yl)methyl)acrylic acid;
2-((3-(1-(4-cyclobutoxyphenyl)cyclopropyl)-1,2,4-oxadiazol-5-yl)methyl)acrylic acid;
2-((3-(4-cyclopentylbenzyl)-1,2,4-oxadiazol-5-yl)methyl)acrylic acid;
2-((3-(1-(4-cyclopropoxyphenyl)cyclopropyl)-1,2,4-oxadiazol-5-yl)methyl)acrylic acid; and
2-((3-(1-(4-cyclopentylphenyl)cyclopropyl)-1,2,4-oxadiazol-5-yl)methyl)acrylic acid;

or a pharmaceutically acceptable salt and/or solvate thereof.

In one embodiment, the compound is selected from the group consisting of:

2-((3-(1-(4-iodophenyl)cyclopropyl)-1,2,4-oxadiazol-5-yl)methyl)acrylic acid;
2-((3-(4-bromophenyl)-1,2,4-oxadiazol-5-yl)methyl)acrylic acid;
2-((3-(4-iodophenyl)-1,2,4-oxadiazol-5-yl)methyl)acrylic acid;
2-((3-(difluoro(4-iodophenyl)methyl)-1,2,4-oxadiazol-5-yl)methyl)acrylic acid;
2-((3-(4-(pentafluoro-$\lambda^6$-sulfaneyl)phenyl)-1,2,4-oxadiazol-5-yl)methyl)acrylic acid;
2-((3-(4-(pentafluoro-$\lambda^6$-sulfaneyl)phenyl)-1,2,4-oxadiazol-5-yl)methyl)acrylic acid;
2-((4,5-dibutyloxazol-2-yl)methyl)acrylic acid;
2,2-((3-(difluoro(4-(pentafluoro-$\lambda^6$-sulfaneyl)phenyl)methyl)-1,2,4-oxadiazol-5-yl)methyl)acrylic acid;
2,2-((3-(difluoro(4-fluorophenyl)methyl)-1,2,4-oxadiazol-5-yl)methyl)acrylic acid;
2-((3-(4-butylphenoxy)-1,2,4-oxadiazol-5-yl)methyl)acrylic acid;
2-((4-(4-butylbenzyl)oxazol-2-yl)methyl)acrylic acid;
2-((3-(4-cyclobutylbenzyl)-1,2,4-oxadiazol-5-yl)methyl)acrylic acid;
2-((3-(4-butoxy-3-fluorophenyl)-1,2,4-oxadiazol-5-yl)methyl)acrylic acid;
2-((3-(3-chloro-4-propoxyphenyl)-1,2,4-oxadiazol-5-yl)methyl)acrylic acid;
2-((3-(1-(4-cyclobutylphenyl)cyclopropyl)-1,2,4-oxadiazol-5-yl)methyl)acrylic acid;
2-((3-(4-(pyrrolidin-1-yl)phenyl)-1,2,4-oxadiazol-5-yl)methyl)acrylic acid;
2-((3-(1-(3,5-dichloro-4-fluorophenyl)cyclopropyl)-1,2,4-oxadiazol-5-yl)methyl)acrylic acid;
2-((3-(3,5-dichloro-4-fluorobenzyl)-1,2,4-oxadiazol-5-yl)methyl)acrylic acid;
2-((3-(1-(4-chloro-3,5-difluorophenyl)cyclopropyl)-1,2,4-oxadiazol-5-yl)methyl)acrylic acid;
2-((3-(1-(3-chloro-4-(trifluoromethyl)phenyl)cyclopropyl)-1,2,4-oxadiazol-5-yl)methyl)acrylic acid;
2-((3-(3-chloro-4-(trifluoromethyl)benzyl)-1,2,4-oxadiazol-5-yl)methyl)acrylic acid;
2-((3-(1-(4-bromo-3-chlorophenyl)cyclopropyl)-1,2,4-oxadiazol-5-yl)methyl)acrylic acid;
2-((3-(4-bromo-3-chlorobenzyl)-1,2,4-oxadiazol-5-yl)methyl)acrylic acid;
2-((3-(1-(3-chloro-4-methoxyphenyl)cyclopropyl)-1,2,4-oxadiazol-5-yl)methyl)acrylic acid;
2-((3-(1-(3-chloro-4-methylphenyl)cyclopropyl)-1,2,4-oxadiazol-5-yl)methyl)acrylic acid;
2-((3-(4-cyclobutoxyphenyl)-1,2,4-oxadiazol-5-yl)methyl)acrylic acid;
2-((3-(4-cyclopentyloxyphenyl)-1,2,4-oxadiazol-5-yl)methyl)acrylic acid;
(R)-2-((3-(4-(sec-butoxy)phenyl)-1,2,4-oxadiazol-5-yl)methyl)acrylic acid;
(S)-2-((3-(4-(sec-butoxy)phenyl)-1,2,4-oxadiazol-5-yl)methyl)acrylic acid;
2-((3-(4-(4,4,4-trifluorobutoxy)phenyl)-1,2,4-oxadiazol-5-yl)methyl)acrylic acid;
2-((3-(4-(1-propylcyclopropyl)benzyl)-1,2,4-oxadiazol-5-yl)methyl)acrylic acid;
2-((3-(4,6-dichloro-2,3-dihydro-1H-inden-1-yl)-1,2,4-oxadiazol-5-yl)methyl)acrylic acid;
2-((3-(4-propoxyphenyl)-1,2,4-oxadiazol-5-yl)methyl)acrylic acid;
2-((3-((3-chloro-4-methoxyphenyl)difluoromethyl)-1,2,4-oxadiazol-5-yl)methyl)acrylic acid;

2-((3-((3-chloro-4-methylphenyl)difluoromethyl)-1,2,4-oxadiazol-5-yl)methyl)acrylic acid;
2-((3-((4-chlorophenyl)fluoromethyl)-1,2,4-oxadiazol-5-yl)methyl)acrylic acid;
2-((3-((3,5-dichloro-4-fluorophenyl)difluoromethyl)-1,2,4-oxadiazol-5-yl)methyl)acrylic acid;
2-((3-((4-bromo-3-chlorophenyl)difluoromethyl)-1,2,4-oxadiazol-5-yl)methyl)acrylic acid;
2-((3-(difluoro(4-((trifluoromethyl)thio)phenyl)methyl)-1,2,4-oxadiazol-5-yl)methyl)acrylic acid;
2-(1-(3-(1-(4-(trifluoromethyl)phenyl)cyclopropyl)-1,2,4-oxadiazol-5-yl)cyclopropyl)acrylic acid;
3-methyl-2-methylene-3-(3-(1-(4-(trifluoromethyl)phenyl)cyclopropyl)-1,2,4-oxadiazol-5-yl)butanoic acid;
2-((3-(1-(4-((trifluoromethyl)sulfinyl)phenyl)cyclopropyl)-1,2,4-oxadiazol-5-yl)methyl)acrylic acid;
2-((3-(4-((trifluoromethyl)thio)phenyl)-1,2,4-oxadiazol-5-yl)methyl)acrylic acid;
2-((3-(4-(3-methoxypropoxy)phenyl)-1,2,4-oxadiazol-5-yl)methyl)acrylic acid;
2-((3-(4-butoxy-3-chlorophenyl)-1,2,4-oxadiazol-5-yl)methyl)acrylic acid;
2-((3-(4-butoxy-3-(trifluoromethyl)phenyl)-1,2,4-oxadiazol-5-yl)methyl)acrylic acid;
2-((3-(4-butoxy-3,5-difluorophenyl)-1,2,4-oxadiazol-5-yl)methyl)acrylic acid;
2-((3-(3-chloro-4-methoxybenzyl)-1,2,4-oxadiazol-5-yl)methyl)acrylic acid;
2-((3-(4-chloro-3,5-difluorobenzyl)-1,2,4-oxadiazol-5-yl)methyl)acrylic acid;
2-((3-(3-chloro-4-methylbenzyl)-1,2,4-oxadiazol-5-yl)methyl)acrylic acid;
(E)-2-methyl-3-(3-octyl-1,2,4-oxadiazol-5-yl)acrylic acid;
(E)-3-(3-(4-butoxyphenyl)-1,2,4-oxadiazol-5-yl)-2-methylacrylic acid;
(E)-3-(3-(1-(4-bromophenyl)cyclopropyl)-1,2,4-oxadiazol-5-yl)-2-methylacrylic acid;
(E)-2-methyl-3-(3-(1-(4-(pentafluoro-$\lambda^6$-sulfaneyl)phenyl)cyclopropyl)-1,2,4-oxadiazol-5-yl)acrylic acid;
(E)-2-methyl-3-(3-(1-(4-((trifluoromethyl)thio)phenyl)cyclopropyl)-1,2,4-oxadiazol-5-yl)acrylic acid;
2-((6-(4-chlorobenzyl)pyridin-2-yl)methyl)acrylic acid trifluoroacetic acid salt;
2-(1-(3-(difluoro(4-(trifluoromethyl)phenyl)methyl)-1,2,4-oxadiazol-5-yl)cyclopropyl)acrylic acid;
2-methylene-3-(3-(1-(4-(trifluoromethyl)phenyl)cyclopropyl)-1,2,4-oxadiazol-5-yl)butanoic acid;
2-((6-(1-(4-chlorophenyl)cyclopropyl)pyridin-2-yl)methyl)acrylic acid; and
2-((3-(1-(4-bromo-3,5-dichlorophenyl)cyclopropyl)-1,2,4-oxadiazol-5-yl)methyl)acrylic acid;

or a pharmaceutically acceptable salt and/or solvate thereof.

In one embodiment, the compound of formula (I) is 2-((3-octyl-1,2,4-oxadiazol-5-yl)methyl)acrylic acid or a pharmaceutically acceptable salt and/or solvate thereof.

In one embodiment, the compound is selected from the group consisting of:

2-((3-(4-butylbenzyl)-1,2,4-oxadiazol-5-yl)methyl)acrylic acid;
2-((3-(1-(4-bromophenyl)cyclopropyl)-1,2,4-oxadiazol-5-yl)methyl)acrylic acid; and
2-((3-(4-butoxyphenyl)-1,2,4-oxadiazol-5-yl)methyl)acrylic acid;

or a pharmaceutically acceptable salt and/or solvate thereof.

In one embodiment, the compound is selected from the group consisting of:

2-((3-(1-(4-((trifluoromethyl)thio)phenyl)cyclopropyl)-1,2,4-oxadiazol-5-yl)methyl)acrylic acid; and
2-((3-(1-(4-(pentafluoro-$\lambda^6$-sulfaneyl)phenyl)cyclopropyl)-1,2,4-oxadiazol-5-yl)methyl)acrylic acid;

or a pharmaceutically acceptable salt and/or solvate thereof.

In one embodiment, there is provided the tromethamine salt of a compound of formula (I). In one particular embodiment, there is provided the tromethamine salt of Example 1.

Figure 2:
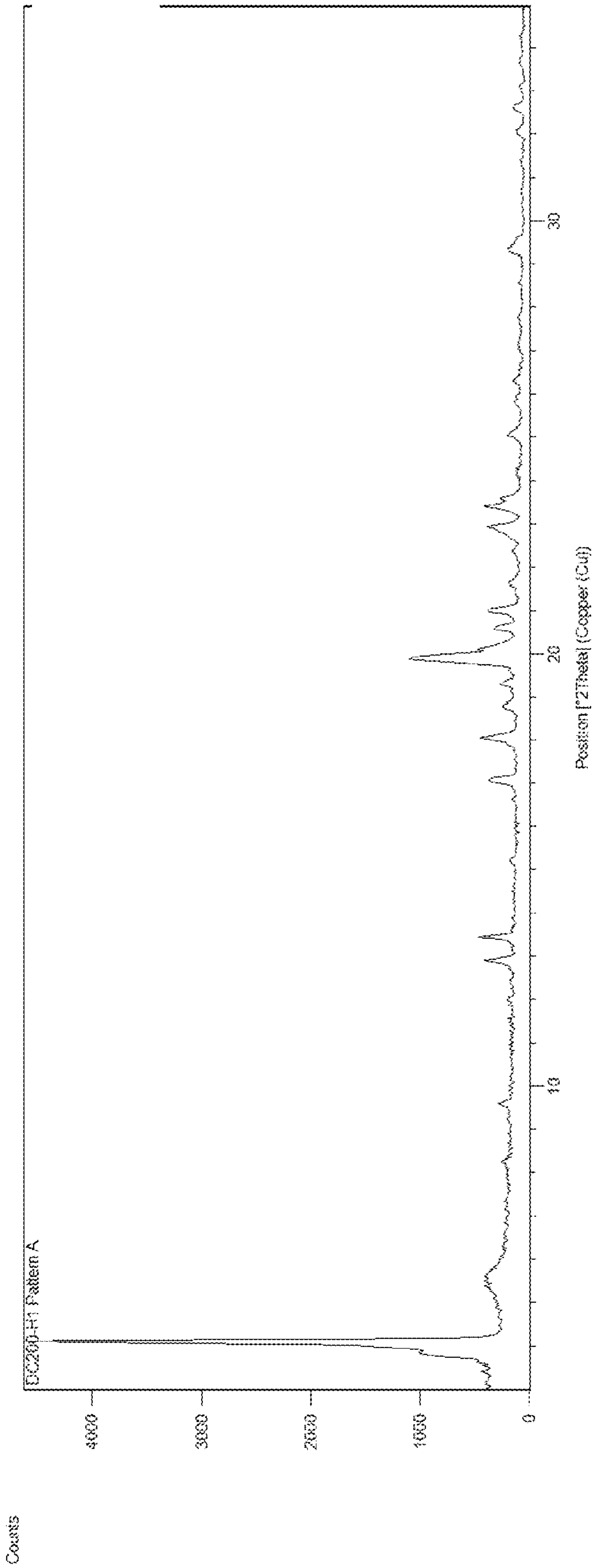
FIG. 2 shows an XRPD pattern of a crystalline form of Example 1, tromethamine salt (2 g scale).
Figure 3:
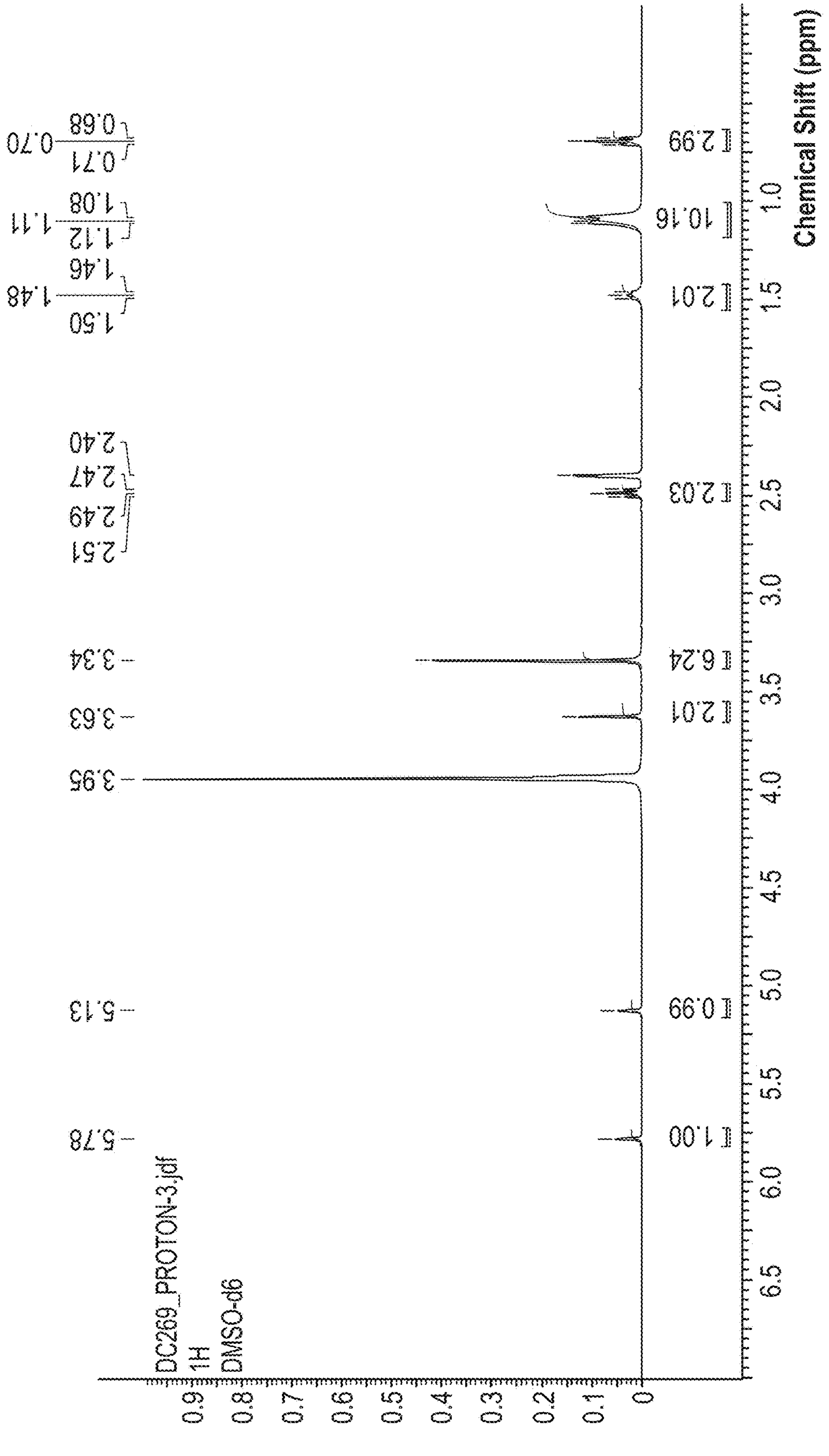
FIG. 3 shows an $^1H$ NMR spectrum of Example 1, tromethamine salt (2 g scale).

The tromethamine salt of Example 1 may exist as a crystalline solid. The tromethamine salt was prepared as described in the Examples and characterising data are shown in FIGS. 1-3.

Thus, in one embodiment, there is provided a tromethamine salt of Example 1 in crystalline form and in particular in a crystalline form having an X-ray powder diffraction pattern with at least one (for example, one, two, three, four, five, six, seven, eight, nine, ten, eleven or twelve) peaks selected from peaks at 12.9, 13.5, 17.0, 18.0, 19.9, 20.1, 20.6, 21.0, 23.0, 23.4, 23.6 or 29.3 (±0.2 degrees, 2-theta values). Particularly characteristic peaks of the crystalline form of the tromethamine salt of Example 1 are selected from peaks at 12.9, 17.0, 19.9, 20.1, 23.0, and 23.4 (±0.2 degrees, 2-theta values) and thus suitably at least one (for example, one, two, three, four, five or six) peaks selected from peaks at 12.9, 17.0, 19.9, 20.1, 23.0, and 23.4 (±0.2 degrees, 2-theta values) are present.

The crystalline form of the tromethamine salt of Example 1 was found to have good physical stability as shown by TGA and DSC analysis.

The compounds of the invention may be prepared by the general methods described herein. In particular, compounds of formula (I) can be prepared as described in the Examples, see for example General Procedures A and B, or by methods analogous thereto, or by other methods known to the skilled person.

Compounds of formula (I) may be prepared using the routes set out in the following schemes.

Scheme 1: Synthesis of certain compounds of formula (I)

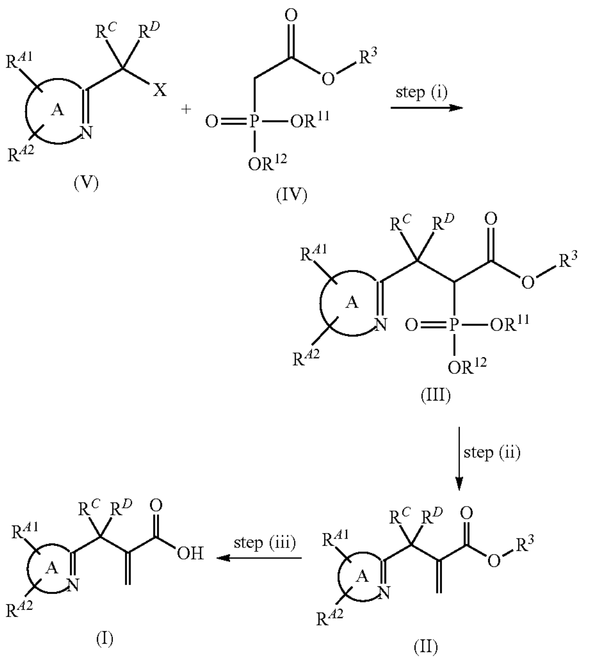

A, $R^{A1}$, $R^{A2}$, $R^C$ and $R^D$ are defined elsewhere herein.

Step (i): compounds of formula (V)—wherein X represents a leaving group, such as chloro, bromo, iodo, alkanesulfonate, e.g., methanesulfonate, or arenesulfonate, e.g., para-toluenesulfonate or benzenesulfonate—are reacted with a trialkylphosphonoacetate of formula (IV)—wherein $R^{11}$, $R^{12}$ and $R^3$ independently represent $C_{1-4}$ alkyl optionally substituted with halo—to provide compounds of formula (III).

Step (ii): compounds of formula (III) undergo a condensation reaction with formaldehyde or a formaldehyde equivalent thereof, e.g., paraformaldehyde, to give α,β-unsaturated esters of formula (II).

Step (iii): compounds of formula (II) are hydrolysed under standard acid or base hydrolysis conditions, e.g., TFA in DCM when $R^3$ is tert-butyl, to give the compound of formula (I).

Scheme 2: Synthesis of certain compounds of formula (III)

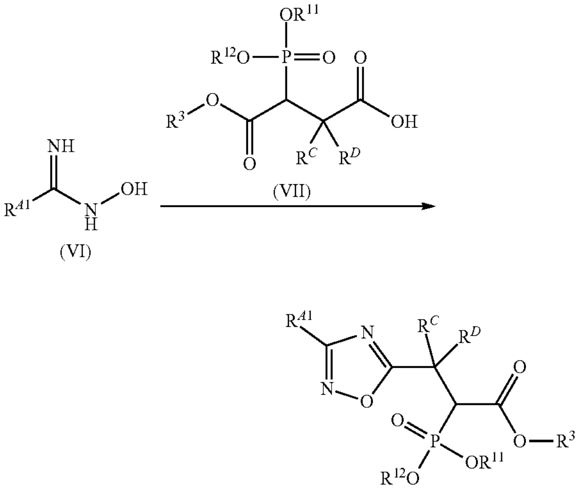

(VII)

(VI)

(III)

$R^{11}$, $R^{12}$ and $R^3$ are defined in Scheme 1 above, $R^{A1}$, $R^C$ and $R^D$ are defined elsewhere herein, and $R^{A2}$ is absent. Compounds of formula (III) may be prepared by reacting amidoxime (VI) with acid (VII) in the presence of a coupling agent such as HATU and a base such as DIPEA.

Compounds of formula (I) may be accessed from compounds of formula (III) as described in Scheme 1.

Scheme 3: Synthesis of certain compounds of formula (III)

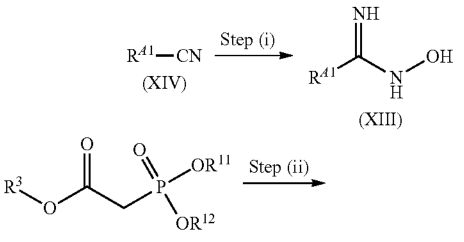

(XIV)

(XIII)

(XII)

-continued

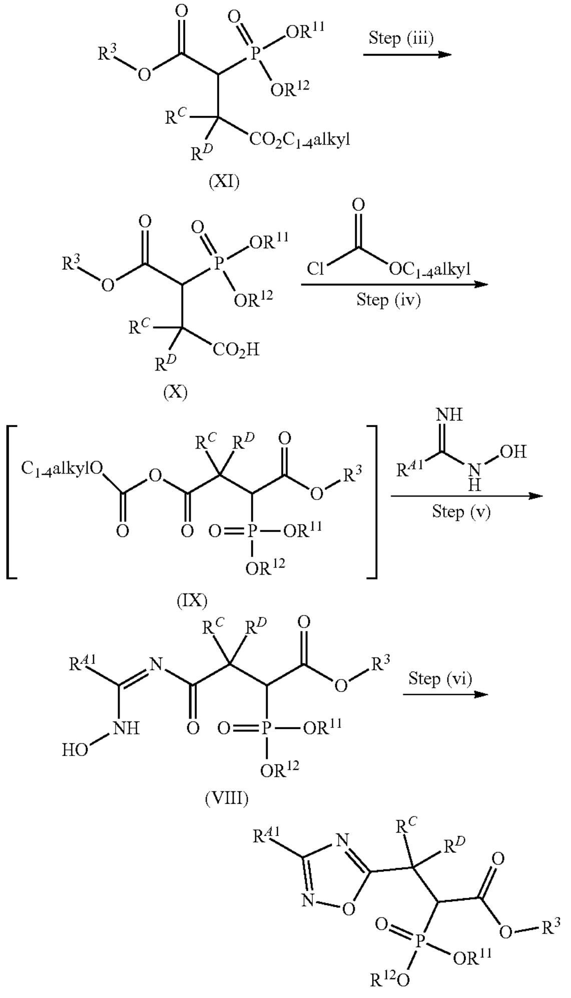

(XI)

(X)

(IX)

(VIII)

(III)

$R^{11}$, $R^{12}$ and $R^3$ are defined in Scheme 1 above, $R^{A1}$, $R^C$ and $R^D$ are defined elsewhere herein, and $R^{A2}$ is absent. Certain compounds of formula (III) may be prepared in 6 steps from commercially available phosphonoacetates of formula (XII) and nitriles of formula (XIV).

Step (i): amidoximes of formula (XIII) can be accessed by reacting nitrile (XIV) with hydroxylamine hydrochloride in the presence of a base such as $NaHCO_3$ in a solvent such as isopropanol.

Step (ii): compounds of formula (XI) can be accessed by reacting phosphonate (XII) with an appropriate ester possessing a leaving group under basic conditions, such as in the presence of NaH in tetrahydrofuran.

Step (iii): carboxylic acids of formula (X) can be accessed by hydrolysis of the ester in compounds of formula (XI), such as under basic conditions, for example aqueous 1M sodium hydroxide solution in tetrahydrofuran.

Step (iv) and (v): compounds of formula (VIII) can be accessed by reacting compounds of formula (X) with a chloroformate in the presence of base, such as 4-methylmorpholine, to form intermediates of formula (IX), followed by addition of the amidoxime of formula (XIII) to compounds of formula (IX) under basic conditions, such as in the presence of triethylamine, to give compounds of formula (VIII).

Step (vi): compounds of formula (III) can be accessed by exposing compounds of formula (VIII) to basic conditions, such as $Cs_2CO_3$ in the presence of tetrahydrofuran, to give compounds of formula (III).

Scheme 4: Synthesis of certain compounds of formula (III)

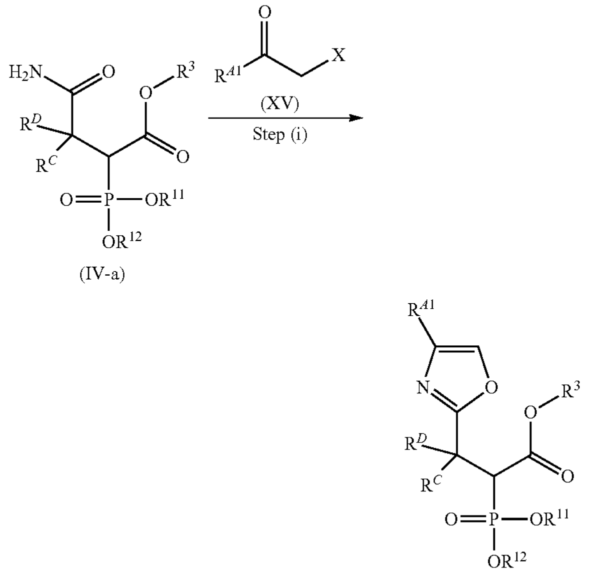

(IV-a) (XV) (III)

Compounds of formula (III) may be accessed in one step by reacting together compounds of formula (IV-a) and compounds of formula (XV) in the presence of an activating agent such as silver trifluoromethanesulfonate or silver tetrafluoroborate, wherein $R^{A1}$, $R^C$, $R^D$, $R^3$, $R^{11}$, $R^{12}$ and X are as defined elsewhere herein.

Scheme 5: Synthesis of certain compounds of formula (I)

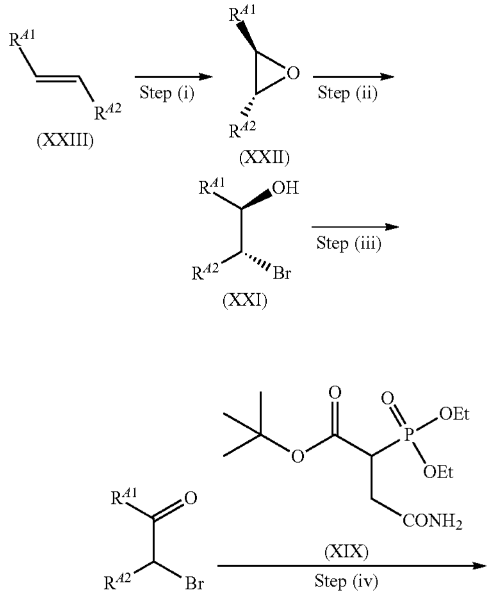

(XXIII) (XXII) (XXI) (XX) (XIX)

-continued

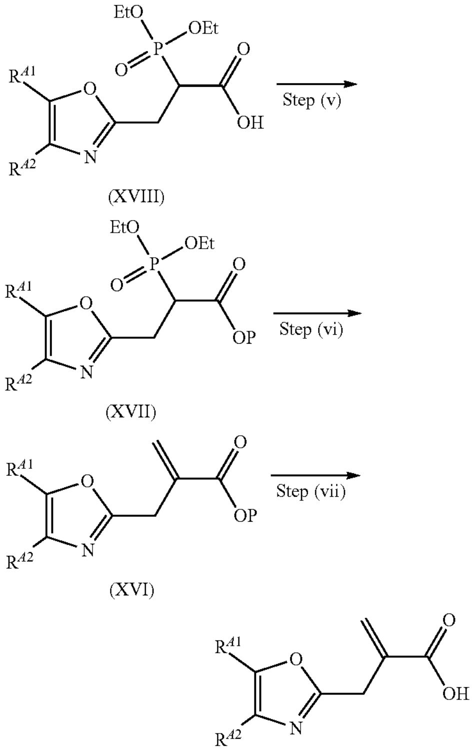

(XVIII) (XVII) (XVI) (I)

$R^{A1}$ and $R^{A2}$ are as defined elsewhere herein and P is carboxylic acid protecting group such as para-methoxybenzyl or tert-butyl. This synthesis has particular utility for compounds of formula (I) wherein $R^{A2}$ is other than absent.

Step (i): oxidation of the double bond in commercially available compounds of formula (XXIII) under conditions known to the person skilled in the art (such as mCPBA in DCM at reduced temperatures) provides epoxides of formula (XXII).

Step (ii): Epoxides of formula (XXII) undergo nucleophilic ring opening, e.g., using HBr in THF, to give haloalcohols of formula (XXI).

Step (iii): oxidation of the alcohol in compounds of formula (XXI) under conditions known to the person skilled in the art (such as DMP in DCM) provides ketones of formula (XX).

Step (iv): reaction of ketones of formula (XX) with amides of formula (XIX), followed by in situ hydrolysis provides acids of formula (XVIII). Upon heating, the tert-butyl ester is hydrolysed and step (v) is necessary. If step (iv) is carried out at room temperature, the tert-butyl ester remains intact, step (v) is not necessary, and P is tert-butyl.

Step (v): protection of acids of formula (XVIII) using a standard carboxylic acid protecting group (e.g. para-methoxybenzyl) gives compounds of formula (XVII).

Step (vi): Olefination with elimination of diethyl phosphate, using conditions described elsewhere herein, provides compounds of formula (XVI).

Step (vii): removal of protecting group P under conditions known to the skilled person provides compounds of formula (I).

Scheme 6: Synthesis of certain compounds of formula (I)

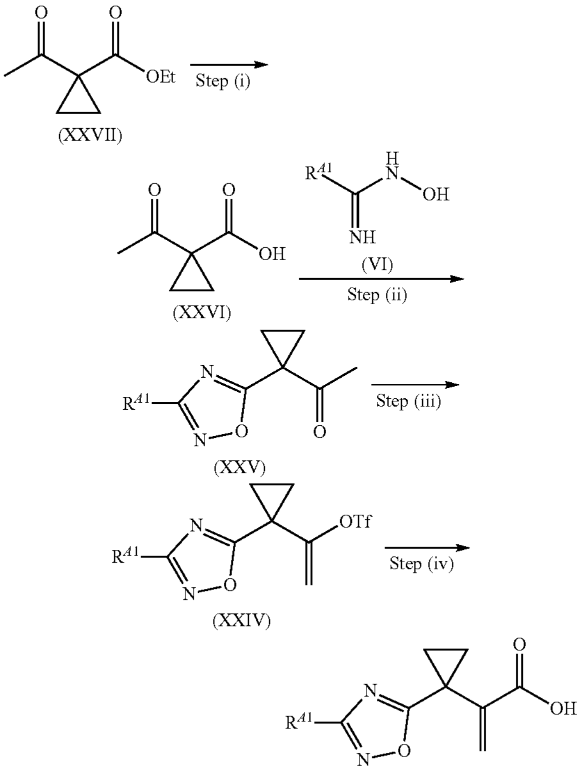

(XXVII)
(XXVI)
(VI)
(XXV)
(XXIV)
(I)

$R^{A1}$ is as defined elsewhere herein. This synthesis has particular utility when $R^C$ and $R^D$ join to form a $C_{3-5}$ cycloalkyl ring, or when both $R^C$ and $R^D$ are other than H.

Step (i): Hydrolysis of ester (XXVII) under e.g. alkali conditions such as aqueous NaOH provides acids of formula (XXVI).

Step (ii): Coupling of acid (XXVI) with compounds of formula (VI) provides compounds of formula (XXV).

Step (iii): Triflation of the ketone in compounds of formula (XXV) under standard conditions (such as a strong base e.g., LDA, and a triflating agent, e.g., $Tf_2NPh$) provides vinyl triflates of formula (XXIV).

Step (iv): Vinyl triflates of formula (XXIV) may be converted to unsaturated carboxylic acids of formula (I) under metal catalysed carbonylation conditions such as a palladium phosphine catalyst in the presence of CO, followed by hydrolysis (such as basic hydrolysis e.g. aqueous $K_2CO_3$, followed by acidification) to give the compounds of formula (I).

Scheme 7: Synthesis of certain compounds of formula (I)

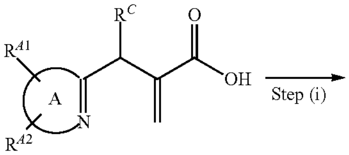

(I)

-continued

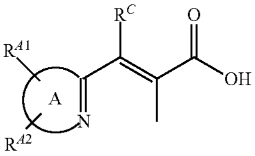
(I)

wherein $R^{A1}$, $R^{A2}$, A and $R^C$ are defined elsewhere herein.

Step (i): certain compounds of formula (I) may be obtained by isomerisation of compounds of formula (I) under basic conditions, for example using an organic base such as diethylamine. Other organic bases suitably for the reaction are known to the skilled person.

The skilled person will appreciate that protecting groups may be used throughout the synthetic scheme described above to give protected derivatives of any of the above compounds or generic formulae. Protective groups and the means for their removal are described in "*Protective Groups in Organic Synthesis*", by Theodora W. Greene and Peter G. M. Wuts, published by John Wiley & Sons Inc; 4th Rev Ed., 2006, ISBN-10: 0471697540. Examples of nitrogen protecting groups include tert-butyloxycarbonyl (BOC), 9-fluorenylmethyloxycarbonyl (Fmoc), acetyl (Ac), benzyl (Bn) and para-methoxy benzyl (PMB). Examples of oxygen protecting groups include acetyl (Ac), methoxymethyl (MOM), para-methoxybenzyl (PMB), benzyl, tert-butyl, methyl, ethyl, tetrahydropyranyl (THP), and silyl ethers and esters (such as trimethylsilyl (TMS), tert-butyldimethylsilyl (TBDMS), tri-iso-propylsilyloxymethyl (TOM), and triisopropylsilyl (TIPS) ethers and esters).

Thus, in one embodiment there is provided a process for preparing the compound of formula (I):

(I)

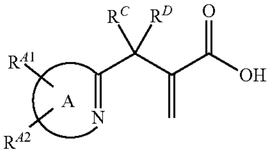

or a salt, such as a pharmaceutically acceptable salt thereof which comprises hydrolysing the ester moiety in a compound of formula (II):

(II)

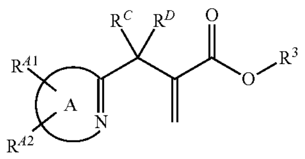

or a salt thereof,
wherein

$R^{A1}$, $R^{A2}$, $R^C$, $R^D$ and $R^3$ are defined elsewhere herein.

In one embodiment there is provided a process for preparing a compound of formula (II):

(II)

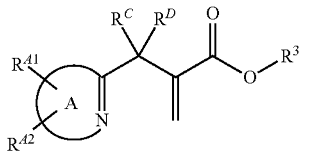

or a salt thereof which comprises reacting a compound of formula (III):

(III)

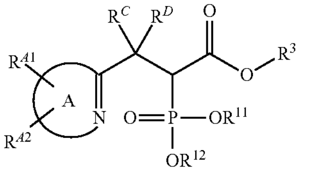

or a salt thereof;

with formaldehyde or an equivalent thereof, wherein

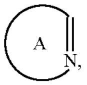

$R^{A1}$, $R^{A2}$, $R^C$, $R^D$, $R^3$, $R^{11}$ and $R^{12}$ are defined elsewhere herein.

In one embodiment there is provided a process for preparing a compound of formula (III):

(III)

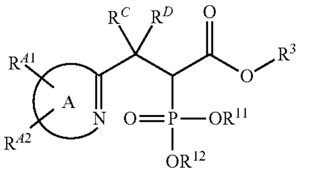

or a salt thereof which comprises reacting a compound of formula (V):

(V)

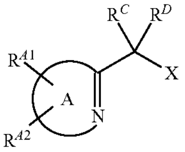

or a salt thereof;

with a compound of formula (IV):

(IV)

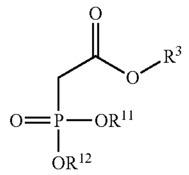

or a salt thereof;

wherein

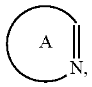

$R^{A1}$, $R^{A2}$, $R^C$, $R^D$, $R^3$, $R^{11}$, $R^{12}$ and X are defined elsewhere herein.

In one embodiment there is provided a process for preparing a compound of formula (III):

(III)

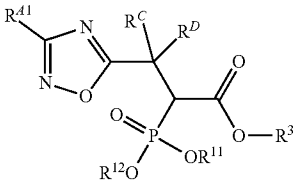

or a salt thereof which comprises reacting a compound of formula (VI):

(VI)

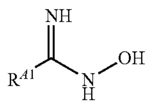

or a salt thereof;

with a compound of formula (VII):

(VII)

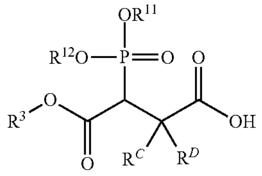

or a salt thereof;

wherein $R^{A1}$, $R^C$, $R^D$, $R^3$, $R^{11}$ and $R^{12}$ are defined elsewhere herein.

In one embodiment, there is provided a process for preparing a compound of formula (III):

(III)

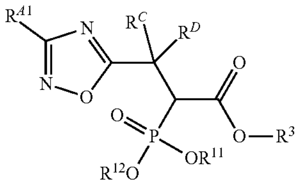

or a salt thereof which comprises reacting a compound of formula (VIII):

(VIII)

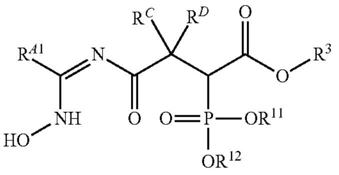

or salt thereof, with a base such as $Cs_2CO_3$;

wherein $R^{A1}$, $R^C$, $R^D$, $R^3$, $R^{11}$ and $R^{12}$ are defined elsewhere herein.

In one embodiment there is provided a process for preparing a compound of formula (III):

(III)

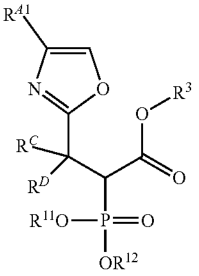

or a salt thereof, which comprises reacting a compound of formula (IV-a):

(IV-a)

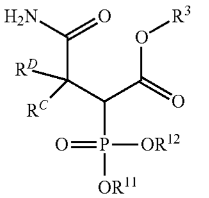

or a salt thereof, with a compound of formula (XV):

(XV)

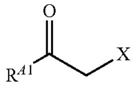

or a salt thereof;

wherein X, $R^{A1}$, $R^C$, $R^D$, $R^3$, $R^{11}$ and $R^{12}$ are defined elsewhere herein.

In one embodiment, there is provided a process for preparing a compound of formula (I) or a salt, such as pharmaceutically acceptable salt thereof, which comprises deprotecting a compound of formula (XVI):

(XVI)

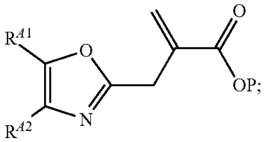

or a salt thereof;

wherein $R^{A1}$ and $R^{A2}$ are defined elsewhere herein and P is a carboxylic acid protecting group such as para-methoxybenzyl.

In one embodiment, there is provided a process for preparing a compound of formula (I) or a salt, such as pharmaceutically acceptable salt thereof, which comprises reacting a compound of formula (XXIV):

(XXIV)

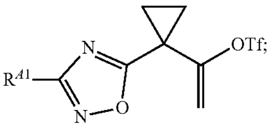

or a salt thereof;

with carbon monoxide in the presence of a metal catalyst, such as a palladium catalyst, followed by hydrolysis (such as basic hydrolysis e.g. aqueous $K_2CO_3$, followed by acidification) to give the compounds of formula (I);

wherein $R^{A1}$ is defined elsewhere herein.

In one embodiment there is provided a compound of formula (II):

(II)

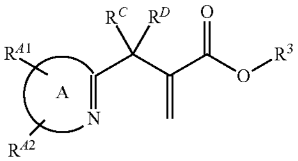

or salt thereof, wherein

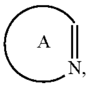

$R^{A1}$, $R^{A2}$, $R^C$, $R^D$ and $R^3$are defined elsewhere herein.

In one embodiment there is provided a compound of formula (III):

(III)

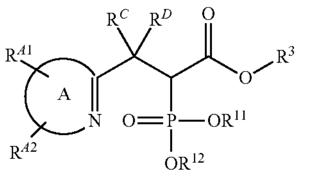

or salt thereof, wherein

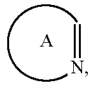

$R^{A1}$, $R^{A2}$, $R^C$, $R^D$, $R^{11}$, $R^{12}$ and $R^3$are defined elsewhere herein.

In one embodiment there is provided a compound of formula (V):

(V)

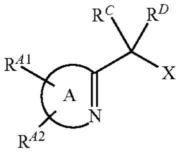

or salt thereof, wherein

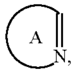

$R^{A1}$, $R^{A2}$, $R^C$, $R^D$ and X are defined elsewhere herein.

In one embodiment there is provided a compound of formula (VIII):

(VIII)

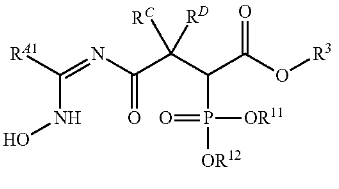

or a salt thereof, wherein $R^{A1}$, $R^C$, $R^D$, $R^3$, $R^{11}$ and $R^{12}$ are as defined elsewhere herein.

In one embodiment there is provided a compound of formula (XVI):

(XVI)

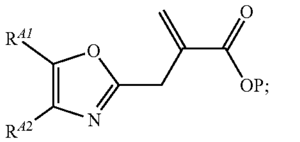

or a salt thereof;

wherein $R^{A1}$ and $R^{A2}$ are defined elsewhere herein and P is a carboxylic acid protecting group such as para-methoxybenzyl.

In one embodiment there is provided a compound of formula (XXIV):

(XXIV)

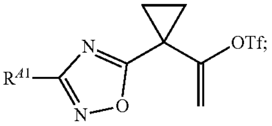

or a salt thereof;

wherein $R^{A1}$ is defined elsewhere herein.

Certain novel compounds may be used in the synthesis of compounds of formula (I). Thus, in one embodiment, there is provided a compound selected from the group consisting of:

5-(chloromethyl)-3-octyl-1,2,4-oxadiazole;

5-(chloromethyl)-3-heptyl-1,2,4-oxadiazole;

5-(chloromethyl)-3-(octan-2-yl)-1,2,4-oxadiazole;

5-(chloromethyl)-3-(naphthalen-2-ylmethyl)-1,2,4-oxadiazole;

5-(chloromethyl)-3-(8,8,8-trifluorooctyl)-1,2,4-oxadiazole; and 9,9,9-trifluorononanenitrile;

or a salt, such as a pharmaceutically acceptable salt, and/or solvate there.

In one embodiment, there is provided a compound selected from the group consisting of intermediates 13 to 85;

or a salt, such as a pharmaceutically acceptable salt, and/or solvate thereof.

In another embodiment, there is provided a compound selected from the group consisting of intermediates 86 to 151;

or a salt, such as a pharmaceutically acceptable salt, and/or solvate thereof.

In another embodiment, there is provided a compound selected from the group consisting of intermediates 152 to 223;

or a salt, such as a pharmaceutically acceptable salt, and/or solvate thereof.

In one embodiment, the molecular weight of the compound of formula (I) is 150 Da-500 Da, especially 200 Da-350 Da.

It will be appreciated that for use in therapy the salts of the compounds of formula (I) should be pharmaceutically acceptable. Suitable pharmaceutically acceptable salts will be apparent to those skilled in the art. Pharmaceutically acceptable salts include basic addition salts such as sodium, potassium, calcium, aluminium, zinc, magnesium and other metal salts. Pharmaceutically acceptable salts may also be formed with organic bases e.g. with ammonia, meglumine, tromethamine, piperazine, arginine, choline, diethylamine, benzathine or lysine. Other pharmaceutically acceptable salts include a trifluoroacetic acid salt. Suitably, the pharmaceutically acceptable salt is a tromethamine salt. Thus, in one embodiment there is provided a compound of formula (I) in the form of a pharmaceutically acceptable salt. Alternatively, there is provided a compound of formula (I) in the form of a free acid. When the compound contains a basic group as well as the free acid it may be Zwitterionic.

The compounds of formula (I) may be prepared in crystalline or non-crystalline form and, if crystalline, may optionally be solvated, e.g. as the hydrate. This invention includes within its scope stoichiometric solvates (e.g. hydrates) as well as compounds containing variable amounts of solvent (e.g. water). Suitably, the compound of formula (I) is not a solvate.

It is to be understood that the present invention encompasses all isomers of compounds of formula (I) including all geometric, tautomeric and optical forms, and mixtures thereof (e.g. racemic mixtures). Insofar as described herein, e.g., in claim 1, certain specific structural isomers are provided as part of the invention. In particular, the invention extends to all tautomeric forms of the compounds of formula (I). Where additional chiral centres are present in compounds of formula (I), the present invention includes within its scope all possible diastereoisomers, including mixtures thereof. The different isomeric forms may be separated or resolved one from the other by conventional methods, or any given isomer may be obtained by conventional synthetic methods or by stereospecific or asymmetric syntheses.

The present invention also includes all isotopic forms of the compounds provided herein, whether in a form (i) wherein all atoms of a given atomic number have a mass number (or mixture of mass numbers) which predominates in nature (referred to herein as the "natural isotopic form") or (ii) wherein one or more atoms are replaced by atoms having the same atomic number, but a mass number different from the mass number of atoms which predominates in nature (referred to herein as an "unnatural variant isotopic form"). It is understood that an atom may naturally exists as a mixture of mass numbers. The term "unnatural variant isotopic form" also includes embodiments in which the proportion of an atom of given atomic number having a mass number found less commonly in nature (referred to herein as an "uncommon isotope") has been increased relative to that which is naturally occurring e.g. to the level of >20%, >50%, >75%, >90%, >95% or >99% by number of the atoms of that atomic number (the latter embodiment referred to as an "isotopically enriched variant form"). The term "unnatural variant isotopic form" also includes embodiments in which the proportion of an uncommon isotope has been reduced relative to that which is naturally occurring. Isotopic forms may include radioactive forms (i.e. they incorporate radioisotopes) and non-radioactive forms. Radioactive forms will typically be isotopically enriched variant forms.

An unnatural variant isotopic form of a compound may thus contain one or more artificial or uncommon isotopes such as deuterium ($^{2}H$ or D), carbon-11 ($^{11}C$), carbon-13 ($^{13}C$), carbon-14 ($^{14}C$), nitrogen-13 ($^{13}N$), nitrogen-15 ($^{15}N$), oxygen-15 ($^{15}O$), oxygen-17 ($^{17}O$), oxygen-18 ($^{18}O$), phosphorus-32 ($^{32}P$), sulphur-35 ($^{35}S$), chlorine-36 ($^{36}Cl$), chlorine-37 ($^{37}Cl$), fluorine-18 ($^{18}F$) iodine-123 ($^{123}I$), iodine-125 ($^{125}I$) in one or more atoms or may contain an increased proportion of said isotopes as compared with the proportion that predominates in nature in one or more atoms.

Unnatural variant isotopic forms comprising radioisotopes may, for example, be used for drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection. Unnatural variant isotopic forms which incorporate deuterium i.e. $^{2}H$ or D may afford certain therapeutic advantages resulting from greater metabolic stability, for example, increased in vivo half-life or reduced dosage requirements, and hence may be preferred in some circumstances. Further, unnatural variant isotopic forms may be prepared which incorporate positron emitting isotopes, such as $^{11}C$, $^{18}F$, $^{15}O$ and $^{13}N$, and would be useful in positron emission topography (PET) studies for examining substrate receptor occupancy.

In one embodiment, the compounds of formula (I) are provided in a natural isotopic form. In one embodiment, the compounds of formula (I) are provided in an unnatural variant isotopic form. In a specific embodiment, the unnatural variant isotopic form is a form in which deuterium (i.e. $^{2}H$ or D) is incorporated where hydrogen is specified in the chemical structure in one or more atoms of a compound of formula (I). In one embodiment, the atoms of the compounds of formula (I) are in an isotopic form which is not radioactive. In one embodiment, one or more atoms of the compounds of formula (I) are in an isotopic form which is radioactive. Suitably radioactive isotopes are stable isotopes. Suitably the unnatural variant isotopic form is a pharmaceutically acceptable form.

In one embodiment, a compound of formula (I) is provided whereby a single atom of the compound exists in an unnatural variant isotopic form. In another embodiment, a compound of formula (I) is provided whereby two or more atoms exist in an unnatural variant isotopic form.

Unnatural isotopic variant forms can generally be prepared by conventional techniques known to those skilled in the art or by processes described herein e.g. processes analogous to those described in the accompanying Examples for preparing natural isotopic forms. Thus, unnatural isotopic variant forms could be prepared by using appropriate isotopically variant (or labeled) reagents in place of the normal reagents employed in the Examples. Since the compounds of formula (I) are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

Therapeutic Indications

Compounds of formula (I) are of use in therapy, particularly for treating or preventing an inflammatory disease or a disease associated with an undesirable immune response. As shown in Biological Example 1 below, the compound of formula (I) of Example 1 reduced cytokine release more effectively than 4-octyl itaconate and 2-(2-chlorobenzyl) acrylic acid, as demonstrated by lower $IC_{50}$ values. This compound also activated NRF2 more potently and with higher efficacy than 4-octyl itaconate and 2-(2-chlorobenzyl)acrylic acid while also demonstrating improved stability in both mouse and human cryopreserved hepatocytes. Other example compounds of formula (I) reduced cytokine release more effectively than 4-octyl itaconate and 2-(2-chlorobenzyl)acrylic acid, as demonstrated by lower $IC_{50}$ values, and/or activated NRF2 more potently and with higher efficacy than 4-octyl itaconate and 2-(2-chlorobenzyl)acrylic acid while also demonstrating improved stability in both mouse and human cryopreserved hepatocytes. Cytokines are important mediators of inflammation and immune-mediated disease as evidenced by the therapeutic benefit delivered by antibodies targeting them.

Thus, in a first aspect, the present invention provides a compound of formula (I) or a pharmaceutically acceptable salt and/or solvate thereof as defined herein, for use as a medicament. Also provided is a pharmaceutical composition comprising a compound of formula (I) or a pharmaceutically acceptable salt and/or solvate thereof as defined herein. Such a pharmaceutical composition contains the compound of formula (I) and a pharmaceutically acceptable carrier or excipient.

In a further aspect, the present invention provides a compound of formula (I) or a pharmaceutically acceptable salt and/or solvate thereof as defined herein, for use in treating or preventing an inflammatory disease or a disease associated with an undesirable immune response. In a further aspect, the present invention provides the use of a compound of formula (I) or a pharmaceutically acceptable salt and/or solvate thereof as defined herein, in the manufacture of a medicament for treating or preventing an inflammatory disease or a disease associated with an undesirable immune response. In a further aspect, the present invention provides a method of treating or preventing an inflammatory disease or a disease associated with an undesirable immune response, which comprises administering a compound of formula (I) or a pharmaceutically acceptable salt and/or solvate thereof as defined herein.

For all aspects of the invention, suitably the compound is administered to a subject in need thereof, wherein the subject is suitably a human subject.

In one embodiment is provided a compound of formula (I) or a pharmaceutically acceptable salt and/or solvate thereof as defined herein, for use in treating an inflammatory disease or disease associated with an undesirable immune response. In one embodiment of the invention is provided the use of a compound of formula (I) or a pharmaceutically acceptable salt and/or solvate thereof as defined herein, in the manufacture of a medicament for treating an inflammatory disease or a disease associated with an undesirable immune response. In one embodiment of the invention is provided a method of treating an inflammatory disease or a disease associated with an undesirable immune response, which comprises administering a compound of formula (I) or a pharmaceutically acceptable salt and/or solvate thereof as defined herein.

In one embodiment is provided a compound of formula (I) or a pharmaceutically acceptable salt and/or solvate thereof as defined herein, for use in preventing an inflammatory disease or a disease associated with an undesirable immune response. In one embodiment of the invention is provided the use of a compound of formula (I) or a pharmaceutically acceptable salt and/or solvate thereof as defined herein, in the manufacture of a medicament for preventing an inflammatory disease or a disease associated with an undesirable immune response. In one embodiment of the invention is provided a method of preventing an inflammatory disease or a disease associated with an undesirable immune response, which comprises administering a compound of formula (I) or a pharmaceutically acceptable salt and/or solvate thereof as defined herein.

In one embodiment is provided a compound of formula (I) or a pharmaceutically acceptable salt and/or solvate thereof as defined herein, for use in treating or preventing an inflammatory disease. In one embodiment of the invention is provided the use of a compound of formula (I) or a pharmaceutically acceptable salt and/or solvate thereof as defined herein, in the manufacture of a medicament for treating or preventing an inflammatory disease. In one embodiment of the invention is provided a method of treating or preventing an inflammatory disease, which comprises administering a compound of formula (I) or a pharmaceutically acceptable salt and/or solvate thereof as defined herein.

In one embodiment is provided a compound of formula (I) or a pharmaceutically acceptable salt and/or solvate thereof as defined herein, for use in treating or preventing a disease associated with an undesirable immune response. In one embodiment of the invention is provided the use of a compound of formula (I) or a pharmaceutically acceptable salt and/or solvate thereof as defined herein, in the manufacture of a medicament for treating or preventing a disease associated with an undesirable immune response. In one embodiment of the invention is provided a method of treating or preventing a disease associated with an undesirable immune response, which comprises administering a compound of formula (I) or a pharmaceutically acceptable salt and/or solvate thereof as defined herein.

An undesirable immune response will typically be an immune response which gives rise to a pathology i.e. is a pathological immune response or reaction.

In one embodiment, the inflammatory disease or disease associated with an undesirable immune response is an auto-immune disease.

In one embodiment, the inflammatory disease or disease associated with an undesirable immune response is, or is associated with, a disease selected from the group consisting of: psoriasis (including chronic plaque, erythrodermic, pustular, guttate, inverse and nail variants), asthma, chronic obstructive pulmonary disease (COPD, including chronic bronchitis and emphysema), heart failure (including left ventricular failure), myocardial infarction, angina pectoris, other atherosclerosis and/or atherothrombosis-related disorders (including peripheral vascular disease and ischaemic stroke), a mitochondrial and neurodegenerative disease (such as Parkinson's disease, Alzheimer's disease, Huntington's disease, amyotrophic lateral sclerosis, retinitis pigmentosa or mitochondrial encephalomyopathy), autoimmune paraneoplastic retinopathy, transplantation rejection (including antibody-mediated and T cell-mediated forms), multiple sclerosis, transverse myelitis, ischaemia-reperfusion injury (e.g. during elective surgery such as cardiopulmonary bypass for coronary artery bypass grafting or other cardiac surgery, following percutaneous coronary intervention, following treatment of acute ST-elevation myocardial infarction or ischaemic stroke, organ transplantation, or acute compartment syndrome), AGE-induced genome damage, an inflammatory bowel disease (e.g. Crohn's disease or ulcerative colitis), primary sclerosing cholangitis (PSC), PSC-autoimmune hepatitis overlap syndrome, non-alcoholic fatty liver disease (non-alcoholic steatohepatitis), rheumatica, granuloma annulare, cutaneous lupus erythematosus (CLE), systemic lupus erythematosus (SLE), lupus nephritis, drug-induced lupus, autoimmune myocarditis or myopericarditis, Dressler's syndrome, giant cell myocarditis, post-pericardiotomy syndrome, drug-induced hypersensitivity syndromes (including hypersensitivity myocarditis), eczema, sarcoidosis, erythema nodosum, acute disseminated encephalomyelitis (ADEM), neuromyelitis optica spectrum disorders, MOG (myelin oligodendrocyte glycoprotein) antibody-associated disorders (including MOG-EM), optic neuritis, CLIPPERS (chronic lymphocytic inflammation with pontine perivascular enhancement responsive to steroids), diffuse myelinoclastic sclerosis, Addison's disease, alopecia areata, ankylosing spondylitis, other spondyloarthritides (including peripheral spondyloarthritis, that is associated with psoriasis, inflammatory bowel disease, reactive arthritis or juvenile onset forms), antiphospholipid antibody syndrome, autoimmune hemolytic anaemia, autoimmune hepatitis, autoimmune inner ear disease, pemphigoid (including bullous pemphigoid, mucous membrane pemphigoid, cicatricial pemphigoid, herpes gestationis or pemphigoid gestationis, ocular cicatricial pemphigoid), linear IgA disease, Behçet's disease, celiac disease, Chagas disease, dermatomyositis, diabetes mellitus type I, endometriosis, Goodpasture's syndrome, Graves' disease, Guillain-Barre syndrome and its subtypes (including acute inflammatory demyelinating polyneuropathy, AIDP, acute motor axonal neuropathy (AMAN), acute motor and sensory axonal neuropathy (AMSAN), pharyngeal-cervical-brachial variant, Miller-Fisher variant and Bickerstaff's brainstem encephalitis), progressive inflammatory neuropathy, Hashimoto's disease, hidradenitis suppurativa, inclusion body myositis, necrotising myopathy, Kawasaki disease, IgA nephropathy, Henoch-Schonlein purpura, idiopathic thrombocytopenic purpura, thrombotic thrombocytopenic purpura (TTP), Evans' syndrome, interstitial cystitis, mixed connective tissue disease, undifferentiated connective tissue disease, morphea, myasthenia gravis (including MuSK antibody positive and seronegative variants), narcolepsy, neuromyotonia, pemphigus vulgaris, pernicious anaemia, psoriatic arthritis, polymyositis, primary biliary cholangitis (also known as primary biliary cirrhosis), rheumatoid arthritis, palindromic rheumatism, schizophrenia, autoimmune (meningo-)encephalitis syndromes, scleroderma, Sjogren's syndrome, stiff person syndrome, polymylagia rheumatica, giant cell arteritis (temporal arteritis), Takayasu arteritis, polyarteritis nodosa, Kawasaki disease, granulomatosis with polyangitis (GPA; formerly known as Wegener's granulomatosis), eosinophilic granulomatosis with polyangiitis (EGPA; formerly known as Churg-Strauss syndrome), microscopic polyarteritis/polyangiitis, hypocomplementaemic urticarial vasculitis, hypersensitivity vasculitis, cryoglobulinemia, thromboangiitis obliterans (Buerger's disease), vasculitis, leukocytoclastic vasculitis, vitiligo, acute disseminated encephalomyelitis, adrenoleukodystrophy, Alexander's disease, Alper's disease, balo concentric sclerosis or Marburg disease, cryptogenic organising pneumonia (formerly known as bronchiolitis obliterans organizing pneumonia), Canavan disease, central nervous system vasculitic syndrome, Charcot-Marie-Tooth disease, childhood ataxia with central nervous system hypomyelination, chronic inflammatory demyelinating polyneuropathy (CIDP), diabetic retinopathy, globoid cell leukodystrophy (Krabbe disease), graft-versus-host disease (GVHD) (including acute and chronic forms, as well as intestinal GVHD), hepatitis C (HCV) infection or complication, herpes simplex viral infection or complication, human immunodeficiency virus (HIV) infection or complication, lichen planus, monomelic amyotrophy, cystic fibrosis, pulmonary arterial hypertension (PAH, including idiopathic PAH), lung sarcoidosis, idiopathic pulmonary fibrosis, paediatric asthma, atopic dermatitis, allergic dermatitis, contact dermatitis, allergic rhinitis, rhinitis, sinusitis, conjunctivitis, allergic conjunctivitis, keratoconjunctivitis sicca, dry eye, xerophthalmia, glaucoma, macular oedema, diabetic macular oedema, central retinal vein occlusion (CRVO), macular degeneration (including dry and/or wet age related macular degeneration, AMD), post-operative cataract inflammation, uveitis (including posterior, anterior, intermediate and pan uveitis), iridocyclitis, scleritis, corneal graft and limbal cell transplant rejection, gluten sensitive enteropathy (coeliac disease), dermatitis herpetiformis, eosinophilic esophagitis, achalasia, autoimmune dysautonomia, autoimmune encephalomyelitis, autoimmune oophoritis, autoimmune orchitis, autoimmune pancreatitis, aortitis and periaortitis, autoimmune retinopathy, autoimmune urticaria, Behcet's disease, (idiopathic) Castleman's disease, Cogan's syndrome, IgG4-related disease, retroperitoneal fibrosis, juvenile idiopathic arthritis including systemic juvenile idiopathic arthritis (Still's disease), adult-onset Still's disease, ligneous conjunctivitis, Mooren's ulcer, pityriasis lichenoides et varioliformis acuta (PLEVA, also known as Mucha-Habermann disease), multifocal motor neuropathy (MMN), paediatric acute-onset neuropsychiatric syndrome (PANS) (including paediatric autoimmune neuropsychiatric disorders associated with streptococcal infections (PANDAS)), paraneoplastic syndromes (including paraneoplastic cerebellar degeneration, Lambert-Eaton myaesthenic syndrome, limbic encephalitis, brainstem encephalitis, opsoclonus myoclonus ataxia syndrome, anti-NMDA receptor encephalitis, thymoma-associated multiorgan autoimmunity), perivenous encephalomyelitis, reflex sympathetic dystrophy, relapsing polychondritis, sperm & testicular autoimmunity, Susac's syndrome, Tolosa-Hunt syndrome, Vogt-Koyanagi-Harada Disease, anti-synthetase syndrome, autoimmune enteropathy, immune dysregulation polyendocrinopathy enteropathy X-linked (IPEX), microscopic colitis, autoimmune lymphoproliferative syndrome (ALPS), autoimmune polyendocrinopathy-candidiasis-ectodermal dystrophy syndrome (APEX), gout, pseudogout, amyloid (including AA or secondary amyloidosis), eosinophilic fasciitis (Shulman syndrome) progesterone hypersensitivity (including progesterone dermatitis), familial Mediterranean fever (FMF), tumour necrosis factor (TNF) receptor-associated periodic fever syndrome (TRAPS), hyperimmunoglobulinaemia D with periodic fever syndrome (HIDS), PAPA (pyogenic arthritis, pyoderma gangrenosum, severe cystic acne) syndrome, deficiency of interleukin-1 receptor antagonist (DIRA), deficiency of the interleukin-36-receptor antagonist (DITRA), cryopyrin-associated periodic syndromes (CAPS) (including familial cold autoinflammatory syndrome [FCAS], Muckle-Wells syndrome, neonatal onset multisystem inflammatory disease [NOMID]), NLRP12-associated autoinflammatory disorders (NLRP12AD), periodic fever aphthous stomatitis (PFAPA), chronic atypical neutrophilic dermatosis with lipodystrophy and elevated temperature (CANDLE), Majeed syndrome, Blau syndrome (also known as juvenile systemic granulomatosis), macrophage activation syndrome, chronic recurrent multifocal osteomyelitis (CRMO), familial cold autoinflammatory syndrome, mutant adenosine deaminase 2 and monogenic interferonopathies (including Aicardi-Goutières syndrome, retinal vasculopathy with cerebral leukodystrophy, spondyloenchondrodysplasia, STING [stimulator of interferon genes]-associated vasculopathy with onset in infancy, proteasome associated autoinflammatory syndromes, familial chilblain lupus, dyschromatosis symmetrica hereditaria), Schnitzler syndrome; familial cylindromatosis, congenital B cell lymphocytosis, OTULIN-related autoinflammatory syndrome, type 2 diabetes mellitus, insulin resistance and the metabolic syndrome (including obesity-associated inflammation), atherosclerotic disorders (e.g. myocardial infarction, angina, ischaemic heart failure, ischaemic nephropathy, ischaemic stroke, peripheral vascular disease, aortic aneurysm), renal inflammatory disorders (e.g. diabetic nephropathy, membranous nephropathy, minimal change disease, crescentic glomerulonephritis, acute kidney injury, renal transplantation).

In one embodiment, the inflammatory disease or disease associated with an undesirable immune response is, or is associated with, a disease selected from the following autoinflammatory diseases: familial Mediterranean fever (FMF), tumour necrosis factor (TNF) receptor-associated periodic fever syndrome (TRAPS), hyperimmunoglobulinaemia D with periodic fever syndrome (HIDS), PAPA (pyogenic arthritis, pyoderma gangrenosum, and severe cystic acne) syndrome, deficiency of interleukin-1 receptor antagonist (DIRA), deficiency of the interleukin-36-receptor antagonist (DITRA), cryopyrin-associated periodic syndromes (CAPS) (including familial cold autoinflammatory syndrome [FCAS], Muckle-Wells syndrome, and neonatal onset multisystem inflammatory disease [NOMID]), NLRP12-associated autoinflammatory disorders (NLRP12AD), periodic fever aphthous stomatitis (PFAPA), chronic atypical neutrophilic dermatosis with lipodystrophy and elevated temperature (CANDLE), Majeed syndrome, Blau syndrome (also known as juvenile systemic granulomatosis), macrophage activation syndrome, chronic recurrent multifocal osteomyelitis (CRMO), familial cold autoinflammatory syndrome, mutant adenosine deaminase 2 and monogenic interferonopathies (including Aicardi-Goutières syndrome, retinal vasculopathy with cerebral leukodystrophy, spondyloenchondrodysplasia, STING [stimulator of interferon genes]-associated vasculopathy with onset in infancy, proteasome associated autoinflammatory syndromes, familial chilblain lupus, dyschromatosis symmetrica hereditaria) and Schnitzler syndrome.

In one embodiment, the inflammatory disease or disease associated with an undesirable immune response is, or is associated with, a disease selected from the following diseases mediated by excess NF-κB or gain of function in the NF-κB signaling pathway or in which there is a major contribution to the abnormal pathogenesis therefrom (including non-canonical NF-κB signaling): familial cylindromatosis, congenital B cell lymphocytosis, OTULIN-related autoinflammatory syndrome, type 2 diabetes mellitus, insulin resistance and the metabolic syndrome (including obesity-associated inflammation), atherosclerotic disorders (e.g. myocardial infarction, angina, ischaemic heart failure, ischaemic nephropathy, ischaemic stroke, peripheral vascular disease, aortic aneurysm), renal inflammatory disorders (e.g. diabetic nephropathy, membranous nephropathy, minimal change disease, crescentic glomerulonephritis, acute kidney injury, renal transplantation), asthma, COPD, type 1 diabetes mellitus, rheumatoid arthritis, multiple sclerosis, inflammatory bowel disease (including ulcerative colitis and Crohn's disease), and SLE.

In one embodiment, the disease is selected from the group consisting of rheumatoid arthritis, psoriatic arthritis, ankylosing spondylitis, systemic lupus erythematosus, multiple sclerosis, psoriasis, Crohn's disease, ulcerative colitis, uveitis, cryopyrin-associated periodic syndromes, Muckle-Wells syndrome, juvenile idiopathic arthritis and chronic obstructive pulmonary disease.

In one embodiment, the disease is multiple sclerosis.

In one embodiment, the disease is psoriasis.

In one embodiment, the compound of formula (I) exhibits a lower $IC_{50}$ compared with 4-octyl itaconate when tested in a cytokine assay e.g. as described in Biological Example 1. In one embodiment, the compound of formula (I) exhibits a lower $EC_{50}$ compared with 4-octyl itaconate when tested in an NRF2 assay e.g. as described in Biological Example 2. In one embodiment, the compound of formula (I) exhibits a higher $E_{max}$ compared with 4-octyl itaconate when tested in an NRF2 assay e.g. as described in Biological Example 2. In one embodiment, the compound of formula (I) exhibits a lower $EC_{50}$ and/or higher $E_{max}$ compared with 4-octyl itaconate when tested in an NRF2 assay e.g. as described in Biological Example 2. In one embodiment, the compound of formula (I) exhibits a lower $EC_{50}$ and higher $E_{max}$ compared with 4-octyl itaconate when tested in an NRF2 assay e.g. as described in Biological Example 2. In one embodiment, the compound of formula (I) exhibits a lower $CI_{int}$ compared with 4-octyl itaconate when tested in a hepatocyte stability assay e.g. as described in Biological Example 3. In one embodiment, the compound of formula (I) exhibits a longer half-life compared with 4-octyl itaconate when tested in a hepatocyte stability assay e.g. as described in Biological Example 3. In one embodiment, the compound of formula (I) exhibits a lower $CI_{int}$ and longer half-life compared with 4-octyl itaconate when tested in a hepatocyte assay e.g. as described in Biological Example 3. In any one of the above embodiments, suitably, the hepatocytes are human cryopreserved hepatocytes.

Administration

The compound of formula (I) is usually administered as a pharmaceutical composition. Thus, in one embodiment, is provided a pharmaceutical composition comprising a compound of formula (I) and one or more pharmaceutically acceptable diluents or carriers.

The compound of formula (I) may be administered by any convenient method, e.g. by oral, parenteral, buccal, sublingual, nasal, rectal, intrathecal or transdermal administration, and the pharmaceutical compositions adapted accordingly.

The compound of formula (I) may be administered topically to the target organ e.g. topically to the eye, lung, nose or skin. Hence the invention provides a pharmaceutical composition comprising a compound of formula (I) optionally in combination with one or more topically acceptable diluents or carriers.

A compound of formula (I) which is active when given orally can be formulated as a liquid or solid, e.g. as a syrup, suspension, emulsion, tablet, capsule or lozenge.

A liquid formulation will generally consist of a suspension or solution of the compound of formula (I) in a suitable liquid carrier(s). Suitably the carrier is non-aqueous e.g. polyethylene glycol or an oil. The formulation may also contain a suspending agent, preservative, flavouring and/or colouring agent.

A composition in the form of a tablet can be prepared using any suitable pharmaceutical carrier(s) routinely used for preparing solid formulations, such as magnesium stearate, starch, lactose, sucrose and cellulose.

A composition in the form of a capsule can be prepared using routine encapsulation procedures, e.g. pellets containing the active ingredient can be prepared using standard carriers and then filled into a hard gelatine capsule; alternatively, a dispersion or suspension can be prepared using any suitable pharmaceutical carrier(s), e.g. aqueous gums, celluloses, silicates or oils and the dispersion or suspension then filled into a soft gelatine capsule.

Typical parenteral compositions consist of a solution or suspension of the compound of formula (I) in a sterile aqueous carrier or parenterally acceptable oil, e.g. polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the compound of formula (I) in a pharmaceutically acceptable aqueous or non-aqueous solvent and are usually presented in single or multidose quantities in sterile form in a sealed container which can take the form of a cartridge or refill for use with an atomising device. Alternatively, the sealed container may be a disposable dispensing device such as a single dose nasal inhaler or an aerosol dispenser fitted with a metering valve. Where the dosage form comprises an aerosol dispenser, it will contain a propellant which can be a compressed gas e.g. air, or an organic propellant such as a chlorofluorocarbon (CFC) or a hydrofluorocarbon (HFC). Aerosol dosage forms can also take the form of pump-atomisers.

Topical administration to the lung may be achieved by use of an aerosol formulation. Aerosol formulations typically comprise the active ingredient suspended or dissolved in a suitable aerosol propellant, such as a chlorofluorocarbon (CFC) or a hydrofluorocarbon (HFC).

Topical administration to the lung may also be achieved by use of a non-pressurised formulation such as an aqueous solution or suspension. These may be administered by means of a nebuliser e.g. one that can be hand-held and portable or for home or hospital use (i.e. non-portable). The formulation may comprise excipients such as water, buffers, tonicity adjusting agents, pH adjusting agents, surfactants and co-solvents.

Topical administration to the lung may also be achieved by use of a dry-powder formulation. The formulation will typically contain a topically acceptable diluent such as lactose, glucose or mannitol (preferably lactose).

The compound of the invention may also be administered rectally, for example in the form of suppositories or enemas, which include aqueous or oily solutions as well as suspensions and emulsions and foams. Such compositions are prepared following standard procedures, well known by those skilled in the art. For example, suppositories can be prepared by mixing the active ingredient with a conventional suppository base such as cocoa butter or other glycerides. In this case, the drug is mixed with a suitable non-irritating excipient which is solid at ordinary temperatures but liquid at the rectal temperature and will therefore melt in the rectum to release the drug. Such materials are cocoa butter and polyethylene glycols.

Generally, for compositions intended to be administered topically to the eye in the form of eye drops or eye ointments, the total amount of the compound of the present invention will be about 0.0001 to less than 4.0% (w/w).

Preferably, for topical ocular administration, the compositions administered according to the present invention will be formulated as solutions, suspensions, emulsions and other dosage forms.

The compositions administered according to the present invention may also include various other ingredients, including, but not limited to, tonicity agents, buffers, surfactants, stabilizing polymer, preservatives, co-solvents and viscosity building agents. Suitable pharmaceutical compositions of the present invention include a compound of the invention formulated with a tonicity agent and a buffer. The pharmaceutical compositions of the present invention may further optionally include a surfactant and/or a palliative agent and/or a stabilizing polymer.

Various tonicity agents may be employed to adjust the tonicity of the composition, preferably to that of natural tears for ophthalmic compositions. For example, sodium chloride, potassium chloride, magnesium chloride, calcium chloride, simple sugars such as dextrose, fructose, galactose, and/or simply polyols such as the sugar alcohols mannitol, sorbitol, xylitol, lactitol, isomaltitol, maltitol, and hydrogenated starch hydrolysates may be added to the composition to approximate physiological tonicity. Such an amount of tonicity agent will vary, depending on the particular agent to be added. In general, however, the compositions will have a tonicity agent in an amount sufficient to cause the final composition to have an ophthalmically acceptable osmolality (generally about 150-450 mOsm, preferably 250-350 mOsm and most preferably at approximately 290 mOsm). In general, the tonicity agents of the invention will be present in the range of 2 to 4% w/w. Preferred tonicity agents of the invention include the simple sugars or the sugar alcohols, such as D-mannitol.

An appropriate buffer system (e.g. sodium phosphate, sodium acetate, sodium citrate, sodium borate or boric acid) may be added to the compositions to prevent pH drift under storage conditions. The particular concentration will vary, depending on the agent employed. Preferably however, the buffer will be chosen to maintain a target pH within the range of pH 5 to 8, and more preferably to a target pH of pH 5 to 7.

Surfactants may optionally be employed to deliver higher concentrations of compound of the present invention. The surfactants function to solubilise the compound and stabilise colloid dispersion, such as micellar solution, microemulsion, emulsion and suspension. Examples of surfactants which may optionally be used include polysorbate, poloxamer, polyosyl 40 stearate, polyoxyl castor oil, tyloxapol, Triton, and sorbitan monolaurate. Preferred surfactants to be employed in the invention have a hydrophile/lipophile/balance "HLB" in the range of 12.4 to 13.2 and are acceptable for ophthalmic use, such as TritonX114 and tyloxapol.

Additional agents that may be added to the ophthalmic compositions of compounds of the present invention are demulcents which function as a stabilising polymer. The stabilizing polymer should be an ionic/charged example with precedence for topical ocular use, more specifically, a polymer that carries negative charge on its surface that can exhibit a zeta-potential of (−)10-50 mV for physical stability and capable of making a dispersion in water (i.e. water soluble). A preferred stabilising polymer of the invention would be polyelectrolyte, or polyelectrolytes if more than one, from the family of cross-linked polyacrylates, such as carbomers and Pemulen(R), specifically Carbomer 974p (polyacrylic acid), at 0.1-0.5% w/w.

Other compounds may also be added to the ophthalmic compositions of the compound of the present invention to increase the viscosity of the carrier. Examples of viscosity enhancing agents include, but are not limited to: polysaccharides, such as hyaluronic acid and its salts, chondroitin sulfate and its salts, dextrans, various polymers of the cellulose family; vinyl polymers; and acrylic acid polymers.

Topical ophthalmic products are typically packaged in multidose form. Preservatives are thus required to prevent microbial contamination during use. Suitable preservatives include: benzalkonium chloride, chlorobutanol, benzododecinium bromide, methyl paraben, propyl paraben, phenylethyl alcohol, edentate disodium, sorbic acid, polyquaternium-1, or other agents known to those skilled in the art. Such preservatives are typically employed at a level of from 0.001 to 1.0% w/v. Unit dose compositions of the present invention will be sterile, but typically unpreserved. Such compositions, therefore, generally will not contain preservatives.

Compositions suitable for buccal or sublingual administration include tablets, lozenges and pastilles where the compound of formula (I) is formulated with a carrier such as sugar and acacia, tragacanth, or gelatine and glycerine.

Compositions suitable for transdermal administration include ointments, gels and patches.

The composition may contain from 0.1% to 100% by weight, for example from 10 to 60% by weight, of the compound of formula (I), depending on the method of administration. The composition may contain from 0% to 99% by weight, for example, 40% to 90% by weight, of the carrier, depending on the method of administration. The composition may contain from 0.05 mg to 1000 mg, for example from 1.0 mg to 500 mg, such as from 1.0 mg to 50 mg, e.g. about 10 mg of the compound of formula (I), depending on the method of administration. The composition may contain from 50 mg to 1000 mg, for example from 100 mg to 400 mg of the carrier, depending on the method of administration. The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 1.0 to 500 mg, such as from 1.0 mg to 50 mg, e.g. about 10 mg and such unit doses may be administered more than once a day, for example two or three times a day. Such therapy may extend for a number of weeks or months.

In one embodiment of the invention, the compound of formula (I) is used in combination with a further therapeutic agent or agents. When the compound of formula (I) is used in combination with other therapeutic agents, the compounds may be administered either sequentially or simultaneously by any convenient route. Alternatively, the compounds may be administered separately.

Therapeutic agents which may be used in combination with the present invention include: corticosteroids (glucocorticoids), retinoids (e.g. acitretin, isotretinoin, tazarotene), anthralin, vitamin D analogues (e.g. cacitriol, calcipotriol), calcineurin inhibitors (e.g. tacrolimus, pimecrolimus), phototherapy or photochemotherapy (e.g. psoralen ultraviolet irradiation, PUVA) or other form of ultraviolet light irradiation therapy, ciclosporine, thiopurines (e.g. azathioprine, 6-mercaptopurine), methotrexate, anti-TNFα agents (e.g. infliximab, etanercept, adalimumab, certolizumab, golimumab and biosimilars), phosphodiesterase-4 (PDE4) inhibition (e.g. apremilast, crisaborole), anti-IL-17 agents (e.g. brodalumab, ixekizumab, secukinumab), anti-IL12/IL-23 agents (e.g. ustekinumab, briakinumab), anti-IL-23 agents (e.g. guselkumab, tildrakizumab), JAK (Janus Kinase) inhibitors (e.g. tofacitinib, ruxolitinib, baricitinib, filgotinib, upadacitinib), plasma exchange, intravenous immune globulin (IVIG), cyclophosphamide, anti-CD20 B cell depleting agents (e.g. rituximab, ocrelizumab, ofatumumab, obinutuzumab), anthracycline analogues (e.g. mitoxantrone), cladribine, sphingosine 1-phosphate receptor modulators or sphingosine analogues (e.g. fingolimod, siponimod, ozanimod, etrasimod), interferon beta preparations (including interferon beta 1b/1a), glatiramer, anti-CD3 therapy (e.g. OKT3), anti-CD52 targeting agents (e.g. alemtuzumab), leflunomide, teriflunomide, gold compounds, laquinimod, potassium channel blockers (e.g. dalfampridine/4-aminopyridine), mycophenolic acid, mycophenolate mofetil, purine analogues (e.g. pentostatin), mTOR (mechanistic target of rapamycin) pathway inhibitors (e.g. sirolimus, everolimus), anti-thymocyte globulin (ATG), IL-2 receptor (CD25) inhibitors (e.g. basiliximab, daclizumab), anti-IL-6 receptor or anti-IL-6 agents (e.g. tocilizumab, siltuximab), Bruton's tyrosine kinase (BTK) inhibitors (e.g. ibrutinib), tyrosine kinase inhibitors (e.g. imatinib), ursodeoxycholic acid, hydroxychloroquine, chloroquine, B cell activating factor (BAFF, also known as BLyS, B lymphocyte stimulator) inhibitors (e.g. belimumab, blisibimod), other B cell targeted therapy including fusion proteins targeting both APRIL (A PRoliferation-Inducing Ligand) and BLyS (e.g. atacicept), PI3K inhibitors including pan-inhibitors or those targeting the p110δ and/or p110γ containing isoforms (e.g. idelalisib, copanlisib, duvelisib), interferon α receptor inhibitors (e.g. anifrolumab, sifalimumab), T cell co-stimulation blockers (e.g. abatacept, belatacept), thalidomide and its derivatives (e.g. lenalidomide), dapsone, clofazimine, leukotriene antagonists (e.g. montelukast), theophylline, anti-IgE therapy (e.g. omalizumab), anti-IL-5 agents (e.g. mepolizumab, reslizumab), long-acting muscarinic agents (e.g. tiotropium, aclidinium, umeclidinium), PDE4 inhibitors (e.g. roflumilast), riluzole, free radical scavengers (e.g. edaravone), proteasome inhibitors (e.g. bortezomib), complement cascade inhibitors including those directed against C5 (e.g. eculizumab), immunoadsor, antithymocyte globulin, 5-aminosalicylates and their derivatives (e.g. sulfasalazine, balsalazide, mesalamine), anti-integrin agents including those targeting α4β1 and/or α4β7 integrins (e.g. natalizumab, vedolizumab), anti-CD11-α agents (e.g. efalizumab), non-steroidal anti-inflammatory drugs (NSAIDs) including the salicylates (e.g. aspirin), propionic acids (e.g. ibuprofen, naproxen), acetic acids (e.g. indomethacin, diclofenac, etodolac), oxicams (e.g. meloxicam) and fenamates (e.g. mefenamic acid), selective or relatively selective COX-2 inhibitors (e.g. celecoxib, etroxicoxib, valdecoxib and etodolac, meloxicam, nabumetone), colchicine, IL-4 receptor inhibitors (e.g. dupilumab), topical/contact immunotherapy (e.g. diphenylcyclopropenone, squaric acid dibutyl ester), anti-IL-1 receptor therapy (e.g. anakinra), IL-1β inhibitor (e.g. canakinumab), IL-1 neutralising therapy (e.g. rilonacept), chlorambucil, specific antibiotics with immunomodulatory properties and/or ability to modulate NRF2 (e.g. tetracyclines including minocycline, clindamycin, macrolide antibiotics), anti-androgenic therapy (e.g. cyproterone, spironolactone, finasteride), pentoxifylline, ursodeoxycholic acid, obeticholic acid, fibrate, cystic fibrosis transmembrane conductance regulator (CFTR) modulators, VEGF (vascular endothelial growth factor) inhibitors (e.g. bevacizumab, ranibizumab, pegaptanib, aflibercept), pirfenidone, and mizoribine.

Compounds of formula (I) may display one or more of the following desirable properties:

- low $IC_{50}$ values for inhibiting release of cytokines e.g. IL-1β and/or IL-6, from cells;
- low $EC_{50}$ and/or high $E_{max}$ values for activating the enzyme NQO1 or the NRF2 pathway;
- enhanced efficacy through improved metabolic stability and/or augmented maximum response;
- reduced dose and dosing frequency through improved pharmacokinetics, especially as a result of enhanced stability in hepatocytes;
- improved oral systemic bioavailability;
- reduced plasma clearance following intravenous dosing;
- improved metabolic stability e.g. as demonstrated by improved stability in plasma and/or hepatocytes;
- augmented cell permeability;
- enhanced aqueous solubility;
- good tolerability, for example, by limiting the flushing and/or gastrointestinal side effects provoked by oral DMF (Hunt T. et al., 2015; WO2014/152494A1, incorporated herein by reference), possibly by reducing or eliminating HCA2 activity;

- low toxicity at the relevant therapeutic dose;
- distinct anti-inflammatory profiles resulting from varied electrophilicities, leading to differential targeting of the cysteine proteome (van der Reest J. et al., 2018) and, therefore, modified effects on gene activation;
- glutathione-sparing actions;
- avoiding the oncometabolite fumaric acid (Kulkarni R. A. et al., 2019);
- improved physical form (solid) or higher melting point.

Abbreviations

Ac acetyl
ACN acetonitrile
aq. aqueous
ATG anti-thymocyte
BBFO broadband fluorine observe
BEH ethylene bridged hybrid
Bn benzyl
BOC tert-butyloxycarbonyl
CSH charged surface hybrid
d doublet
DABCO 1,4-diazabicyclo[2.2.2]octane
DAD diode array detector
DAST diethylaminosulfur trifluoride
DBU 1,8-diazabicyclo(5.4.0)undec-7-ene
DCE dichloroethane
DCM dichloromethane
DIAD diisopropyl azodicarboxylate
DIPEA N,N-diisopropylethylamine
DMAP 4-dimethylaminopyridine
DME dimethyl ether
DMF dimethyl fumarate
DMI dimethyl itaconate
DMP Dess-Martin periodinane
DMSO dimethyl sulfoxide
DSC differential scanning calorimetry
EDC 1-ethyl-3-(3-dimethylaminopropyl)carbodiimide
ee enantiomeric excess
Et ethyl
ES+ electrospray
FBS fetal bovine serum
g gram(s)
GSH glutathione
h hour(s)
HATU 1-[bis(dimethylamino)methylene]-1H-1,2,3-triazolo[4,5-b]pyridinium 3-oxid hexafluorophosphate
HFC hydrofluorocarbon
HPLC high-performance liquid chromatography
IL interleukin
IPA isopropyl alcohol
K kelvin
KHMDS potassium bis(trimethylsilyl)amide
LCMS liquid chromatography-mass spectrometry
LDA lithium diisopropylamide
LPS lipopolysaccharide
m multiplet
M molar concentration/molar mass
m/z mass to charge ratio
mCPBA meta-chloroperoxybenzoic acid
Me methyl
(M)Hz (mega)hertz
mg milligram
min(s) minute(s)
mL millilitre
mm millimetre
MMF monomethyl fumarate
mmol millimole
MOM methoxymethyl
MS mass spectrometry
MSD mass selective detector
MTBE methyl tert-butyl ether
NBS N-bromosuccinimide
nm nanometre
NMP N-methyl-2-pyrrolidone
NMR nuclear magnetic resonance
NQO1 NAD(P)H dehydrogenase [quinone] 1
NRF2 nuclear factor (erythroid-derived 2)-like 2
NSAIDs non-steroidal anti-inflammatory drugs
PAH pulmonary arterial hypertension
PBS phosphate buffered saline
PDA photodiode array
PDE4 phosphodiesterase-4
PET positron emission topography
Pin pinacolato
PMB para-methoxybenzyl
PTFE polytetrafluoroethylene
PUVA psoralen ultraviolet irradiation
4OI 4-octyl itaconic acid
rpm revolutions per minute
RT room temperature
s singlet
sat. saturated
t triplet
T3P propylphosphonic anhydride
TBDMS tert-butyldimethylsilyl
tBu tert-butyl
Tf triflyl
TFA trifluoroacetic acid
TFAA trifluoroacetic anhydride
TGA thermogravimetric analysis
THF tetrahydrofuran
TIPS triisopropylsilyl
TLR Toll-like receptor
TMS trimethylsilyl
TNF tumour necrosis factor
TosMIC toluenesulfonylmethyl isocyanide
TRIS tris(hydroxymethyl)aminomethane; tromethamine
Ts tosyl
TOM tri-iso-propylsilyloxymethyl
μL microlitre
μM micromolar
μmol micromole
UPLC ultra performance liquid chromatography
UV ultra violet
VEGF vascular endothelial growth factor
VWD variable wavelength detector
wt. weight
XRPD X-Ray Powder Diffraction
° C. degrees centigrade

EXAMPLES

Analytical Equipment

NMR spectra were recorded using a Bruker 400 MHz Avance III spectrometer fitted with a BBFO 5 mm probe, or a Bruker 500 MHz Avance III HD spectrometer equipped with a Bruker 5 mm SmartProbe™. Spectra were measured at 298 K, unless indicated otherwise, and were referenced relative to the solvent resonance. The chemical shifts are reported in parts per million. Data were acquired using Bruker TopSpin software.

UPLC/MS analysis was carried out on a Waters Acquity UPLC system using either a Waters Acquity CSH C18 or BEH C18 column (2.1×30 mm) maintained at a temperature of 40° C. and eluted with a linear acetonitrile gradient appropriate for the lipophilicity of the compound over 3 or 10 minutes at a constant flow rate of 0.77 ml/min. The aqueous portion of the mobile phase was either 0.1% Formic Acid (CSH C18 column), 10 mM Ammonium Bicarbonate or 10 mM Ammonia (BEH C18 column). LC-UV chromatograms were recorded using a Waters Acquity PDA detector between 210 and 400 nm. Mass spectra were recorded using a Waters Acquity Qda detector with electrospray ionisation switching between positive and negative ion mode. Sample concentration was adjusted to give adequate UV response.

LCMS analysis was carried out on a Agilent LCMS system using either a Waters Acquity CSH C18 or BEH C18 column (4.6×30 mm) maintained at a temperature of 40° C. and eluted with a linear acetonitrile gradient appropriate for the lipophilicity of the compound over 4 or 15 minutes at a constant flow rate of 2.5 ml/min. The aqueous portion of the mobile phase was either 0.1% Formic Acid (CSH C18 column), 10 mM Ammonium Bicarbonate or 10 mM Ammonia (BEH C18 column). LC-UV chromatograms were recorded using an Agilent VWD or DAD detector at 254 nm. Mass spectra were recorded using an Agilent MSD detector with electrospray ionisation switching between positive and negative ion mode. Sample concentration was adjusted to give adequate UV response.

Alternatively, the following analytical LCMS equipment and methods were also used:

DSC

DSC data was collected on a PerkinElmer Pyris 6000 DSC equipped with a 45-position sample holder. The instrument was verified for energy and temperature calibration using certified indium. A predefined amount of the sample, 0.5-3.0 mg, was placed in a pin holed aluminium pan and heated at 20° C.·$min^{-1}$ from 30 to 350° C. or varied as experimentation dictated. A purge of dry nitrogen at 20 ml $min^{-1}$ was maintained over the sample. The instrument control, data acquisition and analysis was performed with Pyris Software v11.1.1 revision H.

TGA

TGA data were collected on a PerkinElmer Pyris 1 TGA equipped with a 20-position auto-sampler. The instrument was calibrated using a certified weight and certified Alumel and Perkalloy for temperature. A predefined amount of the sample, 1-5 mg, was loaded onto a pre-tared aluminium crucible and was heated at 20° C.·$min^{-1}$ from ambient temperature to 400° C. A nitrogen purge at 20 ml·$min^{-1}$ was maintained over the sample. The instrument control, data acquisition and analysis was performed with Pyris Software v11.1.1 revision H.

XRPD

X-Ray Powder Diffraction patterns were collected on a PANalytical diffractometer using Cu Kα radiation (45 kV, 40 mA), θ-θ goniometer, focusing mirror, divergence slit (½"), soller slits at both incident and divergent beam (4 mm) and a PIXcel detector. The software used for data collection was X'Pert Data Collector, version 2.2f and the data was LCMS/HPLC Instrument Details

| System | Instrument Name | LC Detector | ELS detector | Mass detector |
|---|---|---|---|---|
| 2 | Agilent LCMS 1200 | G1315C DAD | 380 ELSD | Agilent G6110A |

LCMS/HPLC Method Details

| Method Name | Solvent System | Column | Gradient | UV range | Mass Range | Column Temp. °C. | Flow Rate ml/min |
|---|---|---|---|---|---|---|---|
| A | A) water + 10 mM $NH_4HCO_3$ B) acetonitrile | Waters X-Bridge C18 (50 mm × 4.6 mm × 3.5 μm) | From 95:5 to 0:100 in 1.6 min, 0:100 for 1.4 min, from 0:100 to 95:5 in 0.1 min, 95:5 for 0.7 min | 190-400 nm | 100-1800 amu | 40 | 2.0 |
| B | A) water + 0.05% TFA B) acetonitrile + 0.05% TFA | Waters X-Bridge C18 (50 mm × 4.6 mm × 3.5 μm) | From 95:5 to 0:100 in 1.6 min, 0:100 for 1.4 min, from 0:100 to 95:5 in 0.05 min, 95:5 for 0.7 min | 190-400 nm | 100-1100 amu | 40 | 2.0 |
| C | A) water + 0.05% TFA B) acetonitrile + 0.05% TFA | Halo C18 (30 mm × 4.6 mm × 2.7 μm) | From 95:5 0:100 for 0.8 min, 0:100 for 0.4 min, from 0:100 to 95:5 in 0.01 min, 95:5 for 0.2 min | 190-400 nm | 100-1100 amu | 40 | 3.0 |

presented using X'Pert Data Viewer, version 1.2d. XRPD patterns were acquired under ambient conditions via a transmission foil sample stage (polyimide—Kapton, 12.7 μm thickness film) under ambient conditions using a PANalytical X'Pert PRO. The data collection range was 2.994-35°2θ with a continuous scan speed of 0.202004° $s^{-1}$.

General Methods

Unless otherwise stated all reactions were stirred.

General Procedure A

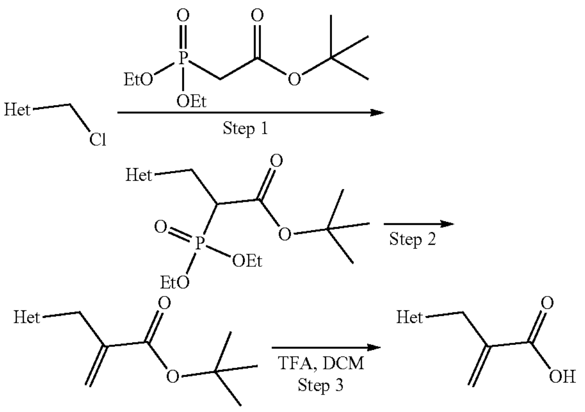

Step 1, Method A

Tert-butyl diethylphosphonoacetate (1 eq.) was added dropwise to a solution of sodium hydride (60 weight % dispersion in mineral oil, 1.1 eq.) in NMP (0.6 M) at 0° C. The reaction was warmed to RT and stirred for 2 h. A solution of chloromethyl-heteroarene (1.1 eq.) in NMP (1.3 M) was added dropwise and the mixture was heated to 60° C. for 2 h. The mixture was cooled to RT, poured into water and extracted with EtOAc (×3). The combined organic extracts were washed with brine, dried ($Na_2SO_4$) and concentrated. The crude product was purified by chromatography on silica gel to afford the required compound Step 1, Method B Sodium hydride (60% dispersion in mineral oil, 1.5 eq.) was added portionwise to a solution of tert-butyl diethylphosphonoacetate (1.4 eq.) in THF (0.6 M) at 0° C. The mixture was allowed to warm to RT and stirred for 1 h. Separately, sodium iodide (1.1 eq.) was added to a chloromethyl-heteroarene (1 eq.) in THF (1.8 M) at RT. The mixture was stirred for 1 h, then added to the mixture of phosphonoacetate and sodium hydride. The reaction was heated to 70° C. and stirred for 3 h, then cooled to RT, before being partitioned between EtOAc and water. The phases were separated and the aqueous phase was extracted with EtOAc (×2). The combined organic phases were washed with brine, dried ($MgSO_4$) and concentrated. The crude product was purified by chromatography on silica gel to afford the required compound.

Step 1, Method C

Sodium hydride (1.3 eq.) was added portionwise to a solution of tert-butyl diethylphosphonoacetate (1.3 eq.) in THF (0.67 M) at 0° C. The mixture was allowed to warm to RT and stirred for 1 h. The solution was added dropwise to a mixture of chloromethyl-heteroarene (1 eq.) and sodium iodide (1.1 eq.) in THF (0.7 M) at RT. The reaction was stirred at RT for 2 h, then water was added, and the mixture concentrated to remove THF. The mixture was diluted with water and EtOAc. The phases were separated and the aqueous phase extracted with EtOAc, then the combined organic phases were washed with brine, dried ($MgSO_4$) and concentrated. The crude product was purified by chromatography on silica gel to afford the required compound.

Step 1, Method D

Sodium hydride suspension in mineral oil (60 wt. %, 1.2 eq.) was added to a solution of tert-butyl 2-(diethoxyphosphoryl)acetate (1.1 eq.) in THF (0.36 M) at 0° C. and the mixture was stirred at 0° C. for 0.5 h. The chloromethyl-heteroarene (1 eq.) was then added and the mixture was stirred at RT overnight. The mixture was quenched with saturated aqueous $NH_4Cl$ solution and extracted with EtOAc (×3). The combined organic phases were washed with brine, dried ($Na_2SO_4$), filtered and concentrated under reduced pressure. The residue was purified by flash column chromatography to afford the required product.

Step 2, Method A

Sodium hydride (60% weight dispersion in mineral oil, 1 eq.) was added to a solution of phosphonate (1 eq.) in THF (0.2 M) at 0° C. After 10 minutes, paraformaldehyde (3 eq.) was added, then the reaction was warmed to RT and stirred for 45 min. The reaction was quenched with sat. aq. $NaHCO_3$ and the mixture was extracted with EtOAc (×3). The combined organic extracts were washed with brine, dried ($Na_2SO_4$) and concentrated. The crude product was purified by chromatography on silica gel to afford the required compound.

Step 2, Method B

Paraformaldehyde (1.1-2.5 eq.) was added to a mixture of phosphonate (1 eq.) and potassium carbonate (1.2-2 eq.) in THF (0.15 M). The mixture was heated to 65° C. and stirred for 4 h, before being cooled to RT and poured into water (150 mL). The phases were separated and the aqueous phase was extracted with EtOAc (×2). The combined organic phases were washed with brine, dried ($MgSO_4$) and concentrated, then the crude product was purified by chromatography on silica gel to afford the required compound.

Step 2, Method C

Formaldehyde solution in water (37 wt. %, 2-30 eq.) was added to a mixture of phosphonate (1 eq.) and potassium carbonate (2-3 eq.) in THF (0.1-0.5 M). The mixture was stirred at RT for 2-5 h, before being extracted with EtOAc (×3) or MTBE (×3). The combined organic phases were washed with brine, dried ($Na_2SO_4$) and concentrated, then the crude product was purified by chromatography on silica gel to afford the required compound.

Step 3

TFA (10-350 eq.) was added to a solution of tert-butyl ester (1 eq.) in DCM (to make a final concentration 30-50% v/v TFA). The mixture was stirred at RT for 1-16 h, before being concentrated and co-evaporated with toluene (×2). The crude product was purified by chromatography on silica gel or by preparative HPLC to afford the required compound.

General Procedure B

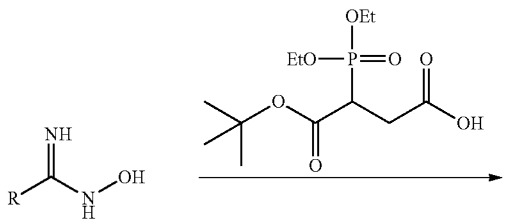

-continued

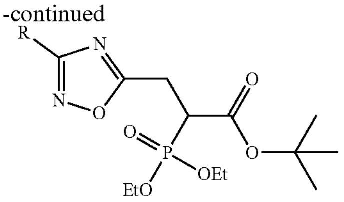

Method A

HATU (1.2-1.5 eq.) and amidoxime (1-1.5 eq.) were added to a solution of 4-(tert-butoxy)-3-(diethoxyphosphoryl)-4-oxobutanoic acid (1 eq.) and DIPEA (5 eq.) in dimethylformamide (0.2 M). The mixture was stirred at RT for 1 h, then heated to 90° C. for 2 h. The mixture was cooled to RT, diluted with water and extracted with EtOAc (3×). The combined organic phases were washed with 1 M HCl (200 mL), brine (200 mL), dried ($MgSO_4$) and concentrated. The crude product was purified by chromatography on silica gel to afford the required compound.

Method B

Triethylamine (2.0-4.0 eq.) was added to a suspension of amidoxime (1.0-1.3 eq.) and 4-(tert-butoxy)-3-(diethoxyphosphoryl)-4-oxobutanoic acid (1 eq.) in EtOAc or dimethylformamide (0.4-0.8 M) at RT. A solution of T3P (50 wt % in EtOAc or dimethylformamide, 2.0-2.5 eq.) was added dropwise at 0° C. or at RT over 20 min. The mixture was heated to 80° C. and stirred 17 h. The mixture was cooled to RT, diluted with brine and 1M HCl and extracted with EtOAc (3×). The combined organic phases were washed with 1M HCl (aq) (3×), dried ($MgSO_4$) and concentrated. The crude product was purified by chromatography on silica gel to afford the required compound.

Method C

Triethylamine (2-3 eq.) was added to a suspension of amidoxime (1 eq.) and 4-(tert-butoxy)-3-(diethoxyphosphoryl)-4-oxobutanoic acid (1 eq.) in EtOAc or dimethylformamide (0.4 M) at RT. A solution of T3P (50 wt % in EtOAc or dimethylformamide, 2.0-2.5 eq.) was added dropwise at RT. The mixture was stirred at RT for 1 h, diluted with water and extracted with EtOAc (3×). The combined organic phases were dried ($MgSO_4$) and concentrated. The residue was taken up in THF (0.2 M) and cesium carbonate (2 eq) was added. The mixture was heated to 70° C. and stirred for 1-5 h, cooled to RT, diluted with water and extracted with EtOAc (3×). The combined organic phases were dried ($MgSO_4$) and concentrated. The crude product was purified by chromatography on silica gel to afford the required compound.

Intermediate 1—5-(chloromethyl)-3-octyl-1,2,4-oxadiazole

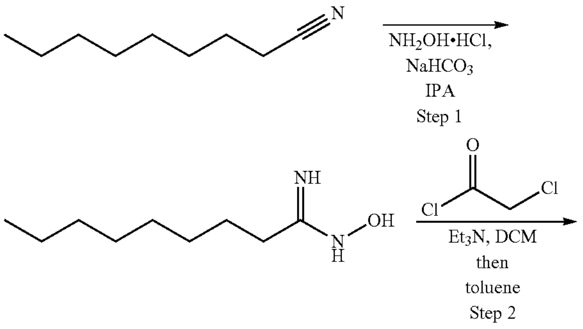

-continued

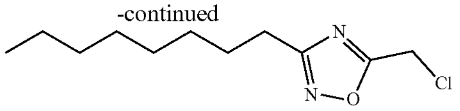

Step 1

Sodium bicarbonate (11.8 g, 141 mmol) was added to a suspension of hydroxylamine hydrochloride (5.88 g, 85 mmol) in isopropanol (100 mL). The mixture was stirred at RT for 10 min then nonanenitrile (10 mL, 57 mmol) was added and the mixture was heated to reflux for 12 h, before being cooled to RT. The mixture was filtered and concentrated in vacuo to afford N-hydroxynonanimidamide (9.74 g, 52.0 mmol, 92% purity) as a white solid. $^1$H NMR (400 MHz, DMSO-d6) δ 8.67 (s, 1H), 5.31 (s, 2H), 2.03-1.87 (m, 2H), 1.58-1.43 (m, 2H), 1.39-1.17 (m, 10H), 0.90-0.83 (m, 3H). (major tautomer assigned) LCMS m/z 173.2 $(M+H)^+$ $(ES^+)$.

Step 2

Chloroacetyl chloride (3.8 mL, 48 mmol) was added dropwise to a solution of N-hydroxynonanimidamide (7.5 g, 44 mmol) and triethylamine (6.9 mL, 50 mmol) in DCM (100 mL) at 0° C. for 10 min. The mixture was allowed to warm to RT and stirred for 2 h, then diluted with EtOAc (100 mL) and washed with water (150 mL). The organic phase was washed with brine (150 mL), dried ($MgSO_4$) and concentrated. The residue was taken up in toluene (100 mL) and heated to 120° C. for 3 h, then cooled to RT and stirred for 15 h. The reaction mixture was concentrated. The crude product was purified by chromatography on silica gel (0-100% EtOAc/isohexane) to afford the title compound (6.79 g, 44 mmol) as a pale yellow oil. $^1$H NMR (400 MHz, DMSO-d6) δ 5.07 (s, 2H), 2.72 (t, J=7.4 Hz, 2H), 1.73-1.50 (m, 2H), 1.41-1.21 (m, 10H), 0.90-0.82 (m, 3H). LCMS m/z 231.0/233.0 $(M+H)^+$ $(ES^+)$.

Intermediate
2-2-(chloromethyl)-5-octyl-1,3,4-oxadiazole

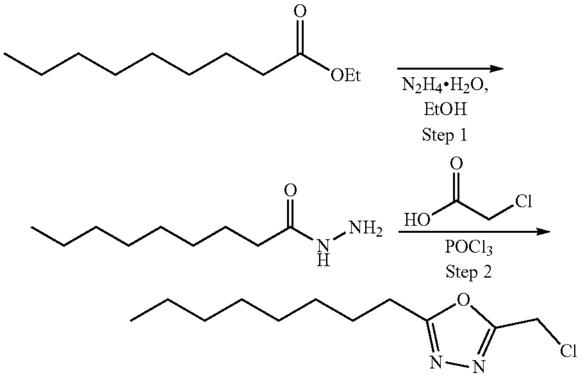

Step 1

A mixture of ethyl nonanoate (10 mL, 46 mmol) and hydrazine hydrate (50%, 5.8 mL, 92 mmol) in ethanol (50 mL) was heated to reflux overnight. The mixture was cooled to RT and concentrated. The residue was co-evaporated with toluene (20 mL), then suspended in MTBE (50 mL). The solid was isolated by filtration, washing with MTBE (2×20 mL) to afford nonanehydrazide (4.9 g, 28 mmol) as a colourless solid. $^1$H NMR (400 MHz, DMSO-d6) δ 8.89 (s, 1H), 4.09 (br. s, 2H), 1.99 (t, J=7.4 Hz, 2H), 1.63-1.41 (m, 2H), 1.24 (s, 10H), 0.94-0.75 (m, 3H). LCMS m/z 173.6 $(M+H)^+$ $(ES^+)$.

Step 2

A suspension of nonanehydrazide (1.00 g, 5.8 mmol), 2-chloroacetic acid (0.55 g, 5.8 mmol) and phosphorus oxychloride (4 mL, 43 mmol) was heated to 80° C. for 2 h. The mixture was cooled to RT and concentrated. The residue was-evaporated with toluene (2×15 mL) then taken up in warm water (45° C.) and extracted with EtOAc (3×15 mL). The combined organic extracts were washed with brine (20 mL), dried ($Na_2SO_4$) and concentrated. The crude product was purified by chromatography on silica gel (0-100% EtOAc/isohexane) to afford the title compound (0.861 g, 3.54 mmol) as a light pink oil. $^1H$ NMR (400 MHz, DMSO-d6) δ 5.02 (s, 2H), 2.88 (t, J=7.4 Hz, 2H), 1.75-1.61 (m, 2H), 1.34-1.22 (m, 10H), 0.90-0.82 (m, 3H). LCMS m/z 231.0/233.0 $(M+H)^+$ $(ES^+)$.

Intermediate 3-3-(chloromethyl)-5-octyl-1,2,4-oxadiazole

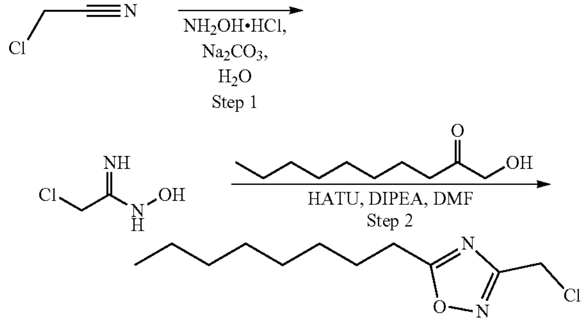

Step 1

Sodium carbonate (7.02 g, 66.2 mmol was added to a mixture of 2-chloroacetonitrile (8.4 mL, 132 mmol) and hydroxylamine hydrochloride (9.20 g, 132 mmol) in water (30 mL) portionwise so the internal temperature did not rise above 30° C. The reaction mixture was stirred at 30° C. for 15 min, then extracted with EtOAc (3×20 mL). The combined organic extracts were dried ($Na_2SO_4$) and concentrated to afford 2-chloro-N-hydroxyacetimidamide (8.0 g, 67 mmol) as an orange solid. $^1H$ NMR (400 MHz, DMSO-d6) δ 9.43 (s, 1H), 5.62 (s, 2H), 4.01 (s, 2H).

Step 2

HATU (17.5 g, 46.1 mmol) was added to a solution of 2-chloro-N-hydroxyacetimidamide (5.0 g, 46 mmol), nonanoic acid (8.0 mL, 46 mmol) and DIPEA (16 mL, 92 mmol) in dimethylformamide (50 mL) at 0° C. The reaction was warmed to RT and stirred for 5 h, before being poured into water (250 mL) and extracted with EtOAc (3×30 mL). The combined organic extracts were washed with brine (2×40 mL), dried ($Na_2SO_4$) and concentrated. The residue was re-dissolved in dimethylformamide (50 mL) and heated to 120° C. with stirring for 16 h. The mixture was cooled to RT and poured into water (250 mL), before being extracted with EtOAc (3×50 mL). The combined organic extracts were washed with brine (2×100 mL), dried ($Na_2SO_4$) and concentrated. The crude product was purified by chromatography on silica gel (0-10% EtOAc/isohexane) to afford the title compound (3.18 g, 11.0 mmol, 80% purity) as a colourless oil. $^1H$ NMR (400 MHz, DMSO-d6) δ 4.85 (s, 2H), 2.95 (t, J=7.5 Hz, 2H), 1.78-1.68 (m, 2H), 1.35-1.21 (m, 10H), 0.88-0.84 (m, 3H). LCMS m/z 231.0/233.0 $(M+H)^+$ $(ES^+)$.

The following compounds were synthesised using the same procedure as used to synthesise Intermediate 1.

| Int. Number | Structure/Name | Characterising data |
|---|---|---|
| 4 | 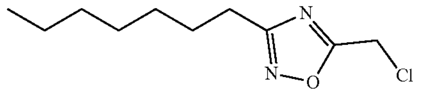 5-(chloromethyl)-3-heptyl-1,2,4-oxadiazole | LCMS m/z 217.1/219.2 $(M + H)^+$ $(ES^+)$. $^1H$ NMR (400 MHz, DMSO-d6) δ 5.07 (s, 2H), 2.72 (t, J = 7.4 Hz, 2H), 1.66 (ddd, J = 14.4, 7.9, 4.9 Hz, 2H), 1.36-1.22 (m, 8H), 0.91-0.81 (m, 3H). |
| 5 | 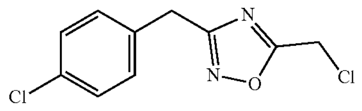 [SMILES: ClCc1nc(Cc2ccc(Cl)cc2)no1] 3-(4-chlorobenzyl)-5-(chloromethyl)-1,2,4-oxadiazole | $^1H$ NMR (400 MHz, DMSO-d6) δ 7.44-7.38 (m, 2H), 7.38-7.32 (m, 2H), 5.07 (s, 2H), 4.15 (s, 2H). |
| 6 | 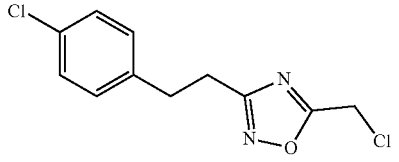 [SMILES: ClCc1nc(CCc2ccc(Cl)cc2)no1] 5-(chloromethyl)-3-(4-chlorophenethyl)-1,2,4-oxadiazole | LCMS m/z 257.4/259.4 $(M + H)^+$ $(ES^+)$. $^1H$ NMR (400 MHz, DMSO-d6) δ 7.36-7.31 (m, 2H), 7.30-7.24 (m, 2H), 5.08 (s, 2H), 3.10-2.97 (m, 4H). |

-continued

| Int. Number | Structure/Name | Characterising data |
|---|---|---|
| 7 | 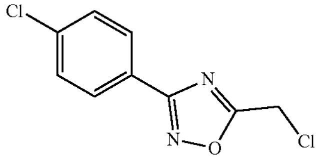 [SMILES: ClCc1nc(-c2ccc(Cl)cc2)no1] 5-(chloromethyl)-3-(4-chlorophenyl)-1,2,4-oxadiazole | $^{1}$H NMR (400 MHz, $CDCl_3$) δ 8.08-7.95 (m, 2H), 7.54-7.41 (m, 2H), 4.75 (s, 2H). |
| 8 | 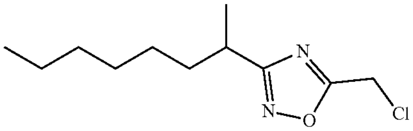 5-(chloromethyl)-3-(octan-2-yl)-1,2,4-oxadiazole | LCMS m/z 231.1/233.2 $(M + H)^+$ $(ES^+)$. $^{1}$H NMR (400 MHz, DMSO-d6) δ 5.08 (s, 2H), 3.03-2.90 (m, 1H), 1.73-1.49 (m, 2H), 1.31-1.09 (m, 11H), 0.91-0.78 (m, 3H). |
| 9 | 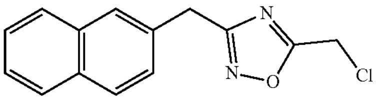 [SMILES: ClCc1nc(Cc2ccc3ccccc3c2)no1] 5-(chloromethyl)-3-(naphthalen-2-ylmethyl)-1,2,4-oxadiazole | LCMS m/z 259.0 $(M + H)^+$ $(ES^+)$. $^{1}$H NMR (400 MHz, DMSO-d6) δ 7.92-7.86 (m, 3H), 7.86-7.83 (m, 1H), 7.53-7.49 (m, 2H), 7.46 (dd, J = 8.5, 1.8 Hz, 1H), 5.07 (s, 2H), 4.31 (s, 2H). |
| 10 | 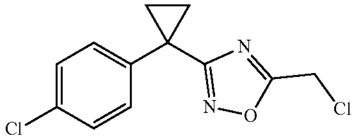 [SMILES: ClCc1nc(C2(c3ccc(Cl)cc3)CC2)no1] 5-(chloromethyl)-3-(1-(4-chlorophenyl)cyclopropyl)-1,2,4-oxadiazole | $^{1}$H NMR (400 MHz, DMSO-d6) δ 7.48-7.39 (m, 4H), 5.04 (s, 2H), 1.55-1.50 (m, 2H), 1.46-1.39 (m, 2H). |
| 11 | 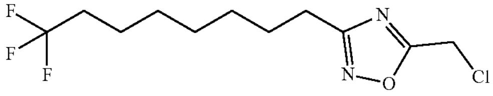 [SMILES: FC(F)(F)CCCCCCCc1noc(CCl)n1] 5-(chloromethyl)-3-(8,8,8-trifluorooctyl)-1,2,4-oxadiazole | $^{1}$H NMR (400 MHz, DMSO-d6) δ 5.07 (s, 2H), 2.73 (t, J = 7.4 Hz, 2H), 2.31-2.14 (m, 2H), 1.73-1.62 (m, 2H), 1.52-1.42 (m, 2H), 1.38-1.27 (m, 6H). |
| 13 | 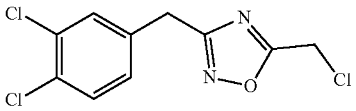 [SMILES: ClCc1nc(Cc2ccc(Cl)c(Cl)c2)no1] 5-(chloromethyl)-3-(3,4-dichlorobenzyl)-1,2,4-oxadiazole | $^{1}$H NMR (400 MHz, DMSO-d6) δ 7.70-7.54 (m, 2H), 7.33 (dd, J = 8.3, 2.1 Hz, 1H), 5.07 (s, 2H), 4.19 (s, 2H). |
| 14 | 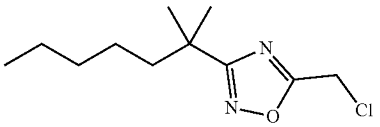 5-(chloromethyl)-3-(2-methylheptan-2-yl)-1,2,4-oxadiazole | LCMS m/z 231.2/233.2 $(M + H)^+$ $(ES^+)$. $^{1}$H NMR (400 MHz, DMSO-d6) δ 5.08 (s, 2H), 1.64-1.58 (m, 2H), 1.52-1.46 (m, 1H), 1.39 (dddd, J = 17.2, 11.2, 8.7, 5.0 Hz, 1H), 1.29 (s, 6H), 1.27-1.15 (m, 2H), 1.14-1.04 (m, 2H), 0.82 (t, J = 7.0 Hz, 3H). |
| 15 | 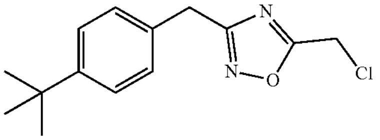 [SMILES: CC(C)(C)c1ccc(Cc2noc(CCl)n2)cc1] 3-(4-(tert-butyl)benzyl)-5-(chloromethyl)-1,2,4-oxadiazole | LCMS m/z 265.1/267.1 $(M + H)^+$ $(ES^+)$. $^{1}$H NMR (400 MHz, DMSO-d6) δ 7.38-7.32 (m, 2H), 7.25-7.19 (m, 2H), 5.06 (s, 2H), 4.07 (s, 2H), 1.26 (s, 9H). |

-continued

| Int. Number | Structure/Name | Characterising data |
|---|---|---|
| 16 | 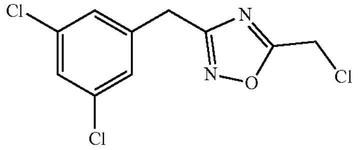 [SMILES: ClCc1nc(Cc2cc(Cl)cc(Cl)c2)no1] 5-(chloromethyl)-3-(3,5-dichlorobenzyl)-1,2,4-oxadiazole | LCMS m/z 278.5 $(M + H)^+$ $(ES^+)$. |
| 17 | 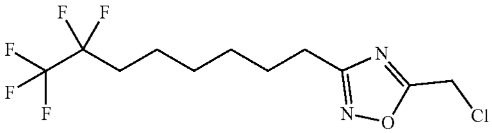 [SMILES: FC(F)(F)C(F)(F)CCCCCCc1noc(CCl)n1] 5-(chloromethyl)-3-(7,7,8,8,8-pentafluorooctyl)-1,2,4-oxadiazole | LCMS m/z 343.9 $(M + Na)^+$ $(ES^+)$. $^1H$ NMR (400 MHz, DMSO-d6) δ 5.07 (s, 2H), 2.73 (t, J = 7.4 Hz, 2H), 2.27-2.10 (m, 2H), 1.68 (p, J = 7.4 Hz, 2H), 1.58-1.28 (m, 6H). |
| 18 | 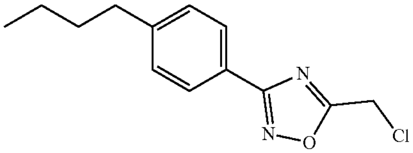 [SMILES: CCCCc1ccc(-c2noc(CCl)n2)cc1] 3-(4-butylphenyl)-5-(chloromethyl)-1,2,4-oxadiazole | LCMS m/z 251.1 $(M + H)^+$ $(ES^+)$. |
| 19 | 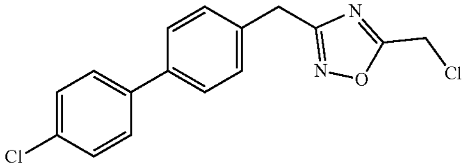 [SMILES: ClCc1nc(Cc2ccc(-c3ccc(Cl)cc3)cc2)no1] 3-((4'-chloro-[1,1'-biphenyl]-4-yl)methyl)-5-(chloromethyl)-1,2,4-oxadiazole | LCMS m/z 342.6 $(M + Na)^+$ $(ES^+)$. $^1H$ NMR (400 MHz, DMSO-d6) δ 7.73-7.60 (m, 4H), 7.55-7.48 (m, 2H), 7.45-7.38 (m, 2H), 5.08 (s, 2H), 4.18 (s, 2H). |
| 20 | 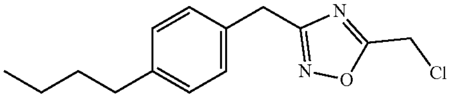 [SMILES: CCCCc1ccc(Cc2noc(CCl)n2)cc1] 3-(4-butylbenzyl)-5-(chloromethyl)-1,2,4-oxadiazole | $^1H$ NMR (400 MHz, DMSO-d6) δ 7.20 (d, J = 8.1 Hz, 2H), 7.15 (d, J = 8.1 Hz, 2H), 5.06 (s, 2H), 4.07 (s, 2H), 2.57-2.52 (m, 2H), 1.60-1.44 (m, 2H), 1.38-1.21 (m, 2H), 0.89 (t, J = 7.3 Hz, 3H). |
| 21 | 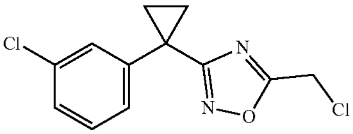 [SMILES: ClCc1nc(C2(c3cccc(Cl)c3)CC2)no1] 5-(chloromethyl)-3-(1-(3-chlorophenyl)cyclopropyl)-1,2,4-oxadiazole | LCMS m/z 269.0/271.0 $(M + H)^+$ $(ES^+)$. $^1H$ NMR (400 MHz, DMSO-d6) δ 7.50-7.46 (m, 1H), 7.40-7.37 (m, 3H), 5.05 (s, 2H), 1.55-1.51 (m, 2H), 1.50-1.45 (m, 2H) |
| 82 | 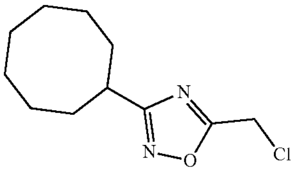 [SMILES: ClCc1nc(C2CCCCCCC2)no1] 5-(chloromethyl)-3-cyclooctyl-1,2,4-oxadiazole | LCMS m/z 229.1 $(M + H)^+$ $(ES^+)$. $^1H$ NMR (400 MHz, DMSO-d6) δ 5.07 (s, 2H), 3.11-3.00 (m, 1H), 1.99-1.44 (m, 14H) |

-continued

| Int. Number | Structure/Name | Characterising data |
|---|---|---|
| 83 | 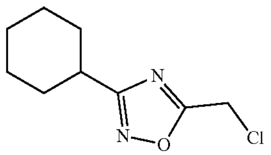 [SMILES: ClCc1nc(C2CCCCC2)no1] 5-(chloromethyl)-3-cyclohexyl-1,2,4-oxadiazole | LCMS m/z 201.1 $(M + H)^+$ $(ES^+)$. $^1H$ NMR (400 MHz, DMSO-d6) δ 5.07 (s, 2H), 2.91-2.77 (m, 1H), 1.98-1.88 (m, 4H), 1.84-1.19 (m, 6H) |
| 84 | 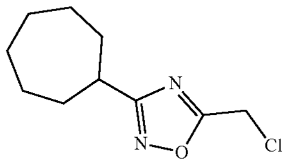 [SMILES: ClCc1nc(C2CCCCCC2)no1] 5-(chloromethyl)-3-cycloheptyl-1,2,4-oxadiazole | LCMS m/z 215.2/217.2 $(M + H)^+$ $(ES^+)$. $^1H$ NMR (400 MHz, DMSO-d6) δ 5.06 (s, 2H), 3.08-2.97 (m, 1H), 2.04-1.91 (m, 2H), 1.90-1.45 (m, 10H) |
| 85 | 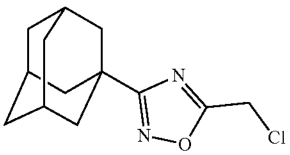 [SMILES: ClCc1nc(C23CC4CC(CC(C4)C2)C3)no1] 3-(adamantan-1-yl)-5-(chloromethyl)-1,2,4-oxadiazole | LCMS m/z 253.1 $(M + H)^+$ $(ES^+)$. $^1H$ NMR (400 MHz, DMSO-d6) δ 5.07 (s, 2H), 2.09-2.01 (m, 3H), 2.01-1.91 (m, 6H), 1.82-1.62 (m, 6H) |

Intermediate 12—9,9,9-trifluorononanenitrile

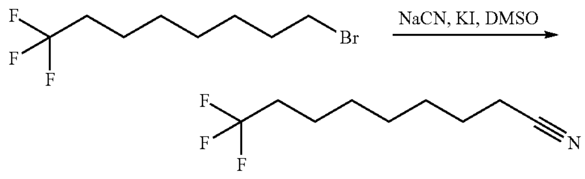

8-bromo-1,1,1-trifluorooctane (5.00 g, 20.2 mmol) was added dropwise to a suspension of sodium cyanide (1.09 g, 22.3 mmol) and potassium iodide (40.0 mg, 0.24 mmol) in DMSO (11 mL) at 40° C. The mixture was stirred at 80° C. for 1 hour and then at 120° C. for 5 hour. The reaction was cooled to RT and poured into water (30 mL). The solution was extracted with MTBE (3x15 mL). The combined organic layers were washed with brine (20 mL), dried ($Na_2SO_4$) and concentrated to afford 9,9,9-trifluorononanenitrile (3.91 g, 20 mmol) as a light yellow oil. $^1H$ NMR (400 MHz, DMSO-d6) δ 2.50-2.46 (m, 2H), 2.31-2.16 (m, 2H), 1.60-1.42 (m, 4H), 1.41-1.26 (m, 6H). $^{19}F$ NMR (376 MHz, DMSO-d6) δ -64.79.

Intermediate 12 was converted to Intermediate 11 using analogous methods as described above.

Intermediate 22—3-(chloromethyl)-1-octyl-1H-1,2,4-triazole

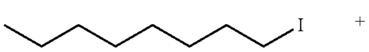

-continued

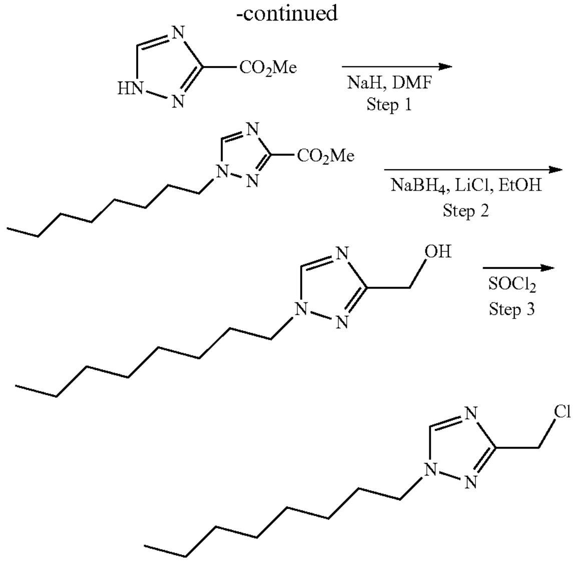

Step 1

Sodium hydride (60 wt % dispersion in mineral oil, 2.05 g, 51.1 mmol) was added portionwise to a solution of methyl 1H-1,2,4-triazole-3-carboxylate (5.00 g, 39.3 mmol) in dimethylformamide (25 mL) at 0° C. The mixture was stirred for 30 min before 1-iodooctane (9.92 g, 7.46 mL, 41.3 mmol) was added dropwise over 10 minutes at 0° C. The reaction was warmed to RT and stirred for 16 h. The reaction mixture was poured into water (100 mL) and extracted with EtOAc (3x30 mL). The combined organic layers were washed with water (50 mL), brine (50 mL), dried ($Na_2SO_4$) and concentrated. The crude product was purified by chromatography on silica gel (0-100% EtOAc/isohexane) to afford methyl 1-octyl-1H-1,2,4-triazole-3-carboxylate (3.83 g, 16 mmol) as a white solid. LCMS m/z 240.2 $(M+H)^+$ $(ES^+)$. $^1H$ NMR (400 MHz, DMSO-d6) δ 8.70 (s, 1H), 4.24 (t, J=7.0 Hz, 2H), 3.84 (s, 3H), 1.87-1.73 (m, 2H), 1.35-1.13 (m, 10H), 0.91-0.80 (m, 3H).

Step 2

Sodium borohydride (3.03 g, 80.0 mmol) was added to a suspension of methyl 1-octyl-1H-1,2,4-triazole-3-carboxylate (3.83 g, 16.0 mmol) and lithium chloride (3.39 g, 80.0 mmol) in ethanol (60 mL) and THF (60 mL) at RT. The mixture was stirred for 18 h, then quenched with sat. aq. $NH_4Cl$ (50 mL). The mixture was stirred for 30 min, then the phases were separated and the aqueous phase extracted with ethyl acetate (3×25 mL). The combined organic layers were washed with brine (50 mL), dried ($Na_2SO_4$) and concentrated. The crude product was purified by chromatography on silica gel (0-10% MeOH/DCM) to afford (1-octyl-1H-1,2,4-triazol-3-yl)methanol (2.22 g, 10 mmol) as a white solid. LCMS m/z 212.2 $(M+H)^+$ $(ES^+)$. $^1H$ NMR (400 MHz, DMSO-d6) δ 8.39 (s, 1H), 5.18 (s, 1H), 4.40 (s, 2H), 4.10 (t, J=7.0 Hz, 2H), 1.80-1.68 (m, 2H), 1.33-1.16 (m, 10H), 0.92-0.78 (m, 3H).

Step 3

Thionyl chloride (20 mL, 273 mmol) was cautiously added to (1-octyl-1H-1,2,4-triazol-3-yl)methanol (2.22 g, 10 mmol). The resulting solution was heated to 80° C. for 1.5 h. The mixture was concentrated and the residue was dissolved in DCM (50 mL) and washed with sat. $NaHCO_3$ (2×25 mL), water (25 mL) and brine (25 mL). The organic layer was then dried ($Na_2SO_4$) and concentrated to afford 3-(chloromethyl)-1-octyl-1H-1,2,4-triazole (2.40 g, 10 mmol) that was used without purification. LCMS m/z 230.2 $(M+H)^+$ $(ES^+)$. $^1H$ NMR (400 MHz, DMSO-d6) δ 8.51 (s, 1H), 4.70 (s, 2H), 4.14 (t, J=7.0 Hz, 2H), 1.80-1.71 (m, 2H), 1.29-1.19 (m, 10H), 0.89-0.81 (m, 3H).

Intermediate 23-8,8-difluoro-N-hydroxynonanimidamide

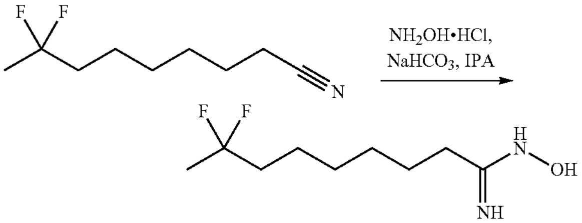

A suspension of hydroxylamine hydrochloride (1.19 g, 17.1 mmol) and sodium bicarbonate (2.40 g, 28.5 mmol) in IPA (14 mL) was stirred at RT for 15 min. 8,8-Difluorononanenitrile (2.00 g, 11.4 mmol) was added and the mixture was heated to 85° C. and stirred for 16 h. The reaction was cooled to RT and filtered. The filtrate was concentrated and co-evaporated with toluene (2×10 mL). The resulting white solid was triturated with iso-hexane (20 mL) and filtered to afford 8,8-difluoro-N-hydroxynonanimidamide (2.08 g, 9.9 mmol) as a white solid. LCMS m/z 209.2 $(M+H)^+$ $(ES^+)$. $^1H$ NMR (400 MHz, DMSO-d6) δ 8.69 (s, 1H), 5.34 (s, 2H), 1.94 (t, J=7.6 Hz, 2H), 1.90-1.76 (m, 2H), 1.58 (t, J=18.9 Hz, 3H), 1.52-1.43 (m, 2H), 1.42-1.34 (m, 2H), 1.32-1.23 (m, 4H).

The following compounds were synthesised using the same procedure.

| Int. Number | Structure/Name | Characterising data |
|---|---|---|
| 24 | 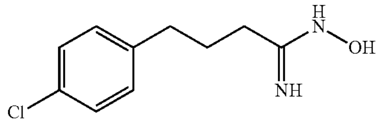 [SMILES: N=C(CCCc1ccc(Cl)cc1)NO] 4-(4-chlorophenyl)-N-hydroxybutanimidamide | LCMS m/z 213.0/215.0 $(M + H)^+$ $(ES^+)$ |
| 25 | 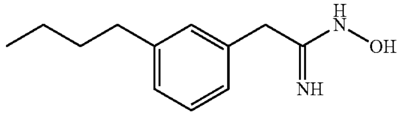 2-(3-butylphenyl)-N-hydroxyacetimidamide | LCMS m/z 207.1 $(M + H)^+$ $(ES^+)$. $^1H$ NMR (400 MHz, DMSO-d6) δ 8.86 (s, 1H), 7.21-7.14 (m, 1H), 7.11-7.05 (m, 2H), 7.04-7.00 (m, 1H), 5.35 (s, 2H), 3.22 (s, 2H), 2.57-2.52 (m, 2H), 1.54 (p, J = 7.4 Hz, 2H), 1.31 (h, J = 7.3 Hz, 2H), 0.90 (t, J = 7.3 Hz, 3H) |
| 26 | 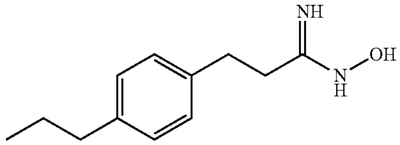 N-hydroxy-3-(4-propylphenyl)propanimidamide | LCMS m/z 207.1 $(M + H)^+$ $(ES^+)$. $^1H$ NMR (400 MHz, DMSO-d6) δ 8.73 (s, 1H), 7.25-7.03 (m, 4H), 5.40 (s, 2H), 2.85-2.71 (m, 2H), 2.55-2.47 (m, 2H), 2.28-2.16 (m, 2H), 1.61-1.51 (m, 2H), 0.88 (t, J = 7.3 Hz, 3H) |
| 27 | 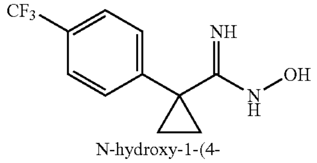 N-hydroxy-1-(4-(trifluoromethyl)phenyl)cyclopropane-1-carboximidamide | LCMS m/z 245.5 $(M + H)^+$ $(ES^+)$. $^1H$ NMR (400 MHz, DMSO-d6) δ 9.14 (s, 1H), 7.63 (d, J = 8.2 Hz, 2H), 7.48-7.43 (m, 2H), 5.44 (s, 2H), 1.32-1.24 (m, 2H), 1.07-0.99 (m, 2H) |

-continued

| Int. Number | Structure/Name | Characterising data |
|---|---|---|
| 28 | 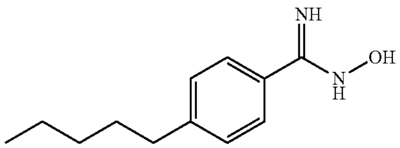 N-hydroxy-4-pentylbenzimidamide | LCMS m/z 207.2 $(M + H)^+$ $(ES^+)$. $^1H$ NMR (400 MHz, DMSO-d6) δ 9.54 (s, 1H), 7.57 (d, J = 7.9 Hz, 2H), 7.17 (d, J = 8.0 Hz, 2H), 5.74 (s, 2H), 2.57 (t, J = 7.6 Hz, 2H), 1.62-1.51 (m, 2H), 1.38-1.20 (m, 4H), 0.86 (t, J = 6.8 Hz, 3H) |
| 29 | 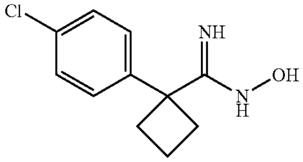 [SMILES: N=C(NO)C1(c2ccc(Cl)cc2)CCC1] 1-(4-chlorophenyl)-N-hydroxycyclobutane-1-carboximidamide | LCMS m/z 225.1 $(M + H)^+$ $(ES^+)$. $^1H$ NMR (400 MHz, DMSO-d6) δ 9.11 (s, 1H), 7.42-7.30 (m, 4H), 5.14 (s, 2H), 2.79-2.60 (m, 2H), 2.31-2.20 (m, 2H), 1.96-1.69 (m, 2H) |
| 30 | 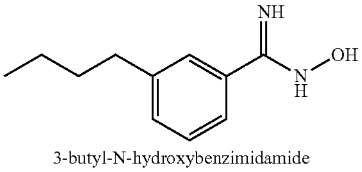 3-butyl-N-hydroxybenzimidamide | LCMS m/z 193.2 $(M + H)^+$ $(ES^+)$. $^1H$ NMR (400 MHz, DMSO-d6) δ 9.56 (s, 1H), 7.55-7.41 (m, 2H), 7.27 (t, J = 7.6 Hz, 1H), 7.23-7.15 (m, 1H), 5.76 (s, 2H), 2.59 (t, J = 7.7 Hz, 2H), 1.62-1.49 (m, 2H), 1.37-1.24 (m, 2H), 0.90 (t, J = 7.4 Hz, 3H) |
| 31 | 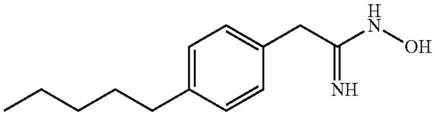 [SMILES: CCCCCc1ccc(CC(=N)NO)cc1] N-hydroxy-2-(4-pentylphenyl)acetimidamide | LCMS m/z 221.1 $(M + H)^+$ $(ES^+)$. $^1H$ NMR (400 MHz, DMSO-d6) δ 8.84 (s, 1H), 7.20-7.13 (m, 2H), 7.12-7.06 (m, 2H), 5.33 (s, 2H), 3.21 (s, 2H), 2.56-2.51 (m, 2H), 1.61-1.46 (m, 2H), 1.36-1.19 (m, 4H), 0.86 (t, J = 7.1 Hz, 3H) |
| 32 | 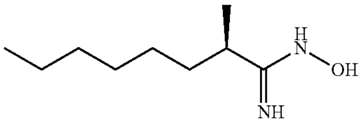 (R)-N-hydroxy-2-methyloctanimidamide | LCMS m/z 173.1 $(M + H)^+$ $(ES^+)$. $^1H$ NMR (400 MHz, DMSO-d6) δ 8.63 (s, 1H), 5.20 (s, 2H), 2.16-1.98 (m, 1H), 1.59-1.44 (m, 2H), 1.43-1.15 (m, 8H), 1.03 (t, J = 6.4 Hz, 3H), 0.86 (t, J = 6.5 Hz, 3H) |
| 33 | 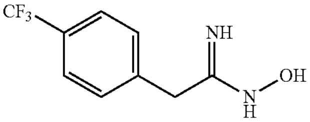 [SMILES: N=C(Cc1ccc(C(F)(F)F)cc1)NO] N-hydroxy-2-(4-(trifluoromethyl)phenyl) acetimidamide | LCMS m/z 219.1 $(M + H)^+$ $(ES^+)$. $^1H$ NMR (400 MHz, DMSO-d6) δ 8.95 (s, 1H), 7.66 (d, J = 8.0 Hz, 2H), 7.50 (d, J = 7.8 Hz, 2H), 5.48 (s, 2H), 3.37 (s, 2H) |
| 34 | 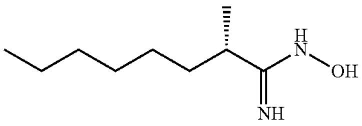 (S)-N-hydroxy-2-methyloctanimidamide | LCMS m/z 173.1 $(M + H)^+$ $(ES^+)$. $^1H$ NMR (400 MHz, DMSO-d6) δ 8.63 (s, 1H), 5.20 (s, 2H), 2.17-1.95 (m, 1H), 1.61-1.43 (m, 2H), 1.38-1.12 (m, 8H), 1.03 (t, J = 6.4 Hz, 3H), 0.96-0.74 (m, 3H) |
| 35 | 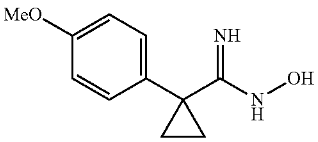 [SMILES: COc1ccc(C2(C(=N)NO)CC2)cc1] N-hydroxy-1-(4-methoxyphenyl)cyclopropane-1-carboximidamide | LCMS m/z 207.2 $(M + H)^+$ $(ES^+)$. $^1H$ NMR (400 MHz, DMSO-d6) δ 8.96 (s, 1H), 7.23 (d, J = 8.7 Hz, 2H), 6.84 (d, J = 8.7 Hz, 2H), 5.17 (s, 2H), 3.72 (s, 3H), 1.20-1.11 (m, 2H), 0.88-0.82 (m, 2H) |

-continued

| Int. Number | Structure/Name | Characterising data |
|---|---|---|
| 36 | 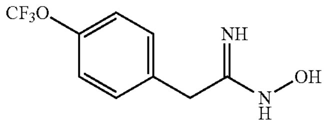 N-hydroxy-2-(4-(trifluoromethoxy)phenyl) acetimidamide | LCMS m/z 235.1 $(M + H)^+$ $(ES^+)$ |
| 37 | 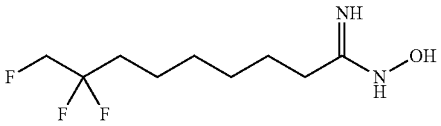 [SMILES: N=C(CCCCCCC(F)(F)CF)NO] 8,8,9-trifluoro-N-hydroxynonanimidamide | LCMS m/z 227.5 $(M + H)^+$ $(ES^+)$ |
| 38 | 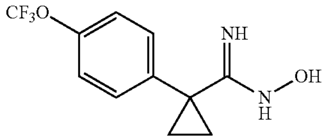 N-hydroxy-1-(4-(trifluoromethoxy)phenyl) cyclopropane-1-carboximidamide | LCMS m/z 261.1 $(M + H)^+$ $(ES^+)$ |
| 39 | 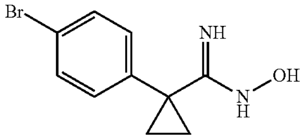 [SMILES: N=C(NO)C1(c2ccc(Br)cc2)CC1] 1-(4-bromophenyl)-N-hydroxycyclopropane-1-carboximidamide | LCMS m/z 255.1/257.1 $(M + H)^+$ $(ES^+)$. $^1H$ NMR (400 MHz, DMSO-d6) δ 9.05 (s, 1H), 7.49-7.43 (m, 2H), 7.26-7.19 (m, 2H), 5.32 (s, br. 2H), 1.27-1.16 (m, 2H), 0.99-0.86 (m, 2H) |
| 40 | 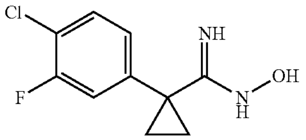 [SMILES: N=C(NO)C1(c2ccc(Cl)c(F)c2)CC1] 1-(4-chloro-3-fluorophenyl)-N-hydroxycyclopropane-1-carboximidamide | LCMS m/z 229.0 $(M + H)^+$ $(ES^+)$. $^1H$ NMR (400 MHz, DMSO-d6) δ 9.10 (s, 1H), 7.47 (t, J = 8.2 Hz, 1H), 7.25 (dd, J = 11.0, 2.1 Hz, 1H), 7.13 (dd, J = 8.4, 2.1 Hz, 1H), 5.40 (s, 2H), 1.23 (q, J = 4.5 Hz, 2H), 1.00 (q, J = 4.5 Hz, 2H) |
| 41 | 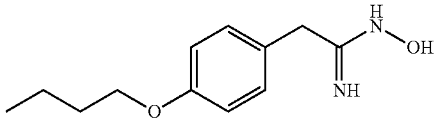 [SMILES: CCCCOc1ccc(CC(=N)NO)cc1] 2-(4-butoxyphenyl)-N-hydroxyacetimidamide | LCMS m/z 223.2 $(M + H)^+$ $(ES^+)$ |
| 42 | 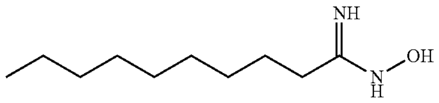 N-hydroxydecanimidamide | LCMS m/z 187.2 $(M + H)^+$ $(ES^+)$. $^1H$ NMR (400 MHz, DMSO-d6) δ 8.65 (s, 1H), 5.27 (s, 2H), 1.93 (t, J = 7.6 Hz, 2H), 1.46 (t, J = 7.4 Hz, 2H), 1.25 (s, 12H), 0.86 (t, J = 6.6 Hz, 3H) |
| 43 | 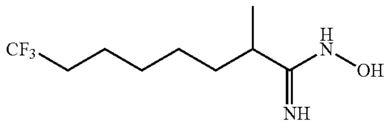 8,8,8-trifluoro-N-hydroxy-2-methyloctanimidamide | LCMS m/z 227.1 $(M + H)^+$ $(ES^+)$. |

-continued

| Int. Number | Structure/Name | Characterising data |
|---|---|---|
| 44 | 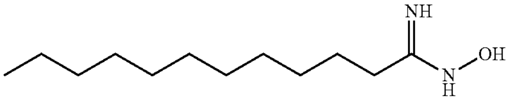 N-hydroxydodecanimidamide | LCMS m/z 215.3 $(M + H)^+$ $(ES^+)$ |
| 45 | 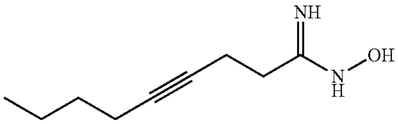 N-hydroxynon-4-ynimidamide | LCMS m/z 169.2 $(M + H)^+$ $(ES^+)$ |
| 46 | 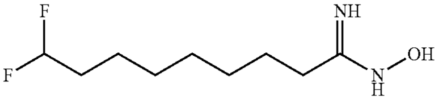 [SMILES: N=C(CCCCCCCC(F)F)NO] 9,9-difluoro-N-hydroxynonanimidamide | LCMS m/z 209.6 $(M + H)^+$ $(ES^+)$ |
| 47 | 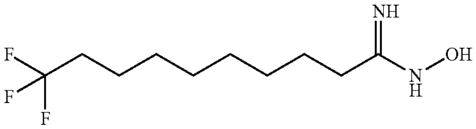 [SMILES: N=C(CCCCCCCCC(F)(F)F)NO] 10,10,10-trifluoro-N-hydroxydecanimidamide | LCMS m/z 241.1 $(M + H)^+$ $(ES^+)$ |
| 48 | 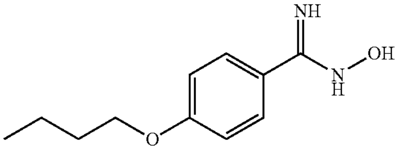 4-butoxy-N-hydroxybenzimidamide | LCMS m/z 209.1 $(M + H)^+$ $(ES^+)$. $^1H$ NMR (400 MHz, DMSO-d6) δ 9.58 (s, 1H), 7.64-7.55 (m, 2H), 6.96-6.90 (m, 2H), 5.99 (s, 2H), 3.99 (t, J = 6.5 Hz, 2H), 1.78-1.64 (m, 2H), 1.53-1.35 (m, 2H), 0.94 (t, J = 7.4 Hz, 3H) |
| 49 | 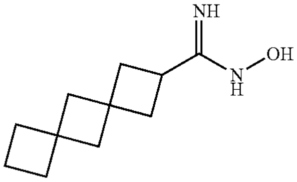 [SMILES: N=C(NO)C1CC2(C1)CC1(CCC1)C2] N-hydroxydispiro [3.1.$3^6$.$1^4$]decane-2-carboximidamide | LCMS m/z 195.2 $(M + H)^+$ $(ES^+)$. $^1H$ NMR (400 MHz, DMSO-d6) δ 8.77 (s, 1H), 5.18 (s, 2H), 2.77-2.67 (m, 1H), 2.13-2.05 (m, 2H), 2.04-1.96 (m, 4H), 1.92-1.85 (m, 6H), 1.80-1.72 (m, 2H) |
| 50 | 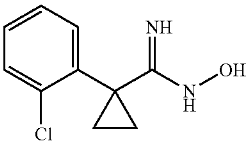 [SMILES: N=C(NO)C1(c2ccccc2Cl)CC1] 1-(2-chlorophenyl)-N-hydroxycyclopropane-1-carboximidamide | LCMS m/z 211.0 $(M + H)^+$ $(ES^+)$. $^1H$ NMR (400 MHz, DMSO-d6) δ 9.10 (s, 1H), 7.49-7.40 (m, 2H), 7.38-7.30 (m, 1H), 7.29-7.21 (m, 1H), 4.99 (s, 2H), 1.54-1.34 (m, 2H), 1.05-0.82 (m, 2H) |
| 51 | 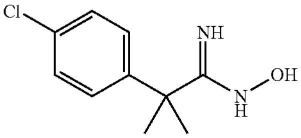 2-(4-chlorophenyl)-N-hydroxy-2-methylpropanimidamide | LCMS m/z 213.5 $(M + H)^+$ $(ES^+)$. $^1H$ NMR (400 MHz, DMSO-d6) δ 9.21 (s, 1H), 7.43-7.26 (m, 4H), 5.22 (s, 2H), 1.42 (d, J = 1.2 Hz, 6H). |

-continued

| Int. Number | Structure/Name | Characterising data |
|---|---|---|
| 52 | 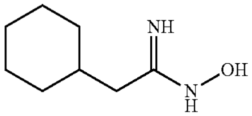 [SMILES: N=C(CC1CCCCC1)NO] 2-cyclohexyl-N-hydroxyacetimidamide | $^{1}$H NMR (400 MHz, DMSO-d6) δ 8.65 (s, 1H), 5.26 (s, 2H), 1.81 (d, J = 7.2 Hz, 2H), 1.72-1.53 (m, 6H), 1.27-1.07 (m, 3H), 0.92-0.78 (m, 2H) |
| 53 | 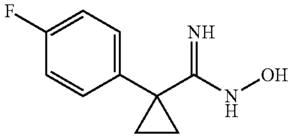 1-(4-fluorophenyl)-N-hydroxycyclopropane-1-carboximidamide | LCMS m/z 195.2 $(M + H)^+$ $(ES^+)$. $^{1}$H NMR (400 MHz, DMSO-d6) δ 9.02 (s, 1H), 7.37-7.28 (m, 2H), 7.13-7.04 (m, 2H), 5.28 (s, br. 2H), 1.25-1.11 (m, 2H), 0.99-0.83 (m, 2H) |
| 54 | 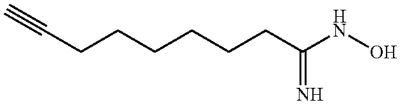 N-hydroxynon-8-ynimidamide | LCMS m/z 169.1 $(M + H)^+$ $(ES^+)$. $^{1}$H NMR (400 MHz, DMSO-d6) δ 8.66 (s, 1H), 5.28 (s, 2H), 2.73 (t, J = 2.7 Hz, 1H), 2.18-2.09 (m, 2H), 1.94 (t, J = 7.6 Hz, 2H), 1.50-1.39 (m, 3H), 1.39-1.30 (m, 3H), 1.30-1.19 (m, 2H) |
| 55 | 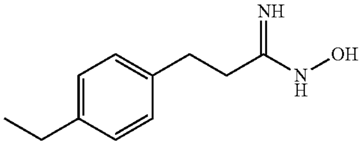 3-(4-ethylphenyl)-N-hydroxypropanimidamide | LCMS m/z 193.1 $(M + H)^+$ $(ES^+)$. $^{1}$H NMR (400 MHz, DMSO-d6) δ 8.72 (s, 1H), 7.15-7.08 (m, 4H), 5.40 (s, 2H), 2.78-2.71 (m, 2H), 2.56 (q, J = 7.6 Hz, 2H), 2.26-2.18 (m, 2H), 1.16 (t, J = 7.6 Hz, 3H) |
| 56 | 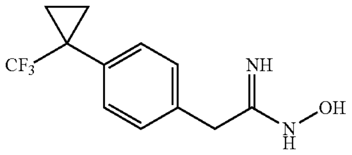 [SMILES: N=C(Cc1ccc(C2(C(F)(F)F)CC2)cc1)NO] N-hydroxy-2-(4-(1-(trifluoromethyl)cyclo-propyl)phenyl)acetimidamide | LCMS m/z 259.1 $(M + H)^+$ $(ES^+)$. $^{1}$H NMR (400 MHz, DMSO-d6) δ 8.88 (s, 1H), 7.41-7.34 (m, 2H), 7.32-7.24 (m, 2H), 5.40 (s, 2H), 3.26 (s, 2H), 1.37-1.27 (m, 2H), 1.13-1.04 (m, 2H) |
| 148 | 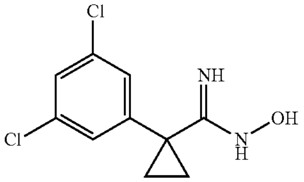 [SMILES: N=C(NO)C1(c2cc(Cl)cc(Cl)c2)CC1] 1-(3,5-dichlorophenyl)-N-hydroxycyclopropane-1-carboximidamide | LCMS m/z 245.1/247.1 $(M + H)^+$ $(ES^+)$. $^{1}$H NMR (400 MHz, DMSO-d6) δ 9.13 (s, 1H), 7.42 (t, J = 1.9 Hz, 1H), 7.27 (d, J = 1.9 Hz, 2H), 5.46 (s, 2H), 1.27-1.18 (m, 2H), 1.07-1.01 (m, 2H) |
| 149 | 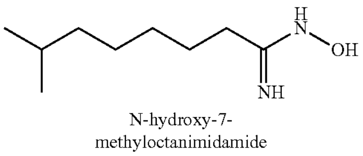 N-hydroxy-7-methyloctanimidamide | LCMS m/z 173.5 $(M + H)^+$ $(ES^+)$. $^{1}$H NMR (400 MHz, DMSO-d6) δ 8.75 (s, 1H), 5.44 (s, 2H), 2.50-2.46 (m, 1H), 1.98-1.92 (m, 2H), 1.59-1.43 (m, 3H), 1.25 (dq, J = 6.6, 4.6, 3.3 Hz, 3H), 1.19-1.11 (m, 2H), 0.87 (d, J = 2.7 Hz, 3H), 0.85 (d, J = 2.7 Hz, 3H) |
| 150 | 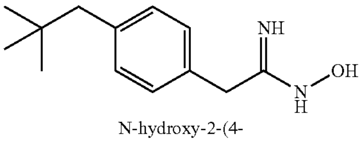 N-hydroxy-2-(4-neopentylphenyl)acetimidamide | LCMS m/z 221.2 $(M + H)^+$ $(ES^+)$. $^{1}$H NMR (400 MHz, DMSO-d6) δ 8.85 (s, 1H), 7.18 (d, J = 8.0 Hz, 2H), 7.06-7.01 (m, 2H), 5.35 (s, 2H), 3.22 (s, 2H), 2.43 (s, 2H), 0.86 (s, 9H) |

-continued

| Int. Number | Structure/Name | Characterising data |
| --- | --- | --- |
| 151 | 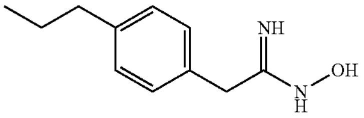 N-hydroxy-2-(4-propylphenyl)acetimidamide | LCMS m/z 193.1 $(M + H)^+$ $(ES^+)$. $^1H$ NMR (400 MHz, DMSO-d6) δ 8.86 (s, 1H), 7.18 (d, J = 8.0 Hz, 2H), 7.12-7.07 (m, 2H), 5.35 (s, 2H), 3.21 (s, 2H), 3.18 (d, J = 5.1 Hz, 2H), 1.62-1.50 (m, 2H), 0.88 (t, J = 7.3 Hz, 3H) |
| 86 | 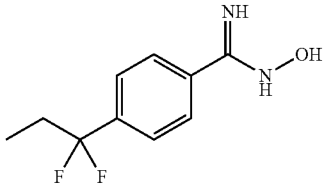 4-(1,1-difluoropropyl)-N-hydroxybenzimidamide | LCMS m/z 214.9 $(M + H)^+$ $(ES^+)$. $^1H$ NMR (400 MHz, DMSO-d6) δ 9.77 (s, 1H), 7.78 (d, J = 8.2 Hz, 2H), 7.51 (d, J = 8.2 Hz, 2H), 5.89 (s, 2H), 2.22 (tq, J = 16.7, 7.4 Hz, 2H), 0.91 (t, J = 7.4 Hz, 3H) |
| 87 | 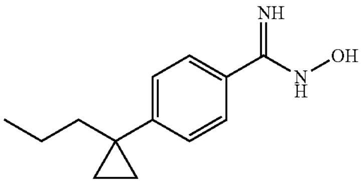 [SMILES: CCCC1(c2ccc(C(=N)NO)cc2)CC1] N-hydroxy-4-(1-propylcyclopropyl)benzimidamide | LCMS m/z 219.1 $(M + H)^+$ $(ES^+)$. $^1H$ NMR (400 MHz, DMSO-d6) δ 9.56 (s, 1H), 7.61-7.53 (m, 2H), 7.29-7.22 (m, 2H), 5.77 (s, 2H), 1.59-1.50 (m, 2H), 1.29-1.14 (m, 2H), 0.82 (t, J = 7.3 Hz, 3H), 0.78-0.72 (m, 2H), 0.72-0.65 (m, 2H) |
| 88 | 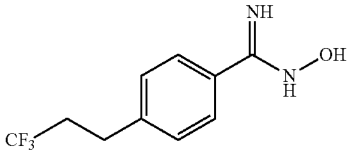 [SMILES: N=C(NO)c1ccc(CCC(F)(F)F)cc1] N-hydroxy-4-(3,3,3-trifluoropropyl)benzimidamide | LCMS m/z 233.0 $(M + H)^+$ $(ES^+)$. $^1H$ NMR (400 MHz, DMSO-d6) δ 9.57 (s, 1H), 7.67-7.57 (m, 2H), 7.34-7.26 (m, 2H), 5.77 (s, 2H), 2.90-2.76 (m, 2H), 2.71-2.54 (m, 2H) |
| 89 | 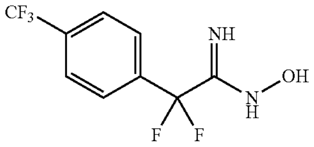 2-(4-chlorophenyl)-2,2-difluoro-N-hydroxyacetimidamide | LCMS m/z 221.2 $(M + H)^+$ $(ES^+)$. |
| 90 | 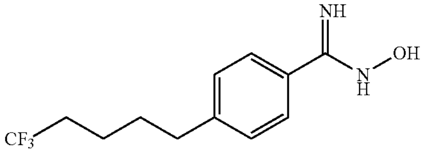 [SMILES: N=C(NO)c1ccc(CCCCC(F)(F)F)cc1] N-hydroxy-4-(5,5,5-trifluoropentyl)benzimidamide | LCMS m/z 261.2 $(M + H)^+$ $(ES^+)$. $^1H$ NMR (400 MHz, DMSO-d6) δ 9.56 (s, 1H), 7.59 (d, J = 8.0 Hz, 2H), 7.21 (d, J = 7.9 Hz, 2H), 5.78 (s, 2H), 2.62 (t, J = 7.5 Hz, 2H), 2.36-2.19 (m, 2H), 1.72-1.60 (m, 2H), 1.55-1.43 (m, 2H) |
| 91 | 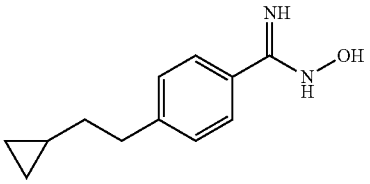 [SMILES: N=C(NO)c1ccc(CCC2CC2)cc1] 4-(2-cyclopropylethyl)-N-hydroxybenzimidamide | LCMS m/z 205.2 $(M + H)^+$ $(ES^+)$. $^1H$ NMR (400 MHz, DMSO-d6) δ 9.53 (s, 1H), 7.57 (d, J = 8.0 Hz, 2H), 7.20 (d, J = 7.8 Hz, 2H), 5.74 (s, 2H), 2.67 (dd, J = 8.8, 6.6 Hz, 2H), 1.47 (q, J = 7.1 Hz, 2H), 0.75-0.63 (m, 1H), 0.44-0.34 (m, 2H), 0.10--0.01 (m, 2H) |

-continued

| Int. Number | Structure/Name | Characterising data |
|---|---|---|
| 92 | 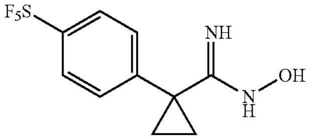 N-hydroxy-1-(4-(pentafluoro-$\lambda^6$-sulfaneyl)phenyl)cyclopropane-1-carboximidamide | LCMS m/z 303.1 $(M + H)^+$ $(ES^+)$. $^1H$ NMR (400 MHz, DMSO-d6) δ 9.13 (s, 1H), 7.86-7.75 (m, 2H), 7.45 (d, J = 8.5 Hz, 2H), 5.43 (s, 2H), 1.33-1.25 (m, 2H), 1.10-1.01 (m, 2H) |
| 93 | 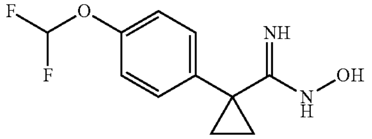 [SMILES: N=C(NO)C1(c2ccc(OC(F)F)cc2)CC1] 1-(4-(difluoromethoxy)phenyl)-N-hydroxycyclopropane-1-carboximidamide | LCMS m/z 243.1 $(M + H)^+$ $(ES^+)$. $^1H$ NMR (400 MHz, DMSO-d6) δ 9.02 (s, 1H), 7.41-7.26 (m, 2H), 7.22-6.94 (m, 3H), 5.28 (s, 2H), 1.29-1.09 (m, 2H), 0.99-0.81 (m, 2H) |
| 94 | 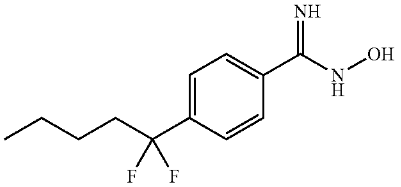 [SMILES: CCCCC(F)(F)c1ccc(C(=N)NO)cc1] 4-(1,1-difluoropentyl)-N-hydroxybenzimidamide | LCMS m/z 243.2 $(M + H)^+$ $(ES^+)$. $^1H$ NMR (400 MHz, DMSO-d6) δ 9.76 (s, 1H), 7.77 (d, J = 8.2 Hz, 2H), 7.51 (d, J = 8.3 Hz, 2H), 5.88 (s, 2H), 2.28-2.10 (m, 2H), 1.33-1.26 (m, 4H), 0.89-0.80 (m, 3H) |
| 95 | 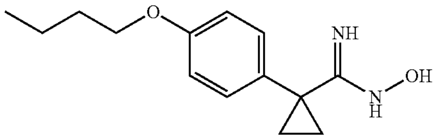 [SMILES: CCCCOc1ccc(C2(C(=N)NO)CC2)cc1] 1-(4-butoxyphenyl)-N-hydroxycyclopropane-1-carboximidamide | LCMS m/z 249.1 $(M + H)^+$ $(ES^+)$. $^1H$ NMR (400 MHz, DMSO-d6) δ 8.94 (s, 1H), 7.22-7.17 (m, 2H), 6.84-6.77 (m, 2H), 5.16 (s, 2H), 3.92 (t, J = 6.5 Hz, 2H), 1.70-1.64 (m, 2H), 1.45-1.38 (m, 2H), 1.15-1.11 (m, 2H), 0.95-0.91 (m, 3H), 0.86-0.82 (m, 2H) |
| 96 | 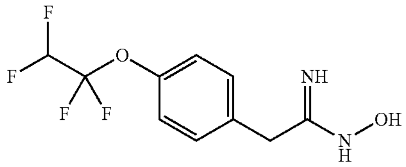 [SMILES: N=C(Cc1ccc(OC(F)(F)C(F)F)cc1)NO] N-hydroxy-2-(4-(1,1,2,2-tetrafluoroethoxy)phenyl) acetimidamide | $^1H$ NMR (400 MHz, $CDCl_3$) δ 7.38-7.27 (m, 2H), 7.25-7.11 (m, 2H), 6.09-5.74 (m, 1H), 4.50 (s, 2H), 3.48 (d, J = 9.3 Hz, 2H) |
| 97 | 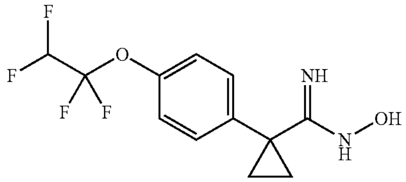 [SMILES: N=C(NO)C1(c2ccc(OC(F)(F)C(F)F)cc2)CC1] N-hydroxy-1-(4-(1,1,2,2-tetrafluoroethoxy)phenyl) cyclopropane-1-carboximidamide | $^1H$ NMR (400 MHz, $CDCl_3$) δ 7.49-7.29 (m, 2H), 7.24-7.14 (m, 2H), 6.07-5.75 (m, 1H), 4.82 (d, J = 49.2 Hz, 2H), 1.67-1.46 (m, 2H), 1.22-1.07 (m, 2H) |
| 98 | 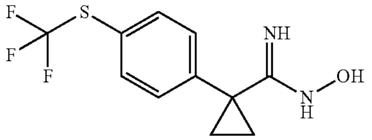 [SMILES: N=C(NO)C1(c2ccc(SC(F)(F)F)cc2)CC1] N-hydroxy-1-(4-((trifluoromethyl)thio)phenyl) cyclopropane-1-carboximidamide | LCMS m/z 277.0 $(M + H)^+$ $(ES^+)$. $^1H$ NMR (400 MHz, DMSO-d6) δ 9.09 (s, 1H), 7.68-7.59 (m, 2H), 7.51-7.37 (m, 2H), 5.42 (s, 2H), 1.38-1.24 (m, 2H), 1.10-0.98 (m, 2H) |

-continued

| Int. Number | Structure/Name | Characterising data |
|---|---|---|
| 99 | 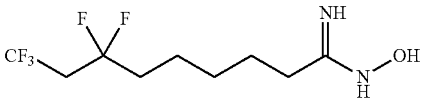 [SMILES: N=C(CCCCCC(F)(F)CC(F)(F)F)NO] 7,7,9,9,9-pentafluoro-N-hydroxynonanimidamide | LCMS m/z 277.0 $(M + H)^+$ $(ES^+)$. $^1$H NMR (400 MHz, DMSO-d6) δ 8.66 (s, 1H), 5.29 (s, 2H), 2.05-1.84 (m, 4H), 1.63-1.36 (m, 6H), 1.35-1.24 (m, 2H) |
| 100 | 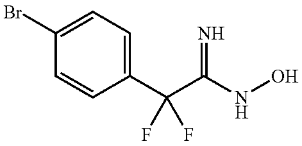 [SMILES: N=C(NO)C(F)(F)c1ccc(Br)cc1] 2-(4-bromophenyl)-2,2-difluoro-N-hydroxyacetimidamide | LCMS m/z 265.0/267.0 $(M + H)^+$ $(ES^+)$. $^1$H NMR (400 MHz, DMSO-d6) δ 9.97 (s, 1H), 7.74-7.62 (m, 2H), 7.49-7.38 (m, 2H), 6.04 (s, 2H) |
| 101 | 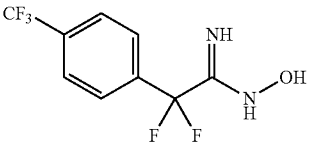 2,2-difluoro-N-hydroxy-2-(4-(trifluoromethyl)phenyl) acetimidamide | LCMS m/z 255.1 $(M + H)^+$ $(ES^+)$. $^1$H NMR (400 MHz, DMSO-d6) δ 10.02 (s, 1H), 7.85 (d, J = 8.2 Hz, 2H), 7.73 (d, J = 8.3 Hz, 2H), 6.12 (s, 2H). $^{19}$F NMR (376 MHz, DMSO-d6) δ −61.39, −96.84. |
| 102 | 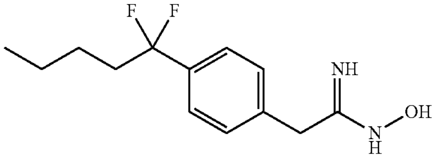 [SMILES: CCCCC(F)(F)c1ccc(CC(=N)NO)cc1] 2-(4-(1,1-difluoropentyl)phenyl)-N-hydroxyacetimidamide | LCMS m/z 257.2 $(M + H)^+$ $(ES^+)$. $^1$H NMR (400 MHz, DMSO-d6) δ 8.90 (s, 1H), 7.42 (d, J = 8.3 Hz, 2H), 7.37 (d, J = 8.3 Hz, 2H), 5.43 (s, 2H), 3.30 (s, 2H), 2.25-2.09 (m, 2H), 1.35-1.23 (m, 4H), 0.88-0.80 (m, 3H). |
| 103 | 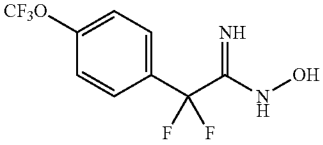 2,2-difluoro-N-hydroxy-2-(4-(trifluoromethoxy)phenyl) acetimidamide | LCMS m/z 271.3 $(M + H)^+$ $(ES^+)$. $^1$H NMR (400 MHz, DMSO-d6) δ 10.01 (s, 1H), 7.64 (d, J = 8.8 Hz, 2H), 7.47 (d, J = 8.3 Hz, 2H), 6.07 (s, 2H). $^{19}$F NMR (376 MHz, DMSO-d6) δ −56.76, −95.71. |
| 104 | 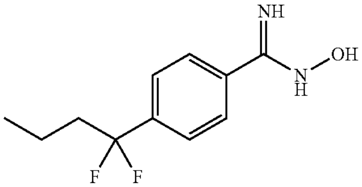 [SMILES: CCCC(F)(F)c1ccc(C(=N)NO)cc1] 4-(1,1-difluorobutyl)-N-hydroxybenzimidamide | LCMS m/z 229.2 $(M + H)^+$ $(ES^+)$. $^1$H NMR (400 MHz, DMSO-d6) δ 9.76 (s, 1H), 7.77 (d, J = 8.3 Hz, 2H), 7.54-7.47 (m, 2H), 5.88 (s, 2H), 2.26-2.10 (m, 2H), 1.40-1.29 (m, 2H), 0.90 (t, J = 7.4 Hz, 3H). $^{19}$F NMR (376 MHz, DMSO-d6) δ −92.70 |
| 105 | 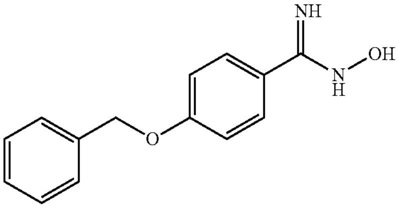 [SMILES: N=C(NO)c1ccc(OCc2ccccc2)cc1] 4-(benzyloxy)-N-hydroxybenzimidamide | LCMS m/z 243.2 $(M + H)^+$ $(ES^+)$. $^1$H NMR (400 MHz, DMSO-d6) δ 9.42 (br. s, 1H), 7.63-7.54 (m, 2H), 7.48-7.43 (m, 2H), 7.42-7.37 (m, 2H), 7.35-7.30 (m, 1H), 7.17-6.85 (m, 2H), 5.71 (br. s, 2H), 5.13 (s, 2H). |

-continued

| Int. Number | Structure/Name | Characterising data |
| --- | --- | --- |
| 139 | 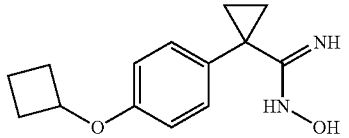 [SMILES: N=C(NO)C1(c2ccc(OC3CCC3)cc2)CC1] 1-(4-cyclobutoxyphenyl)-N-hydroxycyclopropane-1-carboximidamide | LCMS: (System 2, Method C) m/z 247.4 $(M + H)^+$ $(ES^+)$. |
| 141 | 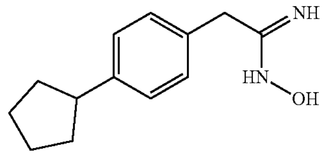 [SMILES: N=C(Cc1ccc(C2CCCC2)cc1)NO] 2-(4-cyclopentylphenyl)-N-hydroxyacetimidamide | LCMS: (System 2, Method C) m/z 219.3 $(M + H)^+$ $(ES^+)$. |
| 144 | 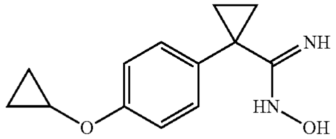 [SMILES: N=C(NO)C1(c2ccc(OC3CC3)cc2)CC1] 1-(4-cyclopropoxyphenyl)-N-hydroxycyclopropane-1-carboximidamide | LCMS: (System 2, Method C) m/z 233.3 $(M + H)^+$ $(ES^+)$. |
| 146 | 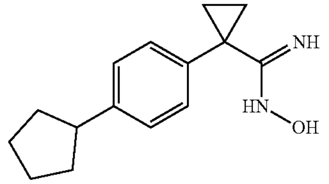 [SMILES: N=C(NO)C1(c2ccc(C3CCCC3)cc2)CC1] 1-(4-cyclopentylphenyl)-N-hydroxycyclopropane-1-carboximidamide | LCMS: (System 2, Method C) m/z 245.3 $(M + H)^+$ $(ES^+)$. |
| 153 | 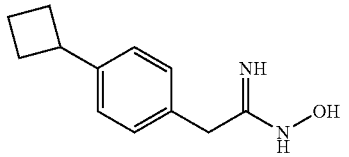 [SMILES: N=C(Cc1ccc(C2CCC2)cc1)NO] 2-(4-cyclobutylphenyl)-N-hydroxyacetimidamide | LCMS: (System 2, Method C) m/z 205.4 $(M + H)^+$ $(ES^+)$. |
| 155 | 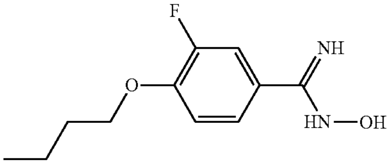 [SMILES: CCCCOc1ccc(C(=N)NO)cc1F] 4-butoxy-3-fluoro-N-hydroxybenzimidamide | LCMS: (System 2, Method C) m/z 227.3 $(M + H)^+$ $(ES^+)$. |
| 157 | 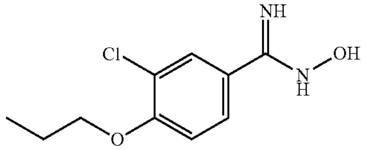 3-chloro-N-hydroxy-4-propoxybenzimidamide | LCMS: (System 2, Method C) m/z 229.2/231.2 $(M + H)^+$ $(ES^+)$. |

-continued

| Int. Number | Structure/Name | Characterising data |
|---|---|---|
| 159 | 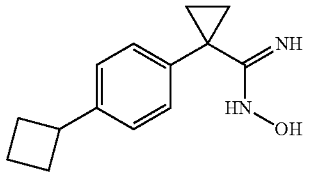 [SMILES: N=C(NO)C1(c2ccc(C3CCC3)cc2)CC1] 1-(4-cyclobutylphenyl)-N-hydroxycyclopropane-1-carboximidamide | LCMS: (System 2, Method C) m/z 231.4 $(M + H)^+$ $(ES^+)$. |
| 160 | 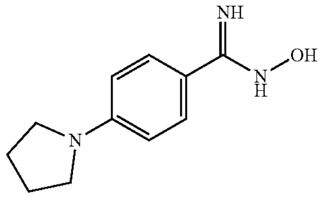 [SMILES: N=C(NO)c1ccc(N2CCCC2)cc1] N-hydroxy-4-(pyrrolidin-1-yl)benzimidamide | LCMS: (System 2, Method C) m/z 206.3 $(M + H)^+$ $(ES^+)$. |
| 162 | 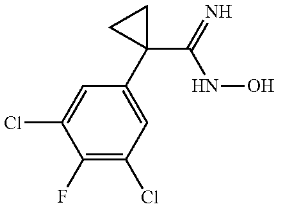 [SMILES: N=C(NO)C1(c2cc(Cl)c(F)c(Cl)c2)CC1] 1-(3,5-dichloro-4-fluorophenyl)-N-hydroxycyclopropane-1-carboximidamide | LCMS: (System 2, Method C) m/z 263.1/265.0 $(M + H)^+$ $(ES^+)$. |
| 163 | 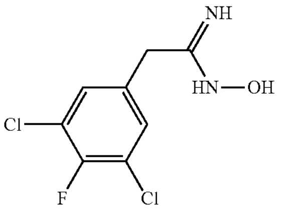 [SMILES: N=C(Cc1cc(Cl)c(F)c(Cl)c1)NO] 2-(3,5-dichloro-4-fluorophenyl)-N-hydroxyacetimidamide | LCMS: (System 2, Method C) m/z 237.0/239.0 $(M + H)^+$ $(ES^+)$. |
| 165 | 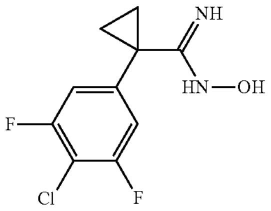 [SMILES: N=C(NO)C1(c2cc(F)c(Cl)c(F)c2)CC1] 1-(4-chloro-3,5-difluorophenyl)-N-hydroxycyclopropane-1-carboximidamide | LCMS: (System 2, Method C) m/z 247.2 $(M + H)^+$ $(ES^+)$. |

-continued

| Int. Number | Structure/Name | Characterising data |
|---|---|---|
| 167 | 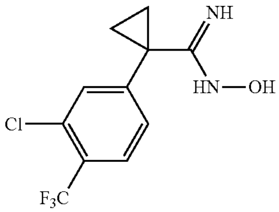 [SMILES: N=C(NO)C1(c2ccc(C(F)(F)F)c(Cl)c2)CC1] 1-(3-chloro-4-(trifluoromethyl) phenyl)-N-hydroxycyclopropane-1-carboximidamide | LCMS: (System 2, Method C) m/z 279.0/281.0 $(M + H)^+$ $(ES^+)$. |
| 168 | 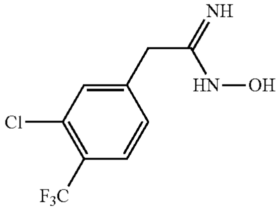 [SMILES: N=C(Cc1ccc(C(F)(F)F)c(Cl)c1)NO] 2-(3-chloro-4-(trifluoromethyl) phenyl)-N-hydroxyacetimidamide | LCMS: (System 2, Method C) m/z 253.2/255.2 $(M + H)^+$ $(ES^+)$. |
| 170 | 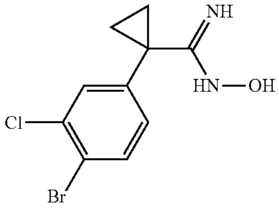 [SMILES: N=C(NO)C1(c2ccc(Br)c(Cl)c2)CC1] 1-(4-bromo-3-chlorophenyl)-N-hydroxycyclopropane-1-carboximidamide | LCMS: (System 2, Method C) m/z 289.1/291.0/293.0 $(M + H)^+$ $(ES^+)$. |
| 171 | 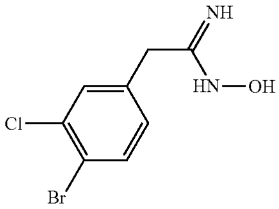 [SMILES: N=C(Cc1ccc(Br)c(Cl)c1)NO] 2-(4-bromo-3-chlorophenyl)-N-hydroxyacetimidamide | LCMS: (System 2, Method C) m/z 263.1/265.0/267.1 $(M + H)^+$ $(ES^+)$. |
| 173 | 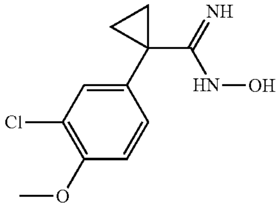 [SMILES: COc1ccc(C2(C(=N)NO)CC2)cc1Cl] 1-(3-chloro-4-methoxyphenyl)-N-hydroxycyclopropane-1-carboximidamide | LCMS: (System 2, Method C) m/z 241.2/243.2 $(M + H)^+$ $(ES^+)$. |

-continued

| Int. Number | Structure/Name | Characterising data |
|---|---|---|
| 175 | 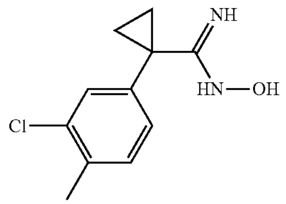 1-(3-chloro-4-methylphenyl)-N-hydroxycyclopropane-1-carboximidamide | LCMS: (System 2, Method C) m/z 225.2/227.2 $(M + H)^+$ $(ES^+)$. |
| 176 | 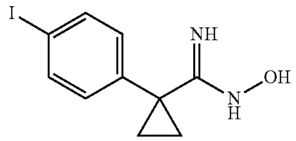 [SMILES: N=C(NO)C1(c2ccc(I)cc2)CC1] N-hydroxy-1-(4-iodophenyl)cyclopropane-1-carboximidamide | LCMS m/z 303.0 $(M + H)^+$ $(ES^+)$. $^1H$ NMR (400 MHz, DMSO-d6) δ 9.04 (s, 1H), 7.71-7.54 (m, 2H), 7.14-7.00 (m, 2H), 5.30 (s, 2H), 1.26-1.13 (m, 2H), 1.03-0.86 (m, 2H) |
| 177 | 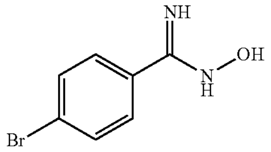 [SMILES: N=C(NO)c1ccc(Br)cc1] 4-bromo-N-hydroxybenzimidamide | LCMS m/z 215.2/217.2 $(M + H)^+$ $(ES^+)$. $^1H$ NMR (400 MHz, DMSO-d6) δ 9.73 (s, 1H), 7.65-7.52 (m, 4H), 5.87 (s, 2H) |
| 178 | 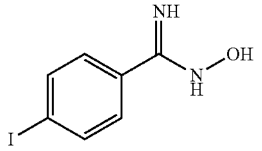 [SMILES: N=C(NO)c1ccc(I)cc1] 4-iodo-N-hydroxybenzimidamide | LCMS m/z 263.1 $(M + H)^+$ $(ES^+)$. $^1H$ NMR (400 MHz, DMSO-d6) δ 9.72 (s, 1H), 7.79-7.68 (m, 2H), 7.51-7.39 (m, 2H), 5.85 (s, 2H) |
| 179 | 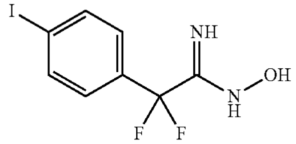 [SMILES: N=C(NO)C(F)(F)c1ccc(I)cc1] 2,2-difluoro-N-hydroxy-2-(4-iodophenyl)acetimidamide | LCMS m/z 313.0 $(M + H)^+$ $(ES^+)$. $^1H$ NMR (400 MHz, DMSO-d6) δ 9.96 (s, 1H), 7.87-7.80 (m, 2H), 7.31-7.25 (m, 2H), 6.03 (s, 2H) |
| 180 | 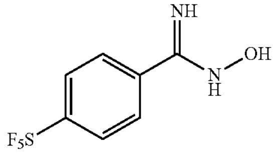 N-hydroxy-4-(pentafluoro-$\lambda^6$-sulfaneyl)benzimidamide | LCMS m/z 263.0 $(M + H)^+$ $(ES^+)$. $^1H$ NMR (400 MHz, DMSO-d6) δ 9.98 (s, 1H), 7.94-7.84 (m, 4H), 6.00 (s, 2H) |
| 181 | 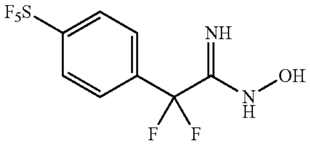 2,2-difluoro-N-hydroxy-2-(4-(pentafluoro-$\lambda^6$-sulfaneyl)phenyl)acetimidamide | LCMS m/z 313.2 $(M + H)^+$ $(ES^+)$. $^1H$ NMR (400 MHz, DMSO-d6) δ 10.06 (s, 1H), 8.09-7.93 (m, 2H), 7.74 (d, J = 8.6 Hz, 2H), 6.16 (s, 2H). $^{19}F$ NMR (376 MHz, DMSO-d6) δ −97.03 |

-continued

| Int. Number | Structure/Name | Characterising data |
|---|---|---|
| 182 | 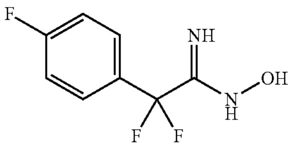 2,2-difluoro-N-hydroxy-2-(4-fluorophenyl)acetimidamide | LCMS m/z 205.3 $(M + H)^+$ $(ES^+)$. $^1H$ NMR (400 MHz, DMSO-d6) δ 9.96 (s, 1H), 7.55 (dd, J = 8.8, 5.4 Hz, 2H), 7.30 (t, J = 8.9 Hz, 2H), 6.02 (s, 2H). $^{19}F$ NMR (376 MHz, DMSO-d6) δ −95.04 (d, J = 2.8 Hz), −111.13. |
| 183 | 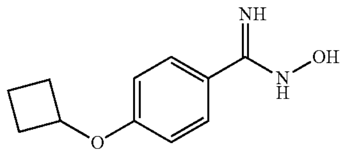 [SMILES: N=C(NO)c1ccc(OC2CCC2)cc1] 4-cyclobutoxy-N-hydroxybenzimidamide | LCMS m/z 207.3 $(M + H)^+$ $(ES^+)$. $^1H$ NMR (400 MHz, DMSO-d6) δ 9.52 (s, 1H), 7.65-7.49 (m, 2H), 6.88-6.75 (m, 2H), 5.87 (s, 2H), 4.80-4.59 (m, 1H), 2.46-2.35 (m, 2H), 2.13-1.94 (m, 2H), 1.85-1.72 (m, 1H), 1.70-1.54 (m, 1H) |
| 184 | 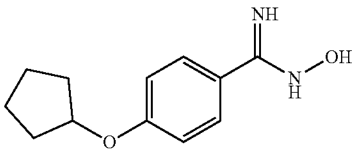 [SMILES: N=C(NO)c1ccc(OC2CCCC2)cc1] 4-cyclopentyloxy-N-hydroxybenzimidamide | LCMS m/z 221.3 $(M + H)^+$ $(ES^+)$. $^1H$ NMR (400 MHz, DMSO-d6) δ 9.64 (s, 1H), 7.63-7.52 (m, 2H), 6.97-6.84 (m, 2H), 6.15 (s, 2H), 4.89-4.76 (m, 1H), 2.04-1.84 (m, 2H), 1.79-1.50 (m, 6H) |
| 185 | 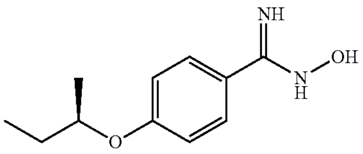 (R)-4-(sec-butoxy)-N-hydroxybenzimidamide | LCMS m/z 209.3 $(M + H)^+$ $(ES^+)$. $^1H$ NMR (400 MHz, DMSO-d6) δ 9.54 (s, 1H), 7.62-7.49 (m, 2H), 6.96-6.85 (m, 2H), 5.93 (s, 2H), 4.48-4.36 (m, 1H), 1.73-1.46 (m, 2H), 1.22 (d, J = 6.1 Hz, 3H), 0.91 (t, J = 7.4 Hz, 3H). |
| 186 | 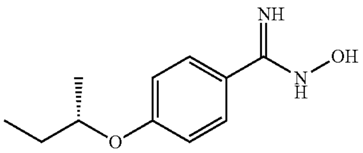 (S)-4-(sec-butoxy)-N-hydroxybenzimidamide | LCMS m/z 209.3 $(M + H)^+$ $(ES^+)$. $^1H$ NMR (400 MHz, DMSO-d6) δ 9.67 (s, 1H), 7.63-7.49 (m, 2H), 7.00-6.89 (m, 2H), 6.21 (s, 2H), 4.49-4.38 (m, 1H), 1.76-1.44 (m, 2H), 1.22 (d, J = 6.1 Hz, 3H), 0.92 (t, J = 7.5 Hz, 3H). |
| 187 | 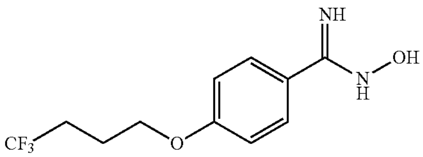 [SMILES: N=C(NO)c1ccc(OCCCC(F)(F)F)cc1] N-hydroxy-4-(4,4,4-trifluorobutoxy)benzimidamide | LCMS m/z 263.3 $(M + H)^+$ $(ES^+)$. $^1H$ NMR (400 MHz, DMSO-d6) δ 9.50 (s, 1H), 7.68-7.53 (m, 2H), 6.98-6.87 (m, 2H), 5.84 (s, 2H), 4.06 (t, J = 6.3 Hz, 2H), 2.48-2.34 (m, 2H), 2.01-1.73 (m, 2H) |
| 188 | 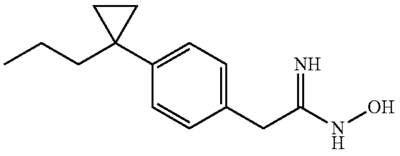 [SMILES: CCCC1(c2ccc(CC(=N)NO)cc2)CC1] N-hydroxy-2-(4-(1-propylcyclopropyl)phenyl) acetimidamide | LCMS m/z 233.3 $(M + H)^+$ $(ES^+)$. $^1H$ NMR (400 MHz, DMSO-d6) δ 8.83 (s, 1H), 7.17 (s, 4H), 5.33 (s, 2H), 3.20 (s, 2H), 1.54-1.45 (m, 2H), 1.26-1.15 (m, 2H), 0.80 (t, J = 7.3 Hz, 3H), 0.72-0.66 (m, 2H), 0.66-0.60 (m, 2H) |

-continued

| Int. Number | Structure/Name | Characterising data |
|---|---|---|
| 189 | 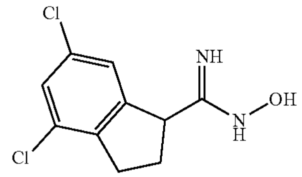 [SMILES: N=C(NO)C1CCc2c(Cl)cc(Cl)cc21] 4,6-dichloro-N-hydroxy-2,3-dihydro-1H-indene-1-carboximidamide | LCMS m/z 245.1/247.1 (M + H)$^+$ (ES$^+$). $^1$H NMR (400 MHz, DMSO-d6) δ 9.02 (s, 1H), 7.41-7.37 (m, 1H), 7.24-7.21 (m, 1H), 5.49 (s, 2H), 3.85 (t, J = 7.8 Hz, 1H), 2.99-2.89 (m, 1H), 2.88-2.77 (m, 1H), 2.28-2.23 (m, 2H) |
| 190 | 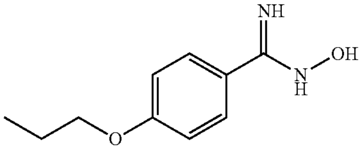 N-hydroxy-4-propoxybenzimidamide | LCMS m/z 195.3 (M + H)$^+$ (ES$^+$) |
| 191 | 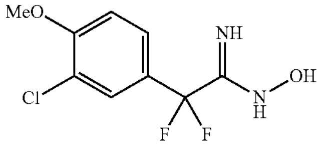 [SMILES: COc1ccc(C(F)(F)C(=N)NO)cc1Cl] 2-(3-chloro-4-methoxyphenyl)-2,2-difluoro-N-hydroxyacetimidamide | LCMS m/z 251.1 (M + H)$^+$ (ES$^+$). $^1$H NMR (400 MHz, DMSO-d6) δ 9.95 (s, 1H), 7.51 (d, J = 2.3 Hz, 1H), 7.45 (dd, J = 8.7, 2.2 Hz, 1H), 7.23 (d, J = 8.7 Hz, 1H), 6.01 (s, 2H), 3.90 (s, 3H) |
| 192 | 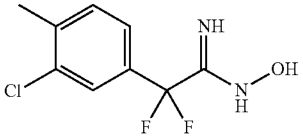 2-(3-chloro-4-methylphenyl)-2,2-difluoro-N-hydroxyacetimidamide | LCMS m/z 235.1 (M + H)$^+$ (ES$^+$). $^1$H NMR (400 MHz, DMSO-d6) δ 9.97 (s, 1H), 7.49 (d, J = 1.8 Hz, 1H), 7.45 (d, J = 8.0 Hz, 1H), 7.37 (dd, J = 8.0, 1.9 Hz, 1H), 6.03 (s, 2H), 2.36 (s, 3H) |
| 193 | 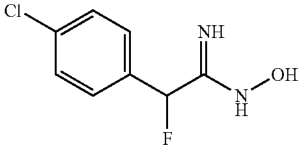 [SMILES: N=C(NO)C(F)c1ccc(Cl)cc1] 2-(4-chlorophenyl)-2-fluoro-N-hydroxyacetimidamide | LCMS m/z 203.1/205.1 (M + H)$^+$ (ES$^+$). $^1$H NMR (400 MHz, DMSO-d6) δ 9.53 (s, 1H), 7.66-7.28 (m, 4H), 5.86 (d, J = 45.6 Hz, 1H), 5.66 (br. s, 2H). $^{19}$F NMR (376 MHz, DMSO) δ −181.53 |
| 194 | 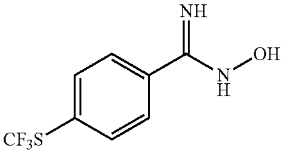 N-hydroxy-4-((trifluoromethyl)thio)benzimidamide | LCMS m/z 237.1 (M + H)$^+$ (ES$^+$). $^1$H NMR (400 MHz, DMSO-d6) δ 9.90 (s, 1H), 7.85-7.76 (m, 2H), 7.72 (d, J = 8.2 Hz, 2H), 5.95 (s, 2H) |
| 195 | 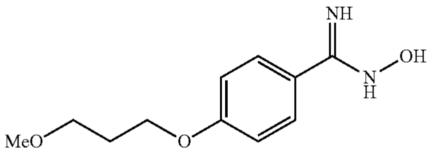 [SMILES: COCCCOc1ccc(C(=N)NO)cc1] N-hydroxy-4-(3-methoxypropoxy)benzimidamide | LCMS m/z 225.1 (M + H)$^+$ (ES$^+$). $^1$H NMR (400 MHz, DMSO-d6) δ 9.44 (s, 1H), 7.65-7.53 (m, 2H), 6.93-6.87 (m, 2H), 5.71 (s, 2H), 4.03 (t, J = 6.4 Hz, 2H), 3.46 (t, J = 6.3 Hz, 2H), 3.25 (s, 3H), 2.00-1.88 (m, 2H) |

-continued

| Int. Number | Structure/Name | Characterising data |
|---|---|---|
| 216 | 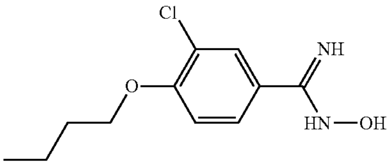 [SMILES: CCCCOc1ccc(C(=N)NO)cc1Cl] 4-butoxy-3-chloro-N-hydroxybenzimidamide | LCMS: (System 2, Method C) m/z 243.2/245.2 $(M + H)^+$ $(ES^+)$. |
| 218 | 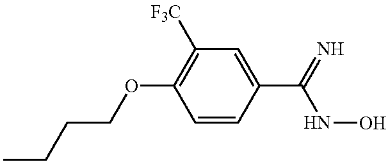 [SMILES: CCCCOc1ccc(C(=N)NO)cc1C(F)(F)F] 4-butoxy-N-hydroxy-3-(trifluoromethyl)benzimidamide | LCMS: (System 2, Method C) m/z 277.2 $(M + H)^+$ $(ES^+)$. |
| 220 | 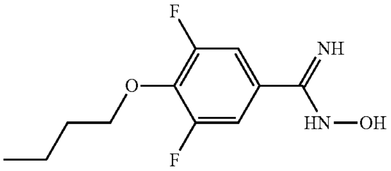 [SMILES: CCCCOc1c(F)cc(C(=N)NO)cc1F] 4-butoxy-3,5-difluoro-N-hydroxybenzimidamide | LCMS: (System 2, Method C) m/z 245.3 $(M + H)^+$ $(ES^+)$. |
| 221 | 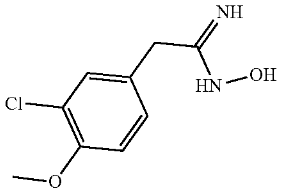 2-(3-chloro-4-methoxyphenyl)-N-hydroxyacetimidamide | LCMS: (System 2, Method C) m/z 215.2/217.2 $(M + H)^+$ $(ES^+)$. |
| 222 | 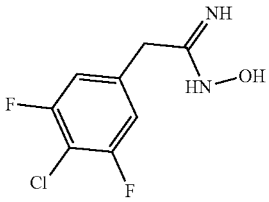 [SMILES: N=C(Cc1cc(F)c(Cl)c(F)c1)NO] 2-(4-chloro-3,5-difluorophenyl)-N-hydroxyacetimidamide | LCMS: (System 2, Method C) m/z 221.2/223.2 $(M + H)^+$ $(ES^+)$. |
| 223 | 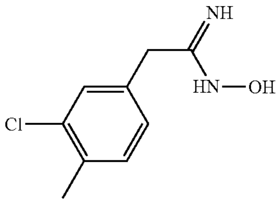 2-(3-chloro-4-methylphenyl)-N-hydroxyacetimidamide | LCMS: (System 2, Method C) m/z 199.2/201.2 $(M + H)^+$ $(ES^+)$. |

Intermediate 57—2.2-dimethylheptanenitrile

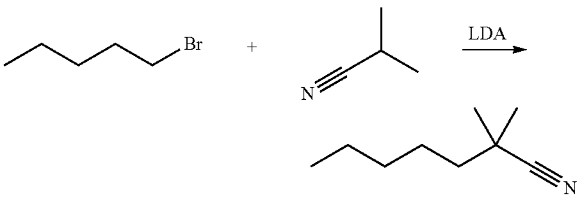

Isobutyronitrile (1.4 mL, 16 mmol) was dissolved in THF (20 mL). LDA (2 M, 8 mL, 16 mmol) was added dropwise at −78° C. and the solution was stirred for 30 min. 1-Bromopentane (1.6 mL, 13 mmol) was added and the mixture was stirred at RT for 18 h. Sat. aq. $NH_4Cl$ (50 mL) was added and the resulting mixture was extracted with DCM (3×50 mL). The combined organic layers were dried (phase separator) and concentrated. The crude product was used directly in the next step.

The following compound was synthesised using the same procedure

| Int. Number | Structure/Name | Characterising data |
|---|---|---|
| 58 | 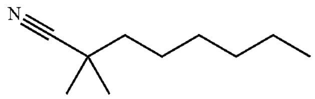 2,2-dimethyloctanenitrile | $^1$H NMR (400 MHz, DMSO-d6) δ 1.53-1.46 (m, 2H), 1.44-1.33 (m, 1H), 1.33-1.22 (m, 13H), 0.92-0.83 (m, 3H) |

Intermediate 59—8,8,9,9,9-pentafluorononanenitrile

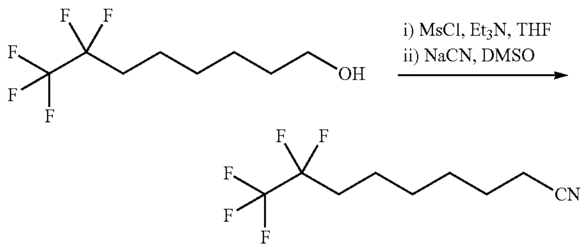

Methanesulfonyl chloride (2.6 mL, 34 mmol) and triethylamine (6.3 mL, 45 mmol) were added dropwise to a cooled solution of 7,7,8,8,8-pentafluorooctan-1-ol (5.00 g, 22.7 mmol) in THF (32 mL). The mixture was stirred at RT for 2 h and quenched with sat. aq. $NaHCO_3$ (50 mL). The mixture was extracted with MTBE (3×50 mL) and the combined organic phases were dried ($MgSO_4$) and concentrated. The residue was dissolved in DMSO (32 mL), sodium cyanide (3.34 g, 68 mmol) was added and the mixture was heated to 120° C. for 24 h. The mixture was cooled to RT, diluted with MTBE (200 mL), and washed with water (3×40 mL). The combined organic phases were dried ($MgSO_4$) and concentrated to afford 8,8,9,9,9-pentafluorononanenitrile (4.58 g, 18 mmol, 91% purity) as a yellowish solid that was used without further purification.

$^1$H NMR (400 MHz, DMSO-d6) δ 2.49 (t, J=7.1 Hz, 2H), 2.18 (tt, J=18.8, 7.9 Hz, 2H), 1.63-1.46 (m, 4H), 1.39 (dq, J=7.4, 3.4 Hz, 4H).

The following compounds were synthesised using the same procedure.

| Int. Number | Structure/Name | Characterising data |
|---|---|---|
| 60 | 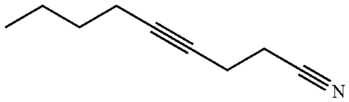 non-4-ynenitrile | $^1$H NMR (400 MHz, DMSO-d6) δ 2.69-2.61 (m, 2H), 2.50-2.44 (m, 2H), 2.22-2.14 (m, 2H), 1.46-1.31 (m, 4H), 0.93-0.82 (m, 3H) |

-continued

| Int. Number | Structure/Name | Characterising data |
|---|---|---|
| 106 | 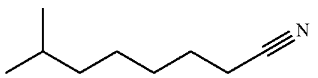 7-methyloctanenitrile | $^1$H NMR (400 MHz, DMSO-d6) δ 2.48 (t, J = 7.1 Hz, 2H), 1.60-1.46 (m, 3H), 1.39-1.23 (m, 4H), 1.20-1.12 (m, 2H), 0.86 (d, J = 6.6 Hz, 6H) |

Intermediate 61—2-(4'-chloro-[1,1-biphenyl]-4-yl) acetonitrile

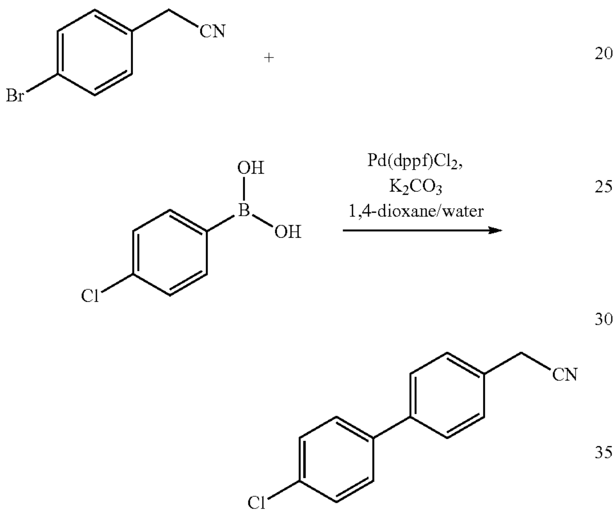

Pd(dppf)$Cl_2$-DCM adduct (1.31 g, 1.60 mmol) was added to a degassed mixture of 2-(4-bromophenyl)acetonitrile (3.13 g, 16.0 mmol), (4-chlorophenyl)boronic acid (2.50 g, 16.0 mmol) and potassium carbonate (6.63 g, 48 mmol) in a mixture of water (11 mL) and 1,4-dioxane (75 ml). The resulting mixture was stirred at 80° C. for 5 hours. The reaction was cooled to RT and filtered using a Whatmans GF/F filter washing with EtOAc (10 ml). The mixture was concentrated and the crude product was purified by chromatography on silica gel (0-50% EtOAc/isohexane) to afford 2-(4'-chloro-[1,1'-biphenyl]-4-yl)acetonitrile (4.32 g, 13 mmol, 71% Purity)as a white solid.

$^1$H NMR (400 MHz, DMSO-d6) δ 7.75-7.66 (m, 4H), 7.55-7.49 (m, 2H), 7.48-7.41 (m, 2H), 4.09 (s, 2H).

Intermediate 62—2-(4-butylphenyl)acetonitrile

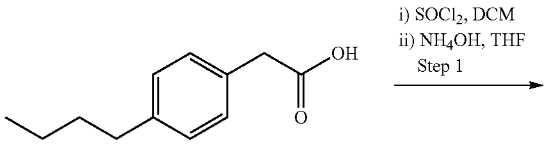

-continued

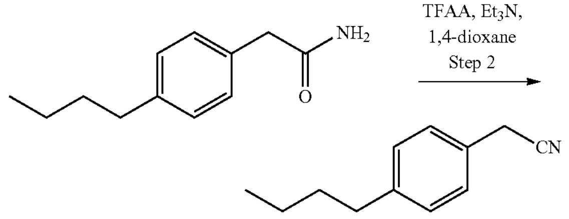

Step 1

Thionyl chloride (9.1 mL, 125 mmol) was added to a solution of 2-(4-butylphenyl)acetic acid (2.00 g, 10.4 mmol) in DCM (33 mL) at 0° C. The reaction mixture was heated to reflux for 2 h, then cooled to RT. The mixture was concentrated and the residue was co-evaporated with toluene (2×10 mL). The residue was dissolved in THF (14 mL), cooled to 0° C. and a solution of ammonium hydroxide (19.2 mL, 28% Wt, 135 mmol) was added dropwise over 10 min. The mixture was warmed to RT and stirred for a further 2 h. The mixture was then extracted with DCM (3×25 mL) and the combined organic layers were dried (phase separator) and concentrated to afford 2-(4-butylphenyl)acetamide (1.90 g, 8.9 mmol, 90% Purity) as an off white solid. LCMS m/z 192.3 $(M+H)^+$ $(ES^+)$. $^1$H NMR (400 MHz, DMSO-d6) δ 7.41 (s, 1H), 7.16 (d, J=8.1 Hz, 2H), 7.10 (d, J=8.1 Hz, 2H), 6.83 (s, 1H), 3.31 (s, 2H), 2.57-2.51 (m, 2H), 1.59-1.47 (m, 2H), 1.37-1.21 (m, 2H), 0.89 (t, J=7.3 Hz, 3H).

Step 2

TFAA (5.5 mL, 40 mmol) was added dropwise to a solution of 2-(4-butylphenyl)acetamide (1.90 g, 9.93 mmol) and triethylamine (5.5 mL, 40 mmol) in 1,4-dioxane (20 mL) at 0° C. The reaction was allowed to warm to RT and stirred for 16 h. The reaction mixture was concentrated and poured into water (30 mL), then extracted with EtOAc (3×25 mL). The combined organic layers were washed with brine (30 mL), dried ($Na_2SO_4$) and concentrated. The crude product was purified by chromatography on silica gel (0-50% EtOAc/isohexane) to afford 2-(4-butylphenyl)acetonitrile (1.75 g, 9.85 mmol) as a brown oil. $^1$H NMR (400 MHz, DMSO-d6) δ 7.28-7.18 (m, 4H), 3.98 (s, 2H), 2.61-2.53 (m, 2H), 1.59-1.49 (m, 2H), 1.36-1.22 (m, 2H), 0.89 (t, J=7.4 Hz, 3H).

The following compounds were synthesised using the same procedure.

| Int. Number | Structure/Name | Characterising data |
|---|---|---|
| 63 | 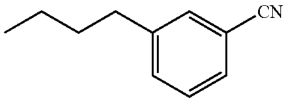 butylbenzonitrile | $^1$H NMR (400 MHz, DMSO-d6) δ 7.70-7.61 (m, 2H), 7.59-7.54 (m, 1H), 7.49 (t, J = 7.6 Hz, 1H), 2.69-2.58 (m, 2H), 1.63-1.48 (m, 2H), 1.37-1.22 (m, 2H), 0.90 (t, J = 7.3 Hz, 3H) |
| 64 | 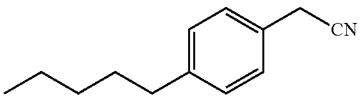 2-(4-pentylphenyl)acetonitrile | $^1$H NMR (400 MHz, DMSO-d6) δ 7.27-7.19 (m, 4H), 3.98 (s, 2H), 2.61-2.52 (m, 2H), 1.64-1.48 (m, 2H), 1.36-1.21 (m, 4H), 0.86 (t, J = 6.9 Hz, 3H) |
| 65 | 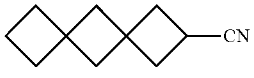 dispiro[3.1.3$^6$.1$^4$]decane-2-carbonitrile | $^1$H NMR (400 MHz, DMSO-d6) δ 3.24-3.13 (m, 1H), 2.35-2.27 (m, 2H), 2.26-2.16 (m, 2H), 2.01 (s, 4H), 1.93-1.86 (m, 4H), 1.80-1.71 (m, 2H) |
| 66 | 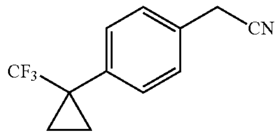 2-(4-(1-(trifluoromethyl)cyclopropyl)phenyl)acetonitrile | $^1$H NMR (400 MHz, DMSO-d6) δ 7.49 (d, J = 8.0 Hz, 2H), 7.37 (d, J = 8.1 Hz, 2H), 4.06 (s, 2H), 1.38-1.32 (m, 2H), 1.16-1.10 (m, 2H) |

Intermediate 67—4-(tert-butoxy)-3-(diethoxyphosphoryl)-4-oxobutanoic acid

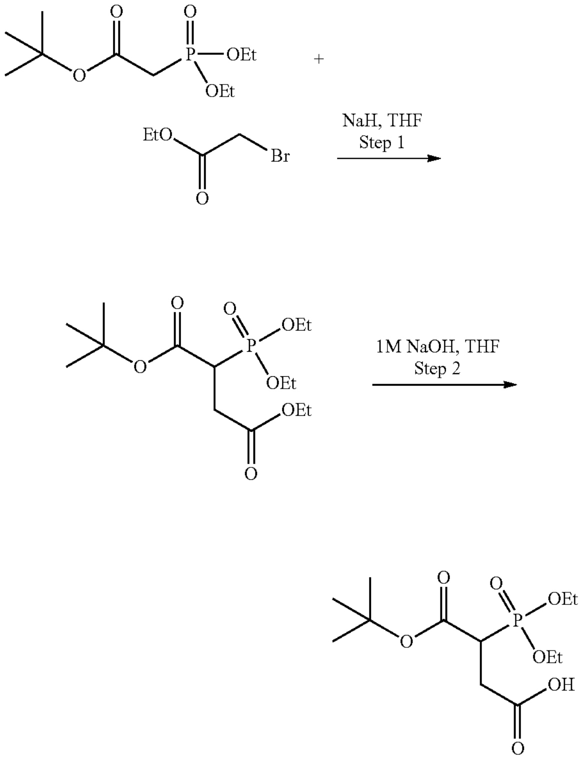

Step 1

Sodium hydride (60 wt % dispersion in mineral oil, 9.00 g, 225 mmol) was added portionwise to a solution of tert-butyl 2-(diethoxyphosphoryl)acetate (50 mL, 213 mmol) in THF (500 mL) at 0° C. The mixture was stirred for 15 min before ethyl bromoacetate (23 mL, 210 mmol) was added dropwise. The mixture was stirred for 1 h then quenched with sat. aq. $NH_4Cl$ (100 mL) and extracted with EtOAc (3×100 mL). The combined organic phases were washed with brine (300 mL), dried ($MgSO_4$) and concentrated to afford 1-(tert-butyl) 4-ethyl 2-(diethoxyphosphoryl) succinate (77.1 g, 182 mmol, 80% purity) as a colourless oil. LCMS m/z 361.2 $(M+Na)^+$ $(ES^+)$. $^1$H NMR (400 MHz, DMSO-d6) δ 4.13-4.01 (m, 6H), 3.28 (ddd, J=23.8, 11.3, 3.9 Hz, 1H), 2.78 (ddd, J=17.2, 11.3, 8.2 Hz, 1H), 2.64 (ddd, J=17.1, 8.5, 4.0 Hz, 1H), 1.40 (s, 9H), 1.28-1.21 (m, 6H), 1.18 (t, J=7.1 Hz, 3H).

Step 2

An aqueous solution of sodium hydroxide (1 M, 250 mL, 250 mmol) was added to a solution of 1-(tert-butyl) 4-ethyl 2-(diethoxyphosphoryl)succinate (77.1 g, 182 mmol, 80% purity) in THF (250 mL). The mixture was stirred at RT for 16 h. The mixture was partially concentrated to ca. 250 mL, then extracted with EtOAc (3×100 mL). The aqueous phase was acidified to pH 1 with conc. HCl and extracted with EtOAc (3×100 mL). The combined organic phases were washed with brine (250 mL), dried ($MgSO_4$) and concentrated. The residue was triturated with hexane (300 mL) and the resulting solid collected by filtration to afford 4-(tert-butoxy)-3-(diethoxyphosphoryl)-4-oxobutanoic acid (53.00 g, 0.15 mol, 90% purity) as a white solid. LCMS m/z 333.2 $(M+Na)^+$ $(ES^+)$. $^1$H NMR (400 MHz, DMSO-d6) δ 12.44 (s, 1H), 4.11-3.99 (m, 4H), 3.22 (ddd, J=23.7, 11.5, 3.7 Hz, 1H), 2.73 (ddd, J=17.3, 11.5, 7.6 Hz, 1H), 2.56 (ddd, J=17.3, 8.6, 3.7 Hz, 1H), 1.40 (s, 9H), 1.25 (dt, J=8.3, 7.0 Hz, 6H). $^{31}$P NMR (162 MHz, DMSO-d6) δ 21.88.

Intermediate 68—2-(3-butylphenyl)acetonitrile

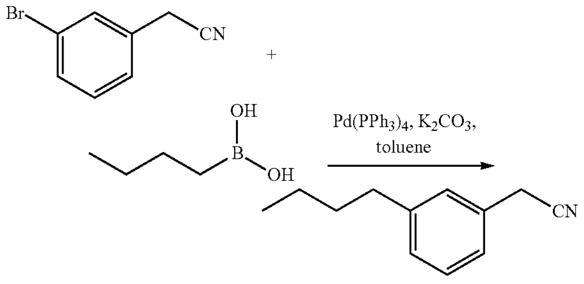

Butylboronic acid (2.73 g, 26.8 mmol). $Pd(PPh_3)_4$ (206 mg, 0.18 mmol)and potassium carbonate (2.47 g, 17.9 mmol) were added to a solution of 2-(3-bromophenyl) acetonitrile (3.50 g, 17.9 mmol) in toluene (50 mL). The reaction mixture was heated to 110° C. and stirred for 10 h, then at RT for 18 h. The solution was diluted with EtOAc (100 mL) and washed with water (100 mL) and brine (100 mL). The organic phase was dried ($MgSO_4$) and concentrated. The crude product was purified by chromatography on silica gel (0-100% EtOAc/isohexane) to afford 2-(3-butylphenyl)acetonitrile (2.50 g, 13 mmol, 90% purity) as a clear colourless oil. $^1$H NMR (400 MHz, DMSO-d6) δ 7.33-7.26 (m, 1H), 7.19-7.11 (m, 3H), 4.00 (s, 2H), 2.58 (t, J=7.7 Hz, 2H), 1.63-1.46 (m, 2H), 1.31 (h, J=7.3 Hz, 2H), 0.90 (t, J=7.3 Hz, 3H).

The following compounds were synthesised using the same procedure.

| Int. Number | Structure/Name | Characterising data |
|---|---|---|
| 69 | 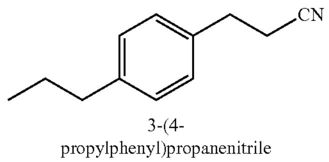 3-(4-propylphenyl)propanenitrile | LCMS m/z 174.1 (M + H)$^+$ (ES$^+$). $^1$H NMR (400 MHz, DMSO-d6) δ 7.19 (d, J = 8.2 Hz, 2H), 7.14 (d, J = 8.1 Hz, 2H), 2.84 (dd, J = 8.1, 4.4 Hz, 2H), 2.81-2.75 (m, 2H), 2.56-2.50 (m, 2H), 1.64-1.51 (m, 2H), 0.89 (t, J = 7.3 Hz, 3H). |
| 70 | 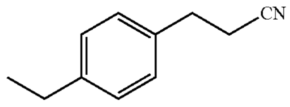 3-(4-ethylphenyl)propanenitrile | LCMS m/z 160.1 (M + H)$^+$ (ES$^+$). $^1$H NMR (400 MHz, DMSO-d6) δ 7.20 (d, J = 8.2 Hz, 2H), 7.16 (d, J = 8.2 Hz, 2H), 2.84 (dd, J = 8.0, 4.4 Hz, 2H), 2.81-2.74 (m, 2H), 2.58 (q, J = 7.6 Hz, 2H), 1.17 (t, J = 7.6 Hz, 3H) |

Intermediate 71—N-hydroxynonanimidamide-d17

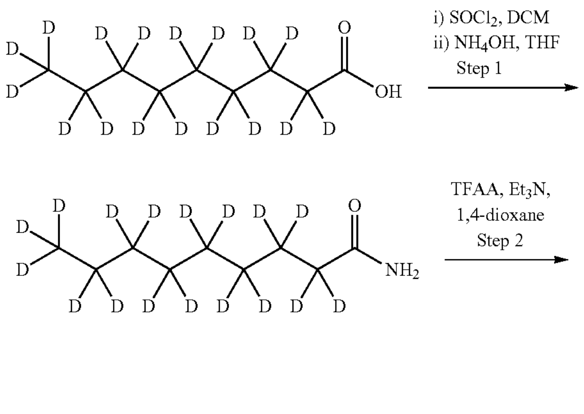

-continued

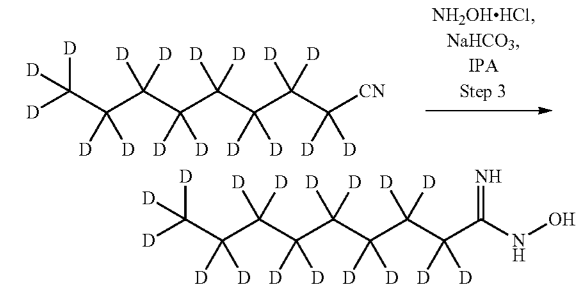

Step 1

A stirred solution of nonanoic-d17 acid (1.00 g, 5.70 mmol) in DCM (20 mL) at 0° C. was treated with thionyl chloride (2.1 mL, 29 mmol) dropwise. The mixture was stirred at 0° C. for 15 min and then at 40° C. for 3 h. The reaction mixture was concentrated and then co-evaporated with toluene (2×10 mL). The residue was taken up in THF (10 mL), cooled to 0° C. and treated with ammonium hydroxide (28% aq., 8.0 mL 57 mmol) dropwise. The reaction mixture was allowed to warm to RT and stirred for 16 h. The mixture was partially concentrated and extracted with DCM (3×10 mL). The combined organic extracts were dried (phase separator) and concentrated to afford nonanamide-d17 (844 mg, 4.84 mmol) as a white solid that was used in the next step without further purification. LCMS m/z 175.3 (M+H)$^+$ (ES$^+$).

Step 2

A stirred suspension of nonanamide-d17 (844 mg, 4.84 mmol) and triethylamine (2.7 mL, 19 mmol) in 1,4-dioxane (10 mL) at 0° C. was treated with TFAA (2.0 mL, 14 mmol) dropwise. The resultant solution was allowed to warm to RT and stirred for 18 h. The reaction mixture was concentrated and the residue was poured into water (20 mL) and extracted with EtOAc (20 mL). The phases were separated and the aqueous phase was extracted with EtOAc (3×20 mL). The combined organic extracts were washed with brine (40 mL), dried (phase separator) and concentrated to afford nonanenitrile-d17 as a yellow oil (1.2 g) that was used in the next step without further purification or analysis, assuming quantitative yield.

Step 3

A suspension of hydroxylamine hydrochloride (685 mg, 9.76 mmol) in IPA (10 mL) was treated with sodium bicarbonate (1.24 g, 14.8 mmol) and stirred for 15 minutes.

A solution of nonanenitrile-d17 (ca. 1.2 g, 4.84 mmol [assumed]) in IPA (5 mL) was added dropwise and then the reaction mixture was stirred at 85° C. for 18 h. The reaction mixture was allowed to cool to RT and filtered, washing with EtOAc (50 mL). The filtrate was concentrated in vacuo to afford N-hydroxynonanimidamide-d17 (1.37 g, 4.84 mmol [assumed]) as a yellow oil that was used in the next step without further purification assuming quantitative yield. LCMS m/z 190.3 $(M+H)^+$ $(ES^+)$.

Intermediate 72—1-bromodecan-2-one

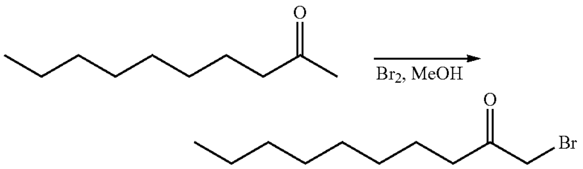

Bromine (1.65 mL, 32 mmol) was added dropwise to a solution of decan-2-one (6.1 mL, 32 mmol) in MeOH (23 mL) at 0° C. The reaction was stirred at 0° C. for 1.5 h, then aqueous potassium carbonate (1 M, 100 mL) was added. The mixture was concentrated under reduced pressure and extracted with EtOAc (3x25 mL). The combined organic layers were washed with potassium carbonate (1 M, 2x20 mL), dried ($Na_2SO_4$) and concentrated. The residue was dissolved in THF (150 mL) and sulfuric acid (1 M, 100 mL). The mixture was vigorously stirred at 70° C. for 1.5 h.

The mixture was concentrated and extracted with EtOAc (3x25 mL). The combined organic extracts were washed with sat. aq. $NaHCO_3$ (2x20 mL), brine (20 mL), dried ($Na_2SO_4$) and concentrated to afford 1-bromodecan-2-one (7.50 g, 31.5 mmol)as a colourless oil that was used without further purification. $^1$H NMR (400 MHz, DMSO-d6) δ 4.33 (s, 2H), 2.57 (t, J=7.3 Hz, 2H), 1.53-1.44 (m, 2H), 1.28-1.21 (m, 10H), 0.89-0.83 (m, 3H).

Intermediate 73—(R)-2-methyloctanenitrile

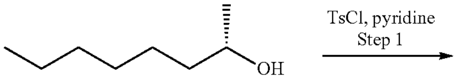

-continued

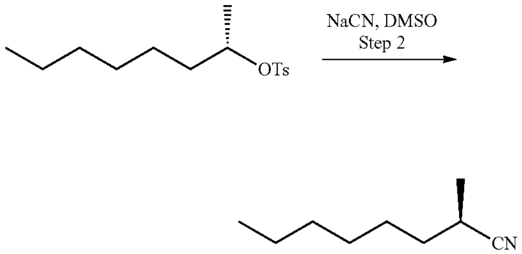

Step 1 p-TsCl (8.1 g, 42 mmol) was added portionwise to a mixture of (S)-octan-2-ol (5.0 g, 38 mmol) in pyridine (11 mL) at −5° C. The mixture was allowed warm to RT and stirred for 18 h. The mixture was quenched with ice and then water (100 mL) was added. The mixture was extracted with EtOAc (3x100 mL). The combined organic layers were washed with 10% citric acid (3x100 mL), water (100 mL), dried ($MgSO_4$) and concentrated to afford (S)-octan-2-yl 4-methylbenzenesulfonate (9.86 g, 33 mmol) as a colourless oil. $^1$H NMR (400 MHz, DMSO-d6) δ 7.84-7.73 (m, 2H), 7.48 (d, J=8.0 Hz, 2H), 4.63-4.46 (m, 1H), 2.42 (s, 3H), 1.56-1.37 (m, 2H), 1.25-0.95 (m, 11H), 0.83 (t, J=7.1 Hz, 3H).

Step 2

Sodium cyanide (1.78 g, 36.2 mmol) was added to a solution of (S)-octan-2-yl 4-methylbenzenesulfonate (9.86 g, 33 mmol) in DMSO (50 mL) at 50° C. The mixture was stirred for 18 h at 50° C. and cooled to RT. Water (500 mL) was added, the phases were separated and the aqueous phase was extracted with DCM (3x100 mL). The combined organic phases were washed with brine (3x100 mL), dried ($MgSO_4$) and concentrated. The crude product was purified by chromatography on silica gel (0-50% MTBE/isohexane) to afford (R)-2-methyloctanenitrile (3.47 g, 22 mmol) as a clear colourless oil. $^1$H NMR (400 MHz, $CDCl_3$) δ 2.67-2.53 (m, 1H), 1.70-1.12 (m, 13H), 0.97-0.81 (m, 3H). $^1$H NMR (400 MHz, DMSO-d6) δ 7.84-7.73 (m, 2H), 7.48 (d, J=8.0 Hz, 2H), 4.63-4.46 (m, 1H), 2.42 (s, 3H), 1.56-1.37 (m, 2H), 1.25-0.95 (m, 11H), 0.83 (t, J=7.1 Hz, 3H).

The following compounds were synthesised using the same procedure.

| Int. Number | Structure/Name | Characterising data |
|---|---|---|
| 74 | 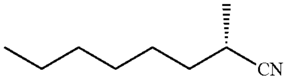 (S)-2-methyloctanenitrile | $^1$H NMR (400 MHz, $CDCl_3$) δ 2.70-2.52 (m, 1H), 1.74-1.23 (m, 13H), 0.98-0.78 (m, 3H) |
| 75 | 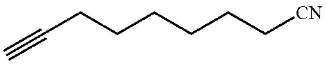 non-8-ynenitrile | $^1$H NMR (400 MHz, DMSO-d6) δ 2.75 (t, J = 2.7 Hz, 1H), 2.48 (t, J = 7.1 Hz, 2H), 2.16 (td, J = 6.9, 2.7 Hz, 2H), 1.60-1.50 (m, 2H), 1.49-1.42 (m, 2H), 1.41-1.31 (m, 4H). |

Intermediate 76—1-(4-(trifluoromethoxy)phenyl) cyclopropane-1-carbonitrile

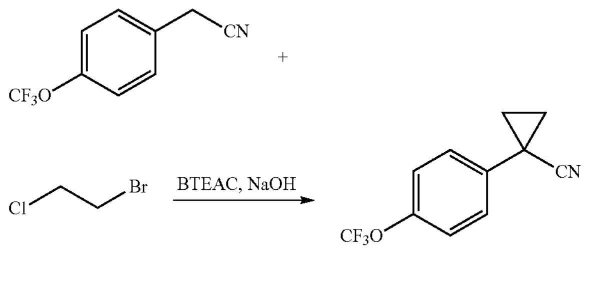

A solution of NaOH (5.97 g, 149 mmol) in water (8 mL) was added dropwise to a mixture of 2-(4-(trifluoromethoxy) phenyl)acetonitrile (5.00 g, 25 mmol), 1-bromo-2-chloroethane (3.1 mL, 37.3 mmol) and benzyl(triethyl)ammonium chloride (113 mg, 0.5 mmol) at 50° C. The mixture was stirred at 50° C. for 16 h, then at RT for 3 days. The mixture was diluted with water (200 mL) and extracted with DCM (3×75 mL). The combined organic phases were washed with 1 M HCl (2×100 mL), water (100 mL), dried ($MgSO_4$) and concentrated to afford 1-(4-(trifluoromethoxy)phenyl)cyclopropane-1-carbonitrile (5.42 g, 21 mmol, 86% purity) as an orange oil. $^1H$ NMR (400 MHz, $CDCl_3$) δ 7.38-7.33 (m, 2H), 7.25-7.18 (m, 2H), 1.84-1.70 (m, 2H), 1.51-1.36 (m, 2H).

The following compounds were synthesised using the same procedure.

| Int. Number | Structure/Name | Characterising data |
|---|---|---|
| 77 | 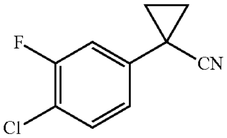 1-(4-chloro-3-fluorophenyl) cyclopropane-1-carbonitrile | $^1H$ NMR (400 MHz, DMSO-d6) δ 7.62 (t, J = 8.2 Hz, 1H), 7.34 (dd, J = 10.7, 2.3 Hz, 1H), 7.29 (dd, J = 8.4, 2.3 Hz, 1H), 1.86-1.75 (m, 2H), 1.66-1.52 (m, 2H) |
| 107 | 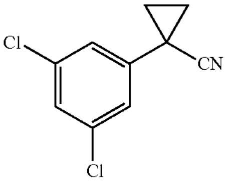 1-(3,5-dichlorophenyl) cyclopropane-1-carbonitrile | $^1H$ NMR (400 MHz, DMSO-d6) δ 7.58 (t, J = 1.8 Hz, 1H), 7.38 (d, J = 1.8 Hz, 2H), 1.83-1.78 (m, 2H), 1.68-1.63 (m, 2H) |
| 108 | 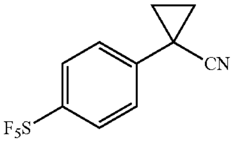 1-(4-(pentafluoro-$\lambda^6$-sulfaneyl)phenyl) cyclopropane-1-carbonitrile | $^1H$ NMR (400 MHz, DMSO-d6) δ 7.98-7.85 (m, 2H), 7.55 (d, J = 8.6 Hz, 2H), 1.99-1.77 (m, 2H), 1.75-1.56 (m, 2H) |
| 109 | 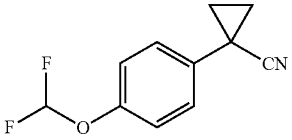 1-(4-(difluoromethoxy)phenyl) cyclopropane-1-carbonitrile | $^1H$ NMR (400 MHz, DMSO-d6) δ 7.47-6.98 (m, 5H), 1.78-1.70 (m, 2H), 1.53-1.44 (m, 2H) |
| 110 | 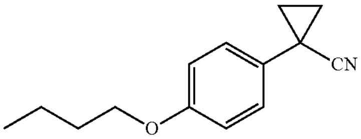 1-(4-butoxyphenyl) cyclopropane-1-carbonitrile | $^1H$ NMR (400 MHz, DMSO-d6) δ 7.28-7.22 (m, 2H), 6.97-6.89 (m, 2H), 3.96 (t, J = 6.5 Hz, 2H), 1.73-1.64 (m, 4H), 1.48-1.37 (m, 4H), 0.93 (t, J = 7.4 Hz, 3H) |

-continued

| Int. Number | Structure/Name | Characterising data |
| --- | --- | --- |
| 111 | 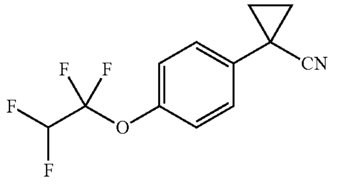 1-(4-(1,1,2,2-tetrafluoroethoxy)phenyl) cyclopropane-1-carbonitrile | $^1$H NMR (400 MHz, $CDCl_3$) δ 7.40-7.28 (m, 2H), 7.27-7.16 (m, 2H), 5.91 (tt, J = 53.1, 2.9 Hz, 1H), 1.79-1.68 (m, 2H), 1.48-1.36 (m, 2H) |
| 112 | 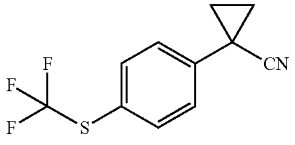 1-(4-((trifluoromethyl)thio)phenyl) cyclopropane-1-carbonitrile | $^1$H NMR (400 MHz, DMSO-d6) δ 7.77-7.70 (m, 2H), 7.52-7.44 (m, 2H), 1.89-1.77 (m, 2H), 1.69-1.57 (m, 2H) |
| 196 | 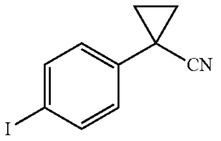 1-(4-iodophenyl) cyclopropane-1-carbonitrile | $^1$H NMR (400 MHz, DMSO-d6) δ 7.89-7.62 (m, 2H), 7.25-7.08 (m, 2H), 1.91-1.67 (m, 2H), 1.54-1.40 (m, 2H) |

Intermediate 78—9,9-difluorononanenitrile

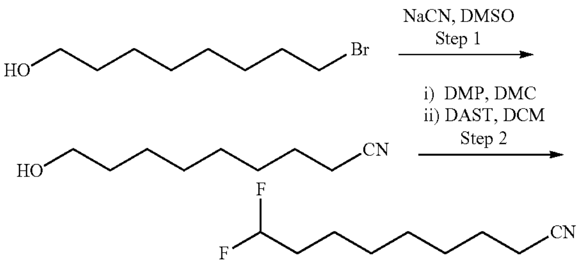

Step 1

Sodium cyanide (0.84 g, 17.2 mmol) was added to a solution of 8-bromooctan-1-ol (3.00 g, 14.4 mmol) in DMSO (24 mL) at RT. The mixture was stirred for 18 h at RT, then diluted with water (50 mL) and extracted with EtOAc (2×100 mL). The combined organic phases were dried ($MgSO_4$) and concentrated. The crude product was purified by chromatography on silica gel (0-100% EtOAc/isohexane) to afford 9-hydroxynonanenitrile (1.45 g, 9.1 mmol) as a translucent oil. $^1$H NMR (400 MHz, DMSO-d6) δ 4.32 (t, J=5.2 Hz, 1H), 3.38 (td, J=6.5, 5.1 Hz, 2H), 2.48 (t, J=7.1 Hz, 2H), 1.61-1.48 (m, 2H), 1.47-1.21 (m, 10H).

Step 2

DMP (5.54 g, 13.1 mmol) was added portionwise to a solution of 9-hydroxynonanenitrile (1.45 g, 9.1 mmol) in DCM (14 mL) at 0° C. The reaction mixture was allowed to warm to RT and stirred for 45 min. The reaction mixture was quenched with sat. aq. $Na_2S_2O_3$ (15 mL). The organic layer was washed with sat. aq. $NaHCO_3$ (15 mL). The aqueous layer was extracted with DCM (3×30 mL). The combined organic phases were dried ($MgSO_4$) and concentrated. The crude product was purified by chromatography on silica gel (0-50% MTBE/isohexane) to afford 9-oxononanenitrile, which was directly diluted in DCM (35 mL), then cooled to 0° C.

Diethylaminosulfur trifluoride (2.46 mL, 18.6 mmol) was added dropwise. The mixture was allowed to warm to RT and stirred for 16 h. The reaction mixture was quenched with sat. aq. $NaHCO_3$ until pH 7. The aqueous phase was extracted with DCM (3×30 mL). The combined organic extracts were dried ($MgSO_4$) and concentrated. The crude product was purified by chromatography on silica gel (0-50% MTBE/isohexane) to afford 9,9-difluorononanenitrile (0.490 g, 2.5 mmol, 90% purity) as a yellow oil. $^1$H NMR (400 MHz, DMSO-d6) δ 6.05 (tt, J=56.9, 4.5 Hz, 1H), 2.48 (t, J=7.1 Hz, 2H), 1.89-1.69 (m, 2H), 1.61-1.48 (m, 2H), 1.46-1.18 (m, 8H).

Intermediate 79-10,10,10-trifluorodecanenitrile

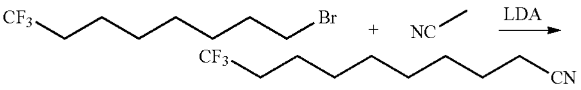

n-Butyllithium (1.6 M in hexanes, 12 mL, 19 mmol) was added to a solution of diisopropylamine (2.8 mL, 19 mmol) in THF (19 mL) at −78° C. The solution was stirred for 15 min at 0° C., then cooled to −78° C. A solution of acetonitrile (1.0 mL, 19 mmol) in THF (16 mL) was added and the mixture was stirred for 30 min at −78° C. 8-bromo-1,1,1-trifluorooctane (4.8 g, 19 mmol) was added. The reaction mixture was allowed to warm to RT and stirred for 20 h, then quenched with sat. aq. $NH_4Cl$ solution (50 mL). The aqueous phase was extracted with ethyl acetate (3×20 mL), the combined organic phases were dried ($MgSO_4$) and concentrated. The crude product was used directly in the next step without further purification. $^1H$ NMR (400 MHz, DMSO-d6) δ 2.48 (t, J=7.1 Hz, 2H), 2.30-2.14 (m, 2H), 1.60-1.42 (m, 3H), 1.41-1.22 (m, 9H).

Intermediate 80—1-aminodecan-2-one hydrochloride

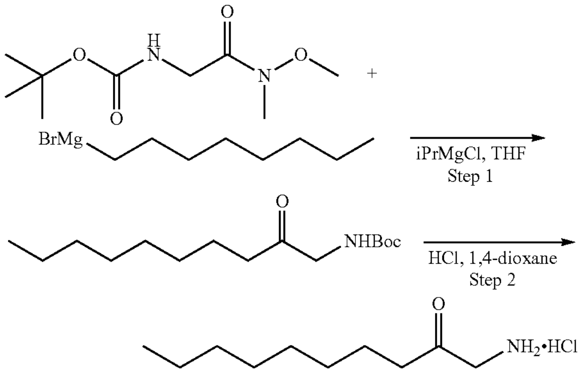

Step 1

Isopropylmagnesium chloride (2 M in THF, 33 mL, 66 mmol) was added dropwise to a suspension of tert-butyl (2-(methoxy(methyl)amino)-2-oxoethyl)carbamate (14.5 g, 66 mmol) in THF (150 mL) at 0° C. Octylmagnesium bromide (2 M in THF, 42 mL, 84 mmol) was added dropwise. The mixture was allowed to warm to RT and stirred for 16 h. The reaction mixture was cooled to 0° C. and quenched with 1M HCl (100 mL). The phases were separated and the aqueous layer was extracted with EtOAc (2×100 mL). The combined organic layers were washed with brine (2×100 mL), dried ($MgSO_4$) and concentrated. The crude product was purified by chromatography on silica gel (0-40% MTBE/isohexane) to afford tert-butyl (2-oxodecyl)carbamate (16.5 g, 55 mmol, 90% purity) as a clear colourless oil. $^1H$ NMR (400 MHz, DMSO-d6) δ 7.02 (t, J=5.9 Hz, 1H), 3.72 (d, J=5.9 Hz, 2H), 2.37 (t, J=7.3 Hz, 2H), 1.49-1.41 (m, 2H), 1.39 (s, 9H), 1.27-1.19 (m, 10H), 0.93-0.80 (m, 3H).

Step 2

HCl (4 M in 1,4-dioxane, 46 mL, 0.18 mol) was added dropwise to a solution of tert-butyl (2-oxodecyl)carbamate (16.5 g, 56 mmol, 90% purity) in 1,4-dioxane (100 mL) at 0° C. The reaction was stirred for 18 h at RT. HCl (4 M in 1,4-dioxane, 18 mL, 72 mmol) was added and the mixture stirred for a further 2 h at RT. The mixture was concentrated to afford 1-aminodecan-2-one hydrochloride (13.0 g, 53 mmol, 85% purity) as a pale brown solid which was used without further purification. $^1H$ NMR (400 MHz, DMSO-d6) δ 7.98 (s, 3H), 3.91 (s, 2H), 2.53-2.48 (m, 2H), 1.55-1.46 (m, 2H), 1.34-1.15 (m, 10H), 0.95-0.75 (m, 3H).

Intermediate 81—2-(4-(1-(trifluoromethyl)cyclopropyl)phenyl)acetic acid

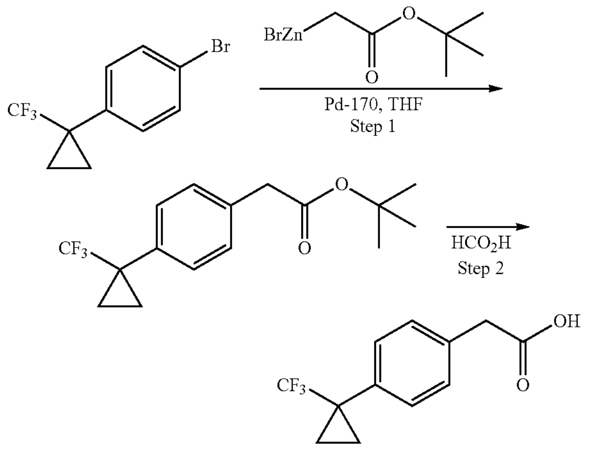

Step 1

A solution of 1-bromo-4-(1-(trifluoromethyl)cyclopropyl)benzene (1.00 g, 3.77 mmol) and Pd-170 (50 mg, 75 μmol) in THF (20 mL) was degassed with nitrogen for 10 min. A solution of (2-(tert-butoxy)-2-oxoethyl)zinc(II) bromide (0.45 M in THF, 9.2 mL) was added dropwise. The reaction was stirred at RT for 1.5 h, then heated to 75° C. and stirred for 16 h. The reaction was cooled to RT and poured into water (20 mL). The phases were separated and the aqueous layer was extracted with EtOAc (3×20 mL). The combined organic layers were washed with brine (20 mL), dried ($Na_2SO_4$) and concentrated. The crude product was purified by chromatography on silica gel (0-10% EtOAc/isohexane) to afford tert-butyl 2-(4-(1-(trifluoromethyl)cyclopropyl)phenyl)acetate (0.653 g, 2.2 mmol) as a clear yellow oil. $^1H$ NMR (400 MHz, DMSO-d6) δ 7.41 (d, J=8.0 Hz, 2H), 7.31-7.20 (m, 2H), 3.57 (s, 2H), 1.41 (s, 9H), 1.35-1.30 (m, 2H), 1.14-1.08 (m, 2H).

Step 2

A mixture of tert-butyl 2-(4-(1-(trifluoromethyl)cyclopropyl)phenyl)acetate (0.653 g, 2.2 mmol) and formic acid (4.1 mL, 109 mmol) was stirred at RT for 16 h. The mixture was concentrated and the residue co-evaporated with toluene (2×10 mL) to afford 2-(4-(1-(trifluoromethyl)cyclopropyl)phenyl)acetic acid (0.625 g, 2.1 mmol, 84% purity) as a colourless oil. $^1H$ NMR (400 MHz, DMSO-d6) δ 12.37 (s, 1H), 7.40 (d, J=8.0 Hz, 2H), 7.28 (d, J=7.9 Hz, 2H), 3.58 (s, 2H), 1.36-1.29 (m, 2H), 1.14-1.07 (m, 2H).

Intermediate 113—2-(3-propylphenyl)acetonitrile

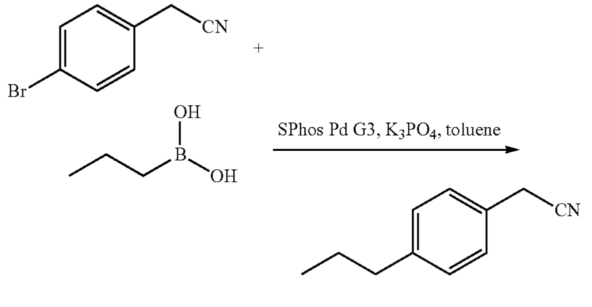

A flask was charged with 2-(4-bromophenyl)acetonitrile (1.5 g, 7.7 mmol), propylboronic acid (1.0 g, 11 mmol) and potassium phosphate (3.2 g, 15 mmol) and SPhos Pd G3 (0.12 g, 0.15 mmol). The flask was evacuated/backfilled with nitrogen (3×). Toluene (20 mL) was added and the mixture was heated to 90° C. for 2 h, then cooled to RT, filtered and concentrated. The crude product was purified by chromatography on silica gel (0-10% EtOAc/isohexane) to afford 2-(4-propylphenyl)acetonitrile (0.98 g, 5.8 mmol) as a clear colourless oil. $^1H$ NMR (400 MHz, DMSO-d6) δ 7.26 (d, J=8.4 Hz, 2H), 7.21 (d, J=8.2 Hz, 2H), 3.98 (s, 2H), 2.58-2.53 (m, 2H), 1.66-1.48 (m, 2H), 0.88 (t, J=7.3 Hz, 3H).

Intermediate 114—4-(1,1-difluoropropyl)benzonitrile

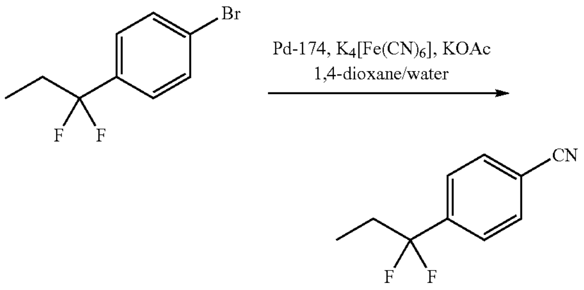

A mixture of potassium acetate (209 mg, 2.1 mmol), potassium ferrocyanide (783 mg, 2.1 mmol) and 1-bromo-4-(1,1-difluoropropyl)benzene (1.00 g, 4.3 mmol) in 1,4-dioxane (10 mL) and water (10 mL) was sparged with nitrogen for 10 min before the addition of Pd-174 (153 mg, 210 μmol). Sparging was continued for an additional 2 min and the mixture was heated to 100° C. for 1 h. The mixture was cooled to RT and poured into water (50 mL) and extracted with EtOAc (35 mL). The aqueous layer was extracted with EtOAc (2×35 mL) and the combined organic layers were washed with brine (50 mL), dried ($Na_2SO_4$) and concentrated. The crude product was purified by chromatography on silica gel (0-10% EtOAc/isohexane) to afford 4-(1,1-difluoropropyl)benzonitrile (0.780 g, 3.3 mmol, 77% purity) as a colourless oil. $^1H$ NMR (400 MHz, DMSO-d6) δ 8.04-7.96 (m, 2H), 7.77-7.71 (m, 2H), 2.25 (tq, J=17.0, 7.4 Hz, 2H), 0.91 (t, J=7.4 Hz, 3H).

The following compounds were synthesised using the same procedure.

| Int. Number | Structure/Name | Characterising data |
| --- | --- | --- |
| 115 | 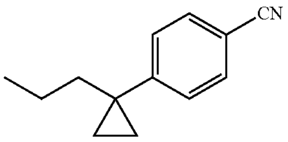 4-(1-propylcyclopropyl)benzonitrile | $^1H$ NMR (400 MHz, DMSO-d6) δ 7.75-7.71 (m, 2H), 7.46-7.42 (m, 2H), 1.62-1.55 (m, 2H), 1.26-1.16 (m, 2H), 0.85-0.75 (m, 7H) |
| 116 | 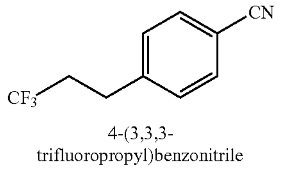 [SMILES: N#Cc1ccc(CCC(F)(F)F)cc1] 4-(3,3,3-trifluoropropyl)benzonitrile | $^1H$ NMR (400 MHz, DMSO-d6) δ 7.79 (d, J = 8.2 Hz, 2H), 7.53 (d, J = 8.0 Hz, 2H), 2.97-2.89 (m, 2H), 2.72-2.58 (m, 2H) |
| 117 | 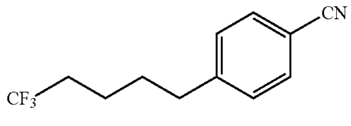 4-(5,5,5-trifluoropentyl)benzonitrile | $^1H$ NMR (400 MHz, DMSO-d6) δ 7.81-7.69 (m, 2H), 7.43 (d, J = 7.9 Hz, 2H), 2.70 (t, J = 7.7 Hz, 2H), 2.37-2.17 (m, 2H), 1.66 (p, J = 7.6 Hz, 2H), 1.48 (tt, J = 9.6, 6.3 Hz, 2H) |
| 118 | 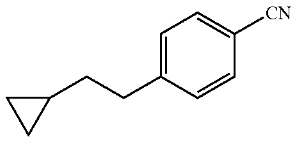 4-(2-cyclopropylethyl)benzonitrile | $^1H$ NMR (400 MHz, DMSO-d6) δ 7.73 (d, J = 8.0 Hz, 2H), 7.42 (d, J = 8.0 Hz, 2H), 2.78-2.71 (m, 2H), 1.48 (q, J = 7.2 Hz, 2H), 0.73-0.61 (m, 1H), 0.43-0.33 (m, 2H), 0.08--0.03 (m, 2H) |

-continued

| Int. Number | Structure/Name | Characterising data |
|---|---|---|
| 119 | 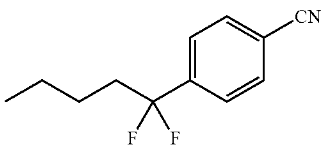 4-(1,1-difluoropentyl)benzonitrile | $^1$H NMR (400 MHz, DMSO-d6) δ 7.99 (d, J = 8.2 Hz, 2H), 7.74 (d, J = 8.2 Hz, 2H), 2.31-2.14 (m, 2H), 1.36-1.23 (m, 4H), 0.89-0.80 (m, 3H) |
| 120 | 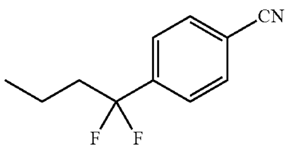 4-(1,1-difluorobutyl)benzonitrile | $^1$H NMR (400 MHz, DMSO-d6) δ 7.99 (d, J = 8.4 Hz, 2H), 7.79-7.71 (m, 2H), 2.29-2.12 (m, 2H), 1.41-1.28 (m, 2H), 0.89 (t, J = 7.4 Hz, 3H). $^{19}$F NMR (376 MHz, DMSO-d6) δ −94.17 |

Intermediate 121—1-bromo-4-(1-propylcyclopropyl)benzene

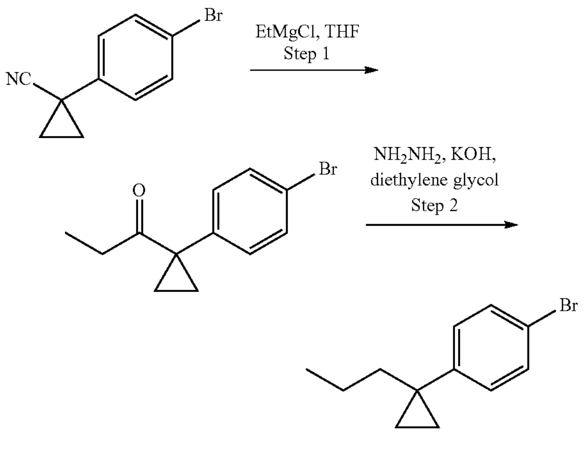

Step 1

A solution of ethylmagnesium chloride (2 M in THF, 14 mL, 28 mmol) was added dropwise to a solution of 1-(4-bromophenyl)cyclopropane-1-carbonitrile (5.00 g, 22.5 mmol) in THF (40 mL) at RT. The mixture was then stirred at 70° C. for 4 h, cooled to RT and poured into sat. $NH_4Cl$ (75 mL). Dilute $H_2SO_4$ (1 M, 15 mL) was added and the mixture was stirred for 10 min, then extracted with EtOAc (3×30 mL). The combined organic layers were washed with brine, dried ($Na_2SO_4$) and concentrated. The crude product was purified by chromatography on silica gel (0-10% EtOAc/isohexane) to afford 1-(1-(4-bromophenyl)cyclopropyl)propan-1-one (4.61 g, 18.2 mmol) as a clear colourless oil. $^1$H NMR (400 MHz, DMSO-d6) δ 7.57-7.51 (m, 2H), 7.39-7.32 (m, 2H), 2.25 (q, J=7.1 Hz, 2H), 1.50-1.42 (m, 2H), 1.17-1.10 (m, 2H), 0.82 (t, J=7.1 Hz, 3H).

Step 2

A solution of 1-(1-(4-bromophenyl)cyclopropyl)propan-1-one (4.61 g 18.2 mmol), hydrazine hydrate (2.7 mL, 54.6 mmol) and potassium hydroxide (3.07 g, 54.6 mmol) in diethylene glycol (35 mL) was heated to 200° C. for 3 h. The mixture was cooled to RT and poured into water (100 mL). The mixture was extracted with EtOAc (3×50 mL) and the combined organic layers were washed with brine (100 mL), dried ($Na_2SO_4$) and concentrated. The crude product was purified by chromatography on silica gel (0-10% EtOAc/isohexane) to afford 1-bromo-4-(1-propylcyclopropyl)benzene (3.73 g, 15 mmol) as a clear colourless oil. $^1$H NMR (400 MHz, DMSO-d6) δ 7.48-7.42 (m, 2H), 7.25-7.19 (m, 2H), 1.55-1.49 (m, 2H), 1.26-1.15 (m, 2H), 0.81 (t, J=7.4 Hz, 3H), 0.75-0.71 (m, 2H), 0.71-0.66 (m, 2H).

Intermediate 122—1-bromo-4-(5,5,5-trifluoropentyl)benzene

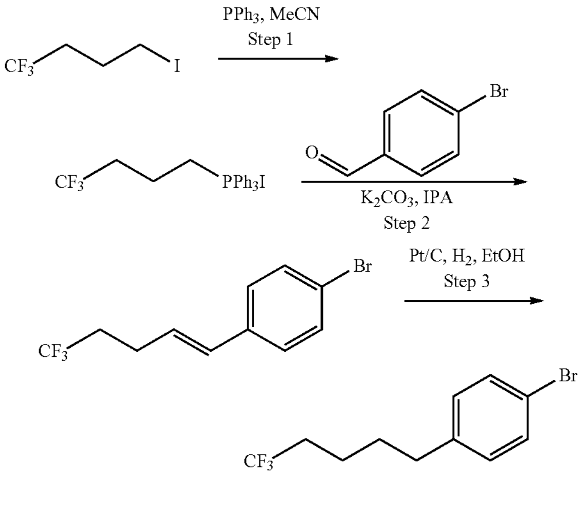

Step 1

A mixture of 1,1,1-trifluoro-4-iodobutane (2.7 mL, 21 mmol) and triphenylphosphane (5.50 g, 21 mmol) in MeCN (20 ml) was heated to reflux for 18 h. The mixture was cooled to RT and concentrated. The residue was suspended in toluene (15 ml) and stirred at 85° C. for 10 min. The mixture was cooled to RT and the precipitate was collected by filtration. The solid was washed with toluene (2×20 mL) to afford triphenyl(4,4,4-trifluorobutyl)phosphonium iodide (10.5 g, 19 mmol, 90% purity) as a white solid. LCMS m/z 373.0 (M–I)$^+$ (ES$^+$). $^1$H NMR (400 MHz, DMSO-d6) δ 7.94-7.80 (m, 9H), 7.80-7.68 (m, 6H), 4.15-4.00 (m, 2H), 2.79-2.64 (m, 2H), 2.05-1.83 (m, 2H).

Step 2

Potassium carbonate (4.66 g, 33.7 mmol) was added to a solution of 4-bromobenzaldehyde (3.40 g, 18.3 mmol) and triphenyl(4,4,4-trifluorobutyl)phosphonium iodide (10.2 g, 18.3 mmol, 90% purity) in IPA (100 mL). The mixture was heated to 80° C. and stirred for 17 h. The mixture was cooled to RT and concentrated. The resulting solid was suspended in DCM (100 mL), filtered and the filtrate concentrated. The crude product was purified by chromatography on silica gel (0-10% DCM/isohexane to afford (E)-1-bromo-4-(5,5,5-trifluoropent-1-en-1-yl)benzene (4.81 g, 16 mmol) as a clear and colourless oil as a 83:17 mixture of isomers. $^1$H NMR (400 MHz, DMSO-d6) δ 7.54-7.48 (m, 2H), 7.39-7.31 (m, 2H), 6.53-6.47 (m, 1H), 6.36-6.31 (m, 1H), 2.49-2.37 (m, 4H) [data corresponds to (E)-isomer].

Step 3

A suspension of (E)-1-bromo-4-(5,5,5-trifluoropent-1-en-1-yl)benzene (4.81 g, 16 mmol) and 1% Pt/C (50% wet, 950 mg) in EtOH (75 mL) was stirred at RT under an atmosphere of hydrogen (1 bar) for 2 h. The mixture was filtered and concentrated. The crude product was purified by chromatography on silica gel (100% iso-hexane) to afford 1-bromo-4-(5,5,5-trifluoropentyl)benzene (4.33 g, 14 mmol, 90% purity) as a clear and colourless liquid. $^1$H NMR (400 MHz, DMSO-d6) δ 7.50-7.44 (m, 2H), 7.20-7.15 (m, 2H), 2.59 (t, J=7.6 Hz, 2H), 2.36-2.18 (m, 2H), 1.69-1.55 (m, 2H), 1.54-1.43 (m, 2H).

Intermediate 123—1-bromo-4-(2-cyclopropylethyl)benzene

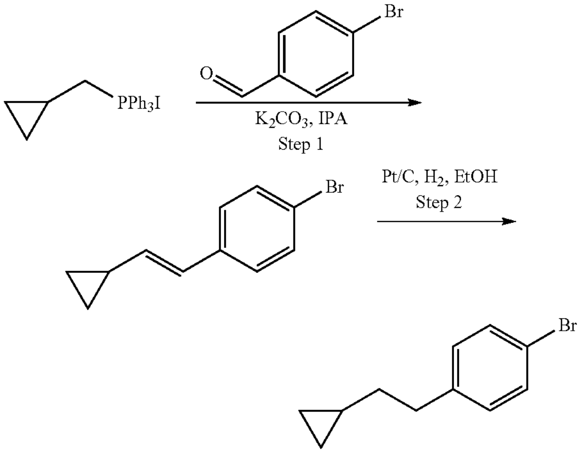

Step 1

Potassium carbonate (5.70 g, 41.2 mmol) was added to a solution of 4-bromobenzaldehyde (4.05 g, 21.9 mmol) and triphenyl(cyclopropylmethyl)phosphonium iodide (9.72 g, 21.9 mmol) in IPA (100 mL). The mixture was heated to 80° C. and stirred for 17 h. The mixture was cooled to RT and concentrated. The resulting solid was suspended in DCM (100 mL), filtered and the filtrate concentrated. The crude product was purified by chromatography on silica gel (0-10% DCM/isohexane to afford (E)-1-bromo-4-(2-cyclopropylvinyl)benzene (4.28 g, 18 mmol) as a white solid as a 76:24 mixture of isomers. $^1$H NMR (400 MHz, DMSO-d6) δ 7.49-7.42 (m, 2H), 7.33-7.26 (m, 2H), 6.44 (d, J=15.9 Hz, 1H), 5.89 (dd, J=15.9, 9.1 Hz, 1H), 1.63-1.46 (m, 1H), 0.87-0.74 (m, 2H), 0.58-0.46 (m, 2H) [data corresponds to (E)-isomer].

Step 2

A suspension of (E)-1-bromo-4-(2-cyclopropylvinyl)benzene (4.28 g, 18 mmol) and 1% Pt/C (50% wet, 800 mg) in EtOH (60 mL) was stirred at RT under an atmosphere of hydrogen (1 bar) for 6 h. The mixture was filtered and concentrated. The crude product was purified by chromatography on silica gel (100% iso-hexane) to afford 1-bromo-4-(2-cyclopropylethyl)benzene (4.46 g, 12 mmol, 61% purity) as a clear and colourless liquid. $^1$H NMR (400 MHz, DMSO-d6) δ 7.49-7.39 (m, 2H), 7.22-7.13 (m, 2H), 2.68-2.58 (m, 2H), 1.49-1.44 (m, 1H), 0.90-0.81 (m, 1H), 0.72-0.59 (m, 1H), 0.43-0.29 (m, 2H), 0.09--0.03 (m, 2H).

Intermediate 124—1-bromo-4-(1,1-difluoropentyl)benzene

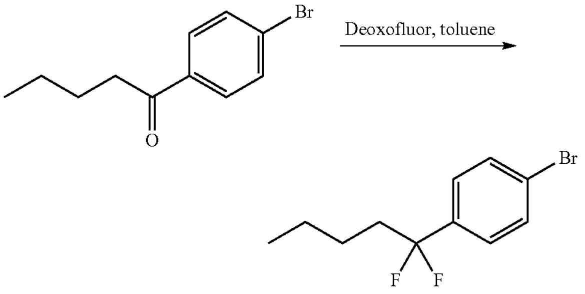

A PTFE flask was charged with 1-(4-bromophenyl)pentan-1-one (2.50 g, 10.4 mmol). Deoxofluor (50 wt % in toluene, 19 mL, 52 mmol) was added dropwise at RT. The mixture was heated to 80° C. for 16 h, then cooled to RT and poured into sat. aq. $NaHCO_3$ (100 mL) and extracted with EtOAc (3×50 mL). The combined organic layers were washed with brine (70 mL), dried ($Na_2SO_4$) and concentrated. The crude product was purified by chromatography on silica gel (0-10% EtOAc/isohexane) to afford 1-bromo-4-(1,1-difluoropentyl)benzene (1.96 g, 7.2 mmol) as a clear colourless oil. $^1$H NMR (400 MHz, DMSO-d6) δ 7.74-7.67 (m, 2H), 7.52-7.44 (m, 2H), 2.27-2.11 (m, 2H), 1.37-1.23 (m, 4H), 0.90-0.81 (m, 3H).

The following compound was synthesised using the same procedure.

| Int. Number | Structure/Name | Characterising data |
| --- | --- | --- |
| 125 | 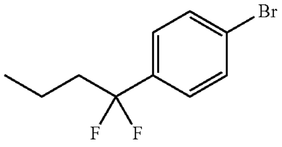 1-bromo-4-(1,1-difluorobutyl)benzene | $^{1}H$ NMR (400 MHz, DMSO-d6) δ 7.70 (d, J = 8.2 Hz, 2H), 7.47 (d, J = 8.2 Hz, 2H), 2.25-2.07 (m, 2H), 1.39-1.27 (m, 2H), 0.89 (t, J = 7.4 Hz, 3H). $^{19}F$ NMR (376 MHz, DMSO-d6) δ −92.91. |

Intermediate 126—2-(4-(1,1,2,2-tetrafluoroethoxy) phenyl)acetonitrile

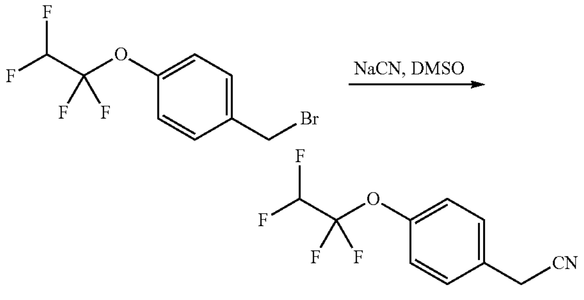

Sodium cyanide (1.54 g, 31.4 mmol) was added to a solution of 1-(bromomethyl)-4-(1,1,2,2-tetrafluoroethoxy) benzene (6.00 g, 20.9 mmol) in DMSO (30 mL) and the mixture was heated to 90° C. for 3 h, then cooled to RT and stirred for 18 h. The mixture was partitioned between EtOAc (150 mL) and 1:1 v/v water/brine (150 mL). The organic layer was washed with 1:1 v/v water/brine (2×150 mL). The combined aqueous washings were extracted with EtOAc (150 ml). The combined organic extracts were washed with 1:1 v/v water/brine (150 mL), dried ($Na_2SO_4$) and concentrated to afford 2-(4-(1,1,2,2-tetrafluoroethoxy)phenyl)acetonitrile (4.76 g, 20 mmol) as a yellow oil. $^{1}H$ NMR (400 MHz, $CDCl_3$) δ 7.42-7.32 (m, 2H), 7.24 (d, J=8.4 Hz, 2H), 5.91 (tt, J=53.0, 2.8 Hz, 1H), 3.77 (s, 2H).

Intermediate 127—tert-butyl 2-(diethoxyphosphoryl)-4-(hydroxyamino)-4-iminobutanoate

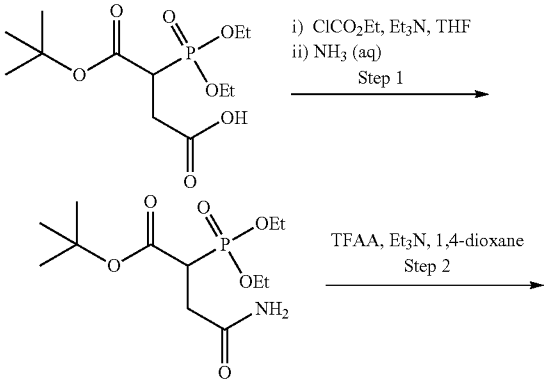

-continued

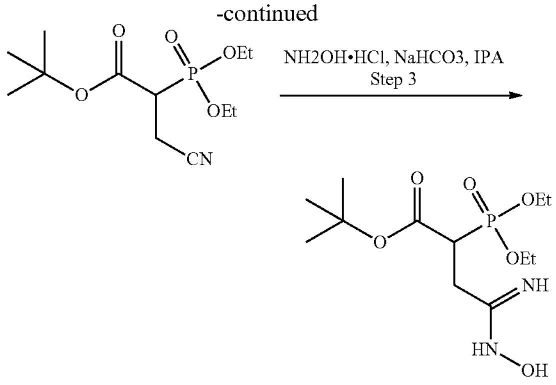

Step 1

Ethyl chloroformate (8.1 mL, 85 mmol) was added dropwise to a solution of 4-(tert-butoxy)-3-(diethoxyphosphoryl)-4-oxobutanoic acid (25.0 g, 80.6 mmol) and triethylamine (12.0 mL, 86 mmol) in THF (200 mL) at 0° C. The mixture was stirred for 30 min, then further triethylamine (3.0 mL, 22 mmol) and ethyl chloroformate (2.0 mL, 21 mmol) were added. After 1 h, ammonia (30% aqueous, 25 mL, 0.39 mol) was added dropwise. The mixture was stirred for 1 h at RT, then concentrated to ca. 50 mL. The mixture was diluted with water (300 mL) and extracted with EtOAc (5×200 mL). The combined organic phases were washed with sat. aq. $NH_4Cl$ (400 mL), brine (400 mL), dried ($Na_2SO_4$) and concentrated. The residue was triturated with MTBE (200 mL) and the resulting solid was isolated by filtration to afford tert-butyl 4-amino-2-(diethoxyphosphoryl)-4-oxobutanoate (10.66 g, 34 mmol) as a white solid. LCMS m/z 254.2 $(M-tBu+H)^+$ $(ES^+)$. $^{1}H$ NMR (400 MHz, DMSO-d6) δ 7.41 (s, 1H), 6.89 (s, 1H), 4.10-3.97 (m, 4H), 3.21 (ddd, J=23.3, 11.5, 3.4 Hz, 1H), 2.69 (ddd, J=16.3, 11.5, 7.2 Hz, 1H), 2.39 (ddd, J=16.4, 9.6, 3.4 Hz, 1H), 1.38 (s, 9H), 1.24 (q, J=7.2 Hz, 6H). $^{31}P$ NMR (162 MHz, DMSO-d6) δ 23.19.

Step 2

Trifluoroacetic anhydride (17.9 mL, 129 mmol) was added portionwise at 0° C. to a stirred solution of tert-butyl 4-amino-2-(diethoxyphosphoryl)-4-oxobutanoate (12.85 g, 41.6 mmol) and triethylamine (18.0 mL, 129 mmol) in 1,4-dioxane (100 mL). The reaction was allowed to warm to RT. and stirred for 60 h. The reaction mixture was quenched with water (100 mL) and mixture was part concentrated. The mixture was extracted with EtOAc (2×150 mL). The combined organic extracts were washed with brine (200 mL), dried ($MgSO_4$) and concentrated. The crude product was purified by chromatography on silica gel (0-100% EtOAc/isohexane) to afford tert-butyl 3-cyano-2-(diethoxyphosphoryl)propanoate (6.63 g, 22 mmol) as a brown oil. LCMS m/z 236.2 $(M-tBu+H)^+$ $(ES^+)$. $^{1}H$ NMR (400 MHz, DMSO-d6)

δ 4.14-4.03 (m, 4H), 3.59 (ddd, J=23.8, 8.1, 5.9 Hz, 1H), 2.90-2.75 (m, 2H), 1.44 (s, 9H), 1.29-1.22 (m, 6H).

Step 3

A mixture of hydroxylamine hydrochloride (2.30 g, 33.1 mmol) and sodium bicarbonate (2.78 g, 33.1 mmol) in 2-propanol (45 mL) was stirred for 15 min before tert-butyl 3-cyano-2-(diethoxyphosphoryl)propanoate (6.63 g, 22.1 mmol) was added and the mixture stirred at reflux for 18 h. The reaction mixture was cooled to RT and filtered. The filtrate was concentrated. The crude product was purified by chromatography on silica gel (0-20% MeOH/DCM) to afford tert-butyl 2-(diethoxyphosphoryl)-4-(hydroxyamino)-4-iminobutanoate (4.83 g, 15 mmol) as a waxy pale green solid. LCMS m/z 325.3 $(M+H)^+$ $(ES^+)$. $^1H$ NMR (400 MHz, DMSO-d6) δ 8.93 (s, 1H), 5.40 (s, 2H), 4.10-3.96 (m, 4H), 3.25 (ddd, J=23.0, 11.8, 3.1 Hz, 1H), 2.57 (ddd, J=15.9, 11.7, 6.8 Hz, 1H), 2.37 (ddd, J=15.9, 10.2, 3.1 Hz, 1H), 1.38 (s, 9H), 1.24 (q, J=7.0 Hz, 6H).

Intermediate 128—2-(4-bromophenyl)-2,2-difluoro-acetonitrile

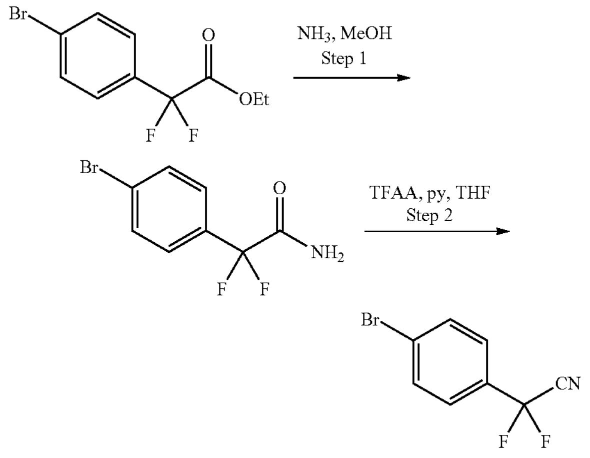

Step 1

A mixture of ethyl 2-(4-bromophenyl)-2,2-difluoroacetate (3.5 g, 13 mmol) and ammonia (7 M in methanol, 20 mL, 0.92 mol) was stirred at RT for 16 h. The mixture was concentrated to afford 2-(4-bromophenyl)-2,2-difluoroacetamide (3.0 g, 10 mmol, 90% purity) as a pale yellow solid. $^1H$ NMR (400 MHz, DMSO-d6) δ 8.38 (s, br. 1H), 8.05 (s, br. 1H), 7.80-7.70 (m, 2H), 7.57-7.47 (m, 2H).

Step 2

TFAA (1.2 mL, 8.6 mmol) was added dropwise to a solution of 2-(4-bromophenyl)-2,2-difluoroacetamide (2.0 g, 7.2 mmol, 90% purity) and pyridine (1.7 mL, 22 mmol) in THF (30 mL) at 0° C. The mixture was stirred at 0° C. for 1 h then allowed to warm to RT and stirred for a further 20 min. The mixture was poured into water (80 mL) and extracted with EtOAc (3×80 mL). The combined organic layers were dried ($MgSO_4$) and concentrated to afford 2-(4-bromophenyl)-2,2-difluoroacetonitrile (1.9 g, 7.2 mmol, 90% purity) as a clear, pale orange oil. $^1H$ NMR (400 MHz, DMSO-d6) δ 7.93-7.84 (m, 2H), 7.82-7.73 (m, 2H).

Intermediate 129—2,2-difluoro-2-(4-(trifluoromethyl)phenyl)acetonitrile

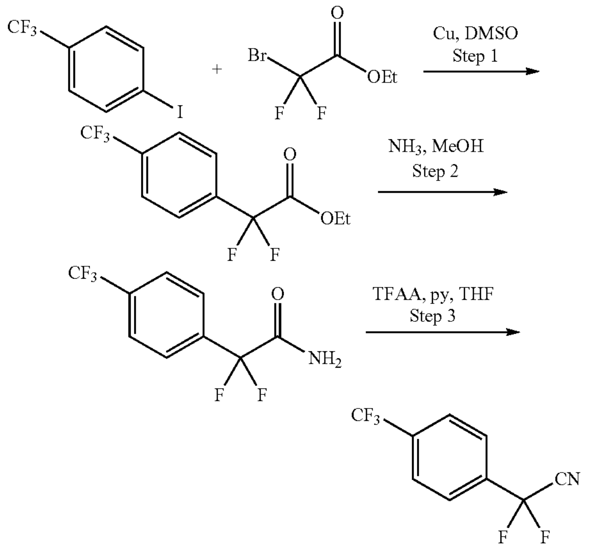

Step 1

1-iodo-4-(trifluoromethyl)benzene (8.0 mL, 54.4 mmol) and ethyl 2-bromo-2,2-difluoroacetate (7.0 mL, 54.4 mmol) were added to a suspension of Copper (8.99 g, 142 mmol) in DMSO (100 mL). The mixture was heated to 60° C. and stirred for 18 h. The mixture was cooled to RT and poured into sat. aq. $NH_4Cl$ (200 mL) and EtOAc (200 mL). The mixture was filtered and the phases were separated. The aqueous phase was extracted with EtOAc (2×100 mL). The combined organic phases were washed with brine (200 mL), dried ($MgSO_4$) and concentrated. The crude product was purified by chromatography on silica gel (0-20% MTBE/isohexane) to afford ethyl 2,2-difluoro-2-(4-(trifluoromethyl)phenyl)acetate (13.17 g, 45 mmol, 92% purity) as a colourless oil. $^1H$ NMR (400 MHz, DMSO-d6) δ 7.95 (d, J=8.2 Hz, 2H), 7.85 (d, J=8.2 Hz, 2H), 4.32 (q, J=7.1 Hz, 2H), 1.23 (t, J=7.1 Hz, 3H). $^{19}F$ NMR (376 MHz, DMSO-d6) δ −61.64, −102.28.

Step 2

Prepared according to the procedure described for Intermediate 128, Step 1 from ethyl 2,2-difluoro-2-(4-(trifluoromethyl)phenyl)acetate (8.00 g, 29.8 mmol) to afford 2,2-difluoro-2-(4-(trifluoromethyl)phenyl)acetamide (5.25 g, 22 mmol) as a white solid. $^1H$ NMR (400 MHz, DMSO-d6) δ 8.47 (br. s, 1H), 8.12 (br. s, 1H), 7.93 (d, J=8.2 Hz, 2H), 7.82 (d, J=8.2 Hz, 2H). $^{19}F$ NMR (376 MHz, DMSO-d6) δ −61.49, −102.79.

Step 3

Prepared according to the procedure described for Intermediate 128, Step 2 from 2,2-difluoro-2-(4-(trifluoromethyl)phenyl)acetamide (5.25 g, 22 mmol) to afford 2,2-difluoro-2-(4-(trifluoromethyl)phenyl)acetonitrile (3.35 g, 15 mmol) as a colourless oil. $^1H$ NMR (400 MHz, DMSO-d6) δ 8.07 (d, J=8.7 Hz, 2H), 8.04 (d, J=8.8 Hz, 2H). $^{19}F$ NMR (376 MHz, DMSO-d6) δ −61.90, −83.33.

The following compounds were synthesised using the same procedure.

| Int. Number | Structure/Name | Characterising data |
|---|---|---|
| 130 | 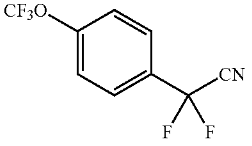 2,2-difluoro-2-(4-(trifluoromethoxy)phenyl)acetonitrile | $^1$H NMR (400 MHz, DMSO-d6) δ 8.09-7.90 (m, 2H), 7.73-7.56 (m, 2H). $^{19}$F NMR (376 MHz, DMSO-d6) δ −56.82, −81.95 |
| 197 | 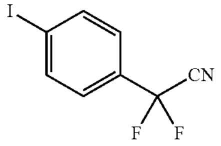 2,2-difluoro-2-(4-iodophenyl)acetonitrile | $^1$H NMR (400 MHz, DMSO-d6) δ 8.12-7.97 (m, 2H), 7.65-7.51 (m, 2H) |
| 198 | 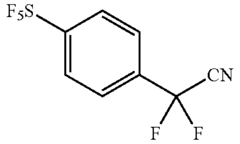 2,2-difluoro-2-(4-(pentafluoro-λ$^6$-sulfaneyl)phenyl)acetonitrile | $^1$H NMR (400 MHz, DMSO-d6) δ 8.25-8.17 (m, 2H), 8.14-8.05 (m, 2H). $^{19}$F NMR (376 MHz, DMSO-d6) δ −83.43 |
| 199 | 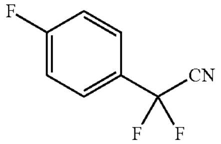 2,2-difluoro-2-(4-fluorophenyl)acetonitrile | $^1$H NMR (400 MHz, DMSO-d6) δ 8.03-7.82 (m, 2H), 7.51 (t, J = 8.8 Hz, 2H). $^{19}$F NMR (376 MHz, DMSO-d6) δ −81.05 (d, J = 3.6 Hz), −105.97 |
| 200 | 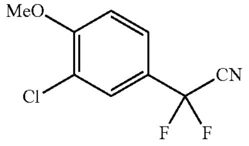 2-(3-chloro-4-methoxyphenyl)-2,2-difluoroacetonitrile | $^1$H NMR (400 MHz, DMSO-d6) δ 7.99-7.87 (m, 1H), 7.82-7.73 (m, 1H), 7.39 (d, J = 8.7 Hz, 1H), 3.96 (s, 3H) |
| 201 | 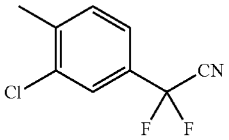 2-(3-chloro-4-methoxyphenyl)-2,2-difluoroacetonitrile | $^1$H NMR (400 MHz, DMSO-d6) δ 7.91-7.88 (m, 1H), 7.74-7.68 (m, 1H), 7.65 (d, J = 8.1 Hz, 1H), 2.43 (s, 3H) |
| 202 | 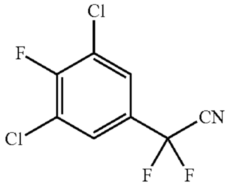 2-(3,5-dichloro-4-methoxyphenyl)-2,2-difluoroacetonitrile | $^1$H NMR (400 MHz, DMSO-d6) δ 8.81-7.95 (m, 2H). $^{19}$F NMR (376 MHz, DMSO-d6) δ −82.95 (d, J = 3.3 Hz), −109.72 |

-continued

| Int. Number | Structure/Name | Characterising data |
|---|---|---|
| 203 | 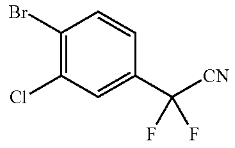 2-(4-bromo-3-chlorophenyl)-2,2-difluoro-N-hydroxyacetimidamide | $^1$H NMR (400 MHz, DMSO-d6) δ 8.19-8.12 (m, 1H), 8.07 (dd, J = 8.4, 1.0 Hz, 1H), 7.73 (ddd, J = 8.4, 2.3, 1.1 Hz, 1H). $^{19}$F NMR (376 MHz, DMSO-d6) δ −83.06 |
| 204 | 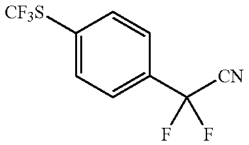 2,2-difluoro-2-(4-((trifluoromethyl)thio)phenyl) acetonitrile | $^1$H NMR (400 MHz, DMSO-d6) δ 8.03-7.97 (m, 4H). $^{19}$F NMR (376 MHz, DMSO-d6) δ −41.22, −82.99. |

Intermediate 131—2-(4-(1,1-difluoropentyl)phenyl) acetonitrile

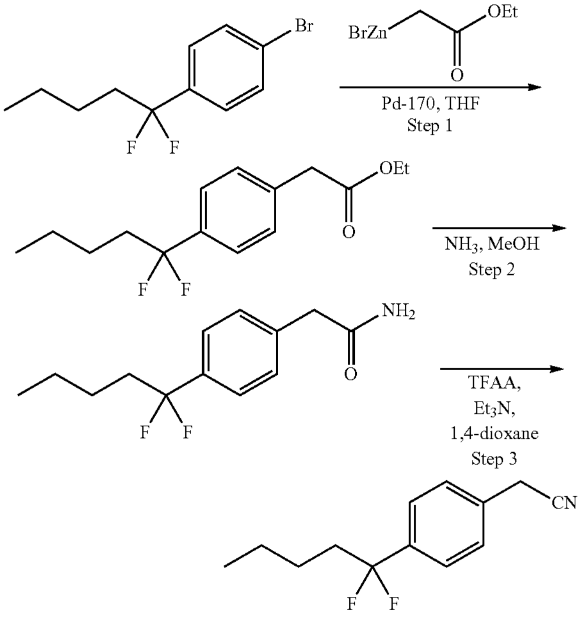

Step 1

A solution of 1-bromo-4-(1,1-difluoropentyl)benzene (1.00 g, 3.80 mmol) and Pd-170 (51 mg, 76 μmol) in THF (20 mL) was sparged for 10 min with nitrogen. (2-Ethoxy-2-oxoethyl)zinc(II) bromide (0.34 M in THF, 25 mL, 8.4 mmol) was added dropwise. The mixture was heated to 75° C. and stirred for 16 h, then cooled to RT and poured into water (20 mL). The mixture was separated and the aqueous layer was extracted with EtOAc (3×20 mL). The combined organic layers were washed with brine (20 mL), dried ($Na_2SO_4$) and concentrated. The crude product was purified by chromatography on silica gel (0-10% EtOAc/isohexane) to afford ethyl 2-(4-(1,1-difluoropentyl)phenyl)acetate (0.651 g, 2.4 mmol) as a clear yellow oil. $^1$H NMR (400 MHz, DMSO-d6) δ 7.46 (d, J=8.2 Hz, 2H), 7.37 (d, J=8.1 Hz, 2H), 4.09 (q, J=7.1 Hz, 2H), 3.73 (s, 2H), 2.26-2.10 (m, 2H), 1.34-1.25 (m, 4H), 1.18 (t, J=7.1 Hz, 3H), 0.87-0.81 (m, 3H). $^{19}$F NMR (376 MHz, DMSO-d6) δ −92.45.

Step 2

A large Biotage microwave vial was charged with ethyl 2-(4-(1,1-difluoropentyl)phenyl)acetate (0.65 g, 2.4 mmol) and ammonia (7 M in MeOH, 6.9 mL, 48 mmol). The vial was sealed and heated to 75° C. for 16 h. The mixture was cooled to RT and concentrated. The vessel was recharged with ammonia (7 M in MeOH, 6.9 mL, 48 mmol) and heated at 75° C. for 16 h. The mixture was concentrated. The crude product was purified by chromatography on silica gel (0-10% MeOH/DCM) to afford 2-(4-(1,1-difluoropentyl) phenyl)acetamide (0.471 g, 1.9 mmol) as a white solid. LCMS m/z 242.1 $(M+H)^+$ $(ES^+)$. $^1$H NMR (400 MHz, DMSO-d6) δ 7.50 (s, 1H), 7.43 (d, J=8.3 Hz, 2H), 7.35 (d, J=8.0 Hz, 2H), 6.91 (s, 1H), 3.42 (s, 2H), 2.25-2.09 (m, 2H), 1.35-1.25 (m, 4H), 0.88-0.81 (m, 3H). $^{19}$F NMR (376 MHz, DMSO-d6) δ −92.25.

Step 3

Prepared according to the procedure described for Intermediate 62, Step 2 from 2-(4-(1,1-difluoropentyl)phenyl) acetamide (0.471 g, 1.9 mmol). The crude product was purified by chromatography on silica gel (0-10% 0-10% EtOAc/isohexane) to afford 2-(4-(1,1-difluoropentyl)phenyl)acetonitrile (0.394 g, 1.7 mmol) as a clear colourless oil. $^1$H NMR (400 MHz, DMSO-d6) δ 7.54 (d, J=8.3 Hz, 2H), 7.46 (d, J=8.1 Hz, 2H), 4.11 (s, 2H), 2.26-2.10 (m, 2H), 1.34-1.22 (m, 4H), 0.90-0.80 (m, 3H). $^{19}$F NMR (376 MHz, DMSO-d6) δ −92.67.

The following compound was synthesised using the same procedure.

| Int. Number | Structure/Name | Characterising data |
|---|---|---|
| 205 | 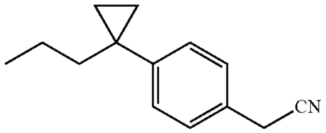 2-(4-(1-propylcyclopropyl)phenyl)acetonitrile | $^1$H NMR (400 MHz, DMSO-d6) δ 7.30-7.22 (m, 4H), 3.97 (s, 2H), 1.55-1.49 (m, 2H), 1.26-1.14 (m, 2H), 0.81 (t, J = 7.3 Hz, 3H), 0.75-0.70 (m, 2H), 0.69-0.64 (m, 2H) |

Intermediate 132—7,7,9,9,9-pentafluorononanenitrile

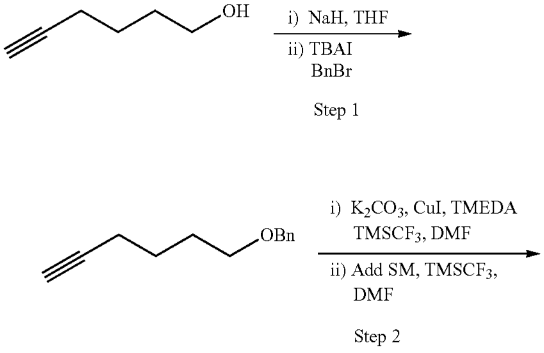

-continued

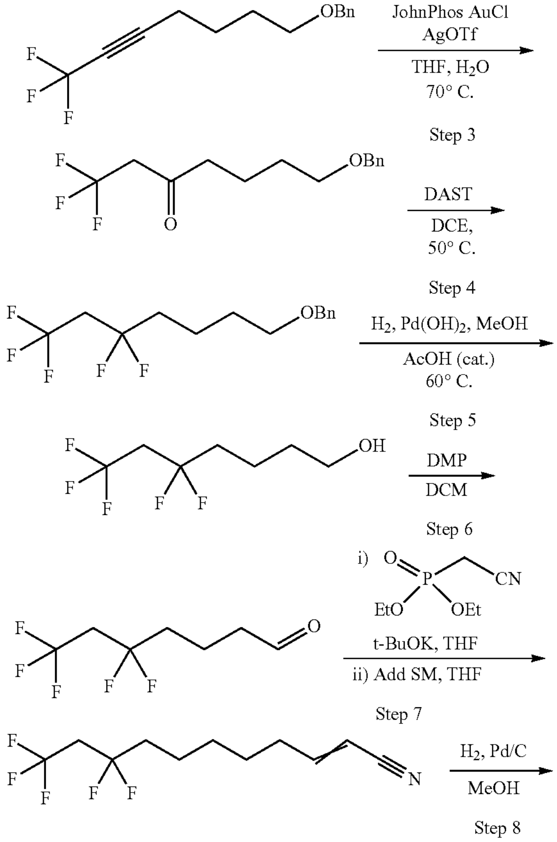

-continued

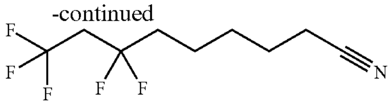

Step 1

NaH suspension in mineral oil (60 wt. %, 16 g, 408 mmol) was added to a solution of hex-5-yn-1-ol (40 g, 408 mmol) in THF (340 mL) at 0° C. and the mixture was stirred until effervescence subsided. Tetrabutylammonium iodide (12.6 g, 34 mmol) and benzyl bromide (58.2 g, 340 mmol) were added, and the mixture was stirred at room temperature for 18 h. Saturated aqueous $NH_4Cl$ solution was added and the reaction mixture was extracted with $Et_2O$. The combined organic phases were washed with brine, dried over $MgSO_4$, filtered, and the filtrate was concentrated under reduced pressure at 40° C. The residue was purified by flash column chromatography (120 g silica, 10-20% EtOAc/petroleum ether) to give ((hex-5-yn-1-yloxy)methyl)benzene (70 g, 372 mmol, 91%) as a pale yellow oil. LCMS: (System 2, Method C) m/z 189.4 $(M+H)^+$ $(ES^+)$.

Step 2

A mixture of CuI (15.2 g, 79.8 mmol), $K_2CO_3$ (36 g, 266 mmol) and N,N,N',N'-tetramethylethylenediamine (9.4 g, 79.8 mmol) in dimethylformamide (540 mL) was vigorously stirred at room temperature under an atmosphere of dry air for 15 min. $TMSCF_3$ (15.2 g, 106 mmol) was added and the resulting deep green mixture was stirred for an additional 5 min, then cooled to 0° C. A solution of ((hex-5-yn-1-yloxy) methyl)benzene (10 g, 53.2 mmol) and $TMSCF_3$ (15.2 g, 106 mmol) in dimethylformamide (540 mL), pre-cooled to 0° C., was then added in one portion. After 30 min at 0° C., the reaction mixture was allowed to warm to room temperature and was stirred for 24 h under an atmosphere of dry air. Water was then added, and the mixture was extracted with $Et_2O$. The combined organic phases were washed with water and brine, then dried over $MgSO_4$ and filtered. The filtrate was concentrated under reduced pressure at 40° C., and the residue was purified by flash column chromatography (120 g silica, 10-20% EtOAc/petroleum ether) to give (((7,7,7-trifluorohept-5-yn-1-yl)oxy)methyl)benzene (6.8 g, 26.5 mmol, 50%) as a pale yellow oil. LCMS: (System 2, Method A) m/z 274.4 $(M+NH_4)^+$ $(ES^+)$.

Step 3

To a solution of (((7,7,7-trifluorohept-5-yn-1-yl)oxy) methyl)benzene (2.5 g, 9.8 mmol) in a mixture of THF (13.5 mL) and $H_2O$ (1.5 mL) was added JohnPhos AuCl (CAS: 854045-93-5) (265 mg, 0.5 mmol) and silver trifluoromethanesulfonate (128 mg, 0.5 mmol) and the vial was wrapped with aluminum foil and heated at 70° C. After 18 h, the reaction mixture was cooled to room temperature, diluted with saturated aqueous $NaHCO_3$ and extracted with DCM (×3). The combined organic phases were dried over $Na_2SO_4$, filtered and concentrated under reduced pressure. The residue was purified by flash column chromatography (80 g silica, 10-30% EtOAc/petroleum ether) to give 7-(benzyloxy)-1,1,1-trifluoroheptan-3-one (2.0 g, 7.3 mmol, 75%) as a pale yellow oil. LCMS: (System 2, Method A) m/z 275.3 $(M+H)^+$ $(ES^+)$.

Step 4

A solution of 7-(benzyloxy)-1,1,1-trifluoroheptan-3-one (6.0 g, 21.9 mmol) and DAST (50 g, 313 mmol) in DCE (60 mL) was stirred at 50° C. overnight. The reaction mixture was poured into ice (50 mL) and extracted with DCM (3×20 mL). The combined organic layers were washed with water (50 mL) and brine (50 mL), dried over $Na_2SO_4$, and filtered. The filtrate was concentrated under reduced pressure at 40° C., and the residue was purified by flash column chromatography (80 g silica, 10-40% EtOAc/petroleum ether) to give (((5,5,7,7,7-pentafluoroheptyl)oxy)methyl)benzene (5.5 g, 18.6 mmol, 85%) as a pale yellow oil. $^1H$ NMR (400 MHz, $CDCl_3$) δ: 7.39-7.25 (m, 5H), 4.50 (s, 2H), 3.49 (t, J=5.9 Hz, 2H), 2.81-2.62 (m, 2H), 2.07-1.88 (m, 2H), 1.73-1.57 (m, 4H). $^{19}F$ NMR (376 MHz, $CDCl_3$) δ: −61.93 (t, J=8.9 Hz), −95.16 (q, J=8.9 Hz).

Step 5

To a solution of (((5,5,7,7,7-pentafluoroheptyl)oxy) methyl)benzene (7.0 g, 23.6 mmol) in MeOH (50 mL) was added 5% $Pd(OH)_2/C$ catalyst (50 wt. % in water, 3.5 g) and AcOH (0.5 mL), and the reaction mixture was stirred at 60° C. overnight under an atmosphere of $H_2$. The reaction mixture was filtered through celite, and the filtrate was concentrated under reduced pressure at 40° C. to 15 give 5,5,7,7,7-pentafluoroheptan-1-ol (4.8 g, 23.3 mmol, 98%) as a pale yellow oil, which was used directly in the next step.

Step 6

To a solution of 5,5,7,7,7-pentafluoroheptan-1-ol (4.8 g, 23.3 mmol) in dichloromethane (80 mL) was added Dess-Martin periodinane (14.8 g, 35 mmol), and the reaction mixture was stirred at room temperature for 30 min. The mixture was quenched with aqueous $Na_2S_2O_3$ (100 mL), diluted with dichloromethane (50 mL) and separated. The aqueous phase was extracted with dichloromethane (2×50 mL), and the combined organic phases were washed with water (2×60 mL) and brine, dried over $MgSO_4$ and filtered. The filtrate was concentrated under reduced pressure at 40° C., and the residue was purified by flash column chromatography (40 g silica, 10-50% EtOAc/petroleum ether) to give 5,5,7,7,7-pentafluoroheptanal (3.6 g, 17.6 mmol, 75%) as a pale yellow oil. $^1H$ NMR (400 MHz, $CDCl_3$) δ: 9.78 (s, 1H), 2.83-2.65 (m, 2H), 2.60-2.51 (m, 2H), 2.08-1.92 (m, 2H), 1.92-1.82 (m, 2H).

Step 7

Potassium tert-butoxide solution in THF (20 wt. %, 15.0 g, 26.4 mmol) was added dropwise to a solution of diethyl cyanomethylphosphonate (4.7 g, 26.4 mmol) in tetrahydrofuran (50 mL) at 0° C. The reaction mixture was warmed to room temperature for 30 min, then cooled to 0° C. and a solution of 5,5,7,7,7-pentafluoroheptanal (3.6 g, 17.6 mmol) in tetrahydrofuran (40 mL) was added. The reaction mixture was allowed to warm to room temperature and was stirred overnight. The mixture was quenched with water and extracted with EtOAc. The combined organic layers were washed with brine, dried over $Na_2SO_4$ and filtered. The filtrate was concentrated under reduced pressure at 40° C., and the residue was purified by flash column chromatography (40 g silica, 10-40% EtOAc/petroleum ether) to give 7,7,9,9,9-pentafluoronon-2-enenitrile (3.5 g, 15.4 mmol, 88%) as a pale yellow oil. $^1H$ NMR (400 MHz, $CDCl_3$) δ: 6.75-6.63 (m, 0.4H), 6.52-6.41 (m, 0.6H), 5.43-5.32 (m, 1H), 2.83-2.64 (m, 2H), 2.55-2.45 (m, 1H), 2.36-2.25 (m, 1H), 2.08-1.89 (m, 2H), 1.79-1.66 (m, 2H). Mixture of E/Z-isomers.

Step 8

A mixture of 7,7,9,9,9-pentafluoronon-2-enenitrile (3.5 g, 15.4 mmol) and 20% Pd/C (50 wt. % in water, 700 mg) in EtOAc (30 mL) was stirred at room temperature overnight under an atmosphere of $H_2$. The reaction mixture was filtered through celite and the filtrate was concentrated under reduced pressure at 40° C. to give 7,7,9,9,9-pentafluorononanenitrile (3.1 g, 13.5 mmol, 88%) as a pale yellow oil. $^1H$ NMR (400 MHz, $CDCl_3$) δ: 2.82-2.64(m, 2H), 2.37 (t, J=7.0 Hz, 2H), 2.06-1.89 (m, 2H), 1.75-1.65 (m, 2H), 1.64-1.47 (m, 4H). $^{19}F$ NMR (376 MHz, $CDCl_3$) δ: −61.97 (t, J=8.9 Hz), −95.23 (q, J=8.9 Hz).

Intermediate 133—tert-butyl 2-(diethoxyphosphoryl)-3-(5-octylisoxazol-3-yl)propanoate

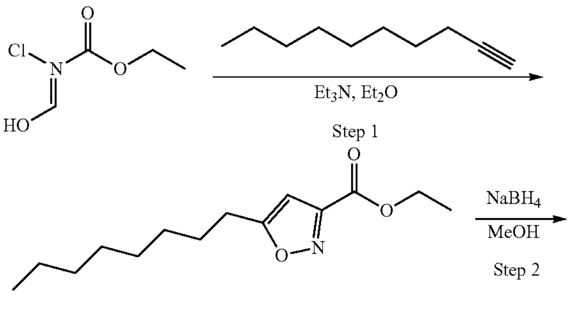

-continued

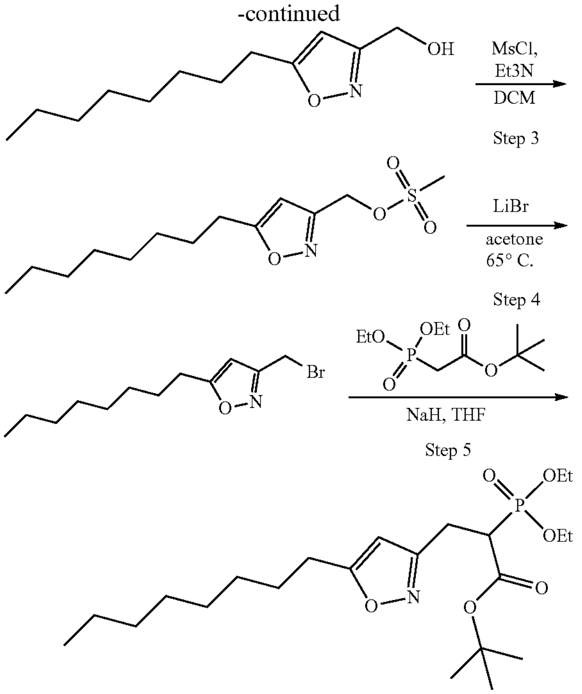

Step 1

To a solution of ethyl 2-chloro-2-(hydroxyimino)acetate (2.00 g, 13.2 mmol) and dec-1-yne (5.48 g 39.7 mmol) in $Et_2O$ (25 mL) at 0° C. was added triethylamine (1.79 mL, 13.2 mmol) and the reaction mixture was stirred at 0° C. for 30 min, then at room temperature for 12 h. The reaction was quenched with water (40 mL), the phases were separated, and the aqueous phase was extracted with ethyl acetate (2×30 mL). The combined organic layers were washed with brine, dried over $Na_2SO_4$ and filtered. The filtrate was concentrated under reduced pressure at 35° C., and the residue was purified by flash column chromatography (1:50-1:10 EtOAc/petroleum ether) to give ethyl 5-octylisoxazole-3-carboxylate (3 g, 11.8 mmol, 90%) as a pale yellow oil. LCMS: (System 2, Method B) m/z 286.3 $(M+H)^+$ $(ES^+)$.

Step 2

To a solution of ethyl 5-octylisoxazole-3-carboxylate (3 g, 11.8 mmol) in MeOH (30 mL) at 0° C. was added $NaBH_4$ (887 mg, 23.7 mmol), and the mixture was stirred at room temperature for 1 h. The mixture was quenched with water (20 mL), concentrated to remove methanol and the residue was extracted with ethyl acetate (4×10 mL). The combined organic phases were washed with brine, dried over $Na_2SO_4$ and filtered. The filtrate was concentrated under reduced pressure at 30° C., and the residue was purified by flash column chromatography (40 g silica, 0-30% MTBE/petroleum ether) to give (5-octylisoxazol-3-yl)methanol (2 g, 9.47 mmol, 80%) as a pale yellow oil. LCMS: (System 2, Method C) m/z 212.4 $(M+H)^+$ $(ES^+)$.

Step 3

To a solution of (5-octylisoxazol-3-yl)methanol (750 mg, 3.6 mmol) and triethylamine (1 mL, 7.2 mmol) in DCM (10 mL) at 0° C. was added methanesulfonyl chloride (0.41 mL, 5.4 mmol), and the reaction mixture was stirred at room temperature for 1.5 h. The mixture was concentrated under reduced pressure at 30° C. to give the crude (5-octylisoxazol-3-yl)methyl methanesulfonate (878 mg, 3.0 mmol, 84%) as a pale yellow oil, which was used directly in next step. LCMS: (System 2, Method C) m/z 290.2 $(M+H)^+$ $(ES^+)$.

Step 4

To a solution of (5-octylisoxazol-3-yl)methyl methanesulfonate (878 mg, 3.0 mmol) in acetone (10 mL) was added LiBr (779 mg, 9.0 mmol), and the mixture was stirred at 65° C. for 2 h. The mixture was quenched with water (20 mL) and extracted with ethyl acetate (4×10 mL). The combined organic phases were washed with brine, dried over $Na_2SO_4$ and filtered. The filtrate was concentrated under reduced pressure at 40° C., and the residue was purified by flash column chromatography (25 g silica, 0-30% MTBE/petroleum ether) to give 3-(bromomethyl)-5-octylisoxazole (600 mg, 2.2 mmol, 73%) as a pale yellow oil. LCMS: (System 2, Method C) m/z 274.2/276.2 $(M+H)^+$ $(ES^+)$.

Step 5

To a solution of tert-butyl 2-(diethoxyphosphoryl)acetate (553 mg, 2.2 mmol) in THF (15 mL) at 0° C. was added NaH suspension in mineral oil (60 wt. %, 96 mg, 2.4 mmol), and the mixture was stirred at 0° C. for 0.5 h. A solution of 3-(bromomethyl)-5-octylisoxazole (600 mg, 2.2 mmol) in THF (5 mL) at 0° C. was then added, and the reaction mixture was stirred at room temperature for 16 h. The mixture was quenched with water (20 mL), the phases were separated and the aqueous phase was extracted with ethyl acetate (4×10 mL). The combined organic layers were washed with brine, dried over $Na_2SO_4$ and filtered. The filtrate was concentrated under reduced pressure at 40° C., and the residue was purified by flash column chromatography (25 g silica, 0-80% MTBE/petroleum ether) to give tert-butyl 2-(diethoxyphosphoryl)-3-(5-octylisoxazol-3-yl)propanoate (500 mg, 1.1 mmol, 50%) as a pale yellow oil. LCMS: (System 2, Method C) m/z 446.2 $(M+H)^+$ $(ES^+)$.

Intermediate 134—2-bromo-1-(1-(4-(trifluoromethyl)phenyl)cyclopropyl)ethan-1-one

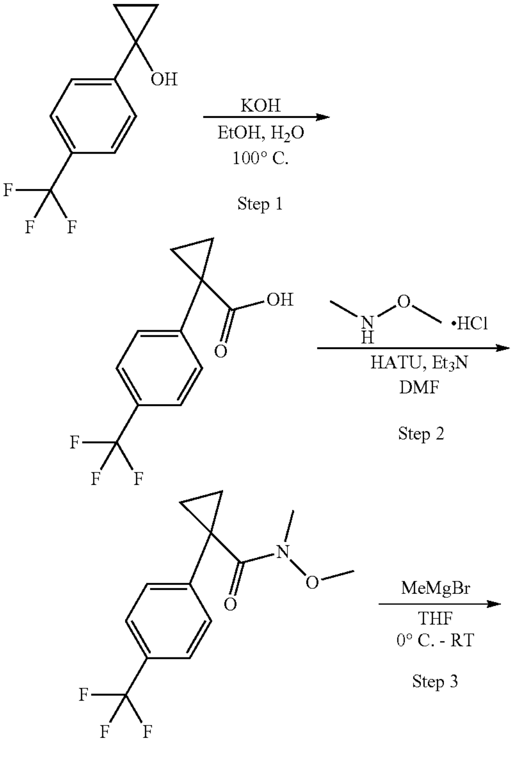

-continued

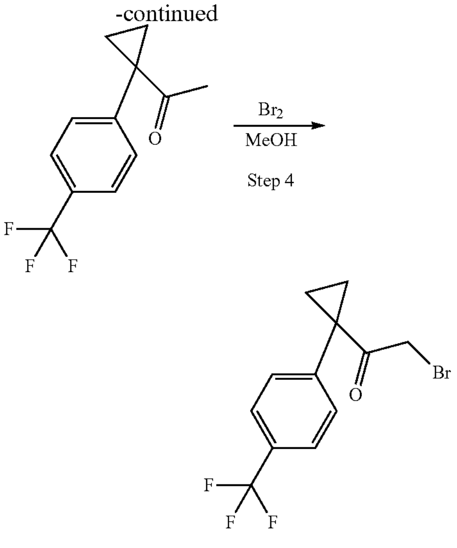

Step 1

A solution of 1-(4-(trifluoromethyl)phenyl)cyclopropane-1-carbonitrile (3.00 g, 14.2 mmol) and KOH (2.38 g, 42.6 mmol) in EtOH (15 mL) and $H_2O$ (15 mL) was stirred at 100° C. for 16 h. The mixture was concentrated under reduced pressure at 35° C. and the residue was washed with EtOAc (2×20 mL). The aqueous layer was adjusted to pH=4 using dilute aqueous HCl (1 M), then extracted with EtOAc (2×20 mL). The combined organic extracts were washed with brine, dried over $Na_2SO_4$ and filtered. The filtrate was concentrated under reduced pressure at 35° C. to give 1-(4-(trifluoromethyl)phenyl)cyclopropane-1-carboxylic acid (3.2 g, 13.9 mmol, 94%) as a yellow oil, which was used directly in the next step. $^1H$ NMR (400 MHz, DMSO-d6) δ: 12.50 (br, 1H), 7.66 (d, J=8.1 Hz, 2H), 7.55 (d, J=8.0 Hz, 2H), 1.49 (q, J=4.0 Hz, 2H), 1.20 (q, J=4.0 Hz, 2H).

Step 2

To a solution of 1-(4-(trifluoromethyl)phenyl)cyclopropane-1-carboxylic acid (3.2 g, 13.9 mmol), N,O-dimethylhydroxylamine hydrochloride (4.07 g, 41.7 mmol) and HATU (10.56 g, 27.8 mmol) in dimethylformamide (70 mL) at 0° C. was added $Et_3N$ (9.83 g, 97.3 mmol). The reaction mixture was stirred at room temperature for 2 h, then quenched with saturated aqueous $NH_4Cl$ solution and extracted with EtOAc (2×100 mL). The combined organic layers were washed with brine, dried over $Na_2SO_4$, filtered and concentrated under reduced pressure at 35° C. The residue was purified by flash column chromatography (20-33% EtOAc/petroleum ether) to give N-methoxy-N-methyl-1-(4-(trifluoromethyl)phenyl)cyclopropane-1-carboxamide (3.5 g, 12.8 mmol, 92%) as a colorless oil. LCMS: (System 2, Method C) m/z 274.2 $(M+H)^+$ $(ES^+)$.

Step 3

To a mixture of N-methoxy-N-methyl-1-(4-(trifluoromethyl)phenyl)cyclopropane-1-carboxamide (3.00 g, 11.0 mmol) in THF (55 mL) at 0° C. was added methylmagnesium bromide solution in diethyl ether (3 M, 5.1 mL, 15.3 mmol), and the reaction mixture was stirred at room temperature for 16 h. The reaction mixture was quenched with saturated aqueous $NH_4Cl$ solution (50 mL) and extracted with EtOAc (2×50 mL). The combined organic layers were washed with brine, dried over $Na_2SO_4$, filtered and concentrated under reduced pressure at 30° C. The residue was purified by flash column chromatography (25 g silica, 0-10% MTBE/petroleum ether) to give 1-(1-(4-(trifluoromethyl)phenyl)cyclopropyl)ethan-1-one (2.5 g, 11.0 mmol, 99%) as a colorless oil. LCMS: (System 2, Method C) m/z 229.3 $(M+Na)^+$ $(ES^+)$.

Step 4

To a solution of 1-(1-(4-(trifluoromethyl)phenyl)cyclopropyl)ethan-1-one (2.2 g, 9.64 mmol) in MeOH (50 mL) at room temperature was added $Br_2$ (2.31 g, 14.46 mmol) dropwise, and the reaction mixture was stirred at room temperature for 16 h. The reaction mixture was adjusted to pH=7 using saturated aqueous $NaHCO_3$, and then concentrated under reduced pressure at 30° C. to remove the MeOH. The residual aqueous mixture was extracted with EtOAc (2×50 mL), and the combined organic phases were dried over $Na_2SO_4$, filtered and concentrated under reduced pressure at 35° C. The residue was purified by flash column chromatography (40 g silica, 0-10% MTBE/petroleum ether) to give 2-bromo-1-(1-(4-(trifluoromethyl)phenyl)cyclopropyl)ethan-1-one (1.4 g, 4.56 mmol, 47%) as a white solid. $^1H$ NMR (400 MHz, DMSO-d6) δ: 7.72 (d, J=8.0 Hz, 2H), 7.67 (d, J=8.2 Hz, 2H), 4.22 (s, 2H), 1.65 (q, J=4.1 Hz, 2H, 1.35 (q, J=4.2 Hz, 2H).

Intermediate 135—2-(chloromethyl)-4-octylpyridine

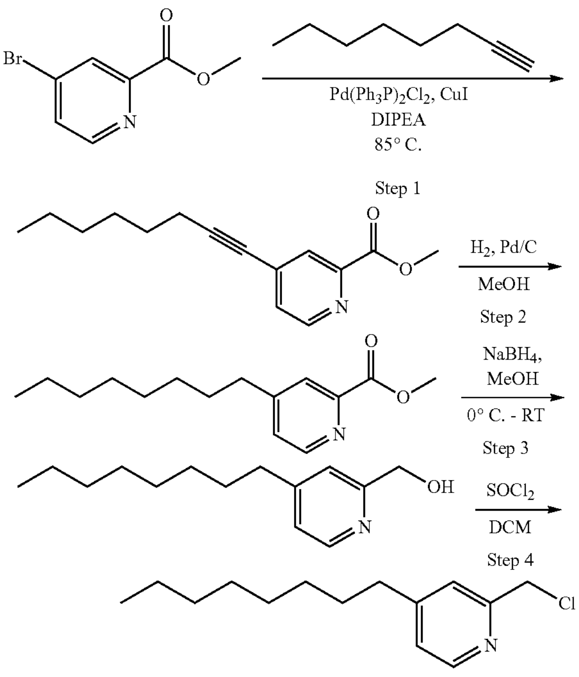

Step 1

A mixture of methyl 4-bromopicolinate (2.80 g, 13.0 mmol), oct-1-yne (5.70 g, 51.8 mmol), $Pd(PPh_3)_2Cl_2$ (0.92 g, 1.30 mmol) and CuI (492 mg, 2.60 mmol) in DIPEA (65 mL) was stirred at 85° C. for 3 h. The mixture was cooled to room temperature, filtered and the filtrate was diluted with water (60 mL), and extracted with ethyl acetate (3×50 mL). The combined organic layers were washed with dilute aqueous HCl (0.5 M, 3×30 mL), water (2×30 mL) and brine, dried over $Na_2SO_4$, filtered and filtrate was concentrated under reduced pressure at 40° C. The residue was purified by flash column chromatography (120 g silica, 0-30% EtOAc/petroleum ether) to give methyl 4-(oct-1-yn-1-yl)picolinate (2.40 g, 9.78 mmol, 75%) as a dark oil. LCMS: (System 2, Method C) m/z 246.4 $(M+H)^+$ $(ES^+)$.

Step 2

A mixture of methyl 4-(oct-1-yn-1-yl)picolinate (2.40 g, 9.78 mmol) and Pd/C catalyst (10 wt. %, 240 mg) in MeOH (20 mL) was stirred under an atmosphere of $H_2$ at room temperature for 12 h. The mixture was filtered and concentrated under reduced pressure at 40° C. The residue was purified by flash column chromatography (80 g silica, 0-30% EtOAc/petroleum ether) to give methyl 4-octylpicolinate (2.20 g, 8.82 mmol, 90%) as a brown oil. LCMS: (System 2, Method C) m/z 250.4 $(M+H)^+$ $(ES^+)$.

Step 3

To a solution of methyl 4-octylpicolinate (2.20 g, 8.82 mmol) in MeOH (44 mL) at 0° C. was added $NaBH_4$ (3.35 g, 88.2 mmol), and the resulting mixture was stirred at room temperature for 12 h, The reaction mixture was quenched with water (40 mL) and concentrated under reduced pressure at 40° C. to remove MeOH. The aqueous residue was extracted with ethyl acetate (3×40 mL), and the combined organic phases were washed with brine, dried over $Na_2SO_4$ and filtered. The filtrate was concentrated under reduced pressure 40° C., and the residue was purified by flash column chromatography (40 g silica, 0-30% EtOAc/petroleum ether) to give (4-octylpyridin-2-yl)methanol (1.20 g, 5.42 mmol, 61%) as a yellow oil. LCMS: (System 2, Method C) m/z 222.4 $(M+H)^+$ $(ES^+)$.

Step 4

To a solution of (4-octylpyridin-2-yl)methanol (1.20 g, 5.42 mmol) in DCM (27 mL) at room temperature was added $SOCl_2$ (1.90 g, 16.3 mmol), and the reaction mixture was stirred at room temperature for 3 h. The solvent was then removed under reduced pressure at 30° C. and the residue was diluted with $H_2O$ (10 mL), adjusted to pH=4 using dilute aqueous HCl (2 M), and extracted with MTBE (3×10 mL). The combined organic layer were washed with $H_2O$ (2×2 mL) and brine, dried over $Na_2SO_4$, filtered and concentrated under reduced pressure at 30° C. The residue was purified by flash column chromatography (20 g silica, 0-30% MTBE/petroleum ether) to give 2-(chloromethyl)-4-octylpyridine (1.30 g, 5.42 mmol, 100%) as a brown oil. LCMS: (System 2, Method C) m/z 240.4/242.4 $(M+H)^+$ $(ES^+)$. $^1H$ NMR (400 MHz, $CDCl_3$) δ: 8.44 (d, J=5.1 Hz, 1H), 7.28 (s, 1H), 7.05 (dd, J=5.1, 1.7 Hz, 1H), 4.65 (s, 2H), 2.62 (t, J=7.8 Hz, 2H), 1.68-1.57 (m, 2H), 1.37-1.20 (m, 10H), 0.88 (t, J=6.8 Hz, 3H).

The following compounds were prepared by an analogous procedure:

| Int. Number | Structure/Name | Characterising data |
|---|---|---|
| 136 | 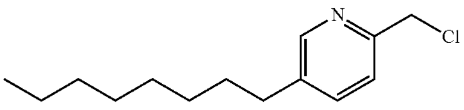 2-(chloromethyl)-5-octylpyridine | LCMS: (System 2, Method C) m/z 240.4/242.4 $(M + H)^+$ $(ES^+)$. |
| 137 | 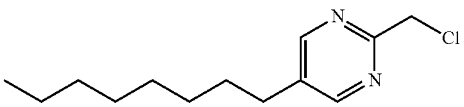 2-(chloromethyl)-5-octylpyrimidine | LCMS: (System 2, Method C) m/z 241.4/243.3 $(M + H)^+$ $(ES^+)$. |
| 142 | 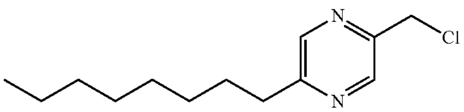 2-(chloromethyl)-5-octylpyrazine | LCMS: (System 2, Method C) m/z 241.3/243.3 $(M + H)^+$ $(ES^+)$. |
| 147 | 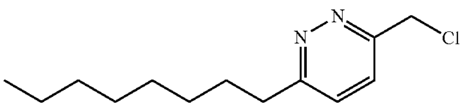 3-(chloromethyl)-6-octylpyridazine | LCMS: (System 2, Method C) m/z 241.4/243.3 $(M + H)^+$ $(ES^+)$. |

Intermediate 138—1-(4-cyclobutoxyphenyl)cyclopropane-1-carbonitrile

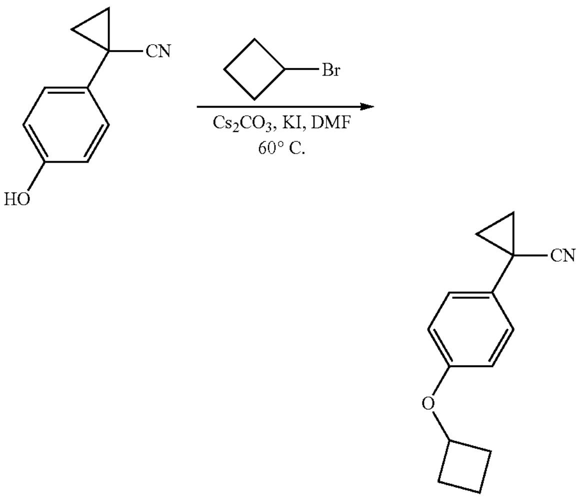

A mixture of 1-(4-hydroxyphenyl)cyclopropane-1-carbonitrile (1.20 g, 7.54 mmol), $Cs_2CO_3$ (7.35 g, 22.6 mmol), KI (125 mg, 0.75 mmol) and bromocyclobutane (4.04 g, 30.2 mmol) in dimethylformamide (14 mL) was stirred at 60° C. overnight. The mixture was cooled to room temperature, diluted with water and extracted with ethyl acetate (3×30 mL). The combined organic layers were washed with saturated aqueous $NH_4Cl$ solution (2×30 mL) and brine, dried over $Na_2SO_4$, filtered and the filtrate was concentrated under reduced pressure at 40° C. The residue was purified by flash column chromatography (40 g silica, 0-20% MTBE/petroleum ether) to give 1-(4-cyclobutoxyphenyl)cyclopropane-1-carbonitrile (1.10 g, 5.16 mmol, 68%) as a pale yellow liquid. LCMS: (System 2, Method C) m/z 214.4 $(M+H)^+$ $(ES^+)$.

Intermediate 140—2-(4-cyclopentylphenyl)acetonitrile

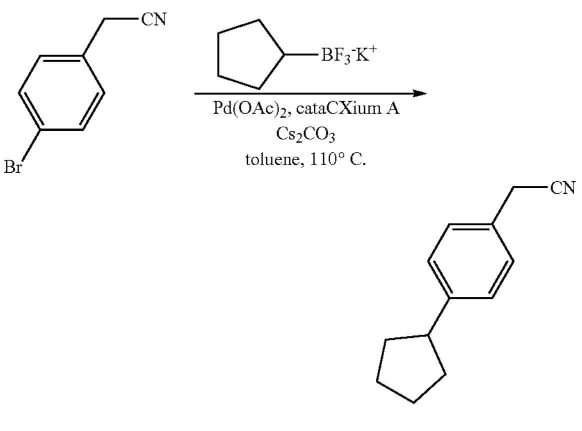

A mixture of 2-(4-bromophenyl)acetonitrile (1.00 g, 5.10 mmol), potassium cyclopentyltrifluoroborate (988 mg, 5.61 mmol), palladium (II) acetate (115 mg, 0.51 mmol), cataCXium A (CAS: 321921-71-5) (366 mg, 1.02 mmol) and cesium carbonate (3.32 g, 10.2 mmol) in toluene (25 mL) was stirred at 110° C. overnight. The mixture was cooled to room temperature, filtered and the filtrate was concentrated under reduced pressure at 40° C. The residue was purified by flash column chromatography (25 g silica, 0-10% EtOAc/petroleum ether) to give 2-(4-cyclopentylphenyl)acetonitrile (470 mg, 2.54 mmol, 50%) as a colorless oil.

$^1H$ NMR (400 MHz, $CDCl_3$) δ: 7.26-7.22 (m, 4H), 3.71 (s, 2H), 3.06-2.92 (m, 1H), 2.13-1.99 (m, 2H), 1.88-1.75 (m, 2H), 1.75-1.63 (m, 2H), 1.63-1.49 (m, 2H).

Intermediate 143—1-(4-cyclopropoxyphenyl)cyclopropane-1-carbonitrile

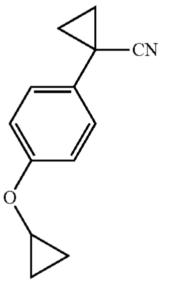 [SMILES: N#CC1(c2ccc(OC3CC3)cc2)CC1]

Prepared by an analogous procedure to Intermediate 138 except that the reaction mixture was heated to 200° C. in a microwave reactor for 1.5 h. LCMS: (System 2, Method C) m/z 200.2 $(M+H)^+$ $(ES^+)$.

Intermediate 145—1-(4-cyclopentylphenyl)cyclopropane-1-carbonitrile

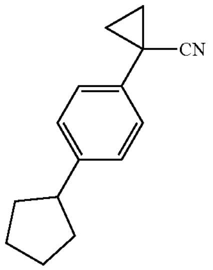 [SMILES: N#CC1(c2ccc(C3CCCC3)cc2)CC1]

Prepared by an analogous procedure to Intermediate 140. LCMS: (System 2, Method C) m/z 212.4 $(M+H)^+$ $(ES^+)$.

Intermediate 152—2-(4-cyclobutylphenyl)acetonitrile

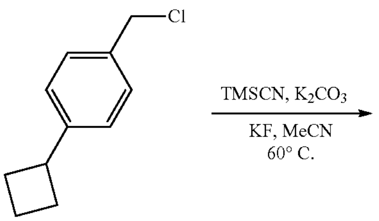

-continued

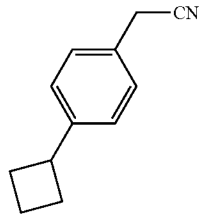

To a solution of 1-(chloromethyl)-4-cyclobutylbenzene (2.7 g, 15 mmol), $K_2CO_3$ (3.1 g, 22.5 mol) and KF (1.3 g, 22.5 mmol) in MeCN (50 mL) at room temperature was slowly added TMSCN (2.2 g, 22.5 mmol) dropwise, and the resulting mixture was stirred at 60° C. for 6 h. The reaction mixture was then diluted with water (30 mL) and MTBE (20 mL), the phases were separated, and the aqueous layer was extracted with MTBE (2×50 mL). The combined organic layers were washed with brine, dried over $Na_2SO_4$, filtered, and concentrated under reduced pressure at 35° C. The residue was purified by flash column chromatography (40 g silica, 0-15% MTBE/petroleum ether) to give 2-(4-cyclobutylphenyl)acetonitrile (1.9 g, 11.1 mmol, 74%) as a colorless oil. LCMS: (System 2, Method C) m/z 172.3 $(M+H)^+$ $(ES^+)$.

Intermediate 154—4-butoxy-3-fluorobenzonitrile

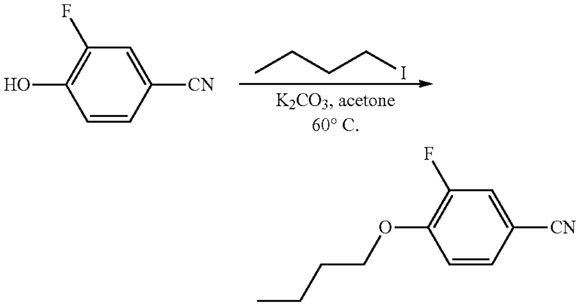

A mixture of 3-fluoro-4-hydroxybenzonitrile (1.00 g, 7.29 mmol), $K200_3$ (2.01 g, 14.6 mmol) and 1-iodobutane (2.01 g, 10.94 mmol) in acetone (15 mL) was stirred at 60° C. for 16 h. The mixture was cooled to room temperature, filtered, and the filtrate was concentrated under reduced pressure at 40° C. The residue was purified by flash column chromatography (40 g silica, 20-40% EtOAc/petroleum ether) to give 4-butoxy-3-fluorobenzonitrile (1.20 g, 6.21 mmol, 85%) as a colorless oil. LCMS: (System 2, Method C) m/z 194.3 $(M+H)^+$ $(ES^+)$.

Intermediate 156—3-chloro-4-propoxybenzonitrile

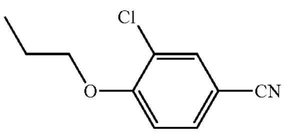

Prepared by an analogous procedure to Intermediate 154, using 3-chloro-4-hydroxybenzonitrile (1.40 g, 9.12 mmol) and 1-iodopropane (1.69 g, 10.0 mmol). Yield: 1.50 g, 7.67 mmol, 84%. LCMS: (System 2, Method C) m/z 196.3/198.3 $(M+H)^+$ $(ES^+)$.

Intermediate 158—1-(4-cyclobutylphenyl)cyclopropane-1-carbonitrile

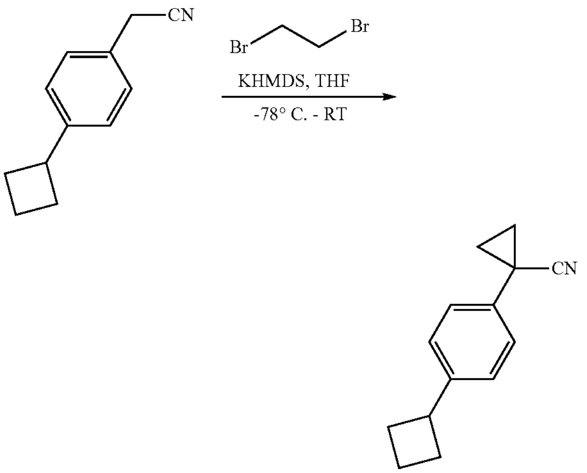

To a solution of 2-(4-cyclobutylphenyl)acetonitrile (Intermediate 152, 1.00 g, 5.84 mmol) in THF (20 mL) at −78° C. was added a solution of KHMDS in THF (1 M, 13.4 mL, 13.4 mmol) and the resulting mixture was stirred at −78° C. for 1 h. A solution of 1,2-dibromoethane (1.21 g, 6.42 mmol) in THF (3 mL) was then added and the mixture was stirred at room temperature overnight. The reaction mixture was quenched with saturated aqueous $NH_4Cl$ solution (20 mL), the phases were separated and the aqueous layer was extracted with MTBE (2×20 mL). The combined organic layers were washed with brine, dried over $Na_2SO_4$, filtered and concentrated under reduced pressure at 30° C. The residue was purified by flash column chromatography (25 g silica, 0-10% MTBE/petroleum ether) to give 1-(4-cyclobutylphenyl)cyclopropane-1-carbonitrile (350 mg, 1.77 mmol, 30%) as a colorless oil. LCMS: (System 2, Method C) m/z 198.4 $(M+H)^+$ $(ES^+)$. $^1H$ NMR (400 MHz, $CDCl_3$) δ: 7.25-7.16 (m, 4H), 3.59-3.46 (m, 1H), 2.40-2.27 (m, 2H), 2.20-1.93 (m, 3H), 1.91-1.78 (m, 1H), 1.73-1.65 (m, 2H), 1.41-1.33 (m, 2H).

Intermediate 161—1-(3,5-dichloro-4-fluorophenyl) cyclopropane-1-carbonitrile

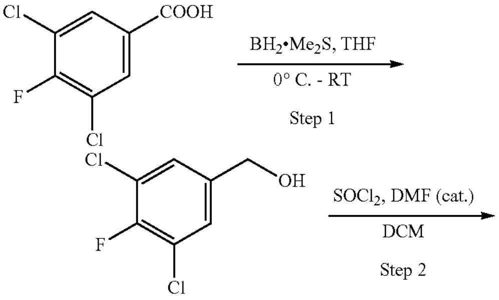

-continued

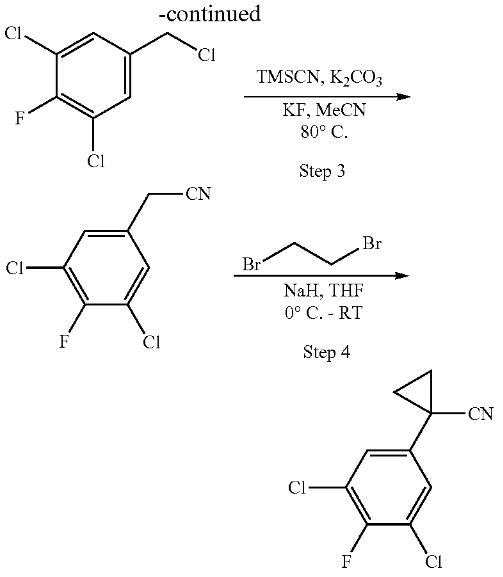

Step 1

To a solution of 3,5-dichloro-4-fluorobenzoic acid (9.00 g, 43.1 mmol) in THF (10 mL) at 0° C. was added a solution of $BH_3 \cdot Me_2S$ complex in THF (2 M, 130 mL, 260 mmol), and the reaction mixture was stirred at room temperature for 12 h. The reaction mixture was quenched with MeOH (20 mL), concentrated under reduced pressure at 30° C., and the residue was diluted with MTBE (30 mL) and water. The phases were separated, and the aqueous phase was extracted with MTBE (3x30 mL). The combined organic layers were washed with brine, dried over $Na_2SO_4$, filtered and concentrated under reduced pressure at 40° C. The residue was purified by flash column chromatography (80 g silica, 0-40% MTBE/petroleum ether) to give (3,5-dichloro-4-fluorophenyl)methanol (8.00 g, 41.0 mmol, 95%) as a colorless oil. $^1$H NMR (400 MHz, $CDCl_3$) δ: 7.32 (d, J=6.2 Hz, 2H), 4.64 (s, 2H). One exchangeable proton not observed.

Step 2

To a solution of (3,5-dichloro-4-fluorophenyl)methanol (8.00 g, 41.0 mmol) in DCM (100 mL) at 0° C. was added $SOCl_2$ (24.2 g, 205 mmol) and three drops of dimethylformamide, and the reaction mixture was stirred at room temperature for 2.5 h. The mixture was quenched with water (40 mL), the phases were separated, and the aqueous phase was extracted with DCM (4x30 mL). The combined organic layers were washed with brine, dried over $Na_2SO_4$, filtered and concentrated under reduced pressure at 40° C. The residue was purified by flash column chromatography (80 g silica, 0-5% MTBE/petroleum ether) to give 1,3-dichloro-5-(chloromethyl)-2-fluorobenzene (7.60 g, 35.6 mmol, 87%) as a pale yellow oil. $^1$H NMR (400 MHz, $CDCl_3$) δ: 7.35 (d, J=6.1 Hz, 2H), 4.48 (s, 2H).

Step 3

A mixture of 1,3-dichloro-5-(chloromethyl)-2-fluorobenzene (7.20 g, 33.7 mmol), TMSCN (5.00 g, 50.6 mmol), $K_2CO_3$ (7.00 g, 50.6 mmol) and KF (2.90 g, 50.6 mmol) in MeCN (80 mL) was stirred at 80° C. for 12 h. The mixture was concentrated under reduced pressure at 40° C., the residue was diluted with DCM (30 mL) and water (20 mL), the phases were separated, and the aqueous layer was extracted with DCM (3x30 mL). The combined organic layers were washed with brine, dried over $Na_2SO_4$, filtered, and concentrated under reduced pressure at 40° C. The residue was purified by flash column chromatography (80 g silica, 0-20% MTBE/petroleum ether) to give 2-(3,5-dichloro-4-fluorophenyl)acetonitrile (3.20 g, 15.7 mmol, 46%) as a yellow solid. $^1$H NMR (400 MHz, $CDCl_3$) δ: 7.31 (d, J=6.0 Hz, 2H), 3.71 (s, 2H).

Step 4

To a solution of 2-(3,5-dichloro-4-fluorophenyl)acetonitrile (1.00 g, 4.90 mmol) in THF (10 mL) at 0° C. was added sodium hydride suspension in mineral oil (60 wt. %, 431 mg, 10.8 mmol), and the mixture was stirred at 0° C. for 30 min. 1,2-dibromoethane (1.00 g, 5.39 mmol) was added, and the resulting suspension was stirred at room temperature for 16 h. The mixture was quenched with saturated aqueous $NH_4Cl$ (10 mL), the phases were separated, and the aqueous phase was extracted with MTBE (3x20 mL). The combined organic layers were washed with $H_2O$ (2x20 mL) and brine, dried over $Na_2SO_4$, filtered and concentrated under reduced pressure at 40° C. The residue was purified by flash column chromatography (25 g silica, 0-20% MTBE/petroleum ether) to give 1-(3,5-dichloro-4-fluorophenyl)cyclopropane-1-carbonitrile (800 mg, 3.48 mmol, 71%) as a white solid. $^1$H NMR (400 MHz, $CDCl_3$) δ: 7.25 (d, J=6.2 Hz, 2H),1.80-1.74 (m, 2H), 1.43-1.36 (m, 2H).

Intermediate 164—1-(4-chloro-3,5-difluorophenyl)cyclopropane-1-carbonitrile

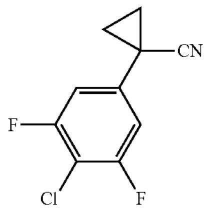 [SMILES: N#CC1(c2cc(F)c(Cl)c(F)c2)CC1]

Prepared by an analogous procedure to Intermediate 161, starting from 4-chloro-3,5-difluorobenzoic acid (2.00 g, 10.39 mmol), except that Step 2 was heated at 40° C. for 2 h. Yield: 400 mg. White solid. $^1$H NMR (400 MHz, $CDCl_3$) δ: 6.96-6.89 (m, 2H), 1.86-1.78 (m, 2H), 1.46-1.37 (m, 2H).

Intermediate 166—1-(3-chloro-4-(trifluoromethyl)phenyl)cyclopropane-1-carbonitrile

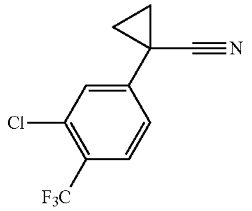 [SMILES: N#CC1(c2ccc(C(F)(F)F)c(Cl)c2)CC1]

Prepared by an analogous procedure to Intermediate 161, Step 2 to Step 4, starting from (3-chloro-4-(trifluoromethyl)phenyl)methanol (5.8 g, 27.5 mmol), except that Step 2 was stirred at room temperature overnight and Step 4 was stirred at room temperature for 3 h. Yield: 480 mg. Off-white solid. $^1$H NMR (400 MHz, $CDCl_3$) δ: 7.67 (d, J=8.3 Hz, 1H), 7.39 (d, J=1.4 Hz, 1H), 7.31-7.26 (m, 1H), 1.89-1.82 (m, 2H), 1.52-1.45 (m, 2H).

Intermediate 169—1-(4-bromo-3-chlorophenyl)cyclopropane-1-carbonitrile

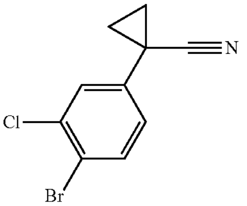 [SMILES: N#CC1(c2ccc(Br)c(Cl)c2)CC1]

Prepared by an analogous procedure to Intermediate 161, Step 2 to Step 4, starting from (4-bromo-3-chlorophenyl) methanol (6.00 g, 27.2 mmol), except that Step 2 was stirred at 0° C. for 2 h and Step 4 was stirred at room temperature for 3 h. Yield: 1.0 g. White solid. $^1$H NMR (400 MHz, $CDCl_3$) δ 7.59 (d, J=8.4 Hz, 1H), 7.36 (d, J=2.3 Hz, 1H), 7.06 (dd, J=8.4, 2.4 Hz, 1H), 1.81-1.74 (m, 2H), 1.44-1.37 (m, 2H).

Intermediate 172—1-(3-chloro-4-methoxyphenyl) cyclopropane-1-carbonitrile

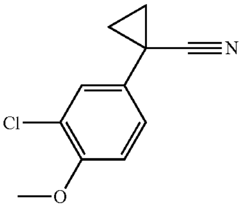

Prepared by an analogous procedure to Intermediate 161, Step 2 to Step 4, starting from (3-chloro-4-methoxyphenyl) methanol (3.30 g, 19.1 mmol), except that Step 2 was stirred at room temperature for 2 h and Step 4 was stirred at room temperature for 3 h. Yield: 425 mg. White solid. $^1$H NMR (400 MHz, $CDCl_3$) δ: 7.26 (d, J=2.4 Hz, 1H), 7.22 (dd, J=8.5, 2.4 Hz, 1H), 6.89 (d, J=8.5 Hz, 1H), 3.90 (s, 3H), 1.72-1.65 (m, 2H),1.37-1.30 (m, 2H).

Intermediate 174—1-(3-chloro-4-methylphenyl) cyclopropane-1-carbonitrile

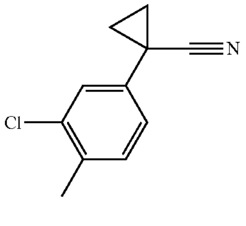

Prepared by an analogous procedure to Intermediate 161, Step 2 to Step 4, starting from (3-chloro-4-methylphenyl) methanol (8.50 g, 54.3 mmol). Yield: 800 mg. Yellow oil. LCMS: (System 2, Method C) m/z 192.2/194.2 $(M+H)^+$ $(ES^+)$.

Intermediate 206—4-cyclobutoxybenzonitrile

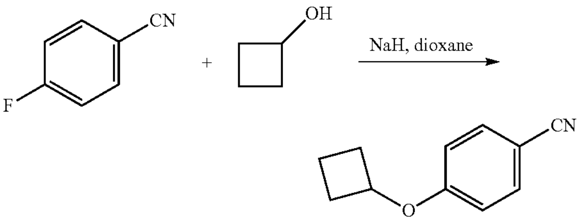

Cyclobutanol (1.2 mL, 15 mmol) was added dropwise to a suspension of NaH (60% suspension in mineral oil, 0.69 g, 17 mmol) in 1,4-dioxane (15 mL). The mixture was stirred for 30 min, before 4-fluorobenzonitrile (0.50 g, 4.1 mmol) was added and the mixture heated at 100° C. for 30 min, then cooled to RT. The mixture was quenched with EtOH (1 mL) then diluted with brine (50 mL) and extracted with EtOAc (3×50 mL). The combined organic layers were dried ($MgSO_4$) and concentrated. The crude product was purified by chromatography on silica gel (0-20% MTBE/isohexane) to afford 4-cyclobutoxybenzonitrile (0.74 g, 3.8 mmol, 90% purity) as a clear and colourless oil. $^1$H NMR (400 MHz, DMSO-d6) δ 7.80-7.68 (m, 2H), 7.05-6.98 (m, 2H), 4.84-4.72 (m, 1H), 2.49-2.39 (m, 2H), 2.11-1.98 (m, 2H), 1.86-1.73 (m, 1H), 1.71-1.58 (m, 1H).

The following compounds were synthesised using the same procedure.

| Int. Number | Structure/Name | Characterising data |
|---|---|---|
| 207 | 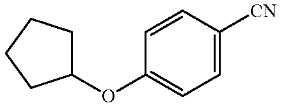 4-cyclopentyloxybenzonitrile | $^1$H NMR (400 MHz, DMSO-d6) δ 7.79-7.66 (m, 2H), 7.14-6.99 (m, 2H), 4.98-4.86 (m, 1H), 2.05-1.85 (m, 2H), 1.78-1.49 (m, 6H) |
| 208 | 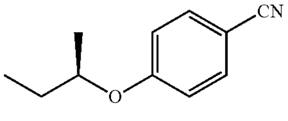 (R)-4-(sec-butoxy)benzonitrile | $^1$H NMR (400 MHz, DMSO-d6) δ 7.82-7.62 (m, 2H), 7.15-7.02 (m, 2H), 4.63-4.43 (m, 1H), 1.76-1.50 (m, 2H), 1.24 (d, J = 6.0 Hz, 3H), 0.91 (t, J = 7.4 Hz, 3H) |
| 209 | 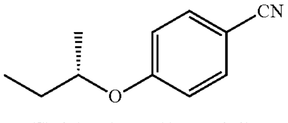 (S)-4-(sec-butoxy)benzonitrile | $^1$H NMR (400 MHz, DMSO-d6) δ 7.82-7.62 (m, 2H), 7.15-7.02 (m, 2H), 4.63-4.43 (m, 1H), 1.76-1.50 (m, 2H), 1.24 (d, J = 6.0 Hz, 3H), 0.91 (t, J = 7.4 Hz, 3H) |
| 210 | 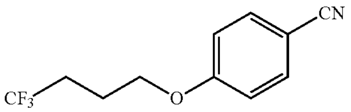 4-(4,4,4-trifluorobutoxy)benzonitrile | $^1$H NMR (400 MHz, DMSO-d6) δ 7.84-7.67 (m, 2H), 7.18-7.04 (m, 2H), 4.21-4.03 (m, 2H), 2.45-2.33 (m, 2H), 2.03-1.85 (m, 2H) |

Intermediate 211—4,6-dichloro-2,3-dihydro-1H-indene-1-carbonitrile

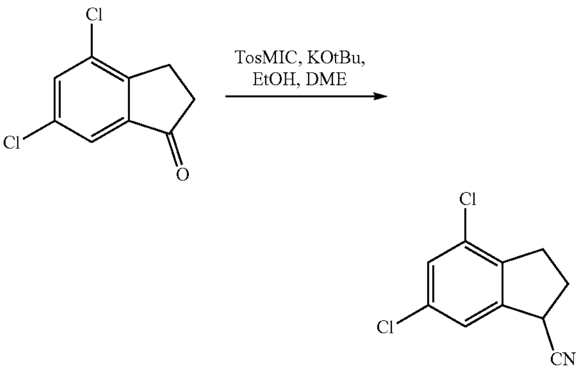

Potassium tert-butoxide (1.67 g, 14.9 mmol) was added portionwise to a solution of 4,6-dichloro-2,3-dihydro-1H-inden-1-one (1.00 g, 4.97 mmol) and TosMIC (2.91 g, 14.9 mmol) in DME (50 mL) and ethanol (2 mL) at 0° C. The mixture was warmed to RT and stirred for 1 h. Water (30 mL) was added and the mixture was extracted with EtOAc (3×15 mL). The combined organic layers were washed with brine (20 mL), dried ($Na_2SO_4$) and concentrated. The crude product was purified by chromatography on silica gel (0-10% EtOAc/isohexane) to afford 4,6-dichloro-2,3-dihydro-1H-indene-1-carbonitrile (0.207 g, 0.93 mmol) as an orange solid. $^1$H NMR (400 MHz, DMSO-d6) δ 7.58-7.54 (m, 1H), 7.52-7.48 (m, 1H), 4.65-4.56 (m, 1H), 3.08-2.98 (m, 1H), 2.96-2.86 (m, 1H), 2.63-2.52 (m, 1H), 2.37-2.26 (m, 1H).

Intermediate 212—2-(3,5-dichloro-4-fluorophenyl)-2,2-difluoro-N-hydroxyacetimidamide

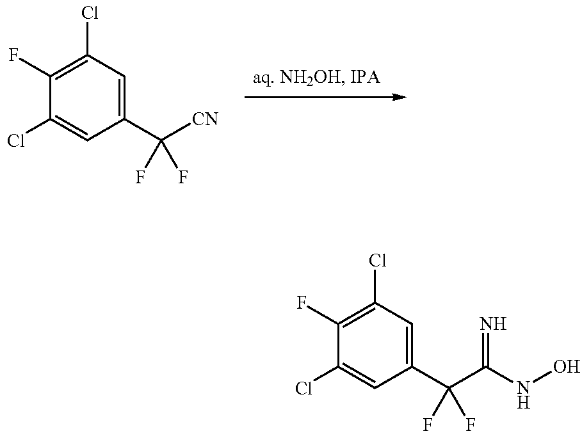 [SMILES: N#CC(F)(F)c1cc(Cl)c(F)c(Cl)c1 ; N=C(NO)C(F)(F)c1cc(Cl)c(F)c(Cl)c1]

Hydroxylamine (50% in water, 1.0 mL, 17.6 mmol) was added to a solution of 2-(3,5-dichloro-4-fluorophenyl)-2,2-difluoroacetonitrile (2.818 g, 11.74 mmol) in IPA (20 mL). The mixture was stirred at RT for 16 h. The mixture was concentrated and the residue was co-evaporated with toluene (3×10 mL) to afford 2-(3,5-dichloro-4-fluorophenyl)-2,2-difluoro-N-hydroxyacetimidamide (3.06 g, 11 mmol) as an orange solid. LCMS m/z 273.0/275.0 $(M+H)^+$ $(ES^+)$. $^1$H NMR (400 MHz, DMSO-d6) δ 7 10.09 (s, 1H), 7.74 (d, J=6.3 Hz, 2H), 6.16 (s, 2H). $^{19}$F NMR (376 MHz, DMSO) δ -96.06 (d, J=2.5 Hz), -113.42--116.00 (m).

The following compounds were synthesised using the same procedure.

| Int. Number | Structure/Name | Characterising data |
|---|---|---|
| 213 | 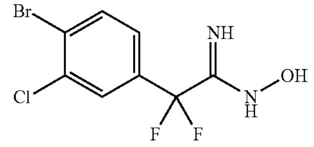 2-(4-bromo-3-chlorophenyl)-2,2-difluoro-N-hydroxyacetimidamide | LCMS m/z 299.1/301.1 $(M + H)^+$ $(ES^+)$. $^1H$ NMR (400 MHz, DMSO-d6) δ 10.03 (s, 1H), 7.89 (d, J = 8.4 Hz, 1H), 7.71 (d, J = 2.1 Hz, 1H), 7.39 (dd, J = 8.4, 2.2 Hz, 1H), 6.12 (s, 2H) |
| 214 | 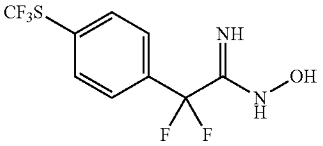 2,2-difluoro-N-hydroxy-2-(4-((trifluoromethyl)thio)phenyl) acetimidamide | LCMS m/z 287.0 $(M + H)^+$ $(ES^+)$. $^1H$ NMR (400 MHz, DMSO-d6) δ 10.02 (s, 1H), 7.82 (d, J = 8.2 Hz, 2H), 7.69-7.63 (m, 2H), 6.11 (s, 2H) |

Intermediate 215—4-butoxy-3-chlorobenzonitrile

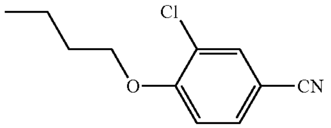

Prepared by an analogous procedure to Intermediate 154, using 3-chloro-4-hydroxybenzonitrile (1.00 g, 6.54 mmol). Yield: 1.20 g, 5.72 mmol, 88%. LCMS: (System 2, Method C) m/z 210.3/212.2 $(M+H)^+$ $(ES^+)$.

Intermediate 217—4-butoxy-3-(trifluoromethyl)benzonitrile

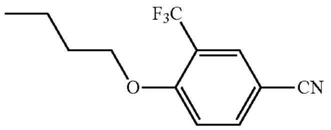 [SMILES: CCCCOc1ccc(C#N)cc1C(F)(F)F]

Prepared by an analogous procedure to Intermediate 154, using 4-hydroxy-3-(trifluoromethyl)benzonitrile (1.40 g, 7.48 mmol). Yield: 1.50 g, 6.17 mmol, 82%. LCMS: (System 2, Method C) m/z 244.2 $(M+H)^+$ $(ES^+)$.

Intermediate 219—4-butoxy-3,5-difluorobenzonitrile

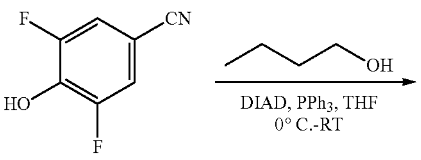

-continued

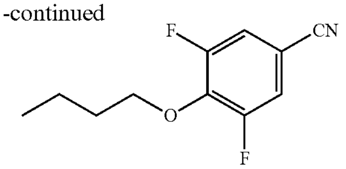

To a solution of 3,5-difluoro-4-hydroxybenzonitrile (750 mg, 4.84 mmol), butan-1-ol (393 mg, 5.32 mmol) and $PPh_3$ (2.54 g, 9.68 mmol) in THF (15 mL) at 0° C. was added DIAD (1.96 g, 9.68 mmol), and the resulting pale yellow mixture was stirred at room temperature for 4 h. The reaction was quenched with water (10 mL), the phases were separated and the aqueous layer was extracted with ethyl acetate (3×20 mL). The combined organic layers were washed with brine, dried over $Na_2SO_4$, filtered and the filtrate was concentrated under reduced pressure at 40° C. The residue was purified by flash column chromatography (25 g silica, 0-2% MTBE/petroleum ether) to give 4-butoxy-3,5-difluorobenzonitrile (750 mg, 3.55 mmol, 73%) as a pale yellow liquid. LCMS: (System 2, Method C) m/z 212.3 $(M+H)^+$ $(ES^+)$.

Intermediate 220—tert-butyl 3-(6-bromopyridin-2-yl)-2-(diethoxyphosphoryl)propanoate

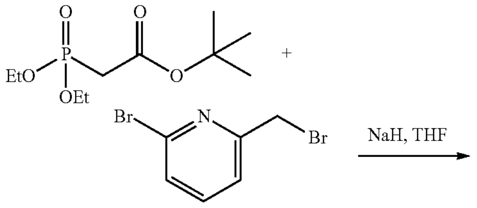

-continued

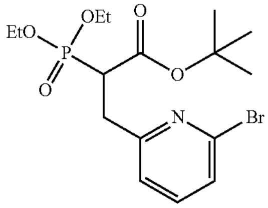

-continued

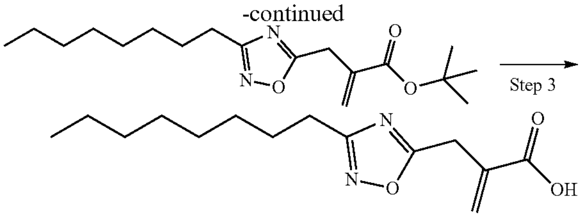

Tert-butyl 2-(diethoxyphosphoryl)acetate (0.94 mL, 4.0 mmol) was added dropwise to a suspension of NaH (60 wt %, 0.18 g, 4.5 mmol) in THF (12 mL). The mixture was stirred at RT for 30 min. 2-Bromo-6-(bromomethyl)pyridine (1.0 g, 4.0 mmol) was added portionwise and the mixture was then heated to 60° C. for 1 h. The mixture was cooled to RT, then poured into brine (40 mL) and extracted with EtOAc (3x50 mL). The combined organic extracts were dried ($MgSO_4$) and concentrated. The crude product was purified by chromatography on RP Flash C18 (5-75% (0.1% Formic acid in MeCN)/(0.1% Formic Acid in Water)) to afford tert-butyl 3-(6-bromopyridin-2-yl)-2-(diethoxyphosphoryl)propanoate (1.07 g, 2.4 mmol) as a colourless oil. LCMS: m/z 442.2/444.4 $(M+H)^+$ $(ES^+)$. $^1$H NMR (400 MHz, DMSO-d6) δ 7.67 (t, J=7.7 Hz, 1H), 7.48 (d, J=7.8 Hz, 1H), 7.38 (d, J=7.5 Hz, 1H), 4.15-3.99 (m, 4H), 3.54-3.37 (m, 1H), 3.29-3.19 (m, 1H), 3.18-3.06 (m, 1H), 1.32 (s, 9H), 1.29-1.20 (m, 6H).

Example 1—2-((3-octyl-1,2,4-oxadiazol-5-yl)methyl)acrylic acid

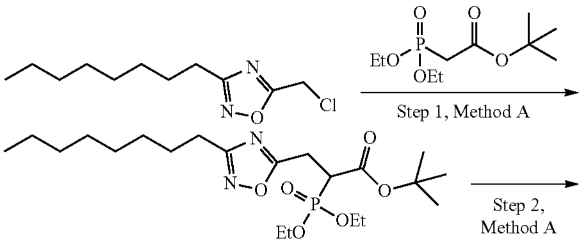

Step 1

Prepared according to General Procedure A, Step 1, Method A from 5-(chloromethyl)-3-octyl-1,2,4-oxadiazole (Intermediate 1, 0.60 g, 2.6 mmol). The crude product was purified by chromatography on silica gel (0-100% EtOAc/isohexane) to afford tert-butyl 2-(diethoxyphosphoryl)-3-(3-octyl-1,2,4-oxadiazol-5-yl)propanoate (0.413 g, 0.92 mmol) as a yellow oil. $^1$H NMR (400 MHz, DMSO-d6) δ 4.15-4.04 (m, 4H), 3.56 (ddd, J=23.4, 11.1, 4.4 Hz, 1H), 3.41-3.32 (m, 1H), 3.28-3.17 (m, 1H), 2.64 (t, J=7.4 Hz, 2H), 1.71-1.55 (m, 2H), 1.37 (s, 9H), 1.32-1.19 (m, 16H), 0.90-0.82 (m, 3H). LCMS m/z 469.3 $(M+Na)^+$ $(ES^+)$.

Step 2

Prepared according to General Procedure A, Step 2, Method A from tert-butyl 2-(diethoxyphosphoryl)-3-(3-octyl-1,2,4-oxadiazol-5-yl)propanoate (0.413 g, 0.93 mmol). The crude product was purified by chromatography on silica gel (0-10% EtOAc/isohexane) to afford tert-butyl 2-((3-octyl-1,2,4-oxadiazol-5-yl)methyl)acrylate (0.105 g, 0.322 mmol) as a colourless oil. $^1$H NMR (400 MHz, DMSO-d6) δ 6.23 (d, J=1.3 Hz, 1H), 5.93-5.86 (m, 1H), 3.91 (s, 2H), 2.64 (t, J=7.3 Hz, 2H), 1.68-1.57 (m, 2H), 1.34 (s, 9H), 1.28-1.21 (m, 10H), 0.91-0.78 (m, 3H). LCMS m/z 323.2 $(M+H)^+$ $(ES^+)$.

Step 3

Prepared according to General Procedure A, Step 3 from tert-butyl 2-((3-octyl-1,2,4-oxadiazol-5-yl)methyl)acrylate (0.105 g, 0.33 mmol). The crude product was purified by chromatography on silica gel (0-100% EtOAc/isohexane) to afford the title compound (0.059 g, 0.22 mmol) as a colourless oil. $^1$H NMR (400 MHz, DMSO-d6) δ 12.81 (s, 1H), 6.28 (d, J=1.2 Hz, 1H), 5.94-5.83 (m, 1H), 3.91 (s, 2H), 2.64 (t, J=7.5 Hz, 2H), 1.66-1.56 (m, 2H), 1.33-1.19 (m, 10H), 0.90-0.81 (m, 3H). LCMS m/z 267.2 $(M+H)^+$ $(ES^+)$.

Example 1 may also be prepared using the following route:

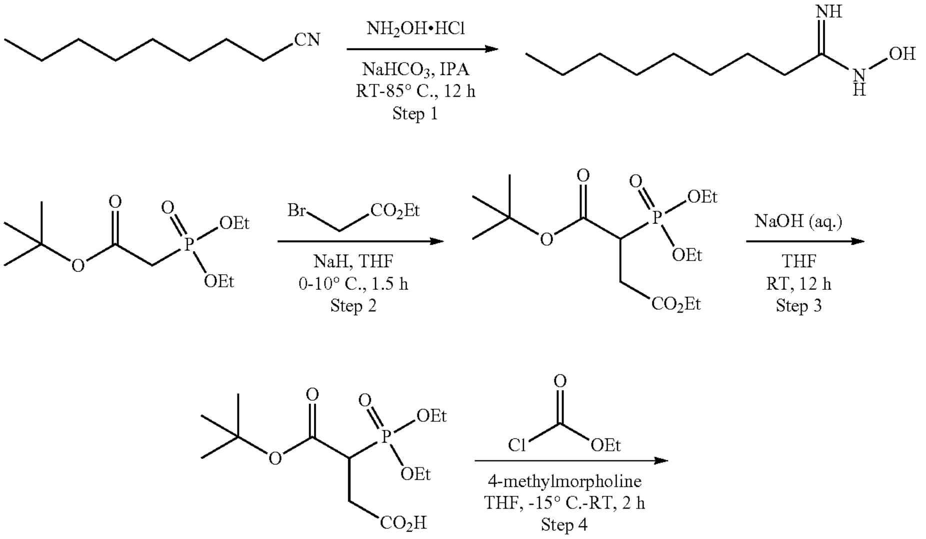

-continued

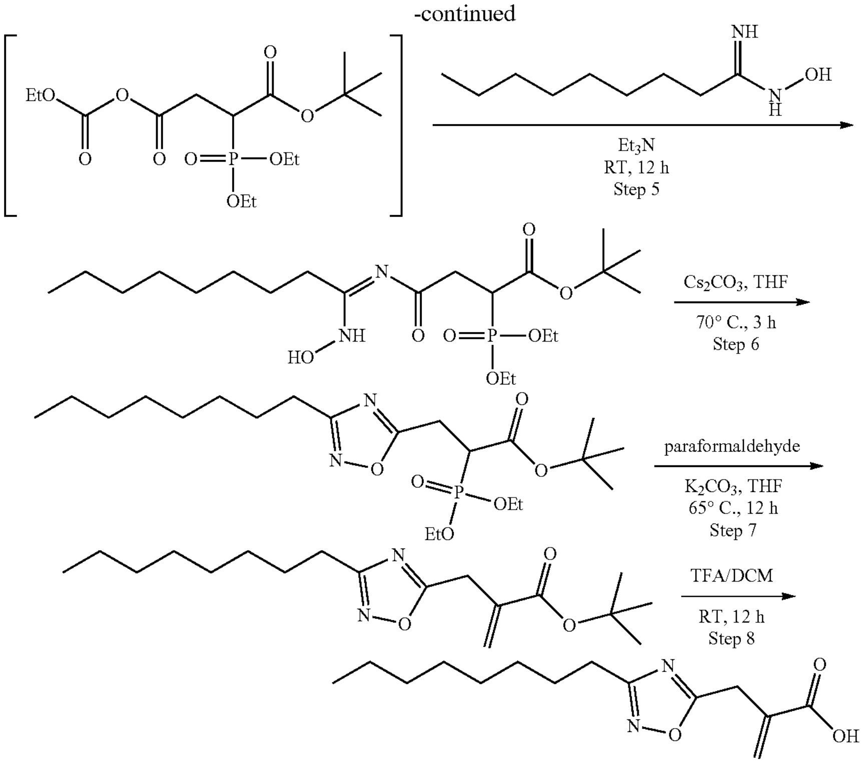

Step 1

To a solution of hydroxylamine hydrochloride (72.9 g, 1.05 mol) in isopropanol (420 mL) was added $NaHCO_3$ (150 g, 1.78 mol) in one portion. The mixture was stirred for 10 min at RT, and then nonanenitrile (73.0 g, 524 mmol) was added into the mixture in one portion. The mixture was heated to 85° C. and stirred for 12 h. The mixture was filtered, and the filter cake was washed with isopropanol (2×200 mL). The filtrate was concentrated under reduced pressure at 45° C. to give the crude N-hydroxynonanimidamide (80 g, 464 mmol, 89%) as a white solid. The crude product was used directly in the next step without further purification. $^1H$ NMR (400 MHz, DMSO-d6) δ: 8.65 (s, 1H), 5.27 (s, 2H), 1.92 (t, J=7.2 Hz, 2H), 1.51-1.40 (m, 2H), 1.31-1.19 (m, 10H), 0.86 (t, J=6.0 Hz, 3H).

Step 2

Five reactions were carried out in parallel. To a solution of tert-butyl 2-(diethoxyphosphoryl)acetate (300 g, 1.19 mol) in THF (3 L) was added NaH suspension in mineral oil (60 wt. %, 50.4 g, 1.26 mol) in portions at 0° C. The mixture was stirred for 0.5 h at 0° C., then ethyl 2-bromoacetate (179 g, 1.07 mol) was added drop-wise into the mixture at such a rate to keep the internal temperature below 10° C. The mixture was stirred for 1 h at 10° C., then poured into aqueous $NH_4Cl$ solution (2 L) in one portion at 0-10° C. Five batches of reactions were combined and the combined mixture was extracted with ethyl acetate (3×2 L). The combined organic layers were washed with brine (500 mL), dried over $Na_2SO_4$, filtered and concentrated under reduced pressure at 45° C. to give 1-(tert-butyl) 4-ethyl 2-(diethoxyphosphoryl)succinate (1.80 kg, 5.32 mol, 89% crude) as a colourless oil. The crude product was used directly in the next step without further purification. $^1H$ NMR (400 MHz, DMSO-d6) δ: 4.12-3.98 (m, 6H), 3.34-3.21 (m, 1H), 2.84-2.71 (m, 1H), 2.68-2.57 (m, 1H), 1.40 (s, 9H), 1.29-1.14 (m, 9H).

Step 3

Four reactions were carried out in parallel. To a solution of 1-(tert-butyl) 4-ethyl 2-(diethoxyphosphoryl)succinate (300 g, 887 mmol) in tetrahydrofuran (1.48 L) was added aqueous NaOH solution (1 M, 1.21 L, 1.21 mol) in one portion. The mixture was stirred at room temperature for 12 h. Four reactions were combined for work up. The reaction mixture was concentrated under reduced pressure at 45° C. to remove tetrahydrofuran, and the residue was extracted with ethyl acetate (2×500 mL). The pH of the aqueous phase was adjusted to 1 with concentrated aqueous HCl (12 M), and the aqueous phase was extracted with ethyl acetate (3×2 L). The combined organic layers were washed with brine (5 L), dried over $Na_2SO_4$, filtered, and concentrated under reduced at 45° C. The crude product was triturated with isopropyl ether (1.1 L) and stirred at RT for 30 min. The suspension was filtered, and the filter cake was washed with isopropyl ether (2×300 mL) and dried under vacuum to give 4-(tert-butoxy)-3-(diethoxyphosphoryl)-4-oxobutanoic acid (840 g, 2.70 mol, 76%) as a white solid. $^1H$ NMR (400 MHz, $CDCl_3$) δ: 10.04 (br.s, 1H), 4.22-4.08 (m, 4H), 3.43-3.29 (m, 1H), 3.08-2.94 (m, 1H), 2.85-2.73 (m, 1H), 1.45 (s, 9H), 1.37-1.27 (m, 6H).

Steps 4 and 5

To a solution of 4-(tert-butoxy)-3-(diethoxyphosphoryl)-4-oxobutanoic acid (100 g, 322 mmol) in THF (600 mL) was added 4-methylmorpholine (32.6 g, 322 mmol) in one portion at RT. The mixture was cooled to −15° C. and ethyl chloroformate (35.0 g, 322 mmol) was added drop-wise to the mixture at such a rate to keep the internal temperature between −15 and −10° C. The mixture was stirred for 2 h at between −15 and −10° C., then N-hydroxynonanimidamide (55.5 g, 322 mmol) and triethylamine (54.5 g, 538 mmol) were added drop-wise at −15 to −10° C. The mixture was stirred at RT for 12 h, then quenched by the addition of dilute aqueous HCl (1 M, 500 mL) at RT. The mixture was extracted with ethyl acetate (3×500 mL) and the combined organic layers were washed with brine (500 mL), dried over $Na_2SO_4$, filtered and concentrated under reduced pressure at 45° C. to give a brown oil. The crude product was purified by flash column chromatography on silica (5-100% ethyl acetate/n-heptane) to give tert-butyl 2-(diethoxyphosphoryl)-4-((1-(hydroxyamino)nonylidene)amino)-4-oxobutanoate (140 g, 301 mmol, 94%) as a yellow oil. LCMS m/z 465.1 $(M+H)^+$ $(ES^+)$. $^1H$ NMR (400 MHz, DMSO-d6) δ: 6.35 (s, 1H), 4.12-3.98 (m, 4H), 3.45-3.33 (m, 1H), 2.97-2.83 (m, 1H), 2.79-2.66 (m, 1H), 2.06-1.95 (m, 2H), 1.57-1.44 (m, 2H), 1.39 (s, 9H), 1.31-1.19 (m, 16H), 0.89-0.81 (m, 3H). One exchangeable proton not observed.

Step 6

To a solution of tert-butyl 2-(diethoxyphosphoryl)-4-((1-(hydroxyamino)nonylidene)amino)-4-oxobutanoate (140 g, 301 mmol) in THF (840 mL) was added $Cs_2CO_3$ (196 g, 603 mmol) in one portion at RT. The mixture was stirred for 3 h at 70° C., then quenched by the addition water (1 L) at RT. The mixture was extracted with ethyl acetate (3×1 L), and the combined organic layers were washed with brine (500 mL), dried over $Na_2SO_4$, filtered and concentrated under reduced pressure at 45° C. to give a brown oil. The crude product was purified by flash column chromatography on silica (5-100% ethyl acetate/n-heptane) to give tert-butyl 2-(diethoxyphosphoryl)-3-(3-octyl-1,2,4-oxadiazol-5-yl) propanoate (109 g, 244 mmol, 81%) as a yellow oil. LCMS m/z 469.2 $(M+Na)^+$ $(ES^+)$. $^1H$ NMR (400 MHz, DMSO-d6) δ: 4.14-4.04 (m, 4H), 3.60-3.48 (m, 1H), 3.39-3.28 (m, 1H), 3.27-3.17 (m, 1H), 2.62 (t, J=7.6 Hz, 2H), 1.66-1.55 (m, 2H), 1.36 (s, 9H), 1.29-1.20 (m, 16H), 0.87-0.82 (m, 3H).

Step 7

To a solution of tert-butyl 2-(diethoxyphosphoryl)-3-(3-octyl-1,2,4-oxadiazol-5-yl)propanoate (100 g, 192 mmol) in THF (600 mL) was added $K_2CO_3$ (79.9 g, 578 mmol) and paraformaldehyde (3.30 g, 193 mmol) in one portion at RT. The mixture was stirred for 12 h at 65° C., then the mixture was concentrated under reduced pressure at 45° C. to give the crude product. The crude product was purified by flash column chromatography on silica (5-100% ethyl acetate/n-heptane) to give tert-butyl 2-((3-octyl-1,2,4-oxadiazol-5-yl) methyl)acrylate (48 g, 149 mmol, 61%) as a yellow oil. LCMS m/z 323.1 $(M+Na)^+$ $(ES^+)$. $^1H$ NMR (400 MHz, DMSO-d6) δ: 6.22 (s, 1H), 5.89 (d, J=1.2 Hz, 1H), 3.90 (s, 2H), 2.63 (t, J=7.2 Hz, 2H), 1.67-1.55 (m, 2H), 1.34 (s, 9H), 1.31-1.18 (m, 10H), 0.85 (t, J=7.2 Hz, 3H).

Step 8

To a solution of tert-butyl 2-((3-octyl-1,2,4-oxadiazol-5-yl)methyl)acrylate (48 g, 149 mmol) in DCM (160 mL) was added TFA (170 g, 1.49 mol) in portions. The mixture was stirred for 12 h at RT and then concentrated under reduced pressure at 45° C. The residue was purified by preparative HPLC (Column: Phenomenex Luna C18 10 μm 100×250 mm; solvent system: MeCN/(0.1% TFA/water) gradient: 40-70% MeCN) to give the product which was lyophilized at RT under vacuum. The product, which still contained some MeCN was co-evaporated with MTBE (100 mL) three times, and then concentrated under reduced pressure at 45° C. for 3 h to give 2-((3-octyl-1,2,4-oxadiazol-5-yl)methyl) acrylic acid (28 g, 105 mmol, 69%) as a yellow oil. LCMS m/z 267.1 $(M+Na)^+$ $(ES^+)$. $^1H$ NMR (400 MHz, DMSO-d6) δ: 12.8 (s, 1H), 6.27 (s, 1H), 5.90 (d, J=0.8 Hz, 1H), 3.90 (s, 2H), 2.67-2.60 (m, 2H), 1.66-1.56 (m, 2H), 1.32-1.18 (m, 10H), 0.85 (t, J=6.8 Hz, 3H).

Tromethamine (TRIS) Salt Isolation of Example 1

Example 1 (38.4 mg, 1 mol eq.) was charged to a vial and dissolved in ACN (400 μL). Tromethamine (17.5 mg, 0.99 mol eq.) was charged to the solution and allowed to stir at 300 rpm for 2 hours at ambient temperature. The resulting solution was evaporated under flux of nitrogen to afford a solid. This was analyzed by XRPD, DSC, TGA and $^1H$ NMR. m.p. 122° C. $^1H$ NMR (400 MHz, DMSO-d6) δ 5.88 (s, 1H), 5.23 (s, 1H), 3.73 (s, 2H), 3.45 (s, 6H), 2.59 (t, J=7.4 Hz, 2H), 1.63-1.53 (m, 2H), 1.27-1.12 (m, 10H), 0.80 (t, J=6.6 Hz, 3H). Six exchangeable protons not observed.

The XRPD data for the tromethamine salt of Example 1 are shown in Table 1.

TABLE 1

XRPD data for the tromethamine salt of Example 1

| Pos. [°2Th.] | Height [cts] | FWHM [°2Th.] | d-spacing [Å] | Rel. Int. [%] |
|---|---|---|---|---|
| 3.7277 | 1255.77 | 0.2047 | 23.70352 | 45.05 |
| 4.1046 | 2787.67 | 0.1023 | 21.52752 | 100.00 |
| 5.5701 | 155.33 | 0.4093 | 15.86655 | 5.57 |
| 9.6096 | 313.57 | 0.1023 | 9.20393 | 11.25 |
| 12.0097 | 158.60 | 0.0768 | 7.36943 | 5.69 |
| 12.9001 | 594.82 | 0.0768 | 6.86271 | 21.34 |
| 13.4570 | 388.74 | 0.1023 | 6.57992 | 13.94 |
| 15.2042 | 171.30 | 0.1535 | 5.82752 | 6.14 |
| 17.0522 | 687.67 | 0.1023 | 5.19989 | 24.67 |
| 17.4190 | 55.27 | 0.8187 | 5.09122 | 1.98 |
| 18.0641 | 591.39 | 0.1279 | 4.91084 | 21.21 |
| 18.7952 | 383.84 | 0.1023 | 4.72143 | 13.77 |
| 19.3351 | 321.64 | 0.1023 | 4.59080 | 11.54 |
| 19.9096 | 2309.21 | 0.1023 | 4.45959 | 82.84 |
| 20.1410 | 821.66 | 0.0768 | 4.40890 | 29.47 |
| 20.6383 | 564.19 | 0.1023 | 4.30377 | 20.24 |
| 21.0239 | 575.90 | 0.1023 | 4.22570 | 20.66 |
| 21.7207 | 194.70 | 0.1023 | 4.09168 | 6.98 |
| 22.4506 | 162.45 | 0.1023 | 3.96028 | 5.83 |
| 23.0003 | 778.19 | 0.1023 | 3.86685 | 27.92 |
| 23.3863 | 890.68 | 0.1023 | 3.80389 | 31.95 |
| 23.6201 | 651.89 | 0.1023 | 3.76677 | 23.38 |
| 24.2091 | 106.02 | 0.1535 | 3.67645 | 3.80 |
| 25.1306 | 120.09 | 0.2558 | 3.54368 | 4.31 |
| 25.8429 | 164.59 | 0.1023 | 3.44761 | 5.90 |
| 26.2850 | 208.98 | 0.1023 | 3.39062 | 7.50 |
| 27.8176 | 64.07 | 0.2558 | 3.20720 | 2.30 |
| 28.6608 | 53.08 | 0.1535 | 3.11473 | 1.90 |
| 29.3303 | 330.96 | 0.1279 | 3.04514 | 11.87 |
| 29.5878 | 261.29 | 0.1279 | 3.01923 | 9.37 |
| 30.7211 | 64.62 | 0.2047 | 2.91038 | 2.32 |
| 31.3887 | 70.70 | 0.1535 | 2.84999 | 2.54 |
| 32.1096 | 126.84 | 0.1023 | 2.78763 | 4.55 |
| 32.6267 | 87.90 | 0.2047 | 2.74462 | 3.15 |
| 33.1134 | 53.21 | 0.1535 | 2.70538 | 1.91 |
| 34.3527 | 87.71 | 0.1535 | 2.61057 | 3.15 |

TGA data (FIG. 1) showed a weight loss of ~0.037% between 25-100° C. DSC analysis (FIG. 1) showed a melting onset at 122° C.

The isolation of the tromethamine salt of Example 1 was scaled up as follows:

Example 1 (2 g, 1 mol eq.) was charged to a round bottom flask and dissolved in ACN (20 mL). TRIS (0.91 g, 1 mol eq.) was dissolved in water (5 mL) and then charged to the solution comprising Example 1. The mixture was stirred at ambient temperature for ~1 hour at which point all the material had dissolved. The resulting solution was initially evaporated using a rotavapor and an oil was isolated. ACN (10 mL) was added to the oil. The system was mixed for 10 min and a white solid was observed. The material was recovered and analysed by $^1H$ NMR. $^1H$ NMR spectra showed the formation of the Example 1 tromethamine salt and the ratio between Example 1: salt was 1:1.04, respectively. No double-bond isomerisation was noted. An XRPD pattern for the crystalline tromethamine salt of Example 1 is shown in FIG. 2 and an $^1$H NMR spectrum for the crystalline tromethamine salt of Example 1 is shown in FIG. 3.

Example 2-2-((5-octyl-1,3,4-oxadiazol-2-yl)methyl) acrylic acid

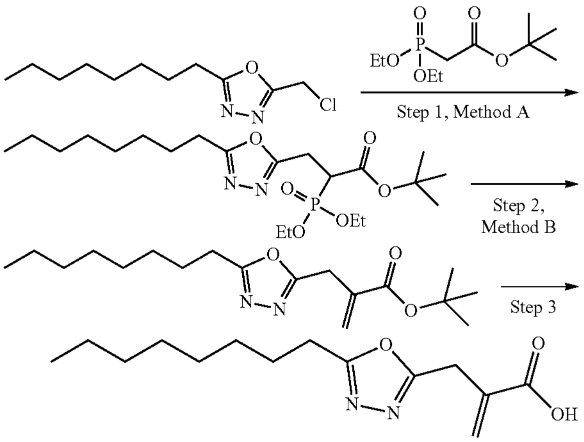

Step 1

Prepared according to General Procedure A, Step 1, Method A from 2-(chloromethyl)-5-octyl-1,3,4-oxadiazole (Intermediate 2, 0.86 g, 3.7 mmol). The crude product was purified by chromatography on silica gel (0-100% EtOAc/isohexane) to afford tert-butyl 2-(diethoxyphosphoryl)-3-(5-octyl-1,3,4-oxadiazol-2-yl)propanoate (1.23 g, 1.1 mmol, 40% purity) as a yellow oil. LCMS m/z 469.3 $(M+Na)^+$ $(ES^+)$.

Step 2

Prepared according to General Procedure A, Step 2, Method B from tert-butyl 2-(diethoxyphosphoryl)-3-(5-octyl-1,3,4-oxadiazol-2-yl)propanoate (1.23 g, 1.1 mmol, 40% purity). The crude product was purified by chromatography on silica gel (0-100% EtOAc/isohexane) to afford tert-butyl 2-((5-octyl-1,3,4-oxadiazol-2-yl)methyl)acrylate (0.197 g, 0.60 mmol) as a colourless oil. $^1$H NMR (400 MHz, DMSO-d6) δ 6.20 (d, J=1.1 Hz, 1H), 5.87-5.79 (m, 1H), 3.86-3.76 (m, 2H), 2.80 (t, J=7.4 Hz, 2H), 1.70-1.57 (m, 2H), 1.38 (s, 9H), 1.34-1.20 (m, 10H), 0.93-0.80 (m, 3H). LCMS m/z 323.2 $(M+H)^+$ $(ES^+)$.

Step 3

Prepared according to General Procedure A, Step 3 from tert-butyl 2-((5-octyl-1,3,4-oxadiazol-2-yl)methyl)acrylate (0.197 g, 0.6 mmol). The crude product was purified by chromatography on silica gel (0-50% EtOAc/isohexane) to afford the title compound (0.132 g, 0.49 mmol) as a white solid. $^1$H NMR (400 MHz, DMSO-d6) δ 12.78 (s, 1H), 6.25 (d, J=1.1 Hz, 1H), 5.86-5.80 (m, 1H), 3.83 (s, 2H), 2.80 (t, J=7.5 Hz, 2H), 1.71-1.60 (m, 2H), 1.34-1.23 (m, 10H), 0.90-0.83 (m, 3H). LCMS m/z 267.1 $(M+H)^+$ $(ES^+)$.

Example 3—2-((5-octyl-1,2,4-oxadiazol-3-yl) methyl)acrylic acid

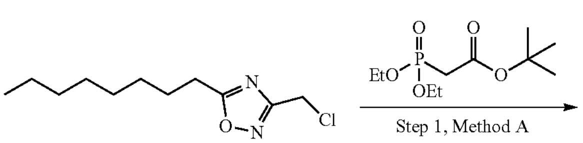

-continued

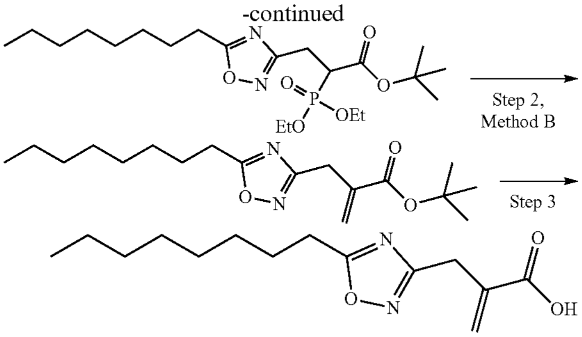

Step 1

Prepared according to General Procedure A, Step 1, Method A from 3-(chloromethyl)-5-octyl-1,2,4-oxadiazole (Intermediate 3, 3.18 g, 13.8 mmol). The crude product was purified by chromatography on silica gel (0-100% EtOAc/isohexane) to afford tert-butyl 2-(diethoxyphosphoryl)-3-(5-octyl-1,2,4-oxadiazol-3-yl)propanoate (3.70 g, 7.3 mmol, 88% purity) as a yellow oil. $^1$H NMR (400 MHz, DMSO-d6) δ 4.14-4.03 (m, 4H), 3.42-3.33 (m, 1H), 3.24-3.12 (m, 1H), 3.07-2.98 (m, 1H), 2.89 (t, J=7.4 Hz, 2H), 1.73-1.65 (m, 2H), 1.36 (s, 9H), 1.29-1.22 (m, 16H), 0.89-0.83 (m, 3H). LCMS m/z 469.3 $(M+Na)^+$ $(ES^+)$.

Step 2

Prepared according to General Procedure A, Step 2, Method B from tert-butyl 2-(diethoxyphosphoryl)-3-(5-octyl-1,2,4-oxadiazol-3-yl)propanoate (3.70 g, 7.3 mmol, 88% purity). The crude product was purified by chromatography on silica gel (0-10% EtOAc/isohexane) to afford tert-butyl 2-((5-octyl-1,2,4-oxadiazol-3-yl)methyl)acrylate (1.75 g, 5.4 mmol) as a colourless oil. $^1$H NMR (400 MHz, DMSO-d6) δ 6.16 (d, J=1.3 Hz, 1H), 5.78-5.70 (m, 1H), 3.68 (s, 2H), 2.88 (t, J=7.4 Hz, 2H), 1.74-1.64 (m, 2H), 1.38 (s, 9H), 1.34-1.19 (m, 10H), 0.89-0.81 (m, 3H). LCMS m/z 267.2 $(M-tBu+H)^+$ $(ES^+)$.

Step 3

Prepared according to General Procedure A, Step 3 from tert-butyl 2-((5-octyl-1,2,4-oxadiazol-3-yl)methyl)acrylate (1.65 g, 5.12 mmol). The crude product was purified by chromatography on silica gel (0-100% EtOAc/isohexane) to afford the title compound (1.32 g, 4.9 mmol) as a pale yellow oil. $^1$H NMR (400 MHz, DMSO-d6) δ 12.57 (s, 1H), 6.22 (d, J=1.3 Hz, 1H), 5.75 (d, J=1.5 Hz, 1H), 3.68 (s, 2H), 2.88 (t, J=7.5 Hz, 2H), 1.78-1.59 (m, 2H), 1.37-1.18 (m, 10H), 0.93-0.78 (m, 3H). LCMS m/z 267.1 $(M+H)^+$ $(ES^+)$.

Example 4—2-((3-(4-chlorobenzyl)-1,2,4-oxadiazol-5-yl)methyl)acrylic acid

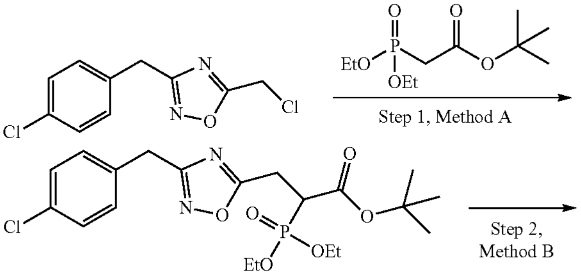

-continued

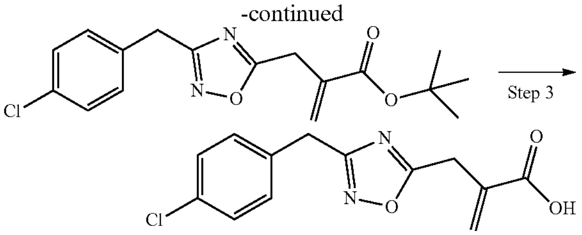

Step 1

Prepared according to General Procedure A, Step 1, Method A from 3-(4-chlorobenzyl)-5-(chloromethyl)-1,2,4-oxadiazole (Intermediate 5, 5.65 g, 23.2 mmol). The crude product was purified by chromatography on silica gel (0-100% EtOAc/isohexane) to afford tert-butyl 3-(3-(4-chlorobenzyl)-1,2,4-oxadiazol-5-yl)-2-(diethoxyphosphoryl) propanoate (7.27 g, 9.0 mmol, 57% purity) as a yellow oil. LCMS m/z 481.2/483.3 $(M+Na)^+$ $(ES^+)$.

Step 2

Prepared according to General Procedure A, Step 2, Method B from tert-butyl 3-(3-(4-chlorobenzyl)-1,2,4-oxadiazol-5-yl)-2-(diethoxyphosphoryl)propanoate (7.27 g, 9.0 mmol, 57% purity). The crude product was purified by chromatography on silica gel (0-30% EtOAc/isohexane) to afford tert-butyl 2-((3-(4-chlorobenzyl)-1,2,4-oxadiazol-5-yl)methyl)acrylate (0.468 g, 1.40 mmol) as a colourless oil. LCMS m/z 279.1/281.0 $(M-tBu+H)^+$ $(ES^+)$. $^1H$ NMR (400 MHz, DMSO-d6) δ 7.42-7.35 (m, 2H), 7.35-7.26 (m, 2H), 6.21 (d, J=1.2 Hz, 1H), 5.94-5.84 (m, 1H), 4.06 (s, 2H), 3.91 (s, 2H), 1.25 (s, 9H).

Step 3

Prepared according to General Procedure A, Step 3 from tert-butyl 2-((3-(4-chlorobenzyl)-1,2,4-oxadiazol-5-yl) methyl)acrylate (0.468 g, 1.40 mmol). The crude product was purified by chromatography on silica gel (0-100% EtOAc/isohexane) to afford 2-((3-(4-chlorobenzyl)-1,2,4-oxadiazol-5-yl)methyl)acrylic acid (0.265 g, 0.94 mmol) as a colourless gum. LCMS m/z 279.5/281.1 $(M+H)^+$ $(ES^+)$. $^1H$ NMR (400 MHz, DMSO-d6) δ 12.80 (s, 1H), 7.44-7.35 (m, 2H), 7.35-7.28 (m, 2H), 6.27 (d, J=1.2 Hz, 1H), 5.95-5.87 (m, 1H), 4.08 (s, 2H), 3.91 (s, 2H).

Example 5—2-((3-(4-chlorophenethyl)-1,2,4-oxadiazol-5-yl)methyl)acrylic acid

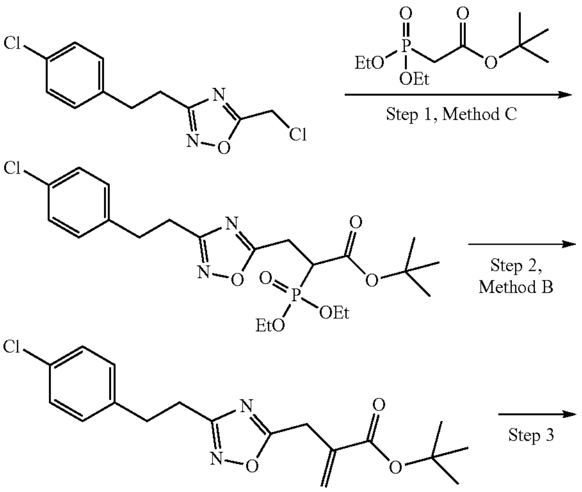

-continued

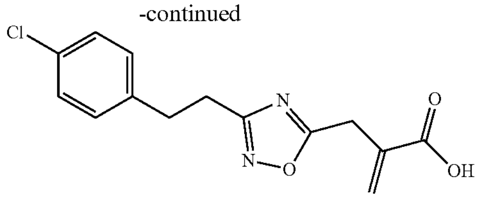

Step 1

Prepared according to General Procedure A, Step 1, Method C from 5-(chloromethyl)-3-(4-chlorophenethyl)-1,2,4-oxadiazole (Intermediate 6, 2.11 g, 8.21 mmol), except the reaction was not heated above RT. The crude product was purified by chromatography on silica gel (0-100% EtOAc/isohexane) to afford tert-butyl 2-(diethoxyphosphoryl)-3-(5-octyl-1,3,4-oxadiazol-2-yl)propanoate (1.87 g, 1.7 mmol, 44% purity) as a yellow oil. LCMS m/z 495.1/497.1 $(M+Na)^+$ $(ES^+)$. $^1H$ NMR (400 MHz, DMSO-d6) δ 7.35-7.20 (m, 4H), 4.15-4.01 (m, 4H), 3.64-3.49 (m, 1H), 3.41-3.32 (m, 1H), 3.29-3.19 (m, 1H), 2.98-2.96 (m, 4H), 1.37 (s, 9H), 1.27-1.22 (m, 6H).

Step 2

Prepared according to General Procedure A, Step 2, Method B from tert-butyl 3-(3-(4-chlorophenethyl)-1,2,4-oxadiazol-5-yl)-2-(diethoxyphosphoryl)propanoate (1.87 g, 1.7 mmol, 44% purity). The crude product was purified by chromatography on silica gel (0-50% EtOAc/isohexane) to afford tert-butyl 2-((3-pentyl-1,2,4-oxadiazol-5-yl)methyl) acrylate (0.413 g, 1.2 mmol) as a yellow oil. LCMS m/z 293.1/295.1 $(M-tBu+H)^+$ $(ES^+)$. $^1H$ NMR (400 MHz, DMSO-d6) δ 7.36-7.29 (m, 2H), 7.29-7.22 (m, 2H), 6.24 (d, J=1.2 Hz, 1H), 5.92-5.85 (m, 1H), 3.92 (s, 2H), 2.97 (s, 4H), 1.34 (s, 9H).

Step 3

Prepared according to General Procedure A, Step 3 from tert-butyl 2-((3-(4-chlorophenethyl)-1,2,4-oxadiazol-5-yl) methyl)acrylate (0.41 g, 1.18 mmol). The crude product was purified by chromatography on silica gel (0-50% EtOAc/isohexane) to afford 2-((3-(4-chlorophenethyl)-1,2,4-oxadiazol-5-yl)methyl)acrylic acid (0.275 g, 0.93 mmol) as a colourless gum. LCMS m/z 293.1/295.1 $(M+H)^+$ $(ES^+)$. $^1H$ NMR (400 MHz, DMSO-d6) δ 12.83 (s, 1H), 7.37-7.28 (m, 2H), 7.27-7.19 (m, 2H), 6.29 (d, J=1.3 Hz, 1H), 5.97-5.86 (m, 1H), 3.92 (s, 2H), 2.97 (m, 4H).

Example 6—2-((3-heptyl-1,2,4-oxadiazol-5-yl) methyl)acrylic acid

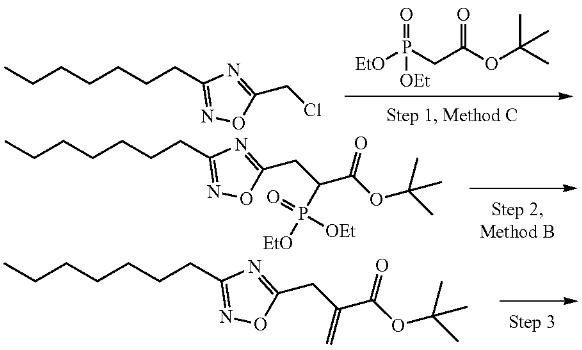

-continued

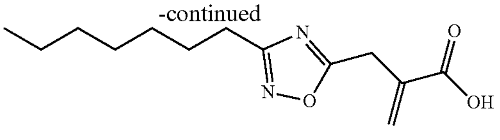

Step 1

Prepared according to General Procedure A, Step 1, Method C from 5-(chloromethyl)-3-heptyl-1,2,4-oxadiazole (Intermediate 4, 7.00 g, 31 mmol). The crude product was purified by chromatography on silica gel (0-70% EtOAc/isohexane) to afford tert-butyl 2-(diethoxyphosphoryl)-3-(3-heptyl-1,2,4-oxadiazol-5-yl)propanoate (5.84 g, 13 mmol) as a colourless oil. LCMS m/z 455.2 $(M+Na)^+$ $(ES^+)$. $^1H$ NMR (400 MHz, DMSO-d6) δ 4.15-4.05 (m, 4H), 3.56 (ddd, J=23.3, 11.1, 4.4 Hz, 1H), 3.40-3.29 (m, 1H), 3.23 (ddd, J=16.8, 8.6, 4.3 Hz, 1H), 2.64 (t, J=7.3 Hz, 2H), 1.68-1.56 (m, 2H), 1.37 (s, 9H), 1.31-1.20 (m, 14H), 0.90-0.83 (m, 3H).

Step 2

Prepared according to General Procedure A, Step 2, Method B from tert-butyl 2-(diethoxyphosphoryl)-3-(3-heptyl-1,2,4-oxadiazol-5-yl)propanoate (5.84 g, 13.5 mmol). The crude product was purified by chromatography on silica gel (0-30% EtOAc/isohexane) to afford tert-butyl 2-((3-heptyl-1,2,4-oxadiazol-5-yl)methyl)acrylate (3.42 g, 11 mmol) as a colourless oil. LCMS m/z 253.2 $(M-tBu+H)^+$ $(ES^+)$. $^1H$ NMR (400 MHz, DMSO-d6) δ 6.23 (d, J=1.2 Hz, 1H), 5.90 (d, J=1.3 Hz, 1H), 3.91 (s, 2H), 2.64 (t, J=7.4 Hz, 2H), 1.62 (s, 2H), 1.34 (s, 9H), 1.30-1.21 (m, 8H), 0.89-0.82 (m, 3H).

Step 3

Prepared according to General Procedure A, Step 3 from tert-butyl 2-((3-heptyl-1,2,4-oxadiazol-5-yl)methyl)acrylate (1.00 g, 3.24 mmol). The crude product was purified by chromatography on silica gel (0-50% EtOAc/isohexane) to afford 2-((3-heptyl-1,2,4-oxadiazol-5-yl)methyl)acrylic acid (0.746 g, 2.9 mmol) as a colourless oil. LCMS m/z 253.3 $(M+H)^+$ $(ES^+)$. $^1H$ NMR (400 MHz, DMSO-d6) δ 12.79 (br. s, 1H), 6.28 (d, J=1.2 Hz, 1H), 5.92 (d, J=1.2 Hz, 1H), 3.91 (s, 2H), 2.65 (t, J=7.5 Hz, 2H), 1.71-1.54 (m, 2H), 1.35-1.19 (m, 8H), 0.95-0.78 (m, 3H).

Example 7—2-((3-(4-chlorophenyl)-1,2,4-oxadiazol-5-yl)methyl)acrylic acid

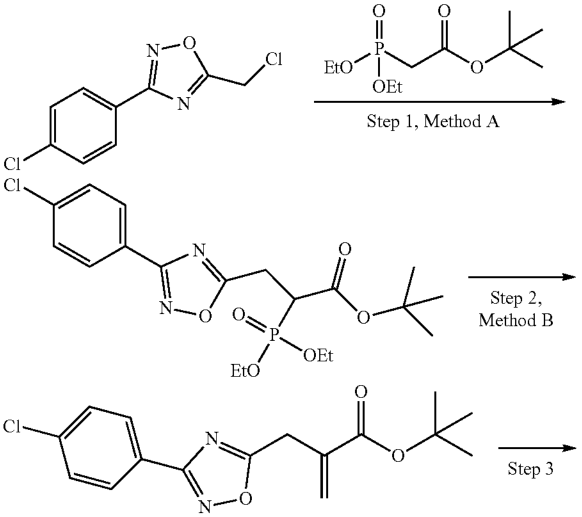

-continued

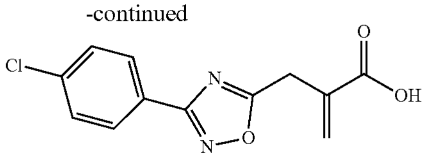

Step 1

Prepared according to General Procedure A, Step 1, Method A using THF in place of NMP from 5-(chloromethyl)-3-(4-chlorophenyl)-1,2,4-oxadiazole (Intermediate 7, 4.00 g, 17 mmol). The crude product was purified by chromatography on RP Flash C18 (5-75% MeCN/Water 0.1% Formic Acid) to afford tert-butyl 3-(3-(4-chlorophenyl)-1,2,4-oxadiazol-5-yl)-2-(diethoxyphosphoryl)propanoate (3.06 g, 6.2 mmol, 90% purity) as a colourless oil. $^1H$ NMR (400 MHz, DMSO-d6) δ 8.03-7.95 (m, 2H), 7.71-7.62 (m, 2H), 4.17-4.05 (m, 4H), 3.75-3.61 (m, 1H), 3.53-3.34 (m, 2H), 1.38 (s, 9H), 1.27 (q, J=6.8 Hz, 6H). LCMS m/z 445.1 $(M+H)^+$ $(ES^+)$.

Step 2

Prepared according to General Procedure A, Step 2, Method B from tert-butyl 3-(3-(4-chlorophenyl)-1,2,4-oxadiazol-5-yl)-2-(diethoxyphosphoryl)propanoate (3.06 g, 6.2 mmol, 90% purity). The crude product was purified by chromatography on RP Flash C18 (5-75% MeCN/Water 0.1% Formic Acid) then by chromatography on silica gel (0-50% EtOAc/isohexane) to afford tert-butyl 2-((3-(4-chlorophenyl)-1,2,4-oxadiazol-5-yl)methyl)acrylate (0.30 g, 0.89 mmol) as a clear and colourless oil. LCMS m/z 265.1 $(M-tBu+H)^+$ $(ES^+)$. $^1H$ NMR (400 MHz, DMSO-d6) δ 8.04-7.94 (m, 2H), 7.69-7.60 (m, 2H), 6.29 (d, J=1.2 Hz, 1H), 6.03-5.95 (m, 1H), 4.05 (s, 2H), 1.34 (s, 9H).

Step 3

Prepared according to General Procedure A, Step 3 from tert-butyl 2-((3-(4-chlorophenyl)-1,2,4-oxadiazol-5-yl)methyl)acrylate (0.300 g, 0.89 mmol). The crude product was purified by chromatography on RP Flash C18 (5-75% MeCN/Water 0.1% Formic Acid) to afford 2-((3-(4-chlorophenyl)-1,2,4-oxadiazol-5-yl)methyl)acrylic acid (0.232 g, 0.83 mmol) as a white solid. LCMS m/z 265.1 $(M+H)^+$ $(ES^+)$. $^1H$ NMR (400 MHz, DMSO-d6) δ 12.88 (s, br. 1H), 8.07-7.91 (m, 2H), 7.70-7.56 (m, 2H), 6.33 (d, J=1.2 Hz, 1H), 6.07-5.90 (m, 1H), 4.04 (s, 2H).

Example 8—2-((3-(octan-2-yl)-1,2,4-oxadiazol-5-yl)methyl)acrylic acid

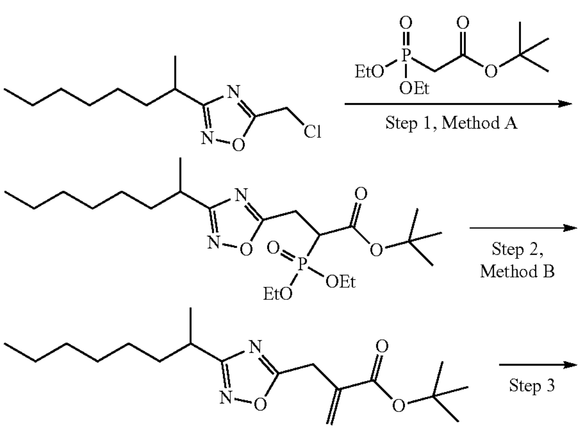

-continued

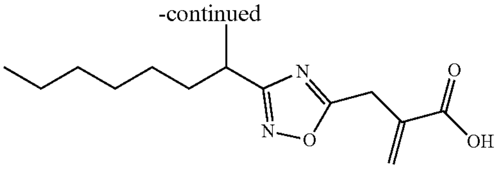

Step 1

Prepared according to General Procedure A, Step 1, Method A using THF in place of NMP from 5-(chloromethyl)-3-(octan-2-yl)-1,2,4-oxadiazole (Intermediate 8, 1.16 g, 4.78 mmol). The crude product was purified by chromatography on silica gel (0-50% EtOAc/isohexane) to afford tert-butyl 2-(diethoxyphosphoryl)-3-(3-(octan-2-yl)-1,2,4-oxadiazol-5-yl)propanoate (0.62 g, 1.2 mmol, 90% purity) as a colourless oil. LCMS m/z 469.1 $(M+Na)^+$ $(ES^+)$. $^1H$ NMR (400 MHz, DMSO-d6) δ 4.14-4.03 (m, 4H), 3.63-3.47 (m, 1H), 3.40-3.32 (m, 1H), 3.28-3.16 (m, 1H), 2.94-2.82 (m, 1H), 1.68-1.44 (m, 2H), 1.37 (s, 9H), 1.32-1.08 (m, 17H), 0.84 (t, J=6.8 Hz, 3H).

Step 2

Prepared according to General Procedure A, Step 2, Method B from tert-butyl 2-(diethoxyphosphoryl)-3-(3-(octan-2-yl)-1,2,4-oxadiazol-5-yl)propanoate (0.62 g, 1.2 mmol, 90% purity). The crude product was purified by chromatography on silica gel (0-10% EtOAc/isohexane) to afford tert-butyl 2-((3-(octan-2-yl)-1,2,4-oxadiazol-5-yl)methyl)acrylate (0.36 g, 1.1 mmol) as a colourless oil. LCMS m/z 267.2 $(M-tBu+H)^+$ $(ES^+)$. $^1H$ NMR (400 MHz, DMSO-d6) δ 6.25-6.21 (m, 1H), 5.92-5.88 (m, 1H), 3.92 (s, 2H), 2.97-2.81 (m, 1H), 1.69-1.45 (m, 2H), 1.34 (s, 9H), 1.29-1.09 (m, 11H), 0.90-0.80 (m, 3H).

Step 3

Prepared according to General Procedure A, Step 3 from tert-butyl 2-((3-(octan-2-yl)-1,2,4-oxadiazol-5-yl)methyl)acrylate (0.38 g, 1.1 mmol). The crude product was purified by chromatography on silica gel (0-50% EtOAc/isohexane) to afford 2-((3-(octan-2-yl)-1,2,4-oxadiazol-5-yl)methyl)acrylic acid (0.32 g, 1.1 mmol) as a colourless oil. LCMS m/z 267.2 $(M+H)^+$ $(ES^+)$. $^1H$ NMR (400 MHz, DMSO-d6) δ 12.80 (s, br. 1H), 6.30-6.26 (m, 1H), 5.92-5.88 (m, 1H), 3.91 (s, 2H), 3.02-2.81 (m, 1H), 1.69-1.57 (m, 1H), 1.57-1.46 (m, 1H), 1.33-1.06 (m, 11H), 0.91-0.79 (m, 3H).

Example 9—2-((3-(naphthalen-2-ylmethyl)-1,2,4-oxadiazol-5-yl)methyl)acrylic acid

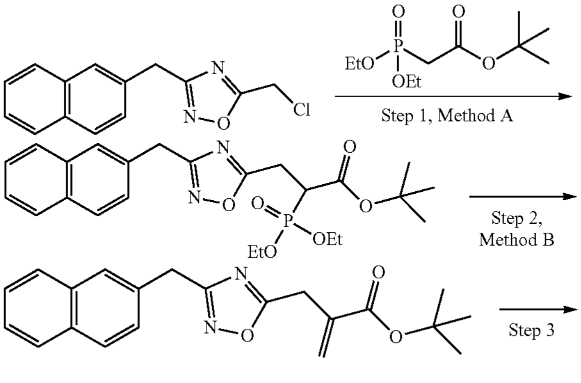

-continued

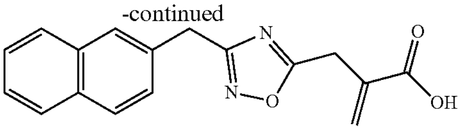

Step 1

Prepared according to General Procedure A, Step 1, Method A using THF in place of NMP from 5-(chloromethyl)-3-(naphthalen-2-ylmethyl)-1,2,4-oxadiazole (Intermediate 9, 1.00 g, 3.7 mmol). The crude product was purified by chromatography on silica gel (0-100% EtOAc/isohexane) to afford tert-butyl 2-(diethoxyphosphoryl)-3-(3-(naphthalen-2-ylmethyl)-1,2,4-oxadiazol-5-yl)propanoate (1.01 g, 1.8 mmol, 84% purity) as an orange oil. LCMS m/z 497.3 $(M+Na)^+$ $(ES^+)$.

Step 2

Prepared according to General Procedure A, Step 2, Method B from tert-butyl 2-(diethoxyphosphoryl)-3-(3-(naphthalen-2-ylmethyl)-1,2,4-oxadiazol-5-yl)propanoate (1.01 g, 1.8 mmol, 84% purity). The crude product was purified by chromatography on silica gel (0-100% EtOAc/isohexane) to afford tert-butyl 2-((3-(naphthalen-2-ylmethyl)-1,2,4-oxadiazol-5-yl)methyl)acrylate (0.30 g, 0.85 mmol) as a pale yellow oil. LCMS m/z 295.2 $(M-tBu+H)^+$ $(ES^+)$. $^1H$ NMR (400 MHz, DMSO-d6) δ 7.92-7.83 (m, 3H), 7.81 (d, J=1.7 Hz, 1H), 7.54-7.45 (m, 2H), 7.42 (dd, J=8.5, 1.8 Hz, 1H), 6.20 (d, J=1.3 Hz, 1H), 5.88 (t, J=1.2 Hz, 1H), 4.22 (s, 2H), 3.91 (s, 2H), 1.20 (s, 9H).

Step 3

Prepared according to General Procedure A, Step 3 from tert-butyl 2-((3-(naphthalen-2-ylmethyl)-1,2,4-oxadiazol-5-yl)methyl)acrylate (0.30 g, 0.85 mmol). The crude product was purified by chromatography on silica gel (0-50% EtOAc/isohexane) to 2-((3-(naphthalen-2-ylmethyl)-1,2,4-oxadiazol-5-yl)methyl)acrylic acid (180 mg, 0.58 mmol) as a white solid. LCMS m/z 295.1 $(M+H)^+$ $(ES^+)$. $^1H$ NMR (400 MHz, DMSO-d6) δ 12.82 (s, 1H), 7.93-7.84 (m, 3H), 7.80 (d, J=1.7 Hz, 1H), 7.54-7.46 (m, 2H), 7.43 (dd, J=8.5, 1.8 Hz, 1H), 6.26 (d, J=1.2 Hz, 1H), 5.90 (d, J=1.3 Hz, 1H), 4.23 (s, 2H), 3.91 (s, 2H).

Example 10—2-((3-(1-(4-chlorophenyl)cyclopropyl)-1,2,4-oxadiazol-5-yl)methyl)acrylic acid

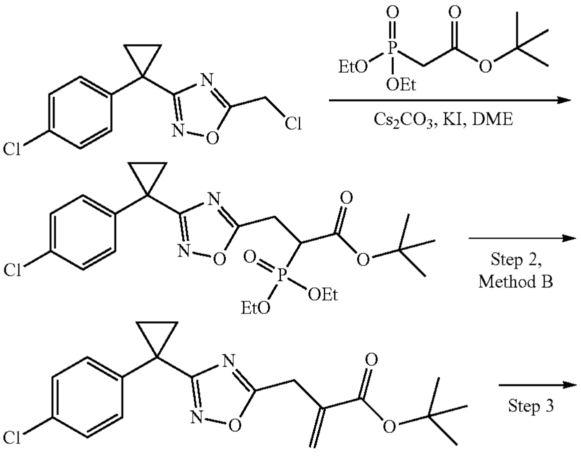

-continued

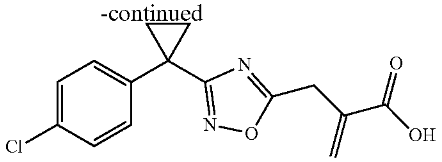

Step 1

Tert-butyl 2-(diethoxyphosphoryl)acetate (1.92 mL, 8.17 mmol) was added to a suspension of 5-(chloromethyl)-3-(1-(4-chlorophenyl)cyclopropyl)-1,2,4-oxadiazole (Intermediate 10, 2.00 g, 7.43 mmol) and cesium carbonate (2.66 g, 8.17 mmol) in DME (20 mL) at RT. The reaction was heated to 80° C. and stirred for 18 h. Potassium iodide (123 mg, 0.74 mmol was added and stirring was continued for 1 h at 80° C. The mixture was cooled to RT and poured into water (50 mL) and extracted with EtOAc (3×25 mL). The combined organic layers were washed with brine (30 mL), dried ($Na_2SO_4$) and concentrated. The crude product was purified by chromatography on silica gel (0-60% EtOAc/isohexane) to afford tert-butyl 3-(3-(1-(4-chlorophenyl)cyclopropyl)-1,2,4-oxadiazol-5-yl)-2-(diethoxyphosphoryl)propanoate (1.12 g, 1.6 mmol, 71% purity) as a yellow oil. LCMS m/z 507.1 $(M+Na)^+$ $(ES^+)$. $^1H$ NMR (400 MHz, DMSO-d6) δ 7.40 (s, 4H), 4.15-3.99 (m, 4H), 3.52 (ddd, J=23.3, 10.9, 4.4 Hz, 1H), 3.37-3.28 (m, 1H), 3.20 (ddd, J=16.8, 8.8, 4.4 Hz, 1H), 1.56-1.37 (m, 4H), 1.36 (s, 9H), 1.25 (q, J=6.8 Hz, 6H).

Step 2

Prepared according to General Procedure A, Step 2, Method B from tert-butyl 3-(3-(1-(4-chlorophenyl)cyclopropyl)-1,2,4-oxadiazol-5-yl)-2-(diethoxyphosphoryl)propanoate (1.12 g, 1.6 mmol, 71% purity). The crude product was purified by chromatography on silica gel (0-30% EtOAc/isohexane) to afford tert-butyl 2-((3-(1-(4-chlorophenyl)cyclopropyl)-1,2,4-oxadiazol-5-yl)methyl)acrylate (396 mg, 1.1 mmol) as a colourless oil. LCMS m/z 305.1/307.1 $(M-tBu+H)^+$ $(ES^+)$. $^1H$ NMR (400 MHz, DMSO-d6) δ 7.40 (s, 4H), 6.21 (d, J=1.2 Hz, 1H), 5.88 (d, J=1.3 Hz, 1H), 3.89 (s, 2H), 1.50-1.41 (m, 2H), 1.41-1.34 (m, 2H), 1.33 (s, 9H).

Step 3

Prepared according to General Procedure A, Step 3 from tert-butyl 2-((3-(1-(4-chlorophenyl)cyclopropyl)-1,2,4-oxadiazol-5-yl)methyl)acrylate (0.394 g, 1.1 mmol). The crude product was purified by chromatography on silica gel (0-60% EtOAc/isohexane) to 2-((3-(1-(4-chlorophenyl)cyclopropyl)-1,2,4-oxadiazol-5-yl)methyl)acrylic acid (206 mg, 0.67 mmol) as a colourless gum. LCMS m/z 305.1/307.1 $(M+H)^+$ $(ES^+)$. $^1H$ NMR (400 MHz, DMSO-d6) δ 12.82 (s, 1H), 7.60-7.27 (m, 4H), 6.27 (d, J=1.2 Hz, 1H), 5.90 (d, J=1.2 Hz, 1H), 3.89 (s, 2H), 1.51-1.34 (m, 4H).

Example 11—2-((3-(8,8,8-trifluorooctyl)-1,2,4-oxadiazol-5-yl)methyl)acrylic acid

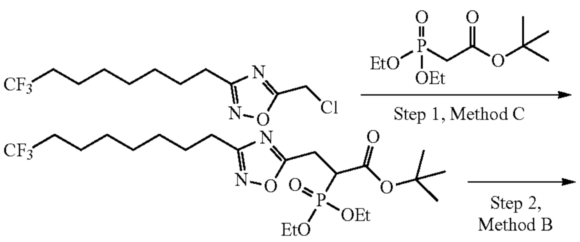

-continued

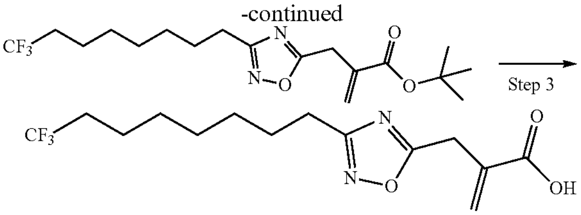

Step 1

Prepared according to General Procedure A, Step 1, Method C from 5-(chloromethyl)-3-(8,8,8-trifluorooctyl)-1,2,4-oxadiazole (Intermediate 11, 4.30 g, 15.1 mmol), except the reaction was not heated above RT. The crude product was purified by chromatography on silica gel (0-60% EtOAc/isohexane) to afford tert-butyl 2-(diethoxyphosphoryl)-3-(3-(8,8,8-trifluorooctyl)-1,2,4-oxadiazol-5-yl)propanoate (4.30 g, 1.7 mmol, 44% purity) as a yellow oil. LCMS m/z 523.2 $(M+Na)^+$ $(ES^+)$. $^1H$ NMR (400 MHz, DMSO-d6) δ 4.21-3.90 (m, 4H), 3.69-3.48 (m, 1H), 3.39-3.30(m, 1H), 3.23 (ddd, J=16.8, 8.7, 4.4 Hz, 1H), 2.69-2.60 (m, 2H), 2.29-2.13 (m, 2H), 1.68-1.55 (m, 2H), 1.50-1.42 (m, 2H), 1.41-1.14 (m, 21H)

Step 2

Prepared according to General Procedure A, Step 2, Method B from tert-butyl 2-(diethoxyphosphoryl)-3-(3-(8,8,8-trifluorooctyl)-1,2,4-oxadiazol-5-yl)propanoate (4.30 g, 8.59 mmol) The crude product was purified by chromatography on silica gel (0-30% EtOAc/isohexane) to afford tert-butyl 2-((3-(8,8,8-trifluorooctyl)-1,2,4-oxadiazol-5-yl)methyl)acrylate (1.84 g, 4.6 mmol) as a clear colourless oil. LCMS m/z 321.2 $(M-tBu+H)^+$ $(ES^+)$. $^1H$ NMR (400 MHz, DMSO-d6) δ 6.23 (d, J=1.2 Hz, 1H), 5.92-5.86 (m, 1H), 3.91 (s, 2H), 2.65 (t, J=7.4 Hz, 2H), 2.29-2.12 (m, 2H), 1.69-1.57 (m, 2H), 1.49-1.41 (m, 2H), 1.36-1.28 (m, 15H).

Step 3

Prepared according to General Procedure A, Step 3 from tert-butyl 2-((3-(8,8,8-trifluorooctyl)-1,2,4-oxadiazol-5-yl)methyl)acrylate (1.84 g, 4.89 mmol). The crude product was purified by chromatography on silica gel (0-30% EtOAc/isohexane) to 2-((3-(8,8,8-trifluorooctyl)-1,2,4-oxadiazol-5-yl)methyl)acrylic acid (1.39 g, 4.33 mmol) as a clear colourless oil. LCMS m/z 321.1 $(M+H)^+$ $(ES^+)$. $^1H$ NMR (400 MHz, DMSO-d6) δ 12.80 (s, 1H), 6.30-6.25 (m, 1H), 5.94-5.87 (m, 1H), 3.91 (s, 2H), 2.65 (t, J=7.5 Hz, 2H), 2.30-2.15 (m, 2H), 1.68-1.56 (m, 2H), 1.51-1.40 (m, 2H), 1.37-1.25 (m, 6H). $^{19}F$ NMR (376 MHz, DMSO-d6) δ −64.76.

Example 12-2-((3-(2-methylheptan-2-yl)-1,2,4-oxadiazol-5-yl)methyl)acrylic acid

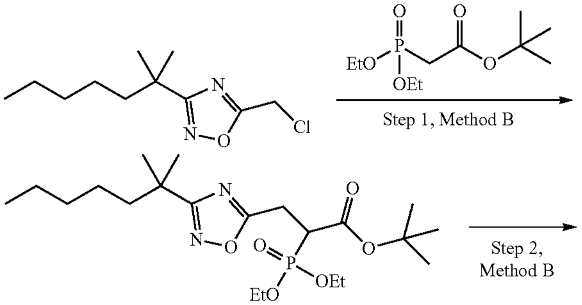

-continued

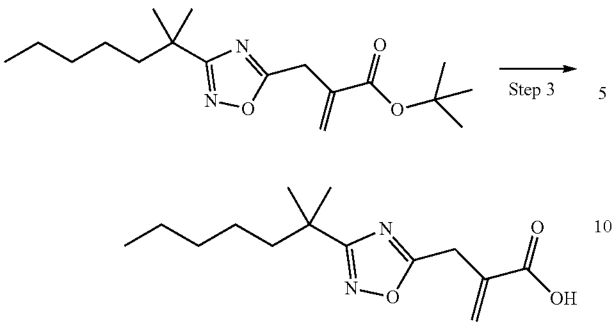

Step 1

Prepared according to General Procedure A, Step 1, Method B from 5-(chloromethyl)-3-(2-methylheptan-2-yl)-1,2,4-oxadiazole (0.60 g, 2.5 mmol), except that sodium iodide was not used and the reaction was not heated above RT. The crude product was purified by chromatography on silica gel (0-50% EtOAc/isohexane) to afford tert-butyl 2-(diethoxyphosphoryl)-3-(3-(2-methylheptan-2-yl)-1,2,4-oxadiazol-5-yl)propanoate (0.55 g, 1.1 mmol, 90% purity) as a yellow oil. LCMS m/z 447.4 $(M+Na)^+$ $(ES^+)$. $^1H$ NMR (400 MHz, DMSO-d6) δ 4.15-4.03 (m, 4H), 3.54 (ddd, J=23.3, 11.1, 4.3 Hz, 1H), 3.40-3.32 (m, 1H), 3.31-3.17 (m, 1H), 1.60-1.52 (m, 2H), 1.37 (s, 10H), 1.31-1.12 (m, 16H), 1.08 (ddd, J=13.8, 7.5, 5.3 Hz, 1H), 0.82 (t, J=7.0 Hz, 3H).

Step 2

Prepared according to General Procedure A, Step 2, Method B from tert-butyl 2-(diethoxyphosphoryl)-3-(3-(2-methylheptan-2-yl)-1,2,4-oxadiazol-5-yl)propanoate (0.55 g, 1.1 mmol, 90% purity). The crude product was purified by chromatography on silica gel (0-100% EtOAc/isohexane) to afford tert-butyl 2-((3-(2-methylheptan-2-yl)-1,2,4-oxadiazol-5-yl)methyl)acrylate (0.30 g, 0.93 mmol) as a colourless oil. LCMS m/z 267.0 $(M-tBu+H)^+$ $(ES^+)$. $^1H$ NMR (400 MHz, DMSO-d6) δ 6.22 (d, J=1.3 Hz, 1H), 5.89 (q, J=1.3 Hz, 1H), 3.90 (s, 2H), 1.60-1.52 (m, 2H), 1.34 (s, 9H), 1.27-1.12 (m, 10H), 1.11-1.01 (m, 2H), 0.81 (t, J=7.0 Hz, 3H).

Step 3

Prepared according to General Procedure A, Step 3 from tert-butyl 2-((3-(2-methylheptan-2-yl)-1,2,4-oxadiazol-5-yl)methyl)acrylate (0.30 g, 0.93 mmol). The crude product was purified by chromatography on silica gel (0-50% EtOAc/isohexane) to afford 2-((3-(2-methylheptan-2-yl)-1,2,4-oxadiazol-5-yl)methyl)acrylic acid (0.16 g, 0.57 mmol) as a white, waxy solid. LCMS m/z 267.0 $(M+H)^+$ $(ES^+)$. $^1H$ NMR (400 MHz, DMSO-d6) δ 12.78 (s, 1H), 6.27 (d, J=1.2 Hz, 1H), 5.88 (q, J=1.3 Hz, 1H), 3.90 (s, 2H), 1.61-1.50 (m, 2H), 1.28-1.11 (m, 10H), 1.11-1.00 (m, 2H), 0.81 (t, J=7.0 Hz, 3H).

Example 13—2-((1-octyl-1H-1,2,4-triazol-3-yl)methyl)acrylic acid

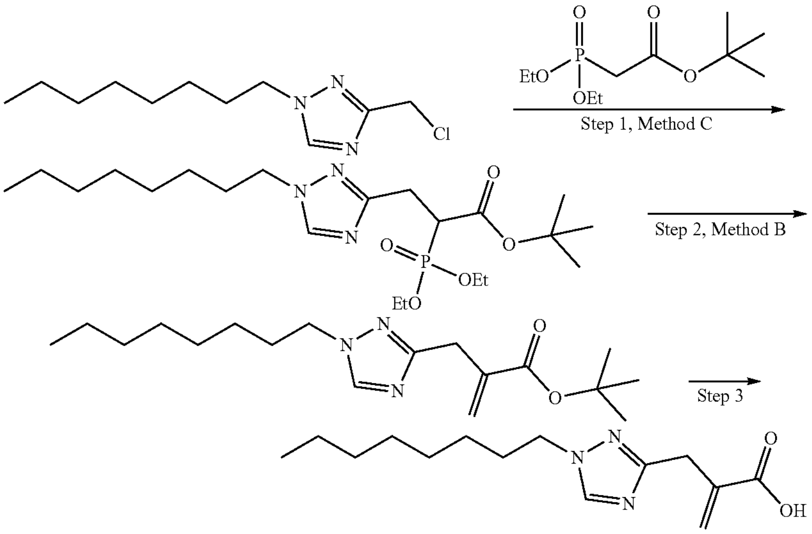

Step 1

Prepared according to General Procedure A, Step 1, Method C from 3-(chloromethyl)-1-octyl-1H-1,2,4-triazole (2.40 g, 10.4 mmol). The crude product was purified by chromatography on silica 15 gel (0-100% EtOAc/isohexane) to afford tert-butyl 2-(diethoxyphosphoryl)-3-(1-octyl-1H-1,2,4-triazol-3-yl)propanoate (3.72 g, 5.4 mmol, 65% purity) as an orange oil. LCMS m/z 466.3 $(M+Na)^+$ $(ES^+)$. $^1H$ NMR (400 MHz, DMSO-d6) δ 8.36 (s, 1H), 4.10-4.03 (m, 6H), 3.39-3.29 (m, 1H), 3.13 (ddd, J=15.5, 11.8, 7.1 Hz, 1H), 2.92 (ddd, J=15.5, 9.6, 3.3 Hz, 1H), 1.74-1.69 (m, 2H), 1.33 (s, 9H), 1.27-1.21 (m, 16H), 0.86-0.83 (m, 3H).

Step 2

Prepared according to General Procedure A, Step 2, Method B from tert-butyl 2-(diethoxyphosphoryl)-3-(1-octyl-1H-1,2,4-triazol-3-yl)propanoate (3.72 g, 5.4 mmol, 65% purity). The crude product was purified by chromatography on silica gel (0-100% EtOAc/isohexane) to afford tert-butyl 2-((1-octyl-1H-1,2,4-triazol-3-yl)methyl)acrylate (1.60 g, 4.98 mmol) as a colourless oil. LCMS m/z 344.3 $(M+Na)^+$ $(ES^+)$. $^1H$ NMR (400 MHz, DMSO-d6) δ 8.36 (s, 1H), 6.05 (d, J=1.6 Hz, 1H), 5.61-5.49 (m, 1H), 4.07 (t, J=6.9 Hz, 2H), 3.57 (s, 2H), 1.80-1.63 (m, 2H), 1.37 (s, 9H), 1.30-1.14 (m, 10H), 0.88-0.82 (m, 3H).

Step 3

Prepared according to General Procedure A, Step 3 from tert-butyl 2-((1-octyl-1H-1,2,4-triazol-3-yl)methyl)acrylate (1.60 g, 4.98 mmol). The crude product was purified by chromatography on silica gel (0-100% EtOAc/isohexane) to afford 2-((1-octyl-1H-1,2,4-triazol-3-yl)methyl)acrylic acid (1.17 g, 4.40 mmol) as a colourless oil. LCMS m/z 266.2 $(M+H)^+$ $(ES^+)$. $^1H$ NMR (400 MHz, DMSO-d6) δ 12.48 (s, 1H), 8.37 (s, 1H), 6.12 (d, J=1.6 Hz, 1H), 5.53 (q, J=1.6 Hz, 1H), 4.08 (t, J=7.0 Hz, 2H), 3.57 (s, 2H), 1.73 (p, J=7.1 Hz, 2H), 1.31-1.15 (m, 10H), 0.85 (t, J=6.8 Hz, 3H).

Example 14—2-((3-(3,4-dichlorobenzyl)-1,2,4-oxadiazol-5-yl)methyl)acrylic acid

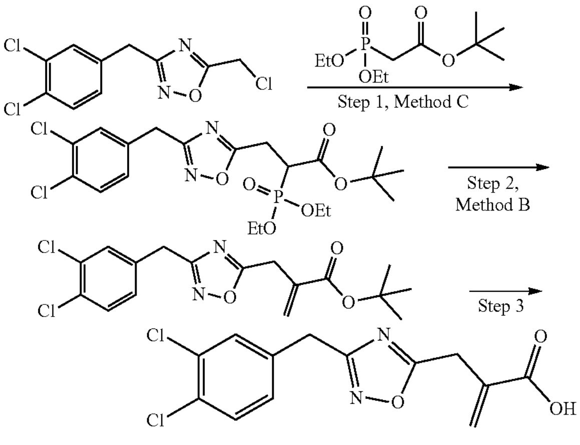

Step 1

Prepared according to General Procedure A, Step 1, Method C from 5-(chloromethyl)-3-(3,4-dichlorobenzyl)-1,2,4-oxadiazole (5.00 g, 18.0 mmol). The crude product was purified by chromatography on silica gel (0-60% EtOAc/isohexane) to afford tert-butyl 3-(3-(3,4-dichlorobenzyl)-1,2,4-oxadiazol-5-yl)-2-(diethoxyphosphoryl)propanoate (2.74 g, 3.1 mmol, 55% purity) as an orange oil. LCMS m/z 437.1/439.1 $(M-tBu+H)^+$ $(ES^+)$.

Step 2

Prepared according to General Procedure A, Step 2, Method B from tert-butyl 3-(3-(3,4-dichlorobenzyl)-1,2,4-oxadiazol-5-yl)-2-(diethoxyphosphoryl)propanoate (2.74 g, 3.1 mmol, 55% purity). The crude product was purified by chromatography on silica gel (0-100% MTBE/isohexane) to afford tert-butyl 2-((3-(3,4-dichlorobenzyl)-1,2,4-oxadiazol-5-yl)methyl)acrylate (0.39 g, 0.80 mmol, 76% Purity) as a colourless oil. LCMS m/z 315.6 $(M-tBu+H)^+$ $(ES^+)$. $^1H$ NMR (400 MHz, DMSO-d6) δ 7.62-7.54 (m, 2H), 7.29 (dd, J=8.2, 2.1 Hz, 1H), 6.21 (s, 1H), 5.89 (s, 1H), 4.10 (s, 2H), 3.91 (s, 2H), 1.23 (s, 9H).

Step 3

Prepared according to General Procedure A, Step 3 from tert-butyl 2-((3-(3,4-dichlorobenzyl)-1,2,4-oxadiazol-5-yl)methyl)acrylate (0.39 g, 0.80 mmol, 76% Purity). The crude product was purified by chromatography on silica gel (0-100% MTBE/isohexane) to afford 2-((3-(3,4-dichlorobenzyl)-1,2,4-oxadiazol-5-yl)methyl)acrylic acid (239.91 mg, 0.76 mmol) as a colourless oil. LCMS m/z 314.8 $(M+H)^+$ $(ES^+)$. $^1H$ NMR (400 MHz, DMSO-d6) δ 12.83 (s, 1H), 7.65-7.54 (m, 2H), 7.29 (dd, J=8.3, 2.1 Hz, 1H), 6.28 (s, 1H), 5.92 (s, 1H), 4.12 (s, 2H), 3.92 (s, 2H).

Example 15—2-((3-(4-(tert-butyl)benzyl)-1,2,4-oxadiazol-5-yl)methyl)acrylic acid

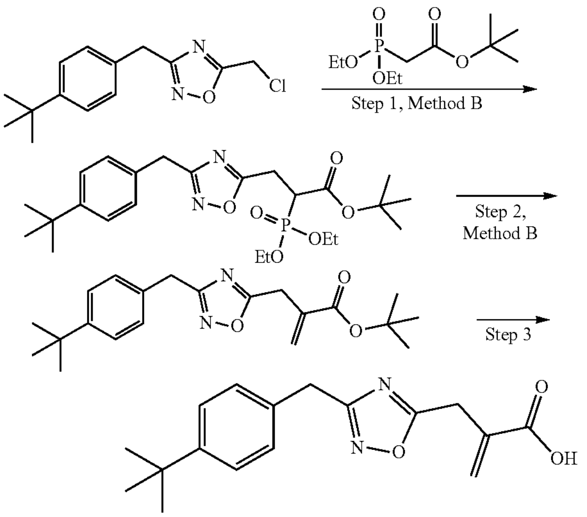

Step 1

Prepared according to General Procedure A, Step 1, Method B from 3-(4-(tert-butyl)benzyl)-5-(chloromethyl)-1,2,4-oxadiazole (2.33 g, 6.51 mmol, 74% purity). The crude product was purified by chromatography on silica gel (0-50% EtOAc/isohexane) to afford tert-butyl 3-(3-(4-(tert-butyl)benzyl)-1,2,4-oxadiazol-5-yl)-2-(diethoxyphosphoryl)propanoate (1.0 g, 2.0 mmol) as an orange oil. LCMS m/z 503.3 $(M-tBu+H)^+$ $(ES^+)$. $^1H$ NMR (400 MHz, DMSO-d6) δ 7.35-7.29 (m, 2H), 7.22-7.15 (m, 2H), 4.12-4.01 (m, 5H), 3.98 (d, J=1.6 Hz, 2H), 3.54 (ddd, J=23.4, 10.9, 4.5 Hz, 1H), 3.22 (ddd, J=16.8, 8.7, 4.5 Hz, 1H), 1.30-1.20 (m, 24H).

Step 2

Prepared according to General Procedure A, Step 2, Method B from tert-butyl 3-(3-(4-(tert-butyl)benzyl)-1,2,4-oxadiazol-5-yl)-2-(diethoxyphosphoryl)propanoate (1.0 g, 2.1 mmol). The crude product was purified by chromatography on silica gel (0-100% EtOAc/isohexane) to afford tert-butyl 2-((3-(4-(tert-butyl)benzyl)-1,2,4-oxadiazol-5-yl)methyl)acrylate (0.30 g, 0.58 mmol, 69% purity) as a pale yellow oil. LCMS m/z 300.8 $(M-tBu+H)^+$ $(ES^+)$. $^1H$ NMR (400 MHz, DMSO-d6) δ 7.33-7.30 (m, 2H), 7.21-7.17 (m, 2H), 6.21 (d, J=1.2 Hz, 1H), 5.88 (q, J=1.3 Hz, 1H), 3.98 (s, 2H), 3.90 (d, J=1.0 Hz, 2H), 1.25 (s, 9H), 1.24 (s, 9H).

Step 3

Prepared according to General Procedure A, Step 3 from tert-butyl 2-((3-(4-(tert-butyl)benzyl)-1,2,4-oxadiazol-5-yl)methyl)acrylate (0.30 g, 0.58 mmol, 69% purity). The crude product was purified by preparative HPLC (Waters X-Select Prep-C18, 5 μm, 30×100 mm column, 40-70% MeCN in Water 0.1% Formic Acid) to afford 2-((3-(4-(tert-butyl)benzyl)-1,2,4-oxadiazol-5-yl)methyl)acrylic acid (100 mg, 0.33 mmol) as a sticky yellow oil. LCMS m/z 300.8 $(M+H)^+$ $(ES^+)$. $^1H$ NMR (400 MHz, DMSO-d6) δ 12.84 (s, 1H), 7.40-7.28 (m, 2H), 7.25-7.14 (m, 2H), 6.26 (d, J=1.2 Hz, 1H), 5.90 (d, J=1.4 Hz, 1H), 4.00 (s, 2H), 3.90 (d, J=1.0 Hz, 2H), 1.26 (s, 9H).

Example 16—2-((3-(3,5-dichlorobenzyl)-1,2,4-oxadiazol-5-yl)methyl)acrylic acid

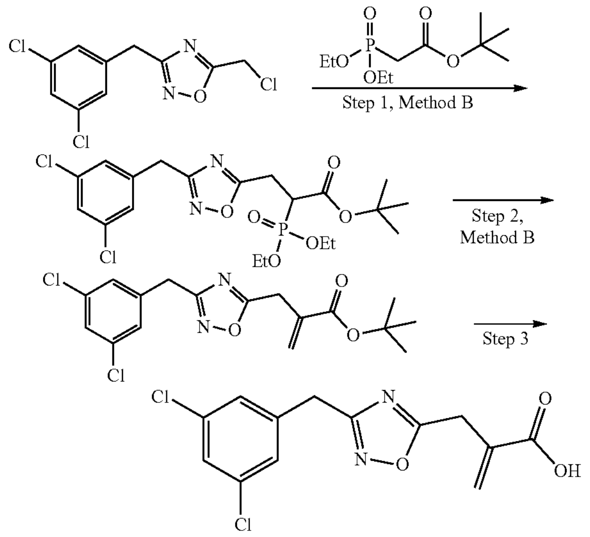

Step 1

Prepared according to General Procedure A, Step 1, Method B from 5-(chloromethyl)-3-(3,5-dichlorobenzyl)-1,2,4-oxadiazole (4.18 g, 9.2 mmol, 61% purity), except sodium iodide was not used. The crude product was purified by chromatography on silica gel (0-50% EtOAc/isohexane) to afford tert-butyl 3-(3-(3,5-dichlorobenzyl)-1,2,4-oxadiazol-5-yl)-2-(diethoxyphosphoryl)propanoate (1.0 g, 2.0 mmol) as an orange oil. LCMS m/z 503.3 $(M-tBu+H)^+$ $(ES^+)$. $^1$H NMR (400 MHz, DMSO-d6) δ 7.35-7.29 (m, 2H), 7.22-7.15 (m, 2H), 4.12-4.01 (m, 5H), 3.98 (d, J=1.6 Hz, 2H), 3.54 (ddd, J=23.4, 10.9, 4.5 Hz, 1H), 3.22 (ddd, J=16.8, 8.7, 4.5 Hz, 1H), 1.30-1.20 (m, 24H).

Step 2

Prepared according to General Procedure A, Step 2, Method B from tert-butyl 3-(3-(3,5-dichlorobenzyl)-1,2,4-oxadiazol-5-yl)-2-(diethoxyphosphoryl)propanoate (1.0 g, 2.0 mmol). The crude product was purified by chromatography on silica gel (0-100% EtOAc/isohexane) to afford tert-butyl 2-((3-(3,5-dichlorobenzyl)-1,2,4-oxadiazol-5-yl)methyl)acrylate (0.61 g, 1.6 mmol) as a colourless oil. LCMS m/z 313.0 $(M-tBu+H)^+$ $(ES^+)$. $^1$H NMR (400 MHz, DMSO-d6) δ 7.52 (t, J=2.0 Hz, 1H), 7.38 (d, J=2.0 Hz, 2H), 6.22 (d, J=1.2 Hz, 1H), 5.90 (q, J=1.3 Hz, 1H), 4.13 (s, 2H), 3.93 (d, J=1.1 Hz, 2H), 1.25 (s, 9H).

Step 3

Prepared according to General Procedure A, Step 3 from tert-butyl 2-((3-(3,5-dichlorobenzyl)-1,2,4-oxadiazol-5-yl)methyl)acrylate (610 mg, 1.57 mmol). The crude product was purified by chromatography on silica gel (0-100% EtOAc/isohexane) to afford 2-((3-(3,5-dichlorobenzyl)-1,2,4-oxadiazol-5-yl)methyl)acrylic acid (230 mg, 0.71 mmol) as a pale yellow oil. LCMS m/z 313.5/315.1 $(M+H)^+$ $(ES^+)$. $^1$H NMR (400 MHz, DMSO-d6) δ 12.82 (s, 1H), 7.52 (t, J=1.9 Hz, 1H), 7.39 (d, J=1.9 Hz, 2H), 6.28 (d, J=1.2 Hz, 1H), 5.93 (q, J=1.2 Hz, 1H), 4.14 (s, 2H), 3.93 (d, J=1.2 Hz, 2H).

Example 17—2-((3-(7,7,8,8,8-pentafluorooctyl)-1,2,4-oxadiazol-5-yl)methyl)acrylic acid

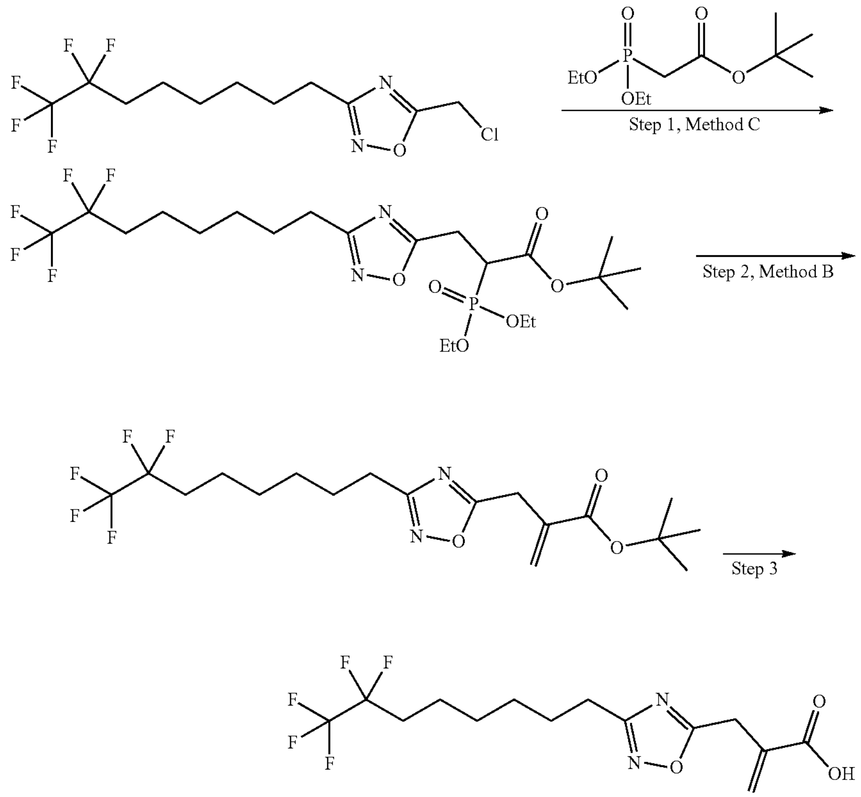

Step 1

Prepared according to General Procedure A, Step 1, Method C from 5-(chloromethyl)-3-(7,7,8,8,8-pentafluorooctyl)-1,2,4-oxadiazole (2.74 g, 8.53 mmol), except that the reaction was heated to 60° C. The crude product was purified by chromatography on silica gel (0-100% MTBE/isohexane) to afford tert-butyl 2-(diethoxyphosphoryl)-3-(3-(7,7,8,8,8-pentafluorooctyl)-1,2,4-oxadiazol-5-yl)propanoate (0.754 g, 1.3 mmol, 90% purity) as a colourless oil. LCMS m/z 558.9 $(M+Na)^+$ $(ES^+)$. $^1H$ NMR (400 MHz, DMSO-d6) δ 4.17-3.95 (m, 4H), 3.55 (ddd, J=23.3, 11.0, 4.4 Hz, 1H), 3.42-3.28 (m, 2H), 3.22 (ddd, J=16.8, 8.6, 4.4 Hz, 1H), 2.65 (t, J=7.4 Hz, 2H), 2.15 (tq, J=16.2, 7.8 Hz, 2H), 1.68-1.55 (m, 2H), 1.48 (p, J=7.6, 6.8 Hz, 14H), 1.29-1.19 (m, 6H).

Step 2

Prepared according to General Procedure A, Step 2, Method B from tert-butyl 2-(diethoxyphosphoryl)-3-(3-(7,7,8,8,8-pentafluorooctyl)-1,2,4-oxadiazol-5-yl)propanoate (0.754 g, 1.3 mmol, 90% purity). The crude product was purified by chromatography on silica gel (0-50% MTBE/isohexane) to afford tert-butyl 2-((3-(7,7,8,8,8-pentafluorooctyl)-1,2,4-oxadiazol-5-yl)methyl)acrylate (0.326 g, 0.78 mmol) as a colourless oil. LCMS m/z 357.6 $(M-tBu+H)^+$ $(ES^+)$. $^1H$ NMR (400 MHz, DMSO-d6) δ 6.23 (s, 1H), 5.90 (s, 1H), 3.91 (s, 2H), 2.66 (t, J=7.4 Hz, 2H), 2.27-2.07 (m, 2H), 1.63 (p, J=7.4 Hz, 2H), 1.55-1.43 (m, 3H), 1.43-1.27 (m, 12H).

Step 3

Prepared according to General Procedure A, Step 3 from tert-butyl 2-((3-(7,7,8,8,8-pentafluorooctyl)-1,2,4-oxadiazol-5-yl)methyl)acrylate (0.326 g, 0.78 mmol). The crude product was purified by chromatography on silica gel (0-50% MTBE/isohexane) to afford 2-((3-(7,7,8,8,8-pentafluorooctyl)-1,2,4-oxadiazol-5-yl)methyl)acrylic acid (0.188 g, 0.52 mmol) as a colourless oil. LCMS m/z 357.0 $(M+H)^+$ $(ES^+)$. $^1H$ NMR (400 MHz, DMSO-d6) δ 12.81 (s, 1H), 6.28 (s, 1H), 5.91 (s, 1H), 3.91 (s, 2H), 2.66 (t, J=7.5 Hz, 2H), 2.17 (tt, J=19.3, 7.8 Hz, 2H), 1.64 (p, J=7.4 Hz, 2H), 1.56-1.44 (m, 2H), 1.44-1.27 (m, 4H).

Example 18—2-((3-(4-butylphenyl)-1,2,4-oxadiazol-5-yl)methyl)acrylic acid

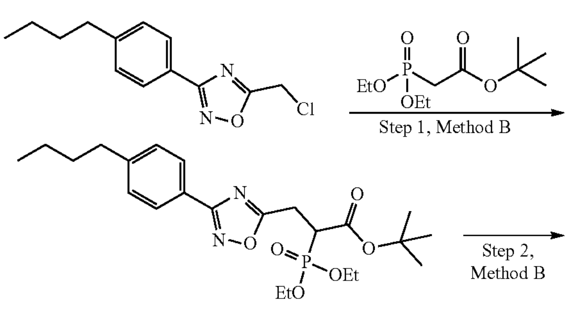

-continued

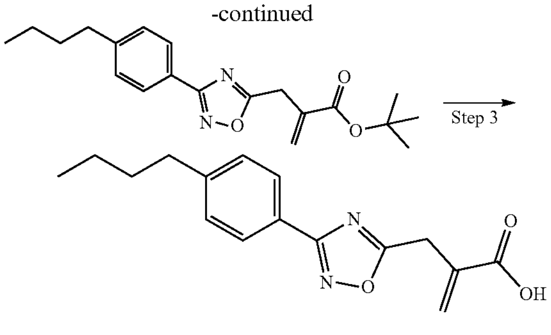

Step 1

Prepared according to General Procedure A, Step 1, Method B from 3-(4-butylphenyl)-5-(chloromethyl)-1,2,4-oxadiazole (2.80 g, 7.37 mmol, 66% purity), except sodium iodide was not used. The crude product was purified by chromatography on silica gel (0-50% EtOAc/isohexane) to afford tert-butyl 3-(3-(4-butylphenyl)-1,2,4-oxadiazol-5-yl)-2-(diethoxyphosphoryl)propanoate (1.72 g, 3.5 mmol) as a yellow oil. LCMS m/z 489.3 $(M+Na)^+$ $(ES^+)$. $^1H$ NMR (400 MHz, DMSO-d6) δ 7.92-7.85 (m, 2H), 7.41-7.35 (m, 2H), 4.11 (qdd, J=7.9, 6.6, 5.0 Hz, 4H), 3.67 (ddd, J=23.4, 10.8, 4.6 Hz, 1H), 3.52-3.33 (m, 2H), 2.69-2.62 (m, 2H), 1.64-1.53 (m, 2H), 1.38 (s, 9H), 1.27 (q, J=6.9 Hz, 8H), 0.91 (t, J=7.3 Hz, 3H).

Step 2

Prepared according to General Procedure A, Step 2, Method B from tert-butyl 3-(3-(4-butylphenyl)-1,2,4-oxadiazol-5-yl)-2-(diethoxyphosphoryl)propanoate (1.72 g, 3.5 mmol). The crude product was purified by chromatography on silica gel (0-100% EtOAc/isohexane) to afford tert-butyl 2-((3-(4-butylphenyl)-1,2,4-oxadiazol-5-yl)methyl)acrylate (1.0 g, 2.8 mmol) as a pale yellow oil. LCMS m/z 287.1 $(M-tBu+H)^+$ $(ES^+)$. $^1H$ NMR (400 MHz, DMSO-d6) δ 7.92-7.86 (m, 2H), 7.42-7.34 (m, 2H), 6.28 (d, J=1.2 Hz, 1H), 5.97 (q, J=1.3 Hz, 1H), 4.03 (s, 2H), 2.69-2.61 (m, 2H), 1.63-1.53 (m, 2H), 1.34 (m, 11H), 0.91 (t, J=7.3 Hz, 3H).

Step 3

Prepared according to General Procedure A, Step 3 from tert-butyl 2-((3-(4-butylphenyl)-1,2,4-oxadiazol-5-yl)methyl)acrylate (1.0 g, 2.8 mmol). The crude product was purified by chromatography on silica gel (0-100% EtOAc/isohexane) to afford 2-((3-(4-butylphenyl)-1,2,4-oxadiazol-5-yl)methyl)acrylic acid (775 mg, 2.7 mmol) as a white solid. LCMS m/z 286.7 $(M+H)^+$ $(ES^+)$. $^1H$ NMR (400 MHz, DMSO-d6) δ 12.81 (s, 1H), 7.94-7.83 (m, 2H), 7.41-7.34 (m, 2H), 6.33 (d, J=1.2 Hz, 1H), 6.00 (d, J=1.3 Hz, 1H), 4.02 (s, 2H), 2.69-2.61 (m, 2H), 1.64-1.53 (m, 2H), 1.32 (h, J=7.4 Hz, 2H), 0.90 (t, J=7.4 Hz, 3H).

Example 19—2-((3-((4'-chloro-[1,1'-biphenyl]-4-yl)methyl)-1,2,4-oxadiazol-5-yl)methyl)acrylic acid

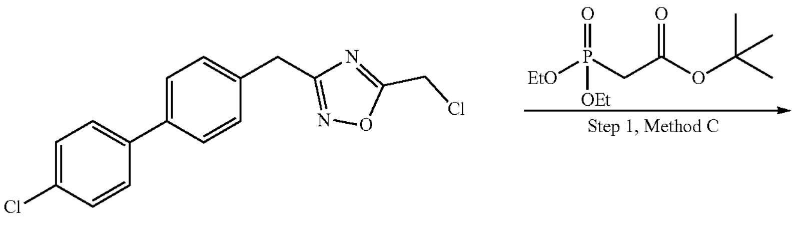

-continued

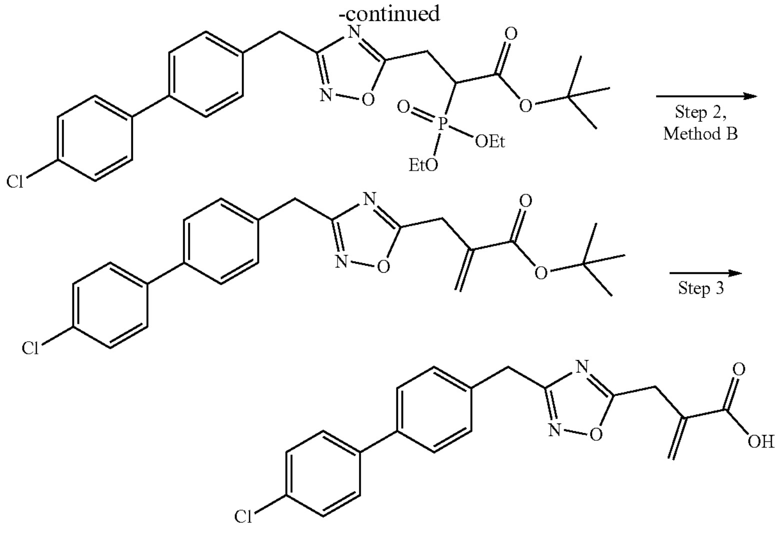

Step 1

Prepared according to General Procedure A, Step 1, Method C from 3-((4'-chloro-[1,1'-biphenyl]-4-yl)methyl)-5-(chloromethyl)-1,2,4-oxadiazole (1.52 g, 1 Eq, 4.76 mmol), except the reaction was heated to 60° C. The crude product was purified by chromatography on silica gel (0-100% MTBE/isohexane) to afford tert-butyl 3-(3-((4'-chloro-[1,1'-biphenyl]-4-yl)methyl)-1,2,4-oxadiazol-5-yl)-2-(diethoxyphosphoryl)propanoate (0.529 g, 0.89 mmol, 90% Purity) as a colourless oil. LCMS m/z 559.5 $(M+Na)^+$ $(ES^+)$. $^1H$ NMR (400 MHz, DMSO-d6) δ 7.71-7.56 (m, 4H), 7.55-7.47 (m, 2H), 7.42-7.32 (m, 2H), 4.14-3.96 (m, 6H), 3.55 (ddd, J=23.3, 10.9, 4.5 Hz, 1H), 3.42-3.18 (m, 2H), 1.31-1.18 (m, 15H).

Step 2

Prepared according to General Procedure A, Step 2, Method B from 3-(3-((4'-chloro-[1,1'-biphenyl]-4-yl)methyl)-1,2,4-oxadiazol-5-yl)-2-(diethoxyphosphoryl)propanoate (0.529 g, 0.89 mmol, 90% Purity). The crude product was purified by chromatography on silica gel (0-50% MTBE/isohexane) to afford tert-butyl 2-((3-((4'-chloro-[1,1'-biphenyl]-4-yl)methyl)-1,2,4-oxadiazol-5-yl)methyl)acrylate (0.178 g, 0.39 mmol, 91% purity) as a colourless oil. LCMS m/z 355.6 $(M-tBu+H)^+$ $(ES^+)$. $^1H$ NMR (400 MHz, DMSO-d6) δ 7.70-7.64 (m, 2H), 7.64-7.58 (m, 2H), 7.54-7.48 (m, 2H), 7.41-7.35 (m, 2H), 6.22 (s, 1H), 5.89 (s, 1H), 4.10 (s, 2H), 3.91 (s, 2H), 1.25 (s, 9H).

Step 3

Prepared according to General Procedure A, Step 3 from tert-butyl 2-((3-((4'-chloro-[1,1'-biphenyl]-4-yl)methyl)-1,2,4-oxadiazol-5-yl)methyl)acrylate (0.178 g, 0.39 mmol, 91% purity). The crude product was purified by chromatography on silica gel (0-100% EtOAc/isohexane) to afford 2-((3-((4'-chloro-[1,1'-biphenyl]-4-yl)methyl)-1,2,4-oxadiazol-5-yl)methyl)acrylic acid (72 mg, 0.20 mmol) as a pale yellow oil. LCMS m/z 355.0 $(M+H)^+$ $(ES^+)$. $^1H$ NMR (400 MHz, DMSO-d6) δ 12.84 (s, 1H), 7.72-7.66 (m, 2H), 7.66-7.58 (m, 2H), 7.54-7.48 (m, 2H), 7.42-7.34 (m, 2H), 6.27 (d, J=1.2 Hz, 1H), 5.91 (d, J=1.3 Hz, 1H), 4.11 (s, 2H), 3.92 (s, 2H).

Example 20—2-((3-(4-butylbenzyl)-1,2,4-oxadiazol-5-yl)methyl)acrylic acid

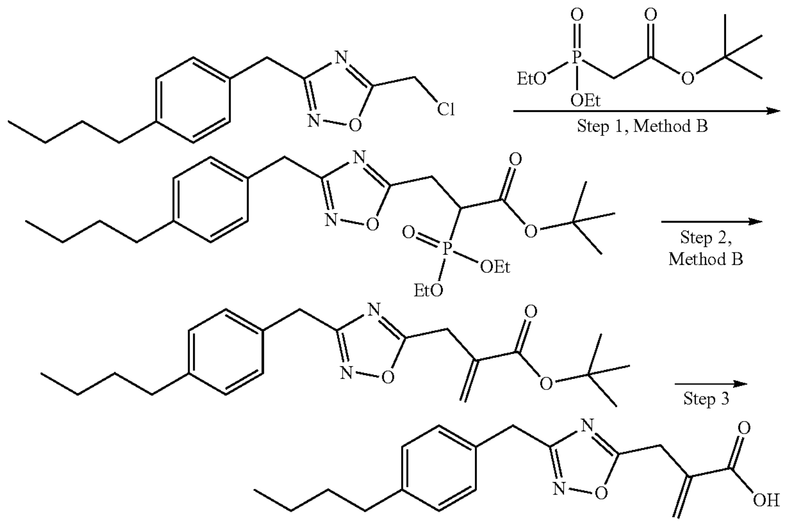

Step 1

Prepared according to General Procedure A, Step 1, Method B from 3-(4-butylbenzyl)-5-(chloromethyl)-1,2,4-oxadiazole (1.10 g, 3.9 mmol), except sodium iodide was not used. The crude product was purified by chromatography on silica gel (0-100% EtOAc/isohexane) to afford tert-butyl 3-(3-(4-butylbenzyl)-1,2,4-oxadiazol-5-yl)-2-(diethoxyphosphoryl)propanoate (0.85 g, 1.8 mmol) as a colourless oil. LCMS m/z 481.1 $(M+H)^+$ $(ES^+)$. $^1$H NMR (400 MHz, DMSO-d6) δ 7.16 (d, J=8.2 Hz, 2H), 7.11 (d, J=8.2 Hz, 2H), 4.13-4.01 (m, 4H), 3.98 (s, 2H), 3.64-3.46 (m, 1H), 3.31-3.27 (m, 1H), 3.27-3.16 (m, 1H), 2.56-2.53 (m, 2H), 1.58-1.45 (m, 2H), 1.28 (s, 9H), 1.26-1.18 (m, 8H), 0.88 (t, J=7.3 Hz, 3H).

Step 2

Prepared according to General Procedure A, Step 2, Method B from 3-(3-(4-butylbenzyl)-1,2,4-oxadiazol-5-yl)-2-(diethoxyphosphoryl)propanoate (0.85 g, 1.8 mmol). The crude product was purified by chromatography on silica gel (0-100% EtOAc/cyclohexane) to afford tert-butyl 2-((3-(4-butylbenzyl)-1,2,4-oxadiazol-5-yl)methyl)acrylate (0.62 g, 1.74 mmol) as a colourless oil. LCMS m/z 301.1 $(M-tBu+H)^+$ $(ES^+)$. $^1$H NMR (400 MHz, DMSO-d6) δ 7.17 (d, J=8.0 Hz, 2H), 7.11 (d, J=8.1 Hz, 2H), 6.23-6.19 (m, 1H), 5.90-5.86 (m, 1H), 3.99 (s, 2H), 3.90 (s, 2H), 2.57-2.52 (m, 2H), 1.59-1.46 (m, 2H), 1.33-1.26 (m, 2H), 1.25 (s, 9H), 0.88 (t, J=7.3 Hz, 3H).

Step 3

Prepared according to General Procedure A, Step 3 from tert-butyl 2-((3-(4-butylbenzyl)-1,2,4-oxadiazol-5-yl) methyl)acrylate (0.62 g, 1.74 mmol). The crude product was purified by chromatography on silica gel (0-50% EtOAc/heptane) to afford 2-((3-(4-butylbenzyl)-1,2,4-oxadiazol-5-yl)methyl)acrylic acid (0.523 g, 1.72 mmol) as a white solid. LCMS m/z 301.1 $(M+H)^+$ $(ES^+)$. $^1$H NMR (400 MHz, DMSO-d6) δ 12.81 (s, br. 1H), 7.17 (d, J=8.2 Hz, 2H), 7.13 (d, J=8.1 Hz, 2H), 6.29-6.25 (m, 1H), 5.93-5.89 (m, 1H), 4.00 (s, 2H), 3.90 (s, 2H), 2.57-2.53 (m, 2H), 1.57-1.47 (m, 2H), 1.34-1.23 (m, 2H), 0.89 (t, J=7.3 Hz, 3H).

Example 21—2-((3-(1-(3-chlorophenyl)cyclopropyl)-1,2,4-oxadiazol-5-yl)methyl)acrylic acid

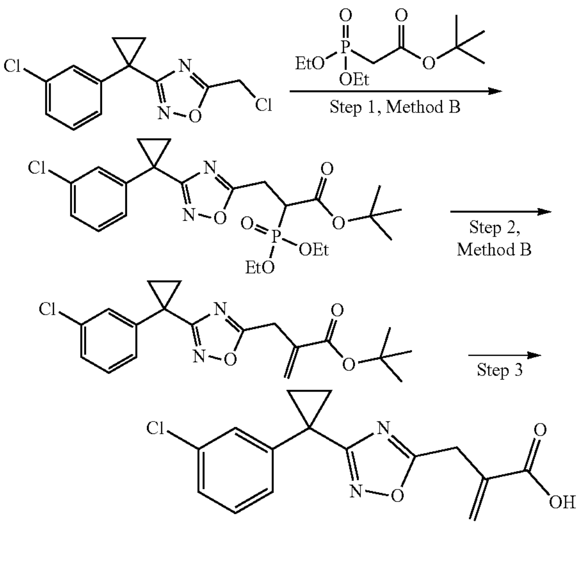

Step 1

Prepared according to General Procedure A, Step 1, Method B from 5-(chloromethyl)-3-(1-(3-chlorophenyl)cyclopropyl)-1,2,4-oxadiazole (2.24 g, 7.41 mmol, 89% purity), except sodium iodide was not used. The crude product was purified by chromatography on silica gel (0-100% EtOAc/isohexane) to afford tert-butyl 3-(3-(1-(3-chlorophenyl)cyclopropyl)-1,2,4-oxadiazol-5-yl)-2-(diethoxyphosphoryl)propanoate (1.60 g, 3.3 mmol) as a sticky yellow oil. LCMS m/z 501.2 $(M+Na)^+$ $(ES^+)$. $^1$H NMR (400 MHz, DMSO-d6) δ 7.43-7.39 (m, 1H), 7.40-7.32 (m, 3H), 4.14-3.99 (m, 4H), 3.53 (ddd, J=23.3, 10.9, 4.4 Hz, 1H), 3.38-3.27 (m, 1H), 3.21 (ddd, J=16.8, 8.9, 4.5 Hz, 1H), 1.54-1.39 (m, 4H), 1.36 (s, 9H), 1.29-1.21 (m, 6H).

Step 2

Prepared according to General Procedure A, Step 2, Method B from tert-butyl 3-(3-(1-(3-chlorophenyl)cyclopropyl)-1,2,4-oxadiazol-5-yl)-2-(diethoxyphosphoryl)propanoate (1.60 g, 3.3 mmol). The crude product was purified by chromatography on silica gel (0-100% EtOAc/cyclohexane) to afford tert-butyl 2-((3-(1-(3-chlorophenyl)cyclopropyl)-1,2,4-oxadiazol-5-yl)methyl)acrylate (0.88 g, 2.3 mmol) as a colourless oil. LCMS m/z 383.1 $(M+Na)^+$ $(ES^+)$. $^1$H NMR (400 MHz, DMSO-d6) δ 7.44-7.41 (m, 1H), 7.41-7.32 (m, 3H), 6.22 (d, J=1.1 Hz, 1H), 5.89 (q, J=1.3 Hz, 1H), 3.90 (s, 2H), 1.48-1.39 (m, 4H), 1.34 (s, 9H).

Step 3

Prepared according to General Procedure A, Step 3 from tert-butyl 2-((3-(1-(3-chlorophenyl)cyclopropyl)-1,2,4-oxadiazol-5-yl)methyl)acrylate (0.88 g, 2.3 mmol). The crude product was purified by chromatography on silica gel (0-100% EtOAc/heptane) to afford 2-((3-(1-(3-chlorophenyl)cyclopropyl)-1,2,4-oxadiazol-5-yl)methyl)acrylic acid (670 mg, 2.1 mmol) as a colourless gum. LCMS m/z 305.1 $(M+H)^+$ $(ES^+)$. $^1$H NMR (400 MHz, DMSO-d6) δ 12.84 (s, 1H), 7.46-7.43 (m, 1H), 7.40-7.33 (m, 3H), 6.27 (d, J=1.2 Hz, 1H), 5.91 (d, J=1.2 Hz, 1H), 3.89 (s, 2H), 1.51-1.38 (m, 4H).

Example 22-2-((3-(1-(4-(trifluoromethyl)phenyl)cyclopropyl)-1,2,4-oxadiazol-5-yl)methyl)acrylic acid

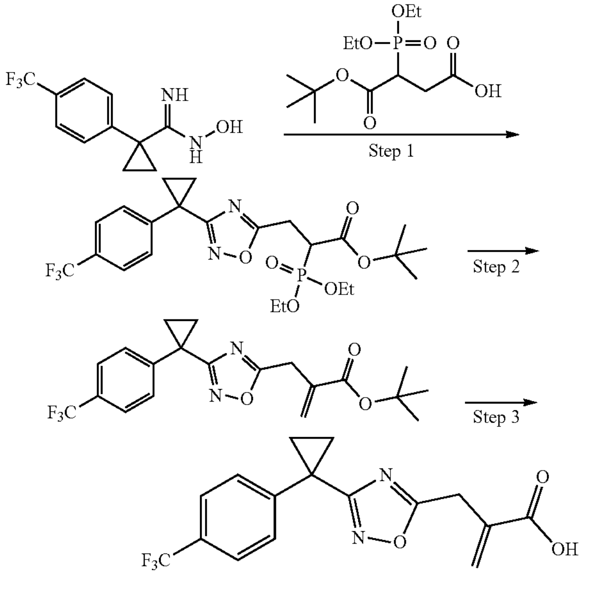

Step 1

Prepared according to General Procedure B, Method A from N-hydroxy-1-(4-(trifluoromethyl)phenyl)cyclopropane-1-carboximidamide (1.12 g, 1.5 eq., 4.59 mmol). The crude product was purified by chromatography on silica gel (0-100% MTBE/isohexane) to afford tert-butyl 2-(diethoxyphosphoryl)-3-(3-(1-(4-(trifluoromethyl)phenyl)cyclopropyl)-1,2,4-oxadiazol-5-yl)propanoate (0.532 g, 0.93 mmol, 91% purity) as a colourless oil. LCMS m/z 541.1 $(M+Na)^+$ $(ES^+)$. $^1H$ NMR (400 MHz, DMSO-d6) δ 7.69 (dd, J=11.6, 8.1 Hz, 2H), 7.57 (dd, J=18.7, 8.0 Hz, 2H), 4.14-3.99 (m, 4H), 3.52 (ddd, J=23.3, 10.9, 4.4 Hz, 1H), 3.39-3.26 (m, 1H), 3.20 (ddd, J=16.8, 8.9, 4.4 Hz, 1H), 1.57-1.14 (m, 19H).

Step 2

Prepared according to General Procedure A, Step 2, Method B from tert-butyl 2-(diethoxyphosphoryl)-3-(3-(1-(4-(trifluoromethyl)phenyl)cyclopropyl)-1,2,4-oxadiazol-5-yl)propanoate (0.532 g, 0.93 mmol, 91% purity). The crude product was purified by chromatography on silica gel (0-50% MTBE/isohexane) to afford tert-butyl 2-((3-(1-(4-(trifluoromethyl)phenyl)cyclopropyl)-1,2,4-oxadiazol-5-yl)methyl)acrylate (0.107 g, 0.27 mmol) as a colourless oil. LCMS m/z 339.1 $(M-tBu+H)^+$ $(ES^+)$. $^1H$ NMR (400 MHz, DMSO-d6) δ 7.70 (d, J=8.1 Hz, 2H), 7.60 (d, J=8.1 Hz, 2H), 6.21 (s, 1H), 5.88 (s, 1H), 3.90 (s, 2H), 1.56-1.39 (m, 4H), 1.32 (s, 9H).

Step 3

Prepared according to General Procedure A, Step 3 from tert-butyl 2-((3-(1-(4-(trifluoromethyl)phenyl)cyclopropyl)-1,2,4-oxadiazol-5-yl)methyl)acrylate (0.107 g, 0.27 mmol). The crude product was purified by chromatography on silica gel (0-50% MTBE/isohexane) to afford 2-((3-(1-(4-(trifluoromethyl)phenyl)cyclopropyl)-1,2,4-oxadiazol-5-yl)methyl)acrylic acid (70 mg, 0.20 mmol) as a colourless oil. LCMS m/z 339.1 $(M+H)^+$ $(ES^+)$. $^1H$ NMR (400 MHz, DMSO-d6) δ 12.82 (s, 1H), 7.71 (d, J=8.2 Hz, 2H), 7.61 (d, J=8.1 Hz, 2H), 6.27 (d, J=1.2 Hz, 1H), 5.91 (d, J=1.3 Hz, 1H), 3.90 (s, 2H), 1.58-1.39 (m, 4H).

Example 23—2-((3-(4-pentylphenyl)-1,2,4-oxadiazol-5-yl)methyl)acrylic acid

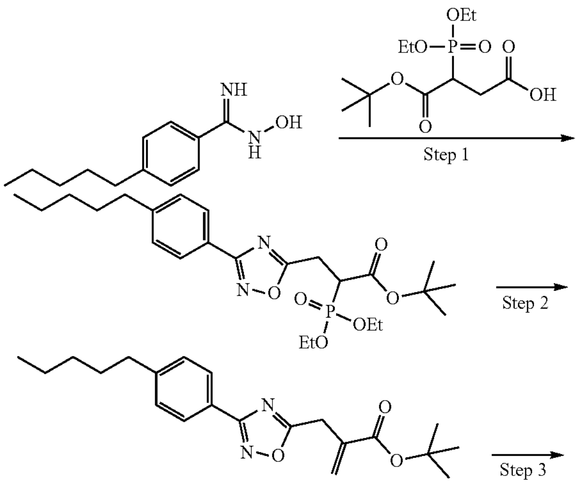

-continued

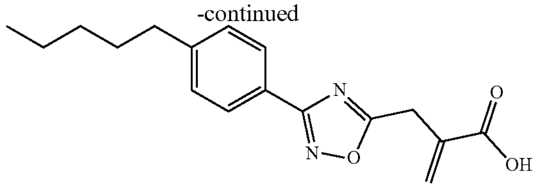

Step 1

Prepared according to General Procedure B, Method A from N-hydroxy-4-pentylbenzimidamide (0.95 g, 1.5 Eq, 4.6 mmol). The crude product was purified by chromatography on silica gel (0-100% MTBE/isohexane) to afford tert-butyl 2-(diethoxyphosphoryl)-3-(3-(4-pentylphenyl)-1,2,4-oxadiazol-5-yl)propanoate (0.509 g, 1.0 mmol) as a colourless oil. LCMS m/z 503.3 $(M+Na)^+$ $(ES^+)$. $^1H$ NMR (400 MHz, DMSO-d6) δ 7.93-7.84 (m, 2H), 7.43-7.34 (m, 2H), 4.18-4.04 (m, 4H), 3.67 (ddd, J=23.4, 10.8, 4.6 Hz, 1H), 3.52-3.27 (m, 2H), 2.65 (t, J=7.7 Hz, 2H), 1.61 (p, J=7.5 Hz, 2H), 1.38 (s, 9H), 1.34-1.22 (m, 10H), 0.88 (t, J=7.1 Hz, 3H).

Step 2

Prepared according to General Procedure A, Step 2, Method B from tert-butyl 2-(diethoxyphosphoryl)-3-(3-(4-pentylphenyl)-1,2,4-oxadiazol-5-yl)propanoate (0.509 g, 1.0 mmol). The crude product was purified by chromatography on silica gel (0-50% MTBE/isohexane) to afford tert-butyl 2-((3-(4-pentylphenyl)-1,2,4-oxadiazol-5-yl)methyl)acrylate (0.268 g, 0.74 mmol) as a colourless oil. LCMS m/z 301.5 $(M-tBu+H)^+$ $(ES^+)$. $^1H$ NMR (400 MHz, DMSO-d6) δ 7.93-7.86 (m, 2H), 7.42-7.35 (m, 2H), 6.28 (d, J=1.2 Hz, 1H), 5.97 (d, J=1.3 Hz, 1H), 4.03 (s, 2H), 2.66 (t, J=7.8 Hz, 2H), 1.60 (p, J=7.4 Hz, 2H), 1.40-1.22 (m, 13H), 0.87 (t, J=6.9 Hz, 3H).

Step 3

Prepared according to General Procedure A, Step 3 from tert-butyl 2-((3-(4-pentylphenyl)-1,2,4-oxadiazol-5-yl)methyl)acrylate (0.268 g, 0.74 mmol). The crude product was purified by chromatography on silica gel (0-50% MTBE/isohexane) to afford 2-((3-(4-pentylphenyl)-1,2,4-oxadiazol-5-yl)methyl)acrylic acid (185 mg, 0.61 mmol) as a colourless oil. LCMS m/z 301.0 $(M+H)^+$ $(ES^+)$. $^1H$ NMR (400 MHz, DMSO-d6) δ 12.87 (s, 1H), 7.95-7.84 (m, 2H), 7.44-7.32 (m, 2H), 6.33 (d, J=1.2 Hz, 1H), 6.00 (s, 1H), 4.02 (d, J=1.1 Hz, 2H), 2.65 (t, J=7.6 Hz, 2H), 1.70-1.52 (m, 2H), 1.41-1.19 (m, 4H), 0.87 (t, J=6.9 Hz, 3H).

Example 24—2-((3-(1-(2-chlorophenyl)cyclopropyl)-1,2,4-oxadiazol-5-yl)methyl)acrylic acid

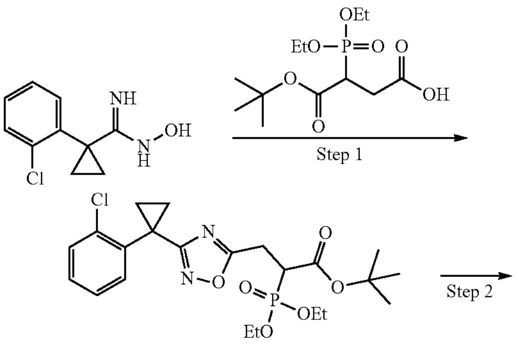

-continued

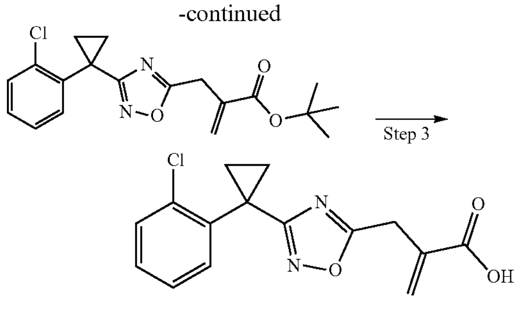

Step 1

Prepared according to General Procedure B, Method A from 1-(2-chlorophenyl)-N-hydroxycyclopropane-1-carboximidamide (729 mg, 2.77 mmol, 80% purity). The crude product was purified by chromatography on RP Flash C18 (5-75% (0.1% Formic acid in MeCN)/(0.1% Formic Acid in Water)) to afford tert-butyl 3-(3-(1-(2-chlorophenyl)cyclopropyl)-1,2,4-oxadiazol-5-yl)-2-(diethoxyphosphoryl)propanoate (0.43 g, 0.84 mmol) as a clear colourless gum. LCMS m/z 485.1 $(M+H)^+$ $(ES^+)$. $^1H$ NMR (400 MHz, DMSO-d6) δ 7.55-7.43 (m, 2H), 7.41-7.29 (m, 2H), 4.14-4.01 (m, 4H), 3.59-3.45 (m, 1H), 3.36-3.13 (m, 2H), 1.66-1.50 (m, 2H), 1.43-1.39 (m, 2H), 1.37 (s, 9H), 1.30-1.20 (m, 6H).

Step 2

Prepared according to General Procedure A, Step 2, Method B from tert-butyl 3-(3-(1-(2-chlorophenyl)cyclopropyl)-1,2,4-oxadiazol-5-yl)-2-(diethoxyphosphoryl)propanoate (0.43 g, 0.84 mmol). The crude product was purified by chromatography on silica gel (0-50% MTBE/isohexane) to afford tert-butyl 2-((3-(1-(2-chlorophenyl)cyclopropyl)-1,2,4-oxadiazol-5-yl)methyl)acrylate (0.300 g, 0.79 mmol) as a clear and colourless oil. LCMS m/z 305.1 $(M-tBu+H)^+$ $(ES^+)$. $^1H$ NMR (400 MHz, DMSO-d6) δ 7.56-7.44 (m, 2H), 7.41-7.32 (m, 2H), 6.24-6.19 (m, 1H), 5.90-5.86 (m, 1H), 3.89 (s, 2H), 1.61-1.54 (m, 2H), 1.44-1.37 (m, 2H), 1.34 (s, 9H).

Step 3

Prepared according to General Procedure A, Step 3 from tert-butyl 2-((3-(1-(2-chlorophenyl)cyclopropyl)-1,2,4-oxadiazol-5-yl)methyl)acrylate (0.300 g, 0.79 mmol). The crude product was purified by chromatography on silica gel (0-50% MTBE/isohexane) to afford 2-((3-(1-(2-chlorophenyl)cyclopropyl)-1,2,4-oxadiazol-5-yl)methyl)acrylic acid (0.225 g, 0.70 mmol) as a colourless gum. LCMS m/z 305.0 $(M+H)^+$ $(ES^+)$. $^1H$ NMR (400 MHz, DMSO-d6) δ 12.83 (s, br. 1H), 7.56-7.50 (m, 1H), 7.49-7.43 (m, 1H), 7.41-7.30 (m, 2H), 6.28-6.23 (m, 1H), 5.91-5.86 (m, 1H), 3.89 (s, 2H), 1.66-1.51 (m, 2H), 1.47-1.28 (m, 2H).

Example 25—2-((3-(1-(4-chlorophenyl)cyclobutyl)-1,2,4-oxadiazol-5-yl)methyl)acrylic acid

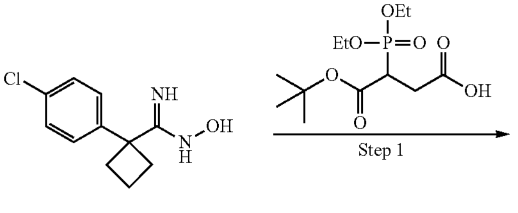

-continued

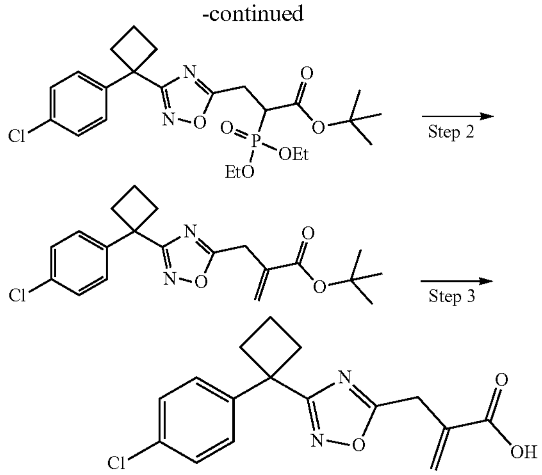

Step 1

Prepared according to General Procedure B, Method A from 1-(4-chlorophenyl)-N-hydroxycyclobutane-1-carboximidamide (596 mg, 1 eq., 2.18 mmol, 82% purity). The crude product was purified by chromatography on silica gel (0-100% EtOAc/isohexane) to afford tert-butyl 3-(3-(1-(4-chlorophenyl)cyclobutyl)-1,2,4-oxadiazol-5-yl)-2-(diethoxyphosphoryl)propanoate (602 mg, 0.72 mmol, 60% purity) as a clear colourless oil. LCMS m/z 520.5 $(M+Na)^+$ $(ES^+)$. $^1H$ NMR (400 MHz, DMSO-d6) δ 7.41-7.36 (m, 2H), 7.32-7.26 (m, 2H), 4.10-4.00 (m, 4H), 3.52 (ddd, J=23.3, 10.9, 4.6 Hz, 1H), 3.38-3.17 (m, 2H), 2.80-2.57 (m, 4H), 2.09-1.86 (m, 2H), 1.27 (s, 9H), 1.25-1.20 (m, 6H).

Step 2

Prepared according to General Procedure A, Step 2, Method B from tert-butyl 3-(3-(1-(4-chlorophenyl)cyclobutyl)-1,2,4-oxadiazol-5-yl)-2-(diethoxyphosphoryl)propanoate (602 mg, 0.72 mmol, 60% purity). The crude product was purified by chromatography on silica gel (0-30% EtOAc/isohexane) to afford tert-butyl 2-((3-(1-(4-chlorophenyl)cyclobutyl)-1,2,4-oxadiazol-5-yl)methyl) acrylate (250 mg, 0.64 mmol) as a colourless oil. LCMS m/z 319.2/321.2 $(M-tBu+H)^+$ $(ES^+)$. $^1H$ NMR (400 MHz, DMSO-d6) δ 7.41-7.35 (m, 2H), 7.33-7.26 (m, 2H), 6.21 (d, J=1.3 Hz, 1H), 5.87 (d, J=1.3 Hz, 1H), 3.90 (s, 2H), 2.80-2.71 (m, 2H), 2.68-2.57 (m, 2H), 2.09-1.85 (m, 2H), 1.20 (s, 9H).

Step 3

Prepared according to General Procedure A, Step 3 from tert-butyl 2-((3-(1-(4-chlorophenyl)cyclobutyl)-1,2,4-oxadiazol-5-yl)methyl)acrylate (250 mg, 0.64 mmol). The crude product was purified by chromatography on silica gel (0-60% EtOAc/isohexane) to afford 2-((3-(1-(4-chlorophenyl)cyclobutyl)-1,2,4-oxadiazol-5-yl)methyl)acrylic acid (164 mg, 0.50 mmol) as a sticky colourless gum. LCMS m/z 319.1/321.1 $(M+H)^+$ $(ES^+)$. $^1H$ NMR (400 MHz, DMSO-d6) δ 12.81 (s, 1H), 7.44-7.36 (m, 2H), 7.34-7.27 (m, 2H), 6.26 (d, J=1.2 Hz, 1H), 5.88 (d, J=1.3 Hz, 1H), 3.90 (s, 2H), 2.81-2.70 (m, 2H), 2.68-2.56 (m, 2H), 2.09-1.98 (m, 1H), 1.97-1.83 (m, 1H).

Example 26—2-((3-(2-methyloctan-2-yl)-1,2,4-oxadiazol-5-yl)methyl)acrylic acid

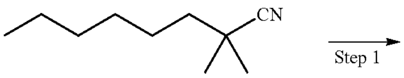

-continued

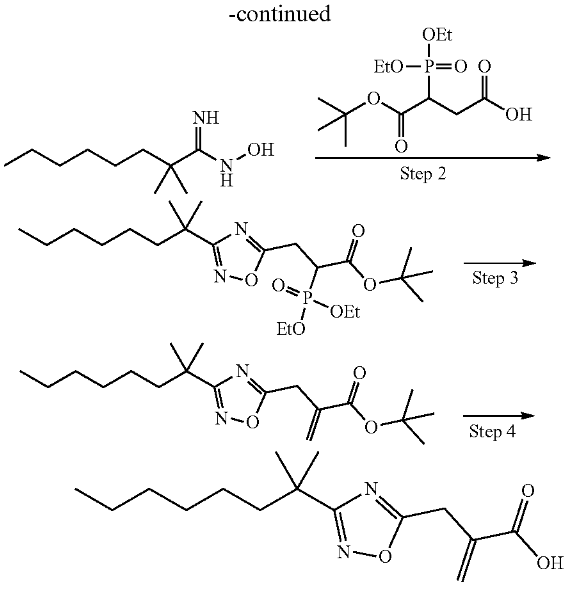

Step 1

A mixture of hydroxylamine hydrochloride (1.22 g, 17.6 mmol) and sodium bicarbonate (1.48 g, 17.6 mmol) in IPA (20 mL) was stirred for 15 min. 2,2-dimethyloctanenitrile (2.50 g, 14.7 mmol, 90% purity) was added and the mixture was heated to 85° C. and stirred for 22 h. The mixture was cooled to RT, filtered and washed with IPA (3×20 mL). The filtrate was concentrated to afford N-hydroxy-2,2-dimethyl-octanimidamide (2.70 g, 14 mmol) as a sticky orange oil, which was used directly in the next step.

Step 2

Prepared according to General Procedure B, Method A from crude N-hydroxy-2,2-dimethyloctanimidamide (1.44 g, 7.35 mmol). The crude product was purified by chromatography on silica gel (0-100% EtOAc/isohexane) to afford tert-butyl 2-(diethoxyphosphoryl)-3-(3-(2-methyloctan-2-yl)-1,2,4-oxadiazol-5-yl)propanoate (1.92 g, 2.1 mmol, 50% purity) as a light brown oil. LCMS m/z 483.3 $(M+Na)^+$ $(ES^+)$. $^1H$ NMR (400 MHz, DMSO-d6) δ 4.15-3.99 (m, 4H), 3.54 (ddd, J=23.3, 11.1, 4.3 Hz, 1H), 3.40-3.28 (m, 1H), 3.23 (ddd, J=16.7, 8.7, 4.3 Hz, 1H), 1.40 (t, J=7.0 Hz, 3H), 1.37 (s, 9H), 1.29-1.16 (m, 10H), 1.03 (s, 6H), 0.88-0.81 (m, 6H).

Step 3

Prepared according to General Procedure A, Step 2, Method B from tert-butyl 2-(diethoxyphosphoryl)-3-(3-(2-methyloctan-2-yl)-1,2,4-oxadiazol-5-yl)propanoate (1.92 g, 2.1 mmol, 50% purity). The crude product was purified by chromatography on silica gel (0-100% EtOAc/isohexane) to afford tert-butyl 2-((3-(2-methyloctan-2-yl)-1,2,4-oxadiazol-5-yl)methyl)acrylate (504 mg, 1.5 mmol) as a colourless oil. LCMS m/z 337.2 $(M+H)^+$ $(ES^+)$. $^1H$ NMR (400 MHz, DMSO-d6) δ 6.23 (d, J=1.2 Hz, 1H), 5.89 (d, J=1.4 Hz, 1H), 3.91 (s, 2H), 1.61-1.53 (m, 2H), 1.34 (s, 9H), 1.25 (s, 6H), 1.23-1.13 (m, 6H), 1.13-1.01 (m, 2H), 0.83 (t, J=6.9 Hz, 3H).

Step 4

Prepared according to General Procedure A, Step 3 from tert-butyl 2-((3-(2-methyloctan-2-yl)-1,2,4-oxadiazol-5-yl)methyl)acrylate (504 mg, 1.5 mmol). The crude product was purified by chromatography on silica gel (0-100% EtOAc/isohexane) to afford 2-((3-(2-methyloctan-2-yl)-1,2,4-oxadiazol-5-yl)methyl)acrylic acid (405 mg, 1.4 mmol) as a yellow oil. LCMS m/z 281.1 $(M+H)^+$ $(ES^+)$. $^1H$ NMR (400 MHz, DMSO-d6) δ 12.67 (s, 1H), 6.27 (d, J=1.2 Hz, 1H), 5.88 (d, J=1.3 Hz, 1H), 3.90 (s, 2H), 1.61-1.50 (m, 2H), 1.30-1.10 (m, 12H), 1.10-0.99 (m, 2H), 0.83 (t, J=6.8 Hz, 3H).

Example 27—2-((3-(3-butylphenyl)-1,2,4-oxadiazol-5-yl)methyl)acrylic acid

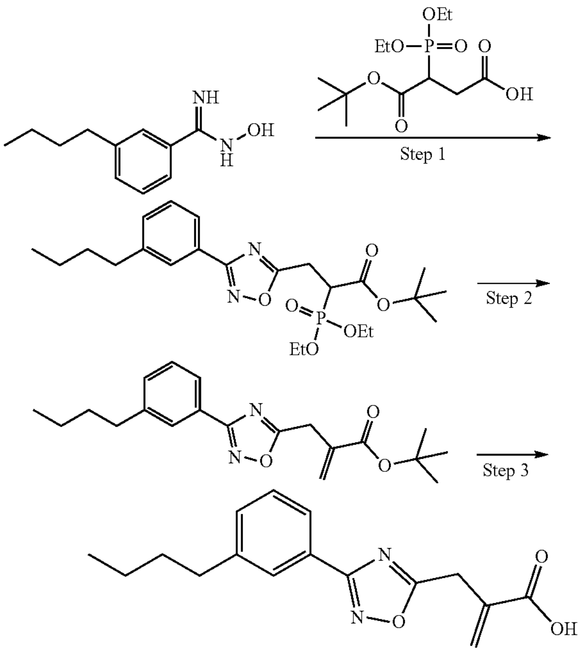

Step 1

Prepared according to General Procedure B, Method A from 3-butyl-N-hydroxybenzimidamide (728 mg, 1.1 Eq, 3.37 mmol, 89% purity). The crude product was purified by chromatography on RP Flash C18 (5-85% (0.1% Formic acid in MeCN)/(0.1% Formic Acid in Water) to afford tert-butyl 3-(3-(3-butylphenyl)-1,2,4-oxadiazol-5-yl)-2-(diethoxyphosphoryl)propanoate (0.65 g, 1.3 mmol, 90% purity) as a clear colourless gum. LCMS m/z 411.1 $(M-tBu+H)^+$ $(ES^+)$. $^1H$ NMR (400 MHz, DMSO-d6) δ 7.85-7.73 (m, 2H), 7.54-7.37 (m, 2H), 4.18-4.07 (m, 4H), 3.76-3.59 (m, 1H), 3.53-3.38 (m, 2H), 2.72-2.61 (m, 2H), 1.65-1.52 (m, 2H), 1.40 (s, 9H), 1.36-1.21 (m, 8H), 0.91 (t, J=7.3 Hz, 3H).

Step 2

Prepared according to General Procedure A, Step 2, Method B from tert-butyl 3-(3-(3-butylphenyl)-1,2,4-oxadiazol-5-yl)-2-(diethoxyphosphoryl)propanoate (0.65 g, 1.3 mmol, 90% purity). The crude product was purified by chromatography on silica gel (0-50% MTBE/isohexane) to afford tert-butyl 2-((3-(3-butylphenyl)-1,2,4-oxadiazol-5-yl)methyl)acrylate (0.400 g, 1.1 mmol) as a clear and colourless oil. LCMS m/z 287.1 $(M-tBu+H)^+$ $(ES^+)$. $^1H$ NMR (400 MHz, DMSO-d6) δ 7.84-7.76 (m, 2H), 7.53-7.37 (m, 2H), 6.31-6.25 (m, 1H), 6.00-5.93 (m, 1H), 4.04 (s, 2H), 2.73-2.61 (m, 2H), 1.64-1.52 (m, 2H), 1.38-1.26 (m, 11H), 0.91 (t, J=7.3 Hz, 3H).

Step 3

Prepared according to General Procedure A, Step 3 from tert-butyl 2-((3-(3-butylphenyl)-1,2,4-oxadiazol-5-yl)methyl)acrylate (0.400 g, 1.1 mmol). The crude product was purified by chromatography on silica gel (0-100% EtOAc/isohexane) to afford 2-((3-(3-butylphenyl)-1,2,4-oxadiazol-5-yl)methyl)acrylic acid (190 mg, 0.66 mmol) as a white solid. LCMS m/z 287.1 $(M+H)^+$ $(ES^+)$. $^1H$ NMR (400 MHz, DMSO-d6) δ 12.87 (s, 1H), 7.82-7.75 (m, 2H), 7.49-7.38 (m, 2H), 6.33 (d, J=1.2 Hz, 1H), 6.00 (d, J=1.3 Hz, 1H), 4.03 (s, 2H), 2.71-2.60 (m, 2H), 1.63-1.51 (m, 2H), 1.38-1.25 (m, 2H), 0.90 (t, J=7.4 Hz, 3H).

Example 28—2-((3-(4-pentylbenzyl)-1,2,4-oxadiazol-5-yl)methyl)acrylic acid

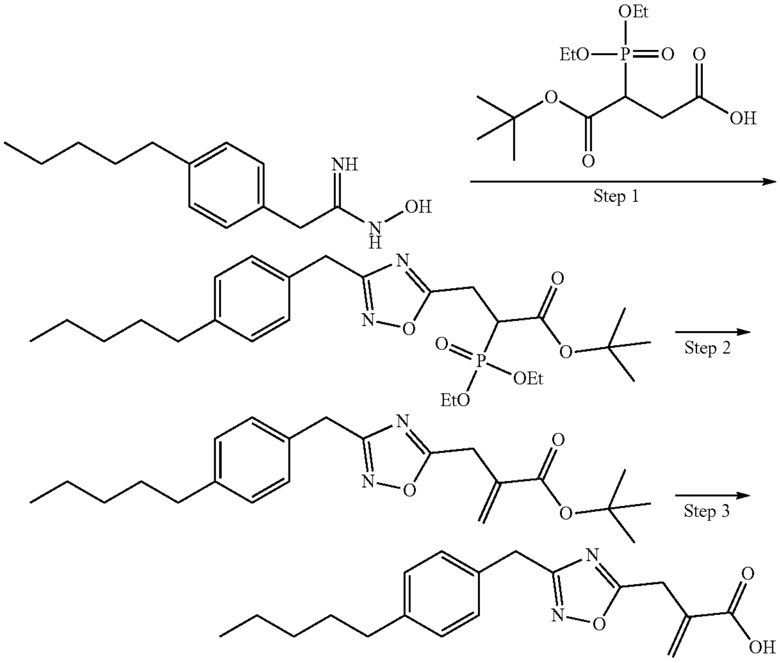

Step 1

Prepared according to General Procedure B, Method A from N-hydroxy-2-(4-pentylphenyl)acetimidamide (780 mg, 1.05 eq., 3.22 mmol, 91% purity). The crude product was purified by chromatography on RP Flash C18 (5-75% (0.1% Formic acid in MeCN)/(0.1% Formic Acid in Water) to afford tert-butyl 2-(diethoxyphosphoryl)-3-(3-(4-pentylbenzyl)-1,2,4-oxadiazol-5-yl)propanoate (0.27 g, 0.52 mmol) as a clear, pale brown gum. LCMS m/z 495 $(M+H)^+$ $(ES^+)$. $^1H$ NMR (400 MHz, DMSO-d6) δ 7.18-7.14 (m, 2H), 7.13-7.09 (m, 2H), 4.13-4.01 (m, 4H), 3.98 (s, 2H), 3.61-3.48 (m, 1H), 3.32-3.16 (m, 4H), 1.60-1.49 (m, 2H), 1.28 (s, 9H), 1.26-1.19 (m, 10H), 0.85 (t, J=6.9 Hz, 3H).

Step 2

Prepared according to General Procedure A, Step 2, Method B from tert-butyl 2-(diethoxyphosphoryl)-3-(3-(4-pentylbenzyl)-1,2,4-oxadiazol-5-yl)propanoate (0.27 g, 0.52 mmol). The crude product was purified by chromatography on silica gel (0-50% MTBE/isohexane) to afford tert-butyl 2-((3-(4-pentylbenzyl)-1,2,4-oxadiazol-5-yl)methyl)acrylate (0.12 g, 0.31 mmol) as a clear and colourless oil. LCMS m/z 315.1 $(M-tBu+H)^+$ $(ES^+)$. $^1H$ NMR (400 MHz, DMSO-d6) δ 7.17 (d, J=8.1 Hz, 2H), 7.11 (d, J=8.2 Hz, 2H), 6.25-6.16 (m, 1H), 5.92-5.81 (m, 1H), 3.99 (s, 2H), 3.90 (s, 2H), 2.56-2.52 (m, 2H), 1.60-1.46 (m, 2H), 1.34-1.18 (m, 13H), 0.85 (t, J=7.0 Hz, 3H).

Step 3

Prepared according to General Procedure A, Step 3 from tert-butyl 2-((3-(4-pentylbenzyl)-1,2,4-oxadiazol-5-yl)methyl)acrylate (0.12 g, 0.31 mmol). The crude product was purified by chromatography on silica gel (0-100% EtOAc/isohexane) to afford 2-((3-(4-pentylbenzyl)-1,2,4-oxadiazol-5-yl)methyl)acrylic acid (50 mg, 0.16 mmol) as a yellow oil. LCMS m/z 315.1 $(M+H)^+$ $(ES^+)$. $^1H$ NMR (400 MHz, DMSO-d6) δ 12.84 (s, 1H), 7.17 (d, J=8.1 Hz, 2H), 7.13 (d, J=8.0 Hz, 2H), 6.26 (s, 1H), 5.90 (d, J=1.4 Hz, 1H), 4.00 (s, 2H), 3.90 (s, 2H), 2.54 (d, J=7.7 Hz, 2H), 1.54 (p, J=7.4 Hz, 2H), 1.28 (dddd, J=14.9, 9.3, 6.8, 2.1 Hz, 4H), 0.86 (t, J=6.9 Hz, 3H).

Example 29—2-((3-(3-butylbenzyl)-1,2,4-oxadiazol-5-yl)methyl)acrylic acid

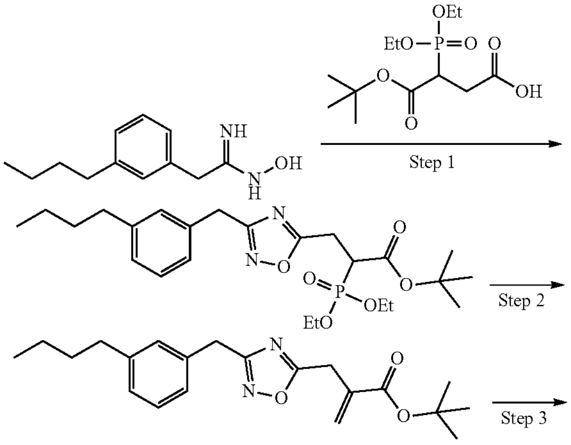

-continued

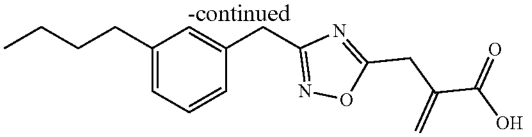

Step 1

Prepared according to General Procedure B, Method B from 2-(3-butylphenyl)-N-hydroxyacetimidamide (2.66 g, 1 eq., 11.2 mmol, 87% purity). The crude product was purified by chromatography on silica gel (0-100% EtOAc/isohexane) to afford tert-butyl 3-(3-(3-butylbenzyl)-1,2,4-oxadiazol-5-yl)-2-(diethoxyphosphoryl)propanoate (1.68 g, 2.9 mmol, 84% purity) as dark orange oil. LCMS m/z 503.3 $(M+Na)^+$ $(ES^+)$.

Step 2

Prepared according to General Procedure A, Step 2, Method B from tert-butyl 3-(3-(3-butylbenzyl)-1,2,4-oxadiazol-5-yl)-2-(diethoxyphosphoryl)propanoate (1.68 g, 2.9 mmol, 84% purity). The crude product was purified by chromatography on silica gel (0-100% EtOAc/isohexane) to afford tert-butyl 2-((3-(3-butylbenzyl)-1,2,4-oxadiazol-5-yl)methyl)acrylate (0.98 g, 2.6 mmol) as a yellow oil. LCMS m/z 300.7 $(M-tBu+H)^+$ $(ES^+)$. $^1H$ NMR (400 MHz, DMSO-d6) δ 7.20 (t, J=7.5 Hz, 1H), 7.07 (td, J=7.9, 1.9 Hz, 3H), 6.21 (d, J=1.3 Hz, 1H), 5.88 (t, J=1.3 Hz, 1H), 4.00 (s, 2H), 3.90 (s, 2H), 2.54 (d, J=7.6 Hz, 2H), 1.52 (tt, J=8.3, 6.5 Hz, 2H), 1.32-1.26 (m, 2H), 1.25 (s, 9H), 0.89 (t, J=7.3 Hz, 3H).

Step 3

Prepared according to General Procedure A, Step 3 from tert-butyl 2-((3-(3-butylbenzyl)-1,2,4-oxadiazol-5-yl)methyl)acrylate (0.98 g, 2.6 mmol). The crude product was purified by chromatography on silica gel (0-100% EtOAc/isohexane) to afford 2-((3-(3-butylbenzyl)-1,2,4-oxadiazol-5-yl)methyl)acrylic acid (700 mg, 2.2 mmol) as a sticky yellow oil. LCMS m/z 301.6 $(M+H)^+$ $(ES^+)$. $^1H$ NMR (400 MHz, DMSO-d6) δ 12.81 (s, 1H), 7.21 (t, J=7.5 Hz, 1H), 7.10 (d, J=1.8 Hz, 1H), 7.09-7.02 (m, 2H), 6.27 (d, J=1.2 Hz, 1H), 5.90 (d, J=1.4 Hz, 1H), 4.01 (s, 2H), 3.91 (s, 2H), 2.54 (t, J=7.7 Hz, 2H), 1.53 (tt, J=7.9, 6.4 Hz, 2H), 1.30 (h, J=7.3 Hz, 2H), 0.89 (t, J=7.3 Hz, 3H).

Example 30—2-((3-(2-(4-chlorophenyl)propan-2-yl)-1,2,4-oxadiazol-5-yl)methyl)acrylic acid

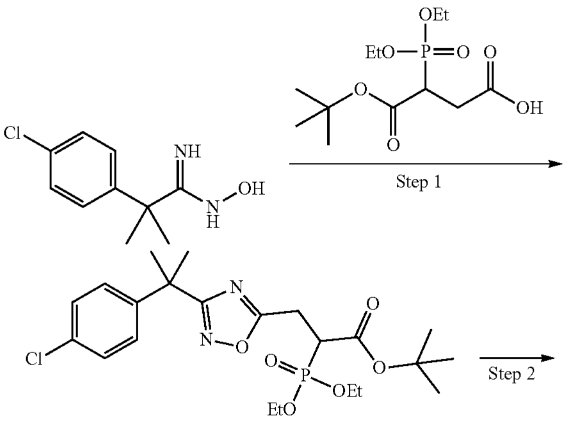

-continued

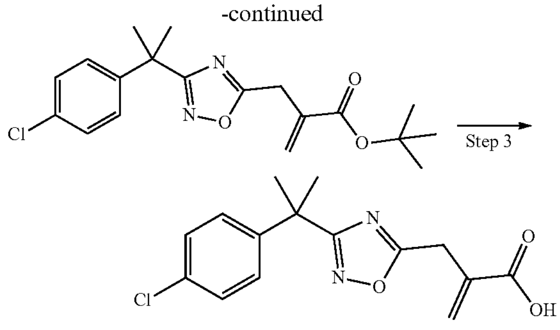

Step 1

Prepared according to General Procedure B, Method A from 2-(4-chlorophenyl)-N-hydroxy-2-methylpropanimidamide (0.98 g, 4.6 mmol). The crude product was purified by chromatography on silica gel (0-100% MTBE/isohexane) to afford tert-butyl 3-(3-(2-(4-chlorophenyl)propan-2-yl)-1,2,4-oxadiazol-5-yl)-2-(diethoxyphosphoryl)propanoate (0.320 g, 0.65 mmol) as a colourless oil. LCMS m/z 509.2 $(M+Na)^+$ $(ES^+)$. $^1H$ NMR (400 MHz, DMSO-d6) δ 7.39-7.33 (m, 2H), 7.32-7.25 (m, 2H), 4.15-3.98 (m, 4H), 3.51 (ddd, J=23.3, 10.9, 4.4 Hz, 1H), 3.40-3.27 (m, 1H), 3.22 (ddd, J=16.8, 8.7, 4.4 Hz, 1H), 1.65 (d, J=3.7 Hz, 6H), 1.28 (s, 9H), 1.26-1.20 (m, 6H).

Step 2

Prepared according to General Procedure A, Step 2, Method B from tert-butyl 3-(3-(2-(4-chlorophenyl)propan-2-yl)-1,2,4-oxadiazol-5-yl)-2-(diethoxyphosphoryl)propanoate (0.320 g, 0.65 mmol). The crude product was purified by chromatography on silica gel (0-50% MTBE/isohexane) to afford tert-butyl 2-((3-(2-(4-chlorophenyl)propan-2-yl)-1,2,4-oxadiazol-5-yl)methyl)acrylate (0.133 g, 0.36 mmol) as a colourless oil. LCMS m/z 307.5 $(M-tBu+H)^+$ $(ES^+)$. $^1H$ NMR (400 MHz, DMSO-d6) δ 7.40-7.26 (m, 4H), 6.20 (s, 1H), 5.87 (s, 1H), 3.90 (s, 2H), 1.66 (s, 6H), 1.27 (s, 9H).

Step 3

Prepared according to General Procedure A, Step 3 from tert-butyl 2-((3-(2-(4-chlorophenyl)propan-2-yl)-1,2,4-oxadiazol-5-yl)methyl)acrylate (0.133 g, 0.36 mmol). The crude product was purified by chromatography on silica gel (0-100% MTBE/isohexane) to afford 2-((3-(2-(4-chlorophenyl)propan-2-yl)-1,2,4-oxadiazol-5-yl)methyl)acrylic acid (78 mg, 0.25 mmol) as a colourless oil. LCMS m/z 307.5 $(M+H)^+$ $(ES^+)$. $^1H$ NMR (400 MHz, DMSO-d6) δ 12.83 (s, br. 1H), 7.56-7.50 (m, 1H), 7.49-7.43 (m, 1H), 7.41-7.30 (m, 2H), 6.28-6.23 (m, 1H), 5.91-5.86 (m, 1H), 3.89 (s, 2H), 1.66-1.51 (m, 2H), 1.47-1.28 (m, 2H).

Example 31—2-((3-(7,7-difluorooctyl)-1,2,4-oxadiazol-5-yl)methyl)acrylic acid

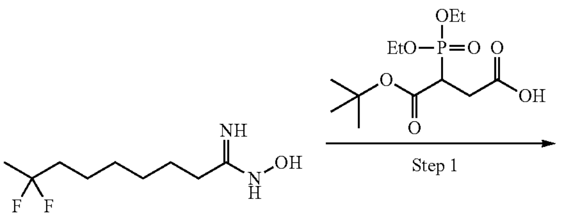

-continued

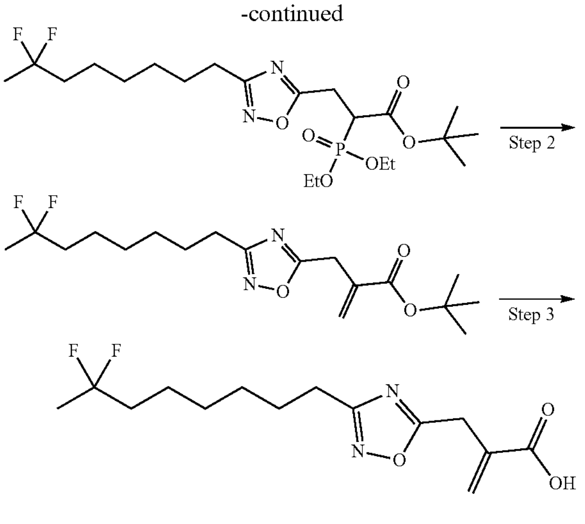

Step 1

Prepared according to General Procedure B, Method B from 8,8-difluoro-N-hydroxynonanimidamide (1.06 g, 5.07 mmol). The crude product was purified by chromatography on silica gel (0-100% EtOAc/isohexane) to afford tert-butyl 2-(diethoxyphosphoryl)-3-(3-(7,7-difluorooctyl)-1,2,4-oxadiazol-5-yl)propanoate (1.28 g, 2.6 mmol) as a clear yellow oil. LCMS m/z 505.2 $(M+Na)^+$ $(ES^+)$. $^1H$ NMR (400 MHz, DMSO-d6) δ 4.15-4.02 (m, 4H), 3.56 (ddd, J=23.3, 11.1, 4.4 Hz, 1H), 3.39-3.33 (m, 1H), 3.23 (ddd, J=16.8, 8.6, 4.4 Hz, 1H), 2.65 (t, J=7.4 Hz, 2H), 1.90-1.76 (m, 2H), 1.66-1.46 (m, 5H), 1.43-1.19 (m, 21H).

Step 2

Prepared according to General Procedure A, Step 2, Method B from tert-butyl 2-(diethoxyphosphoryl)-3-(3-(7,7-difluorooctyl)-1,2,4-oxadiazol-5-yl)propanoate (1.28 g, 2.6 mmol). The crude product was purified by chromatography on silica gel (0-20% EtOAc/isohexane) to afford tert-butyl 2-((3-(7,7-difluorooctyl)-1,2,4-oxadiazol-5-yl)methyl)acrylate (0.650 g, 1.8 mmol) as a clear colourless oil. LCMS m/z 303.2 $(M-tBu+H)^+$ $(ES^+)$. $^1H$ NMR (400 MHz, DMSO-d6) δ 6.23 (d, J=1.3 Hz, 1H), 5.96-5.83 (m, 1H), 3.91 (s, 2H), 2.65 (t, J=7.4 Hz, 2H), 1.90-1.76 (m, 2H), 1.67-1.51 (m, 5H), 1.34 (s, 15H).

Step 3

Prepared according to General Procedure A, Step 3 from tert-butyl 2-((3-(7,7-difluorooctyl)-1,2,4-oxadiazol-5-yl)methyl)acrylate (0.650 g, 1.8 mmol). The crude product was purified by chromatography on silica gel (0-100% EtOAc/isohexane) to afford 2-((3-(7,7-difluorooctyl)-1,2,4-oxadiazol-5-yl)methyl)acrylic acid (0.479 g, 1.6 mmol, 86%, 98% Purity) as a clear colourless oil. LCMS m/z 303.6 $(M+H)^+$ $(ES^+)$. $^1H$ NMR (400 MHz, DMSO-d6) δ 12.81 (s, 1H), 6.28 (d, J=1.2 Hz, 1H), 5.91 (d, J=1.4 Hz, 1H), 3.91 (s, 2H), 2.65 (t, J=7.5 Hz, 2H), 1.92-1.75 (m, 2H), 1.70-1.51 (m, 5H), 1.44-1.25 (m, 6H).

Example 32—2-((3-(cyclohexylmethyl)-1,2,4-oxadiazol-5-yl)methyl)acrylic acid

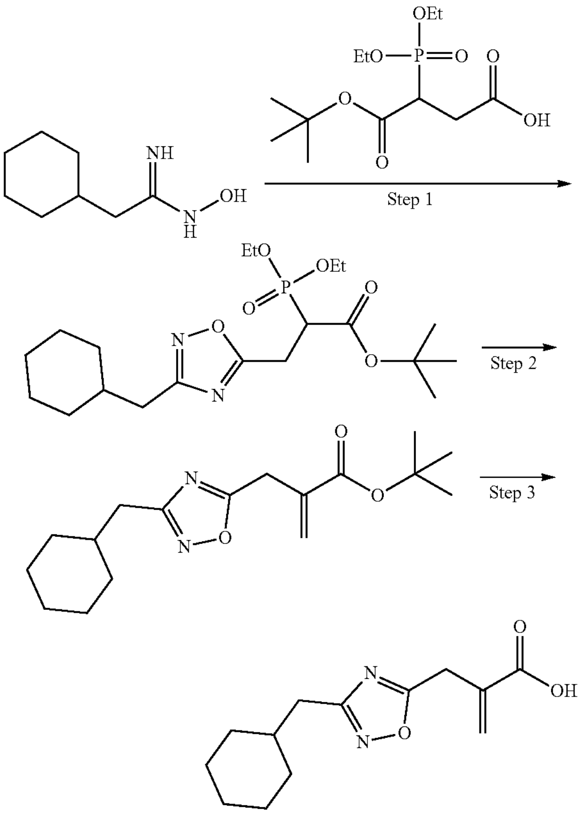

Step 1

Prepared according to General Procedure B, Method B from 2-cyclohexyl-N-hydroxyacetimidamide (553 mg, 2.90 mmol, 82% purity). The crude product was purified by chromatography on silica gel (0-100% EtOAc/isohexane) to afford tert-butyl 3-(3-(cyclohexylmethyl)-1,2,4-oxadiazol-5-yl)-2-(diethoxyphosphoryl)propanoate (356 mg, 0.78 mmol, 94% purity) as a pale brown oil. LCMS m/z 431.1 $(M+H)^+$ $(ES^+)$. $^1H$ NMR (400 MHz, DMSO-d6) δ 0.67 (m, 1H), 4.17-4.01 (m, 4H), 3.56 (m, 1H), 3.41-3.17 (m, 2H), 2.53 (s, 1H), 1.72-1.54 (m, 6H), 1.41 (t, J=7.1 Hz, 1H), 1.37 (s, 9H), 1.26 (m, 6H), 1.19-1.08 (m, 2H), 1.03-0.91 (m, 2H).

Step 2

Prepared according to General Procedure A, Step 2, Method B from tert-butyl 3-(3-(cyclohexylmethyl)-1,2,4-oxadiazol-5-yl)-2-(diethoxyphosphoryl)propanoate (356 mg, 0.78 mmol, 94% purity). The crude product was purified by chromatography on silica gel (0-50% MTBE/isohexane) to afford tert-butyl 2-((3-(cyclohexylmethyl)-1,2,4-oxadiazol-5-yl)methyl)acrylate (125 mg, 0.39 mmol) as a colourless oil. LCMS m/z 251.1 $(M-tBu+H)^+$ $(ES^+)$. $^1H$ NMR (400 MHz, $CD_3OD$) δ 6.34 (s, 1H), 5.86 (s, 1H), 3.90 (s, 2H), 2.58 (d, J=6.9 Hz, 2H), 1.77-1.65 (m, 6H), 1.43 (s, 9H), 1.35-1.17 (m, 3H), 1.09-0.97 (m, 2H).

Step 3

Prepared according to General Procedure A, Step 3 from tert-butyl 2-((3-(cyclohexylmethyl)-1,2,4-oxadiazol-5-yl)methyl)acrylate (125 mg, 0.39 mmol). The crude product was purified by chromatography on silica gel (0-50% MTBE/isohexane) to afford 2-((3-(cyclohexylmethyl)-1,2,4- oxadiazol-5-yl)methyl)acrylic acid (55.6 mg, 0.20 mmol) as a clear colourless oil. LCMS m/z 251.1 $(M+H)^+$ $(ES^+)$. $^1H$ NMR (400 MHz, DMSO-d6) δ 12.82 (br. s, 1H), 6.27 (s, 1H), 5.91 (s, 1H), 3.91 (s, 2H), 3.32 (br. s, 1H), 2.53 (d, J=6.8 Hz, 2H), 1.75-1.55 (m, 5H), 1.31-1.07 (m, 3H), 1.04-0.89 (m, 2H).

Example 33—2-((3-(3-(4-chlorophenyl)propyl)-1,2,4-oxadiazol-5-yl)methyl)acrylic acid

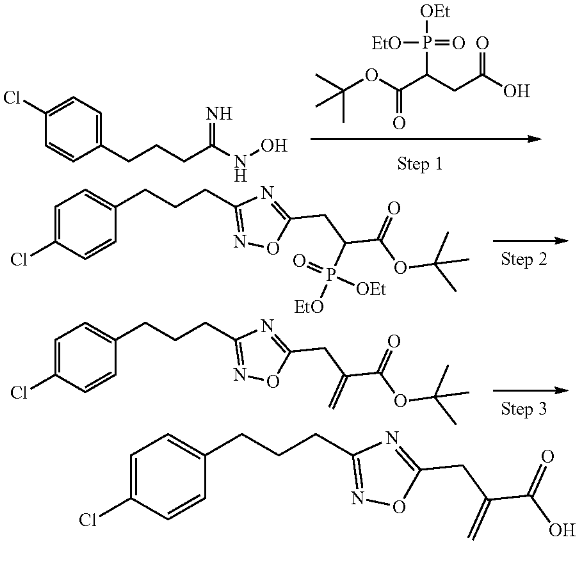

Step 1

Prepared according to General Procedure B, Method A from 4-(4-chlorophenyl)-N-hydroxybutanimidamide (1.00 g, 1 eq., 3.71 mmol, 79% purity). The crude product was purified by chromatography on silica gel (0-50% EtOAc/isohexane) to afford tert-butyl 3-(3-(3-(4-chlorophenyl)propyl)-1,2,4-oxadiazol-5-yl)-2-(diethoxyphosphoryl)propanoate (0.73 g, 1.5 mmol) as a clear orange oil. LCMS m/z 487.1/489.1 $(M+H)^+$ $(ES^+)$. $^1H$ NMR (400 MHz, DMSO-d6) δ 7.37-7.30 (m, 2H), 7.25-7.19 (m, 2H), 4.14-3.99 (m, 5H), 3.40-3.17 (m, 2H), 2.67-2.57 (m, 4H), 1.95-1.84 (m, 2H), 1.34 (s, 9H), 1.29-1.19 (m, 6H).

Step 2

Prepared according to General Procedure A, Step 2, Method B from tert-butyl 3-(3-(3-(4-chlorophenyl)propyl)-1,2,4-oxadiazol-5-yl)-2-(diethoxyphosphoryl)propanoate (0.73 g, 1.5 mmol). The crude product was purified by chromatography on silica gel (0-50% EtOAc/isohexane) to afford tert-butyl 2-((3-(3-(4-chlorophenyl)propyl)-1,2,4-oxadiazol-5-yl)methyl)acrylate (0.345 g, 0.92 mmol) as a pale yellow oil. LCMS m/z 307.0/309.1 $(M-tBu+H)^+$ $(ES^+)$. $^1H$ NMR (400 MHz, DMSO-d6) δ 7.37-7.29 (m, 2H), 7.26-7.19 (m, 2H), 6.22 (d, J=1.2 Hz, 1H), 5.89 (d, J=1.3 Hz, 1H), 3.91 (s, 2H), 2.69-2.57 (m, 4H), 1.97-1.85 (m, 2H), 1.33 (s, 9H).

Step 3

Prepared according to General Procedure A, Step 3 from tert-butyl 2-((3-(3-(4-chlorophenyl)propyl)-1,2,4-oxadiazol-5-yl)methyl)acrylate (0.345 g, 0.92 mmol). The crude product was purified by chromatography on silica gel (0-100% EtOAc/isohexane) to afford 2-((3-(3-(4-chlorophenyl)propyl)-1,2,4-oxadiazol-5-yl)methyl)acrylic acid (0.23 g, 0.74 mmol) as a clear colourless oil. LCMS m/z 307.0/309.1 $(M+H)^+$ $(ES^+)$. $^1H$ NMR (400 MHz, DMSO-d6) δ 12.81 (s, 1H), 7.38-7.29 (m, 2H), 7.27-7.18 (m, 2H), 6.27 (d, J=1.3 Hz, 1H), 5.91 (d, J=1.3 Hz, 1H), 3.90 (s, 2H), 2.65 (t, J=7.4 Hz, 2H), 2.60 (t, J=7.6 Hz, 2H), 1.91 (p, J=7.5 Hz, 2H).

Example 34-2-((3-(octyl-d17)-1,2,4-oxadiazol-5-yl)methyl)acrylic acid

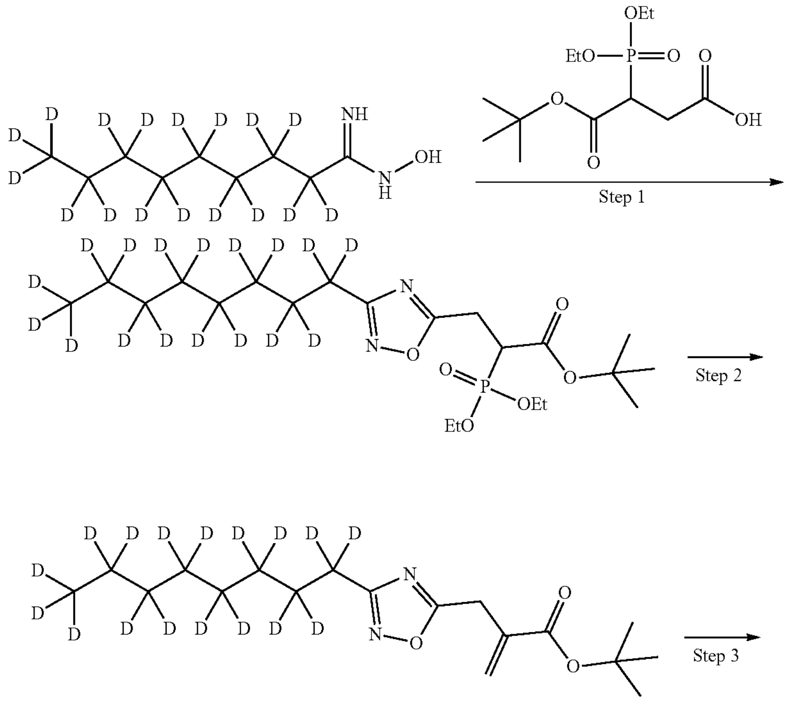

-continued

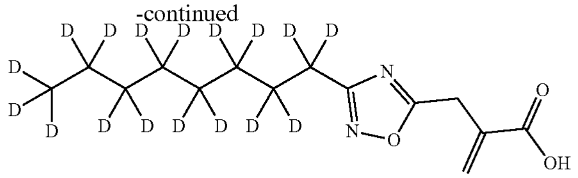

Step 1

Prepared according to General Procedure B, Method A from N-hydroxynonanimidamide-d17 (0.917 g, 1 Eq, 4.84 mmol). The crude product was purified by chromatography on silica gel (0-100% EtOAc/isohexane) to afford tert-butyl 2-(diethoxyphosphoryl)-3-(3-(octyl-d17)-1,2,4-oxadiazol-5-yl)propanoate (145 mg, 0.30 mmol) as a clear orange oil. LCMS m/z 464.4 $(M+H)^+$ $(ES^+)$. $^1H$ NMR (400 MHz, DMSO-d6) δ 4.14-4.03 (m, 4H), 3.55 (ddd, J=23.3, 11.1, 4.3 Hz, 1H), 3.39-3.32 (m, 1H), 3.22 (ddd, J=16.8, 8.6, 4.4 Hz, 1H), 1.36 (s, 9H), 1.29-1.21 (m, 6H).

Step 2

Prepared according to General Procedure A, Step 2, Method B from tert-butyl 2-(diethoxyphosphoryl)-3-(3-(octyl-d17)-1,2,4-oxadiazol-5-yl)propanoate (145 mg, 0.30 mmol). The crude product was purified by chromatography on silica gel (0-50% EtOAc/isohexane) to afford tert-butyl 2-((3-(octyl-d17)-1,2,4-oxadiazol-5-yl)methyl)acrylate (21 mg, 0.6 mmol) as a pale yellow oil. LCMS m/z 284.2 $(M-tBu+H)^+$ $(ES^+)$. $^1H$ NMR (400 MHz, $CDCl_3$) δ 6.35 (d, J=0.9 Hz, 1H), 5.70 (d, J=1.0 Hz, 1H), 3.84 (d, J=0.6 Hz, 2H), 1.44 (s, 9H).

Step 3

Prepared according to General Procedure A, Step 3 from tert-butyl 2-((3-(octyl-d17)-1,2,4-oxadiazol-5-yl)methyl) acrylate (21 mg, 0.6 mmol). The crude product was purified by chromatography on silica gel (0-100% EtOAc/isohexane) to afford 2-((3-(octyl-d17)-1,2,4-oxadiazol-5-yl)methyl) acrylic acid (3.5 mg, 12 μmol, 21%, 100% Purity) as a clear colourless oil. LCMS m/z 284.2 $(M+H)^+$ $(ES^+)$. $^1H$ NMR (400 MHz, $CDCl_3$) δ 6.54 (s, 1H), 5.93 (d, J=1.3 Hz, 1H), 3.90 (dd, J=1.4, 0.7 Hz, 2H). 1 exchangeable proton not observed.

Example 35—2-((3-(oct-7-yn-1-yl)-1,2,4-oxadiazol-5-yl)methyl)acrylic acid

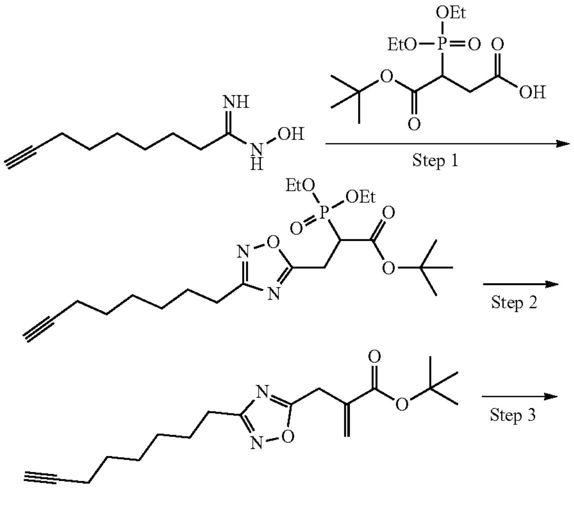

-continued

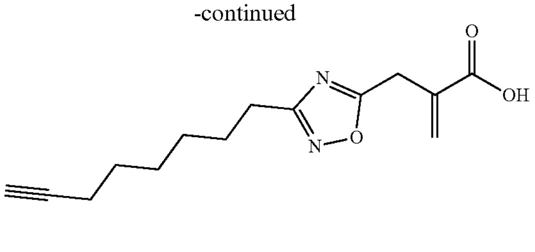

Step 1

Prepared according to General Procedure B, Method B from N-hydroxynon-8-ynimidamide (1.00 g, 5.35 mmol, 90% purity). The crude product was purified by chromatography on silica gel (0-100% EtOAc/isohexane) to afford tert-butyl 2-(diethoxyphosphoryl)-3-(3-(oct-7-yn-1-yl)-1,2,4-oxadiazol-5-yl)propanoate (0.68 g, 1.4 mmol, 90% purity) as a dark orange oil. LCMS m/z 465.1 $(M+Na)^+$ $(ES^+)$. $^1H$ NMR (400 MHz, DMSO-d6) δ 4.15-4.03 (m, 4H), 3.63-3.50 (m, 2H), 3.29-3.12 (m, 1H), 2.73 (t, J=2.6 Hz, 1H), 2.64 (t, J=7.3 Hz, 2H), 2.14 (td, J=6.8, 2.6 Hz, 2H), 1.68-1.57 (m, 2H), 1.45-1.39 (m, 4H), 1.37 (s, 9H), 1.29-1.21 (m, 8H).

Step 2

Prepared according to General Procedure A, Step 2, Method B from tert-butyl 2-(diethoxyphosphoryl)-3-(3-(oct-7-yn-1-yl)-1,2,4-oxadiazol-5-yl)propanoate (0.68 g, 1.4 mmol, 90% purity). The crude product was purified by chromatography on silica gel (0-100% EtOAc/isohexane) to afford tert-butyl 2-((3-(oct-7-yn-1-yl)-1,2,4-oxadiazol-5-yl) methyl)acrylate (0.22 g, 0.62 mmol, 90% purity) as a yellow oil. LCMS m/z 262.9 $(M-tBu+H)^+$ $(ES^+)$. $^1H$ NMR (400 MHz, DMSO-d6) δ 6.23 (d, J=1.2 Hz, 1H), 5.90 (d, J=1.2 Hz, 1H), 3.91 (s, 2H), 2.73 (t, J=2.7 Hz, 1H), 2.65 (t, J=7.4 Hz, 2H), 2.14 (td, J=6.8, 2.6 Hz, 2H), 1.63 (p, J=7.4 Hz, 2H), 1.47-1.20 (m, 15H).

Step 3

Prepared according to General Procedure A, Step 3 from tert-butyl 2-((3-(oct-7-yn-1-yl)-1,2,4-oxadiazol-5-yl) methyl)acrylate (0.22 g, 0.62 mmol, 90% purity). The crude product was purified by chromatography on silica gel (0-100% EtOAc/isohexane) to afford 2-((3-(oct-7-yn-1-yl)-1,2,4-oxadiazol-5-yl)methyl)acrylic acid (171 mg, 0.63 mmol) as a sticky yellow oil. LCMS m/z 267.1 $(M+H)^+$ $(ES^+)$. $^1H$ NMR (400 MHz, DMSO-d6) δ 12.80 (s, 1H), 6.28 (d, J=1.2 Hz, 1H), 5.92 (d, J=1.4 Hz, 1H), 3.91 (s, 2H), 2.74 (t, J=2.7 Hz, 1H), 2.65 (t, J=7.4 Hz, 2H), 2.14 (td, J=6.8, 2.6 Hz, 2H), 1.63 (p, J=7.5 Hz, 2H), 1.48-1.13 (m, 6H).

Example 36—2-((3-(4-propylphenethyl)-1,2,4-oxadiazol-5-yl)methyl)acrylic acid

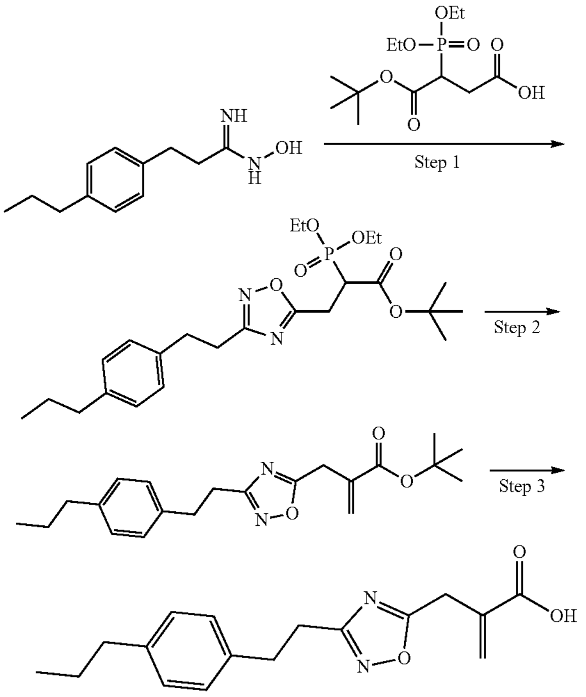

Step 1

Prepared according to General Procedure B, Method B from N-hydroxy-3-(4-propylphenyl)propanimidamide (0.72 g, 1 Eq, 2.7 mmol, 78% purity). The crude product was purified by chromatography on silica gel (0-100% EtOAc/isohexane) to afford tert-butyl 2-(diethoxyphosphoryl)-3-(3-(4-propylphenethyl)-1,2,4-oxadiazol-5-yl)propanoate (0.35 g, 0.60 mmol, 83% purity) as a dark orange oil. LCMS m/z 503.27 $(M+Na)^+$ $(ES^+)$. $^1H$ NMR (400 MHz, DMSO-d6) δ 7.12-7.06 (m, 4H), 4.14-4.04 (m, 4H), 3.63-3.55 (m, 1H), 3.42-3.33 (m, 1H), 3.29-3.14 (m, 1H), 2.98-2.86 (m, 4H), 1.61-1.50 (m, 2H), 1.38 (s, 9H), 1.30-1.22 (m, 8H), 0.88 (t, J=7.3 Hz, 3H).

Step 2

Prepared according to General Procedure A, Step 2, Method B from tert-butyl 2-(diethoxyphosphoryl)-3-(3-(4-propylphenethyl)-1,2,4-oxadiazol-5-yl)propanoate (0.35 g, 0.60 mmol, 83% purity). The crude product was purified by chromatography on silica gel (0-50% EtOAc/isohexane) to afford tert-butyl 2-((3-(4-propylphenethyl)-1,2,4-oxadiazol-5-yl)methyl)acrylate (80 mg, 0.22 mmol) as a yellow oil. LCMS m/z 357.4 $(M+H)^+$ $(ES^+)$. $^1H$ NMR (400 MHz, DMSO-d6) δ 7.12 (d, J=8.2 Hz, 2H), 7.08 (d, J=8.1 Hz, 2H), 6.24 (d, J=1.3 Hz, 1H), 5.89 (q, J=1.2 Hz, 1H), 3.92 (s, 2H), 2.94 (q, J=3.6 Hz, 4H), 2.52-2.51 (m, 2H), 1.60-1.49 (m, 2H), 1.35 (s, 9H), 0.88 (t, J=7.3 Hz, 3H).

Step 3

Prepared according to General Procedure A, Step 3 from tert-butyl 2-((3-(4-propylphenethyl)-1,2,4-oxadiazol-5-yl)methyl)acrylate (80 mg, 0.22 mmol). The crude product was purified by chromatography on silica gel (0-100% EtOAc/isohexane) to afford 2-((3-(4-propylphenethyl)-1,2,4-oxadiazol-5-yl)methyl)acrylic acid (52 mg, 0.16 mmol) as a sticky yellow oil. LCMS m/z 301.1 $(M+H)^+$ $(ES^+)$. $^1H$ NMR (400 MHz, DMSO-d6) δ 12.82 (s, 1H), 7.14-7.05 (m, 4H), 6.29 (d, J=1.3 Hz, 1H), 5.91 (d, J=1.4 Hz, 1H), 3.92 (s, 2H), 2.93 (d, J=3.2 Hz, 4H), 2.53-2.51 (m, 2H), 1.55 (dt, J=14.7, 7.4 Hz, 2H), 0.88 (t, J=7.3 Hz, 3H).

Example 37—2-((5-octyl-1,3,4-thiadiazol-2-yl)methyl)acrylic acid

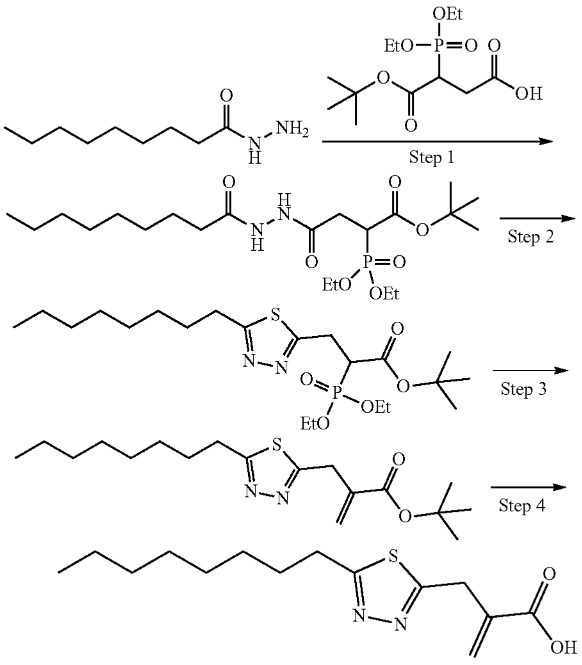

Step 1

N-Ethyl-N'-(3-dimethylaminopropyl)carbodiimide hydrochloride (0.371 g, 1.93 mmol) was added to a mixture of 4-(tert-butoxy)-3-(diethoxyphosphoryl)-4-oxobutanoic acid (0.50 g, 1.61 mmol), nonanehydrazide (0.333 g, 1.93 mmol), DMAP (39 mg, 0.3 mmol) and DIPEA (0.56 mL, 3.2 mmol) in DCM (8 mL). The mixture was stirred for 3.5 days at RT, then diluted with sat. aq. $NH_4Cl$ (20 mL) and the phases were separated. The aqueous phase was extracted with DCM (2×10 mL). The combined organic phases were washed with brine (20 mL), dried ($MgSO_4$) and concentrated. The crude product was purified by chromatography on silica gel (0-10% MeOH/DCM) to afford tert-butyl 2-(diethoxyphosphoryl)-4-(2-nonanoylhydrazineyl)-4-oxobutanoate (0.658 g, 1.1 mmol, 80% purity) as a clear colourless oil that solidified on standing. LCMS m/z 487.2 $(M+Na)^+$ $(ES^+)$. $^1H$ NMR (400 MHz, DMSO-d6) δ 9.83 (s, 1H), 9.72 (s, 1H), 4.15-3.97 (m, 4H), 3.28-3.16 (m, 1H), 2.76 (ddd, J=16.3, 11.5, 6.8 Hz, 1H), 2.49-2.41 (m, 1H), 2.09 (t, J=7.3 Hz, 2H), 1.56-1.45 (m, 2H), 1.39 (s, 9H), 1.33-1.18 (m, 16H), 0.93-0.80 (m, 3H).

Step 2

A mixture of tert-butyl 2-(diethoxyphosphoryl)-4-(2-nonanoylhydrazineyl)-4-oxobutanoate (0.658 g, 1.1 mmol, 80% purity) and Lawesson's Reagent (0.550 g, 1.36 mmol) in THF (10 mL) was stirred for 1 h at 60° C., then at RT for 36 h. The mixture was concentrated. The crude product was purified by chromatography on silica gel (0-100% EtOAc/isohexane) to afford tert-butyl 2-(diethoxyphosphoryl)-3-(5-octyl-1,3,4-thiadiazol-2-yl)propanoate (450 mg, 0.78 mmol, 80% purity) as a yellow oil. LCMS m/z 463.2 $(M+H)^+$ $(ES^+)$. $^1H$ NMR (400 MHz, DMSO-d6) δ 4.16-4.02 (m, 4H), 3.60-3.48 (m, 2H), 3.47-3.30 (m, 1H), 3.03 (t, J=7.4 Hz, 2H), 1.73-1.61 (m, 2H), 1.35 (s, 9H), 1.32-1.20 (m, 16H), 0.88-0.83 (m, 3H).

Step 3

Prepared according to General Procedure A, Step 2, Method B from tert-butyl 2-(diethoxyphosphoryl)-3-(5-octyl-1,3,4-thiadiazol-2-yl)propanoate (450 mg, 0.78 mmol, 80% purity). The crude product was purified by chromatography on silica gel (0-40% EtOAc/isohexane) to afford tert-butyl 2-((5-octyl-1,3,4-thiadiazol-2-yl)methyl)acrylate (175 mg, 0.52 mmol) as a colourless oil. LCMS m/z 339.3 $(M+H)^+$ $(ES^+)$. $^1H$ NMR (400 MHz, DMSO-d6) δ 6.17 (d, J=1.3 Hz, 1H), 5.84 (d, J=1.3 Hz, 1H), 4.01 (s, 2H), 3.02 (t, J=7.4 Hz, 2H), 1.72-1.62 (m, 2H), 1.38 (s, 9H), 1.34-1.19 (m, 10H), 0.89-0.82 (m, 3H).

Step 4

Prepared according to General Procedure A, Step 3 from tert-butyl 2-((5-octyl-1,3,4-thiadiazol-2-yl)methyl)acrylate (175 mg, 0.52 mmol). The crude product was purified by chromatography on silica gel (0-100% MTBE/isohexane) to afford 2-((5-octyl-1,3,4-thiadiazol-2-yl)methyl)acrylic acid (71 mg, 0.25 mmol) as a colourless oil. LCMS m/z 283.5 $(M+H)^+$ $(ES^+)$. $^1H$ NMR (400 MHz, DMSO-d6) δ 12.82 (s, 1H), 6.22 (s, 1H), 5.86 (s, 1H), 4.01 (s, 2H), 3.01 (t, J=7.5 Hz, 2H), 1.68 (p, J=7.5 Hz, 2H), 1.36-1.16 (m, 10H), 0.86 (t, J=7.0 Hz, 3H).

Example 38—2-((4-octylthiazol-2-yl)methyl)acrylic acid

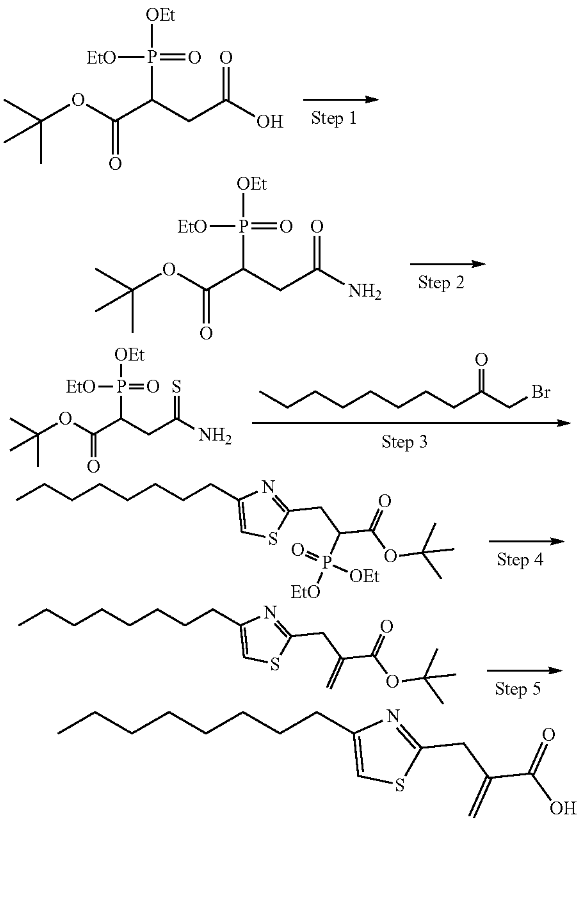

Step 1

A mixture of 4-(tert-butoxy)-3-(diethoxyphosphoryl)-4-oxobutanoic acid (2.00 g, 6.45 mmol), ammonium chloride (517 mg, 9.67 mmol) and DIPEA (1.7 mL, 9.67 mmol) in dimethylformamide (10 mL) was stirred at RT for 15 mins. HATU (2.94 g, 7.73 mmol) was added and the mixture was stirred at RT for 30 min, then poured into water (100 mL) and extracted with EtOAc (3×50 mL). The combined organic layers were washed with water (25 mL), brine (25 mL) dried ($Na_2SO_4$) and concentrated. The crude product was purified by chromatography on silica gel (0-10% MeOH/DCM), then further purified by chromatography on silica gel (0-10% MeOH/DCM) to afford tert-butyl 4-amino-2-(diethoxyphosphoryl)-4-oxobutanoate (1.63 g, 5.2 mmol) as a white solid. LCMS m/z 332.3 $(M+Na)^+$ $(ES^+)$. $^1H$ NMR (400 MHz, DMSO-d6) δ 7.42 (s, 1H), 6.90 (s, 1H), 4.10-3.96 (m, 4H), 3.22 (ddd, J=23.3, 11.5, 3.4 Hz, 1H), 2.69 (ddd, J=16.4, 11.4, 7.2 Hz, 1H), 2.40 (ddd, J=16.4, 9.5, 3.4 Hz, 1H), 1.39 (s, 9H), 1.28-1.22 (m, 6H).

Step 2

Lawesson's reagent (549 mg, 1.36 mmol) was added to a solution of tert-butyl 4-amino-2-(diethoxyphosphoryl)-4-oxobutanoate (0.70 g, 2.26 mmol) in 1,4-dioxane (3 mL) at 60° C. The mixture was stirred for 2 h at 60° C., cooled to RT and concentrated. The crude product was purified by chromatography on silica gel (0-10% MeOH/DCM) to afford tert-butyl 4-amino-2-(diethoxyphosphoryl)-4-thioxobutanoate (0.621 g, 1.8 mmol, 92% purity) as a thick yellow gum. LCMS m/z 348.2 $(M+Na)^+$ $(ES^+)$. $^1H$ NMR (400 MHz, DMSO-d6) δ 9.53 (s, 1H), 9.36 (s, 1H), 4.12-3.98 (m, 4H), 3.83-3.66 (m, 1H), 3.08 (ddd, J=16.0, 11.5, 6.5 Hz, 1H), 2.60 (ddd, J=16.0, 9.8, 3.3 Hz, 1H), 1.39 (s, 9H), 1.31-1.21 (m, 6H).

Step 3

A solution of tert-butyl 4-amino-2-(diethoxyphosphoryl)-4-thioxobutanoate (0.621 g, 1.8 mmol, 92% purity) and 1-bromodecan-2-one (792 mg, 2.86 mmol, 85% purity) in EtOH (19 mL) was heated to 80° C. for 20 min. The mixture was cooled to RT and concentrated. The crude product was purified by chromatography on silica gel (0-100% EtOAc/isohexane) to afford tert-butyl 2-(diethoxyphosphoryl)-3-(4-octylthiazol-2-yl)propanoate (0.602 g, 1.0 mmol, 80% purity) as a clear orange oil. LCMS m/z 462.3 $(M+H)^+$ $(ES^+)$. $^1H$ NMR (400 MHz, DMSO-d6) δ 7.14 (s, 1H), 4.14-4.03 (m, 4H), 3.50-3.41 (m, 2H), 3.32-3.23 (m, 1H), 2.62 (t, J=7.5 Hz, 2H), 1.65-1.55 (m, 2H), 1.34 (s, 9H), 1.29-1.21 (m, 16H), 0.89-0.82 (m, 3H).

Step 4

Prepared according to General Procedure A, Step 2, Method B from tert-butyl 2-(diethoxyphosphoryl)-3-(4-octylthiazol-2-yl)propanoate (0.602 g, 1.0 mmol, 80% purity). The crude product was purified by chromatography on silica gel (0-50% EtOAc/isohexane) to afford tert-butyl 2-((4-octylthiazol-2-yl)methyl)acrylate (0.275 g, 0.77 mmol, 94% purity) as a clear colourless oil. LCMS m/z 338.3 $(M+H)^+$ $(ES^+)$. $^1H$ NMR (400 MHz, DMSO-d6) δ 7.10 (s, 1H), 6.14 (d, J=1.5 Hz, 1H), 5.79-5.73 (m, 1H), 3.90 (d, J=1.1 Hz, 2H), 2.66-2.59 (m, 2H), 1.65-1.54 (m, 2H), 1.37 (s, 9H), 1.32-1.19 (m, 10H), 0.89-0.82 (m, 3H).

Step 5

Prepared according to General Procedure A, Step 3 from tert-butyl 2-((4-octylthiazol-2-yl)methyl)acrylate (0.275 g, 0.77 mmol, 94% purity). The crude product was purified by chromatography on silica gel (0-50% MTBE/isohexane) to afford 2-((4-octylthiazol-2-yl)methyl)acrylic acid (110 mg, 0.37 mmol) as a clear yellow oil. LCMS m/z 282.1 $(M+H)^+$ $(ES^+)$. $^1H$ NMR (400 MHz, DMSO-d6) δ 12.69 (br s, 1H), 7.10 (s, 1H), 6.21 (d, J=1.5 Hz, 1H), 5.79 (d, J=1.4 Hz, 1H), 3.89 (d, J=1.0 Hz, 2H), 2.63 (t, J=7.6 Hz, 2H), 1.60 (t, J=7.5 Hz, 2H), 1.32-1.19 (m, 10H), 0.88-0.80 (m, 3H).

Example 39—2-((4-octyloxazol-2-yl)methyl)acrylic acid

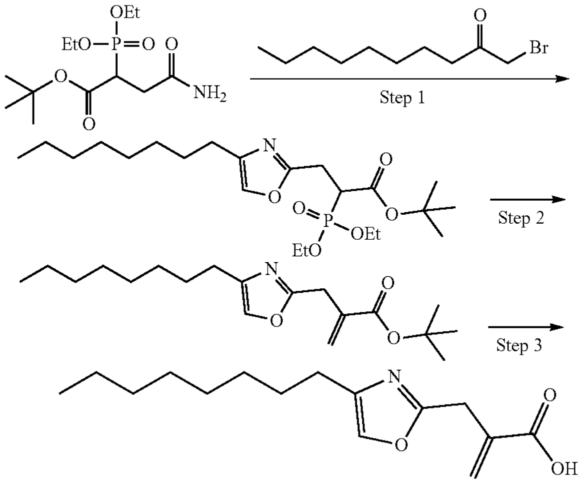

Step 1

Silver trifluoromethanesulfonate (136 mg, 0.53 mmol) was added to a suspension of 1-bromodecan-2-one (100 mg, 0.43 mmol) and tert-butyl 4-amino-2-(diethoxyphosphoryl)-4-oxobutanoate (164 mg, 0.53 mmol) in EtOAc (2 mL) at RT. The mixture was stirred in the dark for 16 h at RT, then diluted with brine (4 mL) and stirred at RT for 3 h. The mixture was filtered and the filtrate was extracted with EtOAc (3×5 mL). The combined organic layers were dried ($Na_2SO_4$) and concentrated. The crude product was purified by chromatography on silica gel (0-10% MeOH/DCM) to afford tert-butyl 2-(diethoxyphosphoryl)-3-(4-octyloxazol-2-yl)propanoate (0.030 g, 56 μmol, 83% purity) as a clear colourless oil. LCMS m/446.3 $(M+H)^+$ $(ES^+)$. $^1$H NMR (400 MHz, DMSO-d6) δ 7.69 (s, 1H), 4.12-4.05 (m, 4H), 3.41 (ddd, J=22.8, 11.5, 3.9 Hz, 1H), 3.17 (ddd, J=16.3, 11.5, 8.3 Hz, 1H), 3.03 (ddd, J=16.4, 8.8, 3.9 Hz, 1H), 2.39-2.32 (m, 2H), 1.55-1.45 (m, 2H), 1.36 (s, 9H), 1.27-1.23 (m, 16H), 0.87-0.84 (m, 3H).

Step 2

Prepared according to General Procedure A, Step 2, Method B from tert-butyl 2-(diethoxyphosphoryl)-3-(4-octyloxazol-2-yl)propanoate (142 mg, 0.32 mmol). The crude product was purified by chromatography on silica gel (0-50% EtOAc/isohexane) to afford tert-butyl 2-((4-octyloxazol-2-yl)methyl)acrylate (0.053 g, 0.12 mmol, 75% purity) as a light yellow oil. LCMS m/z 266.2 $(M-tBu+H)^+$ $(ES^+)$. $^1$H NMR (400 MHz, DMSO-d6) δ 7.68 (t, J=1.1 Hz, 1H), 6.13 (d, J=1.4 Hz, 1H), 5.74-5.68 (m, 1H), 3.68 (s, 2H), 2.41-2.33 (m, 2H), 1.55-1.48 (m, 2H), 1.35 (s, 9H), 1.27-1.24 (m, 10H), 0.87-0.85 (m, 3H).

Step 3

Prepared according to General Procedure A, Step 3 from tert-butyl 2-((4-octyloxazol-2-yl)methyl)acrylate (0.053 g, 0.12 mmol, 75% purity). The crude product was purified by chromatography on silica gel (0-50% EtOAc/isohexane) to afford 2-((4-octyloxazol-2-yl)methyl)acrylic acid (0.020 g, 75 μmol) as a clear colourless oil. LCMS m/z 266.2 $(M+H)^+$ $(ES^+)$. $^1$H NMR (400 MHz, DMSO-d6) δ 12.66 (s, 1H), 7.67 (d, J=1.3 Hz, 1H), 6.19 (d, J=1.4 Hz, 1H), 5.71 (d, J=1.6 Hz, 1H), 3.69 (s, 2H), 2.38 (t, J=7.5 Hz, 2H), 1.58-1.46 (m, 2H), 1.31-1.21 (m, 10H), 0.90-0.81 (m, 3H).

Example 40—(R)-2-((3-(octan-2-yl)-1,2,4-oxadiazol-5-yl)methyl)acrylic acid

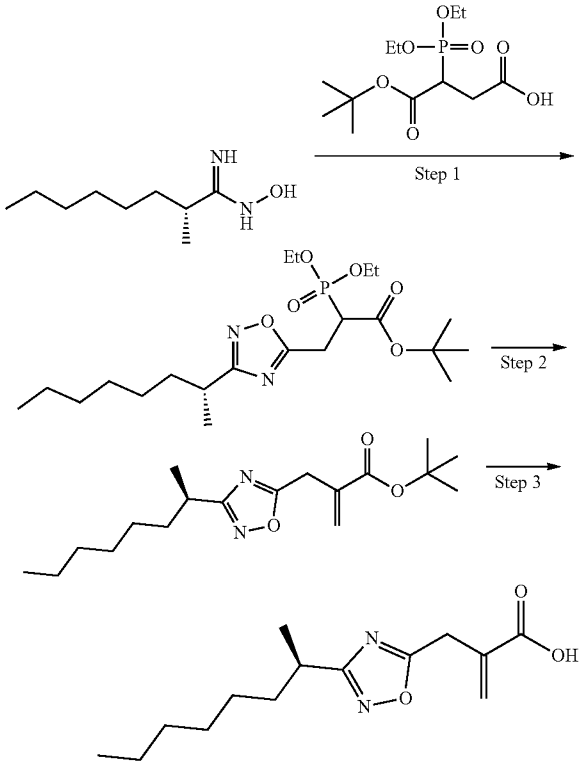

Step 1

Prepared according to General Procedure B, Method B from (R)-N-hydroxy-2-methyloctanimidamide (1.46 g, 7.20 mmol, 85% purity). The crude product was purified by chromatography on silica gel (0-100% MTBE/isohexane) to afford tert-butyl 2-(diethoxyphosphoryl)-3-(3-((R)-octan-2-yl)-1,2,4-oxadiazol-5-yl)propanoate (1.79 g, 2.8 mmol, 70% purity) as a clear, pale yellow oil. LCMS m/z 469.1 $(M+Na)^+$ $(ES^+)$. $^1$H NMR (400 MHz, DMSO-d6) δ 4.18-4.01 (m, 4H), 3.63-3.46 (m, 1H), 3.42-3.33 (m, 1H), 3.28-3.16 (m, 1H), 2.97-2.82 (m, 1H), 1.65-1.49 (m, 2H), 1.37 (s, 9H), 1.30-1.15 (m, 17H), 0.84 (t, J=6.7 Hz, 3H).

Step 2

Prepared according to General Procedure A, Step 2, Method B from tert-butyl 2-(diethoxyphosphoryl)-3-(3-((R)-octan-2-yl)-1,2,4-oxadiazol-5-yl)propanoate (1.79 g, 2.8 mmol, 70% purity). The crude product was purified by chromatography on silica gel (0-20% MTBE/isohexane) to afford tert-butyl (R)-2-((3-(octan-2-yl)-1,2,4-oxadiazol-5-yl)methyl)acrylate (1.0 g, 2.8 mmol, 90% purity) as a clear and colourless oil. LCMS m/z 267.1 $(M-tBu+H)^+$ $(ES^+)$. $^1$H NMR (400 MHz, DMSO-d6) δ 6.29-6.18 (m, 1H), 5.97-5.84 (m, 1H), 3.92 (s, 2H), 2.99-2.78 (m, 1H), 1.70-1.45 (m, 2H), 1.34 (s, 9H), 1.29-1.09 (m, 11H), 0.84 (t, J=6.8 Hz, 3H).

Step 3

Prepared according to General Procedure A, Step 3 from tert-butyl (R)-2-((3-(octan-2-yl)-1,2,4-oxadiazol-5-yl)

methyl)acrylate (1.0 g, 2.8 mmol, 90% purity). The crude product was purified by chromatography on silica gel (0-35% MTBE/isohexane) to afford (R)-2-((3-(octan-2-yl)-1,2,4-oxadiazol-5-yl)methyl)acrylic acid (0.696 g, 2.5 mmol) as a clear, colourless oil. LCMS m/z 267.1 $(M+H)^+$ $(ES^+)$. $^1H$ NMR (400 MHz, DMSO-d6) δ 12.80 (s, br. 1H), 6.37-6.19 (m, 1H), 5.98-5.81 (m, 1H), 3.91 (s, 2H), 3.03-2.76 (m, 1H), 1.75-1.41 (m, 2H), 1.34-1.01 (m, 11H), 0.85 (t, J=6.7 Hz, 3H).

Example 41—2-((3-(4-ethylphenethyl)-1,2,4-oxadiazol-5-yl)methyl)acrylic acid

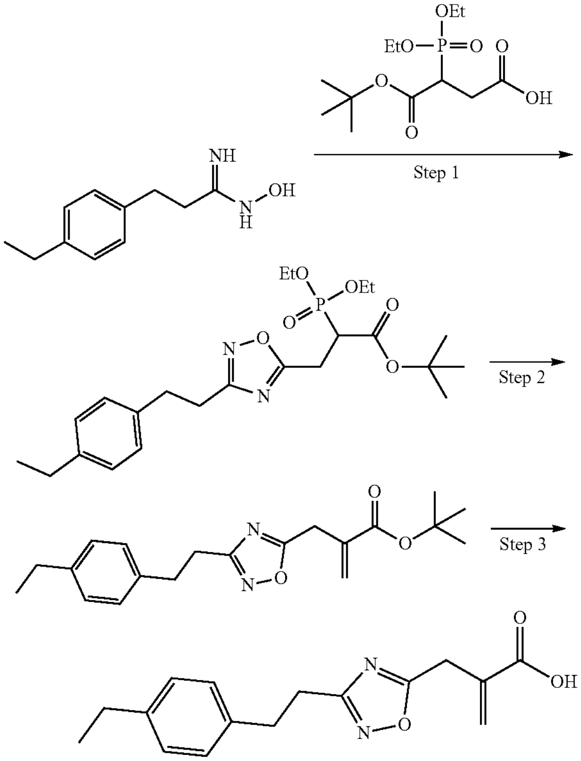

Step 1

Prepared according to General Procedure B, Method B from 3-(4-ethylphenyl)-N-hydroxypropanimidamide (1.10 g, 5.03 mmol, 88% purity). The crude product was purified by chromatography on silica gel (0-100% EtOAc/isohexane) to afford tert-butyl 2-(diethoxyphosphoryl)-3-(3-(4-ethylphenethyl)-1,2,4-oxadiazol-5-yl)propanoate (0.55 g, 1.1 mmol, 94% purity) as a dark orange oil. LCMS m/z 489.3 $(M+Na)^+$ $(ES^+)$. $^1H$ NMR (400 MHz, DMSO-d6) δ 7.11 (s, 4H), 4.15-4.05 (m, 4H), 3.58 (ddd, J=23.3, 10.9, 4.2 Hz, 1H), 3.42-3.33 (m, 1H), 3.24 (ddd, J=16.9, 8.8, 4.4 Hz, 1H), 2.98-2.87 (m, 4H), 2.55 (q, J=7.6 Hz, 2H), 1.38 (s, 9H), 1.30-1.22 (m, 6H), 1.15 (t, J=7.6 Hz, 3H).

Step 2

Prepared according to General Procedure A, Step 2, Method B from tert-butyl 2-(diethoxyphosphoryl)-3-(3-(4-ethylphenethyl)-1,2,4-oxadiazol-5-yl)propanoate (0.55 g, 1.1 mmol, 94% purity). The crude product was purified by chromatography on silica gel (0-100% EtOAc/isohexane) to afford tert-butyl 2-((3-(4-ethylphenethyl)-1,2,4-oxadiazol-5-yl)methyl)acrylate (0.28 g, 0.65 mmol, 79% purity) as a yellow oil. LCMS m/z 287.5 $(M-tBu+H)^+$ $(ES^+)$. $^1H$ NMR (400 MHz, DMSO-d6) δ 7.15-7.07 (m, 4H), 6.24 (d, J=1.3 Hz, 1H), 5.92-5.86 (m, 1H), 3.92 (s, 2H), 2.94 (q, J=3.3 Hz, 4H), 2.55 (q, J=7.7 Hz, 2H), 1.35 (s, 9H), 1.15 (t, J=7.6 Hz, 3H).

Step 3

Prepared according to General Procedure A, Step 3 from tert-butyl 2-((3-(4-ethylphenethyl)-1,2,4-oxadiazol-5-yl)methyl)acrylate (0.28 g, 0.65 mmol, 79% purity). The crude product was purified by HPLC (Waters XSelect CSH column C18, 5 μm 30×100 mm, 40-70% MeCN in Water 0.1% Formic Acid) to afford 2-((3-(4-ethylphenethyl)-1,2,4-oxadiazol-5-yl)methyl)acrylic acid (80 mg, 0.28 mmol) as a white solid. LCMS m/z 286.9 $(M+H)^+$ $(ES^+)$. $^1H$ NMR (400 MHz, DMSO-d6) δ 12.84 (s, 1H), 7.11 (d, J=1.2 Hz, 4H), 6.28 (d, J=1.3 Hz, 1H), 5.90 (d, J=1.6 Hz, 1H), 3.92 (s, 2H), 2.93 (s, 4H), 2.55 (q, J=7.6 Hz, 2H), 1.15 (t, J=7.6 Hz, 3H).

Example 42—2-((3-(4-(trifluoromethyl)benzyl)-1,2,4-oxadiazol-5-yl)methyl)acrylic acid

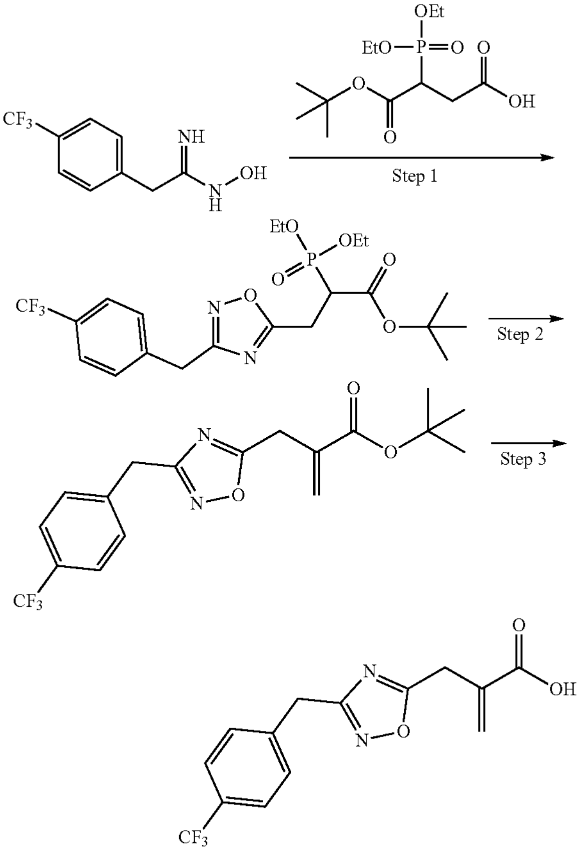

Step 1

Prepared according to General Procedure B, Method B from N-hydroxy-2-(4-(trifluoromethyl)phenyl)acetimidamide (0.60 g, 2.5 mmol, 90% purity). The crude product was purified by chromatography on silica gel (0-100% EtOAc/isohexane) to afford tert-butyl 2-(diethoxyphosphoryl)-3-(3-(4-(trifluoromethyl)benzyl)-1,2,4-oxadiazol-5-yl)propanoate (0.28 g, 0.54 mmol) as dark orange oil. LCMS m/z 515.1 $(M+Na)^+$ $(ES^+)$. $^1H$ NMR (400 MHz, DMSO-d6) δ 7.68 (d, J=8.0 Hz, 2H), 7.51 (d, J=8.0 Hz, 2H), 4.18 (d, J=3.5 Hz, 2H), 4.11-3.96 (m, 4H), 3.53 (ddd, J=23.4, 10.9, 4.5 Hz, 1H), 3.39-3.13 (m, 2H), 1.27-1.19 (m, 15H).

Step 2

Prepared according to General Procedure A, Step 2, Method B from tert-butyl 2-(diethoxyphosphoryl)-3-(3-(4-(trifluoromethyl)benzyl)-1,2,4-oxadiazol-5-yl)propanoate (0.28 g, 0.54 mmol). The crude product was purified by chromatography on silica gel (0-100% EtOAc/isohexane) to afford tert-butyl 2-((3-(4-(trifluoromethyl)benzyl)-1,2,4-oxadiazol-5-yl)methyl)acrylate (130 mg, 0.35 mmol) as a yellow oil. LCMS m/z 313.1 $(M-tBu+H)^+$ $(ES^+)$. $^1H$ NMR (400 MHz, DMSO-d6) δ 7.69 (d, J=8.0 Hz, 2H), 7.53 (d, J=8.0 Hz, 2H), 6.21 (d, J=1.3 Hz, 1H), 5.89 (d, J=1.3 Hz, 1H), 4.18 (s, 2H), 3.91 (s, 2H), 1.22 (s, 9H).

Step 3

Prepared according to General Procedure A, Step 3 from tert-butyl 2-((3-(4-(trifluoromethyl)benzyl)-1,2,4-oxadiazol-5-yl)methyl)acrylate (130 mg, 0.35 mmol). The crude product was purified by chromatography on silica gel (0-100% EtOAc/isohexane to afford 2-((3-(4-(trifluoromethyl)benzyl)-1,2,4-oxadiazol-5-yl)methyl)acrylic acid (110 mg, 0.35 mmol) as a colourless oil. (3135-108). LCMS m/z 313.0 $(M+H)^+$ $(ES^+)$. $^1H$ NMR (400 MHz, DMSO-d6) δ 12.82 (s, 1H), 7.70 (d, J=8.0 Hz, 2H), 7.52 (d, J=7.9 Hz, 2H), 6.27 (d, J=1.3 Hz, 1H), 5.92 (d, J=1.5 Hz, 1H), 4.20 (s, 2H), 3.92 (s, 2H).

Example 43—(S)-2-((3-(octan-2-yl)-1,2,4-oxadiazol-5-yl)methyl)acrylic acid

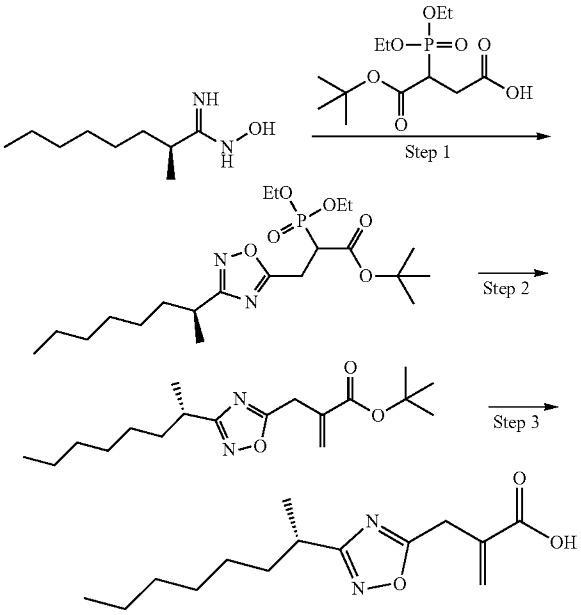

Step 1

Prepared according to General Procedure B, Method B from (S)—N-hydroxy-2-methyloctanimidamide (1.63 g, 8.04 mmol, 85% purity). The crude product was purified by chromatography on silica gel (0-100% MTBE/isohexane) to afford tert-butyl 2-(diethoxyphosphoryl)-3-(3-((S)-octan-2-yl)-1,2,4-oxadiazol-5-yl)propanoate (1.85 g, 2.9 mmol, 71% purity) as a clear, pale yellow oil. LCMS m/z 469.1 $(M+Na)^+$ $(ES^+)$. $^1H$ NMR (400 MHz, DMSO-d6) δ 4.20-3.99 (m, 4H), 3.63-3.46 (m, 1H), 3.40-3.34 (m, 1H), 3.28-3.15 (m, 1H), 2.96-2.83 (m, 1H), 1.67-1.50 (m, 2H), 1.37 (s, 9H), 1.31-1.14 (m, 17H), 0.84 (t, J=6.7 Hz, 3H).

Step 2

Prepared according to General Procedure A, Step 2, Method B from tert-butyl 2-(diethoxyphosphoryl)-3-(3-((S)-octan-2-yl)-1,2,4-oxadiazol-5-yl)propanoate (1.85 g, 2.9 mmol, 71% purity). The crude product was purified by chromatography on silica gel (0-20% MTBE/isohexane) to afford tert-butyl (S)-2-((3-(octan-2-yl)-1,2,4-oxadiazol-5-yl)methyl)acrylate (0.98 g, 2.9 mmol) as a clear and colourless oil. LCMS m/z 267.1 $(M-tBu+H)^+$ $(ES^+)$. $^1H$ NMR (400 MHz, DMSO-d6) δ 6.28-6.19 (m, 1H), 5.95-5.84 (m, 1H), 3.92 (s, 2H), 2.97-2.81 (m, 1H), 1.70-1.46 (m, 2H), 1.34 (s, 9H), 1.28-1.10 (m, 11H), 0.84 (t, J=6.8 Hz, 3H).

Step 3

Prepared according to General Procedure A, Step 3 from tert-butyl (S)-2-((3-(octan-2-yl)-1,2,4-oxadiazol-5-yl)methyl)acrylate (0.98 g, 2.9 mmol). The crude product was purified by chromatography on silica gel (0-35% MTBE/isohexane) to afford (S)-2-((3-(octan-2-yl)-1,2,4-oxadiazol-5-yl)methyl)acrylic acid (0.612 g, 2.2 mmol) as a clear, colourless oil. LCMS m/z 267.1 $(M+H)^+$ $(ES^+)$. $^1H$ NMR (400 MHz, DMSO-d6) δ 12.80 (s, 1H), 6.28 (d, J=1.2 Hz, 1H), 5.90 (q, J=1.3 Hz, 1H), 3.91 (d, J=1.0 Hz, 2H), 2.95-2.81 (m, 1H), 1.68-1.59 (m, 1H), 1.52 (ddt, J=14.6, 12.8, 5.5 Hz, 1H), 1.33-1.11 (m, 11H), 0.85 (t, J=6.9 Hz, 3H).

Example 44—2-((3-(1-(4-fluorophenyl)cyclopropyl)-1,2,4-oxadiazol-5-yl)methyl)acrylic acid

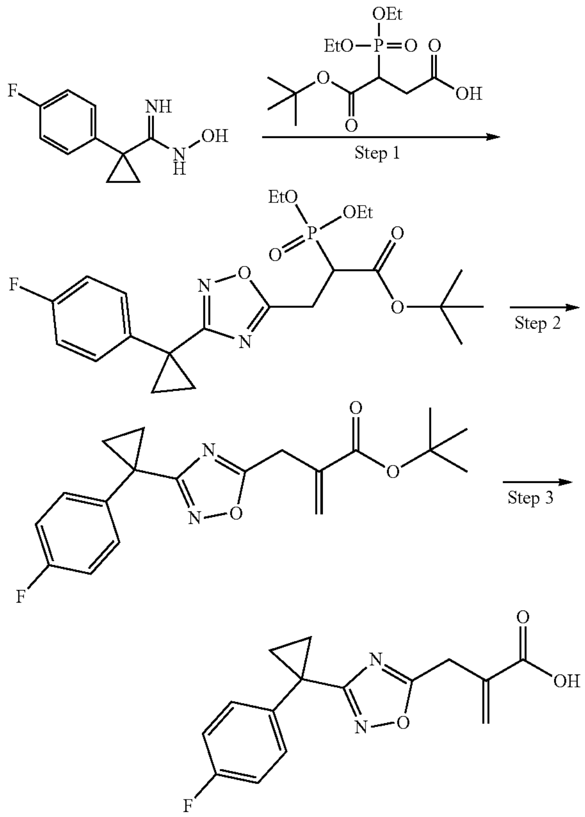

Step 1

Prepared according to General Procedure B, Method B from 1-(4-fluorophenyl)-N-hydroxycyclopropane-1-carboximidamide (1.42 g, 6.58 mmol, 90% purity). The crude product was purified by chromatography on silica gel (0-100% MTBE/isohexane) to afford tert-butyl 2-(diethoxyphosphoryl)-3-(3-(1-(4-fluorophenyl)cyclopropyl)-1,2,4-oxadiazol-5-yl)propanoate (2.27 g, 4.4 mmol, 90% purity) as a clear, pale yellow oil. LCMS m/z 491.1 $(M+Na)^+$ $(ES^+)$. $^1H$ NMR (400 MHz, DMSO-d6) δ 7.47-7.32 (m, 2H), 7.23-7.09 (m, 2H), 4.17-3.95 (m, 4H), 3.61-3.43 (m, 1H), 3.32-3.25 (m, 1H), 3.25-3.12 (m, 1H), 1.53-1.30 (m, 13H), 1.25 (q, J=6.7 Hz, 6H).

Step 2

Prepared according to General Procedure A, Step 2, Method B from tert-butyl 2-(diethoxyphosphoryl)-3-(3-(1-(4-fluorophenyl)cyclopropyl)-1,2,4-oxadiazol-5-yl)propanoate (2.27 g, 4.4 mmol, 90% purity). The crude product was purified by chromatography on silica gel (0-100% MTBE/isohexane) to afford tert-butyl 2-((3-(1-(4-fluorophenyl)cyclopropyl)-1,2,4-oxadiazol-5-yl)methyl)acrylate (0.55 g, 1.5 mmol) as a clear and colourless oil. LCMS m/z 289.2 $(M-tBu+H)^+$ $(ES^+)$. $^1H$ NMR (400 MHz, DMSO-d6) δ 7.50-7.35 (m, 2H), 7.24-7.10 (m, 2H), 6.21 (s, 1H), 5.92-5.84 (m, 1H), 3.89 (s, 2H), 1.49-1.40 (m, 2H), 1.39-1.27 (m, 11H).

Step 3

Prepared according to General Procedure A, Step 3 from tert-butyl 2-((3-(1-(4-fluorophenyl)cyclopropyl)-1,2,4-oxadiazol-5-yl)methyl)acrylate (0.55 g, 1.5 mmol). The crude product was purified by chromatography on silica gel (0-35% MTBE/isohexane) to afford 2-((3-(1-(4-fluorophenyl)cyclopropyl)-1,2,4-oxadiazol-5-yl)methyl)acrylic acid (0.430 g, 1.4 mmol) as a clear and colourless, thick oil. LCMS m/z 289.1 $(M+H)^+$ $(ES^+)$. $^1H$ NMR (400 MHz, DMSO-d6) δ 12.82 (s, 1H), 7.48-7.38 (m, 2H), 7.20-7.11 (m, 2H), 6.27 (d, J=1.2 Hz, 1H), 5.90 (q, J=1.3 Hz, 1H), 3.88 (s, 2H), 1.51-1.43 (m, 2H), 1.40-1.31 (m, 2H).

Example 45—2-((3-(1-(4-methoxyphenyl)cyclopropyl)-1,2,4-oxadiazol-5-yl)methyl)acrylic acid

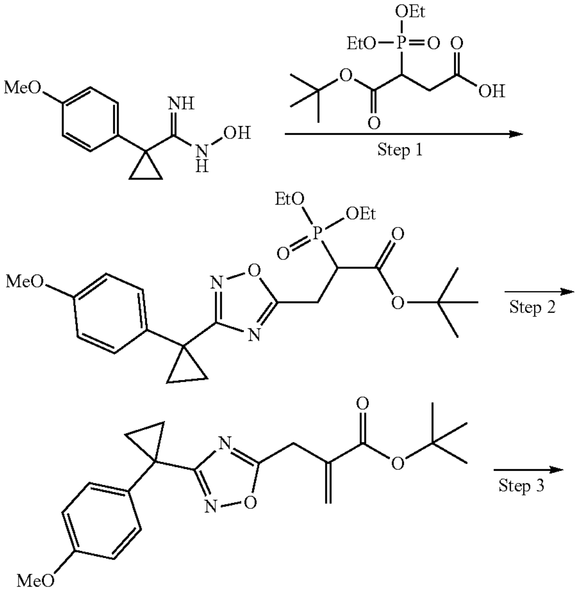

-continued

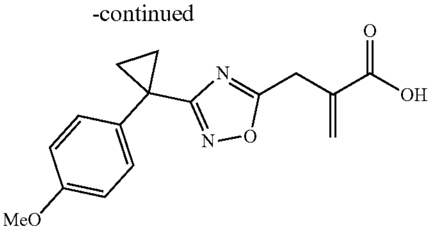

Step 1

Prepared according to General Procedure B, Method B from N-hydroxy-1-(4-methoxyphenyl)cyclopropane-1-carboximidamide (0.90 g, 2.7 mmol, 63% purity). The crude product was purified by chromatography on silica gel (0-100% EtOAc/isohexane) to afford tert-butyl 2-(diethoxyphosphoryl)-3-(3-(1-(4-methoxyphenyl)cyclopropyl)-1,2,4-oxadiazol-5-yl)propanoate (235 mg, 0.32 mmol, 65% purity) as dark orange oil. LCMS m/z 481.1 $(M+H)^+$ $(ES^+)$.

Step 2

Prepared according to General Procedure A, Step 2, Method B from tert-butyl 2-(diethoxyphosphoryl)-3-(3-(1-(4-methoxyphenyl)cyclopropyl)-1,2,4-oxadiazol-5-yl)propanoate (235 mg, 0.32 mmol, 65% purity). The crude product was purified by chromatography on silica gel (0-100% EtOAc/isohexane) to afford tert-butyl 2-((3-(1-(4-methoxyphenyl)cyclopropyl)-1,2,4-oxadiazol-5-yl)methyl) acrylate (60 mg, 0.16 mmol)as a yellow oil. LCMS m/z 301.2 $(M-tBu+H)^+$ $(ES^+)$. $^1H$ NMR (400 MHz, DMSO-d6) δ 7.32-7.26 (m, 2H), 6.92-6.86 (m, 2H), 6.21 (d, J=1.2 Hz, 1H), 5.87 (d, J=1.5 Hz, 1H), 3.88 (s, 2H), 3.75 (s, 3H), 1.40 (q, J=4.2, 3.6 Hz, 2H), 1.34 (s, 9H), 1.30 (q, J=4.8, 4.3 Hz, 2H).

Step 3

Prepared according to General Procedure A, Step 3 from tert-butyl 2-((3-(1-(4-methoxyphenyl)cyclopropyl)-1,2,4-oxadiazol-5-yl)methyl)acrylate (60 mg, 0.16 mmol). The crude product was purified by chromatography on silica gel (0-100% EtOAc/isohexane) to afford 2-((3-(1-(4-methoxyphenyl)cyclopropyl)-1,2,4-oxadiazol-5-yl)methyl)acrylic acid (35 mg, 0.12 mmol) as a white solid. LCMS m/z 301.1 $(M+H)^+$ $(ES^+)$. $^1H$ NMR (400 MHz, DMSO-d6) δ 12.82 (s, 1H), 7.33-7.26 (m, 2H), 6.93-6.84 (m, 2H), 6.26 (d, J=1.2 Hz, 1H), 5.89 (d, J=1.5 Hz, 1H), 3.87 (s, 2H), 3.75 (s, 3H), 1.45-1.38 (m, 2H), 1.32-1.27 (m, 2H).

Example 46—2-((3-(4-(trifluoromethoxy)benzyl)-1,2,4-oxadiazol-5-yl)methyl)acrylic acid

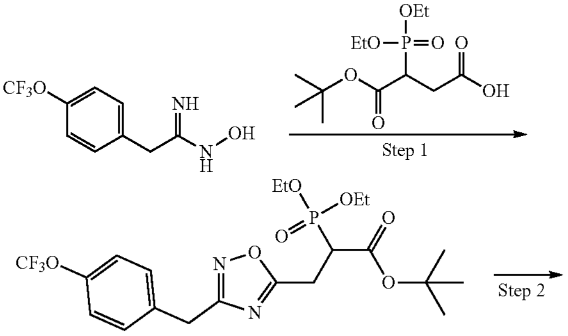

-continued

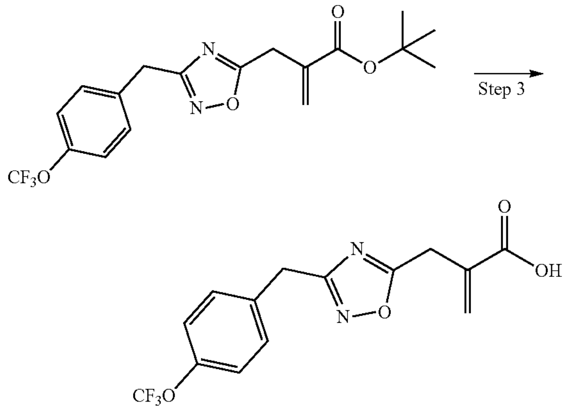

Step 1

Prepared according to General Procedure B, Method B from N-hydroxy-2-(4-(trifluoromethoxy)phenyl)acetimidamide (1.17 g, 5.0 mmol). The crude product was purified by chromatography on silica gel (0-100% MTBE/isohexane) to afford tert-butyl 2-(diethoxyphosphoryl)-3-(3-(4-(trifluoromethoxy)benzyl)-1,2,4-oxadiazol-5-yl)propanoate (1.25 g, 2.2 mmol, 90% purity) as a brown oil. LCMS m/z 531.2 $(M+Na)^+$ $(ES^+)$. $^1H$ NMR (400 MHz, DMSO-d6) δ 7.41 (d, J=9.0 Hz, 2H), 7.31 (d, J=8.1 Hz, 2H), 4.16-3.99 (m, 6H), 3.54 (ddd, J=23.4, 10.9, 4.5 Hz, 1H), 3.41-3.16 (m, 2H), 1.31-1.17 (m, 15H).

Step 2

Prepared according to General Procedure A, Step 2, Method B from tert-butyl 2-(diethoxyphosphoryl)-3-(3-(4-(trifluoromethoxy)benzyl)-1,2,4-oxadiazol-5-yl)propanoate (1.25 g, 2.2 mmol, 90% purity). The crude product was purified by chromatography on silica gel (0-50% MTBE/isohexane) to afford tert-butyl 2-((3-(4-(trifluoromethoxy)benzyl)-1,2,4-oxadiazol-5-yl)methyl)acrylate (0.605 g, 1.5 mmol) as a colourless oil. LCMS m/z 329.2 $(M-tBu+H)^+$ $(ES^+)$. $^1H$ NMR (400 MHz, DMSO-d6) δ 7.42 (d, J=8.6 Hz, 2H), 7.31 (d, J=8.2 Hz, 2H), 6.21 (s, 1H), 5.89 (s, 1H), 4.10 (s, 2H), 3.91 (s, 2H), 1.22 (s, 9H).

Step 3

Prepared according to General Procedure A, Step 3 from tert-butyl 2-((3-(4-(trifluoromethoxy)benzyl)-1,2,4-oxadiazol-5-yl)methyl)acrylate (0.605 g, 1.5 mmol). The crude product was purified by chromatography on silica gel (0-100% MTBE/isohexane) to afford 2-((3-(4-(trifluoromethoxy)benzyl)-1,2,4-oxadiazol-5-yl)methyl)acrylic acid (0.405 g, 1.2 mmol) as a colourless oil. LCMS m/z 329.1 $(M+H)^+$ $(ES^+)$. $^1H$ NMR (400 MHz, DMSO-d6) δ 12.81 (s, 1H), 7.41 (d, J=8.2 Hz, 2H), 7.32 (d, J=8.2 Hz, 2H), 6.27 (s, 1H), 5.91 (s, 1H), 4.12 (s, 2H), 3.91 (s, 2H).

Example 47—2-((3-(7,7,8-trifluorooctyl)-1,2,4-oxadiazol-5-yl)methyl)acrylic acid

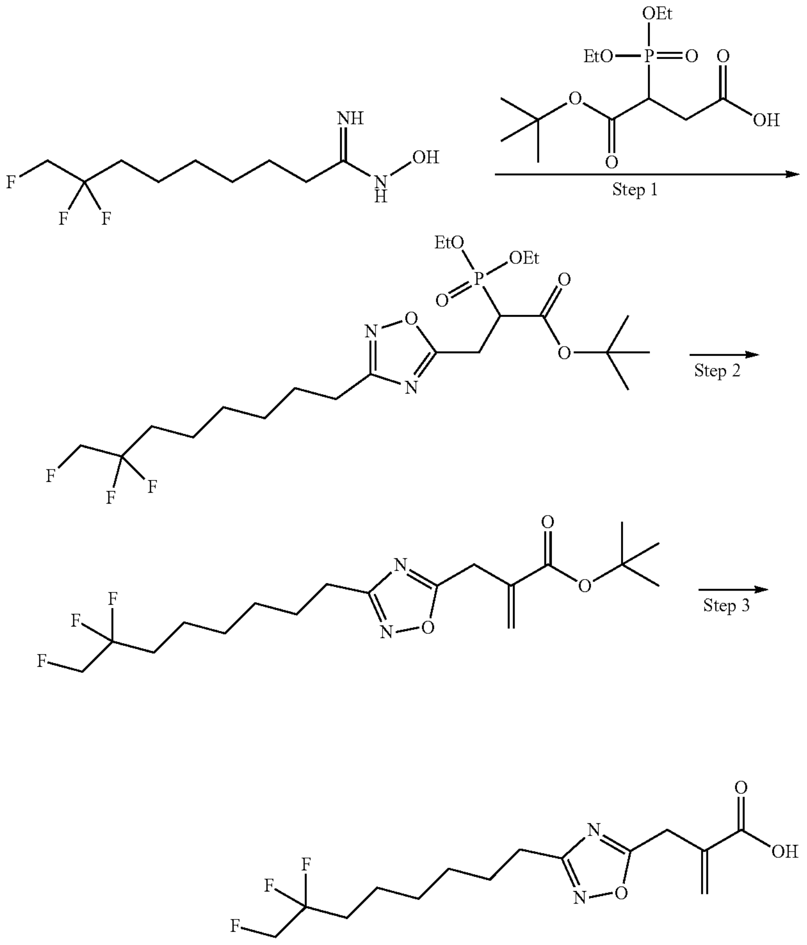

Step 1

Prepared according to General Procedure B, Method B from 8,8,9-trifluoro-N-hydroxynonanimidamide (1.28 g, 5.66 mmol). The crude product was purified by chromatography on silica gel (0-100% MTBE/isohexane) to afford tert-butyl 2-(diethoxyphosphoryl)-3-(3-(7,7,8-trifluorooctyl)-1,2,4-oxadiazol-5-yl)propanoate (1.02 g, 1.9 mmol, 92% purity) as a brown oil. LCMS m/z 523.2 $(M+Na)^+$ $(ES^+)$.

Step 2

Prepared according to General Procedure A, Step 2, Method B from tert-butyl 2-(diethoxyphosphoryl)-3-(3-(7,7,8-trifluorooctyl)-1,2,4-oxadiazol-5-yl)propanoate (1.02 g, 1.9 mmol, 92% purity). The crude product was purified by chromatography on silica gel (0-50% MTBE/isohexane) to afford tert-butyl 2-((3-(7,7,8-trifluorooctyl)-1,2,4-oxadiazol-5-yl)methyl)acrylate (0.516 g, 1.3 mmol, 93% Purity) as a colourless oil. LCMS m/z 321.2 $(M-tBu+H)^+$ $(ES^+)$. $^1H$ NMR (400 MHz, DMSO-d6) δ 6.23 (s, 1H), 5.90 (s, 1H), 4.64 (dt, J=45.9, 13.2 Hz, 2H), 3.91 (s, 2H), 2.65 (t, J=7.4 Hz, 2H), 1.99-1.81 (m, 2H), 1.63 (p, J=7.3 Hz, 2H), 1.49-1.22 (m, 15H).

Step 3

Prepared according to General Procedure A, Step 3 from tert-butyl 2-((3-(7,7,8-trifluorooctyl)-1,2,4-oxadiazol-5-yl)methyl)acrylate (0.516 g, 1.3 mmol, 93% Purity). The crude product was purified by chromatography on silica gel (0-100% MTBE/isohexane) to afford 2-((3-(7,7,8-trifluorooctyl)-1,2,4-oxadiazol-5-yl)methyl)acrylic acid (0.315 g, 0.97 mmol, 71%, 99% Purity) as a colourless oil. LCMS m/z 321.2 $(M+H)^+$ $(ES^+)$. $^1H$ NMR (400 MHz, DMSO-d6) δ 12.81 (s, 1H), 6.28 (s, 1H), 5.92 (s, 1H), 4.64 (dt, J=46.0, 13.2 Hz, 2H), 3.91 (s, 2H), 2.66 (t, J=7.5 Hz, 2H), 2.00-1.83 (m, 2H), 1.64 (p, J=7.3 Hz, 2H), 1.51-1.24 (m, 6H).

Example 48—2-((3-(4-(1-(trifluoromethyl)cyclopropyl)benzyl)-1,2,4-oxadiazol-5-yl)methyl)acrylic acid

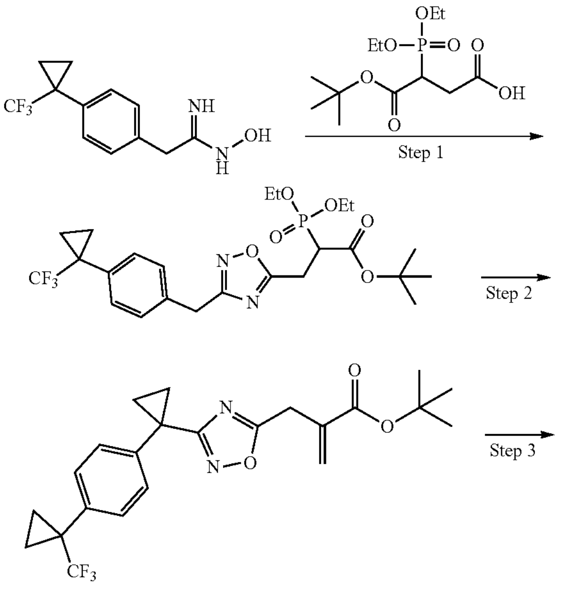

-continued

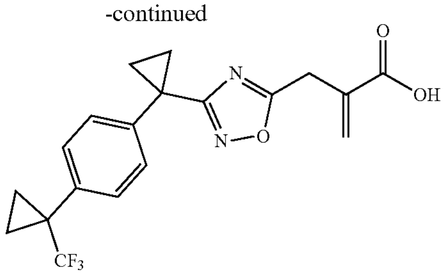

Step 1

Prepared according to General Procedure B, Method B from 8N-hydroxy-2-(4-(1-(trifluoromethyl)cyclopropyl)phenyl)acetimidamide (0.320 g, 1.24 mmol). The crude product was purified by chromatography on silica gel (0-100% EtOAc/isohexane) to afford tert-butyl 2-(diethoxyphosphoryl)-3-(3-(4-(1-(trifluoromethyl)cyclopropyl)benzyl)-1,2,4-oxadiazol-5-yl)propanoate (0.350 g, 0.65 mmol) as a light yellow oil. LCMS m/z 555.2 $(M+Na)^+$ $(ES^+)$. $^1H$ NMR (400 MHz, DMSO-d6) δ 7.40 (d, J=8.0 Hz, 2H), 7.29 (d, J=8.1 Hz, 2H), 4.11-4.00 (m, 6H), 3.54 (ddd, J=23.4, 10.9, 4.5 Hz, 1H), 3.38-3.32 (m, 1H), 3.23 (ddd, J=16.9, 8.7, 4.5 Hz, 1H), 1.35-1.29 (m, 2H), 1.28-1.19 (m, 15H), 1.10-1.04 (m, 2H).

Step 2

Prepared according to General Procedure A, Step 2, Method B from tert-butyl 2-(diethoxyphosphoryl)-3-(3-(4-(1-(trifluoromethyl)cyclopropyl)benzyl)-1,2,4-oxadiazol-5-yl)propanoate (0.350 g, 0.65 mmol). The crude product was purified by chromatography on silica gel (0-100% EtOAc/isohexane) to afford tert-butyl 2-((3-(4-(1-(trifluoromethyl)cyclopropyl)benzyl)-1,2,4-oxadiazol-5-yl)methyl)acrylate (0.226 g, 0.55 mmol) as a clear colourless oil. LCMS m/z 353.2 $(M-tBu+H)^+$ $(ES^+)$. $^1H$ NMR (400 MHz, DMSO-d6) δ 7.40 (d, J=8.0 Hz, 2H), 7.29 (d, J=8.1 Hz, 2H), 6.21 (d, J=1.3 Hz, 1H), 5.92-5.84 (m, 1H), 4.05 (s, 2H), 3.90 (s, 2H), 1.35-1.29 (m, 2H), 1.23 (s, 9H), 1.10-1.05 (m, 2H).

Step 3

Prepared according to General Procedure A, Step 3 from tert-butyl 2-((3-(4-(1-(trifluoromethyl)cyclopropyl)benzyl)-1,2,4-oxadiazol-5-yl)methyl)acrylate (0.226 g, 0.55 mmol). The crude product was purified by chromatography on silica gel (0-50% EtOAc/isohexane) to afford 2-((3-(4-(1-(trifluoromethyl)cyclopropyl)benzyl)-1,2,4-oxadiazol-5-yl)methyl) acrylic acid (0.164 g, 0.46 mmol, 89%, 99% Purity) as a clear colourless oil. LCMS m/z 353.0 $(M+H)^+$ $(ES^+)$. $^1H$ NMR (400 MHz, DMSO-d6) δ 12.83 (s, 1H), 7.41 (d, J=7.9 Hz, 2H), 7.29 (d, J=8.1 Hz, 2H), 6.27 (d, J=1.2 Hz, 1H), 5.91 (d, J=1.4 Hz, 1H), 4.07 (s, 2H), 3.91 (s, 2H), 1.36-1.28 (m, 2H), 1.14-1.07 (m, 2H).

Example 49—2-((3-(1-(4-(trifluoromethoxy)phenyl)cyclopropyl)-1,2,4-oxadiazol-5-yl)methyl)acrylic acid

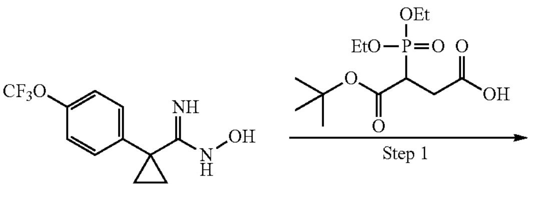

-continued

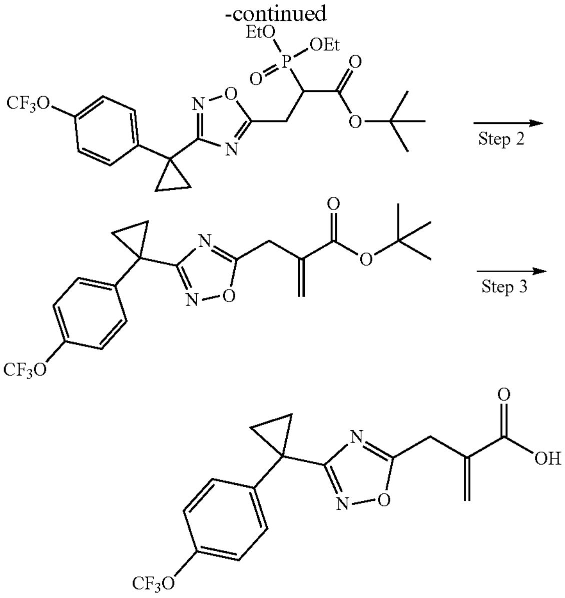

Step 1

Prepared according to General Procedure B, Method B from N-hydroxy-1-(4-(trifluoromethoxy)phenyl)cyclopropane-1-carboximidamide (0.971 g, 3.73 mmol). The crude product was purified by chromatography on silica gel (0-100% MTBE/isohexane) to afford tert-butyl 2-(diethoxyphosphoryl)-3-(3-(1-(4-(trifluoromethoxy)phenyl)cyclopropyl)-1,2,4-oxadiazol-5-yl)propanoate (1.088 g, 1.6 mmol, 77% purity) as a brown oil. LCMS m/z 535.2 $(M+H)^+$ $(ES^+)$.

Step 2

Prepared according to General Procedure A, Step 2, Method B from tert-butyl 2-(diethoxyphosphoryl)-3-(3-(1-(4-(trifluoromethoxy)phenyl)cyclopropyl)-1,2,4-oxadiazol-5-yl)propanoate (1.088 g, 1.6 mmol, 77% purity). The crude product was purified by chromatography on silica gel (0-50% MTBE/isohexane) to afford tert-butyl 2-((3-(1-(4-(trifluoromethoxy)phenyl)cyclopropyl)-1,2,4-oxadiazol-5-yl)methyl)acrylate (0.539 g, 1.3 mmol) as a colourless oil. LCMS m/z 355.1 $(M-tBu+H)^+$ $(ES^+)$. $^1H$ NMR (400 MHz, DMSO-d6) δ 7.51 (d, J=8.1 Hz, 2H), 7.34 (d, J=8.1 Hz, 2H), 6.21 (s, 1H), 5.89 (s, 1H), 3.90 (s, 2H), 1.59-1.23 (m, 13H).

Step 3

Prepared according to General Procedure A, Step 3 from tert-butyl 2-((3-(1-(4-(trifluoromethoxy)phenyl)cyclopropyl)-1,2,4-oxadiazol-5-yl)methyl)acrylate (0.539 g, 1.3 mmol). The crude product was purified by chromatography on silica gel (0-100% MTBE/isohexane) to afford 2-((3-(1-(4-(trifluoromethoxy)phenyl)cyclopropyl)-1,2,4-oxadiazol-5-yl)methyl)acrylic acid (371 mg, 1.0 mmol) as a colourless oil. LCMS m/z 355.1 $(M+H)^+$ $(ES^+)$. $^1H$ NMR (400 MHz, DMSO-d6) δ 12.95-12.70 (m, 1H), 7.61-7.45 (m, 2H), 7.42-7.26 (m, 2H), 6.27 (s, 1H), 5.91 (s, 1H), 3.89 (s, 2H), 1.52-1.35 (m, 4H).

Example 50—2-((3-(1-(4-bromophenyl)cyclopropyl)-1,2,4-oxadiazol-5-yl)methyl)acrylic acid

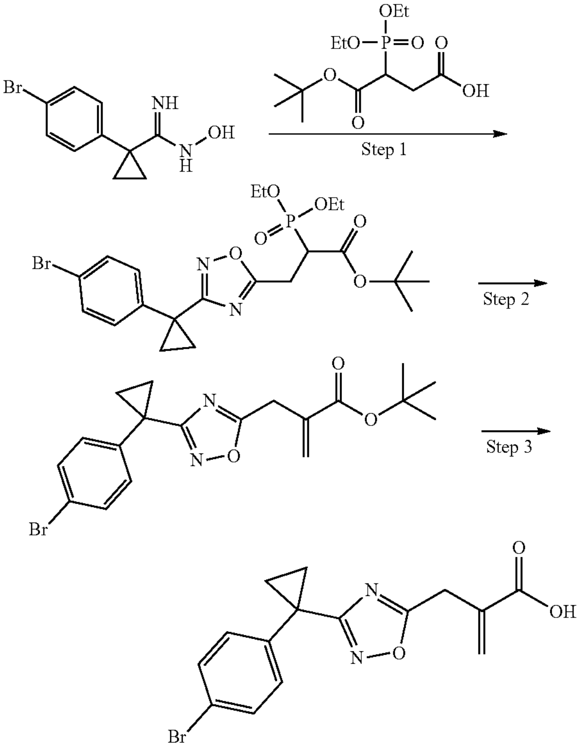

Step 1

Prepared according to General Procedure B, Method B from 1-(4-bromophenyl)-N-hydroxycyclopropane-1-carboximidamide (1.29 g, 4.30 mmol, 85% purity). The crude product was purified by chromatography on silica gel (0-100% MTBE/isohexane) to afford tert-butyl 3-(3-(1-(4-bromophenyl)cyclopropyl)-1,2,4-oxadiazol-5-yl)-2-(diethoxyphosphoryl)propanoate (1.80 g, 3.1 mmol, 90% purity) as a white solid. LCMS m/z 551.1/553.1 $(M+Na)^+$ $(ES^+)$. $^1H$ NMR (400 MHz, DMSO-d6) δ 7.59-7.48 (m, 2H), 7.40-7.25 (m, 2H), 4.15-3.97 (m, 4H), 3.60-3.43 (m, 1H), 3.32-3.26 (m, 1H), 3.25-3.11 (m, 1H), 1.53-1.31 (m, 13H), 1.25 (q, J=6.8 Hz, 6H).

Step 2

Prepared according to General Procedure A, Step 2, Method B from tert-butyl 3-(3-(1-(4-bromophenyl)cyclopropyl)-1,2,4-oxadiazol-5-yl)-2-(diethoxyphosphoryl)propanoate (1.80 g, 3.1 mmol, 90% purity). The crude product was purified by chromatography on silica gel (0-20% MTBE/isohexane) to afford tert-butyl 2-((3-(1-(4-bromophenyl)cyclopropyl)-1,2,4-oxadiazol-5-yl)methyl)acrylate (0.71 g, 1.7 mmol) as a clear and colourless oil. LCMS m/z 349.1/351.1 $(M-tBu+H)^+$ $(ES^+)$. $^1H$ NMR (400 MHz, DMSO-d6) δ 7.58-7.48 (m, 2H), 7.39-7.27 (m, 2H), 6.24-6.19 (m, 1H), 5.90-5.84 (m, 1H), 3.89 (s, 2H), 1.47-1.42 (m, 2H), 1.41-1.35 (m, 2H), 1.33 (s, 9H).

Step 3

Prepared according to General Procedure A, Step 3 from tert-butyl 2-((3-(1-(4-bromophenyl)cyclopropyl)-1,2,4-oxadiazol-5-yl)methyl)acrylate (0.71 g, 1.7 mmol). The crude product was purified by chromatography on silica gel (0-35% MTBE/isohexane), then further purified by preparative HPLC (Waters XSelect CSH C18 OBD prep column, 130 Å, 5 µm, 30 mm×100 mm column, 35-65% MeCN in Water 0.1% Formic Acid) to afford 2-((3-(1-(4-bromophenyl)cyclopropyl)-1,2,4-oxadiazol-5-yl)methyl)acrylic acid (0.447 g, 1.2 mmol) as a white solid. LCMS m/z 349.1/351.1

$(M+H)^+$ ($ES^+$). $^1H$ NMR (400 MHz, DMSO-d6) δ 12.84 (s, 1H), 7.57-7.51 (m, 2H), 7.38-7.32 (m, 2H), 6.26 (d, J=1.2 Hz, 1H), 5.88 (q, J=1.3 Hz, 1H), 3.88 (d, J=1.0 Hz, 2H), 1.48-1.43 (m, 2H), 1.39-1.34 (m, 2H).

Example 51—2-((3-(4-butoxybenzyl)-1,2,4-oxadiazol-5-yl)methyl)acrylic acid

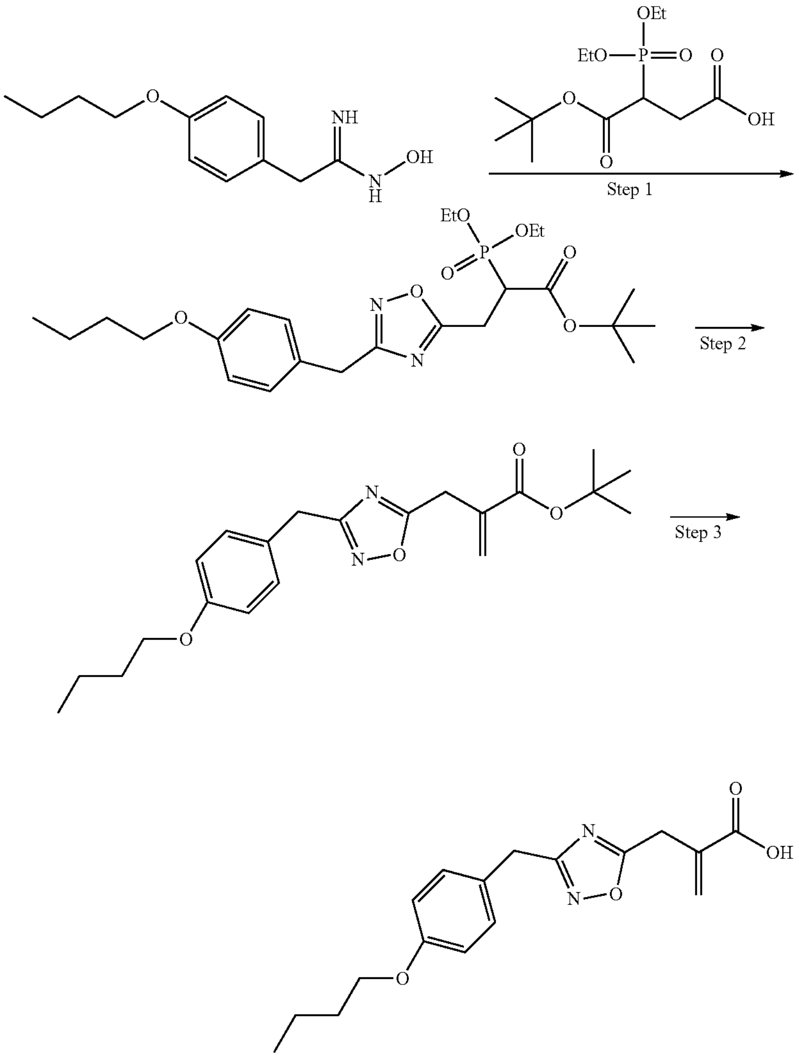

Step 1

Prepared according to General Procedure B, Method B from 2-(4-butoxyphenyl)-N-hydroxyacetimidamide (2.0 g, 7.9 mmol, 88% purity). The crude product was purified by chromatography on silica gel (0-100% EtOAc/isohexane) to afford tert-butyl 3-(3-(4-butoxybenzyl)-1,2,4-oxadiazol-5-yl)-2-(diethoxyphosphoryl)propanoate (1.4 g, 2.3 mmol, 81% purity) as dark orange oil. LCMS m/z 519.2 $(M+Na)^+$ ($ES^+$).

Step 2

Prepared according to General Procedure A, Step 2, Method B from tert-butyl 3-(3-(4-butoxybenzyl)-1,2,4-oxadiazol-5-yl)-2-(diethoxyphosphoryl)propanoate (1.4 g, 2.3 mmol, 81% purity). The crude product was purified by chromatography on silica gel (0-100% EtOAc/isohexane) to afford tert-butyl 2-((3-(4-butoxybenzyl)-1,2,4-oxadiazol-5-yl)methyl)acrylate (400 mg, 1.0 mmol) as a yellow oil. LCMS m/z 317.1 $(M-tBu+H)^+$ ($ES^+$). $^1H$ NMR (400 MHz, DMSO-d6) δ 7.20-7.13 (m, 2H), 6.87-6.82 (m, 2H), 6.21 (d, J=1.3 Hz, 1H), 5.88 (d, J=1.4 Hz, 1H), 3.95 (s, 2H), 3.90 (s, 2H), 1.72-1.62 (m, 2H), 1.49-1.33 (m, 4H), 1.26 (s, 9H), 0.92 (t, J=7.4 Hz, 3H).

Step 3

Prepared according to General Procedure A, Step 3 from tert-butyl 2-((3-(4-butoxybenzyl)-1,2,4-oxadiazol-5-yl)methyl)acrylate (400 mg, 1.0 mmol). The crude product was purified by chromatography on silica gel (0-100% MTBE/isohexane) to afford 2-((3-(4-butoxybenzyl)-1,2,4-oxadiazol-5-yl)methyl)acrylic acid (150 mg, 0.45 mmol) as a sticky orange oil. LCMS m/z 317.1 $(M+H)^+$ ($ES^+$). $^1H$ NMR (400 MHz, DMSO-d6) δ 12.80 (s, 1H), 7.21-7.13 (m, 2H), 6.89-6.82 (m, 2H), 6.27 (d, J=1.2 Hz, 1H), 5.91 (d, J=1.4 Hz, 1H), 3.97 (s, 2H), 3.93 (t, J=6.5 Hz, 2H), 3.90 (s, 2H), 1.74-1.62 (m, 2H), 1.43 (h, J=7.4 Hz, 2H), 0.93 (t, J=7.4 Hz, 3H).

Example 52—2-((3-(1-(4-chloro-3-fluorophenyl)cyclopropyl)-1,2,4-oxadiazol-5-yl)methyl)acrylic acid

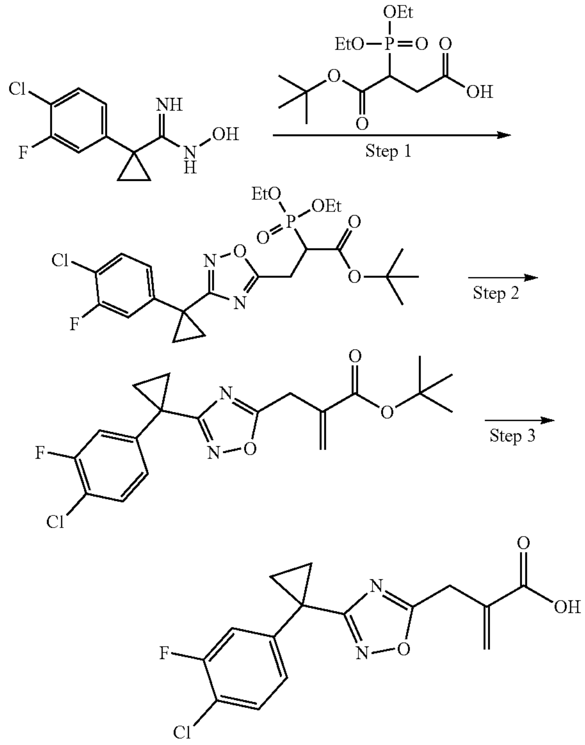

Step 1

Prepared according to General Procedure B, Method B from 1-(4-chloro-3-fluorophenyl)-N-hydroxycyclopropane-1-carboximidamide (2.00 g, 7.0 mmol, 80% purity). The crude product was purified by chromatography on silica gel (0-100% EtOAc/isohexane) to afford tert-butyl 3-(3-(1-(4-chloro-3-fluorophenyl)cyclopropyl)-1,2,4-oxadiazol-5-yl)-2-(diethoxyphosphoryl)propanoate (0.50 g, 0.86 mmol, 87% purity) as dark orange oil. LCMS m/z 503.1 $(M+H)^+$ $(ES^+)$. $^1$H NMR (400 MHz, DMSO-d6) δ 7.56 (t, J=8.2 Hz, 1H), 7.42 (dd, J=10.5, 2.1 Hz, 1H), 7.24 (ddd, J=8.4, 2.1, 0.8 Hz, 1H), 4.13-4.05 (m, 4H), 3.63-3.47 (m, 1H), 3.38-3.27 (m, 1H), 3.25-3.16 (m, 1H), 1.43-1.40 (m, 2H), 1.35 (s, 9H), 1.29-1.21 (m, 8H).

Step 2

Prepared according to General Procedure A, Step 2, Method B from tert-butyl 3-(3-(1-(4-chloro-3-fluorophenyl)cyclopropyl)-1,2,4-oxadiazol-5-yl)-2-(diethoxyphosphoryl)propanoate (0.50 g, 0.86 mmol, 87% purity). The crude product was purified by chromatography on silica gel (0-100% EtOAc/isohexane) to afford tert-butyl 2-((3-(1-(4-chloro-3-fluorophenyl)cyclopropyl)-1,2,4-oxadiazol-5-yl)methyl)acrylate (0.21 g, 0.53 mmol) as a yellow oil. LCMS m/z 379.1 $(M-tBu+H)^+$ $(ES^+)$. $^1$H NMR (400 MHz, DMSO-d6) δ 7.56 (t, J=8.2 Hz, 1H), 7.43 (dd, J=10.5, 2.1 Hz, 1H), 7.25 (ddd, J=8.3, 2.1, 0.8 Hz, 1H), 6.22 (d, J=1.2 Hz, 1H), 5.89 (q, J=1.2 Hz, 1H), 3.92-3.87 (m, 2H), 1.46 (dq, J=6.3, 2.6, 2.1 Hz, 4H), 1.34 (s, 9H).

Step 3

Prepared according to General Procedure A, Step 3 from tert-butyl 2-((3-(1-(4-chloro-3-fluorophenyl)cyclopropyl)-1,2,4-oxadiazol-5-yl)methyl)acrylate (0.21 g, 0.53 mmol). The crude product was purified by chromatography on silica gel (0-100% EtOAc/isohexane) to afford 2-((3-(1-(4-chloro-3-fluorophenyl)cyclopropyl)-1,2,4-oxadiazol-5-yl)methyl)acrylic acid (150 mg, 0.46 mmol) as a yellow oil. LCMS m/z 323.1 $(M+H)^+$ $(ES^+)$. $^1$H NMR (400 MHz, DMSO-d6) δ 12.83 (s, 1H), 7.56 (t, J=8.2 Hz, 1H), 7.46 (dd, J=10.6, 2.1 Hz, 1H), 7.26 (dt, J=8.3, 1.4 Hz, 1H), 6.27 (d, J=1.2 Hz, 1H), 5.91 (q, J=1.3 Hz, 1H), 3.90 (s, 2H), 1.52-1.46 (m, 2H), 1.46-1.40 (m, 2H).

Example 53—2-((3-nonyl-1,2,4-oxadiazol-5-yl)methyl)acrylic acid

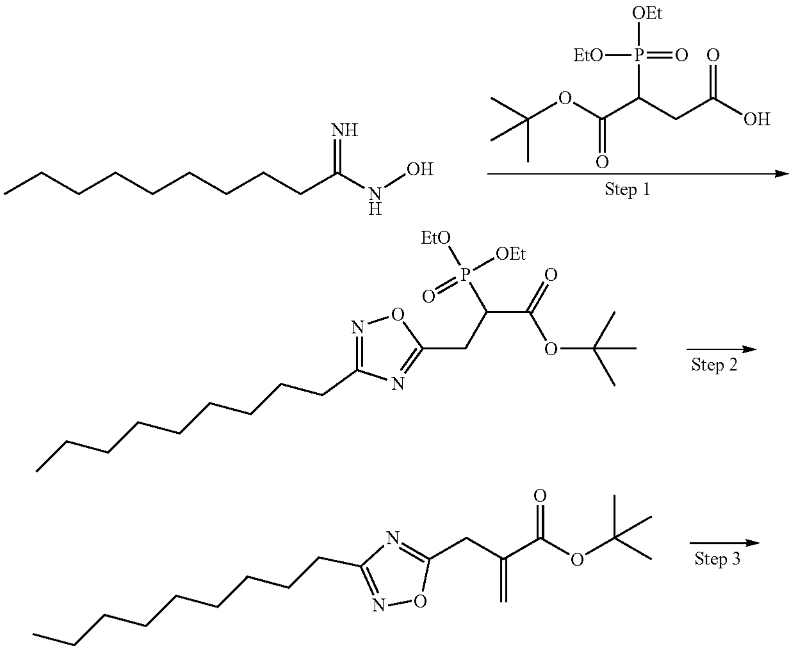

-continued

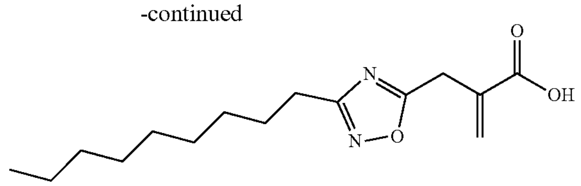

Step 1

Prepared according to General Procedure B, Method B from N-hydroxydecanimidamide (2.50 g, 8.05 mmol). The crude product was purified by chromatography on silica gel (0-100% EtOAc/isohexane) to afford tert-butyl 2-(diethoxyphosphoryl)-3-(3-nonyl-1,2,4-oxadiazol-5-yl)propanoate (0.70 g, 1.4 mmol, 90% purity) as dark orange oil. $^1$H NMR (400 MHz, DMSO-d6) δ 4.14-4.05 (m, 4H), 3.56 (ddd, J=23.5, 11.3, 4.3 Hz, 1H), 3.38-3.33 (m, 1H), 3.23 (ddd, J=16.8, 8.6, 4.3 Hz, 1H), 2.64 (t, J=7.3 Hz, 2H), 1.66-1.56 (m, 2H), 1.37 (s, 9H), 1.27-1.20 (m, 18H), 0.86 (t, J=6.7 Hz, 3H).

Step 2

Prepared according to General Procedure A, Step 2, Method B from tert-butyl 2-(diethoxyphosphoryl)-3-(3-nonyl-1,2,4-oxadiazol-5-yl)propanoate (0.70 g, 1.4 mmol, 90% purity). The crude product was purified by chromatography on silica gel (0-100% EtOAc/isohexane) to afford tert-butyl 2-((3-nonyl-1,2,4-oxadiazol-5-yl)methyl)acrylate (0.20 g, 0.52 mmol, 87% purity) as a yellow oil. LCMS m/z 281.2 (M−tBu+H)$^+$ (ES$^+$). $^1$H NMR (400 MHz, DMSO-d6) δ 6.23 (d, J=1.2 Hz, 1H), 5.90 (q, J=1.2 Hz, 1H), 3.91 (d, J=1.1 Hz, 2H), 2.64 (t, J=7.4 Hz, 2H), 1.61 (p, J=7.0 Hz, 2H), 1.34 (s, 9H), 1.29-1.20 (m, 12H), 0.89-0.80 (m, 3H).

Step 3

Prepared according to General Procedure A, Step 3 from tert-butyl 2-((3-nonyl-1,2,4-oxadiazol-5-yl)methyl)acrylate (0.20 g, 0.52 mmol, 87% purity). The crude product was purified by chromatography on silica gel (0-100% EtOAc/isohexane) to afford 2-((3-nonyl-1,2,4-oxadiazol-5-yl)methyl)acrylic acid (25 mg, 88 μmol) as a colourless oil. LCMS m/z 281.2 (M+H)$^+$ (ES$^+$). $^1$H NMR (400 MHz, DMSO-d6) δ 12.80 (s, 1H), 6.27 (d, J=1.2 Hz, 1H), 5.91 (d, J=1.3 Hz, 1H), 3.90 (s, 2H), 2.64 (t, J=7.5 Hz, 2H), 1.62 (p, J=7.3 Hz, 2H), 1.33-1.18 (m, 12H), 0.91-0.82 (m, 3H).

Example 54—2-((3-(8,8,8-trifluorooctan-2-yl)-1,2,4-oxadiazol-5-yl)methyl)acrylic acid

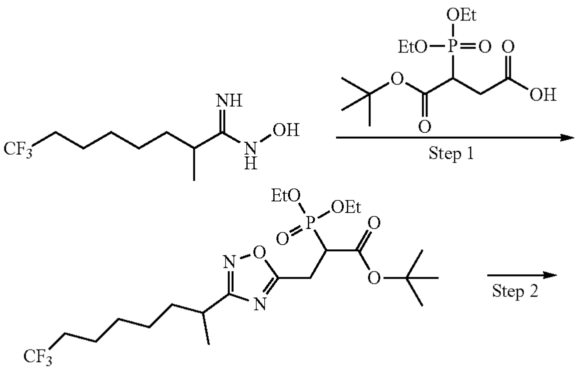

-continued

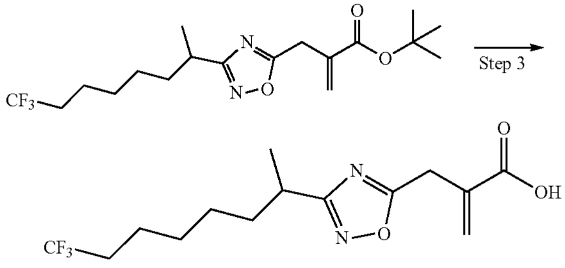

Step 1

Prepared according to General Procedure B, Method B from 8,8,8-trifluoro-N-hydroxy-2-methyloctanimidamide (1.70 g, 6.3 mmol, 84% purity). The crude product was purified by chromatography on silica gel (0-100% EtOAc/isohexane) to afford tert-butyl 2-(diethoxyphosphoryl)-3-(3-(8, 8,8-trifluorooctan-2-yl)-1,2,4-oxadiazol-5-yl)propanoate (0.20 g, 0.40 mmol) as a dark orange oil. LCMS m/z 523.1 (M+Na)$^+$ (ES$^+$). $^1$H NMR (400 MHz, DMSO-d6) δ 4.15-4.00 (m, 4H), 3.56 (ddd, J=23.4, 11.1, 4.4 Hz, 1H), 3.39-3.33 (m, 1H), 3.23 (ddd, J=16.8, 8.5, 4.4 Hz, 1H), 2.91 (dt, J=7.8, 6.4 Hz, 1H), 2.79 (t, J=6.2 Hz, 1H), 2.28-2.12 (m, 3H), 1.66-1.39 (m, 4H), 1.38-1.35 (m, 9H), 1.29-1.22 (m, 7H), 1.23-1.16 (m, 4H).

Step 2

Prepared according to General Procedure A, Step 2, Method B from tert-butyl 2-(diethoxyphosphoryl)-3-(3-(8, 8,8-trifluorooctan-2-yl)-1,2,4-oxadiazol-5-yl)propanoate (0.20 g, 0.40 mmol). The crude product was purified by chromatography on silica gel (0-100% EtOAc/isohexane) to afford tert-butyl 2-((3-(8,8,8-trifluorooctan-2-yl)-1,2,4-oxadiazol-5-yl)methyl)acrylate (80 mg, 0.21 mmol) as a yellow oil. LCMS m/z 321.2 (M−tBu+H)$^+$ (ES$^+$). $^1$H NMR (400 MHz, DMSO-d6) δ 6.23 (d, J=1.3 Hz, 1H), 5.90 (q, J=1.3 Hz, 1H), 3.92 (d, J=1.1 Hz, 2H), 2.95-2.87 (m, 1H), 2.25-2.14 (m, 2H), 1.67-1.58 (m, 1H), 1.57-1.50 (m, 1H), 1.47-1.39 (m, 3H), 1.34 (s, 9H), 1.32-1.23 (m, 3H), 1.20 (d, J=7.0 Hz, 3H). $^{19}$F NMR (471 MHz, DMSO-d6) δ −64.82.

Step 3

Prepared according to General Procedure A, Step 3 from tert-butyl 2-((3-(8,8,8-trifluorooctan-2-yl)-1,2,4-oxadiazol-5-yl)methyl)acrylate (80 mg, 0.21 mmol). The crude product was purified by chromatography on silica gel (0-100% EtOAc/isohexane) to afford 2-((3-(8,8,8-trifluorooctan-2-yl)-1,2,4-oxadiazol-5-yl)methyl)acrylic acid (45 mg, 0.14 mmol) as a clear yellow oil. LCMS m/z 321.1 (M+H)$^+$ (ES$^+$). $^1$H NMR (400 MHz, DMSO-d6) δ 12.82 (s, 1H), 6.27 (d, J=1.2 Hz, 1H), 5.90 (d, J=1.3 Hz, 1H), 3.91 (s, 2H), 2.96-2.85 (m, 1H), 2.28-2.11 (m, 2H), 1.71-1.59 (m, 1H), 1.58-1.49 (m, 1H), 1.49-1.38 (m, 2H), 1.38-1.26 (m, 2H), 1.26-1.13 (m, 5H).

Example 55—2-((5-octylthiazol-2-yl)methyl)acrylic acid

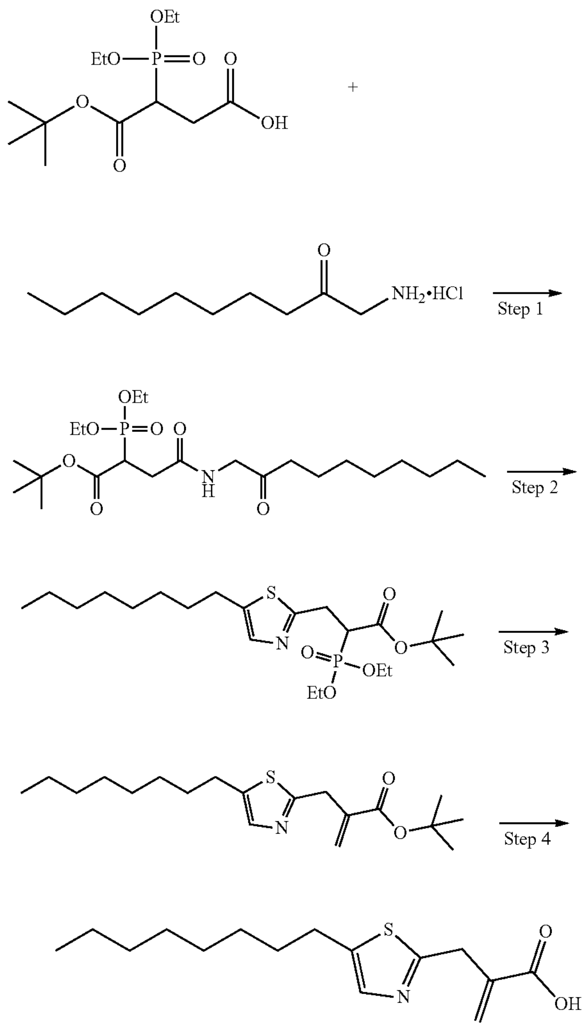

Step 1

1-Hydroxybenzotriazole hydrate (1.04 g, 6.82 mmol) and N-(3-Dimethylaminopropyl)-N'-ethylcarbodiimide hydrochloride (1.31 g, 6.82 mmol) were added to a solution of 4-(tert-butoxy)-3-(diethoxyphosphoryl)-4-oxobutanoic acid (0.347 g, 1.12 mmol) in dimethylformamide (9 mL) at RT. The mixture was stirred at RT for 45 min, before a solution of 1-aminodecan-2-one hydrochloride (1.28 g, 6.15 mmol) in dimethylformamide (7 mL) was added dropwise. Triethylamine (0.86 mL, 6.15 mmol) was added dropwise and the mixture was stirred at RT for 16 h. The reaction was poured into 1M HCl (50 mL) and extracted with EtOAc (3×25 mL). The combined organic layers were washed with sat. aq. $NaHCO_3$ (30 mL), brine (30 mL), dried ($Na_2SO_4$) and concentrated. The crude product was purified by chromatography on silica gel (0-10% MeOH/DCM) to afford tert-butyl 2-(diethoxyphosphoryl)-4-oxo-4-((2-oxodecyl)amino) butanoate (560 mg, 1.1 mmol, 90% purity) as a clear orange oil. LCMS m/z 464.2 $(M+H)^+$ $(ES^+)$. $^1H$ NMR (400 MHz, DMSO-d6) δ 8.30 (t, J=5.7 Hz, 1H), 4.10-4.00 (m, 4H), 3.88 (d, J=5.6 Hz, 2H), 3.23 (ddd, J=23.4, 11.5, 3.4 Hz, 1H), 2.85-2.73 (m, 1H), 2.54-2.52 (m, 1H), 2.42-2.35 (m, 2H), 1.46-1.41 (m, 2H), 1.38 (s, 9H), 1.28-1.23 (m, 16H), 0.86 (s, 3H).

Step 2

Lawesson's reagent (78 mg, 0.19 mmol) was added to a solution of tert-butyl 2-(diethoxyphosphoryl)-4-oxo-4-((2-oxodecyl)amino)butanoate (0.15 g, 0.32 mmol) in THF (2 mL). The mixture was heated to 70° C. for 2 h. Further Lawesson's reagent (65 mg, 0.16 mmol) was added the temperature maintained at 70° C. for 1 h. Further Lawesson's reagent (39 mg, 0.1 mmol) was added and the reaction heated at 70° C. for 16 h. The crude product was purified by chromatography on silica gel (0-10% MeOH/DCM) to afford tert-butyl 2-(diethoxyphosphoryl)-3-(5-octylthiazol-2-yl)propanoate (0.174 g, 0.22 mmol, 59% purity) as a light yellow oil. LCMS m/z 462.2 $(M+H)^+$ $(ES^+)$. $^1H$ NMR (400 MHz, DMSO-d6) δ 7.37 (s, 1H), 4.13-4.05 (m, 4H), 3.87-3.81 (m, 2H), 3.46-3.41 (m, 1H), 2.76 (t, J=7.3 Hz, 2H), 1.58-1.53 (m, 2H), 1.33 (s, 9H), 1.27-1.24 (m, 16H), 0.87-0.85 (m, 3H).

Step 3

Prepared according to General Procedure A, Step 2, Method B from tert-butyl 2-(diethoxyphosphoryl)-3-(5-octylthiazol-2-yl)propanoate (0.174 g, 0.22 mmol, 59% purity). The crude product was purified by chromatography on silica gel (0-50% EtOAc/isohexane) to afford tert-butyl 2-((5-octylthiazol-2-yl)methyl)acrylate (61 mg, 0.14 mmol, 77% purity) as a clear colourless oil. LCMS m/z 282.2 $(M-tBu+H)^+$ $(ES^+)$. $^1H$ NMR (400 MHz, DMSO-d6) δ 7.37 (d, J=1.0 Hz, 1H), 6.14 (d, J=1.5 Hz, 1H), 5.79-5.73 (m, 1H), 3.90-3.84 (m, 2H), 2.76 (t, J=7.4, 1.0 Hz, 2H), 1.60-1.50 (m, 2H), 1.37 (s, 9H), 1.29-1.22 (m, 10H), 0.86-0.83 (m, 3H).

Step 4

Prepared according to General Procedure A, Step 3 from tert-butyl 2-((5-octylthiazol-2-yl)methyl)acrylate (61 mg, 0.14 mmol, 77% purity). The crude product was purified by chromatography on silica gel (0-50% EtOAc/isohexane) to afford 2-((5-octylthiazol-2-yl)methyl)acrylic acid (30 mg, 0.11 mmol) as a yellow oil. LCMS m/z 282.2 $(M+H)^+$ $(ES^+)$. $^1H$ NMR (400 MHz, DMSO-d6) δ 12.68 (s, 1H), 7.42-7.31 (m, 1H), 6.20 (d, J=1.5 Hz, 1H), 5.79 (d, J=1.4 Hz, 1H), 3.88 (s, 2H), 2.79-2.71 (m, 2H), 1.61-1.50 (m, 2H), 1.35-1.21 (m, 10H), 0.90-0.81 (m, 3H).

Example 56—2-((3-undecyl-1,2,4-oxadiazol-5-yl) methyl)acrylic acid

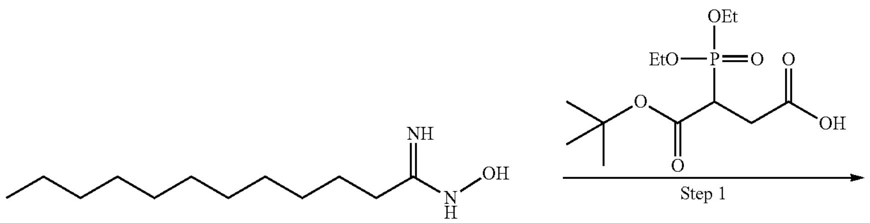

-continued

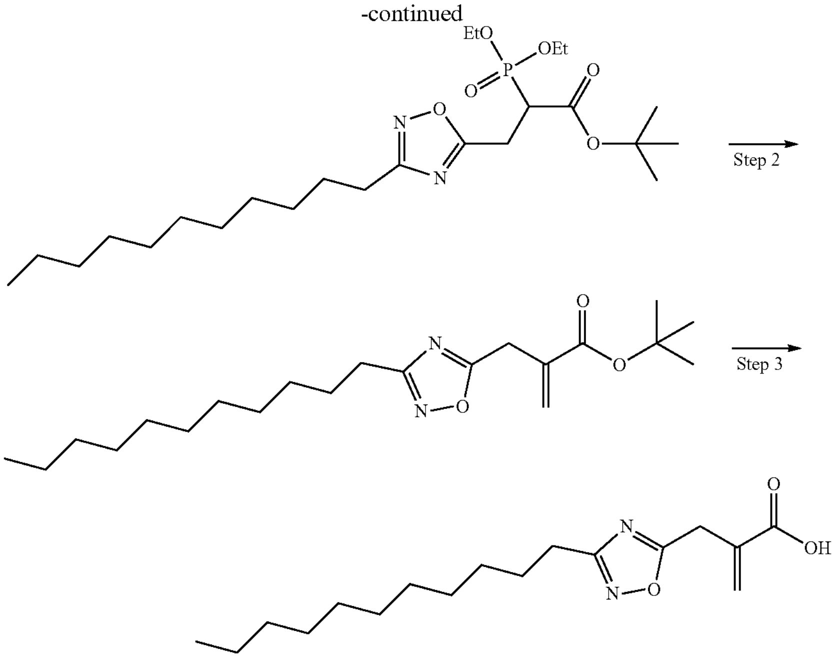

Step 1

Prepared according to General Procedure B, Method B from N-hydroxydodecanimidamide (1.09 g, 5.1 mmol). The crude product was purified by chromatography on silica gel (0-100% MTBE/isohexane) to afford tert-butyl 2-(diethoxyphosphoryl)-3-(3-undecyl-1,2,4-oxadiazol-5-yl)propanoate (1.00 g, 2.0 mmol) as a brown oil. LCMS m/z 489.5 $(M+H)^+$ $(ES^+)$. $^1H$ NMR (400 MHz, DMSO-d6) δ 4.16-4.00 (m, 4H), 3.55 (ddd, J=23.3, 11.1, 4.3 Hz, 1H), 3.40-3.16 (m, 2H), 2.63 (t, J=7.3 Hz, 2H), 1.66-1.54 (m, 2H), 1.36 (s, 9H), 1.32-1.16 (m, 22H), 0.90-0.81 (m, 3H).

Step 2

Prepared according to General Procedure A, Step 2, Method B from tert-butyl 2-(diethoxyphosphoryl)-3-(3-undecyl-1,2,4-oxadiazol-5-yl)propanoate (1.00 g, 2.0 mmol). The crude product was purified by chromatography on silica gel (0-50% MTBE/isohexane) to afford tert-butyl 2-((3-undecyl-1,2,4-oxadiazol-5-yl)methyl)acrylate (0.526 g, 1.4 mmol) as a colourless oil. LCMS m/z 309.2 $(M-tBu+H)^+$ $(ES^+)$. $^1H$ NMR (400 MHz, DMSO-d6) δ 6.23 (d, J=1.2 Hz, 1H), 5.90 (d, J=1.3 Hz, 1H), 3.91 (s, 2H), 2.64 (t, J=7.3 Hz, 2H), 1.62 (t, J=7.3 Hz, 2H), 1.34 (s, 9H), 1.31-1.18 (m, 16H), 0.92-0.80 (m, 3H).

Step 3

Prepared according to General Procedure A, Step 3 from tert-butyl 2-((3-undecyl-1,2,4-oxadiazol-5-yl)methyl)acrylate (0.526 g, 1.4 mmol). The crude product was purified by chromatography on silica gel (0-100% MTBE/isohexane) to afford 2-((3-undecyl-1,2,4-oxadiazol-5-yl)methyl)acrylic acid (318 mg, 1.0 mmol) as a colourless oil. LCMS m/z 309.0 $(M+H)^+$ $(ES^+)$. $^1H$ NMR (400 MHz, DMSO-d6) δ 12.81 (s, 1H), 6.28 (s, 1H), 5.91 (s, 1H), 3.91 (s, 2H), 2.64 (t, J=7.5 Hz, 2H), 1.61 (p, J=7.2 Hz, 2H), 1.35-1.17 (m, 16H), 0.86 (t, J=6.9, 6.2 Hz, 3H).

Example 57—2-((3-(oct-3-yn-1-yl)-1,2,4-oxadiazol-5-yl)methyl)acrylic acid

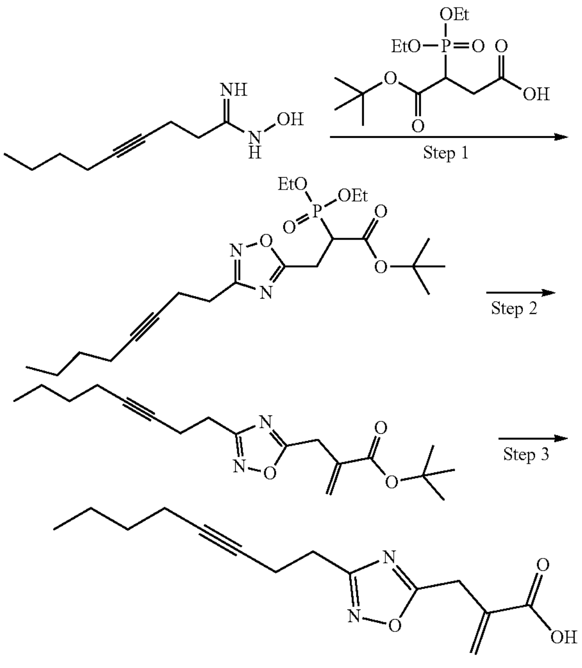

Step 1

Prepared according to General Procedure B, Method B from N-hydroxynon-4-ynimidamide (1.283 g, 7.63 mmol). The crude product was purified by chromatography on silica gel (0-100% MTBE/isohexane) to afford tert-butyl 2-(diethoxyphosphoryl)-3-(3-(oct-3-yn-1-yl)-1,2,4-oxadiazol-5-yl)propanoate (1.71 g, 3.8 mmol) as a brown oil. LCMS m/z 443.2 $(M+H)^+$ $(ES^+)$. $^1H$ NMR (400 MHz, DMSO-d6) δ 4.17-4.00 (m, 4H), 3.54 (ddd, J=23.3, 11.1, 4.2 Hz, 1H), 3.42-3.29 (m, 1H), 3.23 (ddd, J=16.8, 8.8, 4.3 Hz, 1H), 2.80 (t, J=7.1 Hz, 2H), 2.56-2.46 (m, 2H), 2.12-2.01 (m, 2H), 1.43-1.20 (m, 19H), 0.84 (t, J=7.0 Hz, 3H).

Step 2

Prepared according to General Procedure A, Step 2, Method B from tert-butyl 2-(diethoxyphosphoryl)-3-(3-(oct-3-yn-1-yl)-1,2,4-oxadiazol-5-yl)propanoate (1.71 g, 3.8 mmol). The crude product was purified by chromatography on silica gel (0-50% MTBE/isohexane) to afford tert-butyl 2-((3-(oct-3-yn-1-yl)-1,2,4-oxadiazol-5-yl)methyl)acrylate (0.498 g, 1.5 mmol) as a colourless oil. LCMS m/z 263.2 $(M-tBu+H)^+$ $(ES^+)$. $^1H$ NMR (400 MHz, DMSO-d6) δ 6.24 (d, J=1.2 Hz, 1H), 5.89 (d, J=1.3 Hz, 1H), 3.92 (s, 2H), 2.81 (t, J=7.1 Hz, 2H), 2.57-2.47 (m, 2H), 2.11-2.04 (m, 2H), 1.39-1.26 (m, 13H), 0.84 (t, J=7.1 Hz, 3H).

Step 3

Prepared according to General Procedure A, Step 3 from tert-butyl 2-((3-(oct-3-yn-1-yl)-1,2,4-oxadiazol-5-yl)methyl)acrylate (0.498 g, 1.5 mmol). The crude product was purified by chromatography on silica gel (0-100% MTBE/isohexane) to afford 2-((3-(oct-3-yn-1-yl)-1,2,4-oxadiazol-5-yl)methyl)acrylic acid (325 mg, 1.2 mmol) as a colourless oil. LCMS m/z 263.6 $(M+H)^+$ $(ES^+)$. $^1H$ NMR (400 MHz, DMSO-d6) δ 12.82 (s, 1H), 6.28 (s, 1H), 5.91 (s, 1H), 3.92 (s, 2H), 2.82 (t, J=7.2 Hz, 2H), 2.59-2.44 (m, 2H), 2.15-2.02 (m, 2H), 1.42-1.22 (m, 4H), 0.84 (t, J=7.1 Hz, 3H).

Example 58—2-((3-(8,8-difluorooctyl)-1,2,4-oxadiazol-5-yl)methyl)acrylic acid

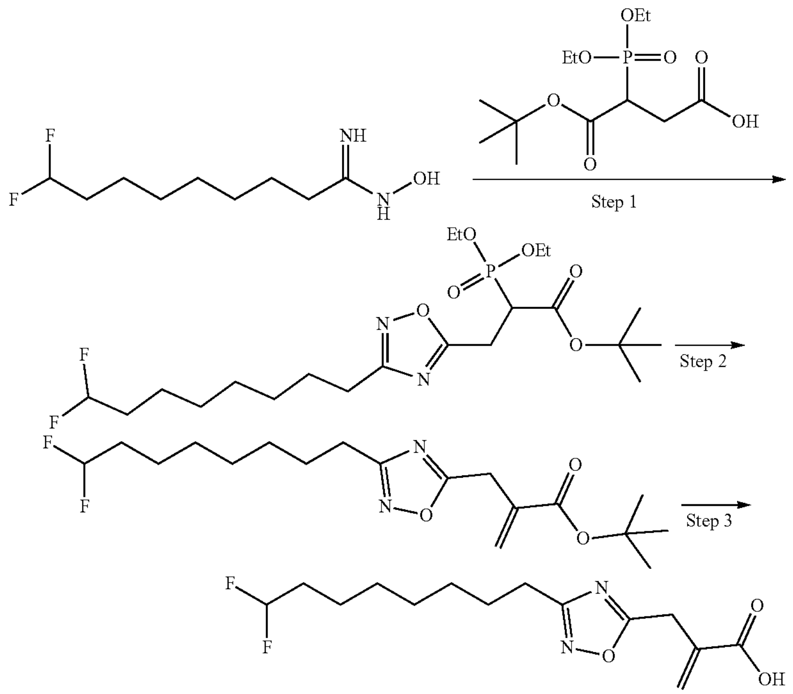

Step 1

Prepared according to General Procedure B, Method B from 9,9-difluoro-N-hydroxynonanimidamide (0.40 g, 1.92 mmol). The crude product was purified by chromatography on silica gel (0-100% MTBE/isohexane) to afford tert-butyl 2-(diethoxyphosphoryl)-3-(3-(8,8-difluorooctyl)-1,2,4-oxadiazol-5-yl)propanoate (400 mg, 0.79 mmol) as a brown oil. LCMS m/z 483.2 $(M+H)^+$ $(ES^+)$. $^1H$ NMR (400 MHz, DMSO-d6) δ 6.04 (tt, J=56.9, 4.5 Hz, 1H), 4.15-4.02 (m, 4H), 3.55 (ddd, J=23.3, 11.0, 4.4 Hz, 1H), 3.40-3.28 (m, 1H), 3.22 (ddd, J=16.8, 8.6, 4.4 Hz, 1H), 2.64 (t, J=7.4 Hz, 2H), 1.87-1.68 (m, 2H), 1.68-1.57 (m, 2H), 1.42-1.20 (m, 23H).

Step 2

Prepared according to General Procedure A, Step 2, Method B from tert-butyl 2-(diethoxyphosphoryl)-3-(3-(8,8-difluorooctyl)-1,2,4-oxadiazol-5-yl)propanoate (400 mg, 0.79 mmol). The crude product was purified by chromatography on silica gel (0-50% MTBE/isohexane) to afford tert-butyl 2-((3-(8,8-difluorooctyl)-1,2,4-oxadiazol-5-yl)methyl)acrylate (0.155 g, 0.39 mmol, 90% purity) as a colourless oil. LCMS m/z 303.2 $(M-tBu+H)^+$ $(ES^+)$. $^1H$ NMR (400 MHz, DMSO-d6) δ 6.23 (s, 1H), 6.21-5.87 (m, 2H), 3.91 (s, 2H), 2.65 (t, J=7.4 Hz, 2H), 1.88-1.69 (m, 2H), 1.63 (q, J=7.1 Hz, 2H), 1.41-1.22 (m, 17H).

Step 3

Prepared according to General Procedure A, Step 3 from tert-butyl 2-((3-(8,8-difluorooctyl)-1,2,4-oxadiazol-5-yl)methyl)acrylate (0.155 g, 0.39 mmol, 90% purity). The crude product was purified by chromatography on silica gel (0-100% MTBE/isohexane) to afford 2-((3-(8,8-difluorooctyl)-1,2,4-oxadiazol-5-yl)methyl)acrylic acid (91 mg, 0.30 mmol) as a colourless oil. LCMS m/z 302.9 $(M+H)^+$ $(ES^+)$. $^1H$ NMR (400 MHz, DMSO-d6) δ 12.81 (s, 1H), 6.28 (s, 1H), 6.22-5.87 (m, 2H), 3.91 (s, 2H), 2.65 (t, J=7.5 Hz, 2H), 1.89-1.69 (m, 2H), 1.64 (p, J=7.2 Hz, 2H), 1.44-1.19 (m, 8H).

Example 59—2-((5-octyloxazol-2-yl)methyl)acrylic acid

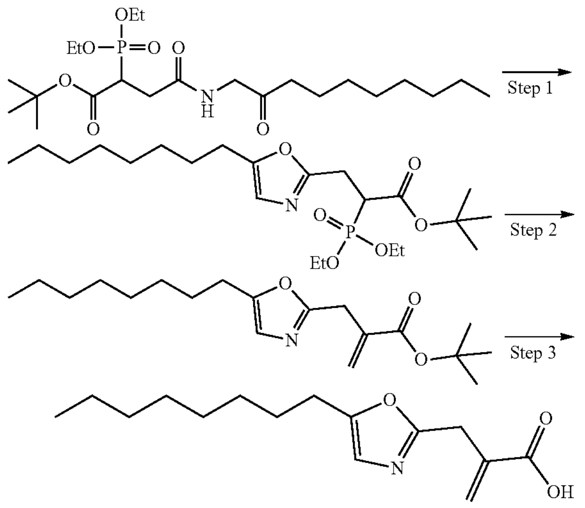

Step 1

Burgess reagent (1.19 g, 5.00 mmol) was added to a solution of tert-butyl 2-(diethoxyphosphoryl)-4-oxo-4-((2-oxodecyl)amino)butanoate (0.772 g, 1.67 mmol) in THF (7 mL). The mixture was heated to 75° C. for 1 h, then cooled to RT and poured into sat. aq. $NaHCO_3$ (20 mL). The mixture was extracted with EtOAc (3×20 mL) and the combined organic layers were washed with brine (50 mL), dried ($Na_2SO_4$) and concentrated. The crude product was purified by chromatography on silica gel (0-10% MeOH/DCM) to afford tert-butyl 2-(diethoxyphosphoryl)-3-(5-octyloxazol-2-yl)propanoate (0.344 g, 0.65 mmol, 84% purity) as a clear orange oil. LCMS m/z 446.4 $(M+H)^+$ $(ES^+)$. $^1H$ NMR (400 MHz, DMSO-d6) δ 6.73 (t, J=1.2 Hz, 1H), 4.14-3.99 (m, 4H), 3.44-3.36 (m, 1H), 3.17 (ddd, J=16.1, 11.4, 8.1 Hz, 1H), 3.02 (ddd, J=16.2, 9.2, 3.8 Hz, 1H), 2.62-2.55 (m, 2H), 1.59-1.50 (m, 2H), 1.36 (s, 9H), 1.30-1.21 (m, 16H), 0.89-0.83 (m, 3H).

Step 2

Prepared according to General Procedure A, Step 2, Method B from tert-butyl 2-(diethoxyphosphoryl)-3-(5-octyloxazol-2-yl)propanoate (0.344 g, 0.65 mmol, 84% purity). The crude product was purified by chromatography on silica gel (0-50% EtOAc/isohexane) to afford tert-butyl 2-((5-octyloxazol-2-yl)methyl)acrylate (0.184 g, 0.54 mmol) as a clear colourless oil. LCMS m/z 322.4 $(M+H)^+$ $(ES^+)$. $^1H$ NMR (400 MHz, DMSO-d6) δ 6.73 (t, J=1.1 Hz, 1H), 6.13 (d, J=1.4 Hz, 1H), 5.73-5.67 (m, 1H), 3.68 (s, 2H), 2.58 (t, J=7.4 Hz, 2H), 1.59-1.49 (m, 2H), 1.37 (s, 9H), 1.31-1.21 (m, 10H), 0.88-0.84 (m, 3H).

Step 3

Prepared according to General Procedure A, Step 3 from tert-butyl 2-((5-octyloxazol-2-yl)methyl)acrylate (0.184 g, 0.54 mmol). The crude product was purified by chromatography on silica gel (0-10% MeOH/DCM) to afford 2-((5-octyloxazol-2-yl)methyl)acrylic acid (0.127 g, 0.47 mmol, 83%, 99% Purity) as a clear orange oil. LCMS m/z 266.0 $(M+H)^+$ $(ES^+)$. $^1H$ NMR (400 MHz, DMSO-d6) δ 12.64 (s, 1H), 6.72 (t, J=1.2 Hz, 1H), 6.19 (d, J=1.4 Hz, 1H), 5.71-5.67 (m, 1H), 3.68 (s, 2H), 2.62-2.55 (m, 2H), 1.59-1.49 (m, 2H), 1.32-1.21 (m, 10H), 0.89-0.83 (m, 3H).

Example 60—2-((3-(9,9,9-trifluorononyl)-1,2,4-oxadiazol-5-yl)methyl)acrylic acid

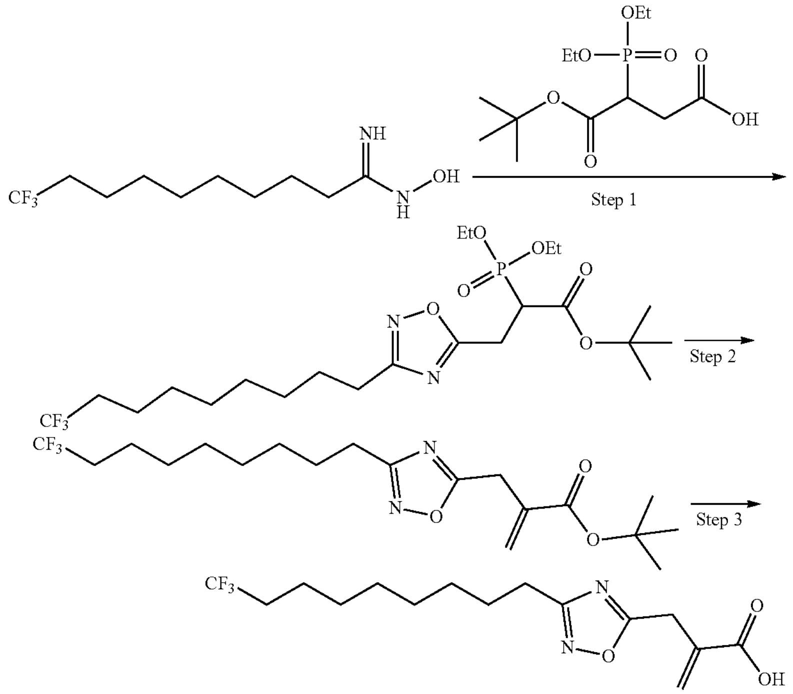

Step 1

Prepared according to General Procedure B, Method B from 10,10,10-trifluoro-N-hydroxydecanimidamide (4.52 g, 11.6 mmol, 60% purity). The crude product was purified by chromatography on silica gel (0-100% EtOAc/isohexane) to afford tert-butyl 2-(diethoxyphosphoryl)-3-(3-(9,9,9-trifluorononyl)-1,2,4-oxadiazol-5-yl)propanoate (0.30 g, 0.58 mmol) as an orange oil. $^1$H NMR (400 MHz, DMSO-d6) δ 4.15-4.05 (m, 4H), 3.63-3.49 (m, 1H), 3.40-3.34 (m, 1H), 3.28-3.14 (m, 1H), 2.64 (t, J=7.4 Hz, 2H), 2.29-2.14 (m, 2H), 1.62 (s, 2H), 1.48 (s, 2H), 1.40-1.36 (m, 10H), 1.34-1.22 (m, 13H).

Step 2

Prepared according to General Procedure A, Step 2, Method B from tert-butyl 2-(diethoxyphosphoryl)-3-(3-(9,9,9-trifluorononyl)-1,2,4-oxadiazol-5-yl)propanoate (0.30 g, 0.58 mmol). The crude product was purified by chromatography on silica gel (0-100% EtOAc/isohexane) to afford tert-butyl 2-((3-(9,9,9-trifluorononyl)-1,2,4-oxadiazol-5-yl)methyl)acrylate (0.11 g, 0.27 mmol) as a yellow oil. LCMS m/z 335.1 (M−tBu+H)$^+$ (ES$^+$). $^1$H NMR (400 MHz, DMSO-d6) δ 6.23 (d, J=1.3 Hz, 1H), 5.90 (d, J=1.2 Hz, 1H), 3.91 (s, 2H), 2.65 (t, J=7.3 Hz, 2H), 2.29-2.14 (m, 2H), 1.67-1.57 (m, 2H), 1.53-1.39 (m, 2H), 1.34 (s, 9H), 1.32-1.25 (m, 8H).

Step 3

Prepared according to General Procedure A, Step 3 from tert-butyl 2-((3-(9,9,9-trifluorononyl)-1,2,4-oxadiazol-5-yl)methyl)acrylate (0.11 g, 0.27 mmol). The crude product was purified by chromatography on silica gel (0-100% EtOAc/isohexane) to afford 2-((3-(9,9,9-trifluorononyl)-1,2,4-oxadiazol-5-yl)methyl)acrylic acid (15 mg, 43 μmol) as a yellow oil. LCMS m/z 335.2 (M+H)$^+$ (ES$^+$). $^1$H NMR (400 MHz, DMSO-d6) δ 12.86 (s, 1H), 6.26 (d, J=1.3 Hz, 1H), 5.93-5.81 (m, 1H), 3.90 (s, 2H), 2.65 (t, J=7.5 Hz, 2H), 2.30-2.14 (m, 2H), 1.71-1.53 (m, 2H), 1.53-1.41 (m, 3H), 1.40-1.21 (m, 7H).

Example 61—2-((3-(4-butoxyphenyl)-1,2,4-oxadiazol-5-yl)methyl)acrylic acid

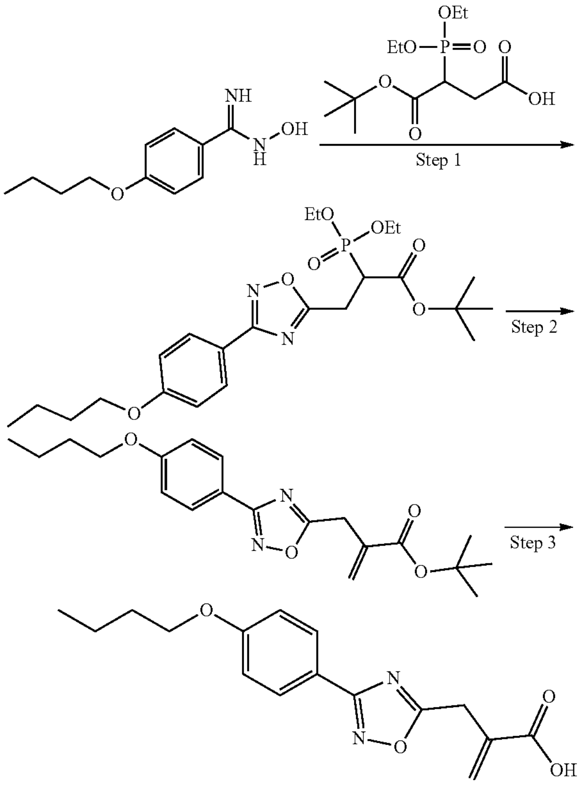

Step 1

Prepared according to General Procedure B, Method B from 4-butoxy-N-hydroxybenzimidamide (1.00 g, 4.8 mmol). The crude product was purified by chromatography on silica gel (0-100% MTBE/isohexane) to afford tert-butyl 3-(3-(4-butoxyphenyl)-1,2,4-oxadiazol-5-yl)-2-(diethoxyphosphoryl)propanoate (1.496 g, 3.0 mmol, 62%, 96% Purity) as a brown oil. LCMS m/z 505.3 (M+Na)$^+$ (ES$^+$). $^1$H NMR (400 MHz, DMSO-d6) δ 7.94-7.86 (m, 2H), 7.14-7.06 (m, 2H), 4.18-4.00 (m, 6H), 3.66 (ddd, J=23.3, 10.8, 4.6 Hz, 1H), 3.51-3.26 (m, 2H), 1.78-1.66 (m, 2H), 1.52-1.34 (m, 11H), 1.27 (q, J=6.8 Hz, 6H), 0.95 (t, J=7.4 Hz, 3H).

Step 2

Prepared according to General Procedure A, Step 2, Method B from tert-butyl 3-(3-(4-butoxyphenyl)-1,2,4-oxadiazol-5-yl)-2-(diethoxyphosphoryl)propanoate (0.70 g, 1.2 mmol, 86% purity). The crude product was purified by chromatography on silica gel (0-100% EtOAc/isohexane) to afford tert-butyl 2-((3-(4-butoxyphenyl)-1,2,4-oxadiazol-5-yl)methyl)acrylate (0.20 g, 0.53 mmol) as a yellow oil. LCMS m/z 303.1 (M−tBu+H)$^+$ (ES$^+$). $^1$H NMR (400 MHz, DMSO-d6) δ 7.93-7.87 (m, 2H), 7.12-7.06 (m, 2H), 6.28 (d, J=1.2 Hz, 1H), 5.96 (q, J=1.3 Hz, 1H), 4.05 (t, J=6.5 Hz, 2H), 4.01 (s, 2H), 1.77-1.68 (m, 2H), 1.51-1.40 (m, 2H), 1.34 (s, 9H), 0.95 (t, J=7.4 Hz, 3H).

Step 3

Prepared according to General Procedure A, Step 3 from tert-butyl 2-((3-(4-butoxyphenyl)-1,2,4-oxadiazol-5-yl)methyl)acrylate (0.20 g, 0.53 mmol). The crude product was purified by chromatography on silica gel (0-100% EtOAc/isohexane) to afford 2-((3-(4-butoxyphenyl)-1,2,4-oxadiazol-5-yl)methyl)acrylic acid (95 mg, 0.31 mmol) as a white solid. LCMS m/z 303.1 (M+H)$^+$ (ES$^+$). $^1$H NMR (400 MHz, DMSO-d6) δ 12.90 (s, 1H), 7.96-7.84 (m, 2H), 7.12-7.04 (m, 2H), 6.31 (d, J=1.3 Hz, 1H), 5.97 (s, 1H), 4.05 (t, J=6.5 Hz, 2H), 4.00 (s, 2H), 1.78-1.68 (m, 2H), 1.51-1.40 (m, 2H), 0.95 (t, J=7.4 Hz, 3H).

Example 62—2-((3-(dispiro[3.1.3$^6$.1$^4$]decan-2-yl)-1,2,4-oxadiazol-5-yl)methyl)acrylic acid

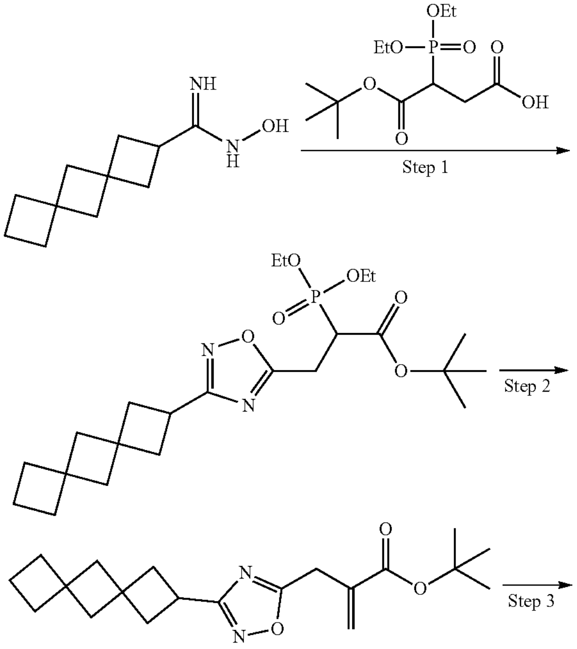

-continued

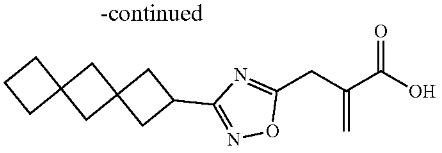

Step 1

Prepared according to General Procedure B, Method B from N-hydroxydispiro[$3.1.3^{6}.1^{4}$]decane-2-carboximidamide (0.263 g, 1.4 mmol). The crude product was purified by chromatography on silica gel (0-100% EtOAc/isohexane) to afford tert-butyl 2-(diethoxyphosphoryl)-3-(3-(dispiro[$3.1.3^{6}.1^{4}$]decan-2-yl)-1,2,4-oxadiazol-5-yl)propanoate (0.326 g, 0.69 mmol) as a light yellow oil. LCMS m/z 491.2 $(M+Na)^+$ $(ES^+)$. $^1$H NMR (400 MHz, DMSO-d6) δ 4.15-4.03 (m, 4H), 3.63-3.50 (m, 1H), 3.51-3.41 (m, 1H), 3.38-3.32 (m, 1H), 3.22 (ddd, J=16.8, 8.6, 4.4 Hz, 1H), 2.34-2.26 (m, 2H), 2.23-2.15 (m, 2H), 2.11 (s, 2H), 1.97-1.85 (m, 6H), 1.80-1.72 (m, 2H), 1.38 (s, 9H), 1.30-1.22 (m, 6H).

Step 2

Prepared according to General Procedure A, Step 2, Method B from tert-butyl 2-(diethoxyphosphoryl)-3-(3-(dispiro[$3.1.3^{6}.1^{4}$]decan-2-yl)-1,2,4-oxadiazol-5-yl)propanoate (0.326 g, 0.69 mmol). The crude product was purified by chromatography on silica gel (0-50% EtOAc/isohexane) to afford tert-butyl 2-((3-(dispiro[$3.1.3^{6}.1^{4}$]decan-2-yl)-1,2,4-oxadiazol-5-yl)methyl)acrylate (0.206 g, 0.60 mmol) as a clear colourless oil. LCMS m/z 289.4 $(M-tBu+H)^+$ $(ES^+)$. $^1$H NMR (400 MHz, DMSO-d6) δ 6.23 (d, J=1.2 Hz, 1H), 5.90 (d, J=1.3 Hz, 1H), 3.91 (s, 2H), 3.46 (p, J=8.4 Hz, 1H), 2.34-2.25 (m, 2H), 2.23-2.15 (m, 2H), 2.11 (s, 2H), 1.98-1.84 (m, 6H), 1.81-1.71 (m, 2H), 1.34 (s, 9H).

Step 3

Prepared according to General Procedure A, Step 3 from tert-butyl 2-((3-(dispiro[$3.1.3^{6}.1^{4}$]decan-2-yl)-1,2,4-oxadiazol-5-yl)methyl)acrylate (0.206 g, 0.60 mmol). The crude product was purified by chromatography on silica gel (0-10% MeOH/DCM) to afford 2-((3-(dispiro[$3.1.3^{6}.1^{4}$]decan-2-yl)-1,2,4-oxadiazol-5-yl)methyl)acrylic acid (0.13 g, 0.45 mmol) as a colourless oil. LCMS m/z 289.1 $(M+H)^+$ $(ES^+)$. $^1$H NMR (400 MHz, DMSO-d6) δ 12.81 (s, 1H), 6.28 (d, J=1.2 Hz, 1H), 5.91 (d, J=1.2 Hz, 1H), 3.90 (s, 2H), 3.46 (p, J=8.5 Hz, 1H), 2.34-2.24 (m, 2H), 2.24-2.16 (m, 2H), 2.11 (s, 2H), 1.97-1.85 (m, 6H), 1.81-1.71 (m, 2H).

Example 63—2-((3-cyclooctyl-1,2,4-oxadiazol-5-yl)methyl)acrylic acid

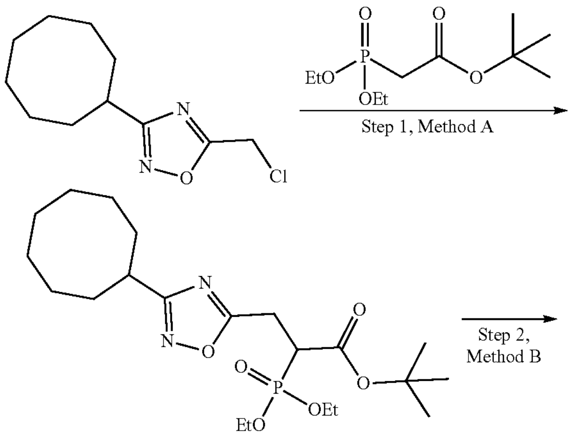

-continued

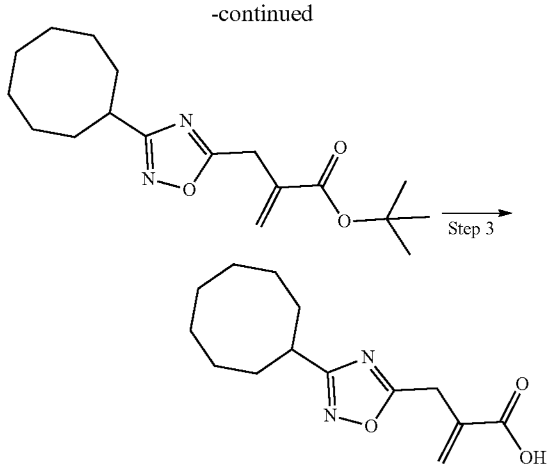

Step 1

Prepared according to General Procedure A, Step 1, Method A using THF in place of NMP from 5-(chloromethyl)-3-cyclooctyl-1,2,4-oxadiazole (1.85 g, 7.3 mmol, 90% purity). The crude product was purified by chromatography on silica gel (0-100% EtOAc/isohexane) to afford tert-butyl 3-(3-cyclooctyl-1,2,4-oxadiazol-5-yl)-2-(diethoxyphosphoryl)propanoate (1.42 g, 2.9 mmol, 90% purity) as a colourless oil. LCMS m/z 445.1 $(M+H)^+$ $(ES^+)$. $^1$H NMR (400 MHz, DMSO-d6) δ 4.17-3.99 (m, 4H), 3.63-3.44 (m, 1H), 3.30 (s, 2H), 3.02-2.91 (m, 1H), 1.95-1.82 (m, 2H), 1.82-1.44 (m, 12H), 1.37 (s, 9H), 1.26 (q, J=6.8 Hz, 6H).

Step 2

Prepared according to General Procedure A, Step 2, Method B from tert-butyl 3-(3-cyclooctyl-1,2,4-oxadiazol-5-yl)-2-(diethoxyphosphoryl)propanoate (1.42 g, 2.9 mmol, 90% purity). The crude product was purified by chromatography on silica gel (0-10% EtOAc/isohexane), then by chromatography on RP Flash C18 (5-80% (0.1% Formic acid in MeCN)/(0.1% Formic Acid in Water) to afford tert-butyl 2-((3-cyclooctyl-1,2,4-oxadiazol-5-yl)methyl)acrylate (0.78 g, 2.2 mmol, 90% Purity) as a colourless oil. LCMS m/z 265.2 $(M-tBu+H)^+$ $(ES^+)$. $^1$H NMR (400 MHz, DMSO-d6) δ 6.23 (s, 1H), 5.91-5.88 (m, 1H), 3.91 (s, 2H), 3.02-2.92 (m, 1H), 1.94-1.82 (m, 2H), 1.81-1.45 (m, 12H), 1.34 (s, 9H).

Step 3

Prepared according to General Procedure A, Step 3 from tert-butyl 2-((3-cyclooctyl-1,2,4-oxadiazol-5-yl)methyl)acrylate (0.78 g, 2.2 mmol, 90% Purity). The crude product was purified by chromatography on RP Flash C18 (5-75% MeCN/Water 0.1% Formic Acid) to afford 2-((3-cyclooctyl-1,2,4-oxadiazol-5-yl)methyl)acrylic acid (0.600 g, 2.2 mmol) as a colourless gum. LCMS m/z 265.2 $(M+H)^+$ $(ES^+)$. $^1$H NMR (400 MHz, DMSO-d6) δ 12.80 (s, 1H), 6.27 (s, 1H), 5.92-5.89 (m, 1H), 3.90 (s, 2H), 3.07-2.87 (m, 1H), 1.96-1.83 (m, 2H), 1.81-1.46 (m, 12H).

Example 64—2-((3-cyclohexyl-1,2,4-oxadiazol-5-yl)methyl)acrylic acid

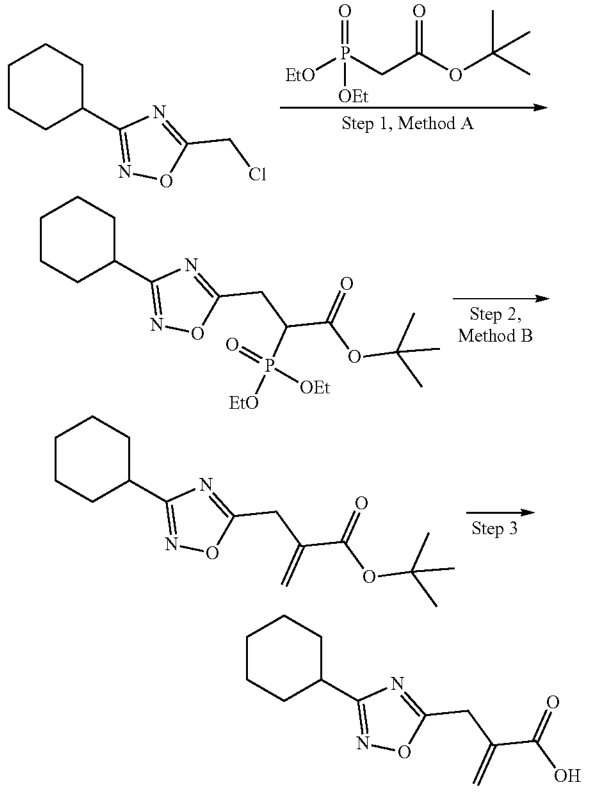

Step 1

Prepared according to General Procedure A, Step 1, Method A using THF in place of NMP from 5-(chloromethyl)-3-cyclohexyl-1,2,4-oxadiazole (6.80 g, 30.5 mmol, 90% purity). The crude product was purified by chromatography on RP Flash C18 (5-75% (0.1% Formic acid in MeCN)/(0.1% Formic Acid in Water)) to afford tert-butyl 3-(3-cyclohexyl-1,2,4-oxadiazol-5-yl)-2-(diethoxyphosphoryl)propanoate (5.7 g, 12 mmol, 90% Purity) as a colourless oil. LCMS m/z 417.1 $(M+H)^+$ $(ES^+)$. $^1H$ NMR (400 MHz, DMSO-d6) δ 4.18-3.96 (m, 4H), 3.64-3.47 (m, 1H), 3.37-3.32 (m, 1H), 3.28-3.18 (m, 1H), 2.81-2.70 (m, 1H), 1.95-1.82 (m, 2H), 1.78-1.59 (m, 2H), 1.36 (s, 15H), 1.26 (q, J=6.8 Hz, 6H).

Step 2

Prepared according to General Procedure A, Step 2, Method B from tert-butyl 3-(3-cyclohexyl-1,2,4-oxadiazol-5-yl)-2-(diethoxyphosphoryl)propanoate (5.7 g, 12 mmol, 90% Purity). The crude product was purified by chromatography on silica gel (0-10% EtOAc/isohexane) to afford tert-butyl 2-((3-cyclohexyl-1,2,4-oxadiazol-5-yl)methyl) acrylate (3.66 g, 12 mmol) as a colourless oil. LCMS m/z 237.2 $(M-tBu+H)^+$ $(ES^+)$. $^1H$ NMR (400 MHz, DMSO-d6) δ 6.27-6.18 (m, 1H), 5.91-5.87 (m, 1H), 3.91 (s, 2H), 2.81-2.70 (m, 1H), 1.94-1.83 (m, 2H), 1.79-1.60 (m, 2H), 1.52-1.21 (m, 15H).

Step 3

Prepared according to General Procedure A, Step 3 from tert-butyl 2-((3-cyclohexyl-1,2,4-oxadiazol-5-yl)methyl) acrylate (3.66 g, 12 mmol). The crude product was purified by chromatography on silica gel (0-50% EtOAc/isohexane) to afford 2-((3-cyclohexyl-1,2,4-oxadiazol-5-yl)methyl) acrylic acid (2.64 g, 11 mmol) as a colourless oil. LCMS m/z 237.2 $(M+H)^+$ $(ES^+)$. $^1H$ NMR (400 MHz, DMSO-d6) δ 12.80 (br. s, 1H), 6.29-6.26 (m, 1H), 5.93-5.90 (m, 1H), 3.91 (s, 2H), 2.83-2.69 (m, 1H), 1.97-1.83 (m, 2H), 1.78-1.59 (m, 3H), 1.54-1.19 (m, 5H).

Example 65—2-((3-cycloheptyl-1,2,4-oxadiazol-5-yl)methyl)acrylic acid

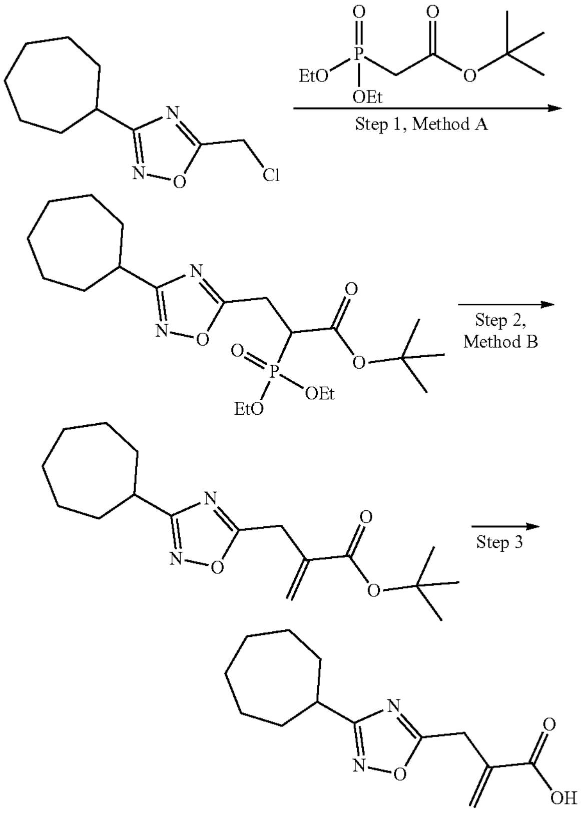

Step 1

Prepared according to General Procedure A, Step 1, Method A using THF in place of NMP from 5-(chloromethyl)-3-cycloheptyl-1,2,4-oxadiazole (5.0 g, 21 mmol, 90% purity). The crude product was purified by chromatography on silica gel (0-50% EtOAc/isohexane) to afford tert-butyl 3-(3-cycloheptyl-1,2,4-oxadiazol-5-yl)-2-(diethoxyphosphoryl)propanoate (4.6 g, 9.6 mmol, 90% purity) as a colourless oil. LCMS m/z 431.1 $(M+H)^+$ $(ES^+)$. $^1H$ NMR (400 MHz, DMSO-d6) δ 4.15-4.05 (m, 4H), 3.63-3.48 (m, 1H), 3.41-3.32 (m, 1H), 3.27-3.17 (m, 1H), 3.02-2.90 (m, 1H), 1.97-1.87 (m, 2H), 1.76-1.44 (m, 10H), 1.37 (s, 9H), 1.31-1.22 (m, 6H).

Step 2

Prepared according to General Procedure A, Step 2, Method B from tert-butyl 3-(3-cycloheptyl-1,2,4-oxadiazol-5-yl)-2-(diethoxyphosphoryl)propanoate (4.6 g, 9.6 mmol, 90% purity). The crude product was purified by chromatography on silica gel (0-50% EtOAc/isohexane) to afford tert-butyl 2-((3-cycloheptyl-1,2,4-oxadiazol-5-yl)methyl) acrylate (2.44 g, 7.6 mmol) as a colourless oil. LCMS m/z 251.2 $(M-tBu+H)^+$ $(ES^+)$. $^1H$ NMR (400 MHz, DMSO-d6)

δ 6.27-6.18 (m, 1H), 5.93-5.83 (m, 1H), 3.91 (s, 2H), 3.03-2.88 (m, 1H), 1.98-1.87 (m, 2H), 1.76-1.44 (m, 10H), 1.33 (s, 9H).

Step 3

Prepared according to General Procedure A, Step 3 from tert-butyl 2-((3-cycloheptyl-1,2,4-oxadiazol-5-yl)methyl) acrylate (2.44 g, 7.6 mmol). The crude product was purified by chromatography on silica gel (0-50% EtOAc/isohexane) to afford 2-((3-cycloheptyl-1,2,4-oxadiazol-5-yl)methyl) acrylic acid (1.92 g, 7.3 mmol) as a colourless oil. LCMS m/z 251.2 $(M+H)^+$ $(ES^+)$. $^1H$ NMR (400 MHz, DMSO-d6) δ 12.80 (br. s, 1H), 6.36-6.18 (m, 1H), 5.97-5.85 (m, 1H), 3.90 (s, 2H), 3.04-2.85 (m, 1H), 2.04-1.85 (m, 2H), 1.82-1.39 (m, 10H).

Example 66—2-((3-(adamantan-1-yl)-1,2,4-oxadiazol-5-yl)methyl)acrylic acid

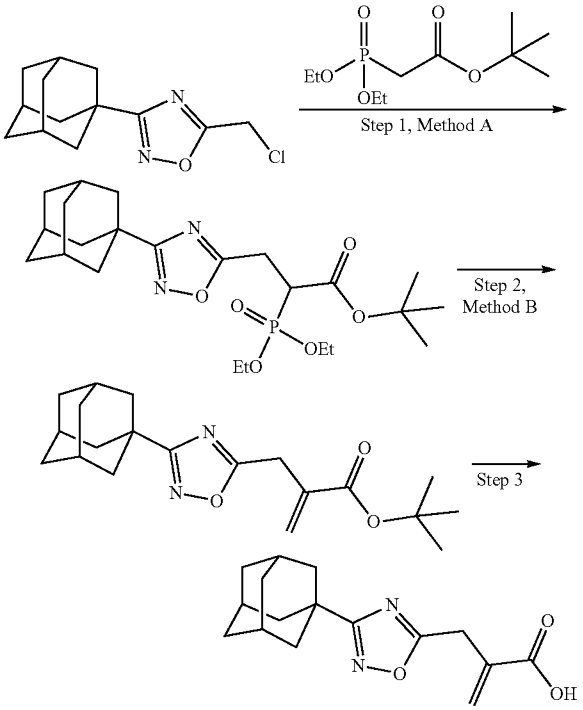

Step 1

Prepared according to General Procedure A, Step 1, Method A using THF in place of NMP from 3-(adamantan-1-yl)-5-(chloromethyl)-1,2,4-oxadiazole (5.32 g, 18.9 mmol 90% purity). The crude product was purified by chromatography on silica gel (0-100% EtOAc/isohexane) to afford tert-butyl 3-(3-(adamantan-1-yl)-1,2,4-oxadiazol-5-yl)-2-(diethoxyphosphoryl)propanoate (4.34 g, 7.9 mmol, 85% purity) as a clear, pale yellow oil. LCMS m/z 491.1 $(M+Na)^+$ $(ES^+)$. $^1H$ NMR (400 MHz, DMSO-d6) δ 4.15-4.03 (m, 4H), 3.63-3.48 (m, 1H), 3.38-3.32 (m, 1H), 3.28-3.16 (m, 1H), 2.07-2.01 (m, 3H), 1.95-1.86 (m, 6H), 1.80-1.66 (m, 6H), 1.37 (s, 9H), 1.30-1.21 (m, 6H).

Step 2

Prepared according to General Procedure A, Step 2, Method B from tert-butyl 3-(3-(adamantan-1-yl)-1,2,4-oxadiazol-5-yl)-2-(diethoxyphosphoryl)propanoate (4.34 g, 7.9 mmol, 85% purity). The crude product was purified by chromatography on silica gel (0-10% EtOAc/isohexane) to afford tert-butyl 2-((3-(adamantan-1-yl)-1,2,4-oxadiazol-5-yl)methyl)acrylate (2.60 g, 6.8 mmol, 90% purity) as a colourless oil. LCMS m/z 289.2 $(M-tBu+H)^+$ $(ES^+)$. $^1H$ NMR (400 MHz, DMSO-d6) δ 6.23 (s, 1H), 5.91-5.88 (m, 1H), 3.91 (s, 2H), 2.06-2.00 (m, 3H), 1.93-1.88 (m, 6H), 1.79-1.67 (m, 6H), 1.33 (s, 9H).

Step 3

Prepared according to General Procedure A, Step 3 from tert-butyl 2-((3-(adamantan-1-yl)-1,2,4-oxadiazol-5-yl) methyl)acrylate (2.60 g, 6.8 mmol, 90% purity). The crude product was purified by chromatography on silica gel (0-50% EtOAc/isohexane) to afford 2-((3-(adamantan-1-yl)-1,2,4-oxadiazol-5-yl)methyl)acrylic acid (0.37 g, 1.3 mmol) as a white solid. LCMS m/z 289.2 $(M+H)^+$ $(ES^+)$. $^1H$ NMR (400 MHz, DMSO-d6) δ 12.80 (br. s, 1H), 6.30-6.24 (m, 1H), 5.93-5.87 (m, 1H), 3.91 (s, 2H), 2.07-1.99 (m, 3H), 1.95-1.85 (m, 6H), 1.80-1.66 (m, 6H).

Example 67—2-((3-(1-(3,5-dichlorophenyl)cyclopropyl)-1,2,4-oxadiazol-5-yl)methyl)acrylic acid

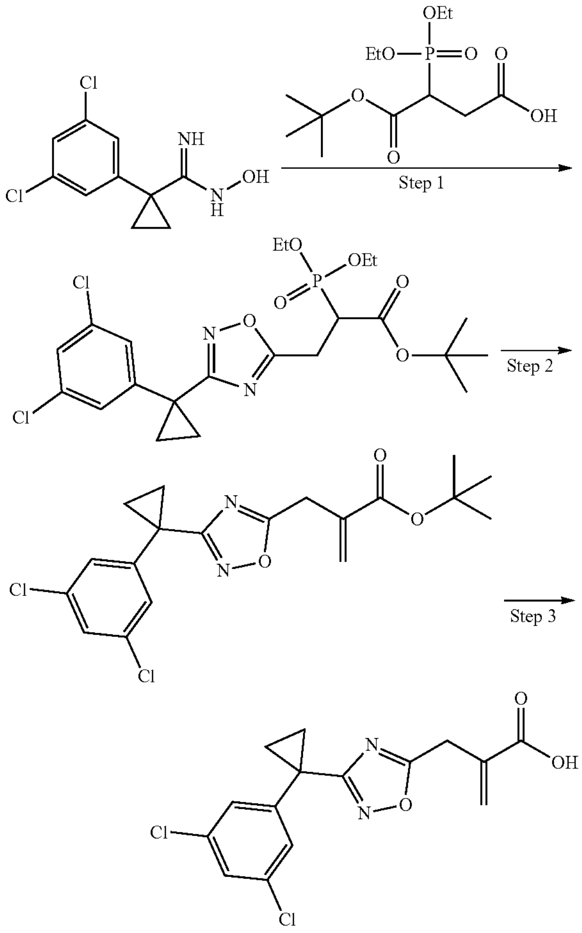

Step 1

Prepared according to General Procedure B, Method B from 1-(3,5-dichlorophenyl)-N-hydroxycyclopropane-1-carboximidamide (2.00 g, 8.2 mmol). The crude product was purified by chromatography on silica gel (0-100% EtOAc/isohexane) to afford tert-butyl 3-(3-(1-(3,5-dichlorophenyl) cyclopropyl)-1,2,4-oxadiazol-5-yl)-2-(diethoxyphosphoryl)

propanoate (1.00 g, 1.7 mmol, 87% purity) as a yellow oil. LCMS m/z 540.6 $(M+Na)^+$ $(ES^+)$. $^1H$ NMR (400 MHz, DMSO-d6) δ 7.56 (t, J=1.9 Hz, 1H), 7.43 (d, J=1.9 Hz, 2H), 4.13-4.05 (m, 4H), 3.53 (ddd, J=23.3, 10.9, 4.4 Hz, 1H), 3.34-3.27 (m, 1H), 3.26-3.17 (m, 1H), 1.53-1.47 (m, 2H), 1.36 (s, 9H), 1.29-1.22 (m, 8H).

Step 2

Prepared according to General Procedure A, Step 2, Method B from tert-butyl 3-(3-(1-(3,5-dichlorophenyl)cyclopropyl)-1,2,4-oxadiazol-5-yl)-2-(diethoxyphosphoryl) propanoate (1.00 g, 1.7 mmol, 87% Purity). The crude product was purified by chromatography on silica gel (0-100% EtOAc/isohexane) to afford tert-butyl 2-((3-(1-(3,5-dichlorophenyl)cyclopropyl)-1,2,4-oxadiazol-5-yl) methyl)acrylate (0.44 g, 1.0 mmol, 91% purity) as a colourless oil. LCMS m/z 341.0 $(M-tBu+H)^+$ $(ES^+)$. $^1H$ NMR (400 MHz, DMSO-d6) δ 7.56 (t, J=1.9 Hz, 1H), 7.44 (d, J=1.9 Hz, 2H), 6.22 (d, J=1.2 Hz, 1H), 5.89 (q, J=1.3 Hz, 1H), 3.91 (s, 2H), 1.49 (t, J=2.5 Hz, 2H), 1.46 (t, J=2.4 Hz, 2H), 1.34 (s, 9H).

Step 3

Prepared according to General Procedure A, Step 3 from tert-butyl 2-((3-(1-(3,5-dichlorophenyl)cyclopropyl)-1,2,4-oxadiazol-5-yl)methyl)acrylate (0.44 g, 1.0 mmol, 91% purity). The crude product was purified by chromatography on silica gel (0-100% EtOAc/isohexane) to afford 2-((3-(1-(3,5-dichlorophenyl)cyclopropyl)-1,2,4-oxadiazol-5-yl) methyl)acrylic acid (215 mg, 0.63 mmol, 99% purity) as a white solid. LCMS m/z 338.8/341.0 $(M+H)^+$ $(ES^+)$. $^1H$ NMR (400 MHz, DMSO-d6) δ 12.84 (s, 1H), 7.56 (t, J=1.9 Hz, 1H), 7.46 (d, J=1.9 Hz, 2H), 6.27 (d, J=1.2 Hz, 1H), 5.91 (d, J=1.3 Hz, 1H), 3.90 (s, 2H), 1.48 (s, 4H).

Example 68—2-((3-(6-methylheptyl)-1,2,4-oxadiazol-5-yl)methyl)acrylic acid

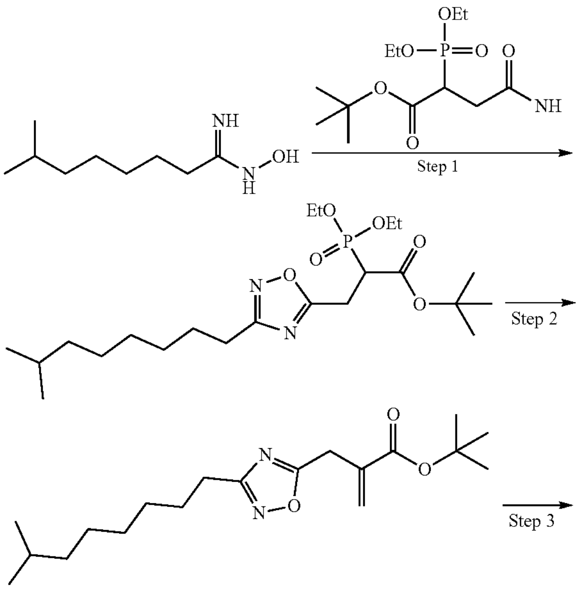

-continued

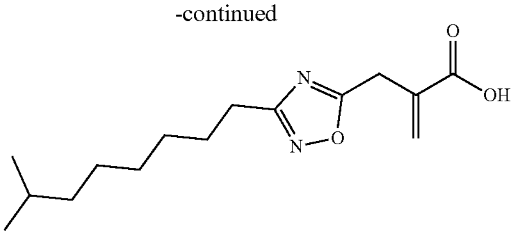

Step 1

Prepared according to General Procedure B, Method B from N-hydroxy-7-methyloctanimidamide (1.70 g, 9.9 mmol). The crude product was purified by chromatography on silica gel (0-100% EtOAc/isohexane) to afford tert-butyl 2-(diethoxyphosphoryl)-3-(3-(6-methylheptyl)-1,2,4-oxadiazol-5-yl)propanoate (1.10 g, 2.0 mmol, 80% purity) as a yellow oil. LCMS m/z 469.0 $(M+Na)^+$ $(ES^+)$. $^1H$ NMR (400 MHz, DMSO-d6) δ 4.15-4.06 (m, 4H), 3.56 (ddd, J=23.4, 11.1, 4.4 Hz, 1H), 3.39-3.33 (m, 1H), 3.23 (ddd, J=16.8, 8.6, 4.4 Hz, 1H), 2.64 (t, J=7.3 Hz, 2H), 1.62 (td, J=7.5, 7.1, 2.6 Hz, 2H), 1.55-1.44 (m, 1H), 1.37 (s, 9H), 1.26 (q, J=6.8 Hz, 10H), 1.16-1.08 (m, 2H), 0.85 (d, J=6.6 Hz, 6H).

Step 2

Prepared according to General Procedure A, Step 2, Method B from tert-butyl 2-(diethoxyphosphoryl)-3-(3-(6-methylheptyl)-1,2,4-oxadiazol-5-yl)propanoate (1.10 g, 2.0 mmol, 80% purity). The crude product was purified by chromatography on silica gel (0-100% EtOAc/isohexane) to afford tert-butyl 2-((3-(6-methylheptyl)-1,2,4-oxadiazol-5-yl)methyl)acrylate (300 mg, 0.78 mmol, 84% purity) as a yellow oil. LCMS m/z 266.9 $(M-tBu+H)^+$ $(ES^+)$. $^1H$ NMR (400 MHz, DMSO-d6) δ 6.23 (d, J=1.3 Hz, 1H), 5.90 (q, J=1.3 Hz, 1H), 3.91 (d, J=1.0 Hz, 2H), 2.64 (t, J=7.3 Hz, 2H), 1.67-1.57 (m, 2H), 1.54-1.45 (m, 1H), 1.34 (s, 9H), 1.26 (p, J=3.4 Hz, 4H), 1.15-1.07 (m, 2H), 0.84 (d, J=6.6 Hz, 6H).

Step 3

Prepared according to General Procedure A, Step 3 from tert-butyl 2-((3-(6-methylheptyl)-1,2,4-oxadiazol-5-yl) methyl)acrylate (300 mg, 0.78 mmol, 84% purity). The crude product was purified by chromatography on silica gel (0-100% EtOAc/isohexane) to afford 2-((3-(6-methylheptyl)-1,2,4-oxadiazol-5-yl)methyl)acrylic acid (0.14 g, 0.50 mmol) as a yellow oil. LCMS m/z 267.1 $(M+H)^+$ $(ES^+)$. $^1H$ NMR (400 MHz, DMSO-d6) δ 12.79 (s, 1H), 6.28 (d, J=1.2 Hz, 1H), 5.91 (d, J=1.3 Hz, 1H), 3.91 (s, 2H), 2.65 (t, J=7.4 Hz, 2H), 1.63 (p, J=7.2 Hz, 2H), 1.56-1.44 (m, 1H), 1.33-1.21 (m, 4H), 1.19-1.08 (m, 2H), 0.85 (d, J=6.6 Hz, 6H).

Example 69—2-((3-(4-neopentylbenzyl)-1,2,4-oxadiazol-5-yl)methyl)acrylic acid

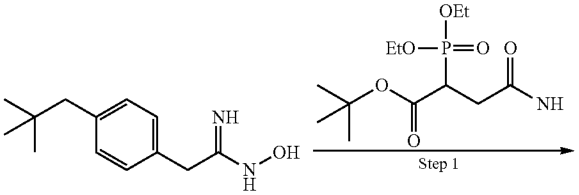

-continued

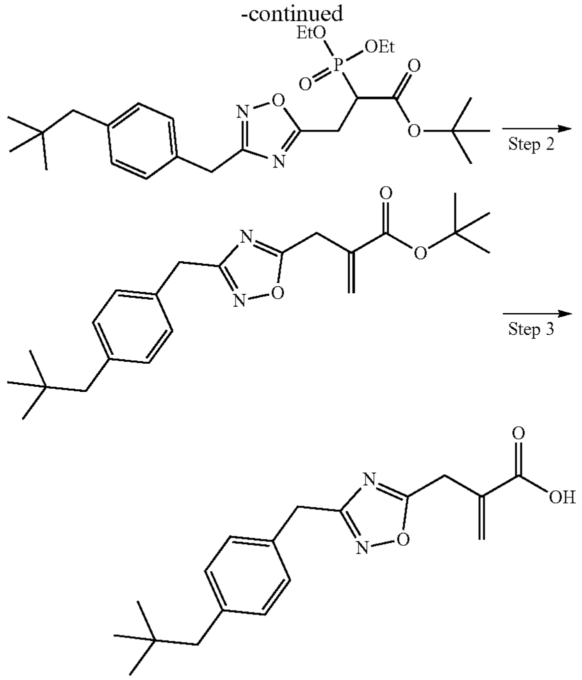

Step 1

Prepared according to General Procedure B, Method B from N-hydroxy-2-(4-neopentylphenyl)acetimidamide (1.40 g, 6.35 mmol). The crude product was purified by chromatography on silica gel (0-100% EtOAc/isohexane) to afford tert-butyl 2-(diethoxyphosphoryl)-3-(3-(4-neopentyl-benzyl)-1,2,4-oxadiazol-5-yl)propanoate (0.70 g, 1.4 mmol) as dark orange oil. LCMS m/z 516.9 $(M+Na)^+$ $(ES^+)$. $^1H$ NMR (400 MHz, DMSO-d6) δ 7.17 (d, J=7.7 Hz, 2H), 7.09-7.01 (m, 2H), 4.07 (dd, J=12.7, 5.5 Hz, 4H), 4.00 (t, J=2.9 Hz, 2H), 3.93 (dt, J=15.2, 7.3 Hz, 1H), 3.55 (ddd, J=23.3, 10.9, 4.5 Hz, 1H), 3.39-3.16 (m, 1H), 2.43 (s, 2H), 1.40 (s, 9H), 1.27-1.22 (m, 6H), 0.85 (s, 9H).

Step 2

Prepared according to General Procedure A, Step 2, Method B from 3-(3-(4-neopentylbenzyl)-1,2,4-oxadiazol-5-yl)propanoate (0.70 g, 1.4 mmol). The crude product was purified by chromatography on silica gel (0-100% EtOAc/isohexane) to afford tert-butyl 2-((3-(4-neopentylbenzyl)-1,2,4-oxadiazol-5-yl)methyl)acrylate (0.20 g, 0.51 mmol) as a yellow oil. LCMS m/z 393.2 $(M+Na)^+$ $(ES^+)$. $^1H$ NMR (400 MHz, DMSO-d6) δ 7.20-7.15 (m, 2H), 7.08-7.03 (m, 2H), 6.21 (d, J=1.2 Hz, 1H), 5.89 (q, J=1.3 Hz, 1H), 4.00 (s, 2H), 3.91 (d, J=1.0 Hz, 2H), 2.43 (s, 2H), 1.25 (s, 9H), 0.85 (s, 9H).

Step 3

Prepared according to General Procedure A, Step 3 from tert-butyl 2-((3-(4-neopentylbenzyl)-1,2,4-oxadiazol-5-yl)methyl)acrylate (0.20 g, 0.51 mmol). The crude product was purified by chromatography on silica gel (0-100% EtOAc/isohexane) to afford 2-((3-(4-neopentylbenzyl)-1,2,4-oxadiazol-5-yl)methyl)acrylic acid (0.12 g, 0.36 mmol) as a yellow oil. LCMS m/z 315.3 $(M+H)^+$ $(ES^+)$. $^1H$ NMR (400 MHz, DMSO-d6) δ 12.80 (s, 1H), 7.20-7.13 (m, 2H), 7.11-7.04 (m, 2H), 6.27 (d, J=1.2 Hz, 1H), 5.91 (q, J=1.3 Hz, 1H), 4.02 (s, 2H), 3.91 (d, J=1.0 Hz, 2H), 2.44 (s, 2H), 0.86 (s, 9H).

Example 70—2-((3-(4-propylbenzyl)-1,2,4-oxadiazol-5-yl)methyl)acrylic acid

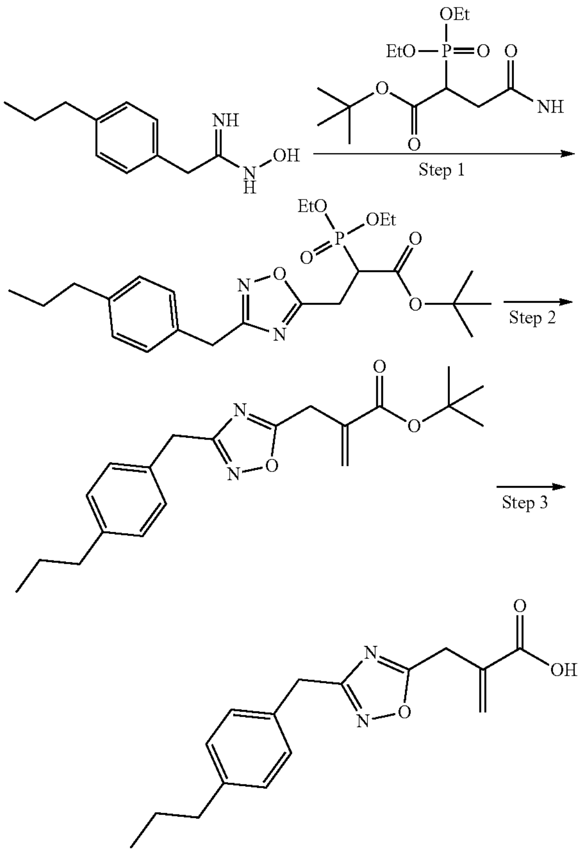

Step 1

Prepared according to General Procedure B, Method B from N-hydroxy-2-(4-propylphenyl)acetimidamide (1.00 g, 3.59 mmol). The crude product was purified by chromatography on silica gel (0-100% EtOAc/isohexane) to afford tert-butyl 2-(diethoxyphosphoryl)-3-(3-(4-propylbenzyl)-1,2,4-oxadiazol-5-yl)propanoate (0.21 g, 0.42 mmol) as a orange oil. LCMS m/z 489.2 $(M+Na)^+$ $(ES^+)$. $^1H$ NMR (400 MHz, DMSO-d6) δ 7.17 (d, J=8.1 Hz, 2H), 7.12 (d, J=8.2 Hz, 2H), 4.11-4.03 (m, 4H), 3.99 (s, 2H), 3.54 (ddd, J=23.3, 10.9, 4.5 Hz, 1H), 3.38-3.33 (m, 1H), 3.22 (ddd, J=16.8, 8.8, 4.5 Hz, 1H), 2.57-2.51 (m, 2H), 1.61-1.50 (m, 2H), 1.29 (s, 9H), 1.23 (t, J=7.0 Hz, 6H), 0.88 (t, J=7.3 Hz, 3H).

Step 2

Prepared according to General Procedure A, Step 2, Method B from tert-butyl 2-(diethoxyphosphoryl)-3-(3-(4-propylbenzyl)-1,2,4-oxadiazol-5-yl)propanoate (0.21 g, 0.42 mmol). The crude product was purified by chromatography on silica gel (0-100% EtOAc/isohexane) to afford tert-butyl 2-((3-(4-propylbenzyl)-1,2,4-oxadiazol-5-yl)methyl)acrylate (90 mg, 0.24 mmol, 90% purity) as a sticky yellow oil. LCMS m/z 287.3 $(M-tBu+H)^+$ $(ES^+)$. $^1H$ NMR (400 MHz, DMSO-d6) δ 7.17 (d, J=8.1 Hz, 2H), 7.12 (d, J=8.2 Hz, 2H), 6.21 (d, J=1.3 Hz, 1H), 5.88 (q, J=1.2 Hz, 1H), 3.99 (s, 2H), 3.90 (s, 2H), 2.54-2.47 (m, 2H), 1.61-1.52 (m, 2H), 1.25 (s, 9H), 0.90-0.83 (m, 3H).

Step 3

Prepared according to General Procedure A, Step 3 from tert-butyl 2-((3-(4-propylbenzyl)-1,2,4-oxadiazol-5-yl)

methyl)acrylate (90 mg, 0.24 mmol, 90% purity). The crude product was purified by chromatography on silica gel (0-100% EtOAc/isohexane) to afford 2-((3-(4-propylbenzyl)-1,2,4-oxadiazol-5-yl)methyl)acrylic acid (55 mg, 0.19 mmol) as a yellow oil. LCMS m/z 287.1 $(M+H)^+$ $(ES^+)$. $^1H$ NMR (400 MHz, DMSO-d6) δ 12.81 (s, 1H), 7.17 (d, J=8.2 Hz, 2H), 7.13 (d, J=8.2 Hz, 2H), 6.27 (d, J=1.2 Hz, 1H), 5.90 (d, J=1.3 Hz, 1H), 4.00 (s, 2H), 3.91 (s, 2H), 2.55-2.52 (m, 2H), 1.64-1.50 (m, 2H), 0.88 (t, J=7.3 Hz, 3H).

Example 71—2-((3-(4-(1,1-difluoropropyl)phenyl)-1,2,4-oxadiazol-5-yl)methyl)acrylic acid

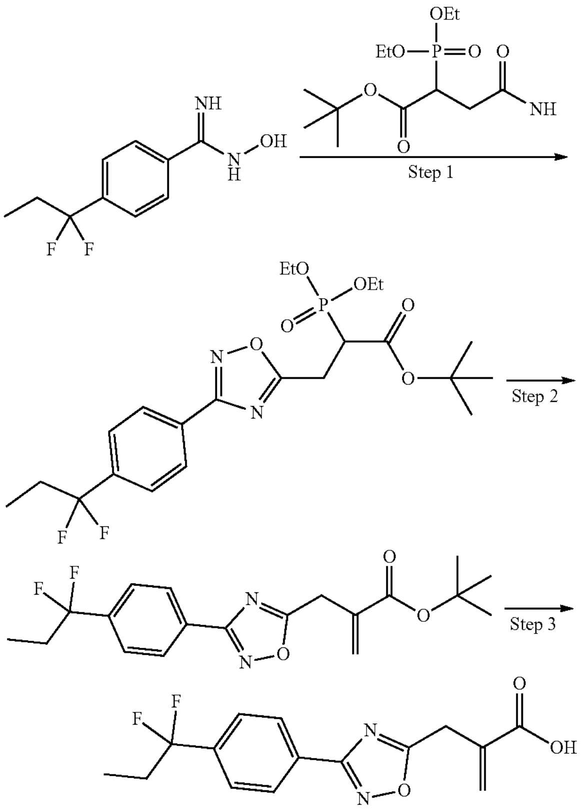

Step 1

Prepared according to General Procedure B, Method B from 4-(1,1-difluoropropyl)-N-hydroxybenzimidamide (0.90 g, 3.8 mmol, 90% purity). The crude product was purified by chromatography on silica gel (0-100% EtOAc/isohexane) to afford tert-butyl 2-(diethoxyphosphoryl)-3-(3-(4-(1,1-difluoropropyl)phenyl)-1,2,4-oxadiazol-5-yl)propanoate (1.10 g, 2.1 mmol) as a dark yellow oil. LCMS m/z 511.2 $(M+Na)^+$ $(ES^+)$. $^1H$ NMR (400 MHz, DMSO-d6) δ 8.10 (d, J=8.1 Hz, 2H), 7.75-7.70 (m, 2H), 4.18-4.07 (m, 4H), 3.69 (ddd, J=23.4, 10.7, 4.7 Hz, 1H), 3.54-3.35 (m, 2H), 2.26 (tq, J=16.9, 7.5 Hz, 2H), 1.39 (s, 9H), 1.31-1.23 (m, 6H), 0.93 (t, J=7.4 Hz, 3H).

Step 2

Prepared according to General Procedure A, Step 2, Method B from tert-butyl 2-(diethoxyphosphoryl)-3-(3-(4-(1,1-difluoropropyl)phenyl)-1,2,4-oxadiazol-5-yl)propanoate (1.10 g, 2.1 mmol). The crude product was purified by chromatography on silica gel (0-100% EtOAc/isohexane) to afford tert-butyl 2-((3-(4-(1,1-difluoropropyl)phenyl)-1,2,4-oxadiazol-5-yl)methyl)acrylate (0.68 g, 1.8 mmol) as a colourless oil. LCMS m/z 309.2 $(M-tBu+H)^+$ $(ES^+)$. $^1H$ NMR (400 MHz, DMSO-d6) δ 8.10 (d, J=8.3 Hz, 2H), 7.71 (d, J=8.4 Hz, 2H), 6.30 (d, J=1.2 Hz, 1H), 5.99 (q, J=1.2 Hz, 1H), 4.07 (s, 2H), 2.34-2.17 (m, 2H), 1.34 (s, 9H), 0.93 (t, J=7.4 Hz, 3H).

Step 3

Prepared according to General Procedure A, Step 3 from tert-butyl 2-((3-(4-(1,1-difluoropropyl)phenyl)-1,2,4-oxadiazol-5-yl)methyl)acrylate (0.68 g, 1.8 mmol). The crude product was purified by chromatography on silica gel (0-100% EtOAc/isohexane) to afford 2-((3-(4-(1,1-difluoropropyl)phenyl)-1,2,4-oxadiazol-5-yl)methyl)acrylic acid (0.47 g, 1.5 mmol) as a white solid. LCMS m/z 309.2 $(M+H)^+$ $(ES^+)$. $^1H$ NMR (400 MHz, DMSO-d6) δ 12.89 (s, 1H), 8.10 (d, J=8.2 Hz, 2H), 7.71 (d, J=8.3 Hz, 2H), 6.34 (d, J=1.2 Hz, 1H), 6.02 (d, J=1.4 Hz, 1H), 4.06 (s, 2H), 2.25 (ddt, J=24.2, 16.8, 7.5 Hz, 2H), 0.93 (t, J=7.4 Hz, 3H).

Example 72—2-((3-(4-(1-propylcyclopropyl)phenyl)-1,2,4-oxadiazol-5-yl)methyl)acrylic acid

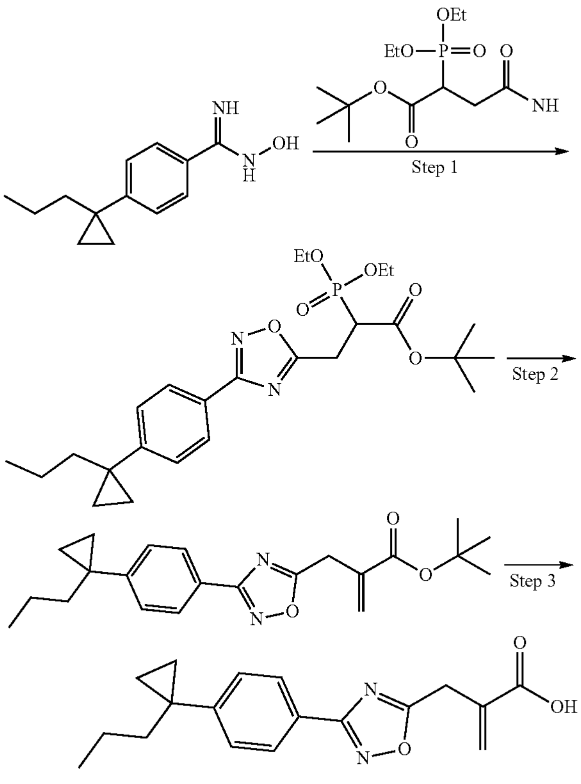

Step 1

Prepared according to General Procedure B, Method B from N-hydroxy-4-(1-propylcyclopropyl)benzimidamide (1.00 g, 4.1 mmol, 90% purity). The crude product was purified by chromatography on silica gel (0-100% EtOAc/isohexane) to afford tert-butyl 2-(diethoxyphosphoryl)-3-(3-(4-(1-propylcyclopropyl)phenyl)-1,2,4-oxadiazol-5-yl)propanoate (1.30 g, 2.4 mmol, 90% purity) as a dark orange oil. LCMS m/z 493.1 $(M+H)^+$ $(ES^+)$. $^1H$ NMR (400 MHz, DMSO-d6) δ 7.89 (d, J=8.3 Hz, 2H), 7.44 (d, J=8.5 Hz, 2H), 4.17-4.06 (m, 4H), 3.66 (ddd, J=23.4, 10.8, 4.6 Hz, 1H), 3.51-3.39 (m, 2H), 1.63-1.55 (m, 2H), 1.37 (s, 10H), 1.31-1.22 (m, 7H), 0.87-0.79 (m, 5H), 0.78-0.72 (m, 2H).

Step 2

Prepared according to General Procedure A, Step 2, Method B from tert-butyl 2-(diethoxyphosphoryl)-3-(3-(4-(1-propylcyclopropyl)phenyl)-1,2,4-oxadiazol-5-yl)propanoate (1.30 g, 2.4 mmol, 90% purity). The crude product was purified by chromatography on silica gel (0-100% EtOAc/isohexane) to afford tert-butyl 2-((3-(4-(1-propylcyclopropyl)phenyl)-1,2,4-oxadiazol-5-yl)methyl)acrylate (0.56 g, 1.4 mmol) as a colourless oil. LCMS m/z 313.3 $(M-tBu+H)^+$ $(ES^+)$. $^1H$ NMR (400 MHz, DMSO-d6) δ 7.92-7.86 (m, 2H), 7.45-7.41 (m, 2H), 6.28 (d, J=1.2 Hz, 1H), 5.97 (q, J=1.3 Hz, 1H), 4.03 (s, 2H), 1.62-1.56 (m, 2H), 1.34 (s, 9H), 1.30-1.20 (m, 2H), 0.87-0.79 (m, 5H), 0.79-0.72 (m, 2H).

Step 3

Prepared according to General Procedure A, Step 3 from tert-butyl 2-((3-(4-(1-propylcyclopropyl)phenyl)-1,2,4-oxadiazol-5-yl)methyl)acrylate (0.56 g, 1.4 mmol). The crude product was purified by chromatography on silica gel (0-100% EtOAc/isohexane) to afford 2-((3-(4-(1-propylcyclopropyl)phenyl)-1,2,4-oxadiazol-5-yl)methyl)acrylic acid (0.47 g, 1.5 mmol) as a yellow oil. LCMS m/z 313.3 $(M+H)^+$ $(ES^+)$. $^1H$ NMR (400 MHz, DMSO-d6) δ 12.87 (s, 1H), 7.89 (d, J=8.0 Hz, 2H), 7.43 (d, J=8.0 Hz, 2H), 6.33 (s, 1H), 6.00 (s, 1H), 4.02 (s, 2H), 1.64-1.52 (m, 2H), 1.25 (p, J=7.6 Hz, 2H), 0.87-0.78 (m, 5H), 0.78-0.72 (m, 2H).

Example 73—2-((3-(4-(3,3,3-trifluoropropyl)phenyl)-1,2,4-oxadiazol-5-yl)methyl)acrylic acid

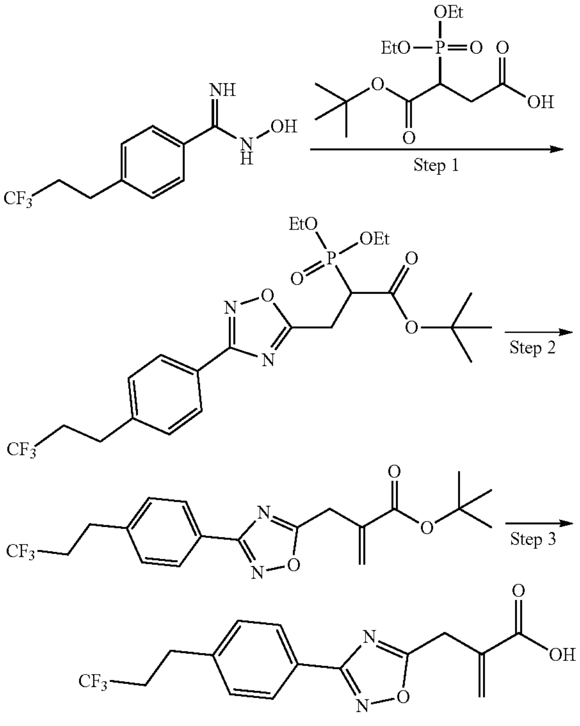

Step 1

Prepared according to General Procedure B, Method B from N-hydroxy-4-(3,3,3-trifluoropropyl)benzimidamide (0.42 g, 1.8 mmol). The crude product was purified by chromatography on silica gel (0-100% EtOAc/isohexane) to afford tert-butyl 2-(diethoxyphosphoryl)-3-(3-(4-(3,3,3-trifluoropropyl)phenyl)-1,2,4-oxadiazol-5-yl)propanoate (0.55 g, 1.1 mmol) as a sticky yellow oil. LCMS m/z 529.1 $(M+Na)^+$ $(ES^+)$. $^1H$ NMR (400 MHz, DMSO-d6) δ 7.95-7.89 (m, 2H), 7.54-7.48 (m, 2H), 4.18-4.07 (m, 4H), 3.68 (ddd, J=23.4, 10.8, 4.6 Hz, 1H), 3.52-3.33 (m, 2H), 2.96-2.88 (m, 2H), 2.74-2.58 (m, 2H), 1.38 (s, 9H), 1.32-1.23 (m, 6H).

Step 2

Prepared according to General Procedure A, Step 2, Method B from tert-butyl 2-(diethoxyphosphoryl)-3-(3-(4-(3,3,3-trifluoropropyl)phenyl)-1,2,4-oxadiazol-5-yl)propanoate (0.55 g, 1.1 mmol). The crude product was purified by chromatography on silica gel (0-100% EtOAc/isohexane) to afford tert-butyl 2-((3-(4-(3,3,3-trifluoropropyl)phenyl)-1,2,4-oxadiazol-5-yl)methyl)acrylate (0.38 g, 0.94 mmol) as a colourless oil. LCMS m/z 327.5 $(M-tBu+H)^+$ $(ES^+)$. $^1H$ NMR (400 MHz, DMSO-d6) δ 7.95-7.88 (m, 2H), 7.52-7.46 (m, 2H), 6.29 (d, J=1.1 Hz, 1H), 5.98 (q, J=1.2 Hz, 1H), 4.05-4.03 (m, 2H), 2.95-2.87 (m, 2H), 2.73-2.58 (m, 2H), 1.34 (s, 9H).

Step 3

Prepared according to General Procedure A, Step 3 from tert-butyl 2-((3-(4-(3,3,3-trifluoropropyl)phenyl)-1,2,4-oxadiazol-5-yl)methyl)acrylate (0.38 g, 0.94 mmol). The crude product was purified by chromatography on silica gel (0-100% EtOAc/isohexane) to afford 2-((3-(4-(3,3,3-trifluoropropyl)phenyl)-1,2,4-oxadiazol-5-yl)methyl)acrylic acid (255 mg, 0.77 mmol) as a white solid. LCMS m/z 327.2 $(M+H)^+$ $(ES^+)$. $^1H$ NMR (400 MHz, DMSO-d6) δ 12.89 (s, 1H), 7.97-7.89 (m, 2H), 7.56-7.43 (m, 2H), 6.33 (d, J=1.2 Hz, 1H), 6.00 (d, J=1.3 Hz, 1H), 4.03 (s, 2H), 2.99-2.86 (m, 2H), 2.74-2.57 (m, 2H).

Example 74—2-((3-((4-chlorophenyl)difluoromethyl)-1,2,4-oxadiazol-5-yl)methyl)acrylic acid

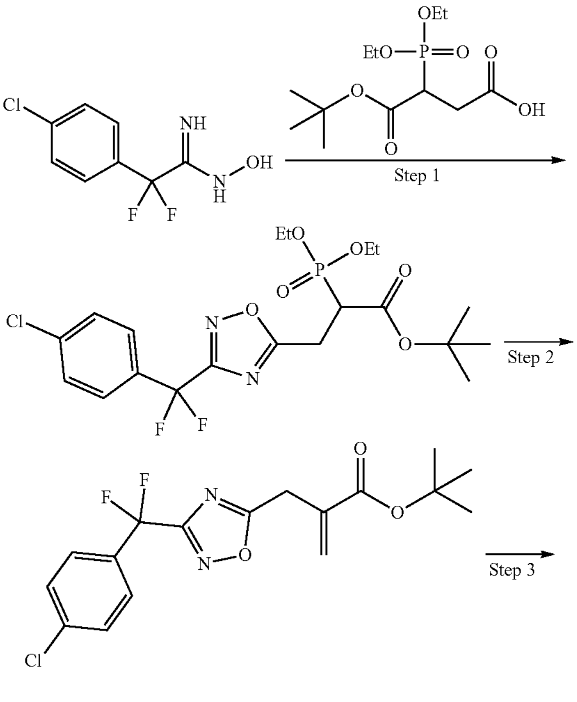

-continued

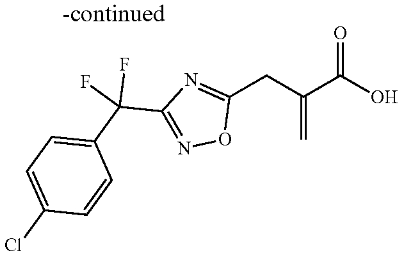

Step 1

Prepared according to General Procedure B, Method B from 2-(4-chlorophenyl)-2,2-difluoro-N-hydroxyacetimidamide (1.11 g, 5.1 mmol). The crude product was purified by chromatography on silica gel (0-100% MTBE/isohexane) to afford tert-butyl 3-(3-((4-chlorophenyl)difluoromethyl)-1,2,4-oxadiazol-5-yl)-2-(diethoxyphosphoryl)propanoate (0.592 g, 0.67 mmol, 56% purity) as a brownish oil. LCMS m/z 517.2 $(M+Na)^+$ $(ES^+)$. $^1H$ NMR (400 MHz, DMSO-d6) δ 7.65 (s, 4H), 4.14-4.00 (m, 4H), 3.64 (ddd, J=23.4, 10.6, 4.8 Hz, 1H), 3.52-3.27 (m, 2H), 1.30 (s, 9H), 1.28-1.20 (m, 6H).

Step 2

Prepared according to General Procedure A, Step 2, Method B from tert-butyl 3-(3-((4-chlorophenyl)difluoromethyl)-1,2,4-oxadiazol-5-yl)-2-(diethoxyphosphoryl)propanoate (0.592 g, 0.67 mmol, 56% purity). The crude product was purified by chromatography on silica gel (0-50% MTBE/isohexane) to afford 2-((3-((4-chlorophenyl)difluoromethyl)-1,2,4-oxadiazol-5-yl)methyl)acrylic acid (0.045 g, 0.14 mmol) as a white solid. LCMS m/z 313.9 $(M-tBu-H)^-$ $(ES^-)$. $^1H$ NMR (400 MHz, DMSO-d6) δ 7.65 (s, 4H), 6.27 (s, 1H), 5.96 (s, 1H), 4.05 (s, 2H), 1.24 (s, 9H).

Step 3

Prepared according to General Procedure A, Step 3 from tert-butyl 2-((5-((4-chlorophenyl)difluoromethyl)-1,2,4-oxadiazol-3-yl)methyl)acrylate (0.072 g, 0.17 mmol, 90% purity). The crude product was purified by chromatography on silica gel (0-100% MTBE/isohexane) to afford 2-((3-(4-(3,3,3-trifluoropropyl)phenyl)-1,2,4-oxadiazol-5-yl)methyl) acrylic acid (255 mg, 0.77 mmol) as a white solid. LCMS m/z 313.4 $(M-H)^-$ $(ES^-)$. $^1H$ NMR (400 MHz, DMSO-d6) δ 12.91 (s, 1H), 7.65 (s, 4H), 6.31 (s, 1H), 5.98 (s, 1H), 4.04 (s, 2H).

Example 75—2-((3-(4-(5,5,5-trifluoropentyl)phenyl)-1,2,4-oxadiazol-5-yl)methyl)acrylic acid

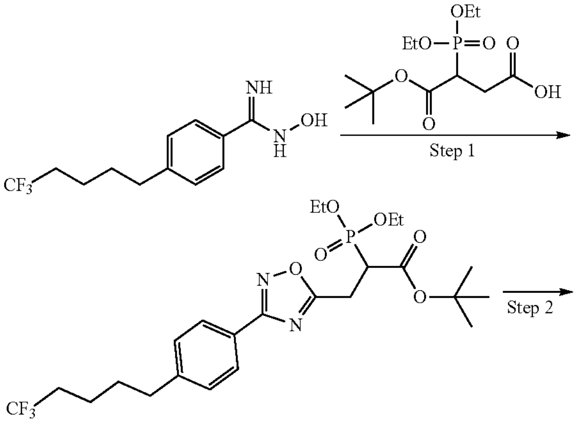

-continued

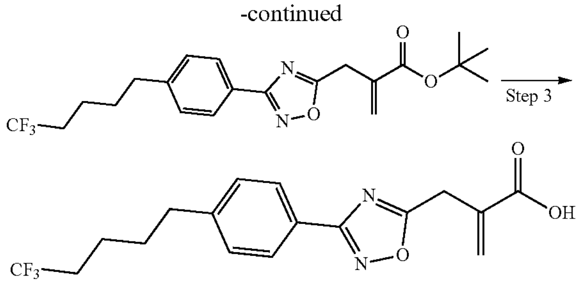

Step 1

Prepared according to General Procedure B, Method B from N-hydroxy-4-(5,5,5-trifluoropentyl)benzimidamide (1.30 g, 4.3 mmol, 86% purity). The crude product was purified by chromatography on silica gel (0-100% EtOAc/isohexane) to afford tert-butyl 2-(diethoxyphosphoryl)-3-(3-(4-(5,5,5-trifluoropentyl)phenyl)-1,2,4-oxadiazol-5-yl)propanoate (1.23 g, 2.3 mmol) as a green oil. LCMS m/z 557.3 $(M+Na)^+$ $(ES^+)$. $^1H$ NMR (400 MHz, DMSO-d6) δ 7.94-7.87 (m, 2H), 7.45-7.36 (m, 2H), 4.20-4.07 (m, 4H), 3.67 (ddd, J=23.3, 10.8, 4.6 Hz, 1H), 3.51-3.33 (m, 2H), 2.69 (t, J=7.6 Hz, 2H), 2.37-2.21 (m, 2H), 1.69 (p, J=7.7 Hz, 2H), 1.58-1.46 (m, 2H), 1.38 (s, 9H), 1.32-1.22 (m, 6H).

Step 2

Prepared according to General Procedure A, Step 2, Method B from tert-butyl 2-(diethoxyphosphoryl)-3-(3-(4-(5,5,5-trifluoropentyl)phenyl)-1,2,4-oxadiazol-5-yl)propanoate (1.23 g, 2.3 mmol). The crude product was purified by chromatography on silica gel (0-100% EtOAc/isohexane) to afford tert-butyl 2-((3-(4-(5,5,5-trifluoropentyl)phenyl)-1,2,4-oxadiazol-5-yl)methyl)acrylate (0.86 g, 1.9 mmol, 90% purity) as a colourless oil. LCMS m/z 433.0 $(M+Na)^+$ $(ES^+)$. $^1H$ NMR (400 MHz, DMSO-d6) δ 7.93-7.88 (m, 2H), 7.42-7.37 (m, 2H), 6.28 (d, J=1.2 Hz, 1H), 5.97 (d, J=1.3 Hz, 1H), 4.03 (s, 2H), 2.69 (t, J=7.7 Hz, 2H), 2.38-2.21 (m, 2H), 1.68 (p, J=7.6 Hz, 2H), 1.57-1.46 (m, 2H), 1.34 (s, 9H).

Step 3

Prepared according to General Procedure A, Step 3 from tert-butyl 2-((3-(4-(5,5,5-trifluoropentyl)phenyl)-1,2,4-oxadiazol-5-yl)methyl)acrylate (0.86 g, 1.9 mmol, 90% purity). The crude product was purified by chromatography on silica gel (0-100% EtOAc/isohexane) to afford 2-((3-(4-(5,5,5-trifluoropentyl)phenyl)-1,2,4-oxadiazol-5-yl)methyl)acrylic acid (488 mg, 1.3 mmol) as a white solid. LCMS m/z 355.1 $(M+H)^+$ $(ES^+)$. $^1H$ NMR (400 MHz, DMSO-d6) δ 12.88 (s, 1H), 7.94-7.87 (m, 2H), 7.43-7.36 (m, 2H), 6.33 (d, J=1.2 Hz, 1H), 6.00 (d, J=1.3 Hz, 1H), 4.02 (s, 2H), 2.69 (t, J=7.6 Hz, 2H), 2.38-2.20 (m, 2H), 1.75-1.62 (m, 2H), 1.57-1.44 (m, 2H).

Example 76—2-((3-(4-(2-cyclopropylethyl)phenyl)-1,2,4-oxadiazol-5-yl)methyl)acrylic acid

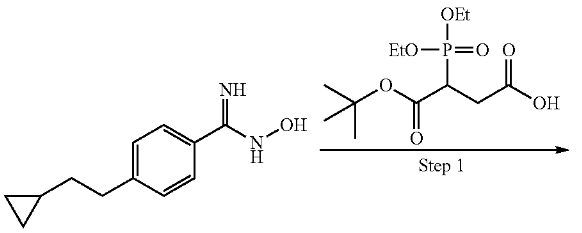

-continued

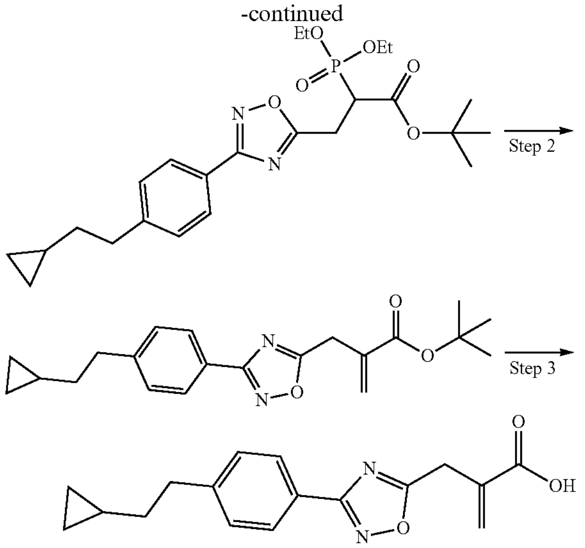

Step 1

Prepared according to General Procedure B, Method B from 4-(2-cyclopropylethyl)-N-hydroxybenzimidamide (1.05 g, 4.0 mmol, 78% purity). The crude product was purified by chromatography on silica gel (0-100% EtOAc/isohexane) to afford tert-butyl 3-(3-(4-(2-cyclopropylethyl)phenyl)-1,2,4-oxadiazol-5-yl)-2-(diethoxyphosphoryl)propanoate (1.80 g, 2.9 mmol, 77% purity) as a yellow oil. LCMS m/z 501.1 $(M+Na)^+$ $(ES^+)$. $^1H$ NMR (400 MHz, DMSO-d6) δ 7.89 (d, J=7.9 Hz, 2H), 7.43-7.38 (m, 2H), 4.17-4.07 (m, 4H), 3.67 (ddd, J=23.3, 10.8, 4.6 Hz, 1H), 3.51-3.33 (m, 2H), 2.74 (t, J=6.6 Hz, 2H), 1.51 (q, J=7.5 Hz, 2H), 1.39 (s, 9H), 1.32-1.23 (m, 6H),0.77-0.64 (m, 1H), 0.44-0.35 (m, 2H), 0.08-0.01 (m, 2H).

Step 2

Prepared according to General Procedure A, Step 2, Method B from tert-butyl 3-(3-(4-(2-cyclopropylethyl)phenyl)-1,2,4-oxadiazol-5-yl)-2-(diethoxyphosphoryl)propanoate (1.80 g, 2.9 mmol, 77% purity). The crude product was purified by chromatography on silica gel (0-100% EtOAc/isohexane) to afford tert-butyl 2-((3-(4-(2-cyclopropylethyl)phenyl)-1,2,4-oxadiazol-5-yl)methyl)acrylate (0.82 g, 1.9 mmol, 84% purity) as a colourless oil. LCMS m/z 377.1 $(M+Na)^+$ $(ES^+)$. $^1H$ NMR (400 MHz, DMSO-d6) δ 7.94-7.84 (m, 2H), 7.42-7.37 (m, 2H), 6.28 (d, J=1.2 Hz, 1H), 5.97 (q, J=1.3 Hz, 1H), 4.03 (s, 2H), 2.78-2.70 (m, 2H), 1.54-1.46 (m, 2H), 1.34 (s, 9H), 0.76-0.65 (m, 1H), 0.44-0.36 (m, 2H), 0.09-0.02 (m, 2H).

Step 3

Prepared according to General Procedure A, Step 3 from tert-butyl 2-((3-(4-(2-cyclopropylethyl)phenyl)-1,2,4-oxadiazol-5-yl)methyl)acrylate (0.82 g, 1.9 mmol, 84% purity). The crude product was purified by preparative HPLC (Waters X-Select Prep-C18, 5 μm, 30×100 mm column, 45-75% MeCN in Water 0.1% Formic Acid) to afford 2-((3-(4-(2-cyclopropylethyl)phenyl)-1,2,4-oxadiazol-5-yl)methyl)acrylic acid as a yellow glass. LCMS m/z 296.7 $(M-H)^-$ $(ES^-)$. $^1H$ NMR (400 MHz, DMSO-d6) δ 12.88 (s, 1H), 7.94-7.82 (m, 2H), 7.43-7.33 (m, 2H), 6.32 (d, J=1.2 Hz, 1H), 5.99 (d, J=1.3 Hz, 1H), 4.01 (s, 2H), 2.78-2.68 (m, 2H), 1.57-1.43 (m, 2H), 0.75-0.61 (m, 1H), 0.44-0.33 (m, 2H), 0.11-0.00 (m, 2H).

Example 77—2-((3-(1-(4-(pentafluoro-$\lambda^6$-sulfaneyl)phenyl)cyclopropyl)-1,2,4-oxadiazol-5-yl)methyl)acrylic acid

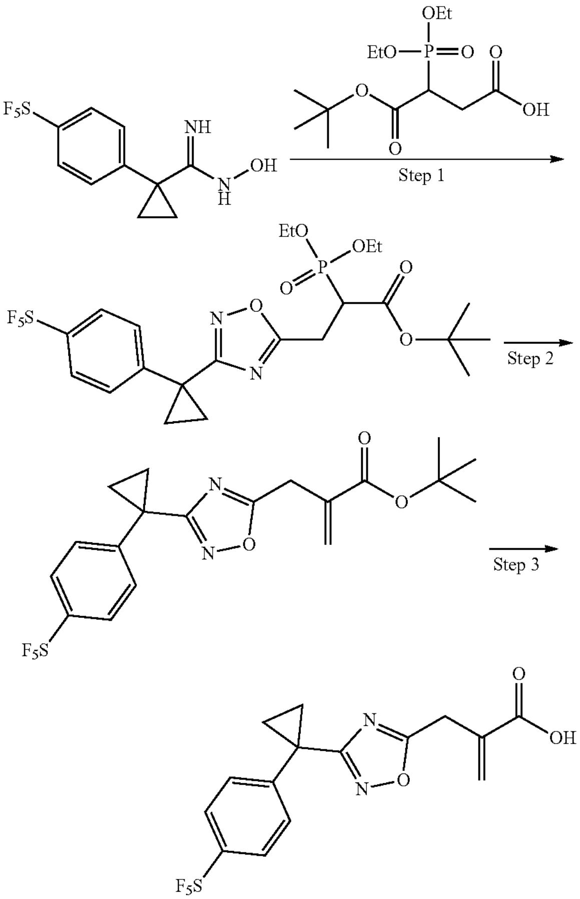

Step 1

Prepared according to General Procedure B, Method C from N-hydroxy-1-(4-(pentafluoro-$\lambda^6$-sulfaneyl)phenyl)cyclopropane-1-carboximidamide (0.97 g, 3.0 mmol). The crude product was purified by chromatography on silica gel (0-100% MTBE/isohexane) to afford tert-butyl 2-(diethoxyphosphoryl)-3-(3-(1-(4-(pentafluoro-$\lambda^6$-sulfaneyl)phenyl)cyclopropyl)-1,2,4-oxadiazol-5-yl)propanoate (1.34 g, 2.0 mmol 85% purity) as a clear and colourless gum. LCMS m/z 521.0 $(M-tBu+H)^+$ $(ES^+)$. $^1H$ NMR (400 MHz, DMSO-d6) δ 7.91-7.82 (m, 2H), 7.59 (d, J=8.4 Hz, 2H), 4.15-3.92 (m, 4H), 3.61-3.44 (m, 1H), 3.39-3.33 (m, 1H), 3.24-3.14 (m, 1H), 1.58-1.42 (m, 4H), 1.33 (s, 9H), 1.30-1.18 (m, 6H).

Step 2

Prepared according to General Procedure A, Step 2, Method B from tert-butyl 2-(diethoxyphosphoryl)-3-(3-(1-(4-(pentafluoro-$\lambda^6$-sulfaneyl)phenyl)cyclopropyl)-1,2,4-oxadiazol-5-yl)propanoate (1.34 g, 2.0 mmol 85% purity). The crude product was purified by chromatography on silica gel (0-30% MTBE/isohexane) to afford tert-butyl 2-((3-(1-(4-(pentafluoro-$\lambda^6$-sulfaneyl)phenyl)cyclopropyl)-1,2,4-oxadiazol-5-yl)methyl)acrylate (0.60 g, 1.2 mmol, 90% purity) as a clear and colourless oil. LCMS m/z 396 $(M-tBu+H)^+$ $(ES^+)$. $^1H$ NMR (400 MHz, DMSO-d6) δ 7.91-7.84 (m, 2H), 7.61 (d, J=8.4 Hz, 2H), 6.23-6.19 (m, 1H), 5.91-5.86 (m, 1H), 3.90 (s, 2H), 1.55-1.42 (m, 4H), 1.32 (s, 9H).

Step 3

Prepared according to General Procedure A, Step 3 from tert-butyl 2-((3-(1-(4-(pentafluoro-$\lambda^6$-sulfaneyl)phenyl)cyclopropyl)-1,2,4-oxadiazol-5-yl)methyl)acrylate (0.60 g, 1.2 mmol, 90% purity). The crude product was purified by chromatography on silica gel (0-50% MTBE/isohexane) to afford 2-((3-(1-(4-(pentafluoro-$\lambda^6$-sulfaneyl)phenyl)cyclopropyl)-1,2,4-oxadiazol-5-yl)methyl)acrylic acid (0.44 g, 1.0 mmol) as a white solid. LCMS m/z 397.5 $(M+H)^+$ $(ES^+)$. $^1H$ NMR (400 MHz, DMSO-d6) δ 12.81 (s, 1H), 7.94-7.75 (m, 2H), 7.61 (d, J=8.4 Hz, 2H), 6.29-6.22 (m, 1H), 5.95-5.84 (m, 1H), 3.90 (s, 2H), 1.62-1.38 (m, 4H).

Example 78—2-((3-(1-(4-(difluoromethoxy)phenyl)cyclopropyl)-1,2,4-oxadiazol-5-yl)methyl)acrylic acid

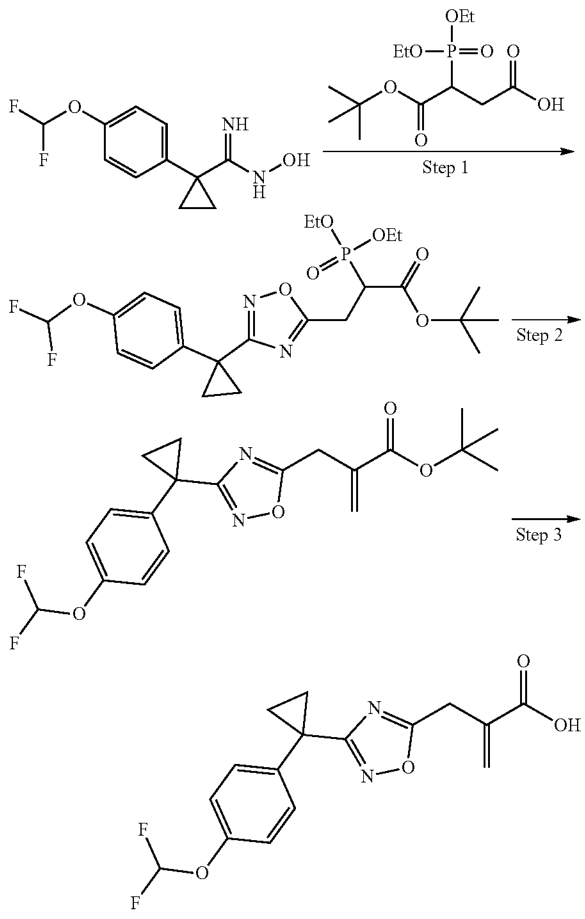

Step 1

Prepared according to General Procedure B, Method C from 1-(4-(difluoromethoxy)phenyl)-N-hydroxycyclopropane-1-carboximidamide (1.27 g, 4.61 mmol, 88% purity). The crude product was purified by chromatography on silica gel (0-100% MTBE/isohexane) to afford tert-butyl 2-(diethoxyphosphoryl)-3-(3-(1-(4-(difluoromethoxy)phenyl)cyclopropyl)-1,2,4-oxadiazol-5-yl)propanoate (1.36 g, 2.5 mmol) as a clear and colourless gum. LCMS m/z 460.0 $(M-tBu+H)^+$ $(ES^+)$. $^1H$ NMR (400 MHz, DMSO-d6) δ 7.48-7.36 (m, 2H), 7.27-6.99 (m, 3H), 4.14-4.01 (m, 4H), 3.60-3.42 (m, 1H), 3.31 (s, 1H), 3.25-3.13 (m, 1H), 1.53-1.37 (m, 4H), 1.35 (s, 9H), 1.29-1.21 (m, 6H).

Step 2

Prepared according to General Procedure A, Step 2, Method B from tert-butyl 2-(diethoxyphosphoryl)-3-(3-(1-(4-(difluoromethoxy)phenyl)cyclopropyl)-1,2,4-oxadiazol-5-yl)propanoate (1.36 g, 2.5 mmol). The crude product was purified by chromatography on silica 10 gel (0-30% MTBE/isohexane) to afford tert-butyl 2-((3-(1-(4-(difluoromethoxy)phenyl)cyclopropyl)-1,2,4-oxadiazol-5-yl)methyl)acrylate (0.98 g, 2.4 mmol) as a clear and colourless oil. LCMS m/z 337.2 $(M-tBu+H)^+$ $(ES^+)$. $^1H$ NMR (400 MHz, DMSO-d6) δ 7.47-7.36 (m, 2H), 7.28-6.99 (m, 3H), 6.25-6.16 (m, 1H), 5.92-5.85 (m, 1H), 3.88 (s, 2H), 1.47-1.40 (m, 2H), 1.38-1.34 (m, 2H), 1.33 (s, 9H).

Step 3

Prepared according to General Procedure A, Step 3 from tert-butyl 2-((3-(1-(4-(difluoromethoxy)phenyl)cyclopropyl)-1,2,4-oxadiazol-5-yl)methyl)acrylate (0.98 g, 2.4 mmol). The crude product was purified by chromatography on silica gel (0-50% MTBE/isohexane) to afford 2-((3-(1-(4-(difluoromethoxy)phenyl)cyclopropyl)-1,2,4-oxadiazol-5-yl)methyl)acrylic acid (0.76 g, 2.1 mmol) as a pale orange gum. LCMS m/z 337.2 $(M+H)^+$ $(ES^+)$. $^1H$ NMR (400 MHz, DMSO-d6) δ 12.82 (s, 1H), 7.48-7.39 (m, 2H), 7.29-6.99 (m, 3H), 6.33-6.20 (m, 1H), 5.97-5.81 (m, 1H), 3.88 (s, 2H), 1.49-1.42 (m, 2H), 1.39-1.32 (m, 2H).

Example 79—2-((3-(4-(1,1-difluoropentyl)phenyl)-1,2,4-oxadiazol-5-yl)methyl)acrylic acid

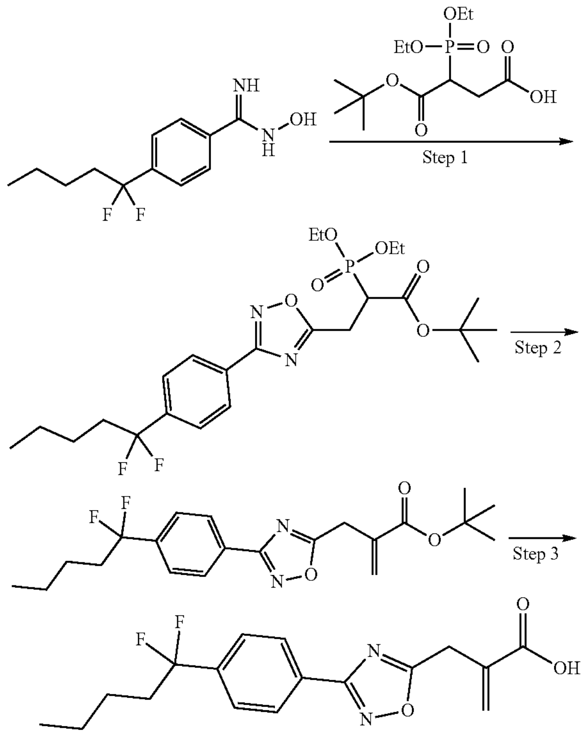

Step 1

Prepared according to General Procedure B, Method B from 4-(1,1-difluoropentyl)-N-hydroxybenzimidamide (0.33 g, 1.26 mmol, 92% purity). The crude product was purified by chromatography on silica gel (0-100% EtOAc/isohexane) to afford tert-butyl 2-(diethoxyphosphoryl)-3-(3-(4-(1,1-difluoropentyl)phenyl)-1,2,4-oxadiazol-5-yl)propanoate (0.430 g, 0.82 mmol) as a light yellow oil. LCMS m/z 539.3 $(M+Na)^+$ $(ES^+)$. $^1H$ NMR (400 MHz, DMSO-d6) δ 8.08 (d, J=8.2 Hz, 2H), 7.72 (d, J=8.3 Hz, 2H), 4.17-4.06 (m, 4H), 3.68 (ddd, J=23.4, 10.7, 4.6 Hz, 1H), 3.53-3.32 (m, 2H), 2.31-2.16 (m, 2H), 1.38 (s, 9H), 1.35-1.22 (m, 10H), 0.88-0.81 (m, 3H).

Step 2

Prepared according to General Procedure A, Step 2, Method B from tert-butyl 2-(diethoxyphosphoryl)-3-(3-(4-(1,1-difluoropentyl)phenyl)-1,2,4-oxadiazol-5-yl)propanoate (0.430 g, 0.82 mmol). The crude product was purified by chromatography on silica gel (0-50% MTBE/isohexane) to afford tert-butyl 2-((3-(4-(1,1-difluoropentyl)phenyl)-1,2,4-oxadiazol-5-yl)methyl)acrylate (0.292 g, 0.73 mmol) as a clear colourless oil. LCMS m/z 337.3 $(M-tBu+H)^+$ $(ES^+)$. $^1H$ NMR (400 MHz, DMSO-d6) δ 8.09 (d, J=8.1 Hz, 2H), 7.75-7.65 (m, 2H), 6.29 (d, J=1.2 Hz, 1H), 6.02-5.95 (m, 1H), 4.06 (s, 2H), 2.30-2.15 (m, 2H), 1.37-1.26 (m, 13H), 0.90-0.80 (m, 3H).

Step 3

A solution of tert-butyl 2-((3-(4-(1,1-difluoropentyl)phenyl)-1,2,4-oxadiazol-5-yl)methyl)acrylate (0.292 g, 0.73 mmol) in formic acid (1.4 mL) was stirred for 18 h, then concentrated. The crude product was purified by chromatography on silica gel (0-100% MTBE/isohexane), then repurified by chromatography on silica gel (0-10% MeOH/DCM) to afford 2-((3-(4-(1,1-difluoropentyl)phenyl)-1,2,4-oxadiazol-5-yl)methyl)acrylic acid (0.170 g, 0.50 mmol) as a white solid. LCMS m/z 335.2 $(M-H)^-$ $(ES^-)$. $^1H$ NMR (400 MHz, DMSO-d6) δ 12.88 (s, 1H), 8.09 (d, J=8.4 Hz, 2H), 7.75-7.67 (m, 2H), 6.34 (d, J=1.2 Hz, 1H), 6.06-5.97 (m, 1H), 4.05 (s, 2H), 2.31-2.14 (m, 2H), 1.31 (h, J=3.7 Hz, 4H), 0.90-0.79 (m, 3H). $^{19}F$ NMR (376 MHz, DMSO-d6) δ −93.47.

Example 80—2-((3-(1-(4-butoxyphenyl)cyclopropyl)-1,2,4-oxadiazol-5-yl)methyl)acrylic acid

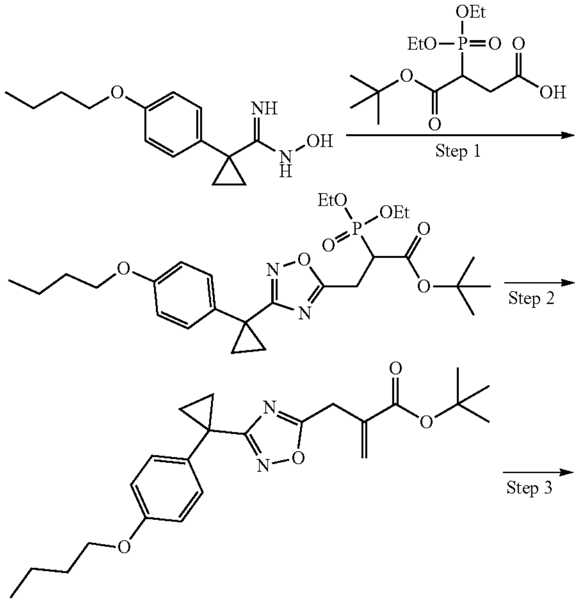

-continued

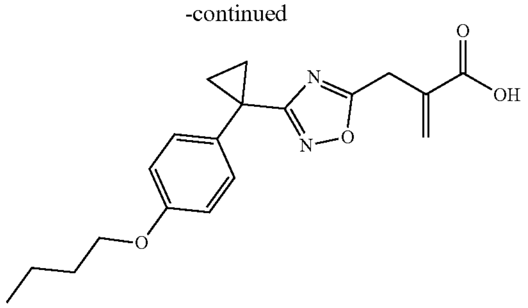

Step 1

Prepared according to General Procedure B, Method B from 1-(4-butoxyphenyl)-N-hydroxycyclopropane-1-carboximidamide (0.262 g, 0.86 mmol, 81% purity). The crude product was purified by chromatography on silica gel (0-100% EtOAc/isohexane) to afford tert-butyl 3-(3-(1-(4-butoxyphenyl)cyclopropyl)-1,2,4-oxadiazol-5-yl)-2-(diethoxyphosphoryl)propanoate (0.291 g, 0.41 mmol, 74% purity) as a light yellow oil. LCMS m/z 523.4 $(M+H)^+$ $(ES^+)$. $^1H$ NMR (400 MHz, DMSO-d6) δ 7.28-7.23 (m, 2H), 6.90-6.86 (m, 2H), 4.12-4.03 (m, 4H), 3.97-3.93 (m, 2H), 3.51 (ddd, J=23.3, 10.9, 4.4 Hz, 1H), 3.30-3.24 (m, 1H), 3.18 (ddd, J=16.8, 8.8, 4.5 Hz, 1H), 1.72-1.66 (m, 2H), 1.46-1.40 (m, 3H), 1.35 (s, 9H), 1.32-1.20 (m, 9H), 0.95-0.91 (m, 3H).

Step 2

Prepared according to General Procedure A, Step 2, Method B from tert-butyl 3-(3-(1-(4-butoxyphenyl)cyclopropyl)-1,2,4-oxadiazol-5-yl)-2-(diethoxyphosphoryl)propanoate (0.291 g, 0.41 mmol, 74% purity). The crude product was purified by chromatography on silica gel (0-50% EtOAc/isohexane) to afford tert-butyl 2-((3-(1-(4-butoxyphenyl)cyclopropyl)-1,2,4-oxadiazol-5-yl)methyl) acrylate (0.143 g, 0.36 mmol) as a clear colourless oil. LCMS m/z 343.0 $(M-tBu+H)^+$ $(ES^+)$. $^1H$ NMR (400 MHz, DMSO-d6) δ 7.29-7.20 (m, 2H), 6.90-6.81 (m, 2H), 6.20 (d, J=1.2 Hz, 1H), 5.90-5.83 (m, 1H), 3.95 (t, J=6.4 Hz, 2H), 3.87 (s, 2H), 1.73-1.63 (m, 2H), 1.47-1.36 (m, 4H), 1.33 (s, 9H), 1.30 (s, 2H), 0.93 (t, J=7.4 Hz, 3H).

Step 3

Prepared according to General Procedure A, Step 3 from tert-butyl 2-((3-(1-(4-butoxyphenyl)cyclopropyl)-1,2,4-oxadiazol-5-yl)methyl)acrylate (0.143 g, 0.36 mmol). The crude product was purified by chromatography on silica gel (0-100% MTBE/isohexane), then repurified by chromatography on silica gel (0-10% MeOH/DCM) to afford 2-((3-(1-(4-butoxyphenyl)cyclopropyl)-1,2,4-oxadiazol-5-yl) methyl)acrylic acid (0.066 g, 0.19 mmol) as a white solid. LCMS m/z 343.7 $(M+H)^+$ $(ES^+)$. $^1H$ NMR (400 MHz, DMSO-d6) δ 12.81 (s, 1H), 7.33-7.23 (m, 2H), 6.91-6.83 (m, 2H), 6.25 (d, J=1.2 Hz, 1H), 5.92-5.84 (m, 1H), 3.95 (t, J=6.5 Hz, 2H), 3.86 (s, 2H), 1.73-1.64 (m, 2H), 1.48-1.37 (m, 4H), 1.31-1.26 (m, 2H), 0.93 (t, J=7.4 Hz, 3H).

Example 81—2-((3-(4-(1,1,2,2-tetrafluoroethoxy)benzyl)-1,2,4-oxadiazol-5-yl)methyl)acrylic acid

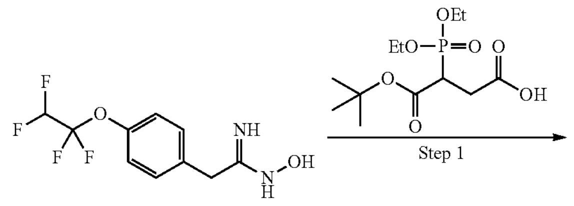

-continued

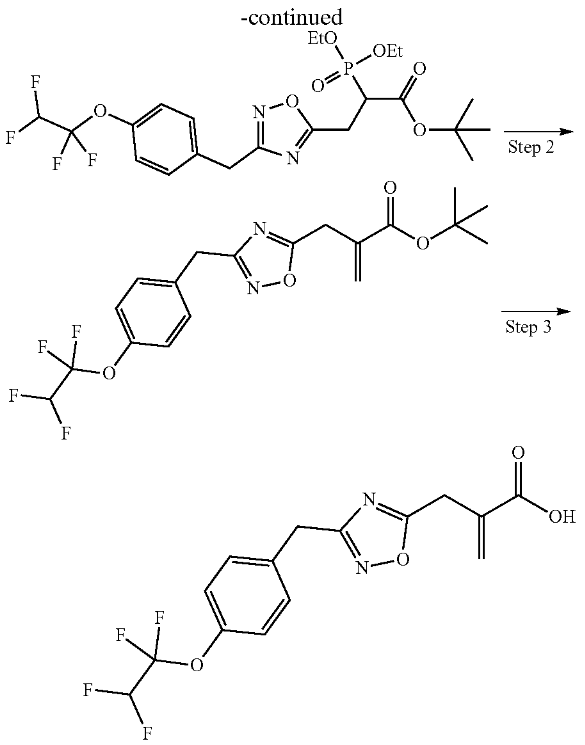

Step 1

Prepared according to General Procedure B, Method B from N-hydroxy-2-(4-(1,1,2,2-tetrafluoroethoxy)phenyl)acetimidamide (2.31 g, 7.55 mmol, 87% purity). The crude product was purified by chromatography on silica gel (0-100% EtOAc/isohexane) to afford tert-butyl 2-(diethoxyphosphoryl)-3-(3-(4-(1,1,2,2-tetrafluoroethoxy)benzyl)-1,2,4-oxadiazol-5-yl)propanoate (2.24 g, 4.1 mmol) as a light yellow oil. LCMS m/z 541.1 $(M+H)^+$ $(ES^+)$. $^1H$ NMR (400 MHz, DMSO-d6) δ 7.41-7.33 (m, 2H), 7.28-7.18 (m, 2H), 6.79 (tt, J=51.9, 3.1 Hz, 1H), 4.10-4.00 (m, 6H), 3.54 (ddd, J=23.4, 10.9, 4.5 Hz, 1H), 3.40-3.17 (m, 2H), 1.30-1.15 (m, 15H).

Step 2

Prepared according to General Procedure A, Step 2, Method B from tert-butyl 2-(diethoxyphosphoryl)-3-(3-(4-(1,1,2,2-tetrafluoroethoxy)benzyl)-1,2,4-oxadiazol-5-yl)propanoate (2.24 g, 4.1 mmol). The crude product was purified by chromatography on silica gel (0-50% EtOAc/isohexane) to afford tert-butyl 2-((3-(4-(1,1,2,2-tetrafluoroethoxy)benzyl)-1,2,4-oxadiazol-5-yl)methyl)acrylate (1.20 g, 2.9 mmol) as a clear colourless oil. LCMS m/z 361.0 $(M-tBu+H)^+$ $(ES^+)$. $^1H$ NMR (400 MHz, DMSO-d6) δ 7.43-7.35 (m, 2H), 7.26-7.18 (m, 2H), 6.79 (tt, J=51.9, 3.1 Hz, 1H), 6.23-6.18 (m, 1H), 5.91-5.86 (m, 1H), 4.08 (s, 2H), 3.91 (s, 2H), 1.22 (s, 9H).

Step 3

Prepared according to General Procedure A, Step 3 from tert-butyl 2-((3-(4-(1,1,2,2-tetrafluoroethoxy)benzyl)-1,2,4-oxadiazol-5-yl)methyl)acrylate (1.20 g, 2.9 mmol). The crude product was purified by chromatography on silica gel (0-100% MTBE/isohexane) to afford 2-((3-(4-(1,1,2,2-tetrafluoroethoxy)benzyl)-1,2,4-oxadiazol-5-yl)methyl)acrylic acid (847 mg, 2.3 mmol) as a colourless oil. LCMS m/z 359.2 $(M-H)^-$ $(ES^-)$. $^1H$ NMR (400 MHz, DMSO-d6) δ 12.81 (s, 1H), 7.42-7.34 (m, 2H), 7.23 (d, J=8.6 Hz, 2H), 6.79 (tt, J=51.9, 3.1 Hz, 1H), 6.27 (d, J=1.3 Hz, 1H), 5.91 (d, J=1.3 Hz, 1H), 4.10 (s, 2H), 3.91 (s, 2H). $^{19}F$ NMR (376 MHz, DMSO-d6) δ −87.41 (t, J=5.9 Hz), −137.71 (t, J=5.9 Hz).

Example 82-2-((3-(1-(4-(1,1,2,2-tetrafluoroethoxy)phenyl)cyclopropyl)-1,2,4-oxadiazol-5-yl)methyl)acrylic acid

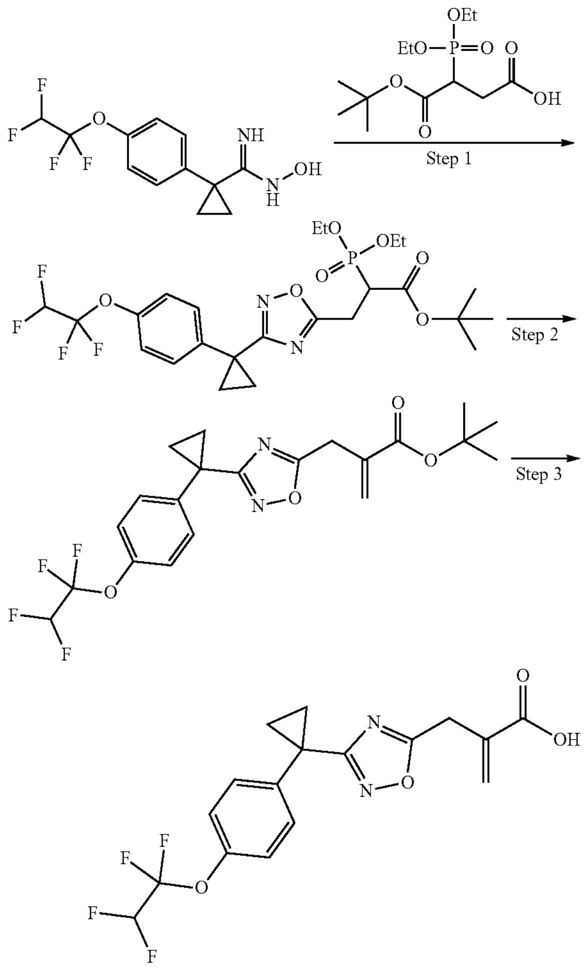

Step 1

Prepared according to General Procedure B, Method B from N-hydroxy-1-(4-(1,1,2,2-tetrafluoroethoxy)phenyl)cyclopropane-1-carboximidamide (0.878 g, 2.37 mmol, 79% purity). The crude product was purified by chromatography on silica gel (0-100% EtOAc/isohexane) to afford tert-butyl 2-(diethoxyphosphoryl)-3-(3-(1-(4-(1,1,2,2-tetrafluoroethoxy)phenyl)cyclopropyl)-1,2,4-oxadiazol-5-yl)propanoate (860 mg, 1.35 mmol, 89% purity) as a light yellow oil. LCMS m/z 567.2 $(M+H)^+$ $(ES^+)$. $^1H$ NMR (400 MHz, DMSO-d6) δ 7.51-7.43 (m, 2H), 7.28-7.20 (m, 2H), 6.99-6.63 (m, 1H), 4.14-4.05 (m, 2H), 4.09-3.98 (m, 2H), 3.52 (ddd, J=23.3, 10.9, 4.4 Hz, 1H), 3.38-3.14 (m, 2H), 1.53-1.37 (m, 2H), 1.40 (s, 2H), 1.35 (s, 9H), 1.25 (dd, J=7.1, 6.0 Hz, 4H), 1.25-1.13 (m, 2H).

Step 2

Prepared according to General Procedure A, Step 2, Method B from tert-butyl 2-(diethoxyphosphoryl)-3-(3-(1-(4-(1,1,2,2-tetrafluoroethoxy)phenyl)cyclopropyl)-1,2,4- oxadiazol-5-yl)propanoate (860 mg, 1.35 mmol, 89% purity). The crude product was purified by chromatography on silica gel (0-50% EtOAc/isohexane) to afford tert-butyl 2-((3-(1-(4-(1,1,2,2-tetrafluoroethoxy)phenyl)cyclopropyl)-1,2,4-oxadiazol-5-yl)methyl)acrylate (357 mg, 0.78 mmol) as a clear colourless oil. LCMS m/z 387.1 $(M-tBu+H)^+$ $(ES^+)$. $^1H$ NMR (400 MHz, DMSO-d6) δ 7.52-7.44 (m, 2H), 7.28-7.21 (m, 2H), 6.97-6.62 (m, 1H), 6.23-6.18 (m, 1H), 5.91-5.85 (m, 1H), 3.89 (s, 2H), 1.49-1.42 (m, 2H), 1.42-1.35 (m, 2H), 1.32 (s, 9H).

Step 3

Prepared according to General Procedure A, Step 3 from tert-butyl 2-((3-(1-(4-(1,1,2,2-tetrafluoroethoxy)phenyl)cyclopropyl)-1,2,4-oxadiazol-5-yl)methyl)acrylate (357 mg, 0.78 mmol). The crude product was purified by chromatography on silica gel (0-100% MTBE/isohexane) to afford 2-((3-(1-(4-(1,1,2,2-tetrafluoroethoxy)phenyl)cyclopropyl)-1,2,4-oxadiazol-5-yl)methyl)acrylic acid (268 mg, 0.67 mmol) as a white solid. LCMS m/z 385.2 $(M-H)^-$ $(ES^-)$. $^1H$ NMR (400 MHz, DMSO-d6) δ 12.81 (s, 1H), 7.53-7.45 (m, 2H), 7.28-7.21 (m, 2H), 6.81 (t, J=3.1 Hz, 1H), 6.26 (d, J=1.2 Hz, 1H), 5.89 (d, J=1.3 Hz, 1H), 3.88 (s, 2H), 1.51-1.42 (m, 2H), 1.44-1.35 (m, 2H). $^{19}F$ NMR (376 MHz, DMSO-d6) δ −87.39 (t, J=5.9 Hz), −137.70 (t, J=5.9 Hz).

Example 83—2-((5-(1,1-difluorooctyl)-1,2,4-oxadiazol-3-yl)methyl)acrylic acid

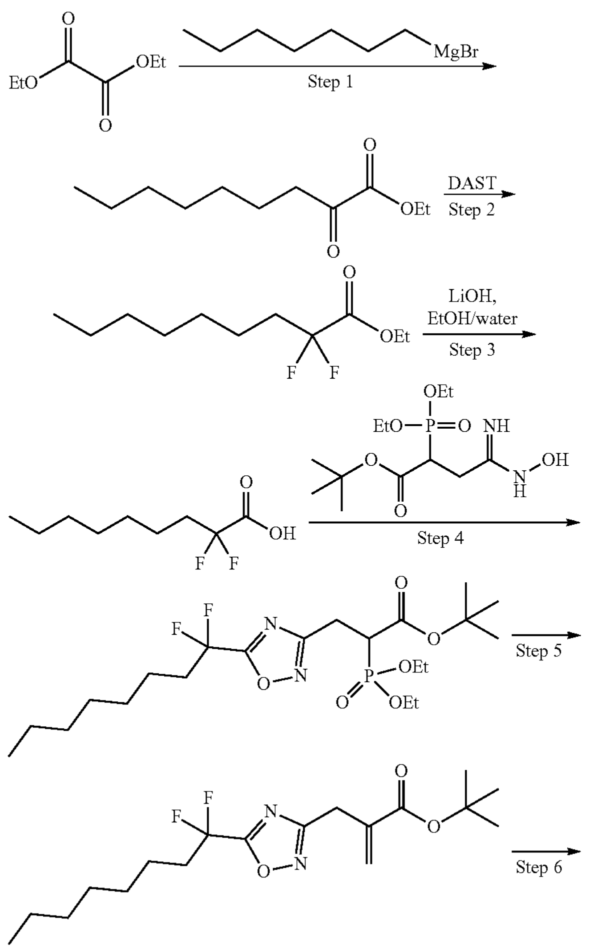

-continued

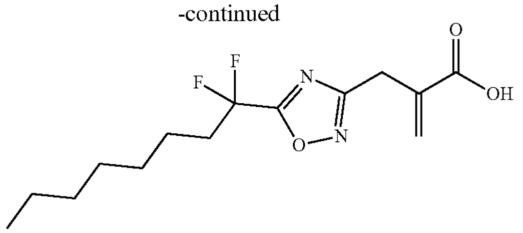

Step 1

Heptylmagnesium bromide (1 M in THF, 50 mL, 50 mmol) was added dropwise to a solution of diethyl oxalate (8.8 mL, 65 mmol) in THF (30 mL) at −78°. The mixture was allowed to warm to RT and stirred for 2 h. The mixture was quenched with sat. aq. $NH_4Cl$ (20 mL). The mixture was extracted with EtOAc (3x60 mL). The combined organic phases were dried ($MgSO_4$) and concentrated. The crude product was purified by chromatography on silica gel (0-50% MTBE/isohexane) to afford ethyl 2-oxononanoate (6.89 g, 31 mmol 90% purity) as a slightly yellow oil. $^1H$ NMR (400 MHz, DMSO-d6) δ 4.22 (q, J=7.1 Hz, 2H), 2.79 (t, J=7.2 Hz, 2H), 1.49 (p, J=7.2 Hz, 2H), 1.36-1.20 (m, 11H), 0.92-0.79 (m, 3H).

Step 2

DAST (6.4 mL, 48.1 mmol) was added dropwise to ethyl 2-oxononanoate (6.89 g, 31 mmol 90% Purity) at 0° C. The mixture was allowed to warm to RT and stirred for 16 h. The mixture was diluted with DCM (50 mL) and quenched with sat. aq. $NaHCO_3$ until pH 7. The aqueous phase was extracted with DCM (3x80 mL). The combined organic phases were dried ($MgSO_4$) and concentrated. The crude product was purified by chromatography on silica gel (0-50% MTBE/isohexane) to afford ethyl 2,2-difluorononanoate (5.12 g, 21 mmol, 90% purity) as a yellow oil. $^1H$ NMR (400 MHz, DMSO-d6) δ 4.30 (q, J=7.1 Hz, 2H), 2.17-1.99 (m, 2H), 1.46-1.17 (m, 13H), 0.91-0.81 (m, 3H).

Step 3

Lithium hydroxide monohydrate (1.18 g, 27.6 mmol) was added over 5 min to a solution of ethyl 2,2-difluorononanoate (5.12 g, 21 mmol, 90% purity) in water (3.8 mL) and EtOH (0.4 mL) at 0° C. The mixture was allowed to warm to RT, then heated to 50° C. for 2 h. The mixture was acidified to pH 1 with 1 M HCl and extracted with MTBE (3x20 mL). The combined organic layers were dried ($MgSO_4$) and concentrated. The crude product was purified by chromatography on silica gel (40 g cartridge, 0-50% EtOAc/isohexane) to afford 2,2-difluorononanoic acid (1.061 g, 4.9 mmol, 90% purity) as a slightly yellow oil. $^1H$ NMR (400 MHz, DMSO-d6) δ 14.55 (s, 1H), 2.12-1.93 (m, 2H), 1.53-1.14 (m, 10H), 0.96-0.78 (m, 3H).

Step 4

T3P (50 wt % in EtOAc, 5.3 mL, 10.3 mmol) was added dropwise to a mixture of 2,2-difluorononanoic acid (800 mg, 4.13 mmol), tert-butyl 2-(diethoxyphosphoryl)-4-(hydroxyamino)-4-iminobutanoate (1.49 g, 4.13 mmol, 90% purity) and triethylamine (1.7 mL, 12.4 mmol) in dimethylformamide (6 mL) at RT. The mixture was heated to 80° C. and stirred for 16 h. The mixture was cooled to RT, diluted with 1M HCl (25 mL) and extracted with EtOAc (3x20 mL). The combined organic phases were washed with brine (3x80 mL), dried ($MgSO_4$) and concentrated. The crude product was purified by chromatography on silica gel (0-100% MTBE/isohexane) to afford tert-butyl 2-(diethoxyphosphoryl)-3-(5-(1,1-difluorooctyl)-1,2,4-oxadiazol-3-yl)propanoate (0.316 g, 0.64 mmol) as a brownish oil. LCMS m/z 505.2 $(M+Na)^+$ $(ES^+)$. $^1H$ NMR (400 MHz, DMSO-d6) δ 4.17-4.03 (m, 4H), 3.47 (ddd, J=22.9, 10.9, 4.2 Hz, 1H), 3.38-3.25 (m, 1H), 3.18 (ddd, J=16.1, 9.4, 4.2 Hz, 1H), 2.47-2.30 (m, 2H), 1.49-1.16 (m, 25H), 0.86 (t, J=7.0 Hz, 3H).

Step 5

Prepared according to General Procedure A, Step 2, Method B from tert-butyl 2-(diethoxyphosphoryl)-3-(5-(1,1-difluorooctyl)-1,2,4-oxadiazol-3-yl)propanoate (0.316 g, 0.64 mmol). The crude product was purified by chromatography on silica gel (0-50% MTBE/isohexane) to afford tert-butyl 2-((5-(1,1-difluorooctyl)-1,2,4-oxadiazol-3-yl)methyl)acrylate (0.104 g, 0.29 mmol) as a colourless oil. $^1H$ NMR (400 MHz, DMSO-d6) δ 6.22 (s, 1H), 5.86 (s, 1H), 3.84 (s, 2H), 2.48-2.30 (m, 2H), 1.49-1.16 (m, 19H), 0.86 (t, J=6.9 Hz, 3H).

Step 3

Prepared according to General Procedure A, Step 3 from tert-butyl 2-((5-(1,1-difluorooctyl)-1,2,4-oxadiazol-3-yl)methyl)acrylate (0.104 g, 0.29 mmol). The crude product was purified by chromatography on silica gel (0-100% MTBE/isohexane) to afford 2-((5-(1,1-difluorooctyl)-1,2,4-oxadiazol-3-yl)methyl)acrylic acid (57 mg, 0.19 mmol) as a colourless oil. LCMS m/z 301.3 $(M-H)^-$ $(ES^-)$. $^1H$ NMR (400 MHz, DMSO-d6) δ 12.78 (s, 1H), 6.26 (s, 1H), 5.84 (s, 1H), 3.82 (s, 2H), 2.47-2.29 (m, 2H), 1.51-1.37 (m, 2H), 1.37-1.16 (m, 8H), 0.86 (t, J=7.2 Hz, 3H).

Example 84—2-((5-((4-chlorophenyl)difluoromethyl)-1,2,4-oxadiazol-3-yl)methyl)acrylic acid

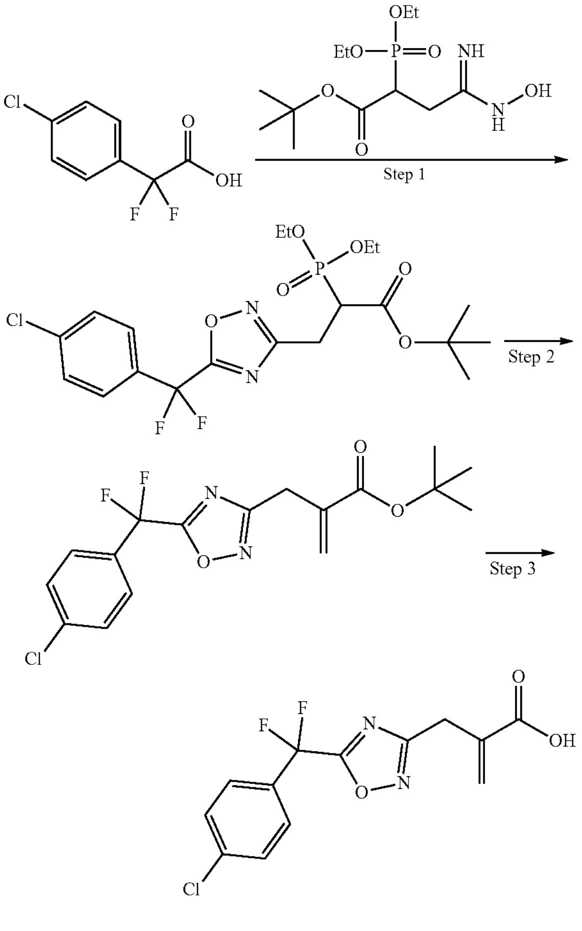

Step 1

T3P (50 wt % in EtOAc, 4.2 mL, 7.1 mmol) was added dropwise to a mixture of 2-(4-chlorophenyl)-2,2-difluoroacetic acid (730 mg, 3.54 mmol), tert-butyl 2-(diethoxyphosphoryl)-4-(hydroxyamino)-4-iminobutanoate (1.26 g, 3.54 mmol, 91% purity) and triethylamine (1.0 mL, 7.1 mmol). in EtOAc (20 mL) The mixture was stirred at RT for 18 hour, then diluted with water (50 mL) and extracted with EtOAc (3×50 mL). The combined organic phases were dried ($MgSO_4$) and concentrated. The crude product was purified by chromatography on silica gel (0-100% MTBE/isohexane) to afford tert-butyl 3-(5-((4-chlorophenyl)difluoromethyl)-1,2,4-oxadiazol-3-yl)-2-(diethoxyphosphoryl)propanoate (0.41 g, 0.79 mmol) as a clear colourless gum. LCMS m/z 517.2 $(M+Na)^+$ $(ES^+)$. $^1H$ NMR (400 MHz, DMSO-d6) δ 7.75-7.63 (m, 4H), 4.13-3.99 (m, 4H), 3.52-3.36 (m, 1H), 3.30-3.22 (m, 1H), 3.22-3.11 (m, 1H), 1.30 (s, 9H), 1.27-1.17 (m, 6H).

Step 2

Prepared according to General Procedure A, Step 2, Method B from tert-butyl 3-(5-((4-chlorophenyl)difluoromethyl)-1,2,4-oxadiazol-3-yl)-2-(diethoxyphosphoryl)propanoate (0.41 g, 0.79 mmol). The crude product was purified by chromatography on silica gel (0-30% MTBE/isohexane) to afford tert-butyl 2-((5-((4-chlorophenyl)difluoromethyl)-1,2,4-oxadiazol-3-yl)methyl)acrylate (0.250 g, 0.61 mmol, 90% purity) as a clear and colourless oil. LCMS m/z 313.1 $(M-tBu+H)^+$ $(ES^+)$. $^1H$ NMR (400 MHz, DMSO-d6) δ 7.77-7.59 (m, 4H), 6.25-6.14 (m, 1H), 5.88-5.77 (m, 1H), 3.82 (s, 2H), 1.29 (s, 9H).

Step 3

Prepared according to General Procedure A, Step 3 from tert-butyl 2-((5-((4-chlorophenyl)difluoromethyl)-1,2,4-oxadiazol-3-yl)methyl)acrylate (0.250 g, 0.61 mmol, 90% purity). The crude product was purified by chromatography on silica gel (0-30% MTBE/isohexane) to afford 2-((5-((4-chlorophenyl)difluoromethyl)-1,2,4-oxadiazol-3-yl)methyl)acrylic acid (0.20 g, 0.6 mmol) as a white solid. LCMS m/z 313.0 $(M-H)^-$ $(ES^-)$. $^1H$ NMR (400 MHz, DMSO-d6) δ 12.78 (s, 1H), 7.79-7.57 (m, 4H), 6.33-6.17 (m, 1H), 5.92-5.73 (m, 1H), 3.81 (s, 2H).

Example 85—2-((5-((4-bromophenyl)difluoromethyl)-1,2,4-oxadiazol-3-yl)methyl)acrylic acid

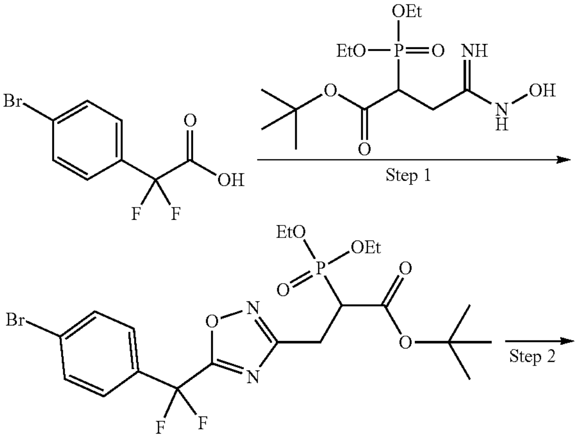

-continued

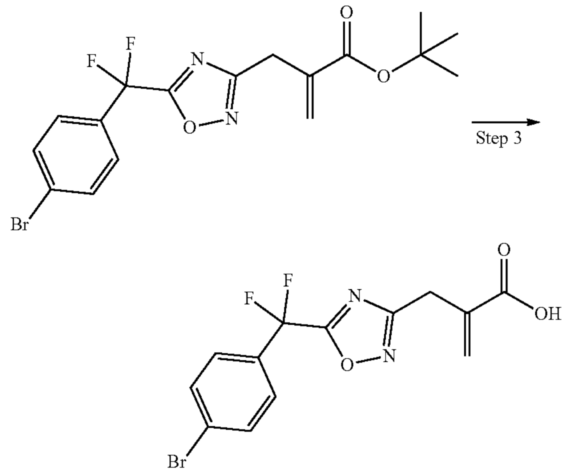

Step 1

Prepared using a similar procedure to Example 84 Step 1 from 2-(4-bromophenyl)-2,2-difluoroacetic acid (888 mg, 3.54 mmol). The crude product was purified by chromatography on silica gel (0-100% MTBE/isohexane) to afford tert-butyl 3-(5-((4-bromophenyl)difluoromethyl)-1,2,4-oxadiazol-3-yl)-2-(diethoxyphosphoryl)propanoate (0.435 g, 0.77 mmol) as a clear colourless gum. LCMS m/z 561.1 $(M+Na)^+$ $(ES^+)$. $^1$H NMR (400 MHz, DMSO-d6) δ 7.87-7.79 (m, 2H), 7.67-7.59 (m, 2H), 4.14-3.97 (m, 4H), 3.52-3.36 (m, 1H), 3.29-3.22 (m, 1H), 3.21-3.10 (m, 1H), 1.30 (s, 9H), 1.26-1.20 (m, 6H).

Step 2

Prepared according to General Procedure A, Step 2, Method B from tert-butyl 3-(5-((4-bromophenyl)difluoromethyl)-1,2,4-oxadiazol-3-yl)-2-(diethoxyphosphoryl)propanoate (0.435 g, 0.77 mmol). The crude product was purified by chromatography on silica gel (0-30% MTBE/isohexane) to afford tert-butyl 2-((5-((4-bromophenyl)difluoromethyl)-1,2,4-oxadiazol-3-yl)methyl)acrylate (0.15 g, 0.32 mmol, 89% purity) as a clear and colourless oil. LCMS m/z 357.1 $(M-tBu+H)^+$ $(ES^+)$. $^1$H NMR (400 MHz, DMSO-d6) δ 7.91-7.75 (m, 2H), 7.70-7.58 (m, 2H), 6.24-6.14 (m, 1H), 5.88-5.77 (m, 1H), 3.82 (s, 2H), 1.29 (s, 9H).

Step 3

Prepared according to General Procedure A, Step 3 from tert-butyl 2-((5-((4-bromophenyl)difluoromethyl)-1,2,4-oxadiazol-3-yl)methyl)acrylate (0.15 g, 0.32 mmol, 89% purity). The crude product was purified by chromatography on silica gel (0-50% MTBE/isohexane) to afford 2-((5-((4-bromophenyl)difluoromethyl)-1,2,4-oxadiazol-3-yl)methyl) acrylic acid (0.090 g, 0.24 mmol) as a clear and colourless gum. LCMS m/z 357.0/359.0 $(M-H)^-$ $(ES^-)$. $^1$H NMR (400 MHz, DMSO-d6) δ 12.78 (s, 1H), 7.89-7.76 (m, 2H), 7.73-7.53 (m, 2H), 6.32-6.12 (m, 1H), 5.92-5.76 (m, 1H), 3.81 (s, 2H).

Example 86—2-((3-(1-(4-((trifluoromethyl)thio)phenyl)cyclopropyl)-1,2,4-oxadiazol-5-yl)methyl)acrylic acid

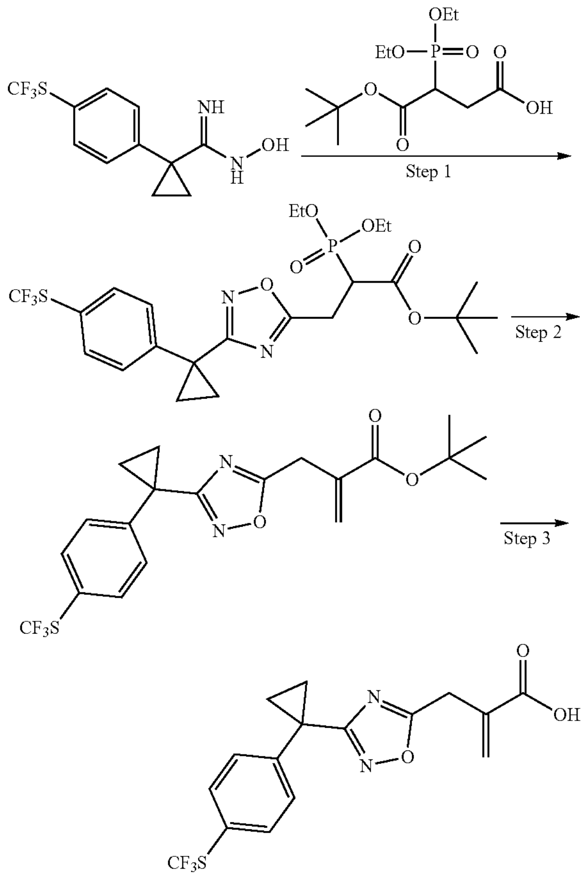

Step 1

Prepared according to General Procedure B, Method B from N-hydroxy-1-(4-((trifluoromethyl)thio)phenyl)cyclopropane-1-carboximidamide (2.82 g, 9.9 mmol). The crude product was purified by chromatography on silica gel (0-100% EtOAc/isohexane) to afford tert-butyl 2-(diethoxyphosphoryl)-3-(3-(1-(4-((trifluoromethyl)thio)phenyl)cyclopropyl)-1,2,4-oxadiazol-5-yl)propanoate (3.04 g, 5.4 mmol) as a light yellow oil. LCMS m/z 551.1 $(M+H)^+$ $(ES^+)$. $^1$H NMR (400 MHz, DMSO-d6) δ 7.72-7.64 (m, 2H), 7.56-7.48 (m, 2H), 4.14-3.98 (m, 4H), 3.53 (ddd, J=23.4, 10.9, 4.4 Hz, 1H), 3.37-3.27 (m, 1H), 3.21 (ddd, J=16.9, 8.9, 4.4 Hz, 1H), 1.54-1.43 (m, 4H), 1.35 (s, 9H), 1.24 (d, J=7.0 Hz, 6H).

Step 2

Prepared according to General Procedure A, Step 2, Method B from tert-butyl 2-(diethoxyphosphoryl)-3-(3-(1-(4-((trifluoromethyl)thio)phenyl)cyclopropyl)-1,2,4-oxadiazol-5-yl)propanoate (3.04 g, 5.4 mmol). The crude product was purified by chromatography on silica gel (0-50% EtOAc/isohexane) to afford tert-butyl 2-((3-(1-(4-((trifluoromethyl)thio)phenyl)cyclopropyl)-1,2,4-oxadiazol-5-yl) methyl)acrylate (1.03 g, 2.4 mmol) as a clear colourless gum. LCMS m/z 371.1 $(M-tBu+H)^+$ $(ES^+)$. $^1$H NMR (400 MHz, DMSO-d6) δ 7.72-7.65 (m, 2H), 7.58-7.49 (m, 2H), 6.23-6.19 (m, 1H), 5.91-5.86 (m, 1H), 3.90 (s, 2H), 1.52-1.40 (m, 4H), 1.33 (s, 9H).

Step 3

Prepared according to General Procedure A, Step 3 from tert-butyl 2-((3-(1-(4-((trifluoromethyl)thio)phenyl)cyclopropyl)-1,2,4-oxadiazol-5-yl)methyl)acrylate (1.03 g, 2.4 mmol). The crude product was purified by chromatography on silica gel (0-50% EtOAc/isohexane) to afford 2-((3-(1-(4-((trifluoromethyl)thio)phenyl)cyclopropyl)-1,2,4-oxadiazol-5-yl)methyl)acrylic acid (815 mg, 2.2 mmol) as a colourless gum. LCMS m/z 371.0 $(M+H)^+$ $(ES^+)$. $^1H$ NMR (400 MHz, DMSO-d6) δ 12.84 (s, 1H), 7.72-7.65 (m, 2H), 7.57-7.50 (m, 2H), 6.26 (d, J=1.2 Hz, 1H), 5.89 (d, J=1.3 Hz, 1H), 3.89 (s, 2H), 1.50 (td, J=5.7, 2.1 Hz, 2H), 1.44 (td, J=5.7, 2.0 Hz, 2H). $^{19}F$ NMR (376 MHz, DMSO-d6) δ −42.00.

Example 87—2-((3-(6,6,8,8,8-pentafluorooctyl)-1,2,4-oxadiazol-5-yl)methyl)acrylic acid

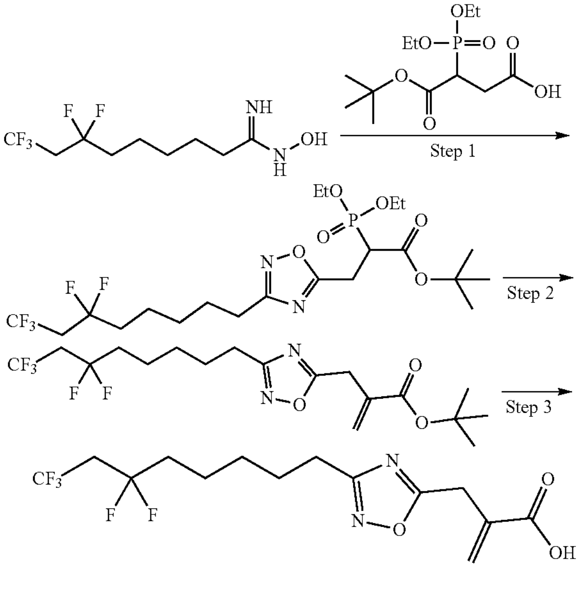

Step 1

Prepared according to General Procedure B, Method B from 7,7,9,9,9-pentafluoro-N-hydroxynonanimidamide (3.46 g, 9.24 mmol, 70% purity). The crude product was purified by chromatography on silica gel (0-100% EtOAc/isohexane) to afford tert-butyl 2-(diethoxyphosphoryl)-3-(3-(6,6,8,8,8-pentafluorooctyl)-1,2,4-oxadiazol-5-yl)propanoate (3.18 g, 5.7 mmol) as a light yellow oil. LCMS m/z 481.3 $(M-tBu+H)^+$ $(ES^+)$. $^1H$ NMR (400 MHz, DMSO-d6) δ 4.15-4.02 (m, 4H), 3.55 (ddd, J=23.4, 11.1, 4.4 Hz, 1H), 3.41-3.12 (m, 2H), 2.65 (t, J=7.3 Hz, 2H), 2.01-1.83 (m, 2H), 1.69-1.58 (m, 2H), 1.54-1.40 (m, 2H), 1.36 (s, 9H), 1.35-1.29 (m, 2H), 1.25 (q, J=6.8 Hz, 6H) [2 protons obscured by DMSO-d6 peak].

Step 2

Prepared according to General Procedure A, Step 2, Method B from tert-butyl 2-(diethoxyphosphoryl)-3-(3-(6,6,8,8,8-pentafluorooctyl)-1,2,4-oxadiazol-5-yl)propanoate (3.18 g, 5.7 mmol). The crude product was purified by chromatography on silica gel (0-50% EtOAc/isohexane) to afford tert-butyl 2-((3-(6,6,8,8,8-pentafluorooctyl)-1,2,4-oxadiazol-5-yl)methyl)acrylate (1.87 g, 4.4 mmol) as a clear colourless oil. LCMS m/z 430.3 $(M+NH_4)^+$ $(ES^+)$. $^1H$ NMR (400 MHz, DMSO-d6) δ 6.22 (d, J=1.2 Hz, 1H), 5.92-5.86 (m, 1H), 3.91 (d, J=1.1 Hz, 2H), 3.30-3.12 (m, 2H), 2.66 (t, J=7.4 Hz, 2H), 2.00-1.84 (m, 2H), 1.70-1.58 (m, 2H), 1.52-1.38 (m, 2H), 1.34 (s, 11H).

Step 3

Prepared according to General Procedure A, Step 3 from tert-butyl 2-((3-(6,6,8,8,8-pentafluorooctyl)-1,2,4-oxadiazol-5-yl)methyl)acrylate (1.875 g, 4.4 mmol). The crude product was purified by chromatography on silica gel (0-50% EtOAc/isohexane) to afford 2-((3-(6,6,8,8,8-pentafluorooctyl)-1,2,4-oxadiazol-5-yl)methyl)acrylic acid (1.22 g, 3.4 mmol) as a colourless oil. LCMS m/z 357.1 $(M+H)^+$ $(ES^+)$. $^1H$ NMR (400 MHz, DMSO-d6) δ 12.80 (s, 1H), 6.27 (d, J=1.2 Hz, 1H), 5.91 (d, J=1.3 Hz, 1H), 3.93-3.88 (m, 2H), 3.29-3.16 (m, 2H), 2.66 (t, J=7.5 Hz, 2H), 2.02-1.84 (m, 2H), 1.65 (p, J=7.5 Hz, 2H), 1.51-1.39 (m, 2H), 1.39-1.27 (m, 2H). $^{19}F$ NMR (376 MHz, DMSO-d6) δ −60.23, −96.59.

Example 88—2-((3-(1,1-difluorooctyl)-1,2,4-oxadiazol-5-yl)methyl)acrylic acid

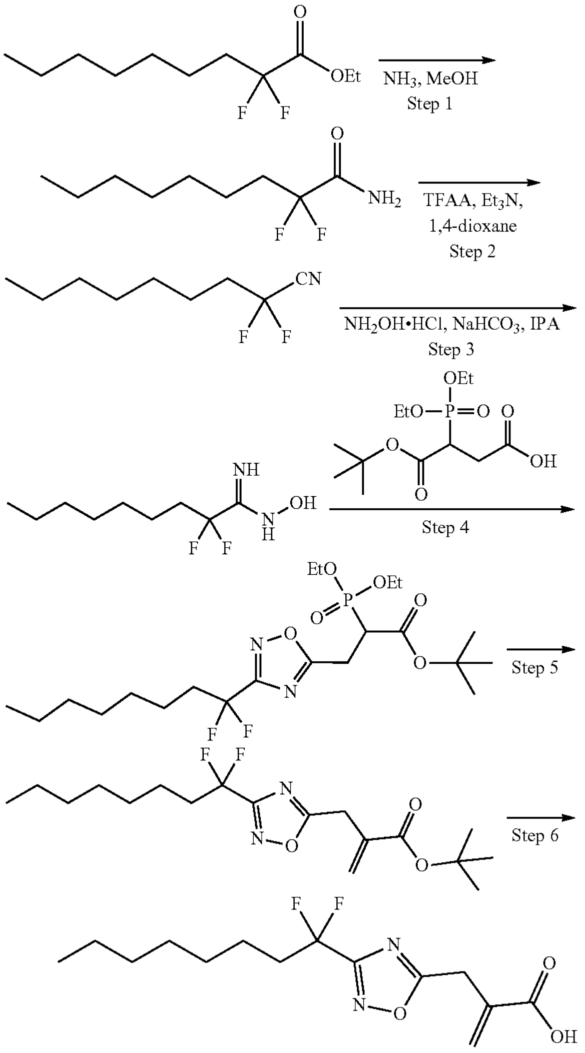

Step 1

A mixture of ethyl 2,2-difluorononanoate (1.00 g, 4.50 mmol) and ammonia (7 M in methanol, 5 mL, 0.2 mol) in methanol (25 mL) was stirred for 16 h at RT. The mixture was concentrated to afford 2,2-difluorononanamide (0.88 g, 4.0 mmol, 88% purity) as a white solid. $^1$H NMR (400 MHz, DMSO-d6) δ 8.05 (s, 1H), 7.84 (s, 1H), 2.06-1.90 (m, 2H), 1.38-1.22 (m, 10H), 0.90-0.81 (m, 3H).

Step 2

TFAA (2.5 mL, 18 mmol) was added dropwise to a solution of 2,2-difluorononanamide (0.88 g, 4.0 mmol, 88% purity) and triethylamine (2.5 mL, 18 mmol) in 1,4-dioxane (10 mL) at 0° C. The mixture was warmed to RT and stirred for 16 h. The mixture was poured into ice-water (20 mL) and extracted with EtOAc (3×15 mL). The combined organic layers were washed with brine (20 mL), dried ($Na_2SO_4$) and concentrated. The crude product was purified by chromatography on silica gel (0-10% EtOAc/isohexane) to afford 2,2-difluorononanenitrile (0.297 g, 1.7 mmol) as a clear colourless oil. $^1$H NMR (400 MHz, DMSO-d6) δ 2.46-2.31 (m, 2H), 1.53-1.43 (m, 2H), 1.40-1.20 (m, 8H), 0.90-0.82 (m, 3H). $^{19}$F NMR (376 MHz, DMSO-d6) δ −88.52.

Step 3

Prepared according to the procedure described for Intermediate 23 from 2,2-difluorononanenitrile (0.297 g, 1.7 mmol), to afford 2,2-difluoro-N-hydroxynonanimidamide (0.210 g, 0.95 mmol, 94% purity) as a white solid. LCMS m/z 209.3 $(M+H)^+$ $(ES^+)$. $^1$H NMR (400 MHz, DMSO-d6) δ 9.78 (s, 1H), 5.75 (s, 2H), 2.10-1.95 (m, 2H), 1.44-1.34 (m, 2H), 1.31-1.23 (m, 8H), 0.89-0.81 (m, 3H). $^{19}$F NMR (376 MHz, DMSO-d6) δ −98.44.

Step 4

Prepared according to General Procedure B, Method C from 2,2-difluoro-N-hydroxynonanimidamide (0.210 g, 0.95 mmol, 94% purity). The crude product was purified by chromatography on silica gel (0-100% MTBE/isohexane) to afford tert-butyl 2-(diethoxyphosphoryl)-3-(3-(1,1-difluorooctyl)-1,2,4-oxadiazol-5-yl)propanoate (0.193 g, 0.40 mmol) as a colourless oil. LCMS m/z 505.3 $(M+Na)^+$ $(ES^+)$. $^1$H NMR (400 MHz, DMSO-d6) δ 4.16-4.02 (m, 4H), 3.65 (ddd, J=23.5, 10.7, 4.8 Hz, 1H), 3.51-3.33 (m, 2H), 2.34-2.19 (m, 2H), 1.41-1.18 (m, 25H), 0.89-0.81 (m, 3H). $^{19}$F NMR (376 MHz, DMSO-d6) δ −97.06 (d, J=267.3 Hz), −97.94 (d, J=267.3 Hz).

Step 5

Prepared according to General Procedure A, Step 2, Method B from tert-butyl 2-(diethoxyphosphoryl)-3-(3-(1,1-difluorooctyl)-1,2,4-oxadiazol-5-yl)propanoate (0.193 g, 0.40 mmol). The crude product was purified by chromatography on silica gel (0-50% MTBE/isohexane) to afford tert-butyl 2-((3-(1,1-difluorooctyl)-1,2,4-oxadiazol-5-yl) methyl)acrylate (0.0767 g, 0.21 mmol) as a clear colourless oil. $^1$H NMR (400 MHz, DMSO-d6) δ 6.28 (d, J=1.1 Hz, 1H), 6.01-5.93 (m, 1H), 4.06 (s, 2H), 2.36-2.20 (m, 2H), 1.32 (m, 19H), 0.89-0.81 (m, 3H). $^{19}$F NMR (376 MHz, DMSO-d6) δ −97.46.

Step 6

Prepared according to General Procedure A, Step 3 from tert-butyl 2-((3-(1,1-difluorooctyl)-1,2,4-oxadiazol-5-yl) methyl)acrylate (0.0767 g, 0.21 mmol). The crude product was purified by chromatography on silica gel (0-10% MeOH/DCM) to afford 2-((3-(1,1-difluorooctyl)-1,2,4-oxadiazol-5-yl)methyl)acrylic acid (0.0485 g, 0.16 mmol) as a white solid. LCMS m/z 303.1 $(M+H)^+$ $(ES^+)$. $^1$H NMR (400 MHz, DMSO-d6) δ 1 2.92 (s, 1H), 6.31 (d, J=1.2 Hz, 1H), 5.98 (d, J=1.4 Hz, 1H), 4.04 (s, 2H), 2.37-2.20 (m, 2H), 1.44-1.35 (m, 2H), 1.34-1.19 (m, 8H), 0.91-0.81 (m, 3H). $^{19}$F NMR (376 MHz, DMSO-d6) δ −97.48.

Example 89—2-((5-((4-chlorophenyl)difluoromethyl)-1,2,4-oxadiazol-3-yl)methyl)acrylic acid

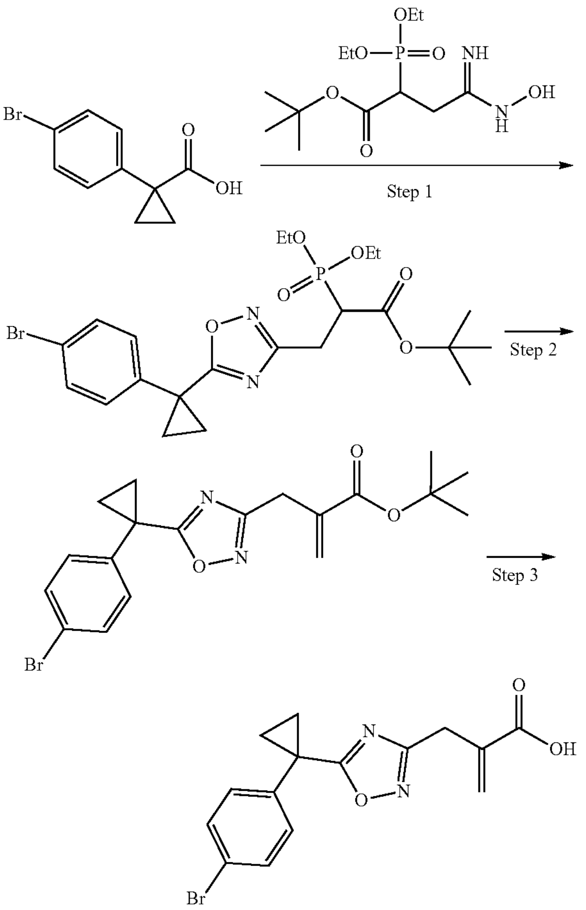

Step 1

T3P (50 wt % in EtOAc, 1.9 mL, 3.2 mmol) was added dropwise to a solution of tert-butyl 2-(diethoxyphosphoryl)-4-(hydroxyamino)-4-iminobutanoate (500 mg, 1.54 mmol), 1-(4-bromophenyl)cyclopropane-1-carboxylic acid (372 mg, 1.54 mmol) and triethylamine (0.7 mL, 5.0 mmol) in EtOAc (10 mL). The mixture was stirred at RT for 1 h, then heated to 50° C. and stirred for 1 h. The mixture was diluted with EtOAc (20 mL) and washed with water (50 mL) and brine (50 mL), dried ($MgSO_4$) and concentrated. The residue was taken up in THF (20 mL) and cesium carbonate (1.51 g, 4.63 mmol) was added. The mixture was heated to 70° C. and stirred for 1 h, then cooled to RT and poured into water (20 mL) and extracted with EtOAc (3×15 mL). The combined organic layers were washed with brine (30 mL), dried ($Na_2SO_4$) and concentrated. The crude product was purified by chromatography on silica gel (0-100% MTBE/isohexane) to afford tert-butyl 3-(5-(1-(4-bromophenyl)cyclopropyl)-1,2,4-oxadiazol-3-yl)-2-(diethoxyphosphoryl)propanoate (0.164 g, 0.26 mmol, 84% purity) as a clear colourless oil. LCMS m/z 529.2/531.2 $(M+H)^+$ $(ES^+)$. $^1$H NMR (400 MHz, DMSO-d6) δ 7.60-7.55 (m, 2H), 7.41-7.36 (m, 2H), 4.09-4.04 (m, 4H), 3.30-3.22 (m, 1H), 3.12 (ddd, J=16.0, 11.1, 8.5 Hz, 1H), 2.97 (ddd, J=16.0, 9.7, 3.9 Hz, 1H), 1.70-1.64 (m, 2H), 1.60-1.56 (m, 2H), 1.33 (s, 9H), 1.26-1.22(m, 6H.

Step 2

Prepared according to General Procedure A, Step 2, Method B from tert-butyl 3-(5-(1-(4-bromophenyl)cyclopropyl)-1,2,4-oxadiazol-3-yl)-2-(diethoxyphosphoryl)propanoate (0.164 g, 0.26 mmol, 84% purity). The crude product was purified by chromatography on silica gel (0-40% MTBE/isohexane) to afford tert-butyl 2-((5-(1-(4-bromophenyl)cyclopropyl)-1,2,4-oxadiazol-3-yl)methyl)acrylate (80 mg, 0.20 mmol) as a colourless oil. LCMS m/z 349.3/351.3 $(M-tBu+H)^+$ $(ES^+)$. $^1H$ NMR (400 MHz, DMSO-d6) δ 7.60-7.54 (m, 2H), 7.42-7.36 (m, 2H), 6.12 (d, J=1.3 Hz, 1H), 5.71 (d, J=1.3 Hz, 1H), 3.62 (s, 2H), 1.71-1.64 (m, 2H), 1.59-1.51 (m, 2H), 1.36 (s, 9H).

Step 3

Prepared according to General Procedure A, Step 3 from tert-butyl 2-((5-(1-(4-bromophenyl)cyclopropyl)-1,2,4-oxadiazol-3-yl)methyl)acrylate (80 mg, 0.20 mmol). The crude product was purified by chromatography on silica gel (0-10% MeOH/DCM) to afford 2-((5-(1-(4-bromophenyl)cyclopropyl)-1,2,4-oxadiazol-3-yl)methyl)acrylic acid (28 mg, 0.08 mmol) as a colourless solid. LCMS m/z 349.1/351.3 $(M+H)^+$ $(ES^+)$. $^1H$ NMR (400 MHz, DMSO-d6) δ 12.66 (s, 1H), 7.61-7.51 (m, 2H), 7.44-7.37 (m, 2H), 6.19 (d, J=1.3 Hz, 1H), 5.72 (d, J=1.4 Hz, 1H), 3.62 (s, 2H), 1.70-1.62 (m, 2H), 1.62-1.51 (m, 2H).

Example 90—2-((3-((4-bromophenyl)difluoromethyl)-1,2,4-oxadiazol-5-yl)methyl)acrylic acid

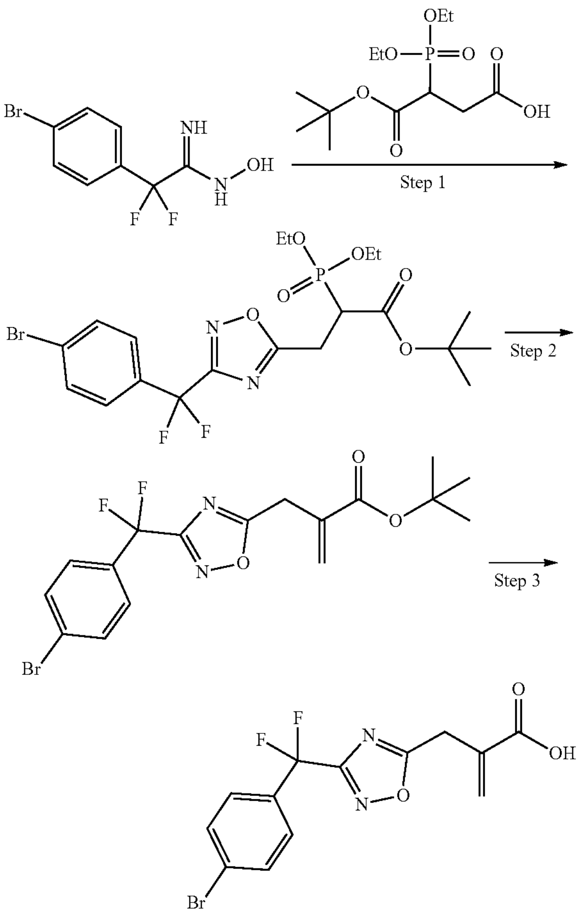

Step 1

Prepared according to General Procedure B, Method C from 2-(4-bromophenyl)-2,2-difluoro-N-hydroxyacetimidamide (2.4 g, 7.7 mmol, 85% purity). The crude product was purified by chromatography on silica gel (0-100% MTBE/isohexane) to afford tert-butyl 3-(3-((4-bromophenyl)difluoromethyl)-1,2,4-oxadiazol-5-yl)-2-(diethoxyphosphoryl)propanoate (1.66 g, 2.8 mmol, 90% purity) as a pale brown gum. LCMS m/z 483.1/485.1 $(M-tBu+H)^+$ $(ES^+)$. $^1H$ NMR (400 MHz, DMSO-d6) δ 7.82-7.72 (m, 2H), 7.60-7.51 (m, 2H), 4.13-4.00 (m, 4H), 3.71-3.55 (m, 1H), 3.51-3.34 (m, 2H), 1.29 (s, 9H), 1.26-1.20 (m, 6H).

Step 2

Prepared according to General Procedure A, Step 2, Method B from tert-butyl 3-(3-((4-bromophenyl)difluoromethyl)-1,2,4-oxadiazol-5-yl)-2-(diethoxyphosphoryl)propanoate (0.800 g, 1.34 mmol, 90% purity). The crude product was purified by chromatography on silica gel (0-30% MTBE/isohexane) to afford tert-butyl 2-((3-((4-bromophenyl)difluoromethyl)-1,2,4-oxadiazol-5-yl)methyl)acrylate (0.200 g, 0.43 mmol, 90% purity) as a clear and colourless oil. $^1H$ NMR (400 MHz, DMSO-d6) δ 7.78 (d, J=8.5 Hz, 2H), 7.61-7.51 (m, 2H), 6.29-6.20 (m, 1H), 5.98-5.91 (m, 1H), 4.04 (s, 2H), 1.23 (s, 9H).

Step 3

Prepared according to General Procedure A, Step 3 from tert-butyl 2-((3-((4-bromophenyl)difluoromethyl)-1,2,4-oxadiazol-5-yl)methyl)acrylate (0.200 g, 0.43 mmol, 90% purity). The crude product was purified by chromatography on silica gel (0-50% MTBE/isohexane) to afford 2-((3-((4-bromophenyl)difluoromethyl)-1,2,4-oxadiazol-5-yl)methyl)acrylic acid (0.15 g, 0.39 mmol) as a white solid. LCMS m/z 357.0/359.0 $(M-H)^-$ $(ES^-)$. $^1H$ NMR (400 MHz, DMSO-d6) δ 12.91 (s, br. 1H), 7.87-7.68 (m, 2H), 7.66-7.50 (m, 2H), 6.36-6.21 (m, 1H), 6.04-5.87 (m, 1H), 4.04 (s, 2H).

Example 91—2-((3-((4-butylphenyl)difluoromethyl)-1,2,4-oxadiazol-5-yl)methyl)acrylic acid

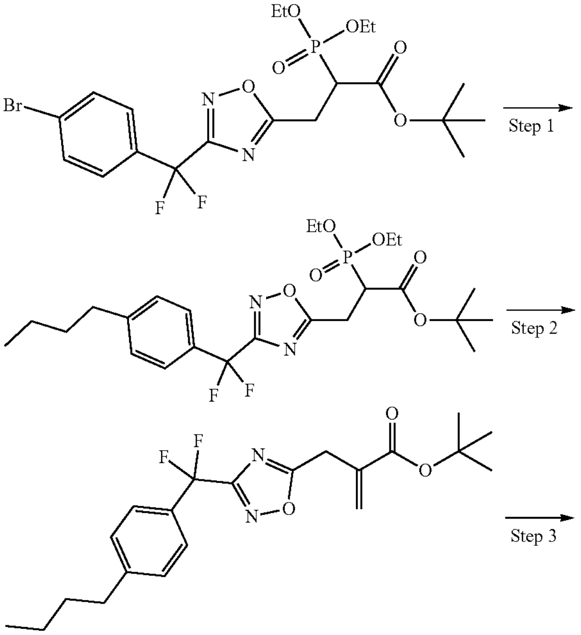

-continued

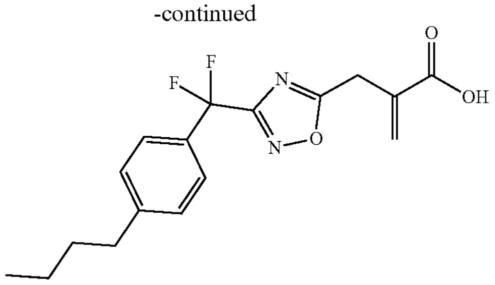

Step 1

A mixture of tert-butyl 3-(3-((4-bromophenyl)difluoromethyl)-1,2,4-oxadiazol-5-yl)-2-(diethoxyphosphoryl)propanoate (0.800 g, 1.34 mmol, 90% purity), butylboronic acid (520 mg, 5.10 mmol) and potassium carbonate (810 mg, 5.86 mmol) in toluene (12 mL) was sparged with nitrogen for 10 min then $Pd(PPh_3)_4$ (0.166 g, 0.14 mol) was added. The mixture was stirred at 100° C. for 1.5 h, then cooled to RT and filtered through celite, washing with EtOAc (3×40 mL). The filtrate was concentrated. The crude product was purified by chromatography on RP Flash C18 (5-100% (0.1% Formic acid in MeCN)/(0.1% Formic Acid in Water)) to afford tert-butyl 3-(3-((4-butylphenyl)difluoromethyl)-1,2,4-oxadiazol-5-yl)-2-(diethoxyphosphoryl)propanoate (0.37 g, 0.68 mmol) as a pale brown oil. LCMS m/z 461.3 $(M-tBu+H)^+$ $(ES^+)$. $^1H$ NMR (400 MHz, DMSO-d6) δ 7.49 (d, J=8.3 Hz, 2H), 7.36 (d, J=8.1 Hz, 2H), 4.15-3.94 (m, 4H), 3.71-3.55 (m, 1H), 3.52-3.33 (m, 2H), 2.63 (t, J=7.7 Hz, 2H), 1.62-1.49 (m, 2H), 1.29 (s, 9H), 1.26-1.16 (m, 6H), 0.89 (t, J=7.3 Hz, 3H) [2 protons not resolved].

Step 2

Prepared according to General Procedure A, Step 2, Method B from tert-butyl 3-(3-((4-butylphenyl)difluoromethyl)-1,2,4-oxadiazol-5-yl)-2-(diethoxyphosphoryl)propanoate (0.37 g, 0.68 mmol). The crude product was purified by chromatography on silica gel (0-50% MTBE/isohexane) to afford tert-butyl 2-((3-((4-butylphenyl)difluoromethyl)-1,2,4-oxadiazol-5-yl)methyl)acrylate (0.16 g, 0.38 mmol, 92% purity) as a clear and colourless oil. $^1H$ NMR (400 MHz, DMSO-d6) δ 7.49 (d, J=8.2 Hz, 2H), 7.36 (d, J=8.0 Hz, 2H), 6.31-6.21 (m, 1H), 6.01-5.90 (m, 1H), 4.04 (s, 2H), 2.63 (t, J=7.7 Hz, 2H), 1.61-1.46 (m, 2H), 1.34-1.25 (m, 2H), 1.23 (s, 9H), 0.89 (t, J=7.3 Hz, 3H).

Step 3

Prepared according to General Procedure A, Step 3 from tert-butyl 2-((3-((4-butylphenyl)difluoromethyl)-1,2,4-oxadiazol-5-yl)methyl)acrylate (0.16 g, 0.38 mmol, 92% purity). The crude product was purified by chromatography on silica gel (0-50% MTBE/isohexane) to afford 2-((3-((4-butylphenyl)difluoromethyl)-1,2,4-oxadiazol-5-yl)methyl) acrylic acid (90 mg, 0.25 mmol) as a pale brown gum. LCMS m/z 335.0 $(M-H)^-$ $(ES^-)$. $^1H$ NMR (400 MHz, DMSO-d6) δ 12.91 (s, br. 1H), 7.53-7.44 (m, 2H), 7.37 (d, J=8.0 Hz, 2H), 6.35-6.24 (m, 1H), 6.03-5.90 (m, 1H), 4.03 (s, 2H), 2.64 (t, J=7.7 Hz, 2H), 1.65-1.46 (m, 2H), 1.38-1.23 (m, 2H), 0.89 (t, J=7.4 Hz, 3H).

Example 92—2-((3-(difluoro(4-(trifluoromethyl)phenyl)methyl)-1,2,4-oxadiazol-5-yl)methyl)acrylic acid

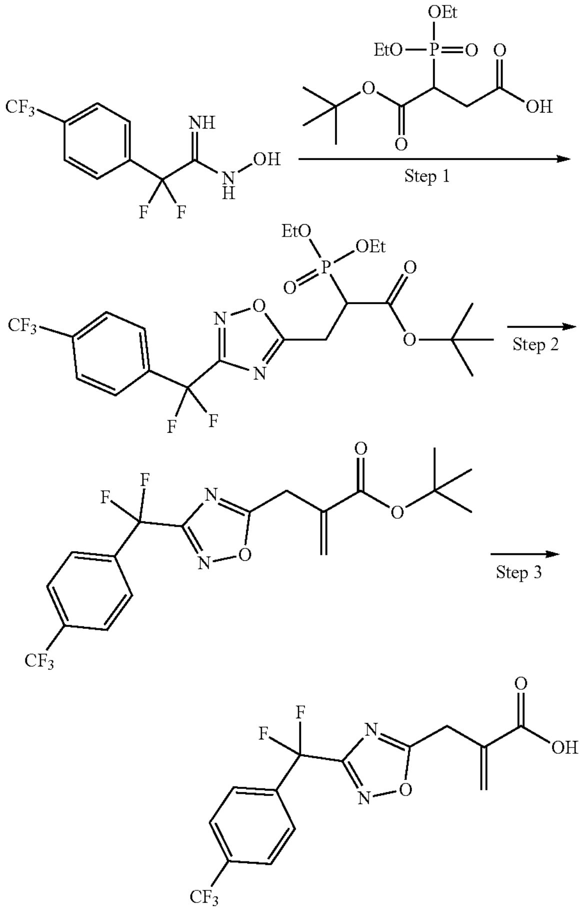

Step 1

Prepared according to General Procedure B, Method C from 2,2-difluoro-N-hydroxy-2-(4-(trifluoromethyl)phenyl)acetimidamide (1.0 g, 3.54 mmol, 90% purity). The crude product was purified by chromatography on silica gel (0-100% MTBE/isohexane) to afford tert-butyl 2-(diethoxyphosphoryl)-3-(3-(difluoro(4-(trifluoromethyl)phenyl)methyl)-1,2,4-oxadiazol-5-yl)propanoate (352 mg, 0.63 mmol) as a yellow oil. LCMS m/z 473.3 $(M-tBu+H)^+$ $(ES^+)$. $^1H$ NMR (400 MHz, DMSO-d6) δ 7.96 (d, J=8.3 Hz, 2H), 7.87 (d, J=8.3 Hz, 2H), 4.12-4.01 (m, 4H), 3.63 (ddd, J=23.4, 10.6, 4.7 Hz, 1H), 3.46 (dd, J=16.9, 10.0 Hz, 1H), 3.41-3.32 (m, 1H), 1.26 (s, 9H), 1.25-1.20 (m, 6H). $^{19}F$ NMR (376 MHz, DMSO-d6) δ −61.69, −95.52. $^{31}P$ NMR (162 MHz, DMSO-d6) δ 19.90.

Step 2

Prepared according to General Procedure A, Step 2, Method B from tert-butyl 2-(diethoxyphosphoryl)-3-(3-(difluoro(4-(trifluoromethyl)phenyl)methyl)-1,2,4-oxadiazol-5-yl)propanoate (352 mg, 0.63 mmol). The crude product was purified by chromatography on silica gel (0-40% MTBE/isohexane) to afford tert-butyl 2-((3-(difluoro(4-(trifluoromethyl)phenyl)methyl)-1,2,4-oxadiazol-5-yl)methyl) acrylate (179 mg, 0.44 mmol) as a colourless oil. $^1H$ NMR (400 MHz, DMSO-d6) δ 7.95 (d, J=8.3 Hz, 2H), 7.88 (d, J=8.3 Hz, 2H), 6.26 (d, J=1.1 Hz, 1H), 5.96 (d, J=1.2 Hz, 1H), 4.05 (s, 2H), 1.20 (s, 9H). $^{19}$F NMR (376 MHz, DMSO-d6) δ −61.69, −96.06.

Step 3

Prepared according to General Procedure A, Step 3 from tert-butyl 2-((3-(difluoro(4-(trifluoromethyl)phenyl)methyl)-1,2,4-oxadiazol-5-yl)methyl)acrylate (179 mg, 0.44 mmol). The crude product was purified by chromatography on silica gel (0-100% MTBE/isohexane) to afford 2-((3-(difluoro(4-(trifluoromethyl)phenyl)methyl)-1,2,4-oxadiazol-5-yl)methyl)acrylic acid (122 mg, 0.35 mmol) as a purple oil. LCMS m/z 347.1 (M−H)$^-$ (ES$^-$). $^1$H NMR (400 MHz, DMSO-d6) δ 12.92 (s, 1H), 7.96 (d, J=8.3 Hz, 2H), 7.88 (d, J=8.3 Hz, 2H), 6.31 (d, J=1.1 Hz, 1H), 5.99 (d, J=1.2 Hz, 1H), 4.05 (s, 2H). $^{19}$F NMR (376 MHz, DMSO-d6) δ −61.63, −94.72.

Example 93—2-((3-(4-(1,1-difluoropentyl)benzyl)-1,2,4-oxadiazol-5-yl)methyl)acrylic acid

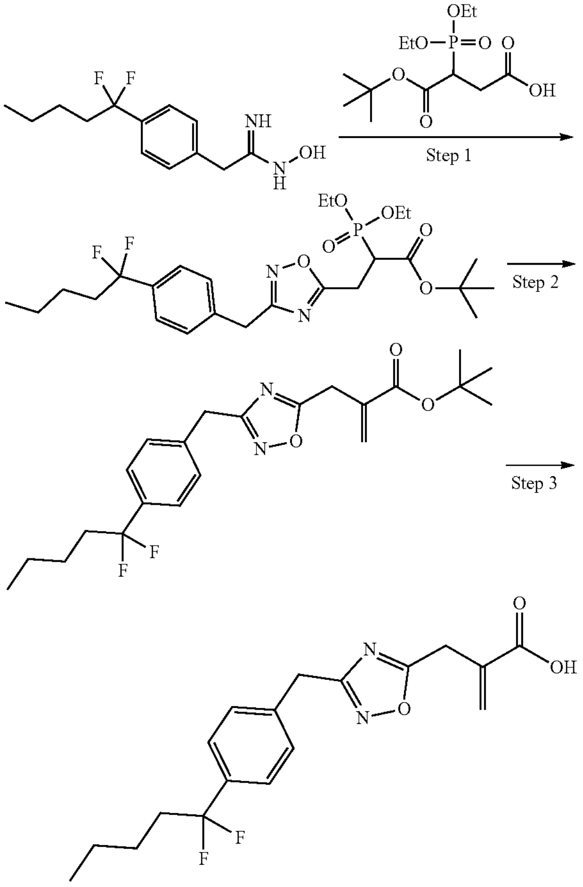

Step 1

Prepared according to General Procedure B, Method B from 2-(4-(1,1-difluoropentyl)phenyl)-N-hydroxyacetimidamide (347 mg, 1.26 mmol, 93% purity). The crude product was purified by chromatography on silica gel (0-100% EtOAc/isohexane) to afford tert-butyl 2-(diethoxyphosphoryl)-3-(3-(4-(1,1-difluoropentyl)benzyl)-1,2,4-oxadiazol-5-yl)propanoate (432 mg, 0.66 mmol, 81% purity) as a light yellow oil. LCMS m/z 553.3 (M+Na)$^+$ (ES$^+$). $^1$H NMR (400 MHz, DMSO-d6) δ 7.44 (d, J=8.2 Hz, 2H), 7.37 (d, J=8.1 Hz, 2H), 4.12-3.99 (m, 6H), 3.53 (ddd, J=23.3, 10.9, 4.5 Hz, 1H), 3.39-3.32 (m, 1H), 3.23 (ddd, J=16.9, 8.8, 4.6 Hz, 1H), 2.24-2.09 (m, 2H), 1.33-1.18 (m, 19H), 0.89-0.79 (m, 3H). $^{19}$F NMR (376 MHz, DMSO-d6) δ −92.44.

Step 2

Prepared according to General Procedure A, Step 2, Method B from tert-butyl 2-(diethoxyphosphoryl)-3-(3-(4-(1,1-difluoropentyl)benzyl)-1,2,4-oxadiazol-5-yl)propanoate (432 mg, 0.66 mmol, 81% purity). The crude product was purified by chromatography on silica gel (0-50% MTBE/isohexane) to afford tert-butyl 2-((3-(4-(1,1-difluoropentyl)benzyl)-1,2,4-oxadiazol-5-yl)methyl)acrylate (0.280 g, 0.69 mmol) as a clear colourless oil. $^1$H NMR (400 MHz, DMSO-d6) δ 7.45 (d, J=8.3 Hz, 2H), 7.39 (d, J=8.1 Hz, 2H), 6.21 (d, J=1.2 Hz, 1H), 5.91-5.84 (m, 1H), 4.10 (s, 2H), 3.90 (s, 2H), 2.24-2.09 (m, 2H), 1.33-1.25 (m, 4H), 1.22 (s, 9H), 0.87-0.80 (m, 3H). $^{19}$F NMR (376 MHz, DMSO-d6) δ −92.43.

Step 3

Prepared according to the procedure described for Example 79, Step 3 from tert-butyl 2-((3-(4-(1,1-difluoropentyl)benzyl)-1,2,4-oxadiazol-5-yl)methyl)acrylate (0.280 g, 0.69 mmol). The crude product was purified by chromatography on silica gel (0-100% MTBE/isohexane) to afford 2-((3-(4-(1,1-difluoropentyl)benzyl)-1,2,4-oxadiazol-5-yl)methyl)acrylic acid (0.168 g, 0.47 mmol) as a white solid. LCMS m/z 349.2 (M−H)$^-$ (ES$^-$). $^1$H NMR (400 MHz, DMSO-d6) δ 12.82 (s, 1H), 7.46 (d, J=8.3 Hz, 2H), 7.38 (d, J=8.1 Hz, 2H), 6.26 (d, J=1.2 Hz, 1H), 5.90 (d, J=1.4 Hz, 1H), 4.12 (s, 2H), 3.91 (s, 2H), 2.26-2.10 (m, 2H), 1.35-1.24 (m, 4H), 0.90-0.79 (m, 3H). $^{19}$F NMR (376 MHz, DMSO-d6) δ −92.49.

Example 94—2-((3-(difluoro(4-(trifluoromethoxy)phenyl)methyl)-1,2,4-oxadiazol-5-yl)methyl)acrylic acid

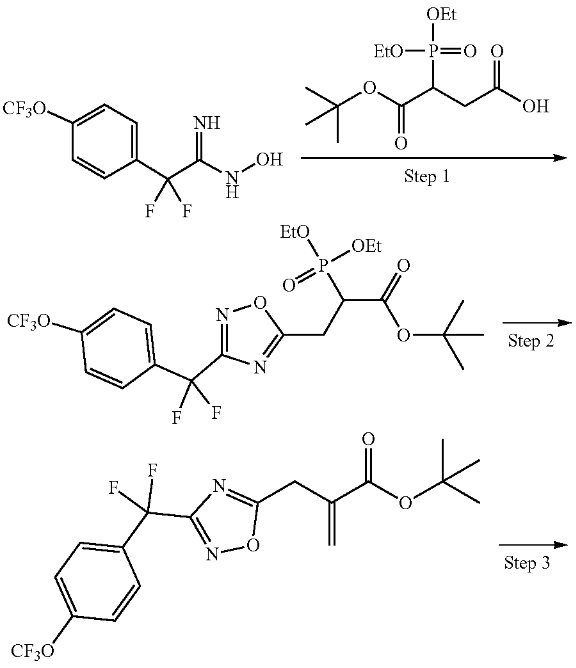

-continued

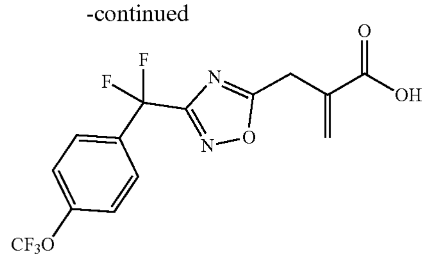

Step 1

Prepared according to General Procedure B, Method C from 2,2-difluoro-N-hydroxy-2-(4-(trifluoromethoxy)phenyl)acetimidamide (1.00 g, 3.33 mmol, 90% purity). The crude product was purified by chromatography on silica gel (0-100% MTBE/isohexane) to afford tert-butyl 2-(diethoxyphosphoryl)-3-(3-(difluoro(4-(trifluoromethoxy)phenyl)methyl)-1,2,4-oxadiazol-5-yl)propanoate (427 mg, 0.78 mmol) as a yellow oil. LCMS m/z 489.4 $(M-tBu+H)^+$ $(ES^+)$. $^1H$ NMR (400 MHz, DMSO-d6) δ 7.81-7.75 (m, 2H), 7.61-7.52 (m, 2H), 4.15-4.02 (m, 4H), 3.63 (ddd, J=23.5, 10.6, 4.8 Hz, 1H), 3.46 (dd, J=16.9, 10.2 Hz, 1H), 3.41-3.33 (m, 1H), 1.28 (s, 9H), 1.26-1.19 (m, 6H). $^{19}F$ NMR (376 MHz, DMSO-d6) δ −56.80, −94.10. $^{31}P$ NMR (162 MHz, DMSO-d6) δ 19.93.

Step 2

Prepared according to General Procedure A, Step 2, Method B from tert-butyl 2-(diethoxyphosphoryl)-3-(3-(difluoro(4-(trifluoromethoxy)phenyl)methyl)-1,2,4-oxadiazol-5-yl)propanoate (427 mg, 0.78 mmol). The crude product was purified by chromatography on silica gel (0-50% MTBE/isohexane) to afford tert-butyl 2-((3-(difluoro(4-(trifluoromethoxy)phenyl)methyl)-1,2,4-oxadiazol-5-yl)methyl)acrylate (242 mg, 0.57 mmol) as a colourless oil. LCMS m/z 363.2 $(M-tBu-H)^-$ $(ES^-)$. $^1H$ NMR (400 MHz, DMSO-d6) δ 7.79 (d, J=8.8 Hz, 2H), 7.60-7.53 (m, 2H), 6.26 (d, J=1.1 Hz, 1H), 5.96 (d, J=1.3 Hz, 1H), 4.05 (s, 2H), 1.21 (s, 9H).

Step 3

Prepared according to General Procedure A, Step 3 from tert-butyl 2-((3-(difluoro(4-(trifluoromethoxy)phenyl)methyl)-1,2,4-oxadiazol-5-yl)methyl)acrylate (242 mg, 0.57 mmol). The crude product was purified by chromatography on silica gel (0-100% MTBE/isohexane) to afford 2-((3-(difluoro(4-(trifluoromethoxy)phenyl)methyl)-1,2,4-oxadiazol-5-yl)methyl)acrylic acid (155 mg, 0.41 mmol) as a purple oil. LCMS m/z 363.2 $(M-H)^-$ $(ES^-)$. $^1H$ NMR (400 MHz, DMSO-d6) δ 12.91 (s, 1H), 7.95-7.68 (m, 2H), 7.68-7.49 (m, 2H), 6.31 (d, J=1.1 Hz, 1H), 5.99 (q, J=1.2 Hz, 1H), 4.05 (s, 2H). $^{19}F$ NMR (376 MHz, DMSO-d6) δ −56.77, −93.40.

Example 95—2-((5-(4-butylbenzyl)-1,2,4-oxadiazol-3-yl)methyl)acrylic acid

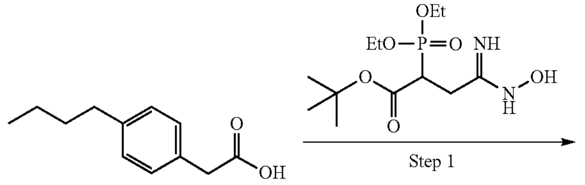

-continued

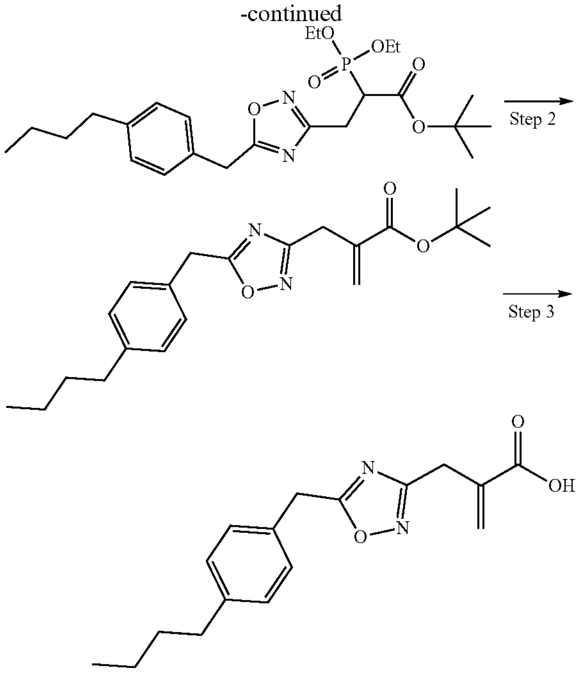

Step 1

EDC (430 mg, 2.24 mmol) was added to a mixture of 2-(4-butylphenyl)acetic acid (316 mg, 1.65 mmol), tert-butyl 2-(diethoxyphosphoryl)-4-(hydroxyamino)-4-iminobutanoate (0.50 g, 1.50 mmol) and DMAP (18 mg, 0.15 mmol) in DCM (10 mL). The mixture was stirred at RT for 2.5 h. The mixture was diluted with water (40 mL) and extracted with DCM (3×20 mL). The combined organic phases were dried ($MgSO_4$), filtered and concentrated. The residue was taken up in THF (10 mL) and $Cs_2CO_3$ (0.93 g, 2.8 mmol) was added and the mixture was stirred at RT for 18 h. The mixture was diluted with water (40 mL) and extracted with EtOAc (3×30 mL). The combined organic phases were dried ($MgSO_4$) and concentrated. The crude product was purified by chromatography on silica gel (0-100% MTBE/isohexane) to afford tert-butyl 3-(5-(4-butylbenzyl)-1,2,4-oxadiazol-3-yl)-2-(diethoxyphosphoryl)propanoate (0.45 g, 0.89 mmol) as a pale brown gum. LCMS m/z 503.3 $(M+Na)^+$ $(ES^+)$. $^1H$ NMR (400 MHz, DMSO-d6) δ 7.25-7.08 (m, 4H), 4.26 (s, 2H), 4.14-3.95 (m, 4H), 3.42-3.34 (m, 1H), 3.25-3.10 (m, 1H), 3.07-2.93 (m, 1H), 2.58-2.52 (m, 2H), 1.57-1.47 (m, 2H), 1.30 (s, 9H), 1.28-1.19 (m, 6H), 0.88 (t, J=7.3 Hz, 3H). Two protons not resolved.

Step 2

Prepared according to General Procedure A, Step 2, Method B from tert-butyl 3-(5-(4-butylbenzyl)-1,2,4-oxadiazol-3-yl)-2-(diethoxyphosphoryl)propanoate (0.45 g, 0.89 mmol). The crude product was purified by chromatography on silica gel (0-50% MTBE/isohexane) to afford tert-butyl 2-((5-(4-butylbenzyl)-1,2,4-oxadiazol-3-yl)methyl)acrylate (231 mg, 0.64 mmol) as a colourless oil. LCMS m/z 301.3 $(M-tBu+H)^+$ $(ES^+)$. $^1H$ NMR (400 MHz, DMSO-d6) δ 7.20 (d, J=8.1 Hz, 2H), 7.15 (d, J=8.1 Hz, 2H), 6.15 (d, J=1.3 Hz, 1H), 5.75 (q, J=1.3 Hz, 1H), 4.26 (s, 2H), 3.67 (s, 2H), 2.57-2.52 (m, 2H), 1.57-1.46 (m, 2H), 1.32 (s, 9H), 1.31-1.23 (m, 2H), 0.88 (t, J=7.3 Hz, 3H).

Step 3

Prepared according to General Procedure A, Step 3 from tert-butyl 2-((5-(4-butylbenzyl)-1,2,4-oxadiazol-3-yl)

methyl)acrylate (231 mg, 0.64 mmol). The crude product was purified by chromatography on silica gel (0-100% MTBE/isohexane) to afford 2-((5-(4-butylbenzyl)-1,2,4-oxadiazol-3-yl)methyl)acrylic acid (163 mg, 0.54 mmol) as a purple oil. LCMS m/z 301.3 $(M+H)^+$ $(ES^+)$. $^1$H NMR (400 MHz, DMSO-d6) δ 12.68 (s, 1H), 7.21 (d, J=8.2 Hz, 2H), 7.16 (d, J=8.2 Hz, 2H), 6.21 (d, J=1.3 Hz, 1H), 5.75 (d, J=1.3 Hz, 1H), 4.26 (s, 2H), 3.67 (s, 2H), 2.60-2.52 (m, 2H), 1.59-1.47 (m, 2H), 1.35-1.23 (m, 2H), 0.88 (t, J=7.3 Hz, 3H).

Example 96—2-((5-(4-butoxyphenyl)-1,2,4-oxadiazol-3-yl)methyl)acrylic acid

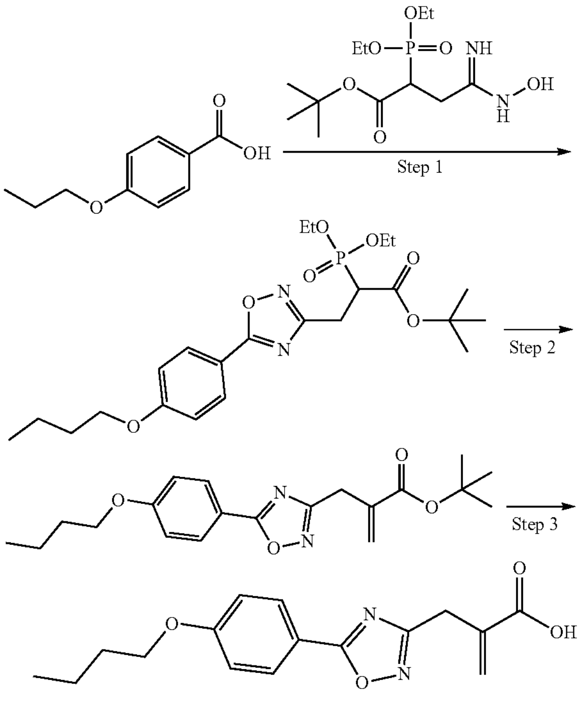

Step 1

Prepared according to the procedure described for Example 95, Step 1 from 4-butoxybenzoic acid (383 mg, 1.97 mmol). The crude product was purified by chromatography on silica gel (0-100% MTBE/isohexane) to afford tert-butyl 3-(5-(4-butoxyphenyl)-1,2,4-oxadiazol-3-yl)-2-(diethoxyphosphoryl)propanoate (0.15 g, 0.25 mmol, 80% purity) as a clear, pale brown gum. LCMS m/z 427.2 $(M-tBu+H)^+$ $(ES^+)$. $^1$H NMR (400 MHz, DMSO-d6) δ 12.72 (s, 1H), 8.03-7.98 (m, 2H), 7.17-7.11 (m, 2H), 6.24 (d, J=1.3 Hz, 1H), 5.81 (s, 1H), 4.08 (t, J=6.5 Hz, 2H), 3.75 (s, 2H), 1.77-1.68 (m, 2H), 1.51-1.39 (m, 2H), 0.94 (t, J=7.4 Hz, 3H).

Step 2

Prepared according to General Procedure A, Step 2, Method B from tert-butyl 3-(5-(4-butoxyphenyl)-1,2,4-oxadiazol-3-yl)-2-(diethoxyphosphoryl)propanoate (0.15 g, 0.25 mmol, 80% purity). The crude product was purified by chromatography on silica gel (0-50% MTBE/isohexane) to afford tert-butyl 2-((5-(4-butoxyphenyl)-1,2,4-oxadiazol-3-yl)methyl)acrylate (82 mg, 0.22 mmol) as a colourless oil. LCMS m/z 303.1 $(M-tBu+H)^+$ $(ES^+)$. $^1$H NMR (400 MHz, DMSO-d6) δ 8.05-7.97 (m, 2H), 7.22-7.11 (m, 2H), 6.19 (d, J=1.3 Hz, 1H), 5.81 (q, J=1.3 Hz, 1H), 4.08 (t, J=6.5 Hz, 2H), 3.76 (s, 2H), 1.78-1.67 (m, 2H), 1.50-1.40 (m, 2H), 1.38 (s, 9H), 0.94 (t, J=7.4 Hz, 3H).

Step 3

Prepared according to General Procedure A, Step 3 from tert-butyl 2-((5-(4-butoxyphenyl)-1,2,4-oxadiazol-3-yl)methyl)acrylate (82 mg, 0.22 mmol). The crude product was purified by chromatography on silica gel (0-100% MTBE/isohexane) to afford 2-((5-(4-butoxyphenyl)-1,2,4-oxadiazol-3-yl)methyl)acrylic acid (50 mg, 0.16 mmol) as a white solid. LCMS m/z 303.2 $(M+H)^+$ $(ES^+)$. $^1$H NMR (400 MHz, DMSO-d6) δ 12.72 (s, 1H), 8.03-7.98 (m, 2H), 7.17-7.11 (m, 2H), 6.24 (d, J=1.3 Hz, 1H), 5.81 (s, 1H), 4.08 (t, J=6.5 Hz, 2H), 3.75 (s, 2H), 1.77-1.68 (m, 2H), 1.51-1.39 (m, 2H), 0.94 (t, J=7.4 Hz, 3H).

Example 97—2-((5-(difluoro(4-(trifluoromethyl)phenyl)methyl)-1,2,4-oxadiazol-3-yl)methyl)acrylic acid

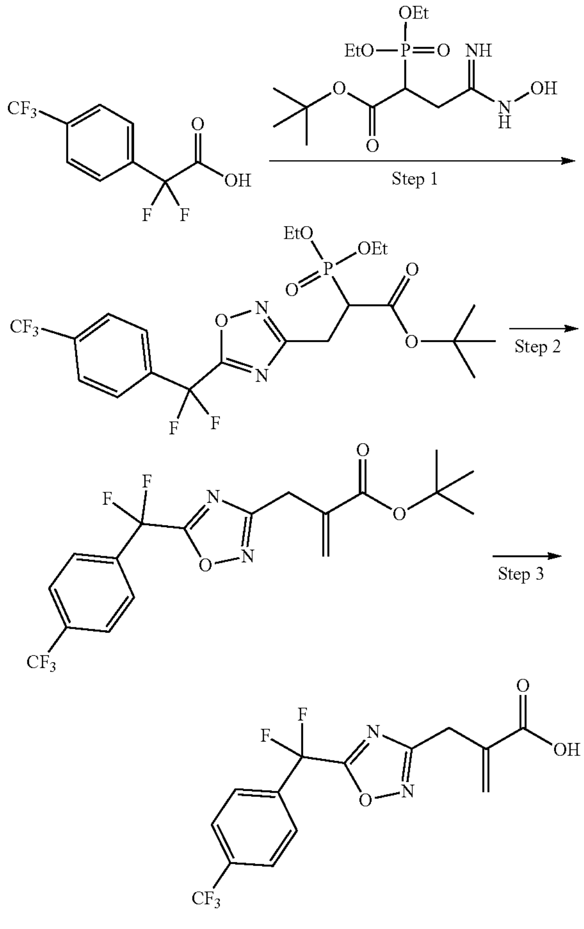

Step 1

Prepared using a similar procedure to Example 84, Step 1 from 2,2-difluoro-2-(4-(trifluoromethyl)phenyl)acetic acid (389 mg, 1.62 mmol). The crude product was purified by chromatography on silica gel (0-100% MTBE/isohexane) to afford tert-butyl 2-(diethoxyphosphoryl)-3-(5-(difluoro(4-(trifluoromethyl)phenyl)methyl)-1,2,4-oxadiazol-3-yl)propanoate (187 mg, 0.33 mmol, 93% purity) as a pale yellow oil. LCMS m/z 551.3 $(M+Na)^+$ $(ES^+)$. $^1$H NMR (400 MHz, DMSO-d6) δ 8.00 (d, J=8.5 Hz, 2H), 7.95 (d, J=8.6 Hz, 2H), 4.12-3.99 (m, 4H), 3.43 (ddd, J=22.8, 10.8, 4.1 Hz, 1H), 3.33-3.23 (m, 1H), 3.16 (ddd, J=16.1, 9.5, 4.2 Hz, 1H), 1.27 (s, 9H), 1.26-1.19 (m, 6H). $^{19}$F NMR (376 MHz, DMSO-d6) δ −61.75, −94.21 (d, J=6.4 Hz). $^{31}$P NMR (162 MHz, DMSO-d6) δ 20.49.

Step 2

Prepared according to General Procedure A, Step 2, Method B from tert-butyl 2-(diethoxyphosphoryl)-3-(5-(difluoro(4-(trifluoromethyl)phenyl)methyl)-1,2,4-oxadiazol-3-yl)propanoate (187 mg, 0.33 mmol, 93% purity). The crude product was purified by chromatography on silica gel (0-50% MTBE/isohexane) to afford tert-butyl 2-((5-(difluoro(4-(trifluoromethyl)phenyl)methyl)-1,2,4-oxadiazol-3-yl)methyl)acrylate (112 mg, 0.27 mmol) as a colourless oil. $^1$H NMR (400 MHz, DMSO-d6) δ 7.99 (d, J=8.9 Hz, 2H), 7.95 (d, J=8.7 Hz, 2H), 6.19 (d, J=1.2 Hz, 1H), 5.83 (d, J=1.3 Hz, 1H), 3.82 (d, J=1.1 Hz, 2H), 1.27 (s, 9H). $^{19}$F NMR (376 MHz, DMSO-d6) δ −61.74, −94.46.

Step 3

Prepared according to General Procedure A, Step 3 from tert-butyl 2-((5-(difluoro(4-(trifluoromethyl)phenyl)methyl)-1,2,4-oxadiazol-3-yl)methyl)acrylate (112 mg, 0.27 mmol). The crude product was purified by chromatography on silica gel (0-100% MTBE/isohexane) to afford 2-((5-(difluoro(4-(trifluoromethyl)phenyl)methyl)-1,2,4-oxadiazol-3-yl)methyl)acrylic acid (61 mg, 0.17 mmol) as a colourless oil. LCMS m/z 347.1 (M−H)$^-$ (ES$^-$). $^1$H NMR (400 MHz, DMSO-d6) δ 12.78 (s, 1H), 8.00 (d, J=8.7 Hz, 2H), 7.96 (d, J=8.7 Hz, 2H), 6.25 (d, J=1.2 Hz, 1H), 5.84 (q, J=1.3 Hz, 1H), 3.81 (s, 2H). $^{19}$F NMR (376 MHz, DMSO-d6) δ −61.69, −93.67.

Example 98—2-((3-(4-(1,1-difluorobutyl)phenyl)-1,2,4-oxadiazol-5-yl)methyl)acrylic acid

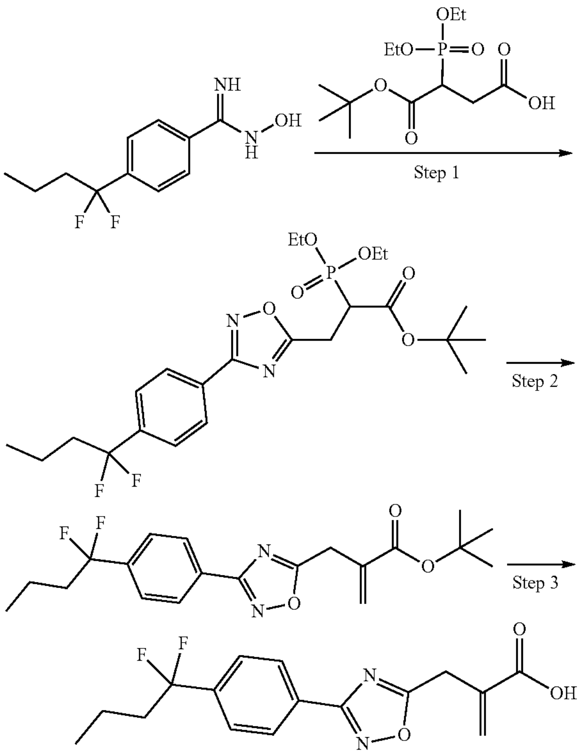

Step 1

Prepared according to General Procedure B, Method B from 4-(1,1-difluorobutyl)-N-hydroxybenzimidamide (0.361 g, 1.53 mmol). The crude product was purified by chromatography on silica gel (0-100% MTBE/isohexane) to afford tert-butyl 2-(diethoxyphosphoryl)-3-(3-(4-(1,1-difluorobutyl)phenyl)-1,2,4-oxadiazol-5-yl)propanoate (0.567 g, 1.1 mmol) as a light yellow oil. LCMS m/z 525.3 (M+Na)$^+$ (ES$^+$). $^1$H NMR (400 MHz, DMSO-d6) δ 8.08 (d, J=8.2 Hz, 2H), 7.72 (d, J=8.3 Hz, 2H), 4.18-4.05 (m, 4H), 3.69 (ddd, J=23.4, 10.7, 4.7 Hz, 1H), 3.53-3.42 (m, 1H), 3.37 (ddd, J=16.8, 8.9, 4.7 Hz, 1H), 2.29-2.14 (m, 2H), 1.41-1.32 (m, 11H), 1.30-1.22 (m, 6H), 0.91 (t, J=7.4 Hz, 3H). $^{19}$F NMR (376 MHz, DMSO-d6) δ −93.44.

Step 2

Prepared according to General Procedure A, Step 2, Method B from tert-butyl 2-(diethoxyphosphoryl)-3-(3-(4-(1,1-difluorobutyl)phenyl)-1,2,4-oxadiazol-5-yl)propanoate (0.567 g, 1.1 mmol). The crude product was purified by chromatography on silica gel (0-50% MTBE/hexane) to afford tert-butyl 2-((3-(4-(1,1-difluorobutyl)phenyl)-1,2,4-oxadiazol-5-yl)methyl)acrylate (0.368 g, 0.92 mmol) as a clear colourless oil. LCMS m/z 323.0 (M−tBu+H)$^+$ (ES$^+$). $^1$H NMR (400 MHz, DMSO-d6) δ 8.09 (d, J=8.1 Hz, 2H), 7.71 (d, J=8.3 Hz, 2H), 6.29 (d, J=1.3 Hz, 1H), 6.00-5.96 (m, 1H), 4.06 (s, 2H), 2.29-2.14 (m, 2H), 1.42-1.30 (m, 11H), 0.91 (t, J=7.4 Hz, 3H). $^{19}$F NMR (376 MHz, DMSO-d6) δ −93.44.

Step 3

Prepared according to the procedure described for Example 79, Step 3 from tert-butyl 2-((3-(4-(1,1-difluorobutyl)phenyl)-1,2,4-oxadiazol-5-yl)methyl)acrylate (0.368 g, 0.92 mmol). The crude product was purified by chromatography on silica gel (0-100% MTBE/isohexane) then repurified by chromatography on silica gel (0-10% MeOH/DCM) to afford 2-((3-(4-(1,1-difluorobutyl)phenyl)-1,2,4-oxadiazol-5-yl)methyl)acrylic acid (0.233 g, 0.72 mmol) as a white solid. LCMS m/z 323.3 (M+H)$^+$ (ES$^+$). $^1$H NMR (400 MHz, DMSO-d6) δ 12.89 (s, 1H), 8.09 (d, J=8.2 Hz, 2H), 7.70 (d, J=8.3 Hz, 2H), 6.33 (d, J=1.2 Hz, 1H), 6.01 (d, J=1.3 Hz, 1H), 4.05 (s, 2H), 2.31-2.13 (m, 2H), 1.43-1.30 (m, 2H), 0.90 (t, J=7.4 Hz, 3H). $^{19}$F NMR (376 MHz, DMSO-d6) δ −93.43.

Example 99—2-((5-(1-(4-(trifluoromethoxy)phenyl)cyclopropyl)-1,2,4-oxadiazol-3-yl)methyl)acrylic acid

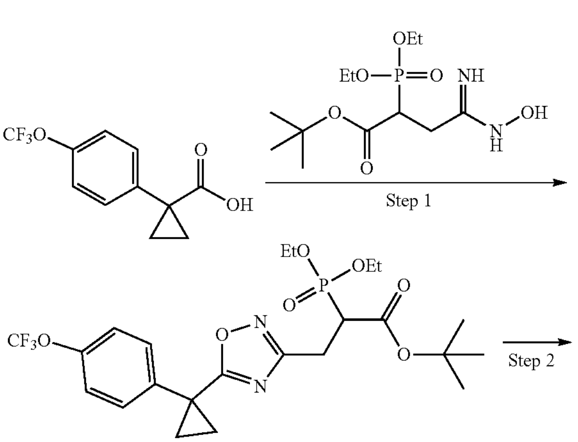

-continued

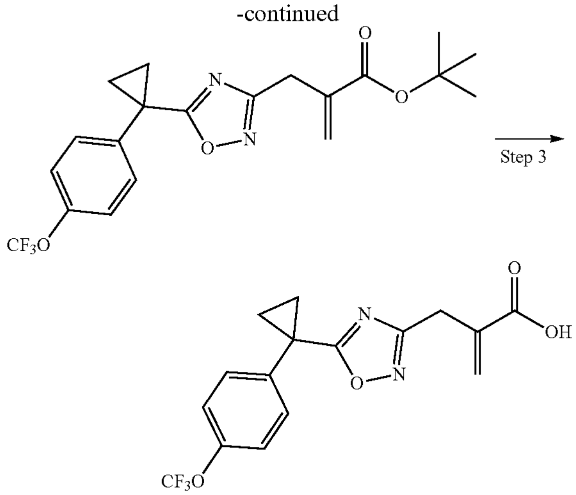

Step 1

Prepared according to the procedure described for Example 95, Step 1 from 1-(4-(trifluoromethoxy)phenyl) cyclopropane-1-carboxylic acid (405 mg, 1.65 mmol). The crude product was purified by chromatography on silica gel (0-100% MTBE/isohexane) to afford tert-butyl 2-(diethoxyphosphoryl)-3-(5-(1-(4-(trifluoromethoxy)phenyl)cyclopropyl)-1,2,4-oxadiazol-3-yl)propanoate (0.31 g, 0.46 mmol, 80% purity) as a pale yellow gum. LCMS m/z 557.3 $(M+Na)^+$ $(ES^+)$. $^1H$ NMR (400 MHz, DMSO-d6) δ 7.61-7.52 (m, 2H), 7.42-7.32 (m, 2H), 4.12-3.99 (m, 4H), 3.29-3.21 (m, 1H), 3.19-3.04 (m, 1H), 3.04-2.91 (m, 1H), 1.74-1.57 (m, 4H), 1.33 (s, 9H), 1.28-1.16 (m, 6H).

Step 2

Prepared according to General Procedure A, Step 2, Method B from tert-butyl 2-(diethoxyphosphoryl)-3-(5-(1-(4-(trifluoromethoxy)phenyl)cyclopropyl)-1,2,4-oxadiazol-3-yl)propanoate (0.31 g, 0.46 mmol, 80% purity). The crude product was purified by chromatography on silica gel (0-20% MTBE/isohexane) to afford tert-butyl 2-((5-(1-(4-(trifluoromethoxy)phenyl)cyclopropyl)-1,2,4-oxadiazol-3-yl)methyl)acrylate (0.17 g, 0.36 mmol, 88% purity) as a clear and colourless oil. LCMS m/z 355.2 $(M-tBu+H)^+$ $(ES^+)$. $^1H$ NMR (400 MHz, DMSO-d6) δ 7.64-7.50 (m, 2H), 7.42-7.31 (m, 2H), 6.17-6.06 (m, 1H), 5.75-5.67 (m, 1H), 3.62 (s, 2H), 1.73-1.65 (m, 2H), 1.62-1.55 (m, 2H), 1.36 (s, 9H).

Step 3

Prepared according to General Procedure A, Step 3 from tert-butyl 2-((5-(1-(4-(trifluoromethoxy)phenyl)cyclopropyl)-1,2,4-oxadiazol-3-yl)methyl)acrylate (0.17 g, 0.36 mmol, 88% purity). The crude product was purified by chromatography on silica gel (0-100% MTBE/isohexane) to afford 2-((5-(1-(4-(trifluoromethoxy)phenyl)cyclopropyl)-1,2,4-oxadiazol-3-yl)methyl)acrylic acid (0.112 g, 0.30 mmol) as a clear and colourless gum. LCMS m/z 355.1 $(M+H)^+$ $(ES^+)$. $^1H$ NMR (400 MHz, DMSO-d6) δ 12.67 (s, 1H), 7.64-7.51 (m, 2H), 7.42-7.29 (m, 2H), 6.23-6.15 (m, 1H), 5.77-5.64 (m, 1H), 3.62 (s, 2H), 1.75-1.66 (m, 2H), 1.63-1.53 (m, 2H).

Example 100—2-((3-(4-(benzyloxy)phenyl)-1,2,4-oxadiazol-5-yl)methyl)acrylic acid

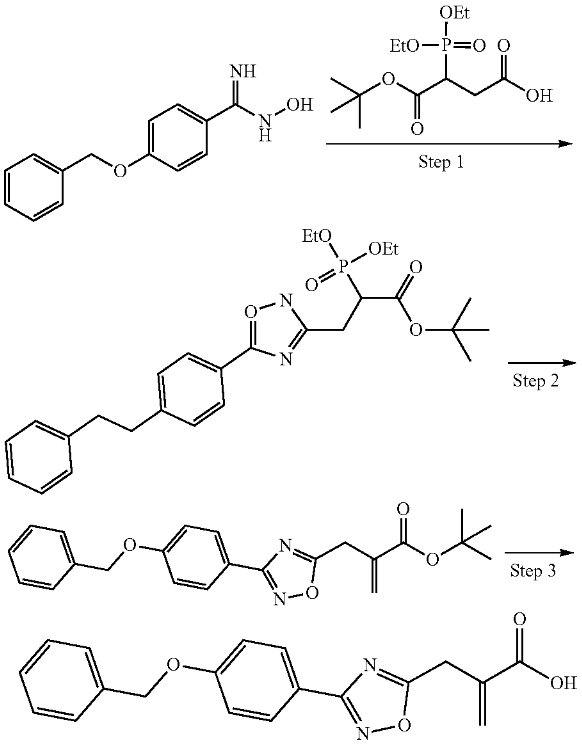

Step 1

Prepared according to General Procedure B, Method B from 4-(benzyloxy)-N-hydroxybenzimidamide (5.97 g, 24.6 mmol). The crude product was purified by chromatography on silica gel (0-100% EtOAc/isohexane) to afford 0-100% MTBE/isohexane) to afford tert-butyl 3-(3-(4-(benzyloxy)phenyl)-1,2,4-oxadiazol-5-yl)-2-(diethoxyphosphoryl)propanoate (8.30 g, 16 mmol) as a brown oil. LCMS m/z 461.3 $(M-tBu+H)^+$ $(ES^+)$. $^1H$ NMR (400 MHz, DMSO-d6) δ 7.95-7.88 (m, 2H), 7.52-7.45 (m, 2H), 7.45-7.38 (m, 2H), 7.38-7.30 (m, 1H), 7.25-7.13 (m, 2H), 5.19 (s, 2H), 4.17-4.06 (m, 4H), 3.65 (ddd, J=23.4, 10.8, 4.6 Hz, 1H), 3.43 (ddd, J=16.8, 10.8, 9.7 Hz, 1H), 3.36-3.27 (m, 1H), 1.38 (s, 9H), 1.30-1.23 (m, 6H).

Step 2

Prepared according to General Procedure A, Step 2, Method B from tert-butyl 3-(3-(4-(benzyloxy)phenyl)-1,2,4-oxadiazol-5-yl)-2-(diethoxyphosphoryl)propanoate (0.300 g, 0.58 mmol). The crude product was purified by chromatography on silica gel (0-50% MTBE/isohexane) to afford tert-butyl 2-((3-(4-(benzyloxy)phenyl)-1,2,4-oxadiazol-5-yl)methyl)acrylate (0.176 g, 0.44 mmol) as a clear colourless oil. LCMS m/z 337.3 $(M-tBu+H)^+$ $(ES^+)$. $^1H$ NMR (400 MHz, DMSO-d6) δ 7.97-7.87 (m, 2H), 7.51-7.31 (m, 5H), 7.23-7.14 (m, 2H), 6.27 (d, J=1.2 Hz, 1H), 6.00-5.91 (m, 1H), 5.19 (s, 2H), 4.01 (s, 2H), 1.33 (s, 9H).

Step 3

Prepared according to General Procedure A, Step 3 from tert-butyl 2-((3-(4-(benzyloxy)phenyl)-1,2,4-oxadiazol-5-yl)methyl)acrylate (0.176 g, 0.44 mmol). The crude product was purified by chromatography on silica gel (0-100% MTBE/isohexane) to afford 2-((3-(4-(benzyloxy)phenyl)-1, 2,4-oxadiazol-5-yl)methyl)acrylic acid (0.0956 g, 0.28 mmol) as a white solid. LCMS m/z 337.3 $(M+H)^+$ $(ES^+)$. $^1H$ NMR (400 MHz, DMSO-d6) δ 12.84 (s, 1H), 12.85 (s, 1H), 7.96-7.89 (m, 2H), 7.50-7.45 (m, 2H), 7.44-7.38 (m, 2H), 7.37-7.32 (m, 1H), 7.21-7.15 (m, 2H), 6.32 (d, J=1.2 Hz, 1H), 6.03-5.95 (m, 1H), 5.19 (s, 2H), 4.00 (s, 2H).

Example 101—2-((4-(4-butylphenyl)oxazol-2-yl)methyl)acrylic acid

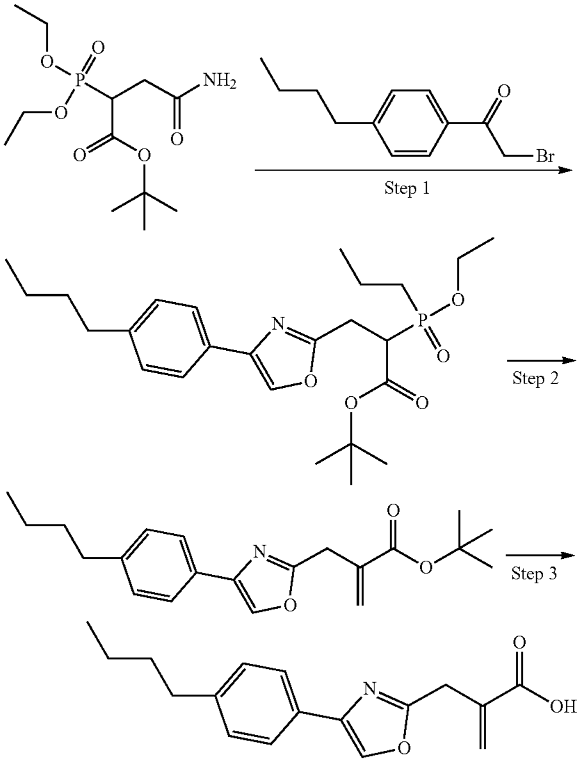

Step 1

Prepared according to Example 39, Step 1 using 2-bromo-1-(4-butylphenyl)ethan-1-one (906 mg, 3.55 mmol). The crude product was purified by flash column chromatography (40 g silica, 0-20% MTBE/petroleum ether) to give tert-butyl 3-(4-(4-butylphenyl)oxazol-2-yl)-2-(diethoxyphosphoryl)propanoate (230 mg, 0.49 mmol, 15%) as a pale yellow oil. LCMS: (System 2, Method C) m/z 466.3 $(M+H)^+$ $(ES^+)$.

Step 2

Prepared according to General Procedure A, Step 2, Method C from tert-butyl 3-(4-(4-butylphenyl)oxazol-2-yl)-2-(diethoxyphosphoryl)propanoate (230 mg, 0.49 mmol). The crude product was purified by flash column chromatography (10% MTBE/petroleum ether) to give tert-butyl 2-((4-(4-butylphenyl)oxazol-2-yl)methyl)acrylate (160 mg, 0.47 mmol, 95%) as a pale yellow oil. LCMS: (System 2, Method C) m/z 254.3 $(M+H)^+$ $(ES^+)$.

Step 3

Prepared according to General Procedure A, Step 3 from tert-butyl 2-((4-(4-butylphenyl)oxazol-2-yl)methyl)acrylate (160 mg, 0.47 mmol). The crude product was purified by preparative HPLC (Column: Waters X-Bridge C18 OBD 10 μm 19×250 mm; Flow Rate: 20 mL/min; solvent system: MeCN/(0.1% TFA/water) gradient: 50-95% MeCN; collection wavelength: 214 nm). The fractions were concentrated under reduced pressure at 30° C. to remove MeCN, and the residue was lyophilized to give 2-((4-(4-butylphenyl)oxazol-2-yl)methyl)acrylic acid (88 mg, 0.31 mmol, 65%) as a white solid. LCMS: (System 2, Method B) m/z 286.3 $(M+H)^+$ $(ES^+)$. $^1H$ NMR (400 MHz, DMSO-d6) δ: 12.70 (br, 1H), 8.44 (s,1H), 7.63 (d, J=8.2 Hz, 2H), 7.22 (d, J=8.2 Hz, 2H), 6.24 (s, 1H), 5.81 (d, J=1.4 Hz, 1H), 3.80 (s, 2H), 2.58 (t, J=7.7 Hz, 2H), 1.61-1.49 (m, 2H), 1.36-1.24 (m, 2H), 0.89 (t, J=7.3 Hz, 3H).

Example 102—2-((5-octylisoxazol-3-yl)methyl)acrylic acid

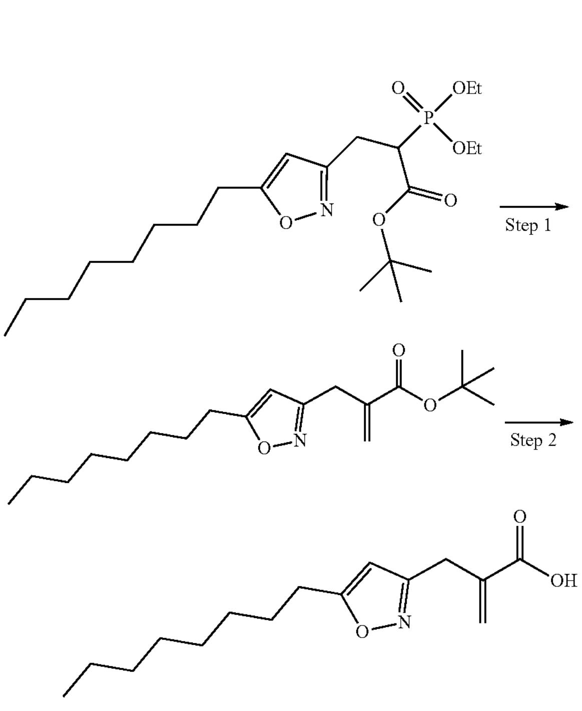

Step 1

Prepared according to General Procedure A, Step 2, Method C from tert-butyl 2-(diethoxyphosphoryl)-3-(5-octylisoxazol-3-yl)propanoate (500 mg, 1.1 mmol). The crude product was purified by flash column chromatography (25 g silica, 0-30% MTBE/petroleum ether) to give tert-butyl 2-((5-octylisoxazol-3-yl)methyl)acrylate (300 mg, 0.93 mmol, 85%) as a pale yellow oil. LCMS: (System 2, Method C) m/z 344.3 $(M+Na)^+$ $(ES^+)$.

Step 2

Prepared according to General Procedure A, Step 3 from tert-butyl 2-((5-octylisoxazol-3-yl)methyl)acrylate (200 mg, 0.62 mmol). The crude product was purified by preparative HPLC (Column: Waters X-Bridge C18 OBD 10 μm 19×250 mm; Flow Rate: 20 mL/min; solvent system: MeCN/(0.05% TFA/water) gradient: 45-95% MeCN; collection wavelength: 214 nm). The fractions were concentrated under reduced pressure at 40° C. to remove MeCN, and the residue was lyophilized to give 2-((5-octylisoxazol-3-yl)methyl) acrylic acid (94 mg, 0.35 mmol, 56%). LCMS: (System 2, Method B) m/z 266.2 $(M+H)^+$ $(ES^+)$. $^1H$ NMR (400 MHz, DMSO-d6) δ: 12.65 (br, 1H), 6.16 (s,1H), 6.06 (s, 1H), 5.67 (d, J=1.5 Hz, 1H), 3.55 (s, 2H), 2.68 (t, J=7.5 Hz, 2H), 1.64-1.53 (m, 2H), 1.32-1.18 (m, 10H), 0.85 (t, J=6.8 Hz, 3H).

Example 103—2-((4-(1-(4-(trifluoromethyl)phenyl)cyclopropyl)oxazol-2-yl)methyl)acrylic acid

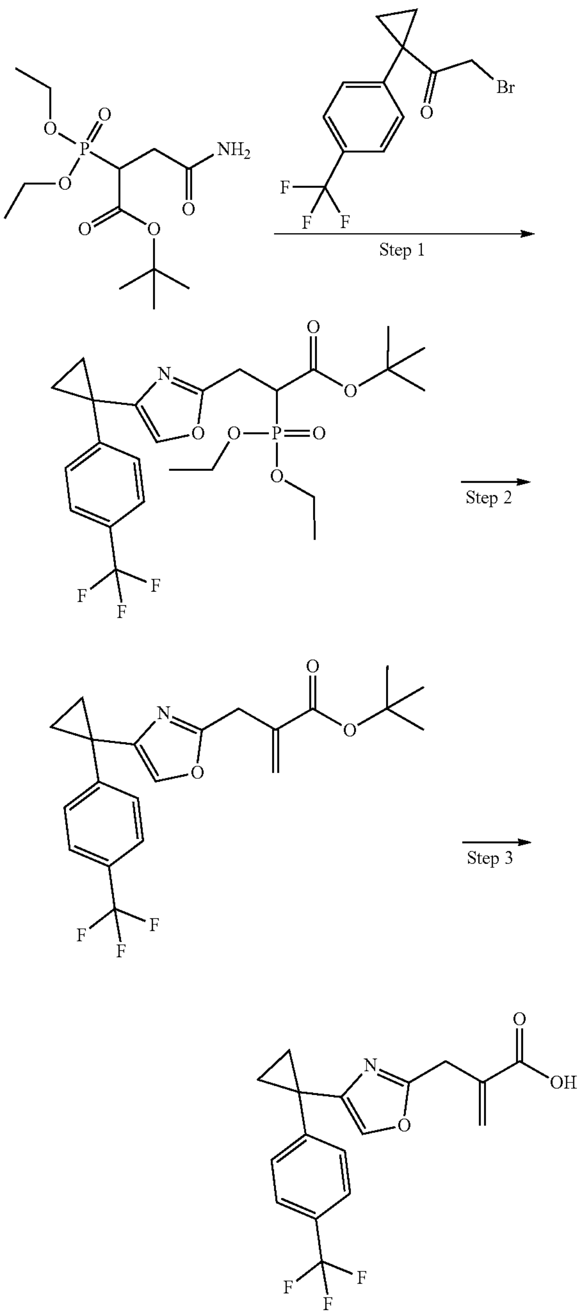

Step 1

Prepared according to Example 39, Step 1 using 2-bromo-1-(1-(4-(trifluoromethyl)phenyl)cyclopropyl)ethan-1-one (1.0 g, 3.26 mmol). The crude product was purified by flash column chromatography (40 g silica, 0-80% MTBE/petroleum ether) to give tert-butyl 2-(diethoxyphosphoryl)-3-(4-(1-(4-(trifluoromethyl)phenyl)cyclopropyl)oxazol-2-yl)propanoate (300 mg, 0.58 mmol, 17%) as a pale yellow oil. LCMS: (System 2, Method C) m/z 518.2 $(M+H)^+$ $(ES^+)$.

Step 2

Prepared according to General Procedure A, Step 2, Method C from tert-butyl 2-(diethoxyphosphoryl)-3-(4-(1-(4-(trifluoromethyl)phenyl)cyclopropyl)oxazol-2-yl)propanoate (300 mg, 0.58 mmol). The crude product was purified by flash column chromatography (25 g silica, 0-20% MTBE/petroleum ether) to give tert-butyl 2-((4-(1-(4-(trifluoromethyl)phenyl)cyclopropyl)oxazol-2-yl)methyl)acrylate (180 mg, 0.46 mmol, 79%) as a pale yellow oil. LCMS: (System 2, Method C) m/z 394.2 $(M+H)^+$ $(ES^+)$.

Step 3

Prepared according to General Procedure A, Step 3 from tert-butyl 2-((4-(1-(4-(trifluoromethyl)phenyl)cyclopropyl)oxazol-2-yl)methyl)acrylate (180 mg, 0.46 mmol). The crude product was purified by preparative HPLC (Column: Waters X-Bridge C18 OBD 10 μm 19×250 mm; Flow Rate: 20 mL/min; solvent system: MeCN/(0.05% TFA/water) gradient: 40-95% MeCN; collection wavelength: 214 nm). The fractions were concentrated under reduced pressure at 30° C. to remove MeCN, and the residue was lyophilized to give 2-((4-(1-(4-(trifluoromethyl)phenyl)cyclopropyl)oxazol-2-yl)methyl)acrylic acid (127 mg, 0.38 mmol, 82%) as a white solid. LCMS: (System 2, Method B) m/z 338.0 $(M+H)^+$ $(ES^+)$. $^1H$ NMR (400 MHz, DMSO-d6) δ: 12.69 (br, 1H), 7.66 (d, J=8.1 Hz, 2H), 7.53 (s,1H), 7.50 (d, J=8.1 Hz, 2H), 6.19 (d, J=1.3 Hz, 1H), 5.73 (d, J=1.4 Hz, 1H), 3.70 (s, 2H), 1.34-1.27 (m, 2H), 1.27-1.19 (m, 2H).

Example 104—2-((4-octylpyridin-2-yl)methyl)acrylic acid trifluoroacetic acid salt

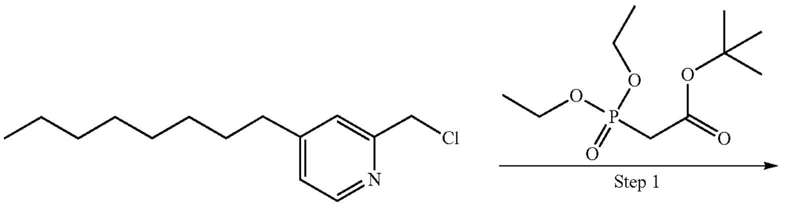

-continued

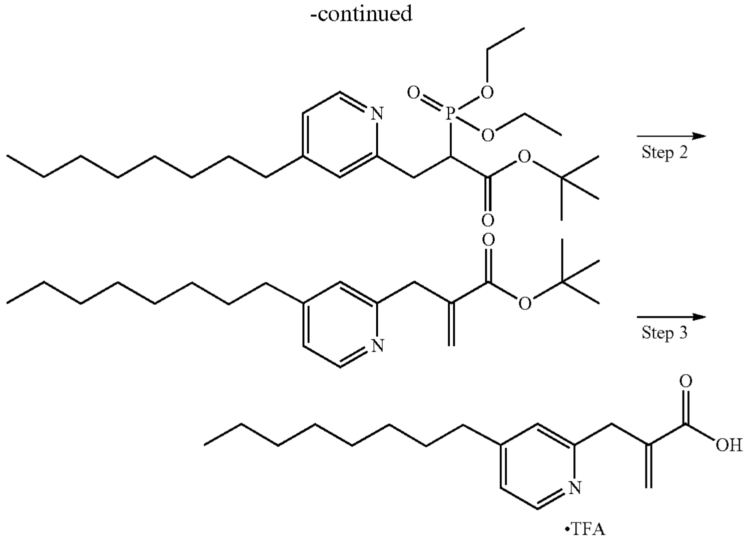

Step 1

Prepared according to General Procedure A, Step 1, Method D from 2-(chloromethyl)-4-octylpyridine (1.3 g, 5.42 mmol). The crude product was purified by flash column chromatography (80 g silica, 0-40% MTBE/petroleum ether) to give tert-butyl 2-(diethoxyphosphoryl)-3-(4-octylpyridin-2-yl)propanoate (1.20 g, 2.63 mmol, 49%) as a brown oil. LCMS: (System 2, Method B) m/z 456.3 $(M+H)^+$ $(ES^+)$.

Step 2

Prepared according to General Procedure A, Step 2, Method C from tert-butyl 2-(diethoxyphosphoryl)-3-(4-octylpyridin-2-yl)propanoate (0.70 g, 1.54 mmol). The crude product was purified by flash column chromatography (40 g silica, 0-20% MTBE/petroleum ether) to give tert-butyl 2-((4-octylpyridin-2-yl)methyl)acrylate (200 mg, 0.60 mmol, 39%) as a colorless oil. LCMS: (System 2, Method C) m/z 332.4 $(M+H)^+$ $(ES^+)$.

Step 3

Prepared according to General Procedure A, Step 3 from tert-butyl 2-((4-octylpyridin-2-yl)methyl)acrylate (180 mg, 0.54 mmol). The crude product was purified by preparative HPLC (Column: Waters X-Bridge C18 OBD 10 μm 19×250 mm; Flow Rate: 20 mL/min; solvent system: MeCN/(0.1% TFA/water) gradient: 50-95% MeCN; collection wavelength: 214 nm). The fractions were concentrated under reduced pressure at 35° C. to remove MeCN, and the residue was lyophilized to give 2-((4-octylpyridin-2-yl)methyl)acrylic acid trifluoroacetic acid salt (112 mg, 0.29 mmol, 54%) as a colorless oil. LCMS: (System 2, Method B) m/z 276.3 $(M+H)^+$ $(ES^+)$. $^1H$ NMR (400 MHz, DMSO-d6) δ: 12.95 (br, 1H), 8.45 (d, J=5.3 Hz, 1H), 7.28 (s, 2H), 6.19 (s, 1H), 5.65 (s, 1H), 3.76 (s, 2H), 2.63 (t, J=7.7 Hz, 2H), 1.62-1.51 (m, 2H), 1.32-1.18 (m, 10H), 0.85 (t, J=6.7 Hz, 3H). One exchangeable proton not observed.

The following compounds were prepared by an analogous procedure:

| Example No. | Starting material used in step 1/ Example Structure/Name | LCMS/$^1H$ NMR data |
|---|---|---|
| 105 | 2-(chloromethyl)-5-octylpyridine 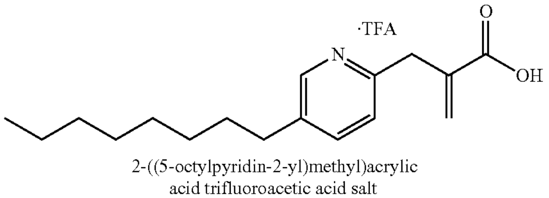 2-((5-octylpyridin-2-yl)methyl)acrylic acid trifluoroacetic acid salt | LCMS (System 2, Method B) m/z 276.3 $(M + H)^+$ $(ES^+)$. $^1H$ NMR (400 MHz, DMSO-d6) δ: 12.77 (br, 1H), 8.34 (d, J = 2.3 Hz, 1H), 7.62 (dd, J = 8.0, 2.3 Hz, 1H), 7.20 (d, J = 8.0 Hz, 1H), 6.15 (d, J = 1.6 Hz, 1H), 5.58 (d, J = 1.7 Hz 1H), 3.70 (s, 2H), 2.55 (t, J = 7.8 Hz, 2H), 1.60-1.48 (m, 2H), 1.33-1.17 (m, 10H), 0.85 (t, J = 6.8 Hz, 3H). One exchangable proton not observed. |
| 106 | 2-(chloromethyl)-5-octylpyrimidine 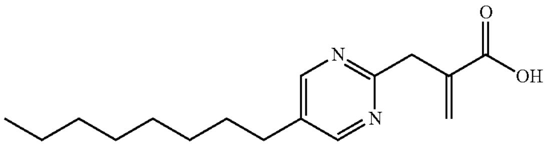 2-((5-octylpyrimidin-2-yl)methyl)acrylic acid | LCMS (System 2, Method B) m/z 277.1 $(M + H)^+$ $(ES^+)$. $^1H$ NMR (400 MHz, DMSO-d6) δ: 12.39 (br, 1H), 8.56 (s, 2H), 6.14 (d, J = 1.7 Hz, 1H), 5.61 (d, J = 1.7 Hz, 1H), 3.84 (s, 2H), 2.53 (t, J = 7.6 Hz, 2H), 1.61-1.49 (m, 2H), 1.32-1.16 (m, 10H), 0.85 (t, J = 6.7 Hz, 3H). |

-continued

| Example No. | Starting material used in step 1/ Example Structure/Name | LCMS/$^1$H NMR data |
|---|---|---|
| 113 | 2-(chloromethyl)-5-octylpyrazine 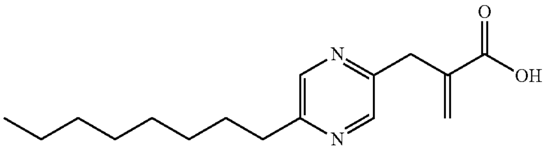 2-((5-octylpyrazin-2-yl)methyl)acrylic acid | LCMS (System 2, Method B) m/z 277.3 $(M + H)^+$ $(ES^+)$. $^1$H NMR (400 MHz, DMSO-d6) δ: 12.57 (br, 1H), 8.42 (s, 2H), 6.16 (d, J = 1.6 Hz, 1H), 5.63 (d, J = 1.4 Hz, 1H), 3.72 (s, 2H), 2.71 (t, J = 7.5 Hz, 2H), 1.70-1.58 (m, 2H), 1.32-1.17 (m, 10H), 0.85 (t, J = 6.9 Hz, 3H). |
| 116 | 3-(chloromethyl)-6-octylpyridazine 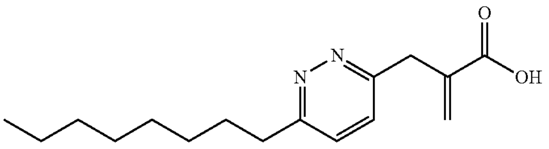 2-((6-octylpyridazin-3-yl)methyl)acrylic acid | LCMS (System 2, Method B) m/z 277.1 $(M + H)^+$ $(ES^+)$. $^1$H NMR (400 MHz, DMSO-d6) δ: 12.59 (br, 1H), 7.51 (d, J = 8.6 Hz, 1H), 7.44 (d, J = 8.6 Hz, 1H), 6.19 (s, 1H), 5.63 (d, J = 1.6 Hz, 1H), 3.86 (s, 2H), 2.85 (t, J = 7.7 Hz, 2H), 1.73-1.60 (m, 2H), 1.35-1.16 (m, 10H), 0.85 (t, J = 6.6 Hz, 3H). |

Example 107—2-((5-methyl-4-octyloxazol-2-yl)methyl)acrylic acid

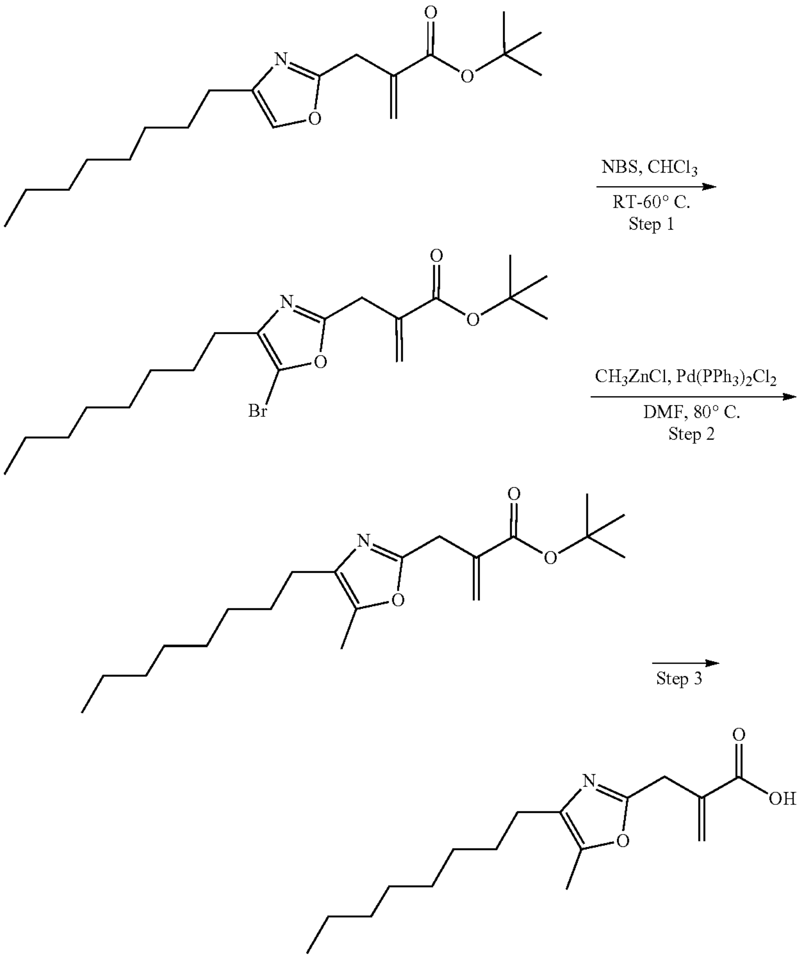

Step 1

A mixture of tert-butyl 2-((4-octyloxazol-2-yl)methyl) acrylate (100 mg, 0.31 mmol) and NBS (109 mg, 0.62 mmol) in $CHCl_3$ (4 mL) was stirred at room temperature for 1 h and heated at reflux for 0.5 h. The reaction mixture was diluted with $H_2O$ (5 mL), the phases were separated and the aqueous layer was extracted with DCM (3x5 mL). The combined organic layers were washed with $H_2O$ (2x5 mL) and brine, dried over $Na_2SO_4$, filtered and concentrated under reduced pressure at 35° C. The residue was purified by flash column chromatography (25 g silica, 0-30% MTBE/petroleum ether) to give tert-butyl 2-((5-bromo-4-octyloxazol-2-yl)methyl)acrylate (100 mg, 0.25 mmol, 80%) as a colorless oil. LCMS: (System 2, Method C) m/z 400.2/402.2 $(M+H)^+$ $(ES^+)$. $^1H$ NMR (400 MHz, $CDCl_3$) δ: 6.28 (d, J=1.0 Hz, 1H), 5.61 (q, J=1.3 Hz, 1H), 3.71 (s, 2H), 2.40 (t, J=7.6 Hz, 2H), 1.57 (s, 2H), 1.45 (s, 9H), 1.34-1.19 (m, 10H), 0.87 (t, J=6.8 Hz, 3H).

Step 2

A mixture of tert-butyl 2-((5-bromo-4-octyloxazol-2-yl) methyl)acrylate (100 mg, 0.25 mmol), $Pd(PPh_3)_2Cl_2$ (526 mg, 0.75 mmol) and $CH_3ZnCl$ solution in diethyl ether (2 M, 2 mL, 4.0 mmol) in dimethylformamide (5 mL) was stirred at 80° C. for 12 h. The reaction mixture was diluted with $H_2O$ (5 mL) and extracted with EtOAc (3x5 mL). The combined organic layers were washed with $H_2O$ (2x5 mL) and brine, dried over $Na_2SO_4$, filtered and concentrated under reduced pressure at 35° C. The residue was purified by flash column chromatography (25 g silica, 0-30% MTBE/petroleum ether) to give tert-butyl 2-((5-methyl-4-octyloxazol-2-yl)methyl)acrylate (42 mg, 0.13 mmol, 50%) as a colorless oil. LCMS: (System 2, Method C) m/z 336.4 $(M+H)^+$ $(ES^+)$.

Step 3

Prepared according to General Procedure A, Step 3 from tert-butyl 2-((5-methyl-4-octyloxazol-2-yl)methyl)acrylate (42 mg, 0.13 mmol). The crude product was purified by preparative HPLC (Column: Waters X-Bridge C18 OBD 10 μm 19x250 mm; Flow Rate: 20 mL/min; solvent system: MeCN/(0.1% TFA/water) gradient: 45-95% MeCN; collection wavelength: 214 nm). The fractions were concentrated under reduced pressure at 35° C. to remove MeCN, and the residue was lyophilized to give 2-((5-methyl-4-octyloxazol-2-yl)methyl)acrylic acid (19 mg, 0.07 mmol, 52%) as colorless oil. LCMS: (System 2, Method B) m/z 280.2 $(M+H)^+$ $(ES^+)$. $^1H$ NMR (400 MHz, $CDCl_3$) δ: 6.42 (s, 1H), 5.74 (s, 1H), 3.74 (s, 2H), 2.38 (t, J=7.6 Hz, 2H), 2.20 (s, 3H), 1.61-1.50 (m, 2H), 1.34-1.18 (m, 10H), 0.87 (t, J=6.7 Hz, 3H). One exchangeable proton not observed.

Example 108—2-(hydroxy(3-octyl-1,2,4-oxadiazol-5-yl)methyl)acrylic acid

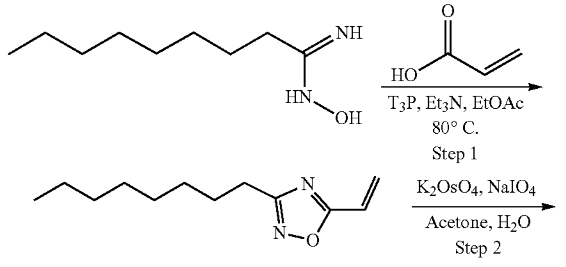

-continued

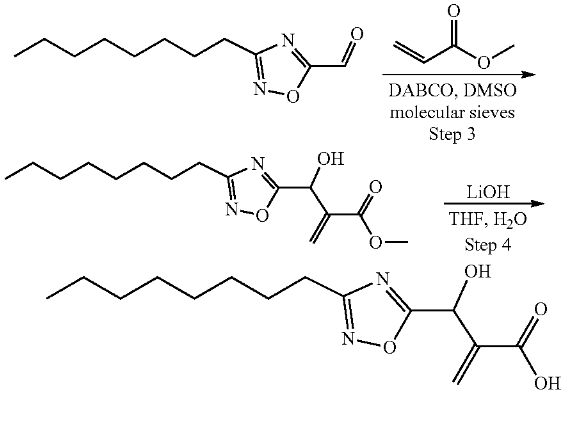

Step 1

To a solution of N-hydroxynonanimidamide (13.28 g, 77.1 mmol), acrylic acid (5.56 g, 77.2 mmol) and triethylamine (23.4 g, 231 mmol) in EtOAc (65 mL) at room temperature was added a solution of $T_3P$ in EtOAc (50 wt. %, 123 g, 193 mmol). The resulting mixture was stirred at 80° C. overnight. The mixture was quenched with water (100 mL), separated and the aqueous phase extracted with EtOAc (3x65 mL). The combined organic layers were washed with brine, dried over $Na_2SO_4$ and filtered. The filtrate was concentrated under reduced pressure at 40° C., and the residue was purified by flash column chromatography (120 g silica, 5% MTBE/petroleum ether) to give 3-octyl-5-vinyl-1,2,4-oxadiazole (6.90 g, 33.1 mmol, 43%) as a pale yellow oil. LCMS: (System 2, Method C) m/z 209.4 $(M+H)^+$ $(ES^+)$.

Step 2

To a solution of 3-octyl-5-vinyl-1,2,4-oxadiazole (6.90 g, 33.1 mmol) and $K_2OsO_4$ (0.55 g, 1.65 mmol) in acetone (128 mL) and water (69 mL) at room temperature was added $NaIO_4$ (21.26 g, 99.4 mmol), and the resulting mixture was stirred at room temperature overnight. The mixture was diluted with water (50 mL) and concentrated under reduced pressure to remove the acetone. The aqueous residue was extracted with EtOAc (3x100 mL), the combined organic phases were washed with brine, dried over $Na_2SO_4$ and filtered. The filtrate was concentrated under reduced pressure at 40° C., and the residue was purified by flash column chromatography (80 g silica, 45% MTBE/petroleum ether) to give 3-octyl-1,2,4-oxadiazole-5-carbaldehyde (6.24 g, 29.7 mmol, 89%) as a white solid. LCMS: (System 2, Method C) m/z 211.3 $(M+H)^+$ $(ES^+)$.

Step 3

A mixture of 3-octyl-1,2,4-oxadiazole-5-carbaldehyde (6.00 g, 28.5 mmol), methyl acrylate (3.69 g, 42.9 mmol), DABCO (1.60 g, 14.3 mmol) and molecular sieves (6.00 g) in DMSO (60 mL) was stirred at room temperature for 3 h. The reaction mixture was filtered, the filtrate was poured into water (300 mL) and the mixture was extracted with EtOAc (3x300 mL). The combined organic phases were washed with brine, dried over $Na_2SO_4$ and filtered. The filtrate was concentrated under reduced pressure at 40° C., and the residue was purified by flash column chromatography (80 g silica, 45% MTBE/petroleum ether) to give methyl 2-(hydroxy(3-octyl-1,2,4-oxadiazol-5-yl)methyl) acrylate (1.35 g, 4.55 mmol, 16%) as a yellow oil. LCMS: (System 2, Method C) m/z 297.2 $(M+H)^+$ $(ES^+)$.

Step 4

LiOH solution in water (2 M, 0.3 mL, 0.6 mmol) was added to a solution of methyl 2-(hydroxy(3-octyl-1,2,4-oxadiazol-5-yl)methyl)acrylate (184 mg, 0.62 mmol) in THF (0.9 mL), and the resulting mixture was stirred at room temperature for 0.5 h. The mixture was adjusted to pH=6 using dilute aqueous HCl (0.5 M) and extracted with EtOAc (3x300 mL). The combined organic layers were washed with brine, dried over $Na_2SO_4$ and filtered. The filtrate was concentrated under reduced pressure at 40° C. and the residue was purified by preparative HPLC (Column: Waters X-Bridge C18 OBD 10 μm 19x250 mm; Flow Rate: 20 mL/min; solvent system: MeCN/(0.1% TFA/water) gradient: 35-95% MeCN; collection wavelength: 214 nm). The fractions were concentrated under reduced pressure at 40° C. to remove MeCN, and the residue was lyophilized to give 2-(hydroxy(3-octyl-1,2,4-oxadiazol-5-yl)methyl)acrylic acid (34 mg, 0.12 mmol, 19%) as a white solid. LCMS: (System 2, Method B) m/z 283.1 $(M+H)^+$ $(ES^+)$. $^1H$ NMR (400 MHz, DMSO-d6) δ: 12.83 (br, 1H), 6.70 (br, 1H), 6.36 (s, 1H), 6.11 (s, 1H), 5.59 (s, 1H), 2.66 (t, J=7.5 Hz, 2H), 1.68-1.55 (m, 2H), 1.34-1.16 (m, 10H), 0.85 (t, J=6.9 Hz, 3H).

Example 109—2-((5-butyl-4-(4-chlorophenyl)oxazol-2-yl)methyl)acrylic acid

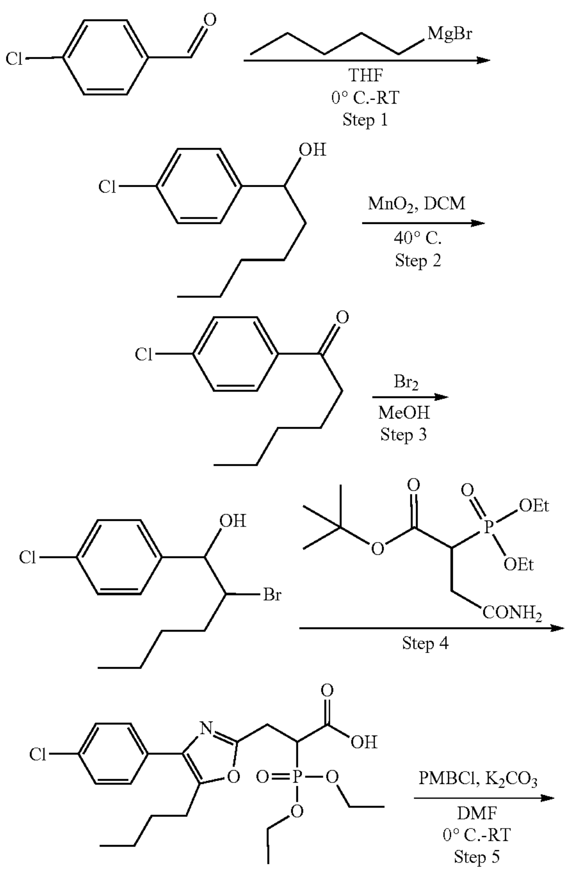

-continued

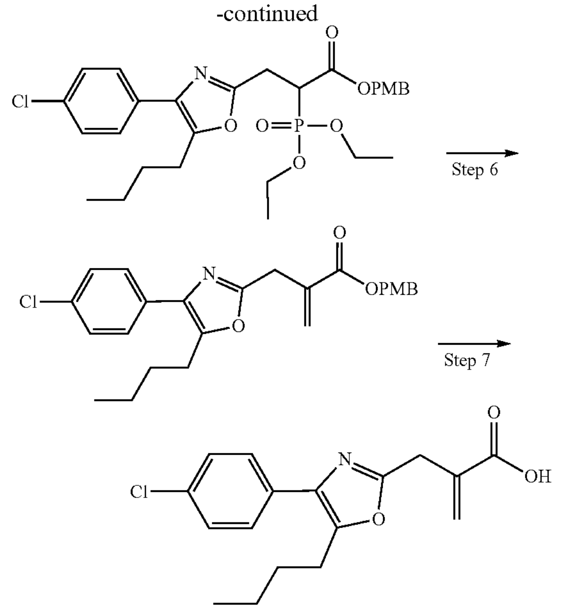

Step 1

To a solution of 4-chlorobenzaldehyde (3.70 g, 26.3 mmol) in THF (132 mL) at 0° C. was added a solution of pentylmagnesium bromide in THF (1 M, 31.6 mL, 31.6 mmol), and the reaction mixture was stirred at room temperature for 16 h. The reaction mixture was quenched with saturated aqueous $NH_4Cl$ solution (100 mL) and extracted with EtOAc (2x100 mL). The combined organic layers were washed with brine, dried over $Na_2SO_4$, filtered and concentrated under reduced pressure at 30° C. The residue was purified by flash column chromatography (80 g silica, 0-10% MTBE/petroleum ether) to give 1-(4-chlorophenyl)hexan-1-ol (4.2 g, 19.7 mmol, 75%) as a yellow oil. $^1H$ NMR (400 MHz, $CDCl_3$) δ: 7.29 (q, J=8.6 Hz, 4H), 4.64 (dd, J=7.5, 5.8 Hz, 1H), 1.81-1.71 (m, 1H), 1.70-1.59 (m, 1H), 1.45-1.33 (m, 1H), 1.33-1.19 (m, 5H), 0.92-0.81 (m, 3H). One exchangeable proton not observed.

Step 2

A mixture of 1-(4-chlorophenyl)hexan-1-ol (4.2 g, 19.7 mmol) and $MnO_2$ (6.87 g, 79.0 mmol) in DCM (100 mL) was stirred at 40° C. for 16 h. The mixture was filtered, and the filtrate was concentrated under reduced pressure at 35° C. to give 1-(4-chlorophenyl)hexan-1-one (3.80 g, 18.0 mmol, 91%) as a yellow oil, which was used directly in the next step. $^1H$ NMR (400 MHz, $CDCl_3$) δ: 7.89 (d, J=8.6 Hz, 2H), 7.43 (d, J=8.5 Hz, 2H), 2.93 (t, J=7.4 Hz, 2H), 1.78-1.67 (m, 2H), 1.42-1.29 (m, 4H), 0.91 (t, J=6.9 Hz, 3H).

Step 3

To a solution of 1-(4-chlorophenyl)hexan-1-one (1.50 g, 7.12 mmol) in MeOH (35 mL) at room temperature was added $Br_2$ (1.46 g, 9.26 mmol) dropwise, and the reaction mixture was stirred at room temperature for 16 h. The reaction mixture was adjusted to pH=7 with saturated aqueous $NaHCO_3$, and the mixture was concentrated under reduced pressure at 35° C. to remove MeOH. The residual aqueous layer was extracted with EtOAc (2x40 mL), and the combined organic layers were dried over $Na_2SO_4$, filtered and concentrated under reduced pressure at 35° C. The residue was purified by flash column chromatography (40 g silica, 0-10% MTBE/petroleum ether) to give 2-bromo-1-

(4-chlorophenyl)hexan-1-one (1.40 g, 4.83 mmol, 68%) as a yellow oil. LCMS: (System 2, Method C) m/z 289.1/291.1 $(M+H)^+$ $(ES^+)$.

Step 4

Prepared according to Example 39, Step 1 using 2-bromo-1-(4-chlorophenyl)hexan-1-one (1.37 g, 4.73 mmol) except that the mixture was stirred at 50° C. for 16 h, not at RT. The reaction mixture was filtered, and the filtrate was concentrated under reduced pressure at 35° C. The residue was purified by reversed phase flash chromatography to give crude 3-(5-butyl-4-(4-chlorophenyl)oxazol-2-yl)-2-(diethoxyphosphoryl)propanoic acid (200 mg, 0.45 mmol, 9%) as a pale yellow oil, which was used directly in the next step. LCMS: (System 2, Method C) m/z 444.2 $(M+H)^+$ $(ES^+)$.

Step 5

To a mixture of 3-(5-butyl-4-(4-chlorophenyl)oxazol-2-yl)-2-(diethoxyphosphoryl)propanoic acid (200 mg, 0.45 mmol) and $K200_3$ (93 mg, 0.68 mmol) in dimethylformamide (3 mL) at 0° C. was added PMBCI (85 mg, 0.54 mmol), and the reaction mixture was stirred at room temperature for 16 h. The reaction mixture was quenched with water and extracted with EtOAc. The combined organic layers were washed with water and saturated aqueous $NH_4Cl$ solution, then dried over $Na_2SO_4$ and filtered. The filtrate was concentrated under reduced pressure at 30° C., and the residue was purified by flash column chromatography (12 g silica, 0-40% MTBE/petroleum ether) to give 4-methoxybenzyl 3-(5-butyl-4-(4-chlorophenyl)oxazol-2-yl)-2-(diethoxyphosphoryl)propanoate (70 mg, 0.12 mmol, 27%) as a yellow oil. LCMS: (System 2, Method C) m/z 564.0 $(M+H)^+$ $(ES^+)$.

Step 6

Prepared according to General Procedure A, Step 2, Method C from 4-methoxybenzyl 3-(5-butyl-4-(4-chlorophenyl)oxazol-2-yl)-2-(diethoxyphosphoryl)propanoate (70 mg, 0.12 mmol). The crude product was purified by flash column chromatography (10% MTBE/petroleum ether) to give 4-methoxybenzyl 2-((5-butyl-4-(4-chlorophenyl)oxazol-2-yl)methyl)acrylate (34 mg, 0.077 mmol, 64%) as a pale yellow oil. LCMS: (System 2, Method C) m/z 440.0 $(M+H)^+$ $(ES^+)$.

Step 7

Prepared according to General Procedure A, Step 3 from 4-methoxybenzyl 2-((5-butyl-4-(4-chlorophenyl)oxazol-2-yl)methyl)acrylate (34 mg, 0.077 mmol). The crude product was purified by preparative HPLC (Column: Waters X-Bridge C18 OBD 10 μm 19×250 mm; Flow Rate: 20 mL/min; solvent system: MeCN/(0.05% TFA/water) gradient: 45-95% MeCN; collection wavelength: 214 nm). The fractions were concentrated under reduced pressure at 30° C. to remove MeCN, and the residue was lyophilized to give 2-((5-butyl-4-(4-chlorophenyl)oxazol-2-yl)methyl)acrylic acid (16 mg, 0.050 mmol 65%) as a white solid. LCMS: (System 2, Method B) m/z 320.1 $(M+H)^+$ $(ES^+)$. $^1H$ NMR (400 MHz, DMSO-d6) δ: 12.71 (s, 1H), 7.63 (d, J=8.7 Hz, 2H), 7.48 (d, J=8.6 Hz, 2H), 6.21 (s,1H), 5.77 (s, 1H), 3.74 (s, 2H), 2.85 (t, J=7.5 Hz, 2H), 1.65-1.54 (m, 2H), 1.38-1.26 (m, 2H), 0.87 (t, J=7.4 Hz, 3H).

Example 110—2-(methoxy(3-octyl-1,2,4-oxadiazol-5-yl)methyl)acrylic acid

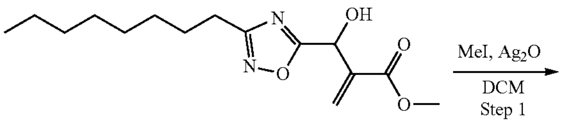

-continued

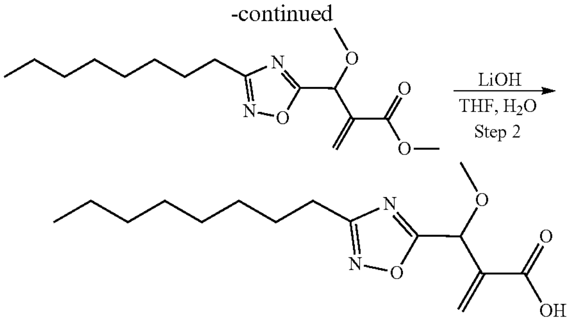

Step 1

To a solution of methyl 2-(hydroxy(3-octyl-1,2,4-oxadiazol-5-yl)methyl)acrylate (300 mg, 1.01 mmol) in DCM (3.1 mL) was added methyl iodide (860 mg, 6.06 mmol) and $Ag_2O$ (470 mg, 2.03 mmol). The mixture was stirred at room temperature under a $N_2$ atmosphere for 16 h. The mixture was filtered through a plug of Celite and the residue was washed with DCM. The filtrate was concentrated under reduced pressure at 40° C. and the residue was purified by flash column chromatography (8 g silica, 15% EtOAc/petroleum ether) to give methyl 2-(methoxy(3-octyl-1,2,4-oxadiazol-5-yl)methyl)acrylate (126 mg, 0.41 mmol, 41%) as a yellow oil. LCMS: (System 2, Method C) m/z 311.2 $(M+H)^+$ $(ES^+)$.

Step 2

To a solution of methyl 2-(methoxy(3-octyl-1,2,4-oxadiazol-5-yl)methyl)acrylate (224 mg, 0.72 mmol) in THF (2.4 mL) was added LiOH solution in water (2 M, 0.8 mL, 1.6 mmol), and the resulting mixture was stirred at room temperature for 2 h. The mixture was adjusted to pH=6 using dilute aqueous HCl (0.5 M) and then extracted with EtOAc (3×30 mL). The combined organic phases were washed with brine, dried over $Na_2SO_4$ and filtered. The filtrate was concentrated under reduced pressure at 40° C. and the residue was purified by preparative HPLC (Column: Waters X-Bridge C18 OBD 10 μm 19×250 mm; Flow Rate: 20 mL/min; solvent system: MeCN/(0.1% TFA/water) gradient: 55-95% MeCN; collection wavelength: 214 nm). The fractions were concentrated under reduced pressure at 40° C. to remove MeCN, and the residue was lyophilized to give 2-(methoxy(3-octyl-1,2,4-oxadiazol-5-yl)methyl)acrylic acid (33 mg, 0.11 mmol, 15%) as a yellow oil. LCMS: (System 2, Method B) m/z 297.2 $(M+H)^+$ $(ES^+)$. $^1H$ NMR (400 MHz, $CDCl_3$) δ: 6.70 (s, 1H), 6.30 (s, 1H), 5.36 (s, 1H), 3.50 (s, 3H), 2.74 (t, J=7.7 Hz, 2H), 1.80-1.68 (m, 2H), 1.40-1.18 (m, 10H), 0.87 (t, J=6.7 Hz, 3H). One exchangeable proton not observed.

Example 111—2-((3-(1-(4-cyclobutoxyphenyl)cyclopropyl)-1,2,4-oxadiazol-5-yl)methyl)acrylic acid

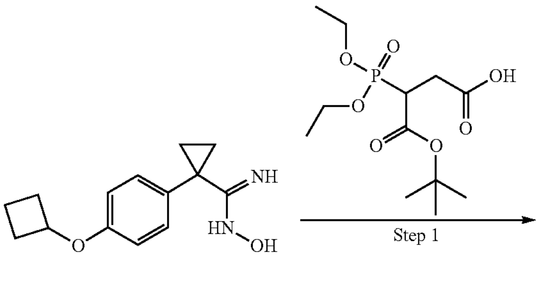

-continued

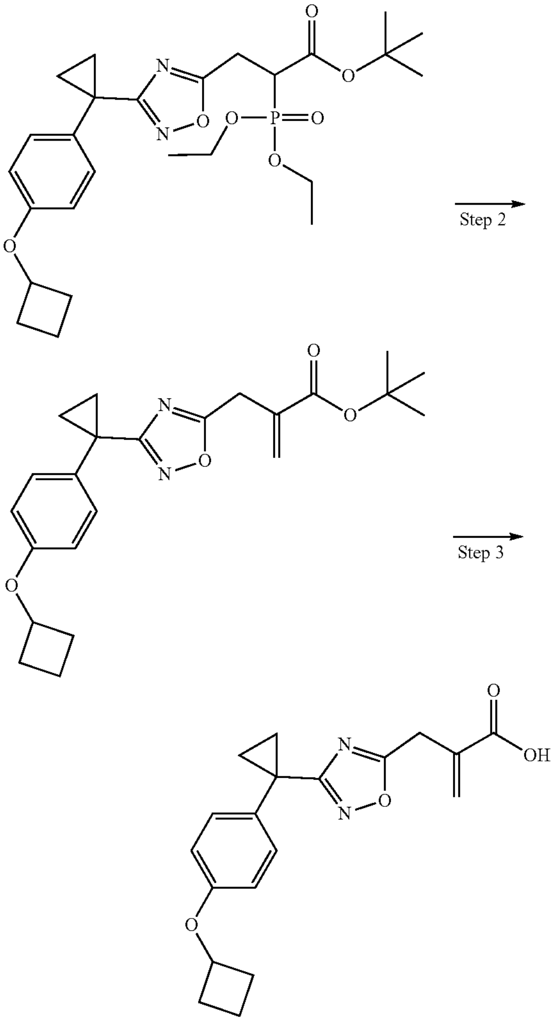

Step 1

Prepared according to General Procedure B, Method B from 1-(4-cyclobutoxyphenyl)-N-hydroxycyclopropane-1-carboximidamide (1.30 g, 5.28 mmol). The crude product was purified by flash column chromatography (50 g silica, 20-40% EtOAC/petroleum ether) to give tert-butyl 3-(3-(1-(4-cyclobutoxyphenyl)cyclopropyl)-1,2,4-oxadiazol-5-yl)-2-(diethoxyphosphoryl)propanoate (2.20 g, 4.23 mmol, 80%) as a colorless oil. LCMS: (System 2, Method C) m/z 521.1 $(M+H)^+$ $(ES^+)$.

Step 2

Prepared according to General Procedure A, Step 2, Method C from tert-butyl 3-(3-(1-(4-cyclobutoxyphenyl)cyclopropyl)-1,2,4-oxadiazol-5-yl)-2-(diethoxyphosphoryl)propanoate (2.20 g, 4.23 mmol). The crude product was purified by flash column chromatography (25 g silica, 0-20% MTBE/petroleum ether) to give tert-butyl 2-((3-(1-(4-cyclobutoxyphenyl)cyclopropyl)-1,2,4-oxadiazol-5-yl)methyl)acrylate (1.20 g, 3.03 mmol, 72%) as a colorless oil. LCMS: (System 2, Method C) m/z 379.3 $(M+H)^+$ $(ES^+)$.

Step 3

Prepared according to General Procedure A, Step 3 from tert-butyl 2-((3-(1-(4-cyclobutoxyphenyl)cyclopropyl)-1,2,4-oxadiazol-5-yl)methyl)acrylate (0.40 g, 1.01 mmol). The crude product was purified by preparative HPLC (Column: Waters X-Bridge C18 OBD 10 μm 19×250 mm; Flow Rate: 20 mL/min; solvent system: MeCN/(0.2% formic acid/water) gradient: 70-95% MeCN; collection wavelength: 214 nm). The fractions were concentrated under reduced pressure at 30° C. to remove MeCN, and the residue was lyophilized to give 2-((3-(1-(4-cyclobutoxyphenyl)cyclopropyl)-1,2,4-oxadiazol-5-yl)methyl)acrylic acid (233 mg, 0.68 mmol, 68%) as a white solid. LCMS: (System 2, Method B) m/z 341.0 $(M+H)^+$ $(ES^+)$. $^1H$ NMR (400 MHz, DMSO-d6) δ: 12.81 (br, 1H), 7.29-7.23 (m, 2H), 6.81-6.74 (m, 2H), 6.26 (d, J=1.2 Hz, 1H), 5.89 (d, J=1.3 Hz, 1H), 4.72-4.61 (m, 1H), 3.86 (s, 2H), 2.47-2.37 (m, 2H), 2.08-1.95 (m, 2H), 1.83-1.71 (m, 1H), 1.70-1.56 (m, 1H), 1.42-1.35 (m, 2H), 1.31-1.24 (m, 2H).

Example 112—2-((3-(4-cyclopentylbenzyl)-1,2,4-oxadiazol-5-yl)methyl)acrylic acid

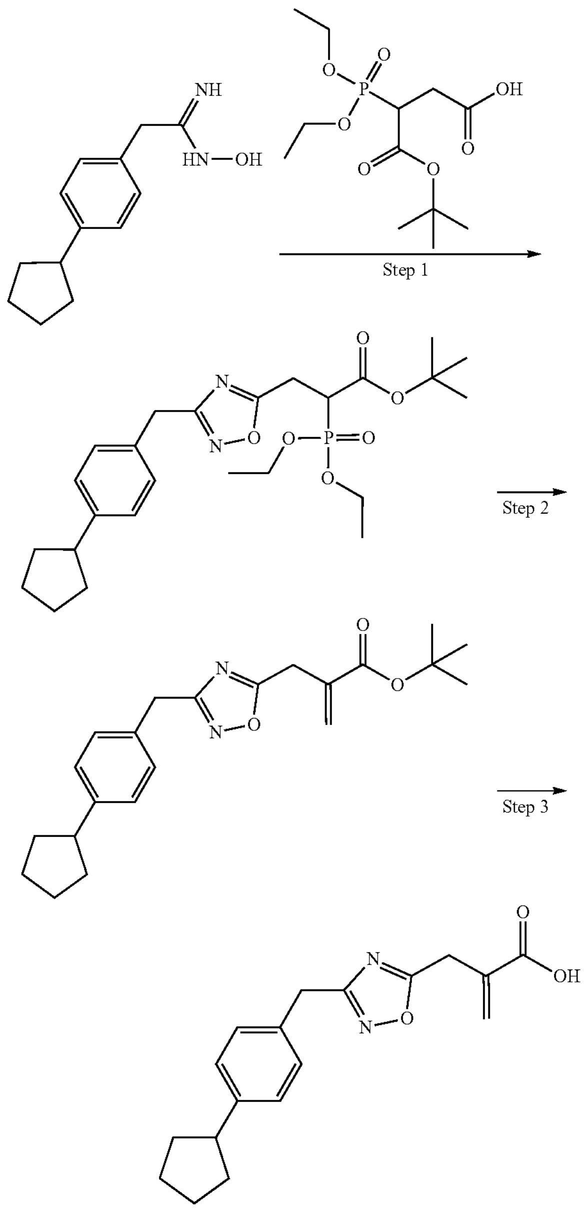

Step 1

Prepared according to General Procedure B, Method B from 2-(4-cyclopentylphenyl)-N-hydroxyacetimidamide (420 mg, 1.92 mmol). The crude product was purified by flash column chromatography (25 g silica, 20-40% EtOAC/petroleum ether) to give tert-butyl 3-(3-(4-cyclopentylbenzyl)-1,2,4-oxadiazol-5-yl)-2-(diethoxyphosphoryl)propanoate (400 mg, 0.81 mmol, 42%) as a colorless oil. LCMS: (System 2, Method C) m/z 493.2 $(M+H)^+$ $(ES^+)$.

Step 2

Prepared according to General Procedure A, Step 2, Method C from tert-butyl 3-(3-(4-cyclopentylbenzyl)-1,2,4-oxadiazol-5-yl)-2-(diethoxyphosphoryl)propanoate (400 mg, 0.81 mmol). The crude product was purified by flash column chromatography (25 g silica, 0-20% MTBE/petroleum ether) to give tert-butyl 2-((3-(4-cyclopentylbenzyl)-1,2,4-oxadiazol-5-yl)methyl)acrylate (180 mg, 0.49 mmol, 60%) as a colorless oil. LCMS: (System 2, Method C) m/z 369.3 $(M+H)^+$ $(ES^+)$.

Step 3

Prepared according to General Procedure A, Step 3 from tert-butyl 2-((3-(4-cyclopentylbenzyl)-1,2,4-oxadiazol-5-yl)methyl)acrylate (180 mg, 0.49 mmol). The crude product was purified by preparative HPLC (Column: Waters X-Bridge C18 OBD 10 μm 19×250 mm; Flow Rate: 20 mL/min; solvent system: MeCN/(0.2% formic acid/water) gradient: 55-95% MeCN; collection wavelength: 214 nm). The fractions were concentrated under reduced pressure at 30° C. to remove MeCN, and the residue was lyophilized to give 2-((3-(4-cyclopentylbenzyl)-1,2,4-oxadiazol-5-yl)methyl)acrylic acid (105 mg, 0.34 mmol, 69%) as a white solid. LCMS: (System 2, Method B) m/z 313.1 $(M+H)^+$ $(ES^+)$. $^1H$ NMR (400 MHz, DMSO-d6) δ: 12.80 (br, 1H), 7.22-7.13 (m, 4H), 6.26 (s, 1H), 5.90 (s, 1H), 3.99 (s, 2H), 3.89 (s, 2H), 2.96-2.86 (m, 1H), 2.03-1.91 (m, 2H), 1.81-1.68 (m, 2H), 1.68-1.55 (m, 2H), 1.55-1.41 (m, 2H).

The following compounds were prepared by analogous procedures to Examples 111 and 112:

| Example No. | Starting material used in step 1/Example Structure/Name | LCMS/$^1H$ NMR data |
|---|---|---|
| 114 | 1-(4-cyclopropoxyphenyl)-N-hydroxycyclopropane-1-carboximidamide 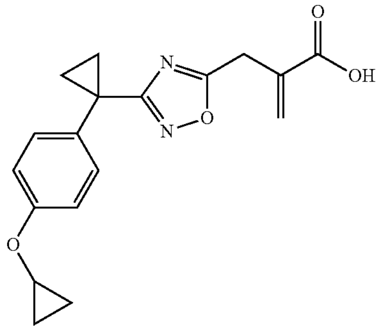 2-((3-(1-(4-cyclopropoxyphenyl)cyclopropyl)-1,2,4-oxadiazol-5-yl)methyl)acrylic acid | LCMS (System 2, Method B) m/z 327.1 $(M + H)^+$ $(ES^+)$. $^1H$ NMR (400 MHz, DMSO-d6) δ: 12.82 (br, 1H), 7.34-7.26 (m, 2H), 7.03-6.95 (m, 2H), 6.26 (d, J = 1.2 Hz, 1H), 5.89 (d, J = 1.3 Hz, 1H), 3.87 (s, 2H), 3.84-3.78 (m, 1H), 1.43-1.37 (m, 2H), 1.32-1.26 (m, 2H), 0.80-0.73 (m, 2H), 0.67-0.60 (m, 2H). |
| 115 | 1-(4-cyclopentylphenyl)-N-hydroxycyclopropane-1-carboximidamide 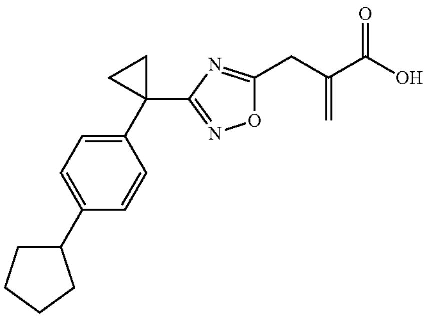 2-((3-(1-(4-cyclopentylphenyl)cyclopropyl)-1,2,4-oxadiazol-5-yl)methyl)acrylic acid | LCMS (System 2, Method B) m/z 339.1 $(M + H)^+$ $(ES^+)$. $^1H$ NMR (400 MHz, DMSO-d6) δ: 12.81 (br, 1H), 7.30-7.25 (m, 2H), 7.23-7.17 (m, 2H), 6.26 (d, J = 1.2 Hz, 1H), 5.89 (d, J = 1.3 Hz, 1H), 3.87 (s, 2H), 3.01-2.88 (m, 1H), 2.06-1.93 (m, 2H), 1.82-1.70 (m, 2H), 1.70-1.57 (m, 2H), 1.57-1.45 (m, 2H), 1.45-1.38 (m, 2H), 1.35-1.28 (m, 2H). |

Example 117—2-((3-(1-(4-iodophenyl)cyclopropyl)-1,2,4-oxadiazol-5-yl)methyl)acrylic acid

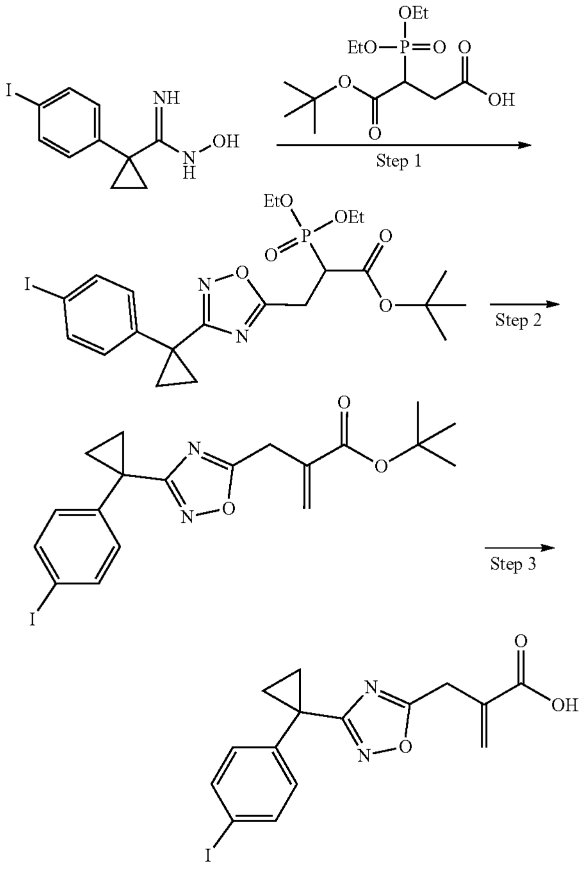

Step 1

HATU (1.23 g, 3.24 mmol) was added to a mixture of 1-(4-iodophenyl)-N-hydroxycyclopropane-1-carboximidamide (0.825 g, 2.70 mmol), 4-(tert-butoxy)-3-(diethoxyphosphoryl)-4-oxobutanoic acid (0.923 g, 2.97 mmol) and triethylamine (1.13 mL, 8.11 mmol) in dimethylformamide (10 mL). The mixture was stirred at RT for 1 h, then sat. aq. $NaHCO_3$ (100 mL) was added. The mixture was extracted with EtOAc (3×80 mL) and the combined organic phases were washed with brine (3×100 mL), dried ($MgSO_4$) and concentrated. The residue was taken up in THF (20 mL) and $Cs_2CO_3$ (1.76 g, 5.39 mmol) was added. The mixture was heated to 70° C. and stirred for 3 h, then cooled to RT, diluted with water (40 mL) and extracted with DCM (3×20 mL). The combined organic phases were dried ($MgSO_4$) and concentrated. The crude product was purified by chromatography on silica gel (0-100% MTBE/isohexane) to afford tert-butyl 2-(diethoxyphosphoryl)-3-(3-(1-(4-iodophenyl)cyclopropyl)-1,2,4-oxadiazol-5-yl)propanoate (1.52 g, 2.5 mmol) as a white solid. LCMS m/z 599.2 $(M+Na)^+$ $(ES^+)$. $^1H$ NMR (400 MHz, DMSO-d6) δ 7.78-7.61 (m, 2H), 7.24-7.07 (m, 2H), 4.16-3.96 (m, 4H), 3.61-3.40 (m, 1H), 3.30-3.24 (m, 1H), 3.24-3.12 (m, 1H), 1.53-1.36 (m, 4H), 1.35 (s, 9H), 1.30-1.17 (m, 6H).

Step 2

Prepared according to General Procedure A, Step 2, Method B from tert-butyl 2-(diethoxyphosphoryl)-3-(3-(1-(4-iodophenyl)cyclopropyl)-1,2,4-oxadiazol-5-yl)propanoate (1.52 g, 2.5 mmol). The crude product was purified by chromatography on silica gel (0-20% MTBE/isohexane) to afford tert-butyl 2-((3-(1-(4-iodophenyl)cyclopropyl)-1,2,4-oxadiazol-5-yl)methyl)acrylate (0.99 g, 2.0 mmol, 90% purity) as a clear and colourless oil. LCMS m/z 397.2 $(M-tBu+H)^+$ $(ES^+)$. $^1H$ NMR (400 MHz, DMSO-d6) δ 7.77-7.62 (m, 2H), 7.23-7.13 (m, 2H), 6.24-6.16 (m, 1H), 5.93-5.82 (m, 1H), 3.88 (s, 2H), 1.46-1.40 (m, 2H), 1.39-1.34 (m, 2H), 1.33 (s, 9H).

Step 3

Prepared according to General Procedure A, Step 3 from tert-butyl 2-((3-(1-(4-iodophenyl)cyclopropyl)-1,2,4-oxadiazol-5-yl)methyl)acrylate (0.99 g, 2.0 mmol, 90% purity). The crude product was purified by chromatography on silica gel (0-30% MTBE/isohexane) to afford 2-((3-(1-(4-iodophenyl)cyclopropyl)-1,2,4-oxadiazol-5-yl)methyl)acrylic acid (0.574 g, 1.4 mmol) as a pale brown solid. LCMS m/z 3971 $(M+H)^+$ $(ES^+)$. $^1H$ NMR (400 MHz, DMSO-d6) δ 12.81 (s, 1H), 7.79-7.56 (m, 2H), 7.28-7.12 (m, 2H), 6.31-6.17 (m, 1H), 5.97-5.79 (m, 1H), 3.88 (s, 2H), 1.48-1.41 (m, 2H), 1.39-1.31 (m, 2H).

Example 118—2-((3-(4-bromophenyl)-1,2,4-oxadiazol-5-yl)methyl)acrylic acid

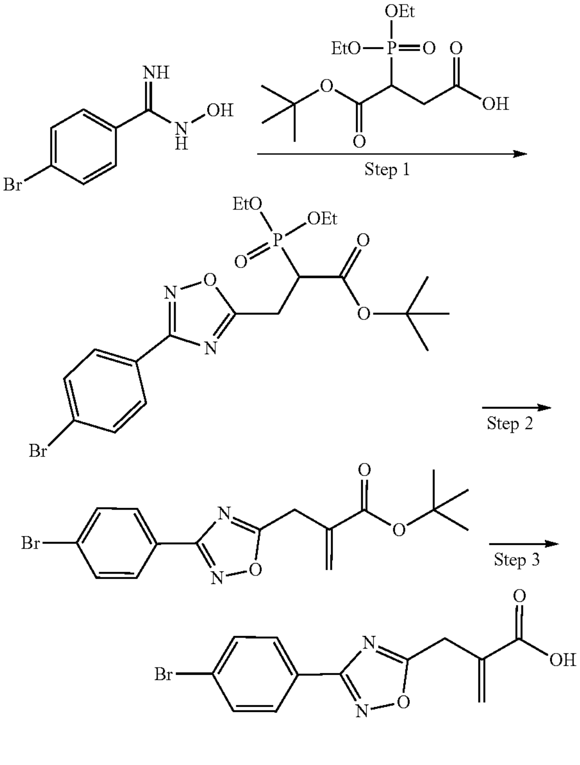

Step 1

Prepared according to General Procedure B, Method A from 4-bromo-N-hydroxybenzimidamide (1.90 g, 8.0 mmol, 90% purity). The crude product was purified by chromatography on RP Flash C18 (5-75% (0.1% Formic acid in MeCN)/(0.1% Formic Acid in Water)) to afford tert-butyl 3-(3-(4-bromophenyl)-1,2,4-oxadiazol-5-yl)-2-(diethoxyphosphoryl)propanoate (1.37 g, 2.5 mmol, 90% purity) as a clear, colourless oil. LCMS m/z 433.2/435.2 $(M-tBu+H)^+$ $(ES^+)$. $^1H$ NMR (400 MHz, DMSO-d6) δ 7.95-7.86 (m, 2H), 7.84-7.75 (m, 2H), 4.18-4.02 (m, 4H), 3.76-3.58 (m, 1H), 3.53-3.34 (m, 2H), 1.37 (s, 9H), 1.26 (q, J=6.8 Hz, 6H).

Step 2

Prepared according to General Procedure A, Step 2, Method B from tert-butyl 3-(3-(4-bromophenyl)-1,2,4-oxadiazol-5-yl)-2-(diethoxyphosphoryl)propanoate (1.37 g, 2.5 mmol, 90% purity). The crude product was purified by chromatography on silica gel (0-20% MTBE/isohexane) to afford tert-butyl 2-((3-(4-bromophenyl)-1,2,4-oxadiazol-5-yl)methyl)acrylate (0.84 g, 2.1 mmol, 90% purity) as a clear and colourless oil. LCMS m/z 309.2/311.2 $(M-tBu+H)^+$ $(ES^+)$. $^1$H NMR (400 MHz, DMSO-d6) δ 7.96-7.88 (m, 2H), 7.83-7.72 (m, 2H), 6.33-6.23 (m, 1H), 6.00-5.93 (m, 1H), 4.04 (s, 2H), 1.33 (s, 9H).

Step 3

Prepared according to General Procedure A, Step 3 from tert-butyl 2-((3-(4-bromophenyl)-1,2,4-oxadiazol-5-yl)methyl)acrylate (0.84 g, 2.1 mmol, 90% purity). The crude product was purified by chromatography on silica gel (0-40% MTBE/isohexane) to afford 2-((3-(4-bromophenyl)-1,2,4-oxadiazol-5-yl)methyl)acrylic acid (0.522 g, 1.6 mmol) as a white solid. LCMS m/z 307.4/309.4 $(M-H)^-$ $(ES^-)$. $^1$H NMR (400 MHz, DMSO-d6) δ 12.88 (s, 1H), 7.95-7.88 (m, 2H), 7.81-7.73 (m, 2H), 6.35-6.29 (m, 1H), 6.03-5.98 (m, 1H), 4.04 (s, 2H).

Example 119—2-((3-(4-iodophenyl)-1,2,4-oxadiazol-5-yl)methyl)acrylic acid

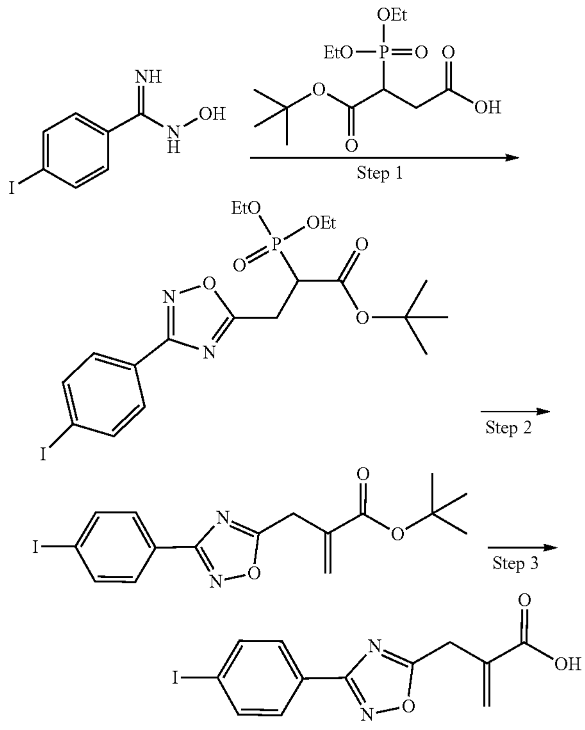

Step 1

Prepared according to General Procedure B, Method A from 4-iodo-N-hydroxybenzimidamide (1.3 g, 4.5 mmol, 90% purity). The crude product was purified by chromatography on RP Flash C18 (5-75% (0.1% Formic acid in MeCN)/(0.1% Formic Acid in Water)) to afford tert-butyl 3-(3-(4-iodophenyl)-1,2,4-oxadiazol-5-yl)-2-(diethoxyphosphoryl)propanoate (1.17 g, 2.1 mmol, 94% purity) as a clear, colourless oil. LCMS m/z 480.8 $(M-tBu+H)^+$ $(ES^+)$. $^1$H NMR (400 MHz, DMSO-d6) δ 8.00-7.90 (m, 2H), 7.80-7.67 (m, 2H), 4.21-4.02 (m, 4H), 3.77-3.58 (m, 1H), 3.53-3.34 (m, 2H), 1.37 (s, 9H), 1.31-1.19 (m, 6H).

Step 2

Prepared according to General Procedure A, Step 2, Method B from tert-butyl 3-(3-(4-iodophenyl)-1,2,4-oxadiazol-5-yl)-2-(diethoxyphosphoryl)propanoate (1.17 g, 2.1 mmol, 94% purity). The crude product was purified by chromatography on silica gel (0-10% MTBE/isohexane) to afford tert-butyl 2-((3-(4-iodophenyl)-1,2,4-oxadiazol-5-yl)methyl)acrylate (0.68 g, 1.5 mmol, 90% purity) as a clear and colourless oil. LCMS m/z 357.1 $(M-tBu+H)^+$ $(ES^+)$. $^1$H NMR (400 MHz, DMSO-d6) δ 8.00-7.89 (m, 2H), 7.83-7.70 (m, 2H), 6.32-6.22 (m, 1H), 6.02-5.89 (m, 1H), 4.04 (s, 2H), 1.32 (s, 9H).

Step 3

Prepared according to General Procedure A, Step 3 from tert-butyl 2-((3-(4-iodophenyl)-1,2,4-oxadiazol-5-yl)methyl)acrylate (0.68 g, 1.5 mmol, 90% purity). The crude product was purified by chromatography on silica gel (0-50% MTBE/isohexane) to afford 2-((3-(4-iodophenyl)-1,2,4-1.0 oxadiazol-5-yl)methyl)acrylic acid (0.411 g, 1.1 mmol) as a white solid. LCMS m/z 354.8 $(M-H)^-$ $(ES^-)$. $^1$H NMR (400 MHz, DMSO-d6) δ 12.87 (s, 1H), 7.99-7.88 (m, 2H), 7.81-7.69 (m, 2H), 6.38-6.25 (m, 1H), 6.06-5.93 (m, 1H), 4.03 (s, 2H).

Example 120—2-((3-(difluoro(4-iodophenyl)methyl)-1,2,4-oxadiazol-5-yl)methyl)acrylic acid

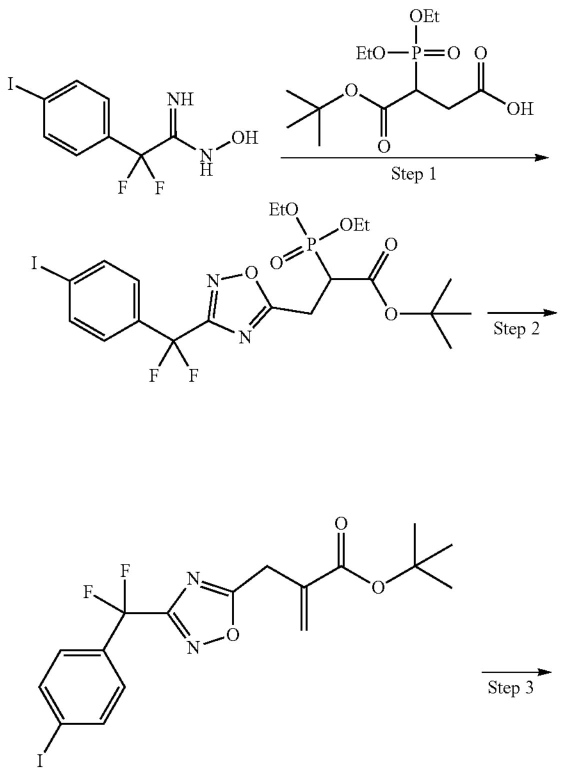

-continued

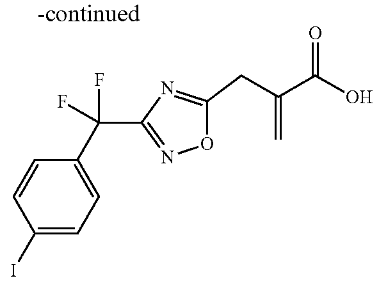

Step 1

Prepared according to General Procedure B, Method A from 2,2-difluoro-N-hydroxy-2-(4-iodophenyl)acetimidamide (4.9 g, 13 mmol, 80% purity). The crude product was purified by chromatography on RP Flash C18 (5-75% (0.1% Formic acid in MeCN)/(0.1% Formic Acid in Water)) to afford tert-butyl 2-(diethoxyphosphoryl)-3-(3-(difluoro(4-iodophenyl)methyl)-1,2,4-oxadiazol-5-yl)propanoate (1.92 g, 2.6 mmol, 79% purity) as a clear, pale yellow oil. LCMS m/z 531.1 $(M-tBu+H)^+$ $(ES^+)$. $^1$H NMR (400 MHz, DMSO-d6) δ 7.99-7.89 (m, 2H), 7.45-7.33 (m, 2H), 4.14-3.99 (m, 4H), 3.71-3.54 (m, 1H), 3.52-3.33 (m, 2H), 1.29 (s, 9H), 1.26-1.19 (m, 6H).

Step 2

Prepared according to General Procedure A, Step 2, Method B from tert-butyl 2-(diethoxyphosphoryl)-3-(3-(difluoro(4-iodophenyl)methyl)-1,2,4-oxadiazol-5-yl)propanoate (1.92 g, 2.6 mmol, 79% purity). The crude product was purified by chromatography on silica gel (0-10% MTBE/isohexane) followed by chromatography on RP Flash C18 (5-75% (0.1% Formic acid in MeCN)/(0.1% Formic Acid in Water)) to afford tert-butyl 2-((3-(difluoro(4-iodophenyl)methyl)-1,2,4-oxadiazol-5-yl)methyl)acrylate (0.50 g, 1 mmol) as a colourless gum. $^1$H NMR (400 MHz, DMSO-d6) δ 8.02-7.84 (m, 2H), 7.47-7.32 (m, 2H), 6.30-6.21 (m, 1H), 6.00-5.90 (m, 1H), 4.04 (s, 2H), 1.23 (s, 9H).

Step 3

Prepared according to General Procedure A, Step 3 from tert-butyl 2-((3-(difluoro(4-iodophenyl)methyl)-1,2,4-oxadiazol-5-yl)methyl)acrylate (0.50 g, 1 mmol). The crude product was purified by chromatography on silica gel (0-50% MTBE/isohexane) to afford 2-((3-(difluoro(4-iodophenyl)methyl)-1,2,4-oxadiazol-5-yl)methyl)acrylic acid (0.326 g, 0.79 mmol) as a white solid. LCMS m/z 405.1 $(M-H)^-$ $(ES^-)$. $^1$H NMR (400 MHz, DMSO-d6) δ 12.90 (s, 1H), 8.01-7.88 (m, 2H), 7.45-7.33 (m, 2H), 6.37-6.24 (m, 1H), 6.04-5.87 (m, 1H), 4.04 (s, 2H).

Example 121—2-((3-(4-(pentafluoro-$\lambda^6$-sulfaneyl)phenyl)-1,2,4-oxadiazol-5-yl)methyl)acrylic acid

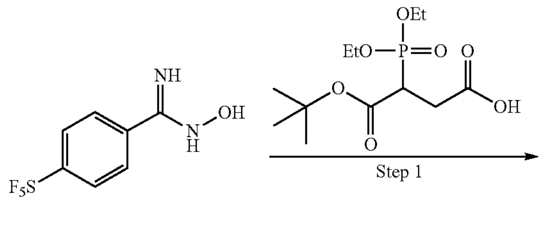

-continued

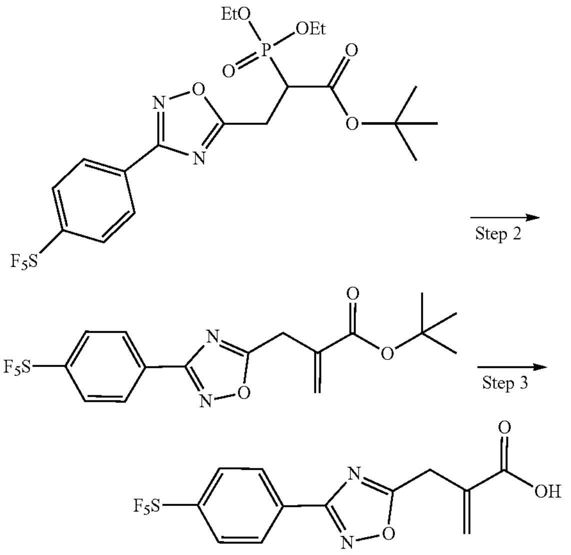

Step 1

Prepared according to General Procedure B, Method B from N-hydroxy-4-(pentafluoro-$\lambda^6$-sulfaneyl)benzimidamide (1.05 g, 4.0 mmol). The crude product was purified by chromatography on silica gel (0-100% MTBE/isohexane) to afford tert-butyl 2-(diethoxyphosphoryl)-3-(3-(4-(pentafluoro-$\lambda^6$-sulfaneyl)phenyl)-1,2,4-oxadiazol-5-yl)propanoate (1.35 g, 2.5 mmol) as a light yellow oil. LCMS m/z 537.3 $(M+H)^+$ $(ES^+)$. $^1$H NMR (400 MHz, DMSO-d6) δ 8.20 (d, J=8.7 Hz, 2H), 8.16-8.11 (m, 2H), 4.17-4.06 (m, 4H), 3.70 (ddd, J=23.4, 10.7, 4.7 Hz, 1H), 3.56-3.44 (m, 1H), 3.39 (ddd, J=16.9, 8.9, 4.7 Hz, 1H), 1.38 (s, 9H), 1.29-1.22 (m, 6H).

Step 2

Prepared according to General Procedure A, Step 2, Method B from tert-butyl 2-(diethoxyphosphoryl)-3-(3-(4-(pentafluoro-$\lambda^6$-sulfaneyl)phenyl)-1,2,4-oxadiazol-5-yl)propanoate (1.35 g, 2.5 mmol). The crude product was purified by chromatography on silica gel (0-50% MTBE/isohexane) to afford tert-butyl 2-((3-(4-(pentafluoro-$\lambda^6$-sulfaneyl)phenyl)-1,2,4-oxadiazol-5-yl)methyl)acrylate (0.858 g, 2.1 mmol) as a clear colourless oil. $^1$H NMR (400 MHz, DMSO-d6) δ 8.21 (d, J=8.9 Hz, 2H), 8.14-8.09 (m, 2H), 6.30 (d, J=1.2 Hz, 1H), 6.02-5.97 (m, 1H), 4.08 (d, J=1.0 Hz, 2H), 1.33 (s, 9H).

Step 3

Prepared according to General Procedure A, Step 3 from tert-butyl 2-((3-(4-(pentafluoro-$\lambda^6$-sulfaneyl)phenyl)-1,2,4-oxadiazol-5-yl)methyl)acrylate (0.858 g, 2.1 mmol). The crude product was purified by chromatography on silica gel (0-50% MTBE/isohexane) to afford 2-((3-(4-(pentafluoro-$\lambda^6$-sulfaneyl)phenyl)-1,2,4-oxadiazol-5-yl)methyl)acrylic acid (0.560 g, 1.6 mmol) as a white solid. LCMS m/z 355.0 $(M-H)^-$ $(ES^-)$. $^1$H NMR (400 MHz, DMSO-d6) δ 12.89 (s, 1H), 8.25-8.17 (m, 2H), 8.14-8.07 (m, 2H), 6.34 (d, J=1.2 Hz, 1H), 6.07-5.99 (m, 1H), 4.07 (s, 2H).

Example 122—2-((3-(4-(pentafluoro-$\lambda^6$-sulfaneyl)phenyl)-1,2,4-oxadiazol-5-yl)methyl)acrylic acid

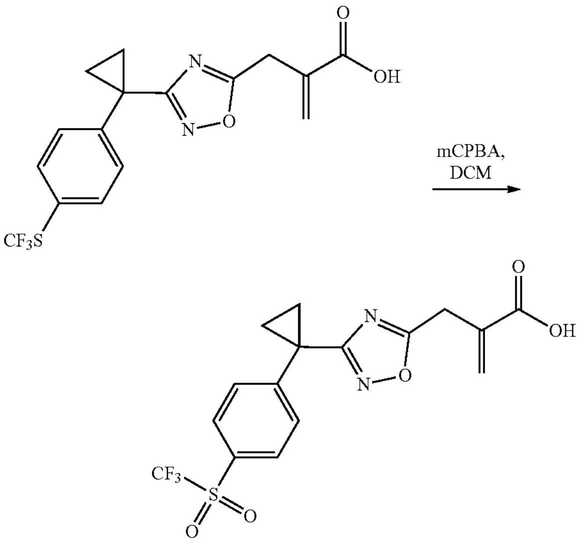

meta-Chloroperbenzoic acid (77 Wt %, 144 mg, 640 μmol was added to a mixture of 2-((3-(1-(4-((trifluoromethyl)thio)phenyl)cyclopropyl)-1,2,4-oxadiazol-5-yl)methyl)acrylic acid (0.100 g, 260 μmol) in DCM (3 mL) at 0° C. The mixture was stirred at 0° C. for 1 h, then at RT for 18 h. The mixture was cooled to 0° C., further meta-Chloroperbenzoic acid (77 Wt %, 100 mg, 450 μmol) was added and the mixture stirred for a further 1 h then warmed to RT and stirred for 18 h. The mixture was diluted with water (20 mL) and extracted with DCM (3x10 mL). The combined organic phases were dried ($MgSO_4$) and concentrated. The crude product was purified by chromatography on silica gel (0-50% MTBE/isohexane) followed by chromatography on RP Flash C18 (5-75% (0.1% Formic acid in MeCN)/(0.1% Formic Acid in Water)) to afford 2-((3-(1-(4-((trifluoromethyl)sulfonyl)phenyl)cyclopropyl)-1,2,4-oxadiazol-5-yl)methyl)acrylic acid (8 mg, 0.02 mmol) as a white solid. LCMS m/z 401.1 $(M-H)^-$ $(ES^-)$. $^1H$ NMR (400 MHz, DMSO-d6) δ 12.85 (s, 1H), 8.18-8.00 (m, 2H), 7.91-7.74 (m, 2H), 6.36-6.15 (m, 1H), 6.00-5.84 (m, 1H), 3.91 (s, 2H), 1.68-1.44 (m, 4H).

Example 123—2-((4,5-dibutyloxazol-2-yl)methyl)acrylic acid

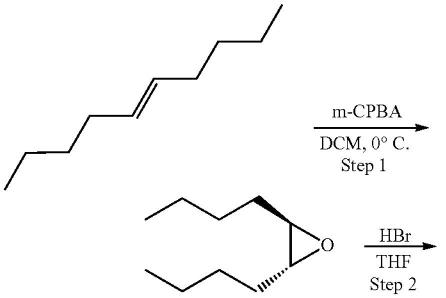

-continued

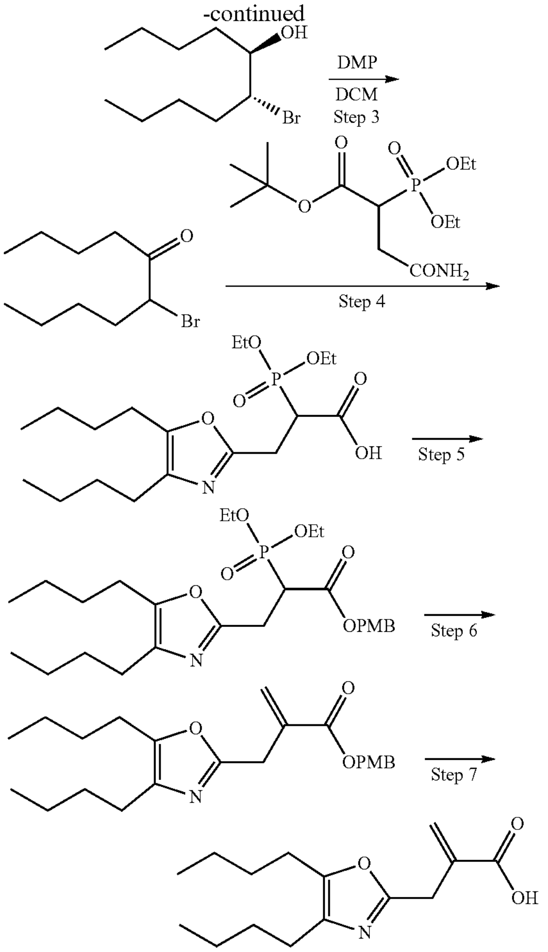

Step 1

To a mixture of (E)-dec-5-ene (1.4 g, 10 mmol) in DCM (100 mL) was added m-CPBA (3.5 g, 20 mmol) at 0° C., and the reaction mixture was stirred at 0° C. for 3 h. The reaction mixture was quenched with dilute aqueous $NaS_2O_3$ (100 mL) and extracted with DCM (2x100 mL). The combined organic layers were washed with brine, dried over $Na_2SO_4$, filtered and concentrated under reduced pressure at 30° C. The residue was purified by flash column chromatography (80 g silica, 0-10% MTBE/petroleum ether) to give (trans)-2,3-dibutyloxirane (1.3 g, 8.3 mmol, 83%) as a yellow oil. $^1H$ NMR (400 MHz, $CDCl_3$) δ: 2.65 (t, J=4.9 Hz, 2H), 1.60-1.20 (m, 12H), 0.99-0.80 (m, 6H).

Step 2

A solution of (trans)-2,3-dibutyloxirane (1.3 g, 8.3 mmol) and aqueous HBr (40 wt. %, 5 mL) in THF (10 mL) was stirred at room temperature for 16 h. The mixture was concentrated under reduced pressure at 35° C. to give crude (trans)-6-bromodecan-5-ol (1.6 g, 6.7 mmol, 81%) as a yellow oil, which was used directly in the next step. $^1H$ NMR (400 MHz, $CDCl_3$) δ: 4.22-4.12 (m, 1H), 3.74-3.63 (m, 1H), 1.94 (d, J=6.5 Hz, 1H), 1.90-1.70 (m, 2H), 1.66-1.45 (m, 4H) 1.45-1.18 (m, 6H), 0.92 (t, J=7.0 Hz 6H).

Step 3

To a solution of (trans)-6-bromodecan-5-ol (1.6 g, 6.7 mmol) in DCM (40 mL), was added Dess-Martin reagent (4.3 g, 10.2 mmol) at room temperature, and the reaction mixture was stirred at room temperature for 30 min. The reaction mixture was quenched with dilute aqueous $Na_2CO_3$ (50 mL) and extracted with MTBE (2×50 mL). The combined organic layers were washed with brine, dried over $Na_2SO_4$, filtered and concentrated under reduced pressure at 30° C. The residue was purified by flash column chromatography (25 g silica, 0-10% MTBE/petroleum ether) to give 6-bromodecan-5-one (1.4 g, 6.0 mmol, 87%) as a yellow oil. $^1$H NMR (400 MHz, $CDCl_3$) δ: 4.23 (dd, J=8.1, 6.5 Hz, 1H), 2.77-2.56 (m, 2H), 2.07-1.84 (m, 2H), 1.70-1.53 (m, 2H), 1.50-1.21 (m, 6H), 0.99-0.81 (m, 6H).

Step 4

Prepared according to Example 109, Step 4 using 6-bromodecan-5-one (0.70 g, 3.0 mmol). The crude product was purified by reversed phase flash chromatography to give crude 3-(4,5-dibutyloxazol-2-yl)-2-(diethoxyphosphoryl)propanoic acid (200 mg, 0.51 mmol, 17%) as a pale yellow oil, which was used directly in next step. LCMS: (System 2, Method C) m/z 390.2 $(M+H)^+$ $(ES^+)$.

Step 5

Prepared according to Example 109, Step 5 using 3-(4,5-dibutyloxazol-2-yl)-2-(diethoxyphosphoryl)propanoic acid (200 mg, 0.51 mmol). The crude product was purified by flash column chromatography (12 g silica, 0-40% MTBE/petroleum ether) to give 4-methoxybenzyl 3-(4,5-dibutyloxazol-2-yl)-2-(diethoxyphosphoryl)propanoate (230 mg, 0.45 mmol, 88%) as a yellow oil. LCMS: (System 2, Method C) m/z 510.2 $(M+H)^+$ $(ES^+)$.

Step 6

Prepared according to General Procedure A, Step 2, Method C from 3-(4,5-dibutyloxazol-2-yl)-2-(diethoxyphosphoryl)propanoate (230 mg, 0.45 mmol). The crude product was purified by flash column chromatography (10% MTBE/petroleum ether) to give 4-methoxybenzyl 2-((4,5-dibutyloxazol-2-yl)methyl)acrylate (90 mg, 0.23 mmol, 52%) as a pale yellow oil. LCMS: (System 2, Method C) m/z 386.2 $(M+H)^+$ $(ES^+)$.

Step 7

Prepared according to General Procedure A, Step 3 from 4-methoxybenzyl 2-((4,5-dibutyloxazol-2-yl)methyl)acrylate (90 mg, 0.23 mmol). The crude product was purified by preparative HPLC (Column: Waters X-Bridge C18 OBD 10 μm 19×250 mm; Flow Rate: 20 mL/min; solvent system: MeCN/(0.1% TFA/water) gradient: 45-95% MeCN; collection wavelength: 214 nm). The fractions were concentrated under reduced pressure at 30° C. to remove MeCN, and the residue was lyophilized to give 2-((4,5-dibutyloxazol-2-yl)methyl)acrylic acid (28 mg, 0.11 mmol, 45%) as a pale yellow oil. LCMS: (System 2, Method B) m/z 266.2 $(M+H)^+$ $(ES^+)$. $^1$H NMR (400 MHz, DMSO-d6) δ: 12.64 (br, 1H), 6.17 (s,1H), 5.66 (d, J=1.5 Hz, 1H), 3.63 (s, 2H), 2.57-2.51 (m, 2H), 2.31 (t, J=7.4 Hz, 2H), 1.53-1.40 (m, 4H), 1.32-1.18 (m, 4H). 0.86 (t, J=7.4 Hz, 6H).

Example 124—2,2-((3-(difluoro(4-(pentafluoro-$\lambda^6$-sulfaneyl)phenyl)methyl)-1,2,4-oxadiazol-5-yl) methyl)acrylic acid

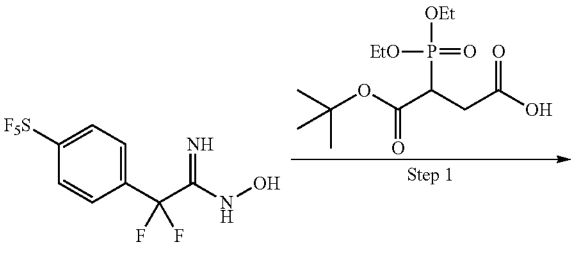

-continued

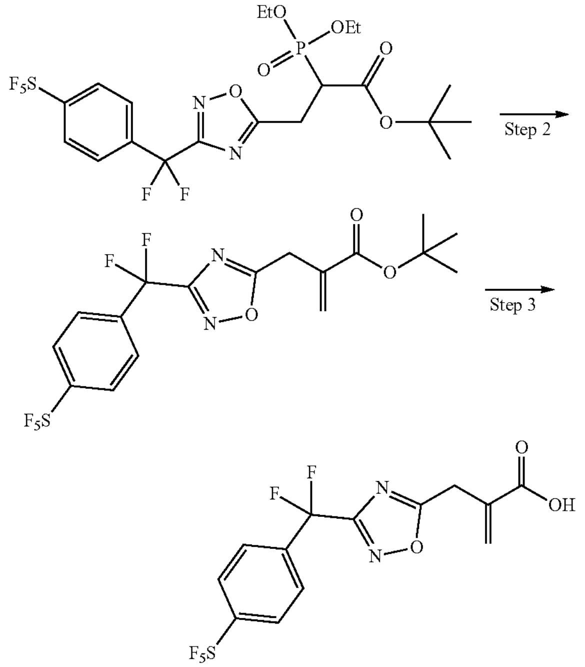

Step 1

Prepared according to General Procedure B, Method C from 2,2-difluoro-N-hydroxy-2-(4-(pentafluoro-$\lambda^6$-sulfaneyl)phenyl)acetimidamide (2.00 g, 5.32 mmol, 83% purity). The crude product was purified by chromatography on silica gel (0-100% MTBE/isohexane) to afford tert-butyl 2-(diethoxyphosphoryl)-3-(3-(difluoro(4-(pentafluoro-$\lambda^6$-sulfaneyl)phenyl)methyl)-1,2,4-oxadiazol-5-yl)propanoate (0.964 g, 1.6 mmol) as a brown oil. LCMS m/z 531.1 $(M-tBu+H)^+$ $(ES^+)$. $^1$H NMR (400 MHz, DMSO-d6) δ 8.16-8.10 (m, 2H), 7.89 (d, J=8.6 Hz, 2H), 4.06 (dddd, J=12.0, 9.5, 7.7, 6.0 Hz, 4H), 3.62 (ddd, J=23.5, 10.6, 4.7 Hz, 1H), 3.51-3.42 (m, 1H), 3.42-3.32 (m, 1H), 1.25 (s, 9H), 1.24-1.19 (m, 6H). $^{19}$F NMR (376 MHz, DMSO) δ −95.88 (d, J=16.8 Hz). $^{31}$P NMR (162 MHz, DMSO) δ 19.88.

Step 2

Prepared according to General Procedure A, Step 2, Method B from tert-butyl 2-(diethoxyphosphoryl)-3-(3-(difluoro(4-(pentafluoro-$\lambda^6$-sulfaneyl)phenyl)methyl)-1,2,4-oxadiazol-5-yl)propanoate (0.964 g, 1.6 mmol). The crude product was purified by chromatography on silica gel (0-50% MTBE/isohexane) to afford tert-butyl 2-((3-(difluoro(4-(pentafluoro-$\lambda^6$-sulfaneyl)phenyl)methyl)-1,2,4-oxadiazol-5-yl)methyl)acrylate (488 mg, 1.0 mmol) as a colourless oil. $^1$H NMR (400 MHz, DMSO-d6) δ 8.16-8.10 (m, 2H), 7.90 (d, J=8.5 Hz, 2H), 6.26 (d, J=1.1 Hz, 1H), 5.96 (d, J=1.2 Hz, 1H), 4.05 (s, 2H), 1.19 (s, 9H). $^{19}$F NMR (376 MHz, DMSO) δ −96.51.

Step 3

Prepared according to General Procedure A, Step 3 from tert-butyl 2-((3-(difluoro(4-(pentafluoro-$\lambda^6$-sulfaneyl)phenyl)methyl)-1,2,4-oxadiazol-5-yl)methyl)acrylate (488 mg, 1.0 mmol). The crude product was purified by chromatography on silica gel (0-50% MTBE/isohexane) to afford 2-((3-(difluoro(4-(pentafluoro-$\lambda^6$-sulfaneyl)phenyl) methyl)-1,2,4-oxadiazol-5-yl)methyl)acrylic acid (367 mg, 0.88 mmol) as a thick colourless gum. LCMS m/z 404.3 $(M-H)^-$ $(ES^-)$. $^1$H NMR (400 MHz, DMSO-d6) δ 12.90 (s, 1H), 8.13 (d, J=8.9 Hz, 2H), 7.90 (d, J=8.6 Hz, 2H), 6.31 (d, J=1.1 Hz, 1H), 5.99 (d, J=1.3 Hz, 1H), 4.05 (s, 2H). $^{19}F$ NMR (376 MHz, DMSO) δ −94.93.

Example 125—2,2-((3-(difluoro(4-fluorophenyl) methyl)-1,2,4-oxadiazol-5-yl)methyl)acrylic acid

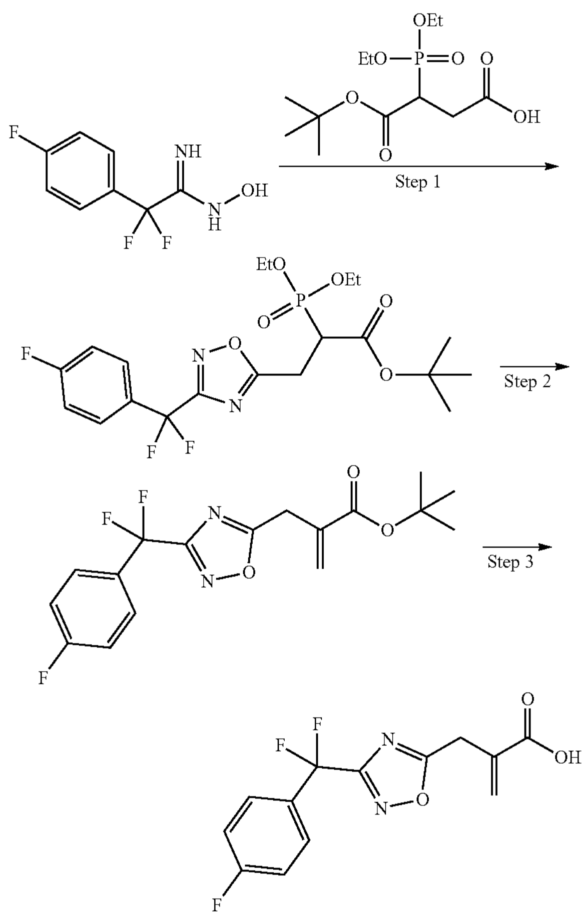

Step 1

Prepared according to General Procedure B, Method C from 2,2-difluoro-2-(4-fluorophenyl)-N-hydroxyacetimidamide (2.14 g, 8.91 mmol, 85% purity). The crude product was purified by chromatography on silica gel (0-100% MTBE/isohexane) to afford tert-butyl 2-(diethoxyphosphoryl)-3-(3-(difluoro(4-fluorophenyl)methyl)-1,2,4-oxadiazol-5-yl)propanoate (1.748 g, 3.2 mmol, 88% purity) as a brown oil. LCMS m/z 423.3 $(M-tBu+H)^+$ $(ES^+)$. $^1H$ NMR (400 MHz, DMSO-d6) δ 7.72-7.64 (m, 2H), 7.45-7.37 (m, 2H), 4.13-4.03 (m, 4H), 3.63 (ddd, J=23.4, 10.6, 4.8 Hz, 1H), 3.46 (dd, J=16.9, 10.2 Hz, 1H), 3.42-3.33 (m, 1H), 1.30 (s, 9H), 1.25-1.20 (m, 6H). $^{19}F$ NMR (376 MHz, DMSO) δ −93.08 (dd, J=13.2, 3.0 Hz), −108.82. $^{31}P$ NMR (162 MHz, DMSO) δ 19.95.

Step 2

Prepared according to General Procedure A, Step 2, Method B from tert-butyl 2-(diethoxyphosphoryl)-3-(3-(difluoro(4-fluorophenyl)methyl)-1,2,4-oxadiazol-5-yl)propanoate (1.748 g, 3.2 mmol, 88% purity). The crude product was purified by chromatography on silica gel (0-50% MTBE/isohexane) to afford tert-butyl 2-((3-(difluoro(4-fluorophenyl)methyl)-1,2,4-oxadiazol-5-yl)methyl)acrylate (812 mg, 2.7 mmol) as a colourless oil. $^1H$ NMR (400 MHz, DMSO-d6) δ 7.72-7.65 (m, 2H), 7.40 (t, J=8.8 Hz, 2H), 6.26 (d, J=1.1 Hz, 1H), 5.96 (d, J=1.2 Hz, 1H), 4.05 (d, J=1.1 Hz, 2H), 1.24 (s, 9H). $^{19}F$ NMR (376 MHz, DMSO) δ −93.59 (d, J=3.0 Hz), −108.85.

Step 3

Prepared according to General Procedure A, Step 3 from tert-butyl 2-((3-(difluoro(4-fluorophenyl)methyl)-1,2,4-oxadiazol-5-yl)methyl)acrylate (812 mg, 2.7 mmol). The crude product was purified by chromatography on silica gel (0-50% MTBE/isohexane) to afford 2-((3-(difluoro(4-fluorophenyl)methyl)-1,2,4-oxadiazol-5-yl)methyl)acrylic acid (508 mg, 1.7 mmol) as a white solid. LCMS m/z 297.5 $(M-H)^-$ $(ES^-)$. $^1H$ NMR (400 MHz, DMSO-d6) δ 12.90 (s, 1H), 7.88-7.59 (m, 2H), 7.40 (t, J=8.8 Hz, 2H), 6.31 (d, J=1.1 Hz, 1H), 5.99 (d, J=1.2 Hz, 1H), 4.04 (s, 2H). $^{19}F$ NMR (376 MHz, DMSO) δ −92.57 (d, J=3.2 Hz), −108.75.

Example 126—2-((3-(4-butylphenoxy)-1,2,4-oxadiazol-5-yl)methyl)acrylic acid

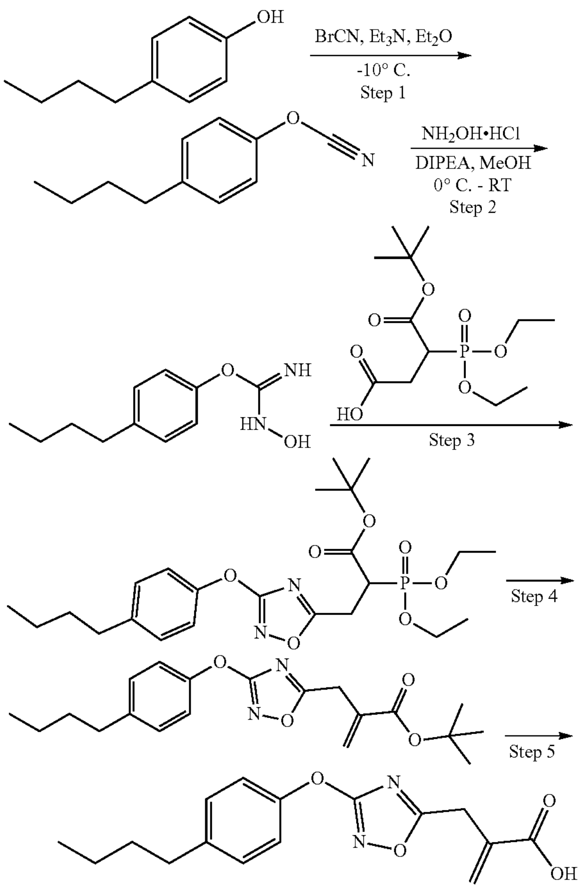

Step 1

To a solution of 4-butylphenol (3.00 g, 20.0 mmol) and $Et_3N$ (2.23 g, 22.0 mmol) in dry diethyl ether (28 mL) at −10° C. was added a solution of cyanogen bromide (2.34 g, 22.1 mmol) in dry diethyl ether (6 mL), dropwise. Then the mixture was vigorously stirred at −10° C. for 1.5 h. The mixture was filtered, and the filter residue was washed with additional dry diethyl ether. The filtrate was washed with water and brine, dried over $Na_2SO_4$, and concentrated under reduced pressure at 35° C. The residue was purified by flash column chromatography to give 1-butyl-4-cyanatobenzene (3.10 g, 17.7 mmol, 89%) as a white solid. LCMS: (System 2, Method C) m/z 176.4 $(M+H)^+$ $(ES^+)$.

Step 2

To a solution of 1-butyl-4-cyanatobenzene (3.00 g, 17.1 mmol) in MeOH (15 mL) was added hydroxylamine hydrochloride (2.39 g, 34.4 mmol). The suspension was cooled to 0° C. and DIPEA (4.44 g, 34.4 mmol) was slowly added, dropwise. The reaction mixture was then warmed to room temperature and stirred for 30 min. The reaction mixture was diluted with aqueous HCl (2 M, 30 mL) and washed with ethyl acetate (3×25 mL). The aqueous layer was basified with aqueous NaOH (2 M) to pH=8 and then extracted with EtOAc (3×25 mL). The combined organic extracts were washed with brine (50 mL), dried over $Na_2SO_4$, filtered and concentrated under reduced pressure at 40° C. to give 4-butylphenyl hydroxycarbamimidate (1.10 g, 5.28 mmol, 31%) as a yellow solid. LCMS: (System 2, Method C) m/z 209.4 $(M+H)^+$ $(ES^+)$.

Step 3

Prepared according to General Procedure B, Method B from 4-butylphenyl hydroxycarbamimidate (1.10 g, 5.28 mmol). The crude product was purified by flash column chromatography (50% EtOAc/petroleum ether) to give tert-butyl 3-(3-(4-butylphenoxy)-1,2,4-oxadiazol-5-yl)-2-(diethoxyphosphoryl)propanoate (1.13 g, 2.34 mmol, 44%) as a pale yellow oil. LCMS: (System 2, Method C) m/z 483.2 $(M+H)^+$ $(ES^+)$.

Step 4

Prepared according to General Procedure A, Step 2, Method C from tert-butyl 3-(3-(4-butylphenoxy)-1,2,4-oxadiazol-5-yl)-2-(diethoxyphosphoryl)propanoate (400 mg, 0.83 mmol). The crude product was purified by flash column chromatography (25 g silica, 45% EtOAc/petroleum ether) to give tert-butyl 2-((3-(4-butylphenoxy)-1,2,4-oxadiazol-5-yl)methyl)acrylate (230 mg, 0.64 mmol, 77%) as a yellow solid. LCMS: (System 2, Method C) m/z 359.3 $(M+H)^+$, 381.2 $(M+Na)^+$ $(ES^+)$.

Step 5

Prepared according to General Procedure A, Step 3 from tert-butyl 2-((3-(4-butylphenoxy)-1,2,4-oxadiazol-5-yl)methyl)acrylate (230 mg, 0.64 mmol). The crude product was purified by preparative HPLC (Column: Waters X-Bridge C18 OBD 10 μm 19×250 mm; Flow Rate: 20 mL/min; solvent system: MeCN/(0.2% formic acid/water) gradient: 55-95% MeCN; collection wavelength: 214 nm). The fractions were concentrated under reduced pressure at 30° C. to remove MeCN, and the residue was lyophilized to give 2-((3-(4-butylphenoxy)-1,2,4-oxadiazol-5-yl)methyl)acrylic acid (130 mg, 0.43 mmol, 67%) as a white solid. LCMS: (System 2, Method B) m/z 303.1 $(M+H)^+$ $(ES^+)$. $^1H$ NMR (400 MHz, DMSO-d6) δ: 12.90 (br, 1H), 7.30-7.16 (m, 4H), 6.29 (s, 1H), 5.96 (d, J=1.3 Hz, 1H), 3.91 (s, 2H), 2.59 (t, J=7.7 Hz, 2H), 1.60-1.49 (m, 2H), 1.37-1.24 (m, 2H), 0.90 (t, J=7.3 Hz, 3H).

Example 127—2-((4-(4-butylbenzyl)oxazol-2-yl)methyl)acrylic acid

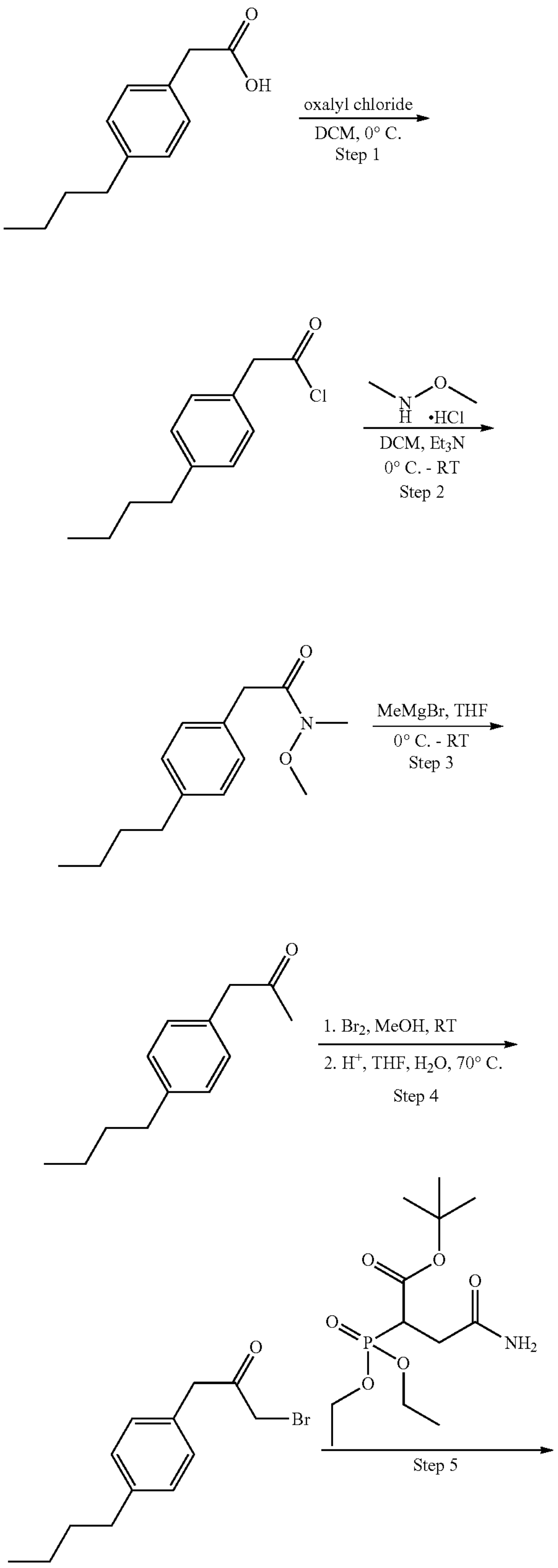

-continued

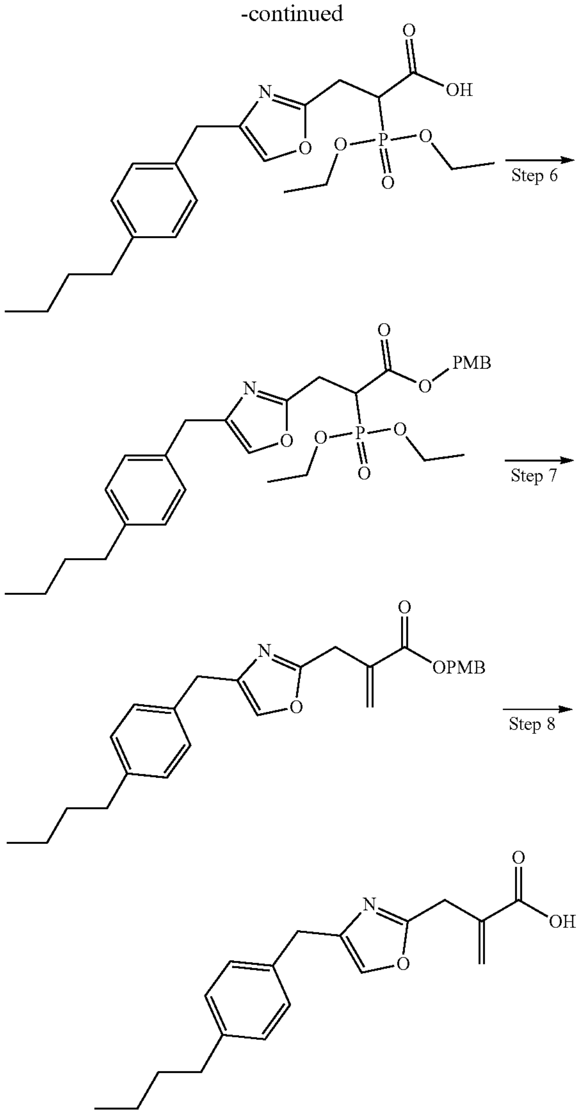

Step 1

A mixture of 2-(4-butylphenyl)acetic acid (4.70 g, 24.5 mmol) and oxalyl chloride (1.55 g, 122.3 mmol) in DCM (80 mL) was stirred at 0° C. for 1 h. The reaction mixture was concentrated under reduced pressure at 35° C. to give crude 2-(4-butylphenyl)acetyl chloride (5.14 g, 24.4 mmol, 100%) as a pale yellow oil. The crude product was used directly to the next step. LCMS: (System 2, Method C) m/z 207.4 (in-situ methyl ester formation+H)$^+$ (ES$^+$).

Step 2

To a solution of N,O-dimethylhydroxylamine hydrochloride (2.38 g, 24.4 mmol) and triethylamine (17.2 g, 171 mmol) in DCM (80 mL) at 0° C. was added 2-(4-butylphenyl)acetyl chloride, and the resulting pale yellow mixture was stirred at room temperature for 12 h. The mixture was quenched with water (40 mL), the phases were separated, and the organic layer was extracted with DCM (2x30 mL). The combined organic layers were washed with water, dried over $Na_2SO_4$ and filtered. The filtrate was concentrated under reduced pressure at 40° C., and the residue was purified by flash column chromatography (80 g silica, 20% MTBE/petroleum ether) to give 2-(4-butylphenyl)-N-methoxy-N-methylacetamide (3.90 g, 16.6 mmol, 68%) as a colorless oil. LCMS: (System 2, Method C) m/z 236.4 (M+H)$^+$ (ES$^+$).

Step 3

To a solution of 2-(4-butylphenyl)-N-methoxy-N-methylacetamide (3.90 g, 16.6 mmol) in THF (40 mL) at 0° C. was added a solution of MeMgBr in diethyl ether (2 M, 20.7 mL, 41.4 mmol), and the reaction mixture was stirred at room temperature for 3 h. The reaction mixture was quenched with saturated aqueous $NH_4Cl$ solution (20 mL), the phases were separated, and the organic layer was extracted with MTBE (3x30 mL). The combined organic layers were washed with $H_2O$ (2x20 mL) and brine, dried over $Na_2SO_4$, filtered and concentrated under reduced pressure at 40° C. The residue was purified by flash column chromatography (80 g silica, 0-20% MTBE/petroleum ether) to give 1-(4-butylphenyl)propan-2-one (2.20 g, 11.6 mmol, 69%) as a colorless oil. LCMS: (System 2, Method C) m/z 191.4 (M+H)$^+$ (ES$^+$).

Step 4

A solution of 1-(4-butylphenyl)propan-2-one (2.20 g, 11.6 mmol) and bromine (5.11 g, 11.6 mmol) in MeOH (38 mL) was stirred at 25° C. for 6 h. The reaction mixture was quenched with dilute aqueous $K200_3$ (3 M, 20 mL) and then concentrated under reduced pressure at 30° C. to remove the volatiles. The aqueous residue was extracted with EtOAc (3x30 mL), the combined organic layers were washed with dilute aqueous $K200_3$ (3 M, 2x20 mL), dried over $Na_2SO_4$, filtered and concentrated under reduced pressure at 40° C. The pale orange residue was dissolved in a mixture of THF (20 mL) and dilute aqueous sulfuric acid (1 M, 30 mL) and stirred at 70° C. for 3 h. The mixture was then concentrated under reduced pressure at 40° C. and the aqueous residue was extracted with EtOAc (3x25 mL). The combined organic layers were washed with dilute aqueous $K_2CO_3$ (3 M, 2x20 mL) and brine (2x20 mL), dried over $Na_2SO_4$, filtered and concentrated under reduced pressure at 40° C. The residue was purified by flash column chromatography (80 g silica, 0-4% MTBE/petroleum ether) to give 1-bromo-3-(4-butylphenyl)propan-2-one (700 mg, 2.60 mmol, 22%) as a pale yellow oil. $^1H$ NMR (400 MHz, $CDCl_3$) δ: 7.19-7.11 (m, 4H), 3.91 (s, 2H), 3.91 (s, 2H), 2.64-2.54 (m, 2H), 1.64-1.52 (m, 2H), 1.41-1.28 (m, 2H), 0.92 (t, J=7.3 Hz, 3H).

Step 5

Prepared according to Example 109, Step 4 using 1-bromo-3-(4-butylphenyl)propan-2-one (700 mg, 2.60 mmol). The mixture was filtered, and the filtrate was diluted with dilute HCl (0.5 M, 20 mL). The phases were separated, and the aqueous layer was extracted with EtOAc (3x20 mL). The combined organic layers were dried over $Na_2SO_4$, filtered and the filtrate was concentrated at 40° C. The residue was purified by reversed phase column chromatography (120 g C18 silica; flow rate: 40 mL/min; 30-50% MeCN/(10 mM formic acid/water); collection wavelength: 214 nm). The collected fractions were concentrated under reduced pressure at 40° C. to remove MeCN, and the residue was lyophilized to give 3-(4-(4-butylbenzyl)oxazol-2-yl)-2-(diethoxyphosphoryl)propanoic acid (270 mg, 0.64 mmol, 24%) as a colorless oil. LCMS: (System 2, Method C) m/z 424.2 (M+H)$^+$ (ES$^+$).

Step 6

Prepared according to Example 109, Step 5 using 3-(4-(4-butylbenzyl)oxazol-2-yl)-2-(diethoxyphosphoryl)propanoic acid (270 mg, 0.64 mmol). The crude product was purified by flash column chromatography (50-90% MTBE/petroleum ether) to give 4-methoxybenzyl 3-(4-(4-butylbenzyl)oxazol-2-yl)-2-(diethoxyphosphoryl)propanoate (175 mg, 0.32 mmol, 50%) as a pale yellow oil. LCMS: (System 2, Method C) m/z 544.2 $(M+H)^+$ $(ES^+)$.

Step 7

Prepared according to General Procedure A, Step 2, Method C from 4-methoxybenzyl 3-(4-(4-butylbenzyl)oxazol-2-yl)-2-(diethoxyphosphoryl)propanoate (175 mg, 0.32 mmol). The crude product was purified by flash column chromatography (25 g silica, 0-20% MTBE/petroleum ether) to give 4-methoxybenzyl 2-((4-(4-butylbenzyl)oxazol-2-yl)methyl)acrylate (125 mg, 0.30 mmol, 92%) as a colorless oil. LCMS: (System 2, Method C) m/z 420.2 $(M+H)^+$ $(ES^+)$.

Step 8

Prepared according to General Procedure A, Step 3 from 4-methoxybenzyl 2-((4-(4-butylbenzyl)oxazol-2-yl)methyl) acrylate (125 mg, 0.30 mmol). The crude product was purified by preparative HPLC (Column: Waters X-Bridge C18 OBD 10 μm 19×250 mm; Flow Rate: 20 mL/min; solvent system: MeCN/(0.2% formic acid/water) gradient: 57-95% MeCN; collection wavelength: 214 nm). The fractions were concentrated under reduced pressure at 35° C. to remove MeCN, and the residue was lyophilized to give 2-((4-(4-butylbenzyl)oxazol-2-yl)methyl)acrylic acid (50 mg, 0.17 mmol, 56%) as a white solid. LCMS: (System 2, Method B) m/z 300.1 $(M+H)^+$ $(ES^+)$. $^1H$ NMR (400 MHz, DMSO-d6) δ: 12.67 (br, 1H), 7.67 (s, 1H), 7.15-7.06 (m, 4H), 6.18 (s, 1H), 5.72 (d, J=1.5 Hz, 1H), 3.71 (s, 2H), 3.68 (s, 2H), 2.56-2.50 (m, 2H), 1.57-1.46 (m, 2H), 1.35-1.22 (m, 2H), 0.88 (t, J=7.3 Hz, 3H).

Example 128—2-((3-(4-cyclobutylbenzyl)-1,2,4-oxadiazol-5-yl)methyl)acrylic acid

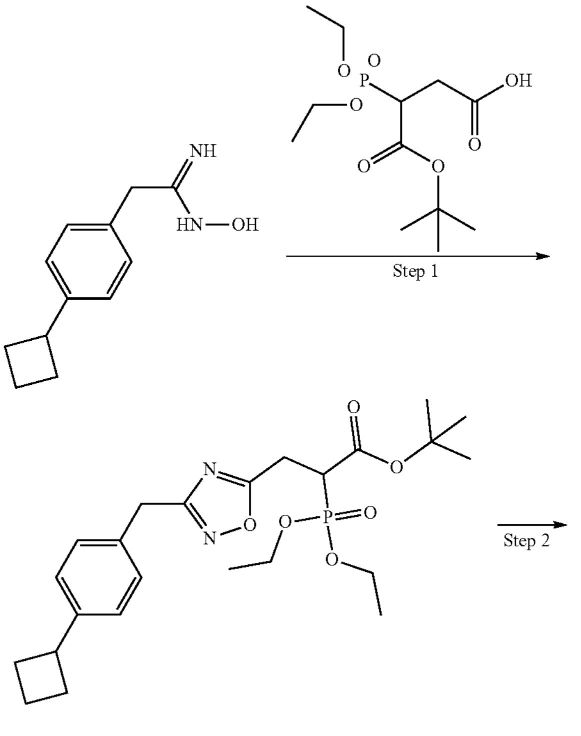

-continued

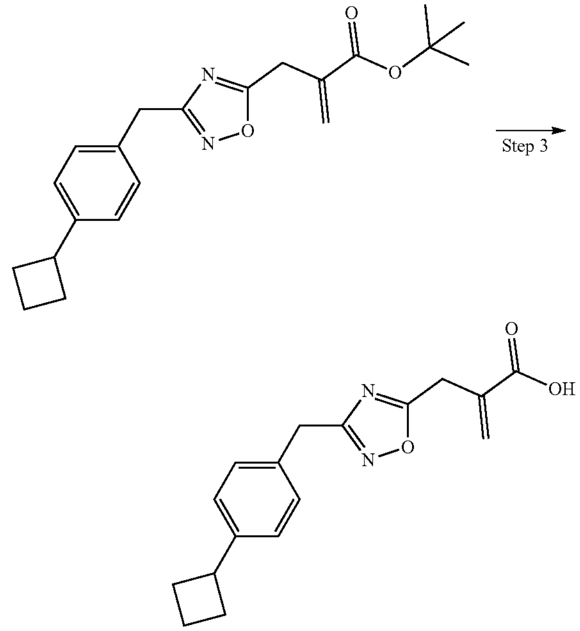

Step 1

Prepared according to General Procedure B, Method B from 2-(4-cyclobutylphenyl)-N-hydroxyacetimidamide (Intermediate 153, 500 mg, 2.45 mmol). The crude product was purified by flash column chromatography (40 g silica, 20-40% EtOAc/petroleum ether) to give tert-butyl 3-(3-(4-cyclobutylbenzyl)-1,2,4-oxadiazol-5-yl)-2-(diethoxyphosphoryl)propanoate (760 mg, 1.59 mmol, 65%) as a colorless oil. LCMS: (System 2, Method C) m/z 479.2 $(M+H)^+$ $(ES^+)$.

Step 2

Prepared according to General Procedure A, Step 2, Method C from tert-butyl 3-(3-(4-cyclobutylbenzyl)-1,2,4-oxadiazol-5-yl)-2-(diethoxyphosphoryl)propanoate (760 mg, 1.59 mmol). The crude product was purified by flash column chromatography (40 g silica, 0-30% MTBE/petroleum ether) to give tert-butyl 2-((3-(4-cyclobutylbenzyl)-1,2,4-oxadiazol-5-yl)methyl)acrylate (480 mg, 1.35 mmol, 85%) as a pale yellow oil. LCMS: (System 2, Method C) m/z 355.3 $(M+H)^+$, 377.2 $(M+Na)^+$ $(ES^+)$.

Step 3

Prepared according to General Procedure A, Step 3 from tert-butyl 2-((3-(4-cyclobutylbenzyl)-1,2,4-oxadiazol-5-yl) methyl)acrylate (480 mg, 1.35 mmol). The crude product was purified by preparative HPLC (Column: Waters X-Bridge C18 OBD 10 μm 19×250 mm; Flow Rate: 20 mL/min; solvent system: MeCN/(0.2% formic acid/water) gradient: 50-95% MeCN; collection wavelength: 214 nm). The fractions were concentrated under reduced pressure at 40° C. to remove MeCN, and the residue was lyophilized to give 2-((3-(4-cyclobutylbenzyl)-1,2,4-oxadiazol-5-yl) methyl)acrylic acid (307 mg, 1.03 mmol, 76%) as a white solid. LCMS: (System 2, Method B) m/z 299.1 $(M+H)^+$, 321.1 $(M+Na)^+$ $(ES^+)$. $^1H$ NMR (400 MHz, DMSO-d6) δ: 12.80 (br, 1H), 7.22-7.13 (m, 4H), 6.26 (d, J=1.2 Hz, 1H), 5.90 (d, J=1.3 Hz, 1H), 4.00 (s, 2H), 3.90 (s, 2H), 3.54-3.41 (m, 1H), 2.32-2.19 (m, 2H), 2.13-1.87 (m, 3H), 1.85-1.72 (m, 1H).

Example 129—2-((3-(4-butoxy-3-fluorophenyl)-1,2,4-oxadiazol-5-yl)methyl)acrylic acid

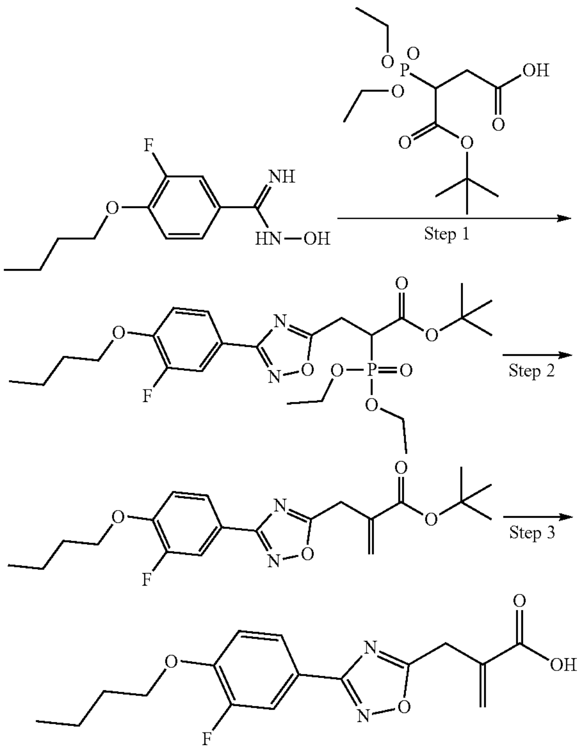

Step 1

Prepared according to General Procedure B, Method B from 4-butoxy-3-fluoro-N-hydroxybenzimidamide (Intermediate 155, 400 mg, 1.77 mmol). The crude product was purified by flash column chromatography (40 g silica, 20-40% EtOAc/petroleum ether) to give tert-butyl 3-(3-(4-butoxy-3-fluorophenyl)-1,2,4-oxadiazol-5-yl)-2-(diethoxyphosphoryl)propanoate (400 mg, 0.80 mmol, 45%) as a yellow solid. LCMS: (System 2, Method C) m/z 501.2 $(M+H)^+$ $(ES^+)$.

Step 2

Prepared according to General Procedure A, Step 2, Method C from tert-butyl 3-(3-(4-butoxy-3-fluorophenyl)-1,2,4-oxadiazol-5-yl)-2-(diethoxyphosphoryl)propanoate (400 mg, 0.80 mmol). The crude product was purified by flash column chromatography (40 g silica, 0-20% MTBE/petroleum ether) to give tert-butyl 2-((3-(4-butoxy-3-fluorophenyl)-1,2,4-oxadiazol-5-yl)methyl)acrylate (290 mg, 0.77 mmol, 96%) as a yellow oil. LCMS: (System 2, Method C) m/z 377.2 $(M+H)^+$ $(ES^+)$.

Step 3

Prepared according to General Procedure A, Step 3 from tert-butyl 2-((3-(4-butoxy-3-fluorophenyl)-1,2,4-oxadiazol-5-yl)methyl)acrylate (290 mg, 0.77 mmol). The crude product was purified by preparative HPLC (Column: Waters X-Bridge C18 OBD 10 μm 19×250 mm; Flow Rate: 20 mL/min; solvent system: MeCN/(0.2% formic acid/water) gradient: 53-95% MeCN; collection wavelength: 214 nm). The fractions were concentrated under reduced pressure at 30° C. to remove MeCN, and the residue was lyophilized to give 2-((3-(4-butoxy-3-fluorophenyl)-1,2,4-oxadiazol-5-yl)methyl)acrylic acid (180 mg, 0.56 mmol, 73%) as a white solid. LCMS: (System 2, Method B) m/z 321.1 $(M+H)^+$ $(ES^+)$. $^1$H NMR (400 MHz, DMSO-d6) δ: 12.86 (br, 1H), 7.80-7.67 (m, 2H), 7.34 (t, J=8.6 Hz, 1H), 6.32 (s, 1H), 6.00 (d, J=1.3 Hz, 1H), 4.13 (t, J=6.5 Hz, 2H), 4.01 (s, 2H), 1.80-1.68 (m, 2H), 1.51-1.38 (m, 2H), 0.94 (t, J=7.4 Hz, 3H).

Example 130—2-((3-(3-chloro-4-propoxyphenyl)-1,2,4-oxadiazol-5-yl)methyl)acrylic acid

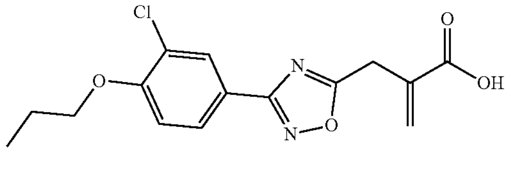 [SMILES: C=C(Cc1nc(-c2ccc(OCCC)c(Cl)c2)no1)C(=O)O]

Prepared by an analogous procedure to Example 129 starting from 3-chloro-N-hydroxy-4-propoxybenzimidamide (Intermediate 157, 409 mg, 1.79 mmol). Yield: 168 mg. White solid. LCMS: (System 2, Method B) m/z 323.0/325.0 $(M+H)^+$ $(ES^+)$. $^1$H NMR (400 MHz, DMSO-d6) δ: 12.86 (br, 1H), 7.96-7.87 (m, 2H), 7.32 (d, J=8.7 Hz, 1H), 6.33 (s, 1H), 6.00 (d, J=1.3 Hz, 1H), 4.11 (t, J=6.4 Hz, 2H), 4.02 (s, 2H), 1.85-1.72 (m, 2H), 1.01 (t, J=7.4 Hz, 3H).

Example 131—2-((3-(1-(4-cyclobutylphenyl)cyclopropyl)-1,2,4-oxadiazol-5-yl)methyl)acrylic acid

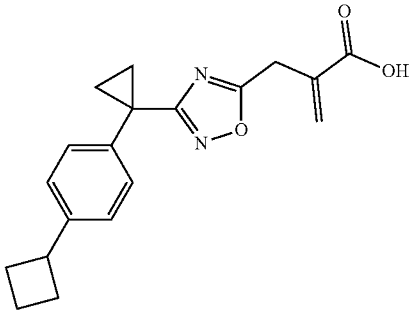 [SMILES: C=C(Cc1nc(C2(c3ccc(C4CCC4)cc3)CC2)no1)C(=O)O]

Prepared by an analogous procedure to Example 128 starting from 1-(4-cyclobutylphenyl)-N-hydroxycyclopropane-1-carboximidamide (Intermediate 159, 380 mg, 1.65 mmol). Yield: 82 mg. White solid. LCMS: (System 2, Method B) m/z 325.1 $(M+H)^+$, 347.0 $(M+Na)^+$ $(ES^+)$. $^1$H NMR (400 MHz, DMSO-d6) δ: 12.80 (br, 1H), 7.29 (d, J=8.2 Hz, 2H), 7.18 (d, J=8.1 Hz, 2H), 6.26 (s, 1H), 5.89 (s, 1H), 3.87 (s, 2H), 3.56-3.43 (m, 1H), 2.35-2.21 (m, 2H), 2.14-1.89 (m, 3H), 1.86-1.74 (m, 1H), 1.45-1.38 (m, 2H), 1.35-1.28 (m, 2H).

Example 132—2-((3-(4-(pyrrolidin-1-yl)phenyl)-1,2,4-oxadiazol-5-yl)methyl)acrylic acid

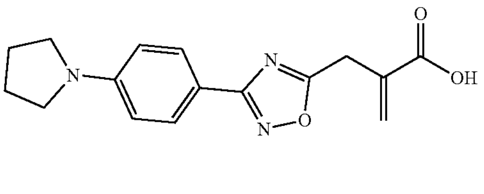 [SMILES: C=C(Cc1nc(-c2ccc(N3CCCC3)cc2)no1)C(=O)O]

Prepared by an analogous procedure to Example 129 starting from N-hydroxy-4-(pyrrolidin-1-yl)benzimidamide (Intermediate 160, 328 mg, 1.44 mmol). Yield: 116 mg. White solid. LCMS: (System 2, Method B) m/z 300.0 $(M+H)^+$ $(ES^+)$. $^1H$ NMR (400 MHz, DMSO-d6) δ: 12.86 (br, 1H), 7.76 (d, J=8.6 Hz, 2H), 6.63 (d, J=8.8 Hz, 2H), 6.31 (s, 1H), 5.97 (s, 1H), 3.96 (s, 2H), 3.32-3.25 m, 4H), 2.02-1.92 (m, 4H).

Example 133—2-((3-(1-(3,5-dichloro-4-fluorophenyl)cyclopropyl)-1,2,4-oxadiazol-5-yl)methyl) acrylic acid

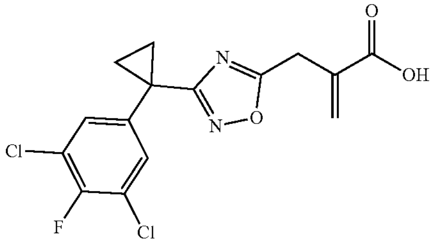 [SMILES: C=C(Cc1nc(C2(c3cc(Cl)c(F)c(Cl)c3)CC2)no1)C(=O)O]

Prepared by an analogous procedure to Example 128 starting from 1-(3,5-dichloro-4-fluorophenyl)-N-hydroxy-cyclopropane-1-carboximidamide (Intermediate 162, 470 mg, 1.79 mmol). Yield: 200 mg. White solid. LCMS: (System 2, Method B) m/z 356.8/358.8 $(M+H)^+$ $(ES^+)$. $^1H$ NMR (400 MHz, DMSO-d6) δ: 12.83 (br, 1H), 7.65 (d, J=6.4 Hz, 2H), 6.27 (s, 1H), 5.91 (d, J=1.3 Hz, 1H), 3.89 (s, 2H), 1.52-1.42 (m, 4H).

Example 134—2-((3-(3,5-dichloro-4-fluorobenzyl)-1,2,4-oxadiazol-5-yl)methyl)acrylic acid

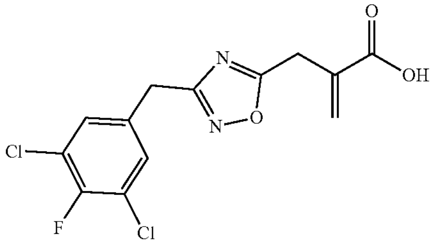 [SMILES: C=C(Cc1nc(Cc2cc(Cl)c(F)c(Cl)c2)no1)C(=O)O]

Prepared by an analogous procedure to Example 128 starting from 2-(3,5-dichloro-4-fluorophenyl)-N-hydroxy-acetimidamide (Intermediate 163, 465 mg, 1.96 mmol). Yield: 194 mg. White solid. LCMS: (System 2, Method B) m/z 330.9/332.8 $(M+H)^+$ $(ES^+)$. $^1H$ NMR (400 MHz, DMSO-d6) δ: 12.83 (br, 1H), 7.56 (d, J=6.4 Hz, 2H), 6.27 (s, 1H), 5.93 (d, J=1.4 Hz, 1H), 4.12 (s, 2H), 3.92 (s, 2H).

Example 135—2-((3-(1-(4-chloro-3,5-difluorophenyl)cyclopropyl)-1,2,4-oxadiazol-5-yl)methyl) acrylic acid

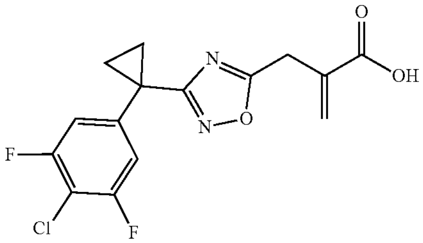 [SMILES: C=C(Cc1nc(C2(c3cc(F)c(Cl)c(F)c3)CC2)no1)C(=O)O]

Prepared by an analogous procedure to Example 128 starting from 1-(4-chloro-3,5-difluorophenyl)-N-hydroxy-cyclopropane-1-carboximidamide (Intermediate 165, 320 mg, 1.30 mmol). Yield: 114 mg. White solid. LCMS: (System 2, Method B) m/z 340.9/342.9 $(M+H)^+$ $(ES^+)$. $^1H$ NMR (400 MHz, DMSO-d6) δ: 12.80 (br, 1H), 7.42-7.35 (m, 2H), 6.27 (s, 1H), 5.92 (d, J=1.3 Hz, 1H), 3.90 (s, 2H), 1.49 (s, 4H).

Example 136—2-((3-(1-(3-chloro-4-(trifluoromethyl)phenyl)cyclopropyl)-1,2,4-oxadiazol-5-yl) methyl)acrylic acid

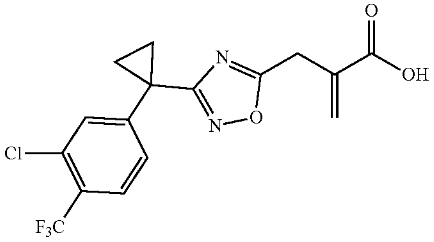 [SMILES: C=C(Cc1nc(C2(c3ccc(C(F)(F)F)c(Cl)c3)CC2)no1)C(=O)O]

Prepared by an analogous procedure to Example 128 starting from 1-(3-chloro-4-(trifluoromethyl)phenyl)-N-hydroxycyclopropane-1-carboximidamide (Intermediate 167, 550 mg, 2.0 mmol). Yield: 82 mg. White solid. LCMS: (System 2, Method B) m/z 372.9/374.8 $(M+H)^+$ $(ES^+)$. $^1H$ NMR (400 MHz, DMSO-d6) δ: 12.83 (br, 1H), 7.83 (d, J=8.2 Hz, 1H), 7.75 (s, 1H), 7.56 (d, J=8.4 Hz, 1H), 6.27 (s, 1H), 5.92 (s, 1H), 3.90 (s, 2H), 1.52 (s, 4H).

Example 137—2-((3-(3-chloro-4-(trifluoromethyl)benzyl)-1,2,4-oxadiazol-5-yl)methyl)acrylic acid

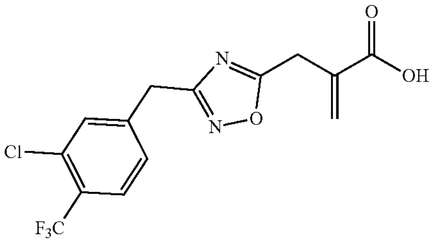 [SMILES: C=C(Cc1nc(Cc2ccc(C(F)(F)F)c(Cl)c2)no1)C(=O)O]

Prepared by an analogous procedure to Example 128 starting from 2-(3-chloro-4-(trifluoromethyl)phenyl)-N-hydroxyacetimidamide (Intermediate 168, 450 mg, 1.78 mmol). Yield: 178 mg. White solid. LCMS: (System 2, Method B) m/z 346.9/348.9 $(M+H)^+$ $(ES^+)$. $^1H$ NMR (400 MHz, DMSO-d6) δ: 12.81 (br, 1H), 7.83 (d, J=8.1 Hz, 1H), 7.69 (s, 1H), 7.47 (d, J=8.1 Hz, 1H), 6.27 (s, 1H), 5.92 (s, 1H), 4.23 (s, 2H), 3.92 (s, 2H).

Example 138—2-((3-(1-(4-bromo-3-chlorophenyl) cyclopropyl)-1,2,4-oxadiazol-5-yl)methyl)acrylic acid

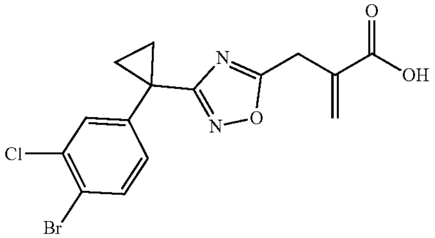 [SMILES: C=C(Cc1nc(C2(c3ccc(Br)c(Cl)c3)CC2)no1)C(=O)O]

Prepared by an analogous procedure to Example 128 starting from 1-(4-bromo-3-chlorophenyl)-N-hydroxycyclopropane-1-carboximidamide (Intermediate 170, 500 mg, 1.93 mmol). Yield: 204 mg. White solid. LCMS: (System 2, Method B) m/z 382.8/384.9 $(M+H)^+$ $(ES^+)$. $^1H$ NMR (400 MHz, DMSO-d6) δ: 12.84 (br, 1H), 7.73 (d, J=8.3 Hz, 1H), 7.64 (d, J=2.1 Hz, 1H), 7.30 (dd, J=8.3, 2.1 Hz, 1H), 6.26 (s, 1H), 5.91 (s, 1H), 3.89 (s, 2H), 1.51-1.38 (m, 4H).

Example 139—2-((3-(4-bromo-3-chlorobenzyl)-1,2,4-oxadiazol-5-yl)methyl)acrylic acid

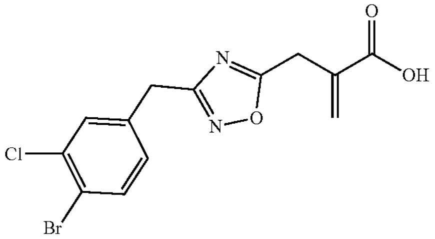 [SMILES: C=C(Cc1nc(Cc2ccc(Br)c(Cl)c2)no1)C(=O)O]

Prepared by an analogous procedure to Example 128 starting from 2-(4-bromo-3-chlorophenyl)-N-hydroxyacetimidamide (Intermediate 171, 350 mg, 1.34 mmol). Yield: 78 mg. White solid. LCMS: (System 2, Method B) m/z 357.0/358.9 $(M+H)^+$ $(ES^+)$. $^1H$ NMR (400 MHz, DMSO-d6) δ: 12.83 (br, 1H), 7.72 (d, J=8.2 Hz, 1H), 7.58 (d, J=2.1 Hz, 1H), 7.20 (dd, J=8.3, 2.1 Hz, 1H), 6.26 (s, 1H), 5.91 (s, 1H), 4.09 (s, 2H), 3.91 (s, 2H).

Example 140—2-((3-(1-(3-chloro-4-methoxyphenyl) cyclopropyl)-1,2,4-oxadiazol-5-yl)methyl)acrylic acid

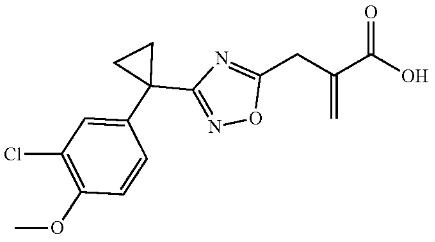 [SMILES: C=C(Cc1nc(C2(c3ccc(OC)c(Cl)c3)CC2)no1)C(=O)O]

Prepared by an analogous procedure to Example 128 starting from 1-(3-chloro-4-methoxyphenyl)-N-hydroxycyclopropane-1-carboximidamide (Intermediate 173, 370 mg, 1.54 mmol). Yield: 90 mg. Colorless oil. LCMS: (System 2, Method B) m/z 335.0/336.9 $(M+H)^+$ $(ES^+)$. $^1H$ NMR (400 MHz, DMSO-d6) δ: 12.80 (br, 1H), 7.42 (d, J=2.2 Hz, 1H), 7.32 (dd, J=8.5, 2.3 Hz, 1H), 7.10 (d, J=8.6 Hz, 1H), 6.26 (s, 1H), 5.90 (s, 1H), 3.88 (s, 2H), 3.85 (s, 3H), 1.47-1.29 (m, 4H).

Example 141—2-((3-(1-(3-chloro-4-methylphenyl) cyclopropyl)-1,2,4-oxadiazol-5-yl)methyl)acrylic acid

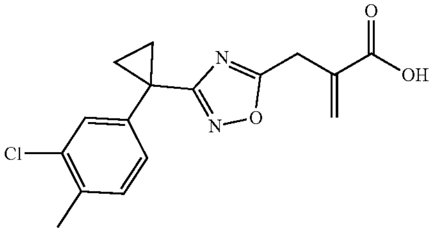 [SMILES: C=C(Cc1nc(C2(c3ccc(C)c(Cl)c3)CC2)no1)C(=O)O]

Prepared by an analogous procedure to Example 128 starting from 1-(3-chloro-4-methoxyphenyl)-N-hydroxycyclopropane-1-carboximidamide (Intermediate 175, 550 mg, 2.45 mmol). Yield: 271 mg. White solid. LCMS: (System 2, Method B) m/z 319.0/321.0 $(M+H)^+$ $(ES^+)$. $^1H$ NMR (400 MHz, DMSO-d6) δ: 12.84 (br, 1H), 7.40 (d, J=1.8 Hz, 1H), 7.31 (d, J=7.9 Hz, 1H), 7.25 (dd, J=7.9, 1.9 Hz, 1H), 6.26 (s, 1H), 5.90 (s, 1H), 3.88 (s, 2H), 2.31 (s, 3H), 1.49-1.30 (m, 4H).

Example 142—2-((3-(4-cyclobutoxyphenyl)-1,2,4-oxadiazol-5-yl)methyl)acrylic acid

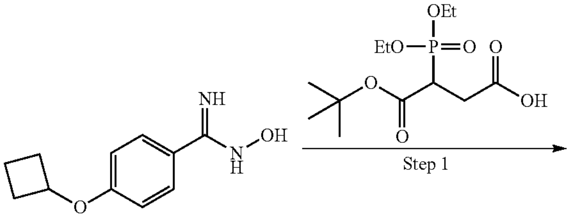

-continued

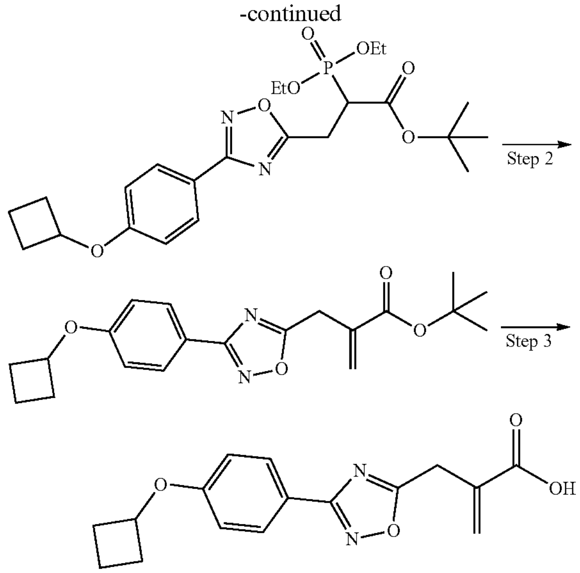

Step 1

Prepared according to General Procedure B, Method B from 4-cyclobutoxy-N-hydroxybenzimidamide (0.81 g, 3.5 mmol, 90% purity). The crude product was purified by chromatography on silica gel (0-100% MTBE/isohexane) to afford tert-butyl 3-(3-(4-cyclobutoxyphenyl)-1,2,4-oxadiazol-5-yl)-2-(diethoxyphosphoryl)propanoate (1.04 g, 1.9 mmol, 90% purity) as a clear and colourless gum. LCMS m/z 425.3 $(M-tBu+H)^+$ $(ES^+)$. $^1$H NMR (400 MHz, DMSO-d6) δ 7.92-7.81 (m, 2H), 7.07-6.93 (m, 2H), 4.84-4.67 (m, 1H), 4.17-4.02 (m, 4H), 3.74-3.54 (m, 1H), 3.51-3.36 (m, 1H), 3.34-3.31 (m, 1H), 2.46-2.40 (m, 2H), 2.16-1.96 (m, 2H), 1.86-1.73 (m, 1H), 1.73-1.57 (m, 1H), 1.37 (s, 9H), 1.30-1.19 (m, 6H).

Step 2

Prepared according to General Procedure A, Step 2, Method B from tert-butyl 3-(3-(4-cyclobutoxyphenyl)-1,2,4-oxadiazol-5-yl)-2-(diethoxyphosphoryl)propanoate (1.04 g, 1.9 mmol, 90% purity). The crude product was purified by chromatography on silica gel (0-50% MTBE/isohexane) to afford tert-butyl 2-((3-(4-cyclobutoxyphenyl)-1,2,4-oxadiazol-5-yl)methyl)acrylate (0.59 g, 1.5 mmol, 90% purity) as a clear and colourless oil. LCMS m/z 301.3 $(M-tBu+H)^+$ $(ES^+)$. $^1$H NMR (400 MHz, DMSO-d6) δ 7.92-7.82 (m, 2H), 7.04-6.93 (m, 2H), 6.32-6.22 (m, 1H), 6.03-5.90 (m, 1H), 4.85-4.67 (m, 1H), 4.00 (s, 2H), 2.48-2.40 (m, 2H), 2.13-1.99 (m, 2H), 1.86-1.74 (m, 1H), 1.73-1.59 (m, 1H), 1.33 (s, 9H).

Step 3

Prepared according to General Procedure A, Step 3 from tert-butyl 2-((3-(4-cyclobutoxyphenyl)-1,2,4-oxadiazol-5-yl)methyl)acrylate (0.59 g, 1.5 mmol, 90% purity). The crude product was purified by chromatography on silica gel (0-50% MTBE/isohexane) to afford 2-((3-(4-cyclobutoxyphenyl)-1,2,4-oxadiazol-5-yl)methyl)acrylic acid (0.441 g, 1.4 mmol) as a white solid. LCMS m/z 301.3 $(M+H)^+$ $(ES^+)$. $^1$H NMR (400 MHz, DMSO-d6) δ 12.85 (s, 1H), 7.96-7.77 (m, 2H), 7.06-6.92 (m, 2H), 6.36-6.25 (m, 1H), 6.04-5.90 (m, 1H), 4.88-4.65 (m, 1H), 4.00 (s, 2H), 2.48-2.40 (m, 2H), 2.13-1.98 (m, 2H), 1.88-1.74 (m, 1H), 1.72-1.58 (m, 1H).

Example 143—2-((3-(4-cyclopentyloxyphenyl)-1,2,4-oxadiazol-5-yl)methyl)acrylic acid

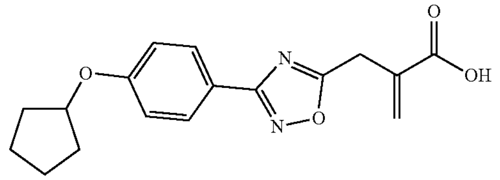 [SMILES: C=C(Cc1nc(-c2ccc(OC3CCCC3)cc2)no1)C(=O)O]

Prepared by an analogous procedure to Example 142 starting from 4-cyclopentyloxy-N-hydroxybenzimidamide (0.79 g, 2.5 mmol, 70% purity). Yield: 318 mg. Pale brown solid. LCMS: m/z 315.3 $(M+H)^+$ $(ES^+)$. $^1$H NMR (400 MHz, DMSO-d6) δ 12.85 (s, 1H), 7.95-7.79 (m, 2H), 7.12-6.97 (m, 2H), 6.38-6.24 (m, 1H), 6.03-5.92 (m, 1H), 4.99-4.81 (m, 1H), 4.00 (s, 2H), 2.05-1.82 (m, 2H), 1.81-1.47 (m, 6H).

Example 144—(R)-2-((3-(4-(sec-butoxy)phenyl)-1,2,4-oxadiazol-5-yl)methyl)acrylic acid

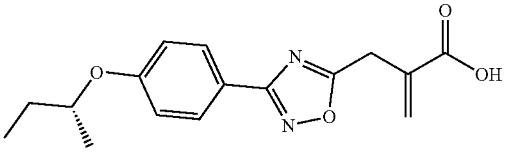 [SMILES: C=C(Cc1nc(-c2ccc(O[C@H](C)CC)cc2)no1)C(=O)O]

Prepared by an analogous procedure to Example 142 starting from (R)-4-(sec-butoxy)-N-hydroxybenzimidamide (0.63 g, 2.1 mmol, 70% purity). Yield: 320 mg. Colourless gum. LCMS: m/z 303.3 $(M+H)^+$ $(ES^+)$. $^1$H NMR (400 MHz, DMSO-d6) δ 12.85 (s, 1H), 7.94-7.83 (m, 2H), 7.12-6.99 (m, 2H), 6.36-6.25 (m, 1H), 6.02-5.94 (m, 1H), 4.55-4.38 (m, 1H), 4.00 (s, 2H), 1.77-1.52 (m, 2H), 1.25 (d, J=6.1 Hz, 3H), 0.93 (t, J=7.4 Hz, 3H).

Example 145—(S)-2-((3-(4-(sec-butoxy)phenyl)-1,2,4-oxadiazol-5-yl)methyl)acrylic acid

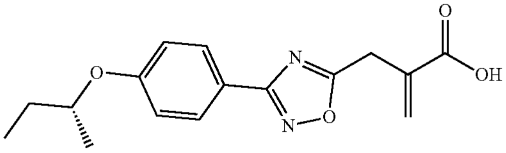 [SMILES: C=C(Cc1nc(-c2ccc(O[C@H](C)CC)cc2)no1)C(=O)O]

Prepared by an analogous procedure to Example 142 starting from (S)-4-(sec-butoxy)-N-hydroxybenzimidamide (0.79 g, 2.7 mmol, 70% purity). Yield: 402 mg. Colourless gum. LCMS: m/z 303.3 $(M+H)^+$ $(ES^+)$. $^1$H NMR (400 MHz, DMSO-d6) δ 12.85 (s, 1H), 7.94-7.83 (m, 2H), 7.12-6.99 (m, 2H), 6.36-6.25 (m, 1H), 6.02-5.94 (m, 1H), 4.55-4.38 (m, 1H), 4.00 (s, 2H), 1.77-1.52 (m, 2H), 1.25 (d, J=6.1 Hz, 3H), 0.93 (t, J=7.4 Hz, 3H).

Example 146—2-((3-(4-(4,4,4-trifluorobutoxy)phenyl)-1,2,4-oxadiazol-5-yl)methyl)acrylic acid

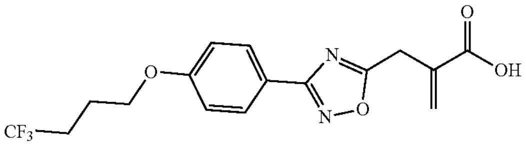 [SMILES: C=C(Cc1nc(-c2ccc(OCCCC(F)(F)F)cc2)no1)C(=O)O]

Prepared by an analogous procedure to Example 142 starting from N-hydroxy-4-(4,4,4-trifluorobutoxy)benzimidamide (0.83 g, 2.7 mmol, 85% purity). Yield: 364 mg. White solid. LCMS: m/z 357.1 $(M+H)^+$ $(ES^+)$. $^1H$ NMR (400 MHz, DMSO-d6) δ 12.86 (s, 1H), 7.96-7.81 (m, 2H), 7.15-7.02 (m, 2H), 6.38-6.27 (m, 1H), 6.06-5.91 (m, 1H), 4.12 (t, J=6.2 Hz, 2H), 4.00 (s, 2H), 2.48-2.36 (m, 2H), 2.03-1.90 (m, 2H).

Example 147—2-((3-(4-(1-propylcyclopropyl)benzyl)-1,2,4-oxadiazol-5-yl)methyl)acrylic acid

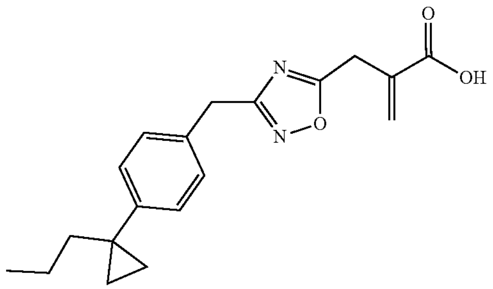 [SMILES: C=C(Cc1nc(Cc2ccc(C3(CCC)CC3)cc2)no1)C(=O)O]

Prepared by an analogous procedure to Example 142 starting from N-hydroxy-2-(4-(1-propylcyclopropyl)phenyl) acetimidamide (0.424 g, 1.82 mmol). The crude product was purified by preparative HPLC (Waters X-Select Prep-C18, 5 μm, 19×50 mm column, 5-95% MeCN in Water 0.1% Formic Acid) then further purified by prep-chiral SFC on a Waters Prep 15 with UV detection by DAD at 210-400 nm, 40° C., 120 bar. The column was IG 10×250 mm, 5 um, flow rate 15 mL/min at 30% MeOH (0.1% Ammonia), 70% $CO_2$. Yield: 159 mg. Colourless oil. LCMS: m/z 327.1 $(M+H)^+$ $(ES^+)$. $^1H$ NMR (400 MHz, DMSO-d6) δ 7.23-7.13 (m, 4H), 6.18 (d, J=1.5 Hz, 1H), 5.76 (s, 1H), 3.99 (s, 2H), 3.86 (s, 2H), 1.54-1.46 (m, 2H), 1.26-1.13 (m, 2H), 0.80 (t, J=7.3 Hz, 3H), 0.73-0.68 (m, 2H), 0.67-0.61 (m, 2H) [exchangeable proton not observed].

Example 148—2-((3-(4,6-dichloro-2,3-dihydro-1H-inden-1-yl)-1,2,4-oxadiazol-5-yl)methyl)acrylic acid

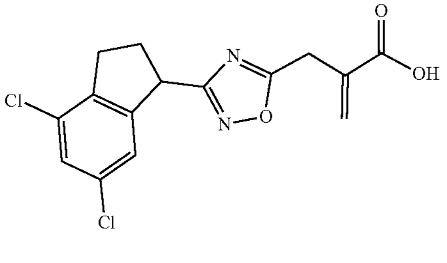 [SMILES: C=C(Cc1nc(C2CCc3c(Cl)cc(Cl)cc32)no1)C(=O)O]

Prepared by an analogous procedure to Example 142 starting from 4,6-dichloro-N-hydroxy-2,3-dihydro-1H-indene-1-carboximidamide (0.185 g, 0.68 mmol, 90% purity). Yield: 61 mg. White solid. LCMS: m/z 337.1/339.1 $(M+H)^+$ $(ES^+)$. $^1H$ NMR (400 MHz, DMSO-d6) δ 12.83 (s, 1H), 7.55-7.40 (m, 1H), 7.17-7.15 (m, 1H), 6.29-6.25 (m, 1H), 5.94-5.90 (m, 1H), 4.72 (t, J=8.0 Hz, 1H), 3.94 (s, 2H), 3.11-2.90 (m, 2H), 2.61-2.52 (m, 1H), 2.37-2.22 (m, 1H).

Example 149—2-((3-(4-propoxyphenyl)-1,2,4-oxadiazol-5-yl)methyl)acrylic acid

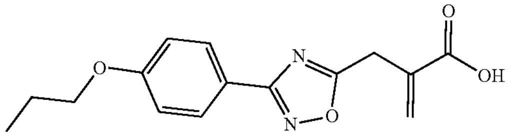 [SMILES: C=C(Cc1nc(-c2ccc(OCCC)cc2)no1)C(=O)O]

Prepared by an analogous procedure to Example 142 starting from N-hydroxy-4-propoxybenzimidamide (1.05 g, 4.8 mmol, 89% purity). Yield: 641 mg. White solid. LCMS: m/z 289.2 $(M+H)^+$ $(ES^+)$. $^1H$ NMR (400 MHz, DMSO-d6) δ 12.85 (s, 1H), 7.98-7.81 (m, 2H), 7.15-6.98 (m, 2H), 6.37-6.26 (m, 1H), 6.05-5.92 (m, 1H), 4.07-3.94 (m, 4H), 1.82-1.67 (m, 2H), 0.99 (t, J=7.4 Hz, 3H).

Example 150—2-((3-((3-chloro-4-methoxyphenyl) difluoromethyl)-1,2,4-oxadiazol-5-yl)methyl)acrylic acid

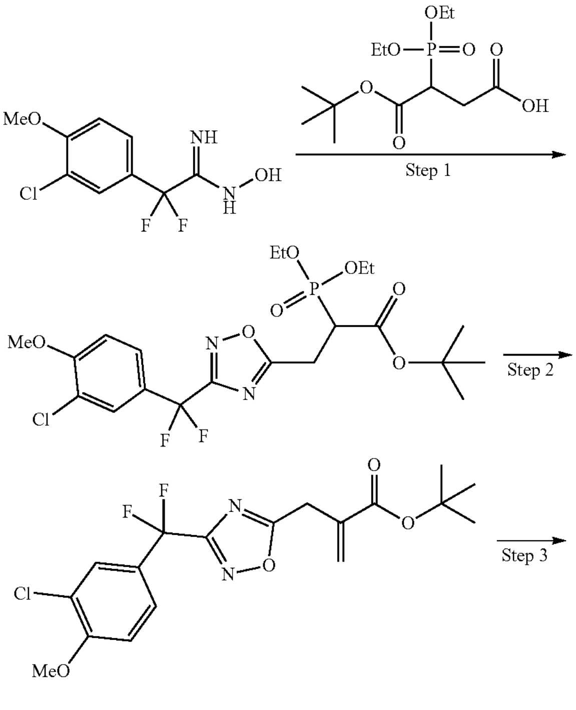

-continued

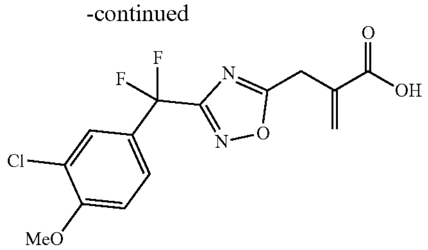

Step 1

HATU (2.85 g, 7.50 mmol) was added to a mixture of 2-(3-chloro-4-methoxyphenyl)-2,2-difluoro-N-hydroxy-acetimidamide (1.74 g, 6.25 mmol, 90% purity), 4-(tert-butoxy)-3-(diethoxyphosphoryl)-4-oxobutanoic acid (2.13 g, 6.87 mmol) and triethylamine (2.6 mL, 18.7 mmol) in DCM (30 mL) The mixture was stirred at RT for 2 h then diluted with 1M HCl (50 mL) and extracted with DCM (2×40 mL). The combined organic phases were dried ($MgSO_4$) and concentrated. The residue was taken up in THF (40 mL) and cesium carbonate (4.7 g, 14 mmol) was added. The reaction was heated to 70° C. and stirred for 3 h. The mixture was cooled to RT, quenched with 1M HCl (50 mL) and extracted with EtOAc (3×40 mL). The combined organic phases were dried ($MgSO_4$) and concentrated. The crude product was purified by chromatography on RP Flash C18 (5-75% (0.1% Formic acid in MeCN)/(0.1% Formic Acid in Water)) to afford tert-butyl 3-(3-((3-chloro-4-methoxyphenyl)difluoromethyl)-1,2,4-oxadiazol-5-yl)-2-(diethoxyphosphoryl)propanoate (1.63 g, 2.1 mmol, 69% purity) as a brown gum. LCMS m/z 547.3 $(M+Na)^+$ $(ES^+)$. $^1$H NMR (400 MHz, DMSO-d6) δ 7.61 (d, J=2.3 Hz, 1H), 7.56 (dd, J=8.7, 2.4 Hz, 1H), 7.31 (d, J=8.7 Hz, 1H), 4.14-3.99 (m, 4H), 3.92 (s, 3H), 3.71-3.55 (m, 1H), 3.52-3.33 (m, 2H), 1.30 (s, 9H), 1.27-1.18 (m, 6H).

Step 2

Prepared according to General Procedure A, Step 2, Method B from tert-butyl 3-(3-((3-chloro-4-methoxyphenyl)difluoromethyl)-1,2,4-oxadiazol-5-yl)-2-(diethoxyphosphoryl)propanoate (1.63 g, 2.1 mmol, 69% purity). The crude product was purified by chromatography on silica gel (0-25% MTBE/isohexane) to afford tert-butyl 2-((3-((3-chloro-4-methoxyphenyl)difluoromethyl)-1,2,4-oxadiazol-5-yl)methyl)acrylate (0.83 g, 1.8 mmol, 87% purity) as a clear and colourless gum. $^1$H NMR (400 MHz, DMSO-d6) δ 7.62 (d, J=2.3 Hz, 1H), 7.60-7.55 (m, 1H), 7.31 (d, J=8.7 Hz, 1H), 6.30-6.17 (m, 1H), 6.00-5.91 (m, 1H), 4.05 (s, 2H), 3.92 (s, 3H), 1.24 (s, 9H).

Step 3

Prepared according to General Procedure A, Step 3 from tert-butyl 2-((3-((3-chloro-4-methoxyphenyl)difluoromethyl)-1,2,4-oxadiazol-5-yl)methyl)acrylate (0.83 g, 1.8 mmol, 87% purity). The crude product was purified by chromatography on silica gel (0-50% MTBE/isohexane) to afford 2-((3-((3-chloro-4-methoxyphenyl)difluoromethyl)-1,2,4-oxadiazol-5-yl)methyl)acrylic acid (0.53 g, 1.5 mmol) as a pale yellow gum. LCMS m/z 343.3 $(M-H)^-$ $(ES^-)$. $^1$H NMR (400 MHz, DMSO-d6) δ 12.87 (s, 1H), 7.65 (d, J=2.3 Hz, 1H), 7.57 (dd, J=8.7, 2.4 Hz, 1H), 7.31 (d, J=8.7 Hz, 1H), 6.33-6.28 (m, 1H), 6.02-5.95 (m, 1H), 4.04 (s, 2H), 3.93 (s, 3H).

Example 151—2-((3-((3-chloro-4-methylphenyl)difluoromethyl)-1,2,4-oxadiazol-5-yl)methyl)acrylic acid

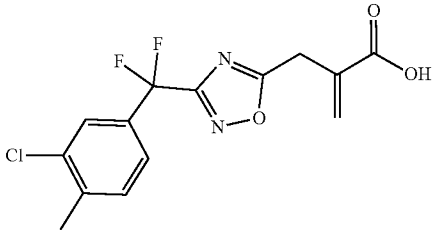 [SMILES: C=C(Cc1nc(C(F)(F)c2ccc(C)c(Cl)c2)no1)C(=O)O]

Prepared by an analogous procedure to Example 148 starting from 2-(3-chloro-4-methylphenyl)-2,2-difluoro-N-hydroxyacetimidamide (3.31 g, 12.0 mmol, 85% purity). Yield: 350 mg. Colourless gum. LCMS: m/z 327.1 $(M-H)^-$ $(ES^-)$. $^1$H NMR (400 MHz, DMSO-d6) δ 12.89 (s, 1H), 7.64 (d, J=1.9 Hz, 1H), 7.56 (d, J=8.1 Hz, 1H), 7.49 (dd, J=8.0, 1.9 Hz, 1H), 6.36-6.25 (m, 1H), 6.06-5.95 (m, 1H), 4.04 (s, 2H), 2.40 (s, 3H).

Example 152—2-((3-((4-chlorophenyl)fluoromethyl)-1,2,4-oxadiazol-5-yl)methyl)acrylic acid

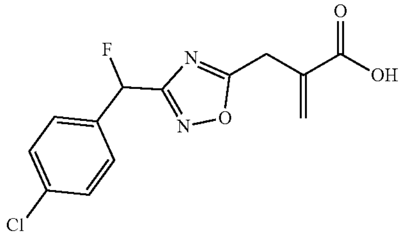 [SMILES: C=C(Cc1nc(C(F)c2ccc(Cl)cc2)no1)C(=O)O]

Prepared by an analogous procedure to Example 125 starting from 2-(4-chlorophenyl)-2-fluoro-N-hydroxy-acetimidamide (0.473 g, 1.98 mmol, 85% purity). Yield: 122 mg. Colourless oil. LCMS: m/z 297.1 $(M+H)^+$ $(ES^+)$. $^1$H NMR (400 MHz, DMSO-d6) δ 12.85 (s, 1H), 7.54 (s, 4H), 6.94 (d, J=44.6 Hz, 1H), 6.29 (d, J=1.1 Hz, 1H), 5.98-5.91 (m, 1H), 3.98 (s, 2H). $^{19}$F NMR (376 MHz, DMSO) δ −174.62.

Example 153—2-((3-((3,5-dichloro-4-fluorophenyl)difluoromethyl)-1,2,4-oxadiazol-5-yl)methyl)acrylic acid

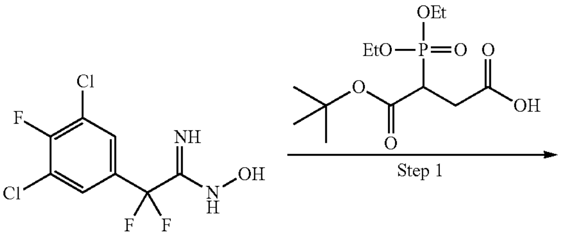

-continued

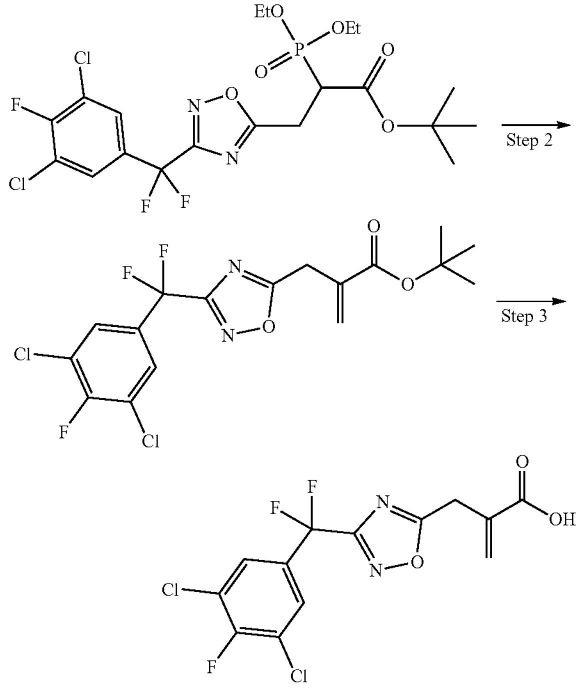

Step 1

HATU (2.30 g, 6.04 mmol) was added to a mixture of 2-(3,5-dichloro-4-fluorophenyl)-2,2-difluoro-N-hydroxy-acetimidamide (1.50 g, 5.49 mmol), 4-(tert-butoxy)-3-(diethoxyphosphoryl)-4-oxobutanoic acid (1.70 g, 5.49 mmol) and DIPEA (2.1 mL, 12 mmol) in DCM (25 mL) at RT. The mixture was stirred for 1 h, then diluted with water (50 mL). The phases were separated and the aqueous phase was extracted with EtOAc (2×25 mL). The combined organic phases were washed with sat. aq. $NaHCO_3$ (50 mL), 1 M HCl (50 mL) and brine (50 mL), then dried ($MgSO_4$) and concentrated. The residue was taken up in THF (25 mL) and cesium carbonate (2.15 g, 6.59 mmol) was added. The mixture was heated to 60° C. and stirred for 1 h, then cooled to RT and stirred for 16 h. The mixture was concentrated. The residue was partitioned between EtOAc (50 mL) and water (50 mL). The phases were separated and the aqueous phase was extracted with EtOAc (25 mL). The combined organic phases were washed with sat. aq. $NaHCO_3$ (50 mL), 1 M HCl (50 mL), brine (50 mL), dried ($MgSO_4$) and concentrated. The crude product was purified by chromatography on silica gel (0-100% MTBE/isohexane) to afford tert-butyl 3-(3-((3,5-dichloro-4-fluorophenyl)difluoromethyl)-1,2,4-oxadiazol-5-yl)-2-(diethoxyphosphoryl)propanoate (2.055 g, 3.6 mmol) as an orange oil. LCMS m/z 491.0/493.0 $(M-tBu+H)^+$ $(ES^+)$. $^1H$ NMR (400 MHz, DMSO-d6) δ 7.91 (d, J=6.2 Hz, 2H), 4.12-4.04 (m, 4H), 3.64 (ddd, J=23.4, 10.7, 4.6 Hz, 1H), 3.53-3.44 (m, 1H), 3.36 (ddd, J=17.1, 9.1, 4.6 Hz, 1H), 1.31 (s, 9H), 1.28-1.21 (m, 6H). $^{19}F$ NMR (376 MHz, DMSO) δ −93.49 (d, J=2.7 Hz), −112.02. $^{31}P$ NMR (162 MHz, DMSO) δ 19.94.

Step 2

Prepared according to General Procedure A, Step 2, Method B from tert-butyl 3-(3-((3,5-dichloro-4-fluorophenyl)difluoromethyl)-1,2,4-oxadiazol-5-yl)-2-(diethoxyphosphoryl)propanoate (2.055 g, 3.6 mmol). The crude product was purified by chromatography on silica gel (0-50% MTBE/isohexane) to afford tert-butyl 2-((3-((3,5-dichloro-4-fluorophenyl)difluoromethyl)-1,2,4-oxadiazol-5-yl)methyl)acrylate (1.052 g, 2.4 mmol) as a yellow oil. $^1H$ NMR (400 MHz, DMSO-d6) δ 7.93 (dd, J=6.1, 0.8 Hz, 2H), 6.27 (d, J=1.1 Hz, 1H), 5.97 (d, J=1.2 Hz, 1H), 4.06 (s, 2H), 1.26 (s, 9H). $^{19}F$ NMR (376 MHz, DMSO) δ −93.91 (d, J=2.8 Hz), −112.03.

Step 3

Prepared according to General Procedure A, Step 3 tert-butyl 2-((3-((3,5-dichloro-4-fluorophenyl)difluoromethyl)-1,2,4-oxadiazol-5-yl)methyl)acrylate (1.052 g, 2.4 mmol). The crude product was purified by chromatography on silica gel (0-100% MTBE/isohexane) to afford 2-((3-((3,5-dichloro-4-fluorophenyl)difluoromethyl)-1,2,4-oxadiazol-5-yl)methyl)acrylic acid (690 mg, 1.9 mmol) as a thick colourless gum. LCMS m/z 365.1/367.1 $(M-H)^-$ $(ES^-)$. $^1H$ NMR (400 MHz, DMSO-d6) δ 12.91 (s, 1H), 7.95 (d, J=6.2 Hz, 2H), 6.32 (d, J=1.0 Hz, 1H), 6.01 (d, J=1.3 Hz, 1H), 4.06 (s, 2H).

Example 154—2-((3-((4-bromo-3-chlorophenyl)difluoromethyl)-1,2,4-oxadiazol-5-yl)methyl)acrylic acid

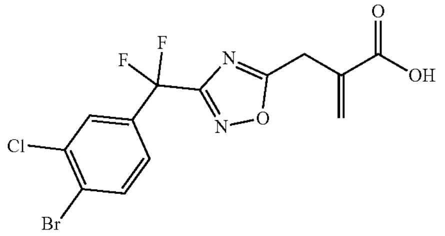 [SMILES: C=C(Cc1nc(C(F)(F)c2ccc(Br)c(Cl)c2)no1)C(=O)O]

Prepared by an analogous procedure to Example 151 starting from 2-(3,5-dichloro-4-fluorophenyl)-2,2-difluoro-N-hydroxyacetimidamide (1.50 g, 5.01 mmol). Yield: 563 mg. Colourless gum. LCMS: m/z 391.0/393.0 $(M-H)^-$ $(ES^-)$. $^1H$ NMR (400 MHz, DMSO-d6) δ 12.90 (s, 1H), 7.99 (d, J=8.4 Hz, 1H), 7.89 (d, J=2.2 Hz, 1H), 7.54 (dd, J=8.4, 2.2 Hz, 1H), 6.31 (d, J=1.1 Hz, 1H), 5.99 (d, J=1.2 Hz, 1H), 4.05 (s, 2H). $^{19}F$ NMR (376 MHz, DMSO) δ −93.94.

Example 155—2-((3-(difluoro(4-((trifluoromethyl)thio)phenyl)methyl)-1,2,4-oxadiazol-5-yl)methyl)acrylic acid

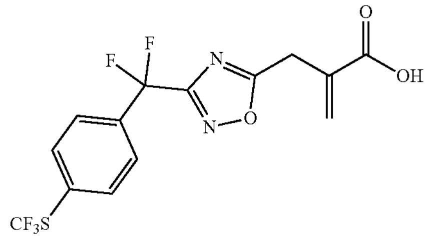

Prepared by an analogous procedure to Example 151 starting from 2,2-difluoro-N-hydroxy-2-(4-((trifluoromethyl)thio)phenyl)acetimidamide (1.68 g, 5.87 mmol). Yield: 1.353 g. Colourless gum.

LCMS: m/z 379.2 $(M-H)^-$ $(ES^-)$. $^1H$ NMR (400 MHz, DMSO-d6) δ 12.90 (s, 1H), 7.92 (d, J=8.2 Hz, 2H), 7.83-

7.76 (m, 2H), 6.31 (d, J=1.1 Hz, 1H), 6.02-5.97 (m, 1H), 4.05 (s, 2H). $^{19}F$ NMR (376 MHz, DMSO) δ −41.41, −94.32.

Example 156—2-(1-(3-(1-(4-(trifluoromethyl)phenyl)cyclopropyl)-1,2,4-oxadiazol-5-yl)cyclopropyl)acrylic acid

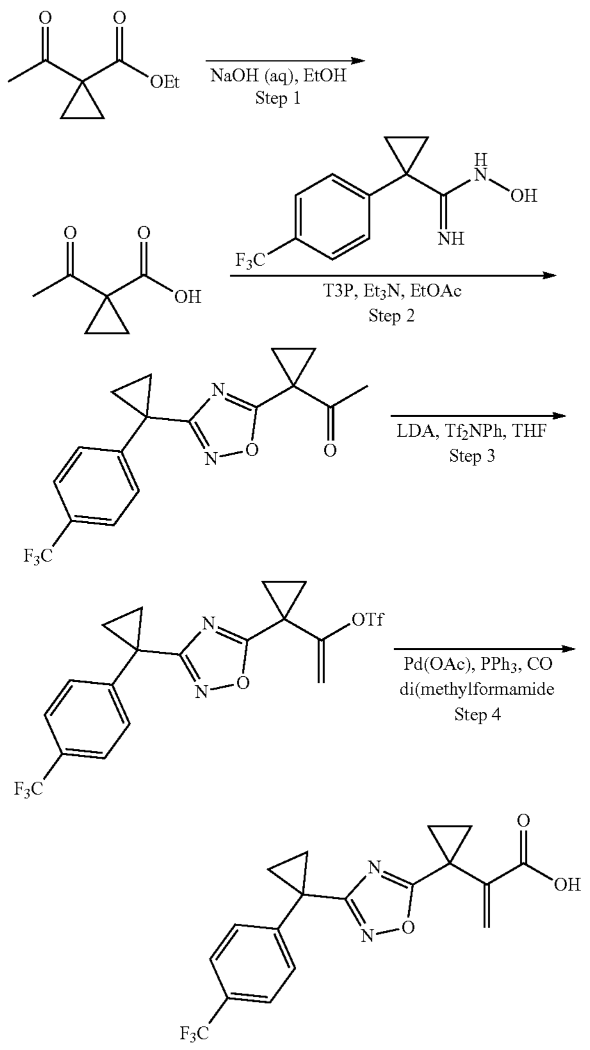

Step 1

Sodium hydroxide (4 M aqueous, 40 mL, 160 mmol) was added to a solution of ethyl 1-acetylcyclopropane-1-carboxylate (5.00 g, 32 mmol) in EtOH (10 mL) at 0° C. The mixture was warmed to RT and stirred for 16 h. The mixture was part-concentrated and extracted with MTBE (3×25 mL). The aqueous layer was then acidified with conc HCl to pH-2 and extracted with DCM (3×25 mL). The combined organic layers were washed with brine (50 mL), dried ($Na_2SO_4$) and concentrated to affod 1-acetylcyclopropane-1-carboxylic acid (3.62 g, 28 mmol, 87%, 99% Purity) as a colourless oil. $^1H$ NMR (400 MHz, DMSO-d6) δ 12.86 (s, 1H), 2.36 (s, 3H), 1.36-1.28 (m, 4H).

Step 2

T3P (50 wt % in EtOAc, 11.8 mL, 20 mmol) was added dropwise to a solution of N-hydroxy-1-(4-(trifluoromethyl)phenyl)cyclopropane-1-carboximidamide (2.00 g, 7.94 mmol), 1-acetylcyclopropane-1-carboxylic acid (1.02 g, 7.94 mmol) and triethylamine (3.3 mL, 24 mmol) in EtOAc (4 mL) at RT. The mixture was heated to 80° C. and stirred for 18 h. The mixture was cooled to RT and poured into ice water (50 mL), then extracted with EtOAc (3×20 mL). The combined organic layers were washed with sat. $NaHCO_3$ (2×25 mL), brine (30 mL), dried ($Na_2SO_4$) and concentrated. The crude product was purified by chromatography on silica gel (0-100% MTBE/hexane) to afford 1-(1-(3-(1-(4-(trifluoromethyl)phenyl)cyclopropyl)-1,2,4-oxadiazol-5-yl)cyclopropyl)ethan-1-one (1.09 g, 2.6 mmol, 80% purity) as a light yellow oil. LCMS: m/z 337.1 $(M+H)^+$ $(ES^+)$.$^1H$ NMR (400 MHz, DMSO-d6) δ 7.73-7.69 (m, 2H), 7.66-7.61 (m, 2H), 2.24 (s, 3H), 1.76-1.72 (m, 2H), 1.63-1.59 (m, 2H), 1.59-1.55 (m, 2H), 1.50-1.45 (m, 2H).

Step 3

LDA (2 M THF/heptane/ethylbenzene, 1.68 mL, 3.35 mmol) was added dropwise to a solution of 1-(1-(3-(1-(4-(trifluoromethyl)phenyl)cyclopropyl)-1,2,4-oxadiazol-5-yl)cyclopropyl)ethan-1-one (1.08 g, 3.19 mmol) in THF (15 mL) -20° C. The mixture was stirred at −20° C. for 30 min, before a solution of N-Phenyl-bis(trifluoromethanesulfonimide) (1.25 g, 3.51 mmol) in THF (2 mL) was added dropwise. The reaction was warmed to −10° C. and stirred for 2 h. Sat. aq. $NH_4Cl$ (20 mL) was added and the mixture extracted with EtOAc (3×20 mL). The combined organic layers were washed with brine (30 mL), dried ($Na_2SO_4$) and concentrated to afford crude 1-(1-(3-(1-(4-(trifluoromethyl)phenyl)cyclopropyl)-1,2,4-oxadiazol-5-yl)cyclopropyl)vinyl trifluoromethanesulfonate (2.28 g) as an amber solid that was used in the next step without analysis/purification.

Step 4

Triphenylphosphine (168 mg, 641 μmol) and palladium (II) acetate (72 mg, 320 μmol) were added to a solution of crude 1-(1-(3-(1-(4-(trifluoromethyl)phenyl)cyclopropyl)-1,2,4-oxadiazol-5-yl)cyclopropyl)vinyl trifluoromethanesulfonate (1.50 g) in dimethyl formamide(7.5 mL). Formic acid (0.2 mL, 5.1 mmol) and triethylamine (0.9 mL, 6.4 mmol) were added. The mixture was stirred at RT under an atmosphere of CO (3 bar) at RT for 18 h. The mixture was poured into 10% aq. $K_2CO_3$ (30 mL) and extracted with MTBE (3×15 mL). The aqueous layer was then acidified with conc. HCl to pH-2 and extracted with MTBE (3×15 mL). The combined organic layers were washed with brine (20 mL), filtered and concentrated. The crude product was purified by chromatography on silica gel (0-50% MTBE/isohexane) to afford 2-(1-(3-(1-(4-(trifluoromethyl)phenyl)cyclopropyl)-1,2,4-oxadiazol-5-yl)cyclopropyl)acrylic acid (21 mg, 59 μmol) as an off-white solid. LCMS: m/z 365.4 $(M+H)^+$ $(ES^+)$. $^1H$ NMR (400 MHz, DMSO-d6) δ 12.76 (s, 1H), 7.69 (d, J=8.2 Hz, 2H), 7.58 (d, J=8.1 Hz, 2H), 6.32 (s, 1H), 5.93 (s, 1H), 1.54-1.45 (m, 4H), 1.45-1.36 (m, 4H). $^{19}F$ NMR (376 MHz, DMSO) δ −60.95.

The following compound was prepared by an analogous procedure:

| Example No. | Starting material used/Example Structure/Name | LCMS/$^1$H NMR data |
|---|---|---|
| 172 | ethyl 2,2-dimethyl-3-oxobutanoate/N-hydroxy-1-(4-(trifluoromethyl)phenyl)cyclopropane-1-carboximidamide 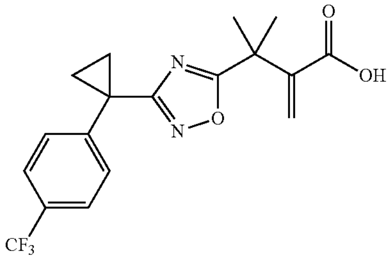 3-methyl-2-methylene-3-(3-(1-(4-(trifluoromethyl)phenyl)cyclopropyl)-1,2,4-oxadiazol-5-yl)butanoic acid | LCMS m/z 367.3 (M + H)$^+$ (ES$^+$). $^1$H NMR (400 MHz, DMSO-d6) δ 12.70 (s, 1H), 7.69 (d, J = 8.2 Hz, 2H), 7.57 (d, J = 8.1 Hz, 2H), 6.31 (s, 1H), 5.95 (s, 1H), 1.55-1.47 (m, 8H), 1.47-1.42 (m, 2H) |

Example 157—2-((3-(1-(4-((trifluoromethyl)sulfinyl)phenyl)cyclopropyl)-1,2,4-oxadiazol-5-yl)methyl)acrylic acid

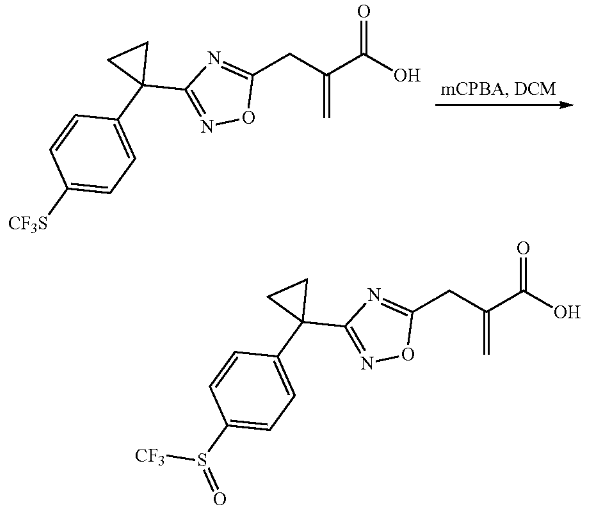

meta-Chloroperbenzoic acid (77 Wt %, 90 mg, 0.4 mmol was added to a mixture of 2-((3-(1-(4-((trifluoromethyl)thio)phenyl)cyclopropyl)-1,2,4-oxadiazol-5-yl)methyl)acrylic acid (0.100 g, 260 μmol) in DCM (3 mL) at 0° C. The mixture was stirred at 0° C. for 1 h, then at RT for 18 h. The mixture was diluted with water (20 mL) and extracted with DCM (3×10 mL). The combined organic phases were dried ($MgSO_4$) and concentrated. The crude product was purified by chromatography on silica gel (0-100% MTBE/isohexane) to afford 2-((3-(1-(4-((trifluoromethyl)sulfinyl)phenyl)cyclopropyl)-1,2,4-oxadiazol-5-yl)methyl)acrylic acid (15 mg, 35 μmol) as a colourless liquid. LCMS m/z 387.2 (M+H)$^+$ (ES$^+$). $^1$H NMR (400 MHz, $CD_3OD$) δ 7.92-7.81 (m, 2H), 7.78-7.71 (m, 2H), 6.45-6.37 (m, 1H), 5.96-5.88 (m, 1H), 3.92 (s, 2H), 1.74-1.63 (m, 2H), 1.54-1.45 (m, 2H) [1 exchangeable proton not observed].

Example 158—2-((3-(4-((trifluoromethyl)thio)phenyl)-1,2,4-oxadiazol-5-yl)methyl)acrylic acid

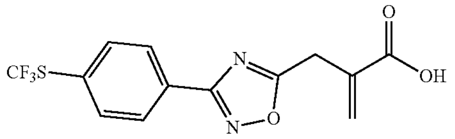

Prepared by an analogous procedure to Example 121 starting from N-hydroxy-4-((trifluoromethyl)thio)benzimidamide (1.08 g, 4.1 mmol, 90% purity). Yield: 649 mg. White solid. LCMS: m/z 329.0 (M−H)$^-$ (ES$^-$). $^1$H NMR (400 MHz, DMSO-d6) δ 12.89 (s, 1H), 8.16-8.09 (m, 2H), 7.94-7.87 (m, 2H), 6.34 (d, J=1.2 Hz, 1H), 6.06-5.97 (m, 1H), 4.06 (s, 2H).

Example 159—2-((3-(4-(3-methoxypropoxy)phenyl)-1,2,4-oxadiazol-5-yl)methyl)acrylic acid

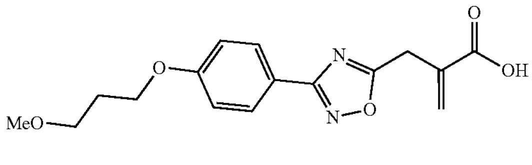 [SMILES: C=C(Cc1nc(-c2ccc(OCCCOC)cc2)no1)C(=O)O]

Prepared by an analogous procedure to Example 142 starting from N-hydroxy-4-(3-methoxypropoxy)benzimidamide (2.41 g, 8.06 mmol, 75% purity). Yield: 681 mg. White solid. LCMS: m/z 319.3 (M+H)$^+$ (ES$^+$). $^1$H NMR (400 MHz, DMSO-d6) δ 12.84 (s, 1H), 7.99-7.80 (m, 2H), 7.16-6.97 (m, 2H), 6.40-6.25 (m, 1H), 6.04-5.91 (m, 1H), 4.09 (t, J=6.4 Hz, 2H), 4.00 (s, 2H), 3.48 (t, J=6.3 Hz, 2H), 3.25 (s, 3H), 2.03-1.90 (m, 2H).

Example 160—2-((3-(4-butoxy-3-chlorophenyl)-1,2,4-oxadiazol-5-yl)methyl)acrylic acid

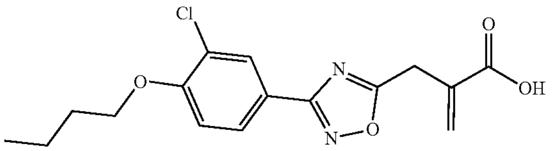 [SMILES: C=C(Cc1nc(-c2ccc(OCCCC)c(Cl)c2)no1)C(=O)O]

Prepared by an analogous procedure to Example 129 starting from 4-butoxy-3-chloro-N-hydroxybenzimidamide (Intermediate 216, 360 mg, 1.49 mmol). Yield: 103 mg. White solid. LCMS: (System 2, Method B) m/z 337.0/339.0 $(M+H)^+$ $(ES^+)$. $^1H$ NMR (400 MHz, DMSO-d6) δ: 12.87 (br, 1H), 7.96-7.87 (m, 2H), 7.32 (d, J=8.7 Hz, 1H), 6.33 (s, 1H), 6.00 (d, J=1.3 Hz, 1H), 4.15 (t, J=6.4 Hz, 2H), 4.01 (s, 2H), 1.81-1.69 (m, 2H), 1.54-1.40 (m, 2H), 0.95 (t, J=7.4 Hz, 3H).

Example 161—2-((3-(4-butoxy-3-(trifluoromethyl)phenyl)-1,2,4-oxadiazol-5-yl)methyl)acrylic acid

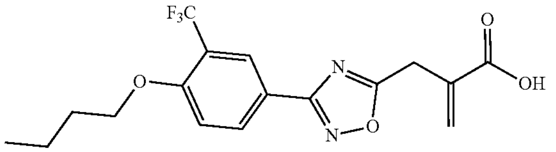 [SMILES: C=C(Cc1nc(-c2ccc(OCCCC)c(C(F)(F)F)c2)no1)C(=O)O]

Prepared by an analogous procedure to Example 129 starting from 4-butoxy-N-hydroxy-3-(trifluoromethyl)benzimidamide (Intermediate 218, 409 mg, 1.48 mmol). Yield: 200 mg. White solid. LCMS: (System 2, Method B) m/z 371.0 $(M+H)^+$ $(ES^+)$. $^1H$ NMR (400 MHz, DMSO-d6) δ: 12.89 (br, 1H), 8.21 (dd, J=8.7 2.2 Hz, 1H), 8.10 (d, J=2.2 Hz, 1H), 7.45 (d, J=8.8 Hz, 1H), 6.33 (s, 1H), 6.01 (s, 1H), 4.21 (t, J=6.2 Hz, 2H), 4.03 (s, 2H), 1.79-1.68 (m, 2H), 1.52-1.39 (m, 2H), 0.94 (t, J=7.4 Hz, 3H).

Example 162—2-((3-(4-butoxy-3,5-difluorophenyl)-1,2,4-oxadiazol-5-yl)methyl)acrylic acid

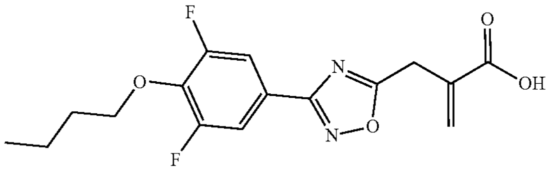 [SMILES: C=C(Cc1nc(-c2cc(F)c(OCCCC)c(F)c2)no1)C(=O)O]

Prepared by an analogous procedure to Example 129 starting from 4-butoxy-3,5-difluoro-N-hydroxybenzimidamide (Intermediate 220, 404 mg, 1.65 mmol). Yield: 211 mg. White solid. LCMS: (System 2, Method B) m/z 339.0 $(M+H)^+$ $(ES^+)$. $^1H$ NMR (400 MHz, DMSO-d6) δ: 12.90 (br, 1H), 7.72-7.63 (m, 2H), 6.33 (s, 1H), 6.00 (d, J=1.4 Hz, 1H), 4.22 (t, J=6.4 Hz, 2H), 4.03 (s, 2H), 1.73-1.63 (m, 2H), 1.51-1.38 (m, 2H), 0.92 (t, J=7.4 Hz, 3H).

Example 163—2-((3-(3-chloro-4-methoxybenzyl)-1,2,4-oxadiazol-5-yl)methyl)acrylic acid

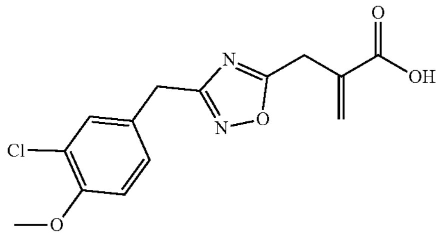 [SMILES: C=C(Cc1nc(Cc2ccc(OC)c(Cl)c2)no1)C(=O)O]

Prepared by an analogous procedure to Example 128 starting from 2-(3-chloro-4-methoxyphenyl)-N-hydroxyacetimidamide (Intermediate 221, 400 mg, 1.86 mmol). Yield: 73 mg. White solid. LCMS: (System 2, Method B) m/z 309.1/311.1 $(M+H)^+$ $(ES^+)$. $^1H$ NMR (400 MHz, DMSO-d6) δ: 12.83 (br, 1H), 7.35 (d, J=2.2 Hz, 1H), 7.21 (dd, J=8.5, 2.2 Hz, 1H), 7.09 (d, J=8.5 Hz, 1H), 6.26 (d, J=1.3 Hz, 1H), 5.91 (s, J=1.3 Hz, 1H), 4.01 (s, 2H), 3.90 (s, 2H), 3.82 (s, 3H).

Example 164—2-((3-(4-chloro-3,5-difluorobenzyl)-1,2,4-oxadiazol-5-yl)methyl)acrylic acid

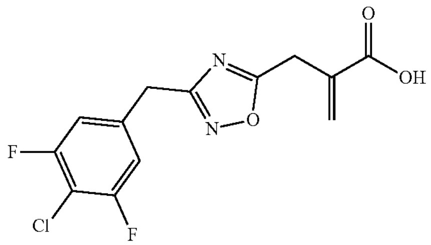 [SMILES: C=C(Cc1nc(Cc2cc(F)c(Cl)c(F)c2)no1)C(=O)O]

Prepared by an analogous procedure to Example 128 starting from 2-(4-chloro-3,5-difluorophenyl)-N-hydroxyacetimidamide (Intermediate 222, 470 mg, 2.10 mmol). Yield: 71 mg. White solid. LCMS: (System 2, Method B) m/z 314.9/316.8 $(M+H)^+$ $(ES^+)$. $^1H$ NMR (400 MHz, DMSO-d6) δ: 12.84 (br, 1H), 7.29 (d, J=8.1 Hz, 2H), 6.27 (s, 1H), 5.92 (d, J=1.2 Hz, 1H), 4.15 (s, 2H), 3.92 (s, 2H).

Example 165—2-((3-(3-chloro-4-methylbenzyl)-1,2,4-oxadiazol-5-yl)methyl)acrylic acid

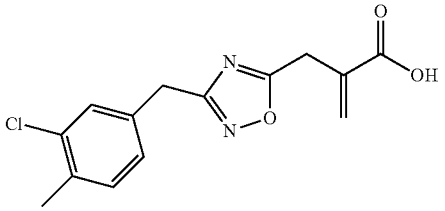 [SMILES: C=C(Cc1nc(Cc2ccc(C)c(Cl)c2)no1)C(=O)O]

Prepared by an analogous procedure to Example 128 starting from 2-(3-chloro-4-methylphenyl)-N-hydroxyacetimidamide (Intermediate 223, 450 mg, 2.21 mmol). Yield: 153 mg. White solid. LCMS: (System 2, Method B)

m/z 293.0/294.9 $(M+H)^+$ $(ES^+)$. $^1H$ NMR (400 MHz, DMSO-d6) δ: 12.80 (br, 1H), 7.34 (d, J=1.8 Hz, 1H), 7.29 (d, J=7.8 Hz, 1H), 7.14 (dd, J=7.8, 1.8 Hz, 1H), 6.26 (s, 1H), 5.91 (d, J=1.2 Hz, 1H), 4.04 (s, 2H), 3.91 (s, 2H), 2.29 (s, 3H).

Example 166—(E)-2-methyl-3-(3-octyl-1,2,4-oxadiazol-5-yl)acrylic acid

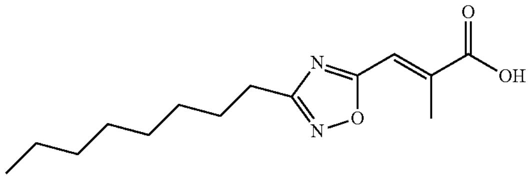 [SMILES: CCCCCCCCc1noc(/C=C(\C)C(=O)O)n1]

Diethylamine (40 μL, 400 μmol was added to a solution of 2-((3-octyl-1,2,4-oxadiazol-5-yl)methyl)acrylic acid (Example 1, 0.100 g, 375 μmol) in DMSO (1 mL). The mixture was stirred for 18 h at RT, then diluted with DMSO (1 mL) and acidified with 2-3 drops of formic acid then filtered and purified by reversed phase preparative HPLC on a Waters X-Select CSH C18 prep column, 130 Å, 5 μm, 30 mm×100 mm, flow rate 40 mL min−1 eluting with a 0.1% formic in water-MeCN gradient over 12.5 mins using UV detection across all wavelengths with PDA as well as a QDA and ELS detector. At-column dilution pump gives 2 mL min−1 MeCN over the entire method, which is included in the following MeCN percentages. Gradient information: 0.0-0.5 min, 50% MeCN; 0.5-10.5 min, ramped from 50% MeCN to 80% MeCN; 10.5-10.6 min, ramped from 80% MeCN to 100% MeCN; 10.6-12.5 min, held at 100% MeCN. The clean fractions were evaporated in a Genevac to affod (E)-2-methyl-3-(3-octyl-1,2,4-oxadiazol-5-yl)acrylic acid (30 mg, 113 μmol) as a white solid. LCMS: m/z 267.1 $(M+H)^+$ $(ES^+)$. $^1H$ NMR (400 MHz, DMSO-d6) δ 13.40 (s, 1H), 7.29 (q, J=1.5 Hz, 1H), 2.75 (t, J=7.4 Hz, 2H), 2.33 (d, J=1.5 Hz, 3H), 1.75-1.61 (m, 2H), 1.37-1.20 (m, 10H), 0.90-0.81 (m, 3H).

The following compounds were prepared by an analogous procedure:

| Example No. | Starting material used/Example Structure/Name | LCMS/$^1H$ NMR data |
|---|---|---|
| 167 | 2-((3-(4-butoxyphenyl)-1,2,4-oxadiazol-5-yl)methylacrylic acid (Example 61) 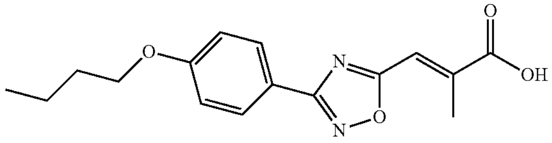 (E)-3-(3-(4-butoxyphenyl)-1,2,4-oxadiazol-5-yl)-2-methylacrylic acid | LCMS m/z 303.5 $(M + H)^+$ $(ES^+)$. $^1H$ NMR (400 MHz, DMSO-d6) δ 13.42 (s, 1H), 8.01-7.95 (m, 2H), 7.37 (q, J = 1.5 Hz, 1H), 7.15-7.09 (m, 2H), 4.06 (t, J = 6.5 Hz, 2H), 2.42 (d, J = 1.5 Hz, 3H), 1.77-1.69 (m, 2H), 1.51-1.40 (m, 2H), 0.95 (t, J = 7.4 Hz, 3H) |
| 168 | 2-((3-(1-(4-bromophenyl)cyclopropyl)-1,2,4-oxadiazol-5-yl)-2-methylacrylic acid (Example 50) 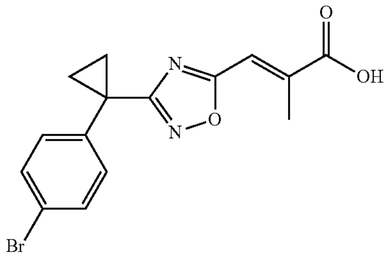 (E)-3-(3-(1-(4-bromophenyl)cyclopropyl)-1,2,4-oxadiazol-5-yl)-2-methylacrylic acid | LCMS m/z 347.3/349.3 $(M + H)^+$ $(ES^+)$. $^1H$ NMR (400 MHz, DMSO-d6) δ 13.38 (s, 1H), 7.58-7.52 (m, 2H), 7.41-7.36 (m, 2H), 7.25 (q, J = 1.5 Hz, 1 H), 2.29 (d, J = 1.5 Hz, 3H), 1.60-1.52 (m, 2H), 1.47-1.40 (m, 2H) |

-continued

| Example No. | Starting material used/Example Structure/Name | LCMS/$^1$H NMR data |
|---|---|---|
| 169 | 2-((3-(1-(4-(pentafluoro-$\lambda^6$-sulfaneyl)phenyl)cyclopropyl)-1,2,4-oxadiazol-5-yl)methyl)acrylic acid (Examplr 77)<br>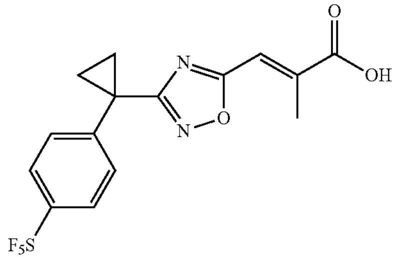<br>(E)-2-methyl-3-(3-(1-(4-(pentafluoro-$\lambda^6$-sulfaneyl)phenyl)cyclopropyl)-1,2,4-oxadiazol-5-yl)acrylic acid | LCMS m/z 395.1 $(M-H)^-$ $(ES^-)$. $^1$H NMR (400 MHz, DMSO-d6) δ 13.46 (s, 1H), 7.94-7.83 (m, 2H), 7.65 (d, J = 8.5 Hz, 2H), 7.29-7.23 (m, 1H), 2.30 (d, J = 1.5 Hz, 3H), 1.67-1.60 (m, 2H), 1.56-1.49 (m, 2H) |
| 170 | 2-((3-(1-(4-((trifluoromethyl)thio)phenyl)cyclopropyl)-1,2,4-oxadiazol-5-yl)methyl)acrylic acid (Example 86)<br>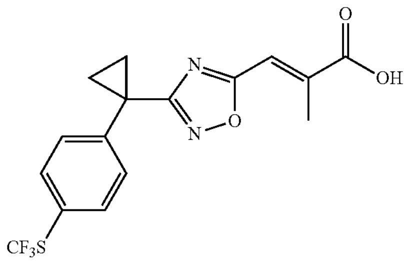<br>(E)-2-methyl-3-(3-(1-(4-((trifluoromethyl)thio)phenyl)cyclopropyl)-1,2,4-oxadiazol-5-yl)acrylic acid | LCMS m/z 369.2 $(M-H)^-$ $(ES^-)$. $^1$H NMR (400 MHz, DMSO-d6) δ 13.36 (s, 1H), 7.74-7.67 (m, 2H), 7.62-7.54 (m, 2H), 7.32-7.21 (m, 2H), 2.29 (d, J = 1.5 Hz, 3H), 1.64-1.57 (m, 2H), 1.57-1.44 (m, 2H) |

Example 171—2-((6-(4-chlorobenzyl)pyridin-2-yl)methyl)acrylic acid trifluoroacetic acid salt

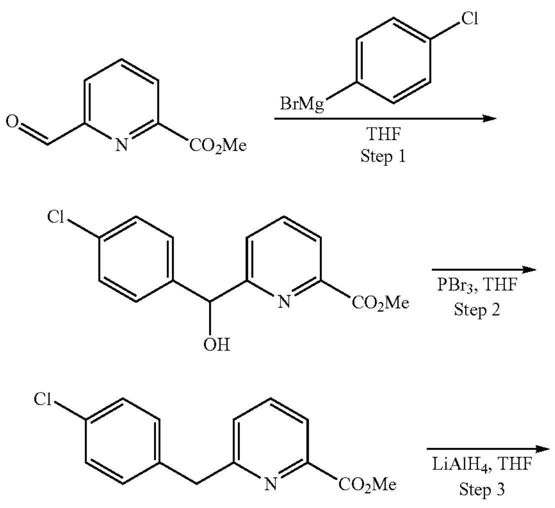

-continued

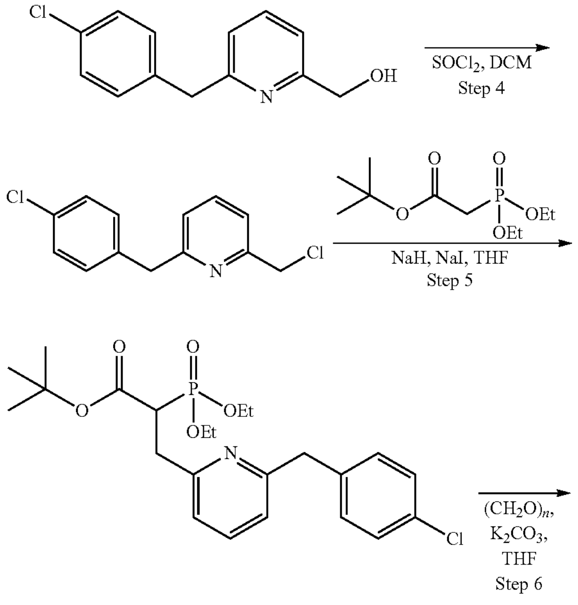

-continued

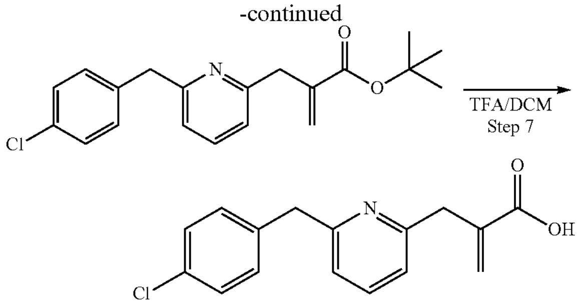

Step 1

(4-chlorophenyl)magnesium bromide (1 M in MeTHF, 73 mL, 73 mmol) was added dropwise to a suspension of methyl 6-formylpicolinate (10.0 g, 60.6 mmol) in THF (200 mL) at −78° C. The mixture was allowed to warm to RT and stirred for 60 h. The mixture was quenched with sat. aq. $NH_4Cl$ (10 mL), then diluted with water (200 mL). The phases were separated and the aqueous phase was extracted with EtOAc (2×100 mL). The combined organic phases were washed with brine (200 mL), dried ($MgSO_4$) and concentrated. The crude product was purified by chromatography on silica gel (0-100% EtOAc/isohexane) to afford methyl 6-((4-chlorophenyl)(hydroxy)methyl)picolinate (6.34 g, 22 mmol) as a yellow oil. LCMS m/z 278.1 $(M+H)^+$ $(ES^+)$. $^1H$ NMR (400 MHz, DMSO-d6) δ 7.99 (t, J=7.7 Hz, 1H), 7.92 (dd, J=7.7, 1.2 Hz, 1H), 7.79 (dd, J=7.8, 1.2 Hz, 1H), 7.44-7.39 (m, 2H), 7.39-7.34 (m, 2H), 6.35 (d, J=4.2 Hz, 1H), 5.78 (d, J=4.2 Hz, 1H), 3.87 (s, 3H).

Step 2

Phosphorus tribromide (0.50 mL, 5.4 mmol) was added to a solution of methyl 6-((4-chlorophenyl)(hydroxy)methyl) picolinate (0.50 g, 1.8 mmol) in THF (15 mL). The mixture was stirred at RT for 20 min, then heated to 80° C. and stirred for 3 h, then cooled to RT and stirred for 18 h. The mixture was cooled in an ice bath and quenched with water (20 mL), then basified with solid $Na_2CO_3$. The phases were separated and the aqueous phase was extracted with EtOAc (3×50 mL). The combined organic phases were washed with brine (50 mL), dried ($MgSO_4$) and concentrated. The crude product was purified by chromatography on silica gel (0-50% EtOAc/isohexane) to afford methyl 6-(4-chlorobenzyl)picolinate (260 mg, 0.98 mmol) as a colourless oil. LCMS m/z 262.2 $(M+H)^+$ $(ES^+)$. $^1H$ NMR (400 MHz, DMSO-d6) δ 7.96-7.87 (m, 2H), 7.52 (dd, J=6.4, 2.4 Hz, 1H), 7.39-7.33 (m, 2H), 7.32-7.26 (m, 2H), 4.17 (s, 2H), 3.87 (s, 3H).

Step 3

Lithium aluminum hydride (4 M in diethylether, 1.2 mL, 4.8 mmol) was added dropwise to a solution of methyl 6-(4-chlorobenzyl)picolinate (1.23 g, 4.70 mmol) in THF (25 mL) at 0° C. The mixture was stirred for 1 h. Sodium sulfate decahydrate was added in small portions until effervescing stopped. The mixture was stirred and the resulting suspension filtered, washing with EtOAc (50 mL). The filtrate was dried ($MgSO_4$) and concentrated to afford (6-(4-chlorobenzyl)pyridin-2-yl)methanol (1.128 g, 4.3 mmol, 90% purity) as a yellow oil. LCMS m/z 234.2/236.2 $(M+H)^+$ $(ES^+)$. $^1H$ NMR (400 MHz, DMSO-d6) δ 7.70 (t, J=7.7 Hz, 1H), 7.38-7.24 (m, 5H), 7.10 (dd, J=7.6, 1.0 Hz, 1H), 5.35 (t, J=5.9 Hz, 1H), 4.52 (d, J=5.9 Hz, 2H), 4.04 (s, 2H).

Step 4

Thionyl chloride (0.80 mL, 11 mmol) was added to a solution of (6-(4-chlorobenzyl)pyridin-2-yl)methanol (1.128 g, 4.3 mmol, 90% purity) in DCM (20 mL). The mixture was stirred at RT for 2 h. The mixture was quenched with water (50 mL) and basified with solid $K_2CO_3$. The phases were separated and the aqueous phase was extracted with EtOAc (2×50 mL). The combined organic phases were washed with brine (50 mL), dried ($MgSO_4$) and concentrated. The crude product was purified by chromatography on silica gel (0-50% EtOAc/isohexane) to afford 2-(4-chlorobenzyl)-6-(chloromethyl)pyridine (0.880 g, 3.4 mmol) as a yellow oil. LCMS m/z 240.3/242.3 $(M+H)^+$ $(ES^+)$. $^1H$ NMR (400 MHz, DMSO-d6) δ 7.76 (t, J=7.7 Hz, 1H), 7.38 (dd, J=7.8, 1.0 Hz, 1H), 7.37-7.32 (m, 2H), 7.32-7.27 (m, 2H), 7.23 (dd, J=7.8, 1.0 Hz, 1H), 4.74 (s, 2H), 4.08 (s, 2H).

Step 5

Tert-butyl 2-(diethoxyphosphoryl)acetate (0.32 mL, 1.4 mmol) was added dropwise to a suspension of sodium hydride (55 mg, 60% Wt, 1.4 mmol) in THF (5 mL) at 0° C. The mixture was stirred for 30 min, then a solution of 2-(4-chlorobenzyl)-6-(chloromethyl)pyridine (300 mg, 1.14 mmol) in THF (2 mL) was added. The mixture was allowed to warm to RT and stirred for 16 h. Sodium iodide (171 mg, 1.14 mmol) was added and the mixture was stirred for a further 24 h. The mixture was quenched with sat. aq. $NH_4Cl$ (2 mL) and diluted with water (20 mL). The mixture was extracted with EtOAc (3×15 mL). The combined organic phases were washed with brine (20 mL), dried ($MgSO_4$) and concentrated. The crude product was purified by chromatography on silica gel (0-100% EtOAc/isohexane) to afford tert-butyl 3-(6-(4-chlorobenzyl)pyridin-2-yl)-2-(diethoxyphosphoryl)propanoate (366 mg, 0.47 mmol, 60% purity) as a yellow oil. LCMS m/z 468.3/470.3 $(M+H)^+$ $(ES^+)$.

Step 6

Prepared according to General Procedure A, Step 2, Method B from tert-butyl 3-(6-(4-chlorobenzyl)pyridin-2-yl)-2-(diethoxyphosphoryl)propanoate (366 mg, 0.47 mmol, 60% purity). The crude product was purified by chromatography on silica gel (0-50% MTBE/isohexane) to afford tert-butyl 2-((6-(4-chlorobenzyl)pyridin-2-yl)methyl)acrylate (145 mg, 0.37 mmol, 88% purity) as a colourless oil. LCMS m/z 344.3/346.3 $(M+H)^+$ $(ES^+)$. $^1H$ NMR (400 MHz, DMSO-d6) δ 7.63 (t, J=7.7 Hz, 1H), 7.35-7.29 (m, 2H), 7.27 (d, J=8.5 Hz, 2H), 7.08 (d, J=7.6 Hz, 1H), 7.03 (d, J=7.7 Hz, 1H), 6.08 (d, J=1.7 Hz, 1H), 5.53 (d, J=1.6 Hz, 1H), 4.01 (s, 2H), 3.69 (s, 2H), 1.30 (s, 9H).

Step 7

Prepared according to General Procedure A, Step 3 from tert-butyl 2-((6-(4-chlorobenzyl)pyridin-2-yl)methyl)acrylate (145 mg, 0.37 mmol, 88% purity) to afford 2-((6-(4-chlorobenzyl)pyridin-2-yl)methyl)acrylic acid trifluoroacetic acid salt (139 mg, 0.34 mmol) as a sticky brown oil. LCMS m/z 288.2/290.2 $(M+H)^+$ $(ES^+)$. $^1H$ NMR (400 MHz, DMSO-d6) δ 13.05 (br. s, 2H), 8.06 (t, J=7.9 Hz, 1H), 7.48-7.30 (m, 6H), 6.25 (s, 1H), 5.72 (s, 1H), 4.24 (s, 2H), 3.87 (s, 2H).

Example 173—2-(1-(3-(difluoro(4-(trifluoromethyl)phenyl)methyl)-1,2,4-oxadiazol-5-yl)cyclopropyl)acrylic acid

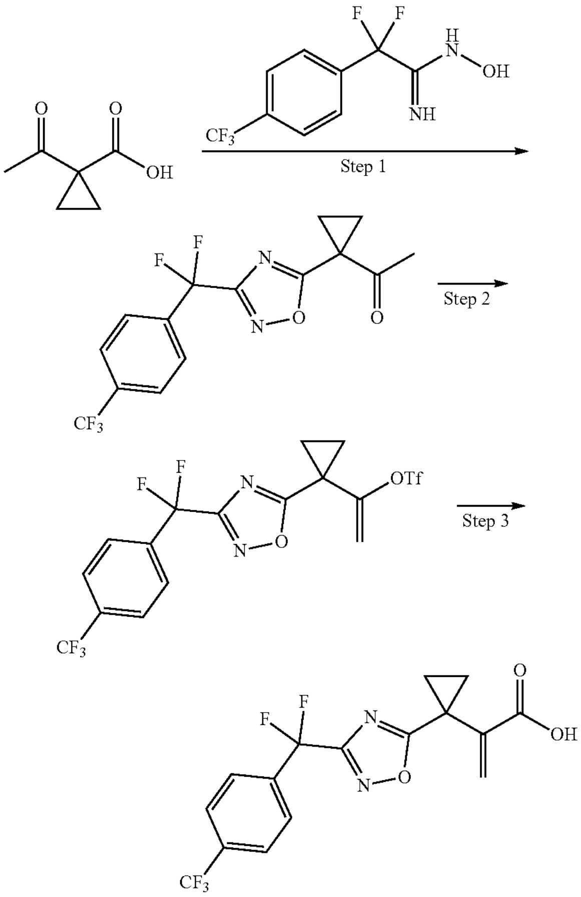

Step 1

HATU (3.29 g, 8.66 mmol) was added to a mixture of 2,2-difluoro-N-hydroxy-2-(4-(trifluoromethyl)phenyl)acetimidamide (2.00 g, 7.87 mmol), 1-acetylcyclopropane-1-carboxylic acid (1.01 g, 7.87 mmol) and DIPEA (3.0 mL, 17.3 mmol) in DCM (35 mL) at RT. The mixture was stirred for 1 h, then diluted with water (50 mL). The phases were separated and the aqueous phase was extracted with EtOAc (2×25 mL). The combined organic phases were washed with sat. aq. $NaHCO_3$ (50 mL), 1 M HCl (50 mL) and brine (50 mL), then dried ($MgSO_4$) and concentrated. The residue was taken up in THF (35 mL) and cesium carbonate (3.08 g, 9.44 mmol) was added. The mixture was heated to 60° C. and stirred for 1 h, then cooled to RT and poured into water (60 mL). The mixture was extracted with EtOAc (3×25 mL). The combined organic phases were washed with 1 M HCl (50 mL), brine (50 mL), dried ($MgSO_4$) and concentrated. The crude product was purified by chromatography on silica gel (0-100% EtOAc/isohexane) to afford 1-(1-(3-(difluoro(4-(trifluoromethyl)phenyl)methyl)-1,2,4-oxadiazol-5-yl)cyclopropyl)ethan-1-one (1.79 g, 5.1 mmol) as an orange oil. $^1H$ NMR (400 MHz, DMSO-d6) δ 7.97 (d, J=8.4 Hz, 2H), 7.92 (d, J=8.4 Hz, 2H), 2.26 (s, 3H), 1.88-1.79 (m, 2H), 1.79-1.71 (m, 2H). $^{19}F$ NMR (376 MHz, DMSO) δ −61.61, −94.17.

Step 2

LDA (2 M THF/heptane/ethylbenzene, 1.5 mL, 3.0 mmol) was added dropwise to a solution of 1-(1-(3-(difluoro(4-(trifluoromethyl)phenyl)methyl)-1,2,4-oxadiazol-5-yl)cyclopropyl)ethan-1-one (0.984 g, 2.84 mmol) in THF (11 mL) at −20° C. The mixture was stirred at −20° C. for 30 min, before N-Phenyl-bis(trifluoromethanesulfonimide) (1.12 g, 3.13 mmol) was added portionwise. The reaction was warmed to −10° C. and stirred for 2 h. Sat. aq. $NH_4Cl$ (20 mL) was added and the mixture extracted with EtOAc (3×20 mL). The combined organic layers were washed with brine (30 mL), dried ($Na_2SO_4$) and concentrated. The crude product was purified by chromatography on silica gel (0-100% DCM/isohexane) to afford 1-(1-(3-(difluoro(4-(trifluoromethyl)phenyl)methyl)-1,2,4-oxadiazol-5-yl)cyclopropyl)vinyl trifluoromethanesulfonate (0.183 g, 0.31 mmol, 80% purity) as a light yellow oil. $^1H$ NMR (400 MHz, DMSO-d6) δ 7.98-7.94 (m, 2H), 7.91-7.87 (m, 2H), 5.82 (d, J=4.7 Hz, 1H), 5.63 (d, J=4.8 Hz, 1H), 1.84-1.82 (m, 2H), 1.80-1.75 (m, 2H).

Step 4

Triphenylphosphine (20 mg, 80 μmol) and palladium(II) acetate (9 mg, 40 μmol) were added to a solution of 1-(1-(3-(difluoro(4-(trifluoromethyl)phenyl)methyl)-1,2,4-oxadiazol-5-yl)cyclopropyl)vinyl trifluoromethanesulfonate (0.183 g, 0.31 mmol, 80% purity) in dimethylformamide (2 mL). Formic acid (23 μL, 610 μmol) and triethylamine (107 μL, 765 μmol) were added. The mixture was stirred at RT under an atmosphere of CO (2 bar) at RT for 18 h. The mixture was poured into 10% aq. $K_2CO_3$ (30 mL) and extracted with MTBE (3×15 mL). The aqueous layer was then acidified with conc. HCl to pH-2 and extracted with MTBE (3×15 mL).

The combined organic layers were washed with brine (20 mL), filtered and concentrated. The crude product was purified by chromatography on silica gel (0-50% MTBE/isohexane) to afford 2-(1-(3-(difluoro(4-(trifluoromethyl)phenyl)methyl)-1,2,4-oxadiazol-5-yl)cyclopropyl)acrylic acid (36 mg, 95 μmol) as an off-white solid. LCMS: m/z 373.1 $(M-H)^-$ $(ES^-)$. $^1H$ NMR (400 MHz, DMSO-d6) δ 12.87 (s, 1H), 7.95 (d, J=8.3 Hz, 2H), 7.87 (d, J=8.3 Hz, 2H), 6.39 (s, 1H), 6.02 (s, 1H), 1.67-1.58 (m, 2H), 1.58-1.48 (m, 2H). $^{19}F$ NMR (376 MHz, DMSO) δ −61.61, −94.33.

Example 174—2-methylene-3-(3-(1-(4-(trifluoromethyl)phenyl)cyclopropyl)-1,2,4-oxadiazol-5-yl)butanoic acid

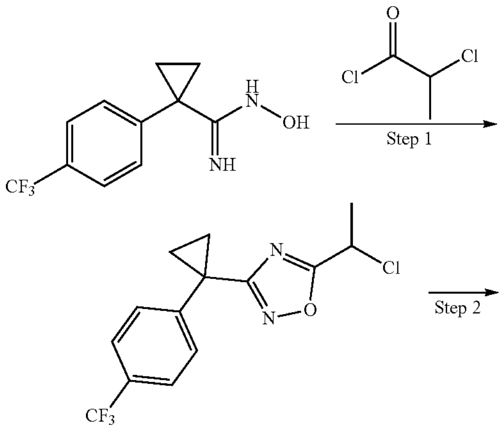

-continued

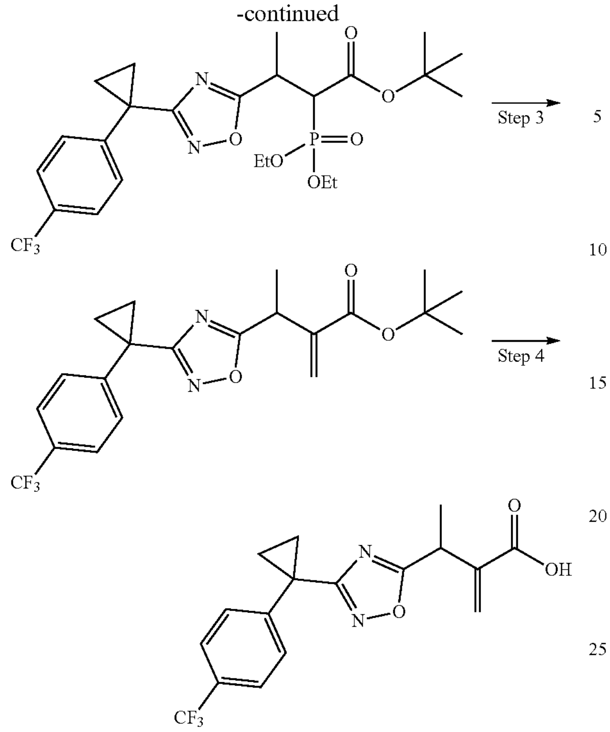

Step 1

2-chloropropanoyl chloride (1.75 mL, 18.0 mmol) was added dropwise to a solution of N-hydroxy-1-(4-(trifluoromethyl)phenyl)cyclopropane-1-carboximidamide (4.00 g, 16.4 mmol) and triethylamine (2.6 mL, 18.8 mmol) in DCM (80 mL) at 0° C. The mixture was warmed to RT and stirred for 2 h. Water (50 mL) was added. The organic layer was separated, passed through a phase separator concentrated. The residue was dissolved in toluene (80 mL) and the mixture was heated to 120° C. for 3 h, then cooled to RT and stirred for 16 h. The mixture was concentrated and the crude product was purified by chromatography on silica gel (0-50% MTBE/isohexane) to afford 5-(1-chloroethyl)-3-(1-(4-(trifluoromethyl)phenyl)cyclopropyl)-1,2,4-oxadiazole (3.76 g, 12 mmol) as a colourless oil. $^{1}$H NMR (400 MHz, DMSO-d6) δ 7.72 (d, J=8.2 Hz, 2H), 7.64 (d, J=8.2 Hz, 2H), 5.60 (q, J=6.9 Hz, 1H), 1.83 (d, J=6.9 Hz, 3H), 1.61-1.54 (m, 2H), 1.54-1.47 (m, 2H).

Step 2

Sodium iodide (1.04 g, 6.95 mmol) was added to a solution of 5-(1-chloroethyl)-3-(1-(4-(trifluoromethyl)phenyl)cyclopropyl)-1,2,4-oxadiazole (2.00 g, 6.31 mmol) in THF (8 mL) at RT.

The mixture was stirred at RT for 1 h. Separately, sodium hydride (60 wt %, 8.2 mmol) was added to a solution of tert-butyl 2-(diethoxyphosphoryl)acetate (1.9 mL, 8.2 mmol) in THF (13 mL) at 0° C. The mixture was stirred at 0° C. for 10 min then warmed to RT and stirred for 1 h. The resulting solution was added dropwise to the initial mixture. The mixture was then heated to 60° C. and stirred for 16 h. The mixture was cooled to RT and poured into water (40 mL), then extracted with EtOAc (3x25 mL). The combined organic layers were washed with brine (50 mL), dried ($Na_2SO_4$) and concentrated. The crude product was purified by chromatography on silica gel (0-100% MTBE/isohexane) to afford tert-butyl 2-(diethoxyphosphoryl)-3-(3-(1-(4-(trifluoromethyl)phenyl)cyclopropyl)-1,2,4-oxadiazol-5-yl)butanoate (1.76 g, 3.2 mmol) as a colourless oil. LCMS: m/z 533.3 $(M+H)^+$ $(ES^+)$. $^{1}$H NMR (400 MHz, DMSO-d6) δ 7.71 (d, J=8.2 Hz, 2H), 7.62-7.56 (m, 2H), 4.12-3.93 (m, 4H), 3.71-3.57 (m, 1H), 3.45-3.34 (m, 1H), 1.52-1.37 (m, 11H), 1.29-1.16 (m, 11H). $^{19}$F NMR (376 MHz, DMSO-d6) δ -60.99, -61.00. $^{31}$P NMR (162 MHz, DMSO-d6) δ 19.62, 19.34.

Step 3

Aqueous formaldehyde (37 wt %, 0.68 mL, 9.2 mmol) was added to a suspension of tert-butyl 2-(diethoxyphosphoryl)-3-(3-(1-(4-(trifluoromethyl)phenyl)cyclopropyl)-1,2,4-oxadiazol-5-yl)butanoate (1.00 g, 1.88 mmol) and potassium carbonate (566 mg, 4.09 mmol) in dimethylformamide (0.7 mL) at RT. The mixture was stirred at RT for 30 min, then poured into water (15 mL). The mixture was extracted with EtOAc (3x15 mL) and the combined organic layers were washed with brine (30 mL), dried ($Na_2SO_4$) and concentrated. The crude product was purified by chromatography on silica gel (0-50% MTBE/isohexane) to afford tert-butyl 2-methylene-3-(3-(1-(4-(trifluoromethyl)phenyl)cyclopropyl)-1,2,4-oxadiazol-5-yl)butanoate (579 mg, 1.4 mmol) as a colourless oil. LCMS: m/z 353.4 $(M-tBu+H)^+$ $(ES^+)$. $^{1}$H NMR (400 MHz, DMSO-d6) δ 7.71 (d, J=8.2 Hz, 2H), 7.60 (d, J=8.1 Hz, 2H), 6.23 (s, 1H), 5.82 (s, 1H), 4.20 (q, J=7.1 Hz, 1H), 1.52-1.48 (m, 2H), 1.48-1.42 (m, 5H), 1.31 (s, 9H).

Step 4

Prepared according to General Procedure A, Step 3 from tert-butyl 2-methylene-3-(3-(1-(4-(trifluoromethyl)phenyl)cyclopropyl)-1,2,4-oxadiazol-5-yl)butanoate (579 mg, 1.4 mmol). The crude product was purified by chromatography on silica gel (0-50% MTBE/isohexane) to afford 2-methylene-3-(3-(1-(4-(trifluoromethyl)phenyl)cyclopropyl)-1,2,4-oxadiazol-5-yl)butanoic acid (331 mg, 0.93 mmol) as a colourless gum. LCMS m/z 353.1 $(M+H)^+$ $(ES^+)$. $^{1}$H NMR (400 MHz, DMSO-d6) δ 12.83 (s, 1H), 7.70 (d, J=8.2 Hz, 2H), 7.60 (d, J=8.1 Hz, 2H), 6.28 (s, 1H), 5.82 (s, 1H), 4.22 (q, J=7.1 Hz, 1H), 1.54-1.49 (m, 2H), 1.48-1.42 (m, 5H). $^{19}$F NMR (376 MHz, DMSO-d6) δ -60.96.

Example 175—2-((6-(1-(4-chlorophenyl)cyclopropyl)pyridin-2-yl)methyl)acrylic acid

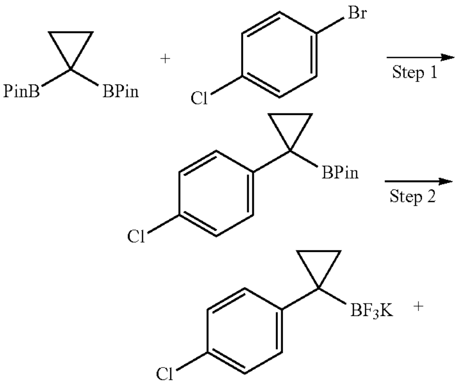

-continued

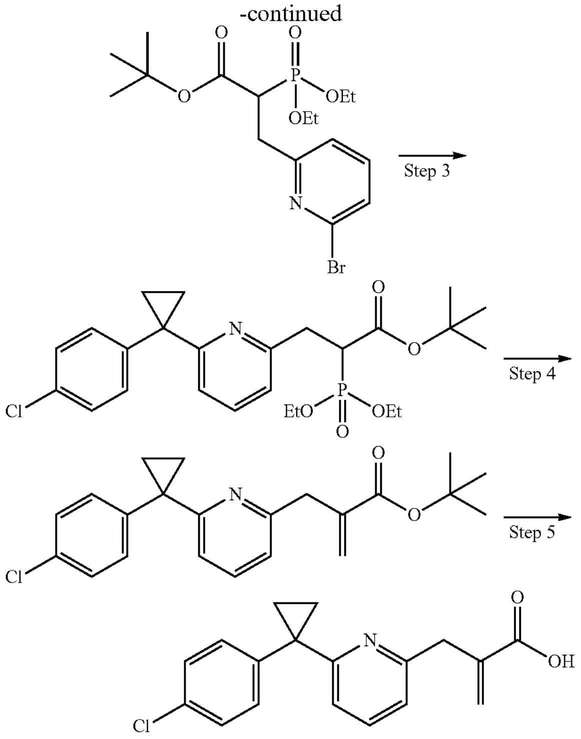

Step 1

A flask was charged with 2,2'-(cyclopropane-1,1-diyl)bis (4,4,5,5-tetramethyl-1,3,2-dioxaborolane) (0.925 g, 3.15 mmol), cataCXium A Pd G3 (115 mg, 0.16 mmol), 1-bromo-4-chlorobenzene (1.20 g, 6.29 mmol), $Cs_2CO_3$ (3.08 g, 9.44 mmol), 1,4-dioxane (75 mL) and water (7.5 mL). The resulting mixture was sparged with nitrogen for 15 min. The mixture was heated to 100° C. for 24 h then cooled to RT. Brine (100 mL) was added and the mixture was extracted with EtOAc (3×80 mL). The combined organic layers were dried ($MgSO_4$) and concentrated. The crude product was purified by chromatography on silica gel (0-5% MTBE/isohexane) to afford 2-(1-(4-chlorophenyl)cyclopropyl)-4,4,5,5-tetramethyl-1,3,2-dioxaborolane (0.469 g, 1.6 mmol) as a pale yellow solid. $^1$H NMR (400 MHz, DMSO-d6) δ 7.35-7.14 (m, 4H), 1.16 (s, 12H), 1.07-0.95 (m, 2H), 0.92-0.79 (m, 2H).

Step 2

A mixture of 2-(1-(4-chlorophenyl)cyclopropyl)-4,4,5,5-tetramethyl-1,3,2-dioxaborolane (0.495 g, 1.78 mmol) and potassium hydrogen fluoride (833 mg, 10.7 mmol) in methanol (15 mL) was stirred at 80° C. for 5 h. The mixture was cooled to RT and concentrated. The residue was triturated with 50% MTBE/isohexane (20 mL) and the resulting precipitate was collected by filtration, rinsing with 50% MTBE/isohexane (2×20 mL). The solid was dissolved in hot acetonitrile (30 mL) and filtered, washing with MeCN (2×20 mL)., The filtrate was concentrated to afford potassium (1-(4-chlorophenyl)cyclopropyl)trifluoroborate (0.355 g, 1.1 mmol, 80% purity) as a pale pink solid. $^1$H NMR (400 MHz, DMSO-d6) δ 7.20-7.13 (m, 2H), 7.11-7.04 (m, 2H), 0.57-0.40 (m, 2H), 0.20-0.08 (m, 2H).

Step 3

A flask was charged with potassium (1-(4-chlorophenyl) cyclopropyl)trifluoroborate (0.355 g, 1.1 mmol, 80% purity), cataCXium A Pd G3 (37 mg, 0.05 mmol), tert-butyl 3-(6-bromopyridin-2-yl)-2-(diethoxyphosphoryl)propanoate (958 mg, 2.04 mmol, 90% purity), 052003 (998 mg, 3.06 mmol), toluene (15.0 mL) and water (1.5 mL). The resulting mixture was sparged with nitrogen for 5 min. The mixture was heated to 95° C. for 24 h, then cooled to RT. Brine (50 mL) was added and the aqueous phase was extracted with EtOAc (3×40 mL). The combined organic layers were dried ($MgSO_4$) and concentrated. The crude product was purified by chromatography on silica gel (0-100% MTBE/isohexane) to afford tert-butyl 3-(6-(1-(4-chlorophenyl)cyclopropyl) pyridin-2-yl)-2-(diethoxyphosphoryl)propanoate (0.090 g, 0.13 mmol, 70% purity) as a pale brown gum. LCMS m/z 494.1/496.1 $(M+H)^+$ $(ES^+)$. $^1$H NMR (400 MHz, DMSO-d6) δ 7.48 (t, J=7.7 Hz, 1H), 7.44-7.40 (m, 2H), 7.37-7.31 (m, 2H), 7.05 (d, J=7.6 Hz, 1H), 6.58 (d, J=7.8 Hz, 1H), 4.17-3.99 (m, 4H), 3.69-3.52 (m, 1H), 3.29-3.18 (m, 1H), 3.10-3.01 (m, 1H), 1.65-1.47 (m, 2H), 1.29 (s, 9H), 1.28-1.23 (m, 6H), 1.23-1.20 (m, 2H).

Step 4

Prepared according to General Procedure A, Step 2, Method B from tert-butyl 3-(6-(1-(4-chlorophenyl)cyclopropyl)pyridin-2-yl)-2-(diethoxyphosphoryl)propanoate (0.090 g, 0.13 mmol, 70% purity). The crude product was purified by chromatography on RP Flash C18 (5-90% (0.1% Formic acid in MeCN)/(0.1% Formic Acid in Water)) to afford tert-butyl 2-((6-(1-(4-chlorophenyl)cyclopropyl)pyridin-2-yl)methyl)acrylate (0.039 g, 84 μmol, 80% purity) as a pale brown gum. LCMS m/z 370.4/372.4 $(M+H)^+$ $(ES^+)$. $^1$H NMR (400 MHz, DMSO-d6) δ 7.48 (t, J=7.8 Hz, 1H), 7.44-7.39 (m, 2H), 7.38-7.32 (m, 2H), 6.96 (d, J=7.6 Hz, 1H), 6.58 (d, J=7.8 Hz, 1H), 6.10-6.04 (m, 1H), 5.58-5.52 (m, 1H), 3.68 (s, 2H), 1.53-1.46 (m, 2H), 1.34 (s, 9H), 1.21-1.15 (m, 2H).

Step 5

Prepared according to General Procedure A, Step 3 from tert-butyl 2-((6-(1-(4-chlorophenyl)cyclopropyl)pyridin-2-yl)methyl)acrylate (0.039 g, 84 μmol, 80% purity). The crude product was purified by chromatography on RP Flash C18 (5-75% MeCN/(0.1% Formic acid in Water)) to afford 2-((6-(1-(4-chlorophenyl)cyclopropyl)pyridin-2-yl)methyl) acrylic acid (0.021 g, 57 μmol, 88% purity) as a brown solid. LCMS m/z 314.2/316.2 $(M+H)^+$ $(ES^+)$. $^1$H NMR (400 MHz, DMSO-d6) δ 12.48 (s, 1H), 7.47 (t, J=7.8 Hz, 1H), 7.44-7.33 (m, 4H), 6.97 (d, J=7.6 Hz, 1H), 6.56 (d, J=7.8 Hz, 1H), 6.14-6.10 (m, 1H), 5.61-5.46 (m, 1H), 3.69 (s, 2H), 1.57-1.47 (m, 2H), 1.21-1.16 (m, 2H).

Example 176—2-((3-(1-(4-bromo-3,5-dichlorophenyl)cyclopropyl)-1,2,4-oxadiazol-5-yl)methyl) acrylic acid

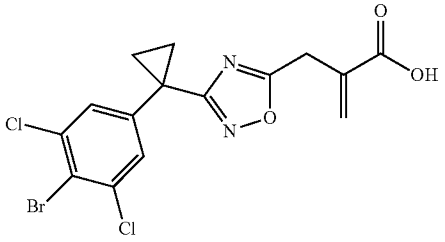 [SMILES: C=C(Cc1nc(C2(c3cc(Cl)c(Br)c(Cl)c3)CC2)no1)C(=O)O]

Prepared by an analogous procedure to Example 128 starting from 1-(4-bromo-3,5-dichlorophenyl)-N-hydroxycyclopropane-1-carboximidamide (Intermediate 225, 800 mg, 2.48 mmol). Yield: 57 mg. White solid. LCMS: (System 2, Method B) m/z 416.8/418.8/420.7 $(M+H)^+$ $(ES^+)$. $^1H$ NMR (400 MHz, DMSO-d6) δ: 12.80 (br, 1H), 7.66 (s, 2H), 6.27 (s, 1H), 5.91 (d, J=1.3 Hz, 1H), 3.90 (s, 2H), 1.54-1.43 (m, 4H).

Biological Example 1—THP-1 AlphaLISA IL-1β

Measuring Inhibitory Effects on IL-1β Cytokine Output from THP-1s

The cytokine inhibition profiles of compounds of formula (I) were determined in a differentiated THP-1 cell assay. All assays were performed in RPMI-1640 growth medium (Gibco), supplemented with 10% fetal bovine serum (FBS; Gibco), 1% penicillin-streptomycin and 1% sodium pyruvate unless specified otherwise. The IL-1β cytokine inhibition assay was run in a background of differentiated THP-1 cells as described below. All reagents described were from Sigma-Aldrich unless specified otherwise. Compounds were prepared as 10 mM DMSO stocks.

Assay Procedure

THP-1 cells were expanded as a suspension up to 80% confluence in appropriate growth medium. Cells were harvested, suspended, and treated with an appropriate concentration of phorbol 12-myristate 13-acetate (PMA) over a 72 hr period (37° C./5% $CO_2$).

Following 72 hrs of THP-1 cell incubation, cellular medium was removed and replaced with fresh growth media containing 1% of FBS. Working concentrations of compounds were prepared separately in 10% FBS treated growth medium and pre-incubated with the cells for 30 minutes (37° C./5% $CO_2$). Following the 30 minute compound pre-incubation, THP-1s were treated with an appropriate concentration of LPS and the cells were subsequently incubated for a 24 hr period (37° C./5% $CO_2$). An appropriate final concentration of Nigericin was then dispensed into the THP-1 plates and incubated for 1 hour (37° C./5% $CO_2$) before THP-1 supernatants were harvested and collected in separate polypropylene 96-well holding plates.

Reagents from an IL-1β and IL-6 commercial kit (Perkin Elmer) were prepared and run according to the manufacturer's instructions. Subsequently, fluorescence signal detection in a microplate reader was measured (EnVision® Multilabel Reader, Perkin Elmer).

Percentage inhibition was calculated per cytokine by normalising the sample data to the high and low controls used within each plate (+/− LPS respectively). Percentage inhibition was then plotted against compound concentration and the 50% inhibitory concentration $(IC_{50})$ was determined from the resultant concentration-response curve.

The compounds of formula (I) were tested and the results are shown in Table 2 below. 4-Octyl itaconate and 2-(2-chlorobenzyl)acrylic acid (Cocco et al., 2017) were included as comparator compounds.

TABLE 2

THP-1 cell IL-1β and IL-6 $IC_{50}$ values (μM)

| Compound | IL-1β $(IC_{50})$ | IL-6 $(IC_{50})$ |
|---|---|---|
| 4-octyl itaconate | 37.8 | 19.1 |
| 2-(2-chlorobenzyl)acrylic acid | >100 | NT[§] |
| Example 1 | 4.9 | 3.7 |
| | 4.7* | 4.0* |
| Example 2 | 36.8 | NT |
| Example 3 | 14.6 | 4.4 |
| Example 4 | 49.3 | NT |
| Example 5 | 45.3 | NT |
| Example 6 | 24.7 | 26.0 |
| Example 7 | >100 | NT |
| Example 8 | 16.8 | 14.0 |
| Example 9 | 54.7 | NT |
| Example 10 | 10.0 | 26.2 |
| Example 11 | 8.2 | NT |
| Example 12 | >100 | NT |
| Example 13 | >100 | NT |
| Example 14 | >100 | NT |
| Example 15 | 23.8 | NT |
| Example 16 | 45.6 | NT |
| Example 17 | 19.3 | 5.3 |
| Example 18 | 15.3 | NT |
| Example 19 | 77 | 3.3 |
| Example 20 | 14.7 | 2.7 |
| Example 21 | >100 | NT |
| Example 22 | 10.9 | NT |
| | 8.7* | 43.5* |
| Example 23 | 4.6 | NT |
| Example 24 | >100 | NT |
| Example 25 | 64.1 | NT |
| Example 26 | 36.3 | 22.6 |
| Example 27 | 29.6 | NT |
| Example 28 | 7.7 | NT |
| Example 29 | 22.8 | NT |
| Example 30 | 53.3 | >100 |
| Example 31 | >100 | NT |
| Example 32 | >100 | >100 |
| Example 33 | 83.5 | NT |
| Example 34 | 9.5 | NT |
| Example 35 | >100 | 34.6 |
| Example 36 | 37.5 | NT |
| Example 37 | 14.6 | NT |
| Example 38 | 7.8 | NT |
| Example 39 | 8.5 | NT |
| Example 40 | 27.0 | 18.1 |
| Example 41 | 45.4 | 22.5 |
| Example 42 | 27.0 | NT |
| Example 43 | 36.9 | 23.1 |
| Example 44 | >100 | 29.9 |
| Example 45 | 38.8 | NT |
| Example 46 | 41.9 | NT |
| Example 47 | >100 | NT |
| Example 48 | 40.2 | 38.5 |
| Example 49 | 12.4 | NT |
| Example 50 | 4.5 | 20.3 |
| Example 51 | 53.4 | 5.3 |
| Example 52 | 19.4 | 25.5 |
| Example 53 | 1.8 | 2.6 |
| Example 54 | >100 | 19.1 |
| Example 55 | 14.9 | 4.2 |
| Example 56 | 3.4 | 3.3 |
| Example 57 | >100 | 24.1 |
| Example 58 | 36.9 | 16.0 |
| Example 59 | 6.9 | 7.2 |
| Example 60 | 11.2 | 6.0 |
| Example 61 | 13.9 | 3.1 |
| Example 62 | 17.9 | 21.5 |
| Example 63 | >100 | NT |
| Example 64 | >100 | NT |
| Example 65 | >100 | NT |
| Example 66 | >100 | NT |
| Example 67 | 69.4 | 4.1 |
| Example 68 | 19.5 | 5.7 |
| Example 69 | 48.6 | 10.1 |
| Example 70 | 25.3 | 9.4 |
| Example 71 | 54.9 | 8.3 |
| Example 72 | 7.0 | 4.4 |
| Example 73 | >100 | 10.4 |
| Example 74 | 6.4 | 9.0 |
| Example 75 | 13.7 | 3.1 |
| Example 76 | 28.2 | 5.1 |
| Example 77 | 7.6 | 14.6 |
| Example 78 | 24.3 | >100 |
| Example 79 | 6.7 | 2.2 |
| Example 80 | 37.2 | 9.6 |

TABLE 2-continued

| THP-1 cell IL-1β and IL-6 $IC_{50}$ values (μM) | | |
|---|---|---|
| Compound | IL-1β ($IC_{50}$) | IL-6 ($IC_{50}$) |
| Example 81 | 22 | 12.8 |
| Example 82 | 14.5 | 20.7 |
| Example 83 | 3.1 | 3.4 |
| Example 84 | 39.0 | 23.1 |
| Example 85 | 13.6 | 18.5 |
| Example 86 | 8.4 | 9.4 |
| Example 87 | >100 | 31.7 |
| Example 88 | 3.1 | 2.8 |
| Example 89 | 12.2 | 33.4 |
| Example 90 | 3.4 | 15.7 |
| Example 91 | 3.8 | 2.4 |
| Example 92 | 6.7 | 19.9 |
| Example 93 | 16.1 | 8.7 |
| Example 94 | 20.5 | NT |
| Example 95 | >31.6 | NT |
| Example 96 | >31.6 | NT |
| Example 97 | 22.1 | NT |
| Example 98 | 37.2 | NT |
| Example 99 | 52.3 | NT |
| Example 100 | 25.8 | NT |
| Example 101 | 52.4 | 4.6 |
| Example 102 | 7.4 | 5.2 |
| Example 103 | 14.4 | 19.7 |
| Example 104 | 11.6 | 2.1 |
| Example 105 | 4.2 | 2.0 |
| Example 106 | 67.8 | 39.3 |
| Example 107 | 9.5 | 8.4 |
| Example 108 | 18.4 | 8.3 |
| Example 109 | >31.6 | 10.6 |
| Example 110 | >31.6 | 9.8 |
| Example 111 | 31.4 | NT |
| Example 112 | 14.2 | 4.4 |
| Example 113 | 20.1 | NT |
| Example 114 | 55.2 | NT |
| Example 115 | 7.9 | NT |
| Example 116 | 27.9 | NT |
| Example 117 | 3.4 | NT |
| Example 118 | 59.6 | NT |
| Example 119 | 59.6 | NT |
| Example 120 | 3.6 | NT |
| Example 121 | 61.8 | NT |
| Example 122 | 75.5 | NT |
| Example 123 | >100 | NT |
| Example 124 | 16.6 | NT |
| Example 125 | >100 | NT |
| Example 126 | 32.1 | NT |
| Example 127 | 14.6 | NT |
| Example 128 | 26.3 | NT |
| Example 129 | 20.6 | NT |
| Example 130 | >100 | NT |
| Example 131 | 7.9 | NT |
| Example 132 | 29.9 | NT |
| Example 133 | 1.6 | NT |
| Example 134 | 15.8 | NT |
| Example 135 | 13.2 | 17.9 |
| Example 136 | 2.9 | 3.9 |
| Example 137 | 60.5 | NT |
| Example 138 | 3.0 | NT |
| Example 139 | 41.1 | NT |
| Example 140 | 29.5 | >100 |
| Example 141 | >56.2 | 32.4 |
| Example 142 | >100 | NT |
| Example 143 | 22.1 | NT |
| Example 144 | >100 | NT |
| Example 145 | 35.6 | NT |
| Example 146 | >31.6 | NT |
| Example 147 | 29.9 | NT |
| Example 148 | 42.6 | NT |
| Example 149 | 50.0 | NT |
| Example 150 | 52.7 | NT |
| Example 151 | 22.7 | NT |
| Example 152 | 36.4 | NT |
| Example 153 | 17.3 | NT |
| Example 154 | 9.5 | NT |
| Example 155 | 9.1 | 13.1 |
| Example 156 | 5.3 | 55.9 |
| Example 157 | >100 | NT |
| Example 158 | >31.6 | NT |
| Example 159 | >100 | NT |
| Example 160 | >10 | NT |
| Example 161 | >10 | NT |
| Example 162 | >46.4 | 6.4 |
| Example 163 | >100 | NT |
| Example 164 | >100 | NT |
| Example 165 | >100 | NT |
| Example 166 | >31.6 | 31.5 |
| Example 167 | >100 | NT |
| Example 168 | 33.6 | 51.2 |
| Example 169 | >31.6 | 20.2 |
| Example 170 | >31.6 | 21.0 |
| Example 171 | >100 | >100 |
| Example 172 | 5.1 | 67.5 |
| Example 173 | 7.6 | >100 |
| Example 174 | 4.2 | >100 |
| Example 175 | 62.2 | 40.6 |
| Example 176 | 3.2 | 7.6 |

NT[§] = not tested;
*data from repeated experiments.

These results reveal that certain compounds of the present invention are expected to have anti-inflammatory activity as shown by their $IC_{50}$ values for inhibition of IL-1β release in this assay. Certain examples exhibit improved or similar IL-1β lowering properties ($IC_{50}$ values) compared to 4-octyl itaconate. Certain examples exhibit improved or similar IL-1β lowering properties ($IC_{50}$ values) compared to 2-(2-chlorobenzyl)acrylic acid. Certain examples (such as Examples 7, 12, 13, 14, 21, 24, 30, 31, 32, 35, 44, 47, 54, 57, 63, 64, 65, 66, 73 and 87, amongst others in Table 2) were not effective when tested in the IL-1β assay. Certain compounds tested in the IL-6 assay showed improved IL-6 lowering properties, in terms of $IC_{50}$ values, compared to 4-octyl itaconate.

Compounds of formula (I) in which the carbon-carbon double bond is exo are generally more potent in this assay than equivalent compounds of formula (I) in which the carbon-carbon double bond is endo, see Table 3.

TABLE 3

| Head to head comparison of exo vs endo carbon-carbon double bond compounds of formula (I) | | | |
|---|---|---|---|
| Compound (exo) | IL-1β ($IC_{50}$) | Compound (endo) | IL-1β ($IC_{50}$) |
| Example 1 | 4.9<br>4.7* | Example 166 | >31.6 |
| Example 50 | 4.5 | Example 168 | 33.6 |
| Example 61 | 13.9 | Example 167 | >100 |
| Example 77 | 7.6 | Example 169 | >31.6 |
| Example 86 | 8.4 | Example 170 | >31.6 |

*Data from repeated experiment

Biological Example 2—NRF2+/−GSH Activation Assay

Measuring Compound Activation Effects on the Anti-Inflammatory Transcription Factor NRF2 in DiscoverX PathHunter NRF2 Translocation Kit Potency and efficacy of compounds of formula (I) against the target of interest to activate NRF2 (nuclear factor erythroid 2-related factor 2) were determined using the PathHunter NRF2 translocation kit (DiscoverX). The NRF2 translocation assay was run using an engineered recombinant cell line, utilising enzyme fragment complementation to determine activation of the Keap1-NRF2 protein complex and subsequent translocation of NRF2 into the nucleus. Enzyme activity was quantified using a chemiluminescent substrate consumed following the formation of a functional enzyme upon PK-tagged NRF2 translocation into the nucleus.

The assay was run under both +/−GSH (glutathione) conditions to determine the sensitivity of the compounds' NRF2-activating abilities to attenuation by GSH.

Additionally, a defined concentration of DMF was used as the 'High' control to normalise test compound activation responses to.

Assay Procedure

U2OS PathHunter eXpress cells were thawed from frozen prior to plating. Following plating, U2OS cells were incubated for 24 hrs (37° C./5% $CO_2$) in commercial kit provided cell medium.

Following 24 hrs of U2OS incubation, cells were directly treated with an appropriate final concentration of compound, for −GSH conditions or, for +GSH conditions, an intermediate plate containing 6× working concentrations of compound stocks was prepared in a 6 mM working concentration of GSH solution (solubilised in sterile PBS). Following a 30 minute compound-GSH pre-incubation (37° C./5% $CO_2$) for +GSH treatment, plated U2OS cells were incubated with an appropriate final concentration of compound and GSH.

Following compound (+/−GSH) treatment, the U2OS plates were incubated for a further 6 hours (37° C./5% $CO_2$) before detection reagent from the PathHunter NRF2 commercial kit was prepared and added to test plates according to the manufacturer's instructions. Subsequently, the luminescence signal detection was measured in a microplate reader (PHERAstar®, BMG Labtech).

Percentage activation was calculated by normalising the sample data to the high and low controls used within each plate (+/−DMF). Percentage activation/response was then plotted against compound concentration and the 50% activation concentration ($EC_{50}$) was determined from the plotted concentration-response curve.

A number of compounds of formula (I) were tested, and the results are shown in Table 4 below. 4-Octyl itaconate was included as a comparator compound. DMF is shown as the high and low control as mentioned above.

TABLE 4

| | NRF2 activation | | | |
|---|---|---|---|---|
| | −GSH | | +GSH | |
| Compound | $EC_{50}$ (μM) | $E_{max}$ (%) | $EC_{50}$ (μM) | $E_{max}$ (%) |
| dimethyl fumarate | 6.1 | 100 | >100 | 20 |
| 4-octyl itaconate | 22.1 | 165 | 28.9 | 148 |
| 2-(2-chlorobenzyl)acrylic acid | >100 | 2 | >100 | 9 |
| Example 1 | 4.5 | 243 | 5.7 | 187 |
| Example 2 | 19.1 | 176 | 26.8 | 169 |
| Example 3 | 3.7 | 218 | 6.9 | 199 |
| Example 4 | 40.5 | 47 | >100 | 23 |
| Example 5 | 42.4 | 74 | 50.4 | 63 |
| Example 6 | 22.9 | 190 | 29.1 | 170 |
| Example 7 | 39.7 | 113 | 44.5 | 89 |
| Example 8 | 20.9 | 175 | 28.1 | 167 |
| Example 9 | 42.7 | 51 | 69.9 | 44 |
| Example 10 | 36.8 | 67 | 45.2 | 53 |
| dimethyl fumarate | 6.1 | 100 | >100 | 20 |

TABLE 4-continued

| | NRF2 activation | | | |
|---|---|---|---|---|
| | −GSH | | +GSH | |
| Compound | $EC_{50}$ (μM) | $E_{max}$ (%) | $EC_{50}$ (μM) | $E_{max}$ (%) |
| 4-octyl itaconate | 22.1 | 165 | 28.9 | 148 |
| 2-(2-chlorobenzyl)acrylic acid | >100 | 2 | >100 | 9 |
| Example 11 | 11.4 | 185 | 13.1 | 149 |
| Example 12 | 53.1 | 85 | 61.9 | 73 |
| Example 13 | 43.1 | 54 | 48.6 | 51 |
| Example 14 | 21.8 | 78 | 52.2 | 46 |
| Example 15 | 57.1 | 41 | >100 | 33 |
| Example 16 | 19.4 | 180 | 23.6 | 149 |
| Example 17 | 5.1 | 179 | 8.7 | 140 |
| Example 18 | 3.5 | 207 | 3.8 | 159 |
| Example 19 | 2.5 | 206 | 7.4 | 140 |
| Example 20 | 2.9 | 206 | 3.0 | 146 |
| Example 21 | 31.7 | 125 | 44.0 | 81 |
| Example 22 | 48.7 | 69 | 60.2 | 62 |
| Example 23 | 1.6 | 209 | 2.2 | 162 |
| Example 24 | 42.4 | 57 | >100 | 17 |
| Example 25 | >100 | 32 | >100 | 31 |
| Example 26 | 27.3 | 205 | 35.6 | 137 |
| Example 28 | 3.0 | 264 | 4.0 | 201 |
| Example 29 | 7.6 | 179 | 11.2 | 183 |
| Example 30 | >100 | 36 | >100 | 12 |
| Example 31 | 35.0 | 178 | 40.9 | 127 |
| Example 32 | 50.1 | 46 | >100 | 35 |
| Example 33 | 18.3 | 150 | 23.3 | 160 |
| Example 34 | 3.7 | 222 | 4.7 | 167 |
| Example 35 | 43.6 | 91 | 48.9 | 55 |
| Example 36 | 10.1 | 216 | 14.2 | 181 |
| Example 37 | 8.4 | 162 | 9.5 | 139 |
| Example 39 | 5.1 | 234 | 7.6 | 172 |
| Example 40 | 25.3 | 168 | 27.5 | 81 |
| Example 41 | 31.7 | 135 | 39.7 | 103 |
| Example 42 | >100 | 63 | >100 | 8 |
| dimethyl fumarate | 6.1 | 100 | >100 | 20 |
| 4-octyl itaconate | 22.1 | 165 | 28.9 | 148 |
| 2-(2-chlorobenzyl)acrylic acid | >100 | 2 | >100 | 9 |
| Example 43 | 30.4 | 166 | 27.4 | 81 |
| Example 44 | 28.7 | 65 | >100 | 23 |
| Example 45 | >100 | 55 | >100 | 9 |
| Example 46 | 31.1 | 106 | 36.2 | 51 |
| Example 47 | 41.4 | 131 | 47.1 | 86 |
| Example 48 | 31.0 | 120 | 50.3 | 61 |
| Example 49 | 49.2 | 109 | 57.5 | 56 |
| Example 50 | 35.9 | 150 | 39.2 | 88 |
| Example 51 | 4.6 | 269 | 6.7 | 181 |
| Example 52 | 15.2 | 78 | >100 | 40 |
| Example 53 | 1.8 | 178 | 1.8 | 71 |
| Example 54 | 44.6 | 115 | 42.4 | 50 |
| Example 55 | 13.3 | 276 | 17.8 | 163 |
| Example 56 | 2.8 | 175 | 3.1 | 110 |
| Example 57 | 41.1 | 102 | 49.9 | 56 |
| Example 58 | 26.4 | 149 | 30.6 | 105 |
| Example 59 | 3.9 | 213 | 5.4 | 136 |
| Example 60 | 8.4 | 195 | 9.0 | 110 |
| Example 61 | 3.2 | 198 | 4.9 | 124 |
| Example 62 | 20.0 | 229 | 27.4 | 149 |
| Example 63 | 25.8 | 114 | 58.0 | 49 |
| Example 64 | >100 | 86 | >100 | 17 |
| Example 65 | >100 | 50 | >100 | 17 |
| Example 66 | >100 | 23 | >100 | 14 |
| Example 70 | 13.4 | 188 | 15.6 | 147 |
| Example 71 | 28.8 | 178 | 37.1 | 146 |
| Example 72 | 14.6 | 189 | 19.5 | 151 |
| Example 74 | 24.4 | 174 | 44.4 | 65 |
| Example 75 | 4.8 | 263 | 7.1 | 188 |
| Example 77 | 48.1 | 210 | 52.7 | 69 |
| dimethyl fumarate | 6.1 | 100 | >100 | 20 |
| 4-octyl itaconate | 22.1 | 165 | 28.9 | 148 |
| 2-(2-chlorobenzyl)acrylic acid | >100 | 2 | >100 | 9 |
| Example 79 | 1.8 | 271 | 2.1 | 181 |
| Example 83 | 3.0 | 185 | 3.8 | 161 |
| Example 85 | 21.6 | 282 | 34.7 | 208 |

TABLE 4-continued

| Compound | NRF2 activation −GSH EC$_{50}$ (μM) | −GSH E$_{max}$ (%) | +GSH EC$_{50}$ (μM) | +GSH E$_{max}$ (%) |
|---|---|---|---|---|
| Example 86 | 18.0 | 320 | 35.0 | 221 |
| Example 87 | 41.4 | 95 | 48.6 | 70 |
| Example 88 | 2.8 | 237 | 3.0 | 205 |
| Example 89 | 30.7 | 99 | 42.2 | 63 |
| Example 90 | 45.3 | 172 | 44.0 | 130 |
| Example 91 | 3.2 | 231 | 3.4 | 190 |
| Example 93 | 12.6 | 224 | 14.3 | 190 |
| Example 94 | 7.9 | 208 | 13.8 | 183 |
| Example 95 | 2.8 | 217 | 3.9 | 183 |
| Example 96 | 11.7 | 170 | 12.4 | 115 |
| Example 102 | 7.2 | 342 | 9.5 | 230 |
| Example 103 | 40.5 | 306 | 42.7 | 190 |
| Example 104 | 7.5 | 293 | 8.2 | 216 |
| Example 105 | 5.3 | 257 | 5.3 | 166 |
| Example 106 | 18.6 | 143 | 24.6 | 101 |
| Example 108 | 19.7 | 299 | 29.0 | 213 |
| Example 110 | 38.9 | 153 | 48.8 | 132 |
| Example 112 | 7.3 | 284 | 10.7 | 283 |
| Example 123 | 6.6 | 111 | 62.4 | 42 |
| Example 125 | >100 | 37 | >100 | 26 |
| Example 130 | 36.5 | 177 | 37.4 | 129 |
| Example 133 | 3.5 | 234 | 4.2 | 281 |
| Example 141 | 16.7 | 177 | 20.1 | 100 |
| Example 142 | 23.3 | 189 | 26.9 | 168 |
| Example 143 | 12.0 | 243 | 14.5 | 195 |
| Example 144 | 28.4 | 167 | 31.1 | 139 |
| Example 145 | 28.4 | 170 | 31.4 | 135 |
| dimethyl fumarate | 6.1 | 100 | >100 | 20 |
| 4-octyl itaconate | 22.1 | 165 | 28.9 | 148 |
| 2-(2-chlorobenzyl)acrylic acid | >100 | 2 | >100 | 9 |
| Example 146 | 13.1 | 177 | 14.6 | 125 |
| Example 155 | 11.2 | 201 | 13.7 | 123 |
| Example 156 | >100 | 0 | −3 | −16.4 |
| Example 157 | >100 | 41 | >100 | −5 |
| Example 158 | 2.6 | 189 | 2.9 | 196 |
| Example 159 | 34.4 | 87 | 39.9 | 85 |
| Example 160 | 5.0 | 216 | 4.1 | 238 |
| Example 161 | 25.1 | 258 | 7.2 | 114 |
| Example 162 | 1.1 | 232 | 1.3 | 269 |
| Example 163 | 61.4 | 61 | >100 | −10 |
| Example 164 | 42.7 | 62 | 63.4 | 5.5 |

TABLE 4-continued

| Compound | NRF2 activation −GSH EC$_{50}$ (μM) | −GSH E$_{max}$ (%) | +GSH EC$_{50}$ (μM) | +GSH E$_{max}$ (%) |
|---|---|---|---|---|
| Example 165 | >100 | 25 | >100 | 16 |
| Example 166 | 28.8 | 189 | 32.2 | 127 |
| Example 167 | >100 | 100 | >100 | 15 |
| Example 168 | 1.4 | 69 | >100 | 16 |
| Example 169 | >100 | 43 | >100 | 15.4 |

TABLE 4-continued

| Compound | NRF2 activation −GSH EC$_{50}$ (μM) | −GSH E$_{max}$ (%) | +GSH EC$_{50}$ (μM) | +GSH E$_{max}$ (%) |
|---|---|---|---|---|
| Example 170 | 38.7 | 177 | 34.9 | 96.5 |
| Example 171 | >100 | 5 | >100 | 0 |
| Example 172 | >100 | 0 | >100 | 7.6 |
| Example 173 | 52.5 | 64 | 61.1 | 2.1 |
| Example 174 | >100 | 24 | >100 | 1.8 |
| Example 175 | >54.8 | 43 | >100 | 4.0 |
| Example 176 | 5.4 | 222 | NT* | NT |

*NT means not tested

These results reveal that compounds of the present invention (including certain Examples which were found to be not effective when tested in the IL-1β assay in Biological Example 1) are expected to have anti-inflammatory activity as shown by their EC$_{50}$ and/or E$_{max}$ values for NRF2 activation in this assay. All compounds shown in Table 4 exhibit lower EC$_{50}$ and/or higher or comparable E$_{max}$ values in one or both of −GSH and +GSH compared to 2-(2-chlorobenzyl)acrylic acid. Certain compounds shown in Table 4 exhibit lower EC$_{50}$ and/or high E$_{max}$ values in one or both of −GSH and +GSH compared to 4-octyl itaconate. Certain examples exhibited higher or similar potencies (lower EC$_{50}$ and higher E$_{max}$ values in both −GSH and +GSH) compared to 4-octyl itaconate and/or 2-(2-chlorobenzyl)acrylic acid.

Compounds of formula (I) in which the carbon-carbon double bond is exo are generally more potent in this assay than equivalent compounds of formula (I) in which the carbon-carbon double bond is endo, see Table 5. However, Example 168 is more potent in NRF2 (-GSH) than Example 50.

TABLE 5

Head to head comparison of exo vs endo double bond compounds of formula (I)

| Compound (exo) | −GSH EC$_{50}$ (μM) | −GSH E$_{max}$ (%) | Compound (endo) | −GSH EC$_{50}$ (μM) | −GSH E$_{max}$ (%) |
|---|---|---|---|---|---|
| Example 1 | 4.5 | 243 | Example 166 | 28.8 | 189 |
| Example 50 | 35.9 | 150 | Example 168 | 1.4 | 69 |
| Example 61 | 3.2 | 198 | Example 167 | >100 | 100 |
| Example 77 | 48.1 | 210 | Example 169 | >100 | 43 |
| Example 86 | 18.0 | 320 | Example 170 | 38.7 | 177 |

Biological Example 3—Hepatocyte Stability Assay

Defrosted cryo-preserved hepatocytes (viability >70%) were used to determine the metabolic stability of a compound via calculation of intrinsic clearance (CI$_{int}$; a measure of the removal of a compound from the liver in the absence of blood flow and cell binding). Clearance data are particularly important for in vitro work as they can be used in combination with in vivo data to predict the half-life and oral bioavailability of a drug.

The metabolic stability in hepatocytes assay involves a time-dependent reaction using both positive and negative controls. The cells were pre-incubated at 37° C. then spiked with test compound (and positive control); samples were taken at pre-determined time intervals and were analysed to monitor the change in concentration of the initial drug compound over 60 minutes. A buffer incubation reaction (with no hepatocytes present) acted as a negative control and two cocktail solutions, containing compounds with known high and low clearance values (verapamil/7-hydroxycoumarin and propranolol/diltiazem), acted as positive controls.

1. The assay was run with a cell concentration of $0.5\times10^6$ cells/mL in Leibovitz buffer.
2. All compounds and controls were run in duplicate.
3. Compound concentration was 10 μM.
4. All compounds and controls were incubated with both cells and buffer to show turnover was due to hepatic metabolism.
5. All wells on the incubation plate had 326.7 μL of either cells or buffer added.
6. Prior to assay, cell and buffer-only incubation plates were preincubated for 10 mins at 37° C.
7. The assay was initiated by adding compounds, 3.3 μL of 1 mM in 10% DMSO—90% Buffer; final DMSO concentration was 0.1%.
8. Samples were taken at regular timepoints (0, 5, 10, 20, 40, 60 min) until 60 mins.
9. Sample volume was 40 μL and was added to 160 μL of crash solvent (acetonitrile with internal standard) and stored on ice.
10. At the end of the assay, the crash plates were centrifuged at 3500 rpm for 20 mins at 4° C.
11. 80 μL of clear supernatant was removed and mixed with 80 μL of deionised water before being analysed by LC-MS/MS.

Raw LC-MS/MS data was exported to, and analysed in, Microsoft Excel for determination of intrinsic clearance. The percentage remaining of a compound was monitored using the peak area of the initial concentration as 100%. Intrinsic clearance and half-life values were calculated using a graph of the natural log of percentage remaining versus the time of reaction in minutes. Half-life (min) and intrinsic clearance ($CI_{int}$ in μL $min^{-1}$ $10^{-6}$ cells) values were calculated using the gradient of the graph (the elimination rate constant, k) and Equations 1 and 2.

$$t_{\frac{1}{2}} = \frac{\ln 2}{k} \qquad \text{\{Equation 1\}}$$

$$Cl_{int} = \left(\frac{\ln 2}{t_{\frac{1}{2}}}\right) \times \left(\frac{350}{0.175}\right) \qquad \text{\{Equation 2\}}$$

A number of compounds of formula (I) were tested, and the results are shown in Table 6 below. 4-Octyl itaconate and 2-(2-chlorobenzyl)acrylic acid (Cocco et al., 2017) were included as comparator compounds.

TABLE 6

| Hepatocyte stability | | | |
|---|---|---|---|
| Compound | Species | $Cl_{int}$ (μL $min^{-1}$ $10^{-6}$ cells) | T½ (min) |
| 4-octyl itaconate | Mouse | 351 | 4 |
| | Human | 401 | 4 |
| 2-(2-chlorobenzyl)acrylic acid | Mouse | 95 | 11 |
| | Human | 21 | 59 |

TABLE 6-continued

| Hepatocyte stability | | | |
|---|---|---|---|
| Compound | Species | $Cl_{int}$ (μL $min^{-1}$ $10^{-6}$ cells) | T½ (min) |
| Example 1 | Mouse | 118 | 12 |
| | Human | 115 | 12 |
| | Mouse[b] | 94 | 13 |
| | Human[c] | 113 | 13 |
| Example 2 | Mouse | 74 | 19 |
| | Human | 95 | 15 |
| Example 3 | Mouse | 117 | 12 |
| | Human[a] | 110 | 15 |
| Example 4 | Mouse[a] | 13 | 93 |
| | Human | <3 | >460 |
| Example 5 | Mouse | 48 | 40 |
| | Human | 8 | 174 |
| Example 6 | Mouse | 185 | 9 |
| | Human | 38 | 31 |
| Example 7 | Mouse | 28 | 49 |
| | Human | <6 | >320 |
| Example 8 | Mouse | 143 | 10 |
| | Human | 28 | 51 |
| Example 9 | Mouse | 41 | 25 |
| | Human | 7 | 181 |
| Example 10 | Mouse | 125 | 8 |
| | Human | 27 | 47 |
| Example 11 | Mouse | 56 | 18 |
| | Human | 30 | 42 |
| Example 12 | Mouse | 15 | 90 |
| | Human | 16 | 90 |
| Example 14 | Mouse | 18 | 72 |
| | Human | 6 | 240 |
| Example 15 | Mouse[a] | 31 | 35 |
| | Human[a] | 7.5 | 167 |
| Example 16 | Mouse | 29 | 45 |
| | Human | <4 | >362 |
| Example 17 | Mouse | 105 | 12 |
| | Human | 42 | 34 |
| Example 18 | Mouse | >460 | <3 |
| | Human | 159 | 11 |
| Example 19 | Mouse | >460 | <3 |
| | Human | 63 | 20 |
| Example 20 | Mouse | 427 | 4 |
| | Human | 70 | 24 |
| Example 21 | Mouse | 62 | 28 |
| | Human | 21 | 83 |
| Example 22 | Mouse | 42 | 41 |
| | Human | 20 | 84 |
| Example 23 | Mouse | >460 | <3 |
| | Human | 321 | 5 |
| Example 25 | Mouse | 17 | 90 |
| | Human | 12 | 104 |
| Example 27 | Mouse | 281 | 5 |
| | Human | 156 | 8 |
| Example 28 | Mouse | >460 | <3 |
| | Human | 103 | 12 |
| Example 31 | Mouse | 42 | 27 |
| | Human | 5 | 246 |
| Example 34 | Mouse[a] | 374 | 4 |
| | Human[a] | 78 | 18 |
| Example 36 | Mouse | 249 | 7 |
| | Human | 23 | 61 |
| Example 37 | Mouse | >481 | <3 |
| | Human | 32 | 40 |
| Example 38 | Mouse | 204 | 9 |
| | Human | >447 | <3 |
| Example 39 | Mouse | >460 | <3 |
| | Human | 386 | 3 |
| Example 40 | Mouse | 82 | 20 |
| | Human | 21 | 66 |
| Example 42 | Mouse | 11 | 118 |
| | Human | <3 | >460 |
| Example 43 | Mouse | 142 | 12 |
| | Human | 33 | 42 |
| Example 44 | Mouse | 37 | 44 |
| | Human | 10 | 144 |
| Example 45 | Mouse | 33 | 49 |
| | Human | 8 | 178 |

TABLE 6-continued

| Hepatocyte stability | | | |
|---|---|---|---|
| Compound | Species | $Cl_{int}$ (μL $min^{-1}$ $10^{-6}$ cells) | T½ (min) |
| Example 46 | Mouse | 17 | 76 |
| | Human | <3 | >447 |
| Example 49 | Mouse | 15 | 86 |
| | Human | 8 | 172 |
| Example 50 | Mouse | 146 | 9 |
| | Human | 25 | 53 |
| Example 51 | Mouse | 278 | 5 |
| | Human | 24 | 55 |
| Example 52 | Mouse | 134 | 10 |
| | Human | 24 | 55 |
| Example 53 | Mouse | >460 | <3 |
| | Human | 329 | 4 |
| Example 54 | Mouse | 13 | 102 |
| | Human | 5 | 268 |
| Example 56 | Mouse | >460 | <3 |
| | Human | >460 | <3 |
| Example 59 | Mouse | >460 | <3 |
| | Human | >460 | <3 |
| Example 60 | Mouse | 257 | 6 |
| | Human | 137 | 11 |
| Example 61 | Mouse | 301 | 4 |
| | Human | 52 | 29 |
| Example 62 | Mouse | 119 | 10 |
| | Human | 57 | 26 |
| Example 63 | Mouse | 23 | 60 |
| | Human | 8 | 169 |
| Example 67 | Mouse | 92 | 13 |
| | Human | 70 | 23 |
| Example 70 | Mouse | 58 | 26 |
| | Human | 13 | 117 |
| Example 72 | Mouse | 28 | 43 |
| | Human | 69 | 27 |
| Example 74 | Mouse | 31 | 47 |
| | Human | <3 | >430 |
| Example 75 | Mouse | 480 | 4 |
| | Human | 80 | 15 |
| Example 77 | Mouse | 10 | 189 |
| | Human | <3 | >460 |
| Example 79 | Mouse | >460 | <3 |
| | Human | 147 | 11 |
| Example 81 | Mouse | 94 | 18 |
| | Human | <3 | >460 |
| Example 82 | Mouse | 30 | 58 |
| | Human | <3 | >460 |
| Example 83 | Mouse | >460 | <3 |
| | Human | 263 | 5 |
| Example 84 | Mouse | 83 | 21 |
| | Human | 14 | 115 |
| Example 85 | Mouse | 131 | 13 |
| | Human | 20 | 77 |
| Example 86 | Mouse | 17 | 103 |
| | Human | 7 | 235 |
| Example 88 | Mouse | >460 | <3 |
| | Human | 134 | 12 |
| Example 89 | Mouse | 336 | 5 |
| | Human | 38 | 41 |
| Example 90 | Mouse | 34 | 56 |
| | Human | 7 | 206 |
| Example 91 | Mouse | 320 | 6 |
| | Human | 74 | 21 |
| Example 92 | Mouse | 23 | 84 |
| | Human | <3 | >460 |
| Example 93 | Mouse | >460 | <3 |
| | Human | 40 | 38 |
| Example 94 | Mouse | 29 | 66 |
| | Human | <3 | >460 |
| Example 97 | Mouse | 79 | 15 |
| | Human | 13 | 125 |
| Example 98 | Mouse | 208 | 6 |
| | Human | 70 | 23 |
| Example 100 | Mouse | >460 | <3 |
| | Human | 77 | 19 |
| Example 102 | Mouse | >460 | <3 |
| | Human | >460 | <3 |

TABLE 6-continued

| Hepatocyte stability | | | |
|---|---|---|---|
| Compound | Species | $Cl_{int}$ (μL $min^{-1}$ $10^{-6}$ cells) | T½ (min) |
| Example 103 | Mouse | 94 | 16 |
| | Human | 43 | 31 |
| Example 104 | Mouse | >460 | <3 |
| | Human | 370 | 3 |
| Example 105 | Mouse | >460 | <3 |
| | Human | >460 | <3 |
| Example 107 | Mouse | >460 | <3 |
| | Human | 161 | 8 |
| Example 108 | Mouse | 438 | 4 |
| | Human | 10 | 163 |
| Example 109 | Mouse | 61 | 28 |
| | Human | 20 | 79 |
| Example 110 | Mouse | >460 | <3 |
| | Human | >460 | <3 |
| Example 111 | Mouse | 382 | 3 |
| | Human | 23 | 71 |
| Example 112 | Mouse | 160 | 12 |
| | Human | 25 | 61 |
| Example 113 | Mouse | >460 | <3 |
| | Human | 290 | 5 |
| Example 115 | Mouse | 87 | 15 |
| | Human | 28 | 55 |
| Example 116 | Mouse | 290 | 5 |
| | Human | 60 | 25 |
| Example 117 | Mouse | 183 | 7 |
| | Human | 36 | 43 |
| Example 120 | Mouse | 66 | 20 |
| | Human | 10 | 154 |
| Example 124 | Mouse | 55 | 27 |
| | Human | 14 | 105 |
| Example 127 | Mouse | 478 | 3 |
| | Human | 245 | 6 |
| Example 128 | Mouse | 256 | 6 |
| | Human | 49 | 30 |
| Example 129 | Mouse | >460 | <3 |
| | Human | 67 | 22 |
| Example 131 | Mouse | 139 | 11 |
| | Human | 34 | 43 |
| Example 133 | Mouse | 338 | 4 |
| | Human | 73 | 19 |
| Example 134 | Mouse | 17 | 75 |
| | Human | 13 | 112 |
| Example 135 | Mouse | 159 | 8 |
| | Human | 31 | 45 |
| Example 136 | Mouse | 79 | 16 |
| | Human | 44 | 32 |
| Example 138 | Mouse | >460 | <3 |
| | Human | 96 | 15 |
| Example 146 | Mouse | 194 | 8 |
| | Human | 36 | 41 |
| Example 147 | Mouse | >460 | <3 |
| | Human | 67 | 22 |
| Example 151 | Mouse | 105 | 19 |
| | Human | 53 | 23 |
| Example 153 | Mouse | 44 | 34 |
| | Human | 23 | 62 |
| Example 154 | Mouse[a] | 203 | 7 |
| | Human | 41 | 35 |
| Example 155 | Mouse[a] | 87 | 17 |
| | Human[a] | 8 | 201 |
| Example 166 | Mouse | 204 | 7 |
| | Human | 260 | 6 |
| Example 167 | Mouse | 331 | 6 |
| | Human | 35 | 35 |
| Example 168 | Mouse | 393 | 5 |
| | Human | 69 | 18 |

[a] n = 2;
[b] n = 3;
[c] n = 4.

These results reveal that compounds of the invention are expected to have acceptable or improved metabolic stabilities compared with 4-octyl itaconate and 2-(2-chlorobenzyl) acrylic acid, as shown by their intrinsic clearance ($CI_{int}$) and half-life ($T_{1/2}$) values in this assay. Certain examples shown in Table 6 were more stable, i.e., they exhibited lower intrinsic clearance ($CI_{int}$) in at least mouse or human cells compared to 4-octyl itaconate. Certain examples in Table 6 also had a longer half-life ($T_{1/2}$) values in at least mouse or human cells compared to 4-octyl itaconate. Certain examples in Table 6 were more stable, i.e., they exhibited lower intrinsic clearance ($CI_{int}$) and longer half-life ($T_{1/2}$) values compared to 2-(2-chlorobenzyl)acrylic acid.

REFERENCES

The following publications cited in this specification are herein incorporated by reference in their entirety.

Ackermann et al. *Proc. Soc. Exp. Bio. Med.* 1949, 72(1), 1-9.
Andersen J. L. et al. *Nat. Commun.* 2018, 9,4344.
Angiari S. and O'Neill L. A. *Cell Res.* 2018, 28,613-615.
Bagavant G. et al. *Indian J. Pharm. Sci.* 1994, 56,80-85.
Bambouskova M. et al. *Nature* 2018, 556,501-504.
Blewett M. M. et al. *Sci. Sign.* 2016, 9 (445), rs10; 6.
Brennan M. S. et al. *PLoS One* 2015, 10, e0120254.
Brück J. et al. *Exp. Dermatol.* 2018, 27,611-624.
Cocco M. et al. *J. Med. Chem.* 2014, 57,10366-10382.
Cocco M. et al. *J. Med. Chem.* 2017, 60,3656-3671.
Cordes T. et al. *J. Biol. Chem.* 2016, 291, 14274-14284.
Cordes T. et al. *Mol. Metab.* 2020, 32, 122-135.
Daly R. et al. *medRxiv* 2019, 19001594; doi: https://doi.org/10.1101/19001594.
Daniels B. P. et al. *Immunity* 2019, 50(1), 64-76. e4.
Dibbert S. et al. *Arch. Dermatol. Res.* 2013, 305,447-451.
ElAzzouny M. et al. *J. Biol. Chem.* 2017, 292, 4766-4769.
Gillard G. O. et al. *J. Neuroimmunol.* 2015, 283, 74-85.
Gu L. et al. *Immunol. Cell Biol.* 2020, 98(3), 229-241.
Hanke T. et al. *Pharmacol. Therapeut.* 2016, 157,163-187.
Hunt T. et al. *Consortium of Multiple Sclerosis Centers* 2015 *Annual Meeting,* 27-30 May 2015, Indianapolis, IN, USA: Poster DX37.
Kobayashi E. H. et al. *Nat. Commun.* 2016, 7, 11624.
Kornberg M. D. et al. *Science* 2018, 360, 449-453.
Kulkarni R. A. et al. *Nat. Chem. Biol.* 2019, 15, 391-400.
Lampropoulou V. et al. *Cell Metab.* 2016, 24, 158-166.
Lehmann J. C. U. et al. *J. Invest. Dermatol.* 2007, 127, 835-845.
Liao S.-T. et al. *Nat. Commun.* 2019, 10(1), 5091.
Liu H. et al. *Cell Commun. Signal.* 2018, 16, 81.
McGuire V. A. et al. *Sci. Rep.* 2016, 6, 31159.
Michelucci A. et al. *Proc. Natl. Acad. Sci. USA* 2013, 110, 7820-7825.
Mills E. A. et al. *Front. Neurol.* 2018, 9, 5.
Mills E. L. et al. *Cell* 2016, 167, 457-470.
Mills E. L. et al. *Nature* 2018, 556, 113-117.
Mrowietz U. et al. *Trends Pharmacol. Sci.* 2018, 39, 1-12.
Müller S. et al. *J. Dermatol. Sci.* 2017, 87, 246-251.
Murphy M. P. and O'Neill L. A. J. *Cell* 2018, 174, 780-784.
O'Neill L. A. J. and Artyomov M. N. *Nat. Rev. Immunol.* 2019 273-281.
Olagnier D. et al. *Nat. Commun.* 2018, 9, 3506.
Schmidt T. J. et al. *Bioorg. Med. Chem.* 2007, 15, 333-342.
Shan Q. et al. *Biochem. Biophys. Res. Commun.* 2019, 517, 538-544.
Straub R. H. and Schradin C. *Evol. Med. Public Health* 2016, 1, 37-51S.
Straub R. H. and Cutolo M. *Rheumatology* 2016, 55 (Suppl. 2), ii6-ii14.
Sun X. et al., *FASEB J.* 2019, 33, 12929-12940.
Tang C. et al. *Cell Physiol. Biochem.* 2018, 51, 979-990.
Tang C. et al. *Biochem. Biophys. Res. Commun.* 2019, 508, 921-927.
Tang H. et al. *Biochem. Biophys. Res. Commun.* 2008, 375, 562-565.
Tian et al. *Eur. J. Pharmacol.* 2020, 873, 172989.
van der Reest J. et al. *Nat. Commun.* 2018, 9, 1581.
von Glehn F. et al. *Mult. Scler. Relat. Disord.* 2018, 23, 46-50.
Yi F. et al. *Hepatology* 2020, 873, 172989.
Yu X.-H. et al. *Immunol. Cell Biol.* 2019, 97, 134-141.
Zhang D. et al. *Int. Immunopharmacol.* 2019, 77, 105924.
Zhang S. et al. *Bioorg. Med. Chem.* 2012, 20, 6073-6079.
Zhao C. et al. *Microb. Pathogen.* 2019, 133, 103541.
Zhao G. et al. *Biochem. Biophys. Res. Commun.* 2014, 448, 303-307.

Miscellaneous

All references referred to in this application, including patent and patent applications, are incorporated herein by reference to the fullest extent possible.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims.

The invention claimed is:

1. A compound of formula (I):

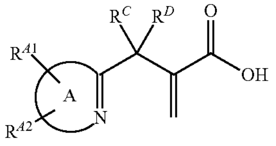

(I)

wherein,

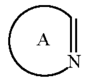

represents a 5 membered heteroaryl ring, which in addition to the C═N shown contains one or more further heteroatoms independently selected from the group consisting of N, O and S;

or

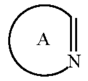

represents a 6 membered heteroaryl ring, which in addition to the C═N shown optionally contains one or more further N atoms;

$R^{A1}$ is $(CH_2)_{0-2}$-phenyl;

wherein $R^{A1}$ is optionally substituted by one or more substituents selected from the group consisting of halo, $C_{1-6}$ alkyl, $C_1$-6 haloalkyl, hydroxy, cyano, $OG^1$, $S(O)_{0-2}G^1$, $SF_5$, $(CH_2)_{0-3}C_3$-7 cycloalkyl and 5-7-membered heterocyclyl wherein said $C_{3-7}$ cycloalkyl and said 5-7-membered heterocyclyl are optionally substituted by one or more groups selected from the group consisting of halo, $C_{1-3}$ alkyl and $C_{1-3}$ haloalkyl; wherein two alkyl groups which are attached to the same carbon atom are optionally joined to form a $C_{3-7}$ cycloalkyl ring; wherein the $C_{3-10}$ cycloalkyl group is optionally fused to a phenyl ring which phenyl ring is optionally substituted by one or more halo atoms; or $R^{A1}$ is optionally substituted by one phenyl ring which is optionally substituted by $C_{1-2}$ haloalkyl, $C_{1-2}$ haloalkoxy or one or more halo atoms;

wherein $G^1$ is $C_{1-6}$ alkyl, $C_{3-7}$ cycloalkyl, $C_{1-6}$ haloalkyl, or $(CH_2)_{0-1}$phenyl wherein $G^1$ is optionally substituted by one or more substituents selected from the group consisting of halo, $C_{1-2}$ alkyl, $C_{1-2}$ haloalkyl, hydroxy, cyano, nitro, $C_{1-2}$ alkoxy and $C_{1-2}$ haloalkoxy;

$R^{A2}$ is selected from the group consisting of halo, $C_{1-6}$ alkyl, $C_{2-6}$ alkenyl, $C_{2-6}$ alkynyl, $C_{1-6}$ haloalkyl, hydroxy, cyano, nitro, $NR^1R^2$, $OG^2$ and $S(O)_{0-2}G^2$;

wherein $G^2$ is $C_{1-6}$ alkyl, $C_{3-7}$ cycloalkyl, $C_{1-6}$ haloalkyl, or phenyl which is optionally substituted by one or more substituents selected from the group consisting of halo, $C_{1-2}$ alkyl, $C_{1-2}$ haloalkyl, hydroxy, cyano, nitro, $C_{1-2}$ alkoxy and $C_{1-2}$ haloalkoxy; and wherein $R^1$ and $R^2$ are independently H or $C_{1-2}$ alkyl or, taken together, $R^1$ and $R^2$ may combine to form a 5-7-membered heterocyclic ring;

or $R^{A2}$ is absent; and $R^C$ and $R^D$ are each independently H, $C_{1-2}$ alkyl, hydroxy, fluoro or $C_{1-2}$ alkoxy; or $R^C$ and $R^D$ may join to form a $C_{3-5}$ cycloalkyl ring;

and wherein the total number of carbon atoms in groups $R^{A1}$ and $R^{A2}$ taken together including their optional substituents is 6-14;

or a pharmaceutically acceptable salt and/or solvate thereof.

2. The compound or pharmaceutically acceptable salt and/or solvate thereof according to claim 1, wherein

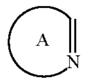

represents an oxadiazole.

3. The compound or pharmaceutically acceptable salt and/or solvate thereof according to claim 1, wherein $R^{A1}$ is substituted by one $OG^1$ group.

4. The compound or pharmaceutically acceptable salt and/or solvate thereof according to claim 3, wherein $G^1$ is $C_{1-6}$ alkyl.

5. The compound or pharmaceutically acceptable salt and/or solvate thereof according to claim 1, wherein $R^{A2}$ is absent, wherein $R^C$ is H and wherein $R^D$ is H.

6. The compound according to claim 1, selected from the group consisting of:

2-((3-(4-chlorobenzyl)-1,2,4-oxadiazol-5-yl)methyl) acrylic acid;

2-((3-(4-chlorophenethyl)-1,2,4-oxadiazol-5-yl)methyl) acrylic acid;

2-((3-(4-chlorophenyl)-1,2,4-oxadiazol-5-yl)methyl) acrylic acid;

2-((3-(1-(4-chlorophenyl)cyclopropyl)-1,2,4-oxadiazol-5-yl)methyl)acrylic acid;

2-((3-(3,4-dichlorobenzyl)-1,2,4-oxadiazol-5-yl)methyl) acrylic acid;

2-((3-(4-(tert-butyl)benzyl)-1,2,4-oxadiazol-5-yl)methyl) acrylic acid;

2-((3-(3,5-dichlorobenzyl)-1,2,4-oxadiazol-5-yl)methyl) acrylic acid;

2-((3-(4-butylphenyl)-1,2,4-oxadiazol-5-yl)methyl) acrylic acid;

2-((3-((4'-chloro-[1,1'-biphenyl]-4-yl)methyl)-1,2,4-oxadiazol-5-yl)methyl)acrylic acid;

2-((3-(4-butylbenzyl)-1,2,4-oxadiazol-5-yl)methyl) acrylic acid;

2-((3-(1-(3-chlorophenyl)cyclopropyl)-1,2,4-oxadiazol-5-yl)methyl)acrylic acid;

2-((3-(1-(4-(trifluoromethyl)phenyl)cyclopropyl)-1,2,4-oxadiazol-5-yl)methyl)acrylic acid;

2-((3-(4-pentylphenyl)-1,2,4-oxadiazol-5-yl)methyl) acrylic acid;

2-((3-(1-(2-chlorophenyl)cyclopropyl)-1,2,4-oxadiazol-5-yl)methyl)acrylic acid;

2-((3-(1-(4-chlorophenyl) cyclobutyl)-1,2,4-oxadiazol-5-yl)methyl)acrylic acid;

2-((3-(3-butylphenyl)-1,2,4-oxadiazol-5-yl)methyl) acrylic acid;

2-((3-(4-pentylbenzyl)-1,2,4-oxadiazol-5-yl)methyl) acrylic acid;

2-((3-(3-butylbenzyl)-1,2,4-oxadiazol-5-yl)methyl) acrylic acid;

2-((3-(2-(4-chlorophenyl) propan-2-yl)-1,2,4-oxadiazol-5-yl)methyl)acrylic acid;

2-((3-(3-(4-chlorophenyl) propyl)-1,2,4-oxadiazol-5-yl) methyl)acrylic acid;

2-((3-(4-propylphenethyl)-1,2,4-oxadiazol-5-yl)methyl) acrylic acid;

2-((3-(4-ethylphenethyl)-1,2,4-oxadiazol-5-yl)methyl) acrylic acid;

2-((3-(4-(trifluoromethyl)benzyl)-1,2,4-oxadiazol-5-yl) methyl)acrylic acid;

2-((3-(1-(4-fluorophenyl)cyclopropyl)-1,2,4-oxadiazol-5-yl)methyl)acrylic acid;

2-((3-(1-(4-methoxyphenyl)cyclopropyl)-1,2,4-oxadiazol-5-yl)methyl)acrylic acid;

2-((3-(4-(trifluoromethoxy)benzyl)-1,2,4-oxadiazol-5-yl) methyl)acrylic acid;

2-((3-(4-(1-(trifluoromethyl)cyclopropyl)benzyl)-1,2,4-oxadiazol-5-yl)methyl)acrylic acid;

2-((3-(1-(4-(trifluoromethoxy)phenyl)cyclopropyl)-1,2,4-oxadiazol-5-yl)methyl)acrylic acid;

2-((3-(1-(4-bromophenyl)cyclopropyl)-1,2,4-oxadiazol-5-yl)methyl)acrylic acid;

2-((3-(4-butoxybenzyl)-1,2,4-oxadiazol-5-yl)methyl) acrylic acid;

2-((3-(1-(4-chloro-3-fluorophenyl)cyclopropyl)-1,2,4-oxadiazol-5-yl)methyl)acrylic acid;

2-((3-(4-butoxyphenyl)-1,2,4-oxadiazol-5-yl)methyl) acrylic acid;

2-((3-(1-(3,5-dichlorophenyl)cyclopropyl)-1,2,4-oxadiazol-5-yl)methyl)acrylic acid;

2-((3-(4-neopentylbenzyl)-1,2,4-oxadiazol-5-yl)methyl) acrylic acid;
2-((3-(4-propylbenzyl)-1,2,4-oxadiazol-5-yl)methyl) acrylic acid;
2-((3-(4-(1,1-difluoropropyl)phenyl)-1,2,4-oxadiazol-5-yl)methyl)acrylic acid;
2-((3-(4-(1-propylcyclopropyl)phenyl)-1,2,4-oxadiazol-5-yl)methyl)acrylic acid;
2-((3-(4-(3,3,3-trifluoropropyl)phenyl)-1,2,4-oxadiazol-5-yl)methyl)acrylic acid;
2-((3-((4-chlorophenyl)difluoromethyl)-1,2,4-oxadiazol-5-yl)methyl)acrylic acid;
2-((3-(4-(5,5,5-trifluoropentyl)phenyl)-1,2,4-oxadiazol-5-yl)methyl)acrylic acid;
2-((3-(4-(2-cyclopropylethyl)phenyl)-1,2,4-oxadiazol-5-yl)methyl)acrylic acid;
2-((3-(1-(4-(pentafluoro-$\lambda^6$-sulfaneyl)phenyl)cyclopropyl)-1,2,4-oxadiazol-5-yl)methyl)acrylic acid;
2-((3-(1-(4-(difluoromethoxy)phenyl)cyclopropyl)-1,2,4-oxadiazol-5-yl)methyl)acrylic acid;
2-((3-(4-(1,1-difluoropentyl)phenyl)-1,2,4-oxadiazol-5-yl)methyl)acrylic acid;
2-((3-(1-(4-butoxyphenyl)cyclopropyl)-1,2,4-oxadiazol-5-yl)methyl)acrylic acid;
2-((3-(4-(1,1,2,2-tetrafluoroethoxy)benzyl)-1,2,4-oxadiazol-5-yl)methyl)acrylic acid;
2-((3-(1-(4-(1,1,2,2-tetrafluoroethoxy)phenyl)cyclopropyl)-1,2,4-oxadiazol-5-yl)methyl)acrylic acid;
2-((5-((4-chlorophenyl)difluoromethyl)-1,2,4-oxadiazol-3-yl)methyl)acrylic acid;
2-((5-((4-bromophenyl)difluoromethyl)-1,2,4-oxadiazol-3-yl)methyl)acrylic acid;
2-((3-(1-(4-((trifluoromethyl)thio)phenyl)cyclopropyl)-1,2,4-oxadiazol-5-yl)methyl)acrylic acid;
2-((5-((4-chlorophenyl)difluoromethyl)-1,2,4-oxadiazol-3-yl)methyl)acrylic acid;
2-((3-((4-bromophenyl)difluoromethyl)-1,2,4-oxadiazol-5-yl)methyl)acrylic acid;
2-((3-((4-butylphenyl)difluoromethyl)-1,2,4-oxadiazol-5-yl)methyl)acrylic acid;
2-((3-(difluoro(4-(trifluoromethyl)phenyl)methyl)-1,2,4-oxadiazol-5-yl)methyl)acrylic acid;
2-((3-(4-(1,1-difluoropentyl)benzyl)-1,2,4-oxadiazol-5-yl)methyl)acrylic acid;
2-((3-(difluoro(4-(trifluoromethoxy)phenyl)methyl)-1,2,4-oxadiazol-5-yl)methyl)acrylic acid;
2-((5-(4-butylbenzyl)-1,2,4-oxadiazol-3-yl)methyl) acrylic acid;
2-((5-(4-butoxyphenyl)-1,2,4-oxadiazol-3-yl)methyl) acrylic acid;
2-((5-(difluoro(4-(trifluoromethyl)phenyl)methyl)-1,2,4-oxadiazol-3-yl)methyl)acrylic acid;
2-((3-(4-(1,1-difluorobutyl)phenyl)-1,2,4-oxadiazol-5-yl) methyl)acrylic acid;
2-((5-(1-(4-(trifluoromethoxy)phenyl)cyclopropyl)-1,2,4-oxadiazol-3-yl)methyl)acrylic acid;
2-((3-(4-(benzyloxy)phenyl)-1,2,4-oxadiazol-5-yl) methyl)acrylic acid;
2-((4-(4-butylphenyl)oxazol-2-yl)methyl)acrylic acid;
2-((4-(1-(4-(trifluoromethyl)phenyl)cyclopropyl)oxazol-2-yl)methyl)acrylic acid;
2-((5-butyl-4-(4-chlorophenyl)oxazol-2-yl)methyl) acrylic acid;
2-((3-(1-(4-cyclobutoxyphenyl)cyclopropyl)-1,2,4-oxadiazol-5-yl)methyl)acrylic acid;
2-((3-(4-cyclopentylbenzyl)-1,2,4-oxadiazol-5-yl) methyl)acrylic acid;
2-((3-(1-(4-cyclopropoxyphenyl)cyclopropyl)-1,2,4-oxadiazol-5-yl)methyl)acrylic acid;
2-((3-(1-(4-cyclopentylphenyl)cyclopropyl)-1,2,4-oxadiazol-5-yl)methyl)acrylic acid;
2-((3-(1-(4-iodophenyl)cyclopropyl)-1,2,4-oxadiazol-5-yl)methyl)acrylic acid;
2-((3-(4-bromophenyl)-1,2,4-oxadiazol-5-yl)methyl) acrylic acid;
2-((3-(4-iodophenyl)-1,2,4-oxadiazol-5-yl)methyl)acrylic acid;
2-((3-(difluoro(4-iodophenyl)methyl)-1,2,4-oxadiazol-5-yl)methyl)acrylic acid;
2-((3-(4-(pentafluoro-$\lambda^6$-sulfaneyl)phenyl)-1,2,4-oxadiazol-5-yl)methyl)acrylic acid;
2-((3-(4-(pentafluoro-$\lambda^6$-sulfaneyl)phenyl)-1,2,4-oxadiazol-5-yl)methyl)acrylic acid;
2,2-((3-(difluoro(4-(pentafluoro-$\lambda^6$-sulfaneyl)phenyl) methyl)-1,2,4-oxadiazol-5-yl)methyl)acrylic acid;
2,2-((3-(difluoro(4-fluorophenyl)methyl)-1,2,4-oxadiazol-5-yl)methyl)acrylic acid;
2-((4-(4-butylbenzyl)oxazol-2-yl)methyl)acrylic acid;
2-((3-(4-cyclobutylbenzyl)-1,2,4-oxadiazol-5-yl)methyl) acrylic acid;
2-((3-(4-butoxy-3-fluorophenyl)-1,2,4-oxadiazol-5-yl) methyl)acrylic acid;
2-((3-(3-chloro-4-propoxyphenyl)-1,2,4-oxadiazol-5-yl) methyl)acrylic acid;
2-((3-(1-(4-cyclobutylphenyl)cyclopropyl)-1,2,4-oxadiazol-5-yl)methyl)acrylic acid;
2-((3-(4-(pyrrolidin-1-yl)phenyl)-1,2,4-oxadiazol-5-yl) methyl)acrylic acid;
2-((3-(1-(3,5-dichloro-4-fluorophenyl)cyclopropyl)-1,2,4-oxadiazol-5-yl)methyl)acrylic acid;
2-((3-(3,5-dichloro-4-fluorobenzyl)-1,2,4-oxadiazol-5-yl)methyl)acrylic acid;
2-((3-(1-(4-chloro-3,5-difluorophenyl)cyclopropyl)-1,2,4-oxadiazol-5-yl)methyl)acrylic acid;
2-((3-(1-(3-chloro-4-(trifluoromethyl)phenyl)cyclopropyl)-1,2,4-oxadiazol-5-yl)methyl)acrylic acid;
2-((3-(3-chloro-4-(trifluoromethyl)benzyl)-1,2,4-oxadiazol-5-yl)methyl)acrylic acid;
2-((3-(1-(4-bromo-3-chlorophenyl)cyclopropyl)-1,2,4-oxadiazol-5-yl)methyl)acrylic acid;
2-((3-(4-bromo-3-chlorobenzyl)-1,2,4-oxadiazol-5-yl) methyl)acrylic acid;
2-((3-(1-(3-chloro-4-methoxyphenyl)cyclopropyl)-1,2,4-oxadiazol-5-yl)methyl)acrylic acid;
2-((3-(1-(3-chloro-4-methylphenyl)cyclopropyl)-1,2,4-oxadiazol-5-yl)methyl)acrylic acid;
2-((3-(4-cyclobutoxyphenyl)-1,2,4-oxadiazol-5-yl) methyl)acrylic acid;
2-((3-(4-cyclopentyloxyphenyl)-1,2,4-oxadiazol-5-yl) methyl)acrylic acid;
(R)-2-((3-(4-(sec-butoxy)phenyl)-1,2,4-oxadiazol-5-yl) methyl)acrylic acid;
(S)-2-((3-(4-(sec-butoxy)phenyl)-1,2,4-oxadiazol-5-yl) methyl)acrylic acid;
2-((3-(4-(4,4,4-trifluorobutoxy)phenyl)-1,2,4-oxadiazol-5-yl)methyl)acrylic acid;
2-((3-(4-(1-propylcyclopropyl)benzyl)-1,2,4-oxadiazol-5-yl)methyl)acrylic acid;
2-((3-(4-propoxyphenyl)-1,2,4-oxadiazol-5-yl)methyl) acrylic acid;
2-((3-((3-chloro-4-methoxyphenyl)difluoromethyl)-1,2,4-oxadiazol-5-yl)methyl)acrylic acid;
2-((3-((3-chloro-4-methylphenyl)difluoromethyl)-1,2,4-oxadiazol-5-yl)methyl)acrylic acid;

2-((3-((4-chlorophenyl) fluoromethyl)-1,2,4-oxadiazol-5-yl)methyl)acrylic acid;

2-((3-((3,5-dichloro-4-fluorophenyl)difluoromethyl)-1,2,4-oxadiazol-5-yl)methyl)acrylic acid;

2-((3-((4-bromo-3-chlorophenyl)difluoromethyl)-1,2,4-oxadiazol-5-yl)methyl)acrylic acid;

2-((3-(difluoro(4-((trifluoromethyl)thio)phenyl)methyl)-1,2,4-oxadiazol-5-yl)methyl)acrylic acid;

2-(1-(3-(1-(4-(trifluoromethyl)phenyl)cyclopropyl)-1,2,4-oxadiazol-5-yl)cyclopropyl)acrylic acid;

3-methyl-2-methylene-3-(3-(1-(4-(trifluoromethyl)phenyl)cyclopropyl)-1,2,4-oxadiazol-5-yl)butanoic acid;

2-((3-(1-(4-((trifluoromethyl)sulfinyl)phenyl)cyclopropyl)-1,2,4-oxadiazol-5-yl)methyl)acrylic acid;

2-((3-(4-((trifluoromethyl)thio)phenyl)-1,2,4-oxadiazol-5-yl)methyl)acrylic acid;

2-((3-(4-(3-methoxypropoxy)phenyl)-1,2,4-oxadiazol-5-yl)methyl)acrylic acid;

2-((3-(4-butoxy-3-chlorophenyl)-1,2,4-oxadiazol-5-yl)methyl)acrylic acid;

2-((3-(4-butoxy-3-(trifluoromethyl)phenyl)-1,2,4-oxadiazol-5-yl)methyl)acrylic acid;

2-((3-(4-butoxy-3,5-difluorophenyl)-1,2,4-oxadiazol-5-yl)methyl)acrylic acid;

2-((3-(3-chloro-4-methoxybenzyl)-1,2,4-oxadiazol-5-yl)methyl)acrylic acid;

2-((3-(4-chloro-3,5-difluorobenzyl)-1,2,4-oxadiazol-5-yl)methyl)acrylic acid;

2-((3-(3-chloro-4-methylbenzyl)-1,2,4-oxadiazol-5-yl)methyl)acrylic acid;

2-(1-(3-(difluoro(4-(trifluoromethyl)phenyl)methyl)-1,2,4-oxadiazol-5-yl)cyclopropyl)acrylic acid;

2-methylene-3-(3-(1-(4-(trifluoromethyl)phenyl)cyclopropyl)-1,2,4-oxadiazol-5-yl)butanoic acid;

2-((6-(1-(4-chlorophenyl)cyclopropyl) pyridin-2-yl)methyl)acrylic acid; and 2-((3-(1-(4-bromo-3,5-dichlorophenyl)cyclopropyl)-1,2,4-oxadiazol-5-yl)methyl)acrylic acid;

or a pharmaceutically acceptable salt and/or solvate of any one thereof.

7. A pharmaceutical composition comprising a compound or pharmaceutically acceptable salt and/or solvate thereof according to claim 1 and one or more pharmaceutically acceptable diluents or carriers.

8. A method of treating or preventing an inflammatory disease or a disease associated with an undesirable immune response, which comprises administering a compound or pharmaceutically acceptable salt and/or solvate thereof according to claim 1.

9. The method according to claim 8, wherein the inflammatory disease or disease associated with an undesirable immune response is, or is associated with, a disease selected from the group consisting of: psoriasis (including chronic plaque, erythrodermic, pustular, guttate, inverse and nail variants), asthma, chronic obstructive pulmonary disease (COPD, including chronic bronchitis and emphysema), heart failure (including left ventricular failure), myocardial infarction, angina pectoris, other atherosclerosis and/or atherothrombosis-related disorders (including peripheral vascular disease and ischaemic stroke), a mitochondrial and neurodegenerative disease, autoimmune paraneoplastic retinopathy, transplantation rejection (including antibody-mediated and T cell-mediated forms), multiple sclerosis, transverse myelitis, an ischaemia-reperfusion injury, AGE-induced genome damage, an inflammatory bowel disease, primary sclerosing cholangitis (PSC), a PSC-autoimmune hepatitis overlap syndrome, non-alcoholic fatty liver disease (non-alcoholic steatohepatitis), rheumatica, granuloma annulare, cutaneous lupus erythematosus (CLE), systemic lupus erythematosus (SLE), lupus nephritis, a drug-induced lupus, autoimmune myocarditis or myopericarditis, Dressler's syndrome, giant cell myocarditis, post-pericardiotomy syndrome, drug-induced hypersensitivity syndromes (including hypersensitivity myocarditis), eczema, sarcoidosis, erythema nodosum, acute disseminated encephalomyelitis (ADEM), neuromyelitis optica spectrum disorders, MOG (myelin oligodendrocyte glycoprotein) antibody-associated disorders (including MOG-EM), optic neuritis, CLIPPERS (chronic lymphocytic inflammation with pontine perivascular enhancement responsive to steroids), diffuse myelinoclastic sclerosis, Addison's disease, alopecia areata, ankylosing spondylitis, other spondyloarthritides (including peripheral spondyloarthritis, that is associated with psoriasis, inflammatory bowel disease, reactive arthritis or juvenile onset forms), antiphospholipid antibody syndrome, autoimmune hemolytic anaemia, autoimmune hepatitis, autoimmune inner ear disease, pemphigoid (including bullous pemphigoid, mucous membrane pemphigoid, cicatricial pemphigoid, herpes gestationis or pemphigoid gestationis, ocular cicatricial pemphigoid), linear IgA disease, Behçet's disease, celiac disease, Chagas disease, dermatomyositis, diabetes mellitus type I, endometriosis, Goodpasture's syndrome, Graves' disease, Guillain-Barre syndrome and its subtypes (including acute inflammatory demyelinating polyneuropathy, AIDP, acute motor axonal neuropathy (AMAN), acute motor and sensory axonal neuropathy (AMSAN), pharyngeal-cervical-brachial variant, Miller-Fisher variant and Bickerstaff's brainstem encephalitis), progressive inflammatory neuropathy, Hashimoto's disease, hidradenitis suppurativa, inclusion body myositis, necrotising myopathy, Kawasaki disease, IgA nephropathy, Henoch-Schonlein purpura, idiopathic thrombocytopenia purpura, thrombotic thrombocytopenia purpura (TTP), Evans' syndrome, interstitial cystitis, mixed connective tissue disease, undifferentiated connective tissue disease, morphea, myasthenia gravis (including MuSK antibody positive and seronegative variants), narcolepsy, neuromyotonia, pemphigus vulgaris, pernicious anaemia, psoriatic arthritis, polymyositis, primary biliary cholangitis (also known as primary biliary cirrhosis), rheumatoid arthritis, palindromic rheumatism, schizophrenia, autoimmune (meningo-) encephalitis syndromes, scleroderma, Sjogren's syndrome, stiff person syndrome, polymylagia rheumatica, giant cell arteritis (temporal arteritis), Takayasu arteritis, polyarteritis nodosa, Kawasaki disease, granulomatosis with polyangitis (GPA; formerly known as Wegener's granulomatosis), eosinophilic granulomatosis with polyangiitis (EGPA; formerly known as Churg-Strauss syndrome), microscopic polyarteritis/polyangiitis, hypocomplementaemic urticarial vasculitis, hypersensitivity vasculitis, cryoglobulinemia, thromboangiitis obliterans (Buerger's disease), vasculitis, leukocytoclastic vasculitis, vitiligo, acute disseminated encephalomyelitis, adrenoleukodystrophy, Alexander's disease, Alper's disease, balo concentric sclerosis or Marburg disease, cryptogenic organising pneumonia (formerly known as bronchiolitis obliterans organizing pneumonia), Canavan disease, central nervous system vasculitic syndrome, Charcot-Marie-Tooth disease, childhood ataxia with central nervous system hypomyelination, chronic inflammatory demyelinating polyneuropathy (CIDP), diabetic retinopathy, globoid cell leukodystrophy (Krabbe disease), graft-versus-host disease (GVHD) (including acute and chronic forms, as well as intestinal GVHD), hepatitis C (HCV) infection or complication, herpes simplex viral infection or complication, human immunodeficiency virus (HIV) infection or complication, lichen planus, monomelic amyotrophy, cystic fibrosis, pulmonary arterial hypertension (PAH, including idiopathic PAH), lung sarcoidosis, idiopathic pulmonary fibrosis, paediatric asthma, atopic dermatitis, allergic dermatitis, contact dermatitis, allergic rhinitis, rhinitis, sinusitis, conjunctivitis, allergic conjunctivitis, keratoconjunctivitis sicca, dry eye, xerophthalmia, glaucoma, macular oedema, diabetic macular oedema, central retinal vein occlusion (CRVO), macular degeneration (including dry and/or wet age related macular degeneration, AMD), post-operative cataract inflammation, uveitis (including posterior, anterior, intermediate and pan uveitis), iridocyclitis, scleritis, corneal graft and limbal cell transplant rejection, gluten sensitive enteropathy (coeliac disease), dermatitis herpetiformis, eosinophilic esophagitis, achalasia, autoimmune dysautonomia, autoimmune encephalomyelitis, autoimmune oophoritis, autoimmune orchitis, autoimmune pancreatitis, aortitis and periaortitis, autoimmune retinopathy, autoimmune urticaria, Behcet's disease, (idiopathic) Castleman's disease, Cogan's syndrome, IgG4-related disease, retroperitoneal fibrosis, juvenile idiopathic arthritis including systemic juvenile idiopathic arthritis (Still's disease), adult-onset Still's disease, ligneous conjunctivitis, Mooren's ulcer, pityriasis lichenoides et varioliformis acuta (PLEVA, also known as Mucha-Habermann disease), multifocal motor neuropathy (MMN), paediatric acute-onset neuropsychiatric syndrome (PANS) (including paediatric autoimmune neuropsychiatric disorders associated with streptococcal infections (PANDAS)), paraneoplastic syndromes (including paraneoplastic cerebellar degeneration, Lambert-Eaton myaesthenic syndrome, limbic encephalitis, brainstem encephalitis, opsoclonus myoclonus ataxia syndrome, anti-NMDA receptor encephalitis, thymoma-associated multiorgan autoimmunity), perivenous encephalomyelitis, reflex sympathetic dystrophy, relapsing polychondritis, sperm & testicular autoimmunity, Susac's syndrome, Tolosa-Hunt syndrome, Vogt-Koyanagi-Harada Disease, anti-synthetase syndrome, autoimmune enteropathy, immune dysregulation polyendocrinopathy enteropathy X-linked (IPEX), microscopic colitis, autoimmune lymphoproliferative syndrome (ALPS), autoimmune polyendocrinopathy-candidiasis-ectodermal dystrophy syndrome (APEX), gout, pseudogout, an amyloid disease (including AA or secondary amyloidosis), eosinophilic fasciitis (Shulman syndrome) progesterone hypersensitivity (including progesterone dermatitis), familial Mediterranean fever (FMF), a tumour necrosis factor (TNF) receptor-associated periodic fever syndrome (TRAPS), hyperimmunoglobulinaemia D with periodic fever syndrome (HIDS), a PAPA (pyogenic arthritis, pyoderma gangrenosum, severe cystic acne) syndrome, deficiency of interleukin-1 receptor antagonist (DIRA), deficiency of the interleukin-36-receptor antagonist (DITRA), cryopyrin-associated periodic syndromes (CAPS) (including familial cold autoinflammatory syndrome [FCAS], Muckle-Wells syndrome, neonatal onset multisystem inflammatory disease [NOMID]), NLRP12-associated autoinflammatory disorders (NLRP12AD), periodic fever aphthous stomatitis (PFAPA), chronic atypical neutrophilic dermatosis with lipodystrophy and elevated temperature (CANDLE), Majeed syndrome, Blau syndrome (also known as juvenile systemic granulomatosis), macrophage activation syndrome, chronic recurrent multifocal osteomyelitis (CRMO), familial cold autoinflammatory syndrome, mutant adenosine deaminase 2 and monogenic interferonopathies (including Aicardi-Goutières syndrome, retinal vasculopathy with cerebral leukodystrophy, spondyloenchondrodysplasia, STING [stimulator of interferon genes]-associated vasculopathy with onset in infancy, proteasome associated autoinflammatory syndromes, familial chilblain lupus, dyschromatosis symmetrica hereditaria), Schnitzler syndrome, familial cylindromatosis, congenital B cell lymphocytosis, OTULIN-related autoinflammatory syndrome, type 2 diabetes mellitus, insulin resistance and the metabolic syndrome (including obesity-associated inflammation), atherosclerotic disorders, and renal inflammatory disorders.

10. The method according to claim 8, for use in combination with a further therapeutic agent, selected from the group consisting of a corticosteroid (glucocorticoid), retinoid, anthralin, vitamin D analogue, calcineurin inhibitors, phototherapy or photochemotherapy or other form of ultraviolet light irradiation therapy, cyclosporine, a thiopurine, methotrexate, an anti-TNFα agent, a phosphodiesterase-4 (PDE4) inhibitor, an anti-IL-17 agent, an anti-IL12/IL-23 agent, an anti-IL-23 agent, a JAK (Janus Kinase) inhibitor, plasma exchange, intravenous immune globulin (IVIG), cyclophosphamide, an anti-CD20 B cell depleting agent, an anthracycline analogue, cladribine, a sphingosine 1-phosphate receptor modulator or a sphingosine analogue, an interferon beta preparation (including interferon beta 1b/la), glatiramer, an anti-CD3 therapy, an anti-CD52 targeting agent, leflunomide, teriflunomide, gold compound, laquinimod, a potassium channel blocker, mycophenolic acid, mycophenolate mofetil, a purine analogue, a mTOR (mechanistic target of rapamycin) pathway inhibitor, anti-thymocyte globulin (ATG), an IL-2 receptor (CD25) inhibitor, an anti-IL-6 receptor or an anti-IL-6 agent, a Bruton's tyrosine kinase (BTK) inhibitor, a tyrosine kinase inhibitor, ursodeoxycholic acid, hydroxychloroquine, chloroquine, a B cell activating factor (BAFF, also known as BLyS, B lymphocyte stimulator) inhibitor, other B cell targeted therapy including a fusion protein targeting both APRIL (A PRoliferation-Inducing Ligand) and BLyS, a PI3K inhibitor including pan-inhibitor or one targeting the p1108 and/or p110γ containing isoforms, an interferon α receptor inhibitor, a T cell co-stimulation blocker, thalidomide and its derivatives, dapsone, clofazimine, a leukotriene antagonist, theophylline, an anti-IgE therapy, an anti-IL-5 agent, a long-acting muscarinic agent, a PDE4 inhibitor, riluzole, a free radical scavenger, a proteasome inhibitor, a complement cascade inhibitor including one directed against C5, immunoadsor, antithymocyte globulin, 5-aminosalicylates and their derivatives, an anti-integrin agent including one targeting α4β1 and/or α4β7 integrins, an anti-CD11-α agent, a non-steroidal anti-inflammatory drug (NSAID) including a salicylate, a propionic acid, an acetic acid, an oxicam a fenamate, a selective or relatively selective COX-2 inhibitor, colchicine, an IL-4 receptor inhibitor, topical/contact immunotherapy, an anti-IL-1 receptor therapy, an IL-1B inhibitor, an IL-1 neutralising therapy, chlorambucil, a specific antibiotic with immunomodulatory properties and/or ability to modulate NRF2, anti-androgenic therapy, pentoxifylline, ursodeoxycholic acid, obeticholic acid, fibrate, a cystic fibrosis transmembrane conductance regulator (CFTR) modulator, a VEGF (vascular endothelial growth factor) inhibitor, pirfenidone or mizoribine.

11. The compound or pharmaceutically acceptable salt and/or solvate thereof according to claim 2, wherein

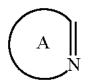

is 1,2,4-oxadiazole.

12. The compound or pharmaceutically acceptable salt and/or solvate thereof according to claim 6, which is 2-((3-(4-butylbenzyl)-1,2,4-oxadiazol-5-yl)methyl)acrylic acid.

13. The compound or pharmaceutically acceptable salt and/or solvate thereof according to claim 6, which is the pharmaceutically acceptable salt of 2-((3-(4-butylbenzyl)-1,2,4-oxadiazol-5-yl)methyl)acrylic.

14. The compound or pharmaceutically acceptable salt and/or solvate thereof according to claim 6, which is 2-((3-(1-(4-bromophenyl)cyclopropyl)-1,2,4-oxadiazol-5-yl)methyl)acrylic acid.

15. The compound or pharmaceutically acceptable salt and/or solvate thereof according to claim 6, which is the pharmaceutically acceptable salt of 2-((3-(1-(4-bromophenyl)cyclopropyl)-1,2,4-oxadiazol-5-yl)methyl)acrylic acid.

16. The compound or pharmaceutically acceptable salt and/or solvate thereof according to claim 6, which is 2-((3-(4-butoxyphenyl)-1,2,4-oxadiazol-5-yl)methyl)acrylic acid.

17. The compound or pharmaceutically acceptable salt and/or solvate thereof according to claim 6, which is the pharmaceutically acceptable salt of 2-((3-(4-butoxyphenyl)-1,2,4-oxadiazol-5-yl)methyl)acrylic acid.

18. The compound or pharmaceutically acceptable salt and/or solvate thereof according to claim 6, which is 2-((3-(1-(4-((trifluoromethyl)thio)phenyl)cyclopropyl)-1,2,4-oxadiazol-5-yl)methyl)acrylic acid.

19. The compound or pharmaceutically acceptable salt and/or solvate thereof according to claim 6, which is the pharmaceutically acceptable salt of 2-((3-(1-(4-((trifluoromethyl)thio)phenyl)cyclopropyl)-1,2,4-oxadiazol-5-yl)methyl)acrylic.

20. The compound or pharmaceutically acceptable salt and/or solvate thereof according to claim 6, which is 2-((3-(1-(4-(pentafluoro-$\lambda^6$-sulfaneyl)phenyl)cyclopropyl)-1,2,4-oxadiazol-5-yl)methyl)acrylic acid.

21. The compound or pharmaceutically acceptable salt and/or solvate thereof according to claim 6, which is the pharmaceutically acceptable salt of 2-((3-(1-(4-(pentafluoro-$\lambda^6$-sulfaneyl)phenyl)cyclopropyl)-1,2,4-oxadiazol-5-yl)methyl)acrylic.

* * * * *